(12) United States Patent
Grossman

(10) Patent No.: US 11,197,884 B2
(45) Date of Patent: Dec. 14, 2021

(54) MODULATION OF THE NOTCH SIGNALING PATHWAY FOR TREATMENT OF RESPIRATORY DISORDERS

(71) Applicant: Ionis Pharmaceuticals, Inc., Carlsbad, CA (US)

(72) Inventor: Tamar R. Grossman, La Jolla, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/638,018

(22) PCT Filed: Aug. 17, 2018

(86) PCT No.: PCT/US2018/046905
§ 371 (c)(1),
(2) Date: Feb. 10, 2020

(87) PCT Pub. No.: WO2019/036613
PCT Pub. Date: Feb. 21, 2019

(65) Prior Publication Data
US 2020/0171071 A1 Jun. 4, 2020

Related U.S. Application Data

(60) Provisional application No. 62/672,939, filed on May 17, 2018, provisional application No. 62/547,580, filed on Aug. 18, 2017.

(51) Int. Cl.
| | |
|---|---|
| *C07H 21/04* | (2006.01) |
| *A61K 31/7115* | (2006.01) |
| *A61P 11/12* | (2006.01) |
| *A61P 11/06* | (2006.01) |
| *C07K 14/705* | (2006.01) |
| *C12N 15/113* | (2010.01) |
| *A61K 9/00* | (2006.01) |
| *A61K 45/06* | (2006.01) |

(52) U.S. Cl.
CPC ........... *A61K 31/7115* (2013.01); *A61P 11/06* (2018.01); *A61P 11/12* (2018.01); *C07K 14/705* (2013.01); *C12N 15/113* (2013.01); *A61K 9/007* (2013.01); *A61K 9/0019* (2013.01); *A61K 45/06* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,501,729 A | 2/1985 | Boucher et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |

(Continued)

FOREIGN PATENT DOCUMENTS

| | | |
|---|---|---|
| WO | WO 1999/014226 | 3/1999 |
| WO | WO 2000/063364 | 10/2000 |

(Continued)

OTHER PUBLICATIONS

Zong, Dandan, et al. "Notch signaling in lung diseases: focus on Notch1 and Notch3." Therapeutic advances in respiratory disease 10.5 (2016): 468-484.*
Kim, Min Ju, et al. "Notch1 targeting siRNA delivery nanoparticles for rheumatoid arthritis therapy." Journal of Controlled Release 216 (2015): 140-148.*
Taichman, Darren B., et al. "Notch1 and Jagged1 expression by the developing pulmonary vasculature." Developmental dynamics: an official publication of the American Association of Anatomists 225.2 (2002): 166-175.*
Anderson "Use of Respimat Soft Mist inhaler in COPD patients" Int J Chron Obstruct Pulmon Dis. (2006): 251-259.

(Continued)

*Primary Examiner* — Kimberly Chong
(74) *Attorney, Agent, or Firm* — Sheppard Mullin Richter & Hampton LLP

(57) ABSTRACT

Provided herein are methods, compounds, and compositions for modulating expression of at least one member of the Notch signaling pathway in a cell or individual. Such methods, compounds, and compositions are useful to treat, prevent, delay, or ameliorate a respiratory disorder associated with excessive mucus production in an individual.

25 Claims, No Drawings
Specification includes a Sequence Listing.

(56) References Cited

U.S. PATENT DOCUMENTS

| | | |
|---|---|---|
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,811,534 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,673,661 B1 | 1/2004 | Liu et al. |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 7,015,315 B1 | 3/2006 | Cook et al. |
| 7,034,133 B2 | 4/2006 | Wengel et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,796,437 B2 | 8/2014 | Swayze et al. |
| 8,828,956 B2 | 9/2014 | Manoharan et al. |
| 9,005,906 B2 | 4/2015 | Swayze et al. |

(56) References Cited

U.S. PATENT DOCUMENTS

| | | | |
|---|---|---|---|
| 9,012,421 B2 | 4/2015 | Migawa et al. | |
| 9,096,636 B2 * | 8/2015 | Crooke | C07H 21/04 |
| 9,127,276 B2 | 8/2015 | Prakash et al. | |
| 9,290,760 B2 | 3/2016 | Rajeev et al. | |
| 9,518,121 B2 | 12/2016 | Chinn et al. | |
| 10,011,661 B2 | 7/2018 | Chinn et al. | |
| 2001/0053519 A1 | 12/2001 | Fodor et al. | |
| 2003/0082807 A1 | 5/2003 | Wengel | |
| 2003/0158403 A1 | 8/2003 | Manoharan et al. | |
| 2003/0175906 A1 | 9/2003 | Manoharan et al. | |
| 2003/0207841 A1 | 11/2003 | Kaneko et al. | |
| 2003/0224377 A1 | 12/2003 | Wengel et al. | |
| 2003/0228597 A1 | 12/2003 | Cowsert et al. | |
| 2004/0102401 A1 | 5/2004 | Dean et al. | |
| 2004/0143114 A1 | 7/2004 | Imanishi et al. | |
| 2004/0171570 A1 | 9/2004 | Allerson et al. | |
| 2004/0192918 A1 | 9/2004 | Imanishi et al. | |
| 2005/0130923 A1 | 6/2005 | Bhat et al. | |
| 2006/0148740 A1 | 7/2006 | Platenburg | |
| 2007/0031844 A1 | 2/2007 | Khvorova et al. | |
| 2008/0039618 A1 | 2/2008 | Allerson et al. | |
| 2010/0119474 A1 | 5/2010 | Crystal et al. | |
| 2010/0190837 A1 | 7/2010 | Migawa et al. | |
| 2010/0197762 A1 | 8/2010 | Swayze et al. | |
| 2011/0123520 A1 | 5/2011 | Manoharan et al. | |
| 2012/0053112 A1 | 3/2012 | Whitsett | |
| 2013/0130378 A1 | 5/2013 | Manoharan et al. | |
| 2013/0203836 A1 | 8/2013 | Rajeev et al. | |
| 2014/0107330 A1 | 4/2014 | Freier et al. | |
| 2015/0018540 A1 | 1/2015 | Prakash et al. | |
| 2015/0184153 A1 | 7/2015 | Freier et al. | |
| 2015/0191727 A1 | 7/2015 | Migawa et al. | |
| 2015/0267195 A1 | 9/2015 | Seth et al. | |
| 2015/0275212 A1 | 10/2015 | Albaek et al. | |

FOREIGN PATENT DOCUMENTS

| | | |
|---|---|---|
| WO | WO 2004/106356 | 12/2004 |
| WO | WO 2005/073250 | 8/2005 |
| WO | WO 2007/134181 | 11/2007 |
| WO | WO 2008/101157 | 8/2008 |
| WO | WO 2009/114726 | 9/2009 |
| WO | WO 2011/133876 | 10/2011 |
| WO | WO 2014/141064 | 9/2014 |
| WO | WO 2014/179620 | 11/2014 |
| WO | WO 2015/106128 | 7/2015 |
| WO | WO 2015/123325 | 8/2015 |
| WO | WO 2016/046151 | 3/2016 |
| WO | WO 2017/106210 | 6/2017 |

OTHER PUBLICATIONS

Albaek et al., "Analogues of a Locked Nucleic Acid with Three-Carbon 2',4'-Linkages: Synthesis by Ring-Closing Metathesis and Influence on Nucleic Acid Duplex Stability and Structure" J. Org. Chem. (2006) 71, 7731-7740.
Altschul et al., "Basic Local Alignment Search Tool" J. Mol. Biol. (1990) 215, 403-410.
Braasch et al., "Novel Antisense and Peptide Nucleic Acid Strategies for Controlling Gene Expression" Biochemistry (2002) 41: 4503-4510.
Branch et al., "A good antisense molecule is hard to find," TIBS (1998) 23:45-50.
Bray, "Notch signalling in context" Nat. Rev. Mol. Cell Biol. (2016) 17: 722-735.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Crooke et al., "Pharmacokinetic Properties of Several Novel Oligonucleotide Analogs in mice" J. Pharmacol. Exp. Ther. (1996) 277: 923-937.
Crooke, ST., et al., "Antisense Drug Technology" Second Edition, CRC Press (2008) Chapters 1-28.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Elayadi et al., "Application of PNA and LNA oligomers to chemotherapy" Curr. Opinion Invens. Drugs (2001) 2:558-561.
Englisch et al., "Chemically Modified Oligonucleotides as Probes and Inhibitors" Angewandte Chemie International Edition (1991) 30: 613-722.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Gautschi et al., "Activity of a novel bcl-2/bcl-xLbispecific antisense oligonucleotide against tumors of diverse histologic origins" J. Natl. Cancer Inst. (2001) 93:463-471.
International Search Report for PCT/US18/046905 dated Dec. 18, 2018.
Johnson et al., "Continuous exposure to house dust mite elicits chronic airway inflammation and structural remodeling" Am J Respir Crit Care Med vol. (2004) 169: 378-385.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz The Concise Encyclopedia Of Polymer Science And Engineering, Kroschwitz, J.I., Ed., John Wiley & Sons, 1990, 858-859.
Kumar et al., "The first analogues of LNA (locked nucleic acids): phosphorothioate-LNA and 2'-thio-LNA" Bioorg Med Chem Lett. (1998) 8:2219-2222.
Kumar et al., "Design, synthesis, biophysical and primer extension studies of novel acyclic butyl nucleic acid (BuNA)" Org. Biomol. Chem. (2013) 11: 5853-5865.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.
Manoharan et al., "Chemical Modifications to Improve Uptake and Bioavailability of Antisense Oligonucleotides" Ann. N.Y. Acad. Sci. (1992) 660:306.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Manoharan et al., "Oligonucleotide Conjugates: Alteration of the Pharmacokinetic Properties of Antisense Agents" Nucleosides & Nucleotides (1995) 14(3-5):969-973.
Mishra et al., "Improved leishmanicidal effect of phosphorotioate antisense oligonucleotides by LDL-mediated delivery" Biochim. Biophys. Acta (1995) 1264:229-237.
New England Biolabs 1998/99 Catalog (cover page and pp. 121 and 284).

(56) References Cited

OTHER PUBLICATIONS

Nishina et al., "Chimeric Antisense Oligonucleotide Conjugated to α-Tocopherol" Molecular Therapy Nucleic Acids (2015) 4:e220.

Nishina et al., "Efficieny In Vivo Delivery of siRNA to the Liver by Conjugation of α-Tocopherol" Molecular Therapy (2008) 16: 734-740.

Oberhauser et al., "Effective incorporation of 2'-O-methyl-oligoribonucleotides into liposomes and enhanced cell association through modifications with thiocholesterol" Nucl. Acids Res. (1992) 20(3):533-538.

Reynolds et al., "Rational siRNA design for RNA interference" Nature Biotechnology (2004) 22(3):326-330.

Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.

Sanghvi et al., "Heterocyclic Base Modifications in Nucleic Acids and Their Applications in Antisense Oligonucleotides" Antisense Research and Applications (1993) pp. 273-288.

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Shea et al., "Synthesis, hybridization properties and antiviral activity of lipid-oligodeoxynucleotide conjugates" Nucl. Acids Res. (1990) 18(13):3777-3783.

Singh et al., "LNA (locked nucleic acids): synthesis and high-affinity nucleic acid recognition" Chem. Commun. (1998) 4:455-456.

Singh et al., "Synthesis of 2'-Amino-LNA: A Novel Conformationally Restricted High-Affinity Oligonucleotide Analogue with a Handle" J. Org. Chem. (1998) 63:10035-10039.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Svinarchuk et al., "Inhibition of HIV proliferation in MT-4 cells by antisense oligonucleotide conjugated to lipophilic groups" Biochimie (1993) 75:49-54.

Tsao et al., "Notch signaling prevents mucous metaplasia in mouse conducting airways during postnatal development" Development (2011) 138: 3533-3543.

Woolf et al., "Specificity of antisense oligonucleotides in vivo" PNAS (1992) 89: 7305-7309.

Zhang et al., "PowerBLAST: A New Network BLAST Application for Interactive or Automated Sequence Analysis and Annotation" Genome Res. (1997) 7: 649-656.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

Zimrin et al., "An antisense oligonucleotide to the notch ligand jagged enhances fibroblast growth factor-induced angiogenesis in vitro" J Biol Chem (1996) 271: 32499-32502.

Tilley et al., "Down-regulation of the notch pathway in human airway epithelium in association with smoking and chronic obstructive pulmonary disease" Am J Respir Crit Care Med (2009) 179: 457-466.

Mori et al., "Notch3-Jagged signaling controls the pool of undifferentiated airway progenitors" Development (2015) 142: 258-267.

Guo et al., "Small interfering RNA-mediated knockdown of Notch1 in lung T cells of asthmatic mice affects T cell differentiation" Chin Med J (2009) 122: 2647-2651.

Hu et al., "Mesenchymal Deficiency of Notch1 Attenuates Bleomycin-Induced Pulmonary Fibrosis" Am J Pathol (2015) 185: 3066-3075.

Luan et al., "Roles of FIZZ1 and NOTCH1 in asthma" Chin. J. of Contemporary Pediatrics (2011) 13: 219-222.

Partial Search Report for EP 18846461.4 dated Apr. 14, 2021.

Sanghvi et al., "Carbohydrate Modifications in Antisense Research" ACS Symposium Series (1994) 580; Chapters 3 and 4, 40-65.

Zhang et al., "PI3K ad Notch signal pathways coordinately regulate the activation and proliferation of T lymphocytes in asthma" Life Sciences (2013) 92: 890-895.

\* cited by examiner

SEQUENCE LISTING

<160> NUMBER OF SEQ ID NOS: 250

<210> SEQ ID NO 1
<211> LENGTH: 42000
<212> TYPE: DNA
<213> ORGANISM: Mus musculus

<400> SEQUENCE: 1

```
acttagagtg accctccggc ctcccaagtg ctagctaggc tttaatacct tactactttc      60
tttaggcagt ttatctaacc atccagccat tctccacatt ttatgcattt gaagtttcat     120
tgtaggtcca tatcatttca aacatcccga agtgttcttt ttactgataa aagcaaccac     180
tgtgtgcctt caaaaaaaaa aaaaaaaaaa aaaacataat gaatggcact ggtttcaaat     240
gtgcttggta ctgaaagttg ataatccaca cacctgtgtc atccatcccc caattaagac     300
acagatagct gatttatgcc cagaaaagga ccaagcacat caaacctcca agcacacacc     360
accctaacca tacgtgcacg caagactggc gtttcctgtc ctcatccacc tttgtatata     420
ggagctctaa aggagctcat acgcgctgaa ctcttggtac ccgacttatt ttcctcacgt     480
ggcgttcttt agatcagtca cactacggca tacaacagta cttttcaata aatattgatt     540
agctgattct tctcagtgtt gataaataat tttggttgat tagaagcttt aaaatacaat     600
```

```
tataacataa atgcctctta ttaagtccca tgggaagtca gggctgtttg ttgatgaatg    660
aatgaaggtt gggtatgttt tgtagaaagg gaattgaggc atcatatttt taaaatcaga    720
gaagatatcc aaacacctgc aacaggttgc tatctggctc ggagcaacct ggggtggaag    780
caatggtgat ggctaagtgt tgttttccat gggaatgttt ccttaactat acacttatag    840
ttggaaagca aagctcaaag ggaggctatg gcttggcaag gggaaatgtc cattttgaa     900 ttctttgagc agtagttccc cattctccag gtttcagggg tgatcaagga agttgaggac    960
agaagttcca cccagtgcct gttgcagtat aaaaaagctt cttgggggag tcccagctca   1020
ctggaagagc accaaatgaa aacatttta aagaatcccc tatagcccac aactgccttc    1080
ctcaaatgtg ggttcccagg cacagaaaag actagaggct ctgtgttatt gctgtgcct   1140 ttggtgtttc ttagtgattt gacattccca gtatgccatt aggtgctttt tactcctcaa   1200
aactttcctt ttagtgaagt gagctaaact cactgttaga taggtactga tctcagcttt   1260
cacgaagccc agattgttag cagcagagca actataaatc tcaggtagtc ttccaatgta   1320
actcaggtgg ctggctcaaa ccttctgaac taaaaactct ggctccatag ccgccttcta   1380
ggggttagtg tgggacatgg ggcatgcatc attggataca gctttacatt ttaaaacagc   1440
tttagacctt gggacctcaa gaaatataga ctctaagacc actgcagtct ttgtgggcta   1500
tgtggctttt ccacaccacc aatcctttgc tataaaagcg ttattgagca ccctaacttg   1560
gcgactagag atgcaggtaa gaagtccaat cagaagtgag gactgttata tttctggaaa   1620
ctttagtggg aaaaaaacaa aaacaaaaac aaaaacctgt gttgaattaa tgttgaaaac   1680
gggatgcttt gcattcgtga tcattgggtg gaggaggact gggcacactg gaaaatgccc   1740
aggtggctgc tgtgtaggcc aggtgcttct gtgaccagtt gcaaactcat tctgatttgg   1800
gatatgccct tcccaattat ggattaagtt actcgggaat ggttagaatg agatgcattg   1860
ccattaagaa atcacctatc tcaggtggtt aaaatgccca agttacgaaa ccatctttgt   1920
tagcctggaa ctcagctttc tcaaccccat caagtggtat ggggcactat ctatgctggg   1980
ccactcttta aacgtagata accacaaata acctgtgttg ttatgttgtc gtgttcagca   2040
tgttggaaac tgttttccc tttacccatc atgccctgat gtctagaagg gttgaggcgc    2100
taaagcaatc tcggaaaaat cagagctttt cttcaggaca ggctcaacgc aagttaagaa   2160
acccttttcg tcctttaatg gaaatctgtt ttcctaaaga gctccgttta aacccgcctg   2220
gagtggagct ggcagagact tcagccagcc tttgggttcc ctttgacctt gattatgacc   2280
aggagtgtcg ctgctaattg cgaggcctgc ctcaaggtgg aaaatggcat cggtttccac   2340
caccacccag gagaagccaa gttctgtgga ccacgacagc ggttaggttc ttttcaggcc   2400
gcgtctcgcc acccagagag cagcgcggag gccgcctaca ggtgcagtcc cgccactgcg   2460
cccgggctgg aggctggcgg agccctcggc gtctcagaaa gcccttcccg aagtccgggc   2520
tgagcccccg ggtgcccgcc ggccactccc cctgcttccc ccacgcctct gccccggcgc   2580
ggtctggaaa ggacgctggg agcccctccg aggctccacg acatggatt tgggaaggga   2640 tggcgcgcgg ccgaggcttt ccctcgagtt tgcggcaagt ctgactccgg gaaagttttt   2700
caaagttccc agcagagtct gcccaggtcg cctctgcggg gcgaggagac ggcggcgagc   2760
gcgccagtct cgccgccgcc agcacagggc tctgggctcg cttgctggga gcggccgggt  2820 ttccggcgg gcaggccctc ctccccgggg caaaagccgc agctgacgca ggcggctccg    2880
aaggcggaag ccgcccgccc caactgctcc ggccgtaccg cggcgcctac acctgggct    2940
```

```
tgcaagggag cccaggccgt gcaccgaggg ggcggtccag cggaggcgct ctgggcttct    3000
cagagccatg ggctcctcca cggtccttcc aggttccttt ctcctggccc gggctccccg    3060
ggacactgat ctgcgtgtgg gggcccctcg ggcggccatg ccacccggtc cgtcccgcaa    3120
cttccaaccc cttctcaatt tctccctcc ccaacaaccc ggaggaaagg ggcgtgccca    3180
atagatggca cgcccttat gaatattaac aatcgcgcat gcgccttgtt ccgcgtgttg    3240
agaagaggtg gccagccgga gtcccggctc ccagaccggc gctccgggtc ccttcgagag    3300
ccaggcgggc acgcgtcatt gtgttacctg cagccggccg gcgagctagg ctcaggtttt    3360
tttttttttt ttcctcccct ccctcccgc gtttcatgca gctgatctga aagggaataa    3420
aaggctgcgc ataatcataa taataaaaga aggggagcgc gagagaagga aagaaagccg    3480
agaggtggaa gaggggggag cgcctcaaag aagcgatcag aataataaaa ggaggccggg    3540
ctctttgcct tctggaacgc gcggctcttg aaagggcttt tgaaaagtag tgttgttttc    3600
cagtcgtgca tgctccaatc cacggagtat attagagccg ggacgcggcg gccgcggggg    3660
cagcgacgac ggcagcctcg gcgggagcac cagcgctagc agcggcggcg gcgtccggag    3720
tgcccgtggc gcgcggcgca gcgatgcggt ccccacggac gcgcggccgg cccgggcgcc    3780
ccctgagtct tctgctcgcc ctgctctgtg ccctgcgagc caaggtagga gtctctctcc    3840
cgctcttgct ccccgcggtc ctctcccttc cctcgtggcg ttctggacgg gagcggctgt    3900
ggctcccagt gcaagttccg gagcccttga gtacaaggct ccctgaccct gacttttcac    3960
ccgagaggca gcacccggtg agggaacgct ggttccccag aggggagccc ctggcctcga    4020
aagataaact cctccaggct gggcaaaatg cgatcattac gttctcacgg tccttcgggg    4080
cacttgtctt agttttcccg cacttgtgtt ttttatgccc ccaaaccagg ttgagcccta    4140
aacctagttt ttgcaaaatt attttcactt gccaccgagg atctttggca gcctggggtg    4200
tgtgtattgg gggtgggggg tgtcaaggag tctccacctc caccttcaga gaaaactttc    4260
tcatgcgttg accttccttc ctcgctggca ggtgtgcggg gcctcgggtc agtttgagct    4320
ggagatcctg tccatgcaga acgtgaatgg agagctacag aatgggaact gttgtggtgg    4380
agtccggaac cctggcgacc gcaagtgcac ccgcgacgag tgtgatacgt acttcaaagt    4440
gtgcctcaag gagtatcagt cccgcgtcac tgccggggga ccctgcagct tcggctcagg    4500
gtctacgcct gtcatcgggg gtaacacctt caatctcaag gccagccgtg caacgaccg    4560 taatcgcatc gtactgcctt tcagtttcgc ctggccggtg agtgagcgac acaccgacag    4620
agtcgaacgc ggggccgagc cctatattgc cttgagaagg atttaatgcc acttgaaact    4680
tggcactaag ttgagaggct ttgggggtgg caagtttgag agtccagact acagctggac    4740
ctggacaaga tgagcgggc gggtcttcca ttctgggtgg tgtctgctta gcgcagcgaa    4800 atgggtctc tgaagagcat tgctggggga aagtacgcaa ggatgctaat tttatgcttg    4860
ctacttccag ttcccacccct cgaccaggcg gtcattatag atgatttctt tgcttaacta    4920
attaaaactc gtagtgccct ggaaggcgac tgcgcatagt ctgccctgca tacgctgtcc    4980
aagttggcac cctcccctttt cccgtgagcc gccccgaggg cgggtgtgtc cttcctgcag    5040
ggtgtggggg agcaggcttc ccgcggctct agtggggaga ttttagtgtg ttggagggggt    5100 gctctcccag cctgaagtgg cggctgcagg agggggggttg tctccggctg gcgtccaagc    5160
tttagtctgg gaacctccgc cccctgccgg cccctttcctc ccgccccgc tcggtgcagc    5220 ccaggctgcc ttactcccag cggttcccca gttctggaac agctgtgttt gcaaacttcc    5280
ccgggaaggg cgggcgcact ctctcgtccg gagggcaccc ggcctccgca agcccttccc    5340
```

```
gcgccctagt aaggcttaga agaggcagcc cgctataagt cgtgtttgcg ggtgcaactg    5400
cgtgcgccct catctccccc ttttccctcg gagctgcttg aggccggcgt accgctggca    5460
gactgcggca gaaccttgc aacatcccaa aatgggtgga aggaagatgg gtgcgattgc    5520
agaaggggag gaaagggaaa tggtgggggg tgtgcccgtt gtccaggagg cgtgactcgc    5580
tgccaggact ggtgctccgc caagcttgag ctccgagggt gggtggtaag aggggagat    5640 ctgtgcccca gaggattgct ttccgccacg tgctcggatg gggtgcgctc tgctgcctcc    5700
tacccgcggc tttgggctgt gatttgaaac tctgaagagg ggcgggagag aagcctgtct    5760
ggctgtctgt gtgtgaagct gagctggctc ttaatgtctg cgtttacagg agttggcctt    5820
tgctgtgggt gcgataagac agttatcgaa aacatgctat taaaaagggt cttatttttgg    5880 caggggactg ccgctgtagg tgaaatctct tcagatctga aggctgtgtc cgctgtggga    5940
tttcactttt acaaagaatg tttgtcttgt ttgttaatcc cctattaggg agaactttaa    6000
gctaaagagg ttggccacct ctaaatctgg ctgggtccat tcgagcttag ggtgagtact    6060
ggctgccctt gagctgtgtt tggagtttcg ggaggaaggg gcctgcaggt ggttccaccc    6120
tccctaggat cagtccgagc ccctcgcttt tcacaagacc ataaaaggaa tcttattagt    6180
gatgtggaaa gaacggcagg cctggctgag gtttattttg gagagagggg tcaggggag    6240 gatggcttgg atgaaagcag acagacttgc tccacaggct ggctgggga aagtgaccca    6300 gaagtgtggc tgtctgcttt tgacacctgg aagagagagt ttctcaccga caaggagcag    6360
aaatggtgtg agtggatgga tggagggttg ccaccactgc tgggctccta ctgttcagtg    6420
ccttcaggcc ccacgggtca ccgaccatga aatagactcg ggttttctag aaagagggag    6480
ccccactggg tcagcaccga gaatgtggtt cttttttgaa gctgggccaa gtacatggat    6540
cactcctaaa caagtctcca cactgctgcc cccaaacagg cctcctgcga aacacaggct    6600
ttacttccga agagaaactc aagtgggggg ggggggtggg gtgggtgtgt gtgtgtgtgt    6660
gtgtgtgtgt gtgtgtgtgt gtgtgtgtgt gtgtgtgtgt gtgtgtgtgt gtgtgtgtgt    6720
gtgtataaac tcaagtgggg tgtgtatgtg tgtgtgttgt tttagtttat tttcctcagt    6780
gtggttagag aaccgctgct gtctggaact tccaagaatg gctccagggt gagtcttagc    6840
ttcaatgaaa gccttaagct tcacaagtgt tagtaatggg tcgcacagct tcattcgctt    6900
tgataattaa cacgagaggc ttgttttaa acgggctgg gggtgtagct catcaaaata    6960
ggtatttgcc taccattctt aaaggtcctg ggtttgaatt caagcccac aaacttaatt    7020 tttatttctc ctccttctta gttagtttac agtggaattg tgtgggagat gttggaattt    7080
cagagtaggc cataatttaa aaggcaaaca aagcctccag cctaccttgg cctcatagcc    7140
acataagctg ccaaccccta agcaggcaca gttgtctttt gggctaagta ctcctaaatt    7200
ggcttacgga gaaaggaaac actgtgtttg gtaaagctag ttcagtgaag aaagtcatgt    7260
aattcctttc ttttgattgc tagtatggcc cctgttcgtg gcctatagag gaagaggagg    7320
aaatgatctg gtaggattga aacacagtct acatcccagc ttgtgagacg ctctgcagtg    7380
gacgtccctg ccatctcagt atcgcattcg cttatattgc ccttgggcta catcctactc    7440
cagtatcagt tgctctggcc ccagtctttt agctttgtgc ttctgattgg gttgtcatcc    7500
atgctgtgag ggagctcaac ttgcagcagc tagcttgatt tattatttc caatttggat    7560 actaggtgat aagagcatag ttatgacagg taattgggc taacaagaaa tgatttggga    7620
ataaccatta ataaatcacc gaaatggtta atttgcacct ccccaaacta gctcaaaatc    7680
```

-continued

```
ccagtagtgc ctgctcatta aaaatgcatt agtataatta cttctgtttt tgaaaacctc    7740
agtcatatgg ctgcattggt ggccctaaat ttgtaatgac ttggggtaaa gcaacagggg    7800
tgtctggctt tatcttaaa taccactgac cctattcaga gtcttgctga gagcaacttt    7860
aattatttta ggaaaagcca atgaaacgtg accaatgtag cagaagagga tgccagcttg    7920
aacccgtgtc acacttatag cctcagtaac taaataacag gagttagagt caagttgcca    7980
tcaggtagtt aatcacagaa tctaaattgc cagtccttgg gtatgattat gctgtctgct    8040
gtctttcctc tagatgtgtg tggacacatg aagagagag gaataagact ctctttaagt    8100
tagcttttt tctgtacctc acctgtgtgc cgagcatgta tgcagacagt gcgcttgtgt    8160
aagtgctaag cacaagggat gatgtgtgta tggagagaac attgtttctt cttcttgttg    8220
ttgttctaag aaacctgcct caaatgttta agttgcttta ctgggctttt ggggaacacg    8280
gaggtagagt ggctttcaag cactgtaaaa cagctgtgac ctggagtact ttcttggttc    8340
ctaatagttt tccttttcct gcaggtatag acctctctgt gttttcttcc tcctttctt    8400
gtttcttagc aacttgctca aacctccagt acgtaaaaga atctgcaacc catcaactcc    8460
acacccatag ctgtgtaggg ccttggaaca tttgtagaga atagtgaagg ctcagtgctg    8520
ttggtagctg aattgggcag aggcagaggc agcagcaatg tggtaggggt aaacctccta    8580
gagagccagc aatctgaatg ctgcctaagg tctttacaag ctctggtacc ttcagggaca    8640
cttgtacag agggcaggtg ggaaatttac catggaggga aaaggcgctt tgtgagaaaa    8700
caaggctaag gctacaagga gtcctcactt cacatgggag ccagattcgg agtagccatg    8760
ttgtggaaag gcctaacttg gttccagagt gtcaggcttt ctattcacat agattatttc    8820
tgcgtggacg catagtctgt ggttgtgcac actgccagct tggtaatcca tagtgacaaa    8880
tattcctgag aattcttctt ggtggagctt tagagacata cccctaacta gcccaaggtt    8940
ttaggattca aactgttccc aagtgacatt tggctccagc ccttaaatct actttaacaa    9000
taatgagaac aaaataaact tttcttccaa gggctggaag atgtatctgg aggcatgaaa    9060
gtgaggactc tgacaggatg ggagggagg tgagtcttgg gctcagaaaa ctggtgttgc    9120
taggttactg cttggcccac agcagcccct tggtccttac tcatagtgtc agtaacatct    9180
ctctctggag cagcatgtgg actgggaaga cattcccagg gtggctccta gtggttaaag    9240
ggggcatgta aataatcaaa ctgagccctc taccagctca gcctagtttt tatgcacttt    9300
tggtaaatca gtagaaaggc ttcttgtttg ggcttgctct gtgtgaactg gacggttgtg    9360
cttggctggc tccctggtat tctatctatt aacctcacca cccttttgta actggtgcat    9420
ttaattatca gtgggatgcc tttcaaacag gtaagggtaa tgatgggaaa ggggttaggg    9480
gcctctcatt gagagcctgc aatctgggta tgagctctgg ggccccttgg tgagtctttg    9540
aggtgggctt tgatgagaaa atcactcttt gtggccagat cacactctat tgacatgtca    9600
aatcctgcaa aaatggtcgc tttctgtggc tggagcctca gcttgcatgc acgaggggag    9660
tggtcttttt ttccaccct caccttgcca aaaccctaaa agacaggaat tgtgtgtgcc    9720
cacacatgga ctctctgaac tcgttttttg tttcccatgt tttgtgactg aatattta    9780
tactctggcc acccagactc aggcaggaca atagagttgg ctggactgac tgaagtgcgg    9840
attacagaga agaatggggc ctctccagaa atactgctaa tacaggacaa gtgacaggaa    9900
gcaacgttg agtcagcaga gcgcatgcag ggccctgac agacctgggg ccagcaggct    9960
gtgtacaatg gctgtgttgg cactcggac attctcagga tgtgcatgcc tctggcgggc   10020
ctgcctgtcg cagcggtctg gggttttgga ctccccacgc gtgccatttg gatggcggtt   10080
```

```
tgtttgtgtc ggtcagcttg gcaggagggg aggcagccgc ttcttagggc ttggtttggc    10140
taccactgtt gccaggaaaa ggaagctccc agctgccaac acaatcacct ttgtttctta    10200 catcccccc tgtttaatgt ggcaattaag tgcttactgc tttgcccagt gccaaggtaa     10260
cctccataga gtggagcagg acaaagaatg aaccctagac cagcagctca agtgtggaga   10320
ataggaggag gaggaggtgc ctggtggccc agccttggta aggtgaccct gtgaccgtgg    10380
tatacctgga gggctttgat gccaaggtaa aattgtatgg aaatctccca aaagtccgtt   10440
ctgaaagctg accagtactt ttgacgcttc acaagcatgg aagccagcca ccttactgcc    10500
agatgtcctt gagcctcaag ctgggaaggg gcagaagtga ctcacttgca aatccagatg   10560
gatgatctgg taactatcgt gtgtctcttg ttttgcctct cagacaacta ctctgggaag   10620
actcaggaca aaatatgaaa tctgagtaat tcatcaaaaa tttctttat tgtttgaact     10680 acagcaaaac tcaggatttg cttgttgttt gcttttttgg gtgtaaagtt aagatcaagg   10740
aaaacttgcc ttttgaagcc ccttacaaac tcccatagga ctggggactt ggcctctgct   10800
gaggatgggt tttgtagcat ccaatcccat gtgggtgatt tgtggctggg tggcatgagg   10860
tccacatggt ctaaaatctc agtgtccgga catatagctg gggatgtaca gaggtcaagc   10920
gtgggcctgg gaaaaattaa agctccctag caactaataa tcattgccaa attatcttga   10980
ttgttgatct atagtgtggg gatggagtgg gagggaagaa tgcctcttaa tagaagcctt   11040
ggagggaatc ctttctctaa aggcagggca cccatgcccc aggaaacctg gaactccaat   11100
gcatgctttc aagagaaagc aaagtccagg cttggctagt ctctctccac gcccttaccc   11160
ttattctagc ccaccttcaa ccccaaaag gaaggcactt gattagggga aaatactgcc    11220
agcccatggg gctgtgggac atttcttttc catccagctg gggtagtgtt ggtcagcaac   11280
ttttgagtcc aagacgaacc tggcagatgg cttgatctta caagttcttg tgcaaggtct   11340
aaggatgcct tctgccttga gaatgaagct gagttaatac tgctgtgcca gctggttcca    11400
aggcaccttc ctttgcagtg gtgtttgtgg gtatgatgtg tgtttagtgc ttgtgcaagt   11460
ctgtcaaaac tcttggtatc aatgcattta gtcagaggat taattacagc gatattgttg   11520
aagtgaagga tgtgggcctc aacgtgacca acaaatgaag ggcttaatta tacagaatca   11580
gccacacatc tggcctcatt tcgacttggc tctcactgtg aaccagtaga gaaatataat   11640
ttcttactgc tcttcgggaa gagtcctata atttgtagga agtcctaggg aacttaaaga   11700
ggctgtaaat aaggtgtaac tttcactaat aaaatattaa cgacaataac aatgtattcg   11760
gacctacaac cactaacagg agagcgtgag gtatgtgtcc tggcttgccc ggttttgctt   11820
gctttgtgag cattttccca cagttatcag tgaacgaaat ggaatcctgc tgtaagtatg   11880
aagcatattt aggctgaatt ccaaagcagg ggcctatcac aagatatttt tgtcgtcaga   11940
gcagacctgc tgtgtcaccg agagaggagt gagcttcctt gatttatgaa tgaaacctcc    12000
tgcttttctc tcatgccttt cccctatcgg tgccatctct tcccctggca gcagtgtttt   12060
ctggtggcat tgtggttatc tgagcaacag aagcattgtg gcaggcagag cagcgctgca   12120
caaacctgtt gcagtcctgt ttctccgctg tatttctcca gcacccagat aggcttagca   12180
agattcacct caatgcctgt tgtaagtgaa ggttggagta aaagtggaaa tttgctaatg   12240
gtttgggtct tggggtgaag cggagatggg gttcagagac atgcttagaa gattaaaaaa   12300
aaaaaacagg tttcagtagg ataactggca tcttgccagc ctccagggaa ttgtttagtt   12360
actgaactga ttattccagg aatgttagat cttattgaca gatacattca tcaataaaca   12420
```

```
taacccatgg gtgtgcggtg cccgtctcct ttgtgctttc tcccacagac agccacaacc    12480 cacccacca tggaagctag gttgctgcct ttgtcttaag tctttgagcc ttaccccctcc    12540 ttttttccta gagtcacctg atacttgtgg gagctgggat ggtctcacac agacagggct    12600
ttcaaagggg ttctgaaaag gaaaagggg cctccctggg gactgctcca ccagggccca    12660
aagcgtaacc ttagcagttc tctctcagga caaatacctg agtaggttgg cttgggataa    12720
attctttgtg tgggttttt tctcatgcac taagactagg gactgaaaag ttttgggaaa    12780
cctatatgct acgtgttccc ataggcag gtactacttt ctgatcaggg tttggagcag    12840
cttggcttgc tgggtgtgag ccccagtgtt cccctgccag gtgaaaggag ttatttgtca    12900
acctgtgaag agcgctgcag cgagaagagg ttggtcaggc ttcaaatacc ctgttgcctt    12960
ttttctgcct tctatttgg gttggttcct ggtaccagag caccagagac tgcaggcagc    13020
atcagcatcg tagagttgac ccctgtatgt gaatcactaa actttgctta tctgtcttgc    13080
agaggtccta cactttgctg gtggaggcct gggattccag taatgacact attcgtaagt    13140
atctcatcag gaattcttct ttaaatgctg gtgcgtttaa agtgctgtgc ttggaagcac    13200
agaggaaagc ctccagtgcc ccaccccac acaggctga acctatccgg ggactctatt    13260
ccttaacttc tagaactttc aactgaaata ttaagtagcc agaatagact cccagtttat    13320
tcagtccttg cagaaaggga catagtttat ctctggatag agatcttaat ggttttacaa    13380 cttttaaaacc ttgtagactg ccaaaggatc aaagtagtga cttttaaaa gtccatttaa    13440 actttaagtg agcatttaat ctctcatcag aaagataaag ctgtaaaggg tggtgctggg    13500
ctctaaagac caaccttaaa tttcactcag tgggcaggtg agccccacgt cagcctgagt    13560
ttcccacact gctcaccaca aacctcccat tgaagccgaa tttcagagcc cccgcagtc    13620 aggacctgcc ctgtccgttt tgaaagatgg ctctgttctc tgggcaggtt gcttttcagg    13680
cctgcagaga agtggctggg gcttgtgggg tgtgtggaga ggtagtgaag gtgtactctg    13740
ctgatggtgg tcaactctat tgtaacacgt tcgttctccc tcccagtgag atacacagtt    13800
cctcctttat caccagagcc tggttgcctt tggaaaacct gattcactcg gacagttttg    13860
atctgttcag gaaagagagt tgatccattt ttttgccttt gcccactgct ctcagagtgc    13920
ctcacacctt ctacttctct cacttattca cccttttctta tttttttttt ttctcaacat    13980
cactgtgctt tcccaccata ggtgaaggta ctgagtgtcc agcatgggcc tagtcacagc    14040
tgctcataaa ctcaatggca gctcaacatg gccgactcct tgggcctctt agggtcacac    14100
aatccttggc aagccctggt gtgcagcagg ctgcctgtca ctgggattac tttcttgctt    14160
tggtattcag ctatttagac agcagccctg cctaggaggg agtttgtgga aggccaggat    14220
ctgcgctgtc tcattgtgat agacattat atgttgaggt tagtggtagg acacattgcc    14280
aggcttggtt gatgccagcc aaggtcatag ataccgtta gtcctcccca caaaacactg    14340
agctctgcat ggcatcccta tcattgtacc cttaatgtac aaaacgctgg gtaggggaca    14400
gaagtgggcc ttctgagtgc actggtgcca gaactaaagc tgggagagga ttcctgccca    14460
gcatctgtag aatctctgct aagctatctg tcctctcact ttccagggct atgcctccag    14520
ggacctgagg cctgcccaca gttccccata cttatccaca tttccaggca atggaaatct    14580
ctacattttg ggactcctgg atatctcatt tcttcctagg gtaactagtc tctggatagg    14640
agacaaagaa gactgagatg agaacagttt gctttcagat ctttcagatt ttagaaagtg    14700
agacacagtc ccagatgccc atcacagtta tagaaactta cagtatgagc cttgggcttt    14760
gtggtttatc tgtttttctg ttgactctca ttatttttca tctgtatttt ccaaggtacc    14820
```

```
acaaattgcc gagtcaaagc caaattggag gtccaagagc actcccctttt aatggagccc   14880 tttctgggtg acaagcacca gtattgggac agctagtgcc ataagccatt catttggaag   14940 gccctatgt actttatgta gcatctgtac ctatacagcc tccaacttct gaatagtctt    15000
gatcttttgc tctccatatg aacccagctg cgtcctgcca tgtctactgc tgccctgatc   15060
cacttcactg cctgcttata ccttcagagt tagtgttact gctacatggc ctgtccttac   15120
tggctctccc tggtcaactt tcaatatctt ctccattctt gggccatctt attttttttt   15180
tccttgagca taacatttga tggtcaccct ggtggtagaa gctaacagct cacgggcttt   15240
ctatagctct tggtcagatc tttgtatgcc ttttcttcct gatggcttgt cttaacacac   15300
cgtgtctact gtgtctgttt cctagccatt cttgattcac ttgtatcctg gagtgtatca   15360
cattactttc ttgtctcagg acctttgtgc gcactgtttg tatgtttggc tccctgtttt   15420
ctttaccctc tgcccttaca aagcatctga ggatgtcaag gaggagcccg gtagtgtggg   15480
ctgttctttg gttgcaaagt tcatcaagtt gcaaacatcc tggctttgct tgtatcttat   15540
aggcagatcc ccaagtttgg gtcagaattc cttttcacat cagctctgta attatcccca   15600
aggaaggttt tgctcgccat tctttggtct gtgtctattt gcaaaaactc aagtataagt   15660
ctagaccgga ttaagctcag gtgcttctga agttccaagg ctggctccca gcctcagtct   15720
tccagttgtt cctaatatgg ctcaggagta taacatcttt atagatctct ttttccacct   15780
gagcaaatga ttttagtata ttgtaacatt taactgattg atgggcaagc atacccagga   15840
gtcctggaga ccaaggtttc catacagcag agacttctct cagctaaggt cattatctag   15900
gttttctgat tggtccttga gttgtgttcc tggtggtccc tcctcctttc ttctgggtgt   15960
acaaagctct gtgtatgctt catgatgcat ctttacacca gtgacattaa cagggaagtg   16020
tgctaatact ctttttccagc cctaaggctg gagctacccc aggtgagctg cccctgtcc   16080 ttagtggttt aagccaatgg gagagctgag tcaggtggta gtatcgaatc atcacacagt   16140
aaactcgggc tctgtaaccc agacagtgta gagcatgcta catatttcgt agcctcatgg   16200
ctccgtggtt gtaaagttat ttccatagct ttgttagcca cctacccttc tgtggattct   16260
gaagttacct tcacagaatt tcctgaaagt taggtagaaa gtgcaccaaa ctatacagag   16320
tcctttgtta aggcacatgg ctactgtgtt taataattcc ttcattaagc tcttagagca   16380
acaccggaat agcccactac atttctcaac ggaaccagca aagcaaacag gcagttagtg   16440
gagaggcatt tttgccattc tctagtctgt gtgtatttgc aaaaacttga gtacagtgtg   16500
acatgcatgc acgtggttct acatgttact gaatgtaagc tacagatacg tgggctttca   16560
aggattgccc tacccacacc atggtccaga ctggctgggg ctgtgttggt tgtgcataga   16620
gccacccagg agttgttctc ctggtcacct gtagggcttg tctagctttg tcaaagagca   16680
caggctcaag gcctagaaaa acagtggtgt gggtgtacag gaatcacaaa gacattgaaa   16740
gtaggtccta agttgcctct ccaaggtggc cttgaatttg acaaggtgat gactagcagg   16800
tttaagaaaa caaacacagc accaggttga gtgctgactt agagccttgt ctgttcacat   16860
cctcctgtac ttcttgcttc tgggctttaa agctattta gtacctgtct cttagactag   16920
cttgtaggtg acctcaggag aggggccagt catactgctt ctgggaactg ttgggctcta   16980
gacatttgct ttgcctctca ggcatcttta aggtacctga cttaaaacag acacaaacaa   17040
accgaatgcc ttgacctacc tgtctgcagg ctgagatgaa tttagtcata tgatgagaag   17100
agtgaactga attatgtttt tgctgttgct gatggaatgc cagcttaaaa gagtttatta   17160
```

```
gtggtttgtt tttcacatat tacaattcac cccttggccc tcagtgagga atttttgaaat    17220 ggaactttt  ctaagcaaga cttgcaagta aatgtaaaaa aagaaaaaac caaaacaaaa    17280
caaaacacta accttgtctg aatagtaaaa atttctttca gagcaaaatc tcctaaggcg    17340 cagcttcta  taacatttag gagtttttga acatttgcta tggacagcaa tatgttagaa    17400
aagttggcaa aggatacgga tcacaggaac aaataaaaat actgtcacta aaggtcagtt    17460
aaaacaggag atactattgt atctgttgga cctgttgtgc agagatgaga aactgagctg    17520
tgatactgtt gctgaggtag caccttatgc tgagggtctg caggttttgc tggcaggtat    17580
ctgtgcatca cctggggatg aatgtgttg  tttgtgtcca ctgaatctgt tagggtattt    17640
cttgctgctg gccaacatgc attcaacatg cttattgtag ctttgaataa caagaggcta    17700
acttaaaaaa aaaatatata tatatatata tattttaaag acttttttt  ttatgtatgt    17760 gagtacactg ttggtgtctt cagacacacc agaagagggc atctgatccc attacagatg    17820
gttgtaagct accatgtggt cgctaggaat tgaactcagg acagtgctct taaccactga    17880
gccatctatc tctccatccc tgcaagagac taactctaat gtcttgaatg cctacagatc    17940
aaggaagagg tgcatttatt caatgttgtt tccaggcacc tgacaactag tttgaatggt    18000
aaattggcat acaaaaacga gggtacagct cttgttacta ttttttttta ataacagttt    18060 gattttgta  ctgtgtgtgt ttctagtccg aaagtaggca aaatggtcaa atcggaagat    18120
gcttatgtga ctgttaatga gtttcatctt cttctccccc tctagaacct gatagcataa    18180
ttgaaaaggc ttctcactca ggcatgataa accctagccg gcaatggcag acactgaaac    18240
aaaacacagg gattgcccac ttcgagtatc agatccgagt gacctgtgat gaccactact    18300
atggctttgg ctgcaataag ttctgtcgtc ccagagatga cttctttgga cattatgcct    18360
gtgaccagaa cggcaacaaa acttgcatgg aaggctggat gggtcctgat tgcaacaaag    18420
gtatccaagc atgcaactgg atgcataaaa ctgcaaatga tgttggctta tcagtttggg    18480
taccaggttc tcacccttat agcagtcggg tggcagggtg gatgctgcc  gctatcatta    18540 tcttagactg aagcatgtag atgctgtatg tagaagattc tgttagtgcc ctgtctggag    18600
tccccgttac cagctggtgt ccccatcccc cagctgctgt gagtgttggc tgctaagagc    18660
tcgcagctgc tccttctcca gggagttgtc cttggccagg caggagccac tctctgcccc    18720
atccctgcag cgaacagtta ctgagtggct gacacggggg gatggggatg ttgggaaggc    18780
cagcctcttt gctttaacac tgtggagtaa gattcacact ctggaggttc ccctgggatc    18840
acactgaagt cagaccccag ctgagaccac atccttgctc agctcctcct taggcctcat    18900
ctggctcccc attccttcct cctattacca aatctcctcc tcagactgct tctgagaaga    18960
gcctgatgcc aaacaggacc aggccaagcc agtggtgttt gaacagacag tgctatgggc    19020
aatgactgtc actgagctca catgtcactg cagcacgttt cactgggcat ctttgaggtt    19080
gcggcattaa aggaggcggg ggaagtaggt ggtaaccttg ggagtccctt actgtctttt    19140
gccccttata ctagaattaa ataattctaa ttcctagcaa tagagttgga ggtcacagca    19200
caacagatgc tatgccctca cggacatata atataccttg gtggtcttgg aaaatcatta    19260
gataaactcc ttcttttagc tttaaattgt gtggaatgat gcaggagagg atatttggtc    19320
tctgaggaag tagtcctgtc tcctggtatc tggcgacagt agtttgctta aactggaatt    19380
gatgacagaa ggaattgctc aatattttaa aattcagtag caattactga ggttctgtgt    19440
tcttttttaa gtgtccactt gatttctttc tttctgtgag caagtataga acagcttgta    19500
agcttacttg tctgcaagat cagcttgcct ggttttttag ctccatggga ttgttgaaac    19560
```

```
caggcattta gtgggaggct cacctgaaaa taccatgcta ggaccatgtt ggggcaggga    19620
aggcaaatga atgaatgaat atcttcattt ttcctcttga tgagggggga actaggcccc    19680
gacagggctc aaggaataag catgttgagg aacccccaa tcatttgtcc ccaaacaatg     19740
ttgtgacttg aggttctact aacatggcct tggagtttga acctggattt attgggcccc    19800
caattctatg tactagacca tttacataac tgtggcccga aaggcataga cagcgctaat    19860
gtaactttcc gatttttttt ccagctatct gccgacaggg ctgcagtccc aagcatgggt    19920
cttgtaaact tccaggtgac tgcaggtaaa tgaccaacta attgaactct agtaatcaat    19980
cactttctcc cctccccacc ccaccccctgc cctttctctc cctttctctt tgatgcaaga    20040
cagaaaaact gacttcctta tgaatgtgcc tcgttatttt ctttggagga tgaaaaaatt    20100
aggggaaaac acaaaacaaa acaagcacat gagaagcata atgaatcata ccagctgttt    20160
ggtggaatgc acccttcttc attggtgctg gcgggtgggt ttagtcaaaa ccccaaacca    20220
aaatccttaa tgggcatagc tggcatcttt gtgtattaac tgttctgtaa attggtaaga    20280
cctatttgta atcttcctta agtgctaatg tactggactg ggacgaagct ttgtttcccc    20340
tgtctcctcc tccaccctgg cttttcctct ggcaccctcc cccactttc ccatcaatag     20400 gcaaaagtcc agcattcttt agaatgggat tagtacaatc tcctggcccc tttgcagtgg    20460
gagctgcgct gttgctggag gttaatggct gtgctggaat ctgctcggtg gagcctgatg    20520
aatgtagact ttgctgctgg cctttgaagt ctgctcttta tggtccaggg acaatactga    20580
aaccaaacgg aaacctaccc agcctgtttc cccttccgat gccggttttg ggggcttttt    20640
gaaatgtaca ttatgccaat ttggaaaaag acttgtttca ggaaataccct ttggggtctg    20700 tggcatttt gactggtctc aggctttatt ctccctgaag cctttcagaa ttagcaaatt     20760
tgatgagaca ctaagtggac cctcttcaag tcctgtcacc tttgctctga aaggctgcac    20820
tgacttgagc caaagacagt tttgaaacag tctaaaggca caaacccata gaaggaggtg    20880
cctggtgccc ttactaaaac aaaacaaaac aaaaaaacag ttttggtca ccaaactgta     20940 gaatttacag agaattgtta gaagtgcagg ttcccagttc ccacaactgg cacagatttc    21000
ccaggccttg gttgggccta ggagtctgta tttgacaact ttgctcagtg atttatccct    21060
cagcaaacac gcgggctact gctttaacca gccacccata ggtttaacct tgatgactct    21120
tagccccacc ctgagttctc ttccccaacc atgggagtgc aaacttgatg cttaagagat    21180
ccaaggcagc gggagtaaac taagaacagg ttgtcctgga attgtttctt cctgcttttg    21240
aaagttgatt tccaggaagc ctgaatagga tttgcccact aaggaacggg cctggtcaca    21300
gctgacccgg catccaacag catctttgtc agaggtggag cagaaaccta ccttcaatga    21360
ctctgctaat taaggctgtt ctggagaaag taagagcgct agttattctc cagcctctga    21420
gcctgctccc tgctccgata gcatcagcga gatgtgtgct actgtcatca gaataaacac    21480
cctgctgggc aggggagggc cctcctagcc agaacaacag gctttgtttc cagaattgag    21540 cccttttctct ttcgaagtct cacctcccac tccctgccca gacatgcacc agtgctctta    21600
tttacttaag gtgcaactttt cccacacgcc atttgcatag tctcccagcc cagttccttc   21660
tctctgcctt gaaagaaaat caaaacagaa ccttccagct aaggaagttc aggttgagtc    21720
ctgctcccga aatagttgca ttacaagtta cctgtaagtt gtcttttggg ttatgtatta    21780
catgagcttt gttgttgttg ttgttgttgt tgttgactca cccacaggag aaaacttcac    21840
tgattttgtt ggtctcaggt ggacttgggt tgtcccttac tgggtgtaca gactggtttc    21900
```

-continued

```
gtgccagcct gacaataata tcaaacttaa ttatgaatca tcatctccag aacgtcagct    21960
tctcatgggg ctgctaatca tctatcatta ccccgggata acgtggtaga tgcctctgtt    22020
agggtcagga ttttatttg ttcttgtttg aagtcatcca tggcctccta tggttgcttt    22080
tttaggcttg ggcattgagc cttcattaat taggaggttg gttgggtcct cagccgtccg    22140
gcttggtttt attaggcaaa ctgaagacgt gtagtgacgc ttcacttggg acaacgcggg    22200
aggacagagg attgtggtcc catcagttac ctcatgtctt ctaagctaag aatattgatc    22260
tgacagaatg gcttcccacc ctcctacctc ccactgactt gggtgtctgc ctctgaagag    22320
aatggttccc atctagtggc atactctgtc cttagatcag tcttttcaat agtcatttgt    22380
catttaaact gatggtctag tttagagatg ccagactcct gtgtctgatt aacttttaag    22440
ccccacattc tagtggttgt ctgtcggtgt ttgggtgtag atagaggtta ggaagtagtc    22500
aggattctca agggttcagt ggcttctcag cctgggtgat tagctaatag ctagatttct    22560
ataattttcc catgaccagg atttgctcct ttgcctccag ctctctggaa ctgaaagcaa    22620
agttcctccc ctcccctcc gccccgccc cccgctcccc gcccccaag agtcacagca    22680 gagaagttca cagggctttg gatctgatcc tgcatttccc taggccctgc tctgggctga    22740
ttctgcaggc ccaacatctg ctccatcttc actctgttat cagcatgccg gtgggtggct    22800
gggccctgcc tttccaagag gcccctttgt taaagcttga ttttgagagg gaggttcaaa    22860
ttgcagaggg cttgaaacta acttaagggg aaagtggttt tgagaccttg ccctgtccca    22920
ccccaggtga aggttcatgt ttgtggtttt gtttgggcat cagacattcc atctgacctc    22980 aaagaagtc ttgaactctt agaaaggaga cccagctccc tcaaagctag acaaatcaag    23040
cttggcccct ctcttctgac ccccccctc ttttttcta aagtgaaaaa taactataaa    23100
tcagcatgcc tggcttgggt aatgggtcat aaattatata tgaattggtt cccagtgttg    23160
ccgttccccg ttcccctctc tccttcctac agagattggt ttagagatcc agggctctgt    23220
aaggaggcca ttctccttcc catttgagtc tacaaaacca gcgaggtgct accctggcac    23280
cctgtggccc tgaatcctgt gcactctgag cagagtgggg cttcatgtgc attgttgcag    23340
agctgcacag ctggtgtcac cagaggctcc ttccctttgta tggtctgtcc tgatgaggac    23400
ttgggattga tttattccca tccccacccc ttggttcaat tcctgagaga ctgagaagag    23460
aatggctttg tgcagggcac cccatgctgg ccgctccctg gatagctctt cttttgtcag    23520
ggtatgctga gaggacacac tttgggccaa ctgtgaggtt actcatacag aaccctgtga    23580
aagtctgaaa aatctgccat cctgtccttt tcaggggggca aaacccagaa atagctgtgt    23640
gttgtaacta tgtgcatccc cggctgtttg tctgcaggtg ccagtacggt tggcagggcc    23700
tgtactgcga caagtgcatc ccgcacccag gatgtgtcca cggcacctgc aatgaaccct    23760
ggcagtgcct ctgtgagacc aactggggtg gacagctctg tgacaaaggt atgaccattg    23820
tgaagccttg gggggtggca tgagggctta gtgggcggga actgaggtta tgggacaggt    23880
tatgtatgtg aacagacacc gtgaccaagg caactctaat aaggacaaca tttcatgggg    23940
gctggcttac aggttcagag gttcagtcca ttatcaccaa ggtgggagca tagcagcatc    24000
caggcaggca tggcacagga gaagctgaga gttctaaatc ttcatctgaa ggctgctagc    24060
aaagtactgt cttccaggca gctagggtga gggtcttaaa gcccacgccc accagtgaca    24120
caccctctaa tagtgccatt ctctgggcca agcatatgca aaccgtcaca aacagtaata    24180
gccactctgt attttggtg ttgctggggc aaccccaggtc ctctgagatg ttagtgctca    24240
gctgtagcca caccctggc cctgtttaag ttgttatagg ggctcttatt aggaatgtgt    24300
```

```
ttcaatttgc ctttaaagtt ggtttatttg gggataagcc atattttttt aaaatggcat   24360
ggcctagaac tgggatcaat taggagtttt tttccctaac tttggttttt ttttttttt    24420 ttttttttg gcagatctga attactgtgg gactcatcag ccctgtctca accggggaac    24480
atgtagcaac actgggcctg acaaatacca gtgctcctgc cagagggct actcgggccc    24540 caactgtgaa attggtaagt ggccgagctg ggaggggag gggtcccttt gcgtttgtgt    24600
cctgcacatc cagtttcaaa accaaatagg tttttgtttg tttgtttgtt tgttttgatt   24660 cactttttt tttaaaaaaa gacacaaaat tgggtgggta gaaaggggt gttggctgtg     24720 ataggatttg gggggaggag tgaatatgat caaaagtata ttgtaggaaa ttcttaaaat    24780
atttaaaaat ttggagctgg aaagtggtag cttaaggtca caggtggatg atcaccaaag   24840
gatccaagga tgttttttgta gctaaattca gtgacgcagt gaagaggtgc aggacagagc   24900
tagacaagtg gtgagaagac gctagattat cctatttaaa tcactacaga tggcattatt   24960
ttgatatggc cttcataata ttcatggaga aacatgatac gtgagtgtga gtgtgtgtgt   25020
gtatgtatgt gagagacaga cagacagaca gatggagaga gagagagact atacactgaa   25080
ctcacttgtg aaaagaaga aaaccgcttc aaagttgaga ctggttatcc cagaccttct    25140
gtgaacctat gaaatcccca acactttgtg ttgagtaggt tgcaggcttt taaatgaacc   25200
ggagttctaa aaaggtattg aaatctgcct tgagccagct tagttggaga gtgtcttccc   25260
ttttgcgtca cagcacagca ttgttacatc tcaagcttgc ttttgttgtt ggtttgtcat    25320
cggcttcaac tagtcgcaga ggcagggac tggcccttgg agggaaggc cagttttacc     25380 gcattttacc gcgttgtttt accaccttgc tgactgtctt tctcttgtat gcagctgagc   25440
atgcttgtct ctctgacccc tgccataacc gaggcagctg caaggagacc tcctcaggct   25500
ttgagtgtga gtgttctcca ggctggactg gccccacgtg ttccacaagt aagtcagtcc   25560
aggttttgcc atgtgcctgt tctgcaaggt tattgtgttg agaggagggg ttggtgggag   25620
agacttaggc tgttcaatat atctatcttg gtgacagagg gctgggtgca ttcgacaggt   25680
tagtggctgg tctagtagct cttgtatgat tcctagaatc tctttcctac ccactaaggt   25740
ggctggtgat gtctgtggta gaaatcaatc agattccctt gcatgtgtgt ttggagtggt   25800
ctcctccaat cctataggaa aggaatttag atcaactact gaatgttgtc ttgaggtgcc   25860
actttgcttt gaggcttggc catattattg gggtactttt cagtgaagaa ctctggtcat   25920
atatgatctc ctccagaatt aggcagtctg tggtctttag agagttagtt cctgaaactt   25980
tgagggttac cgaagcctga taatctactg tctttgacac cttaggagca gtgtgtggca   26040
tggctaagat tgttctggag gctgtaggtg cttctgtgac taatggaact cagcaggcct   26100 ttcaacctt cctgggccgt ctttaaccag ggaagcagca gttcccattt gggagggttg    26160
ttatatagtc ttggtgagca aatttgtgaa gagtgtgtgg cacacattgt aaatgaatga    26220
gatctctggc aggggctcag aaaaatcttc taaggaaatc acaggcctaa gatttctcta   26280
tgtgtaaaga agaatgcctt ttccatgcct cctcttggtg tgcagcctct gaaccatgaa   26340
ggaaagagtt cttttaaaag tgaagattaa gcagataaga atgtcccttg tcaccactga   26400
gttgatgccc tgtgtgtctc cggctatctt tctttccctc gatgcttagg gacggattaa   26460
ctgaactagg gcagtgaggg atttcaagct aaaataaggg cttgggtcct ttcatcacct   26520
cccttccctg ttgtggcttt tcttagattt gtagcaggtg tccgtccggt tcctaggtga   26580
agactcttct tgtggagagt gctgttgcat tatctaattg ccaagtggat caaatgaaat   26640
```

```
taaattgccg cccctttctt gttctcattg cattggacag acatcgatga ctgttctcca    26700
aataactgtt cccatggggg cacctgccag gatctggtga atggattcaa gtgtgtgtgc    26760 ccgcccccagt ggactggcaa gacttgtcag ttaggtaagg aaactctcgt gactgtaatt   26820
ctttgccaag gttggctgtg ctcctcagag ctgtgaggag ggacgagcat gtggccagca    26880
gtgtgtgcgt atctgtatcc catcatacga agtaatttat tatcagggtc taacgagcct    26940
gggagaaata ccttgcatgc aaatggccta gggttttag gtcctgtggg aaagccctgg     27000
gattccttga accatgtcaa ttgtcccagg agtgttcagc tgggttctaa acagggatga    27060
cctcgtgagg aacgagctgt ctgcattctt tttgccacat ttaaagccca gcaactggat    27120
tgtgctgggt tttgcacaca agtgcctggt ggcttgctgt ttgtcagcca gcagcccaaa    27180
agaaagttat caattagcaa cccttgatgg ataaaggctg ggagagggtt ccaacgctcc    27240
aaatagaaga cacctcctat ttcttattta gctagcttgt taaaatgtct catatttcag    27300
accagcacta tggtgttttc atttcaaggg gacagcagtg gggtggggc agtcccccat     27360 ttgtcactgt tcatccttgc tgcttttcag atgcaaatga gtgcgaggcc aaaccttgtg    27420
taaatgccag atcctgtaag aatctgattg ccagctacta ctgtgattgc cttcctggct    27480
ggatgggtca gaactgtgac ataagtgagt gactttgttt tgattttcat gaaacttggg    27540
tgacaagtct ttttccatt catccccctc aacccctgc tcgggttctg ggactctttt      27600
ccccttactt tgtgatgtta aggacggaac ccacagcttc ttgatataag ctgtttaagc    27660
accttccagc tgaatagaag gaaaaacctt attaggggga ggggaaggga atgttttgg     27720 agagggaggg gccaggctaa agcagtaagg aaaacataca atttatcagg cttgttagtt    27780
gctaaaattg ggcatattct gataaggtga tgagaacaat gaggtgaagt ttcactccct   27840
cgtctgggag gattagggag ggtccccacc ctgtggcata gccttatctc accggaagca    27900
cagggaaatc tgattgaaac ttttatcagt cttgtacttt tcaggtgaac ccgaattcaa    27960
tgtcacgtgc ctccttaatg tgacggcttg tttatttttt tcagatatca atgactgcct    28020
tggccagtgt cagaatgacg cctcctgtcg ggtacgtaag tcattgcttg aacagaaacc    28080
ttgtcattgc ttgaacagaa accttgcttg acacatgaca acaatctttt aagatttatg    28140
tgacacggga gagtcttgct cctatgggat ttaaaatgct ggtgagaagc tgagtccctc    28200
accaacccta gcttgtcagg agcctcttaa aggcaggcat tcggaaccgc tagtctgggc    28260
ccaggcttag cacgaggcca tttcagtgaa tggcctgaac cacagcagtc ttgtcaaatc    28320
cctgacgacg tcctgggttc gtggatacat agataaatat gtatgtgttt ctccccttc     28380 tcttctccca ggatttggtt aatggttatc gctgtatctg tccacctggc tatgcaggcg    28440
atcactgtga gagagacatc gatgagtgtg ctagcaaccc ctgcttgaat ggggtcact     28500 gtcagaatga aatcaacaga ttccagtgtc tctgtccac tggtttctct ggaaacctct     28560
gtcaggtgag cggaggcaaa aacttccagg t caccaagctt tagtgttgaa ccctattctc  28620
catcaccatt ctttcccctc cttgccccac tctagttgtt tagaccctg acaccaacta    28680 gcaccccact gactggagga tgtctgctag acaaatgctg tagaaggcag agttgaatga    28740
tttcttattg attactgtgg cctgtttgct tggctgagtg tcatcccata gcctgtttt     28800 ctatgctgtc accgtgccct gggctttaat gctttcctgg gacctgacga ccttaagggt    28860
tacatgggtg tattctgtat aggggtctc cttgtggaag gggttggagc aatcaattgt     28920
ttactgccca gagaagtgat gatgacgcct ttgttttcct ttgatctgct ccttcccact    28980
cttgccatat ggcagctgga catcgattac tgcgagccca acccttgcca gaatggcgcc    29040
```

```
cagtgctaca atcgtgccag tgactatttc tgcaagtgcc ccgaggacta tgagggcaag    29100
aactgctcac acctgaaaga ccactgccgt accaccacct gcgaaggtat ctccctcacc    29160
cagggcccat ctatccacag atgggctcct gccacctccc cctagagctc tgataagtgg    29220
taaatgggtg aggaaggttt tcagatgaaa cttaatctga tcacttaggg aaacaaaacc    29280
atacggaggt aatctgtcag gctgctgttg ggagagcccg agtaccgttg cccaagggag    29340
agaatgtgaa atccatttat catcccagtt cagaggtggc caagtttgtg acagaagaga    29400
agaattgctc tgaggagcgc tgtcagcagg ggtctatagc agtggggaag ttaggcgttt    29460
gtatcagtta tttgtagcca tggctggcta tggtgcttga cacttttt tggagtagtt     29520 catataaaaa tacgtacacg tggcctatgg ctactatatt gggaggcata acttaaagac    29580
ttgtctagat aggtttgtcc tttagttttg gttaagatga aggagggctg acagtggtg     29640 gcgcacgcct ttagtcccag cactcaggag gcagaggcag gcagttctct gaattggaag    29700
caagcctggt ctacaaaatg agttccagga cagccaggc tacacagaga aaccctgtca     29760 aggggggaagc tggggtgggg tagcagggaa gtatagaggt gaccttcttt gacaagcatt   29820
taacatgaga tagatattaa ggtgccatta aagaaacttt aaaaagactt tctgtccact    29880
tgggagtctt acatttttacc tgtcataaga acattgttgg gttttagttc ccaagcacct   29940
cttgatgagt taactcatta gcccaaggag tggccctatc caatcaggca ggcatacatg    30000
ggctaagtcc tctacttaga aatgctgtcg gtgggtatgt ggctggagtc tgatcccaag    30060
cctgtgttca gtgattgaca gctgcactgt ggccatggcc tccaacgaca cgcctgaagg    30120
ggtgcggtat atctcttcta acgtctgtgg tccccatggg aagtgcaaga gccagtcggg    30180
aggcaaattc acctgtgact gtaacaaagg cttcaccggc acctactgcc atgaaagtaa    30240
gattccactt ggaacggggg agcccagtgg gtacccagct tgggggagca gatgtatttg    30300
aattgcttta ggaagaaaat aaggtagagg acaagtagtg gcttccttag gcccctgatg    30360
gaggcattag tcagttgata agaccaccaa tagtctcttg agctcttcaa gatgattttg    30420
gaatgttgta gaaccttcct ttatttgagt ggtccctctt ttctatagaa gctttccccc    30480
caggcctacc aaataagcca atgtgtgagg gtcttaaaat ggggaggtac catctagaag    30540
ccccggcaca gaaagggtag tgatgtatcc aggtacgttt gctaaggagg cagctgtgac    30600
aatgaccagg cggtgccccg gtggctgcat gactggccct tcggctcctc agtttgccca    30660
tgcttccttt cccagatatc aacgactgcg agagcaaccc ctgtaaaaac ggtggcacct    30720
gcatcgatgg cgttaactcc tacaagtgta tctgtagtga cggctgggag ggagcgcact    30780
gtgagaacag tgagtctgct gctgcttttg gggacagatg gctccagggt gagggctcgg    30840
ggtagagcag ggataacacc ttcccttggg ggaagccctt ttttttttt tttccagaga    30900 tttctattat ggtggctgta atgatctcct gtatctcctt ggtatttatt aaggctgctg    30960
ggcagtagtg ggaggagcca ccactggggg atgatagaat tagattggca gttaggttct    31020
ttccaggcac gtattctgac ttgttgacat ttctgaccat cttgatttta attgccatgg    31080
gcattccgga ggattgtgtg ctctttataa cttgtattct ttccgcctag ccgagaactt    31140
gtctaaaagg ttgatgatga agttgaggtc ctaggacatc tcacttgttc ttggaagata    31200
gcatagaaag ccagggttgg atcttctcat agtcgagctt tgccccttat catgacggac    31260
ttcttcagcc ttgtgtctct ttggttctag acataaatga ctgtagccag aacccttgtc    31320
actacggggg tacatgtcga gacctggtca atgacttttta ctgtgactgc aaaaatggct    31380
```

```
ggaaaggaaa gacttgccat tcccgtaagt gttgctgccg gggtctcctg tctgtcttct   31440
gagggagggg aactctctag cagagagact catgctaagg tctttcttca ggtgacagcc   31500
agtgtgacga agccacgtgt aataatggtg gtacctgcta tgatgaagtg gacacgttta   31560
agtgcatgtg tcccggtggc tgggaaggaa caacctgtaa tataggtaac cttctgcccc   31620
ctaggtggga tttgctgcgg gcaaggctat tgtctgaggt ggtctgccgc caggctctta   31680
ggaaatgatc atttccttgg gtctggttct gccccttaga ccaccttgga tcctctggaa   31740
aagggtggtc ttaacctgtt tttgttttat agctagaaac agtagctgcc tgccgaaccc   31800
ctgtcataat ggaggtacct gcgtggtcaa tggagactcc ttcacctgtg tctgcaaaga   31860
aggctgggag gggcctattt gtactcaaag tgagtggcct cccctgaact ctttctgggt   31920
tgctgcagcc tacccaaaat acccatgggg acttggaatc gaaaccagaa gcacagctgt   31980
ttgatgtctg ctttcgtatc acctgggtcc ttactaatga cttgatgggc tgcagccctg   32040
acctgggcat gagaaagttc cctgggagat aagtggagac agatgctgac tctgttccca   32100
gccgcgggtc tgaccagcag cctgcctcct cccattctca gccctcccta ctccctgttc   32160
cctacaaggg cctcttcctg tatacatgtg tcccacagca aatgaaactg agtatggtcc   32220
aggcctgctt ccaatttaga ctaggttttc ggcgtatttg actggtatta agtgtgactt   32280
ttatcatttg ggtgctatgg aaataagtaa atggtgctgt gatggagacc cccaaggctg   32340
ttgtcttttc tttgcagata ccaacgactg cagtccccat ccttggtaag tgcggcaacc   32400
tcttaagctg gttcttggct gttaggatgc atgggaatct cccgggatga tgctgaaaat   32460
gtaggttctg attcaggagg tctgcggtgg ggctgtgtgt ttctaacaag ctcccaggtg   32520
accctgccct gctgctccgc ggaccacact ttaattatcc aggttgtgtc ttcatttagt   32580
gcaatgattc tcaacctcag gctgcacagg gaatcacct ggggagcttt taaaagtccc   32640
aatccctggg ttgcgactga gacctaggaa atgagattct caggggtag gacccaggca   32700
tcagtatttt taagctcctc ggtcagcagc agatatggcc tggggtgaaa gcctgtgttt   32760
gtggcaggca cggcttccaa gtgctgggta tgttgtggac ctggatgtcg gtaactaagg   32820
tcacctttgg tttcttagtt acaatagcgg gacctgtgtg gacggagaca actggtatcg   32880
gtgcgaatgt gccccgggtt ttgctgggcc agactgcagg ataagtaagt gtcactgtat   32940
ctgatgtccc cttgtctgtc ctcctcagca ttcaaatctt tcctctttaa aaacaatgaa   33000
gaccataatt ccaaataacc ctgacaactc aagccctctc ctccctctag cttggattta   33060
aaagtccctc gctgttgtcc tccctcgtca ttctctgggt ggcacagcct tctttgttct   33120
cggggagagt gccaaccata gaatttgaca attaagctat gagagagccc tgagggaaaa   33180
aagtgtatgc atccctcgtg attagcatga aattatggcc aagccattgt ccatgaagac   33240
ggctgtctct ggctccatag actgttttgt agtgggtttg accaggcccc agagaaacaa   33300
ttagtaggat caaggagtaa ggttttttct tagtgtttgt tttgtttgtt tttctttttg   33360
cctactttt aaaacatctt tttcccacac aaaacagtgt aggaaaactc ttattttgt    33420
tgttgttgtt tttttttttc ctcaaaactt taaaatgtta gttgtatttg aagtcccata   33480
atctgagatg ggctggactt gagcactagg tgagtaagtt atatctgttt caccttctaa   33540
agcgggtttg gcaaaggcat ctgtcccacc tgttttgta aatgaagttt attggcactt    33600
ggctgtcctt acttgggctt gtctatttcc tgcatctgct tacagggtgc caccagacac   33660
cactggttat gaccgacttt atggcctatg aagttaaaat gctcgctctg acccattttc   33720
agggaacgat ggtcagcctt ggtgtaaagt cagaggagag agaagctaag ggaaaattgc   33780
```

```
tcccttttgca gaggttctca gatttaggaa tcagaactgt tgtggtctttt ggtagtcagg   33840
ggctggtaca ggctttgtgt gttgtgtgca tggaaattca ccaagtttgt atcagcattt   33900
ggatgctttt gggcaatgtc tgtgaaaaaa cttcccaccg aagtctgaac ttgacctcat   33960
ttctcctaga catcaatgag tgccagtctt cccttgtgc ctttgggcc acctgtgtgg    34020
atgagatcaa tggctaccag tgtatctgcc ctccaggaca tagtggtgcc aagtgccatg   34080
aaggtaggca tgccagggtg tgtcttctga attgagtggg cttcacagtt accacagctc   34140
acagtgggggg ggggggggtgc accatgctca acggggaagg gaacaaagca gggtggtacc  34200
tatgggtttc tgttgccact tagttgccat gtaacaaagt tccttaaaac ccaatagctt   34260
gcagtatcca tttttgtggc ttgtagcatg atagctgggc agagcactga ttccaggcgc   34320
agttctggtc aactggtcct tagctatctc tgaggcatgt tcttcttctc atgatagatg   34380
gcaggcacac gggaggccag ctcaactggg aaagctctgt tacagggcct ctcgggtcac   34440
atctgctgag actgctttag tcaagtgacc caagtgagca gtcagagggg atggatggcc   34500
agtgcacgtg cctgacattg tgggaggagc tgtcatcacg tggcagagga aggacacggg   34560
tgtaaccaat ttcttaacag ggagggggta aacaaattca gtctgtggga aaagaaactc   34620
ctacttaagc gtctccacct ctcagtttca gggcgatctt gcatcaccat ggggagagtg   34680
atacttgatg gggccaagtg ggatgatgac tgtaacacct gccagtgcct gaatggacgg   34740
gtggcctgct ccaaggtagg gcaatgaaag ttgctgaagc tcccaagtgt taatcatggg   34800
tggacattcc tgctaagcca ccagttcctc ttctctcctc tctaggtctg gtgtggcccg   34860
agaccttgca ggctccacaa aagccacaat gagtgcccca gtgggcagag ctgcatcccg   34920
gtcctggatg accagtgttt cgtgcgcccc tgcactggtg ttggcgagtg tcggtcctcc   34980
agcctccagc cagtgaagac caagtgcaca tctgactcct attaccagga taactgtgca   35040
aacatcactt tcaccttttaa caaagagatg atgtctccag tgcgtaactt ctttaatggg   35100
gatgagaacg tggctgcttg tttcaaagta gtacaacagt ttcagagtag catgagggag   35160
tcctctcctc ccctttagccg aaatctgtct cttagaacag actgaggctt ctatctagcc   35220
cgttgaggag acttgtgagc cttttatttc atccattatt tgacatttgt gttaacctttt  35280
ctaaaaattt atagggtctt accaccgaac acattttgcag cgaattgagg aatttgaata   35340
tcctgaagaa tgtttctgct gaatattcga tctacatagc ctgtgagcct tccctgtcag   35400
caaacaatga aatacacgtg ccatcgtga gtagaagacc atttcactcc taattatttg    35460
attacaaggg atttaagtta gcaagtatca gacaacaatt gcaatgaaaa cattagctag   35520
tcttgttaag tttgagtgat aactaccatg ggtttgcttt tattttagtc tgcagaagac   35580
atccgggatg atgggaaccc tgtcaaggaa attaccgata aaataataga tctcgttagt   35640
aaacgggatg gaaacagctc acttattgct gcggttgcag aagtcagagt tcagaggcgt   35700
cctctgaaaa acagaacagg tgggtgtcta tttggaagat acccttgcct ggtgactgtg   35760
aaaatgattc tcctgcacca tccaggaaag tcctcaccta gggaatgatc ttccagccat   35820
cttagaagcc cctcacttcc agcctcctgg cccaggctca caaatcaat attggtattg    35880
gctgaggaag gcagagaggt acacctgacc cattatccca ctagcgtgct gtatgcattt   35940
tcttcttgga aagctcccat gcataagagg tatgatttag atccagtgca aagccctggg   36000
gcacagcagt gcctgctctg agctgttgat gctctacaga gccagttttta gggttctagc   36060
acagctgacc ctgaacacta aacagcatca ctgacgcttg atggtgactc agggtattca   36120
```

```
aactgaccct ttgatgattc agagcctcgc tgtttaggct gagctgaaat caggacttct    36180
attttggggg aattggagtt gtctgtgctt gcactgggtt tctgatgatt ctgaactcag    36240
tcctaatcct gagccaccga agtcctctgg aactggaaat aacccaatgt ggagttggaa    36300
gaaagacata ggagtgctat tctatccacc tggtgcactg aacacaggtg tcctaaagac    36360
cagcttctgg caatagtgaa cctatctgtg aagtttcaaa gaggttcttg tccccacagt    36420
gcccctctta gggaccgaat acaggaagac cactgttggc attctgttcc tatggcaata    36480
gctcttcttg agttaactgg tccttggctt gtcttccaga tttcctggtt cctctgctga    36540
gctctgtctt aacagtggct tgggtctgtt gcttggtgac agccttctac tggtgtgtaa    36600
ggaagcggcg gaagcccagc agccacactc actccgcccc cgaggacaac accaccaaca    36660
atgtgcggga gcagctgaac caaatcaaaa accccatcga gaaacacgga gccaacacgg    36720
tccccattaa ggattacgag aacaaaaact cgaaaatgtc aaaaatcagg acacacaact    36780
cggaagtgga ggaggatgac atggataaac accagcagaa agtccgcttt gccaaacagc    36840
cagtgtatac gctggtagac agagaggaga aggcccccag cggcacgccg acaaaacacc    36900
cgaactggac aaataaacag gacaacagag acttggaaag tgcccagagc ttgaaccgga    36960
tggaatacat cgtatagcag acagtgggct gccgccatag gtagagtttg agggcaccgc    37020
ggggcttgta gtttctttaa actgttgtcc tattccagtc tgaggctgtt gttgacttag    37080
aatcctgtgt taatttaagt ttcgacaagc tggcttccac tggcactggt agtttctgtg    37140
gttggctggg aaattgagtg cagcgctctc acagctatgc aaaaactagt gaatgtgccc    37200
tggtgtccat tcccctgccg cagacacatc gggctcccag gagctgccca gccctaggcc    37260
tggagcttcc acatctgcca gcggtcctaa tggtgatggc agccttagga tcatagtttt    37320
atttatattt attgactctt gagttgtttt tgtatattgg ttttatgatg acgttcgagt    37380
agttctgtat ttgaaagtgc ctttgcagct cagaaccaca gcaactatca caaatgactt    37440
tattatttat ttttttttat tgtattttg ttgttggggg agggggggatt tgatgtcagc    37500 agttgctggt aaaatgaaga atttaaagag gaaaaatgtg tcaaagtaga attttttgtat   37560 agttatgtaa ataattcttt ttttattaat cactgtgtat atttgattta ttaacttaat    37620
aatcaagagc cttaaaacat cattccttt tatttatatg tatgtgttta gaattgaagg    37680
tttttgatag tgttgtaagc atatgactct ttttttgtg aacttttctc ataacgtgtt    37740
gcctgtaagc caaaattaag gtgtttggaa atagtttctc ttgaaaggat gggataggct    37800
ttttcccctg ggaatactga tggaattttt tttttttttt ttttttttgt acgacgtcag    37860
gtgttgaaac acttccttga tagcatcact ttaagtttaa gacacatttt aaggactgac    37920
tgaggcagat taagaattgc tctagaacag gtttctttct ttcttttttt ttttttttc    37980 ctctttcttt cctgctttag acttgaaaag agacaggcag gcgatctgct acagagcagt    38040
cagttttaag ggaacagact gagctatatg acttatgtag ccagaaagtg actggttgaa    38100
tctcattaca aatatcaaat taattgtgtg aagttggaag catcccaatc ttactttgta    38160
aattctgatt tattttcacc attcgttatg taatgctgaa ccacttgtag acttgatttc    38220
gttgttgttg tctactgcat ttagggagta ttctcataag ctagttgaat acttgaaccg    38280
taaaatgtcc agttagatca ctgtttagat ttgccgtaga gtacactgcc tgccttaagt    38340
gaggaaatca aagtgctatt accaagctca agatcaaaaa aaaggcttat aaaacagagt    38400
gatccaggtt caccaccggg actggggaga tacttggtgt tgttctatt agtgtttatat    38460 gaacagaaaa tacatctttg atgtgttgtt cctggcaata aattttgaaa agtaatatttt   38520
```

```
attaaatttt ttgtatgaaa acatggaaca gtgtggagtc ttgtgagctt atggaatcct    38580
tgctggtttt tccatcctgt ggttgtttgg cactgctcat tctgctccat gtagcatctg    38640
aaaggggtgg gggtgtgggt gggggtgggg ttgaagcaaa cagcaaaatt tctgagttct    38700
caaaaaaccc gtgaggctgc tgtgtaggtg cgagctgtgg tgggggagcc cccgattctc    38760
ttgtcatttg acaagtgtga atactgctga catagtgcta ctggattgca gtgtggagat    38820
gaatggtttc ggagcactca cagggaatgc ccattgcaca aacagtggtt taaacagctt    38880
ggatttggca ttgagctgaa ggagtgagac ttggcgcctt ctcactttt ggattggatt    38940 aatagtgatt ccttgctgtc attatacgcc acacccatg ctttatgtg tacgcttatc    39000 cccagagggt ctctttgcca caacgtgggt agtctgatgt tagggtccac ctagtcacca    39060
ccttggccca gggaatgagt gttgggctgc cttaccacgc agaccttagg agctgggtat    39120
ccgactttcc aagggggcg gggcgtgtta caagatcaaa ctgccttcaa tatctgtaaa    39180
tagcaaaagc catagctccc tgtggctcca ggggccttgc ccgttcccac actgggaggt    39240
gcaggaagct ggcctctggt tcctcttcgg caagggatga gttgtggtga aagccatgtg    39300
gacacgttcc agcagccgtg tagagtcatc aggagttccc tgtttctggt taggaagtca    39360
aaggttacct ttctcagaat gctctttagc aacctagcat ccaggcctgc ccactagccc    39420
ctggacttaa tggtctaaca aacttggtca ctcaaaggtg aagagatatg ccctcctcct    39480
gtacccatcc cccacaggga agttttctct aacagtctag gggttattct cagttaggta    39540
gctcatttca ggatggatga agagttttaa atgtcccaaa tatctctgca tagacagact    39600
atcaagggat tcaatgtctc ttaacatccc taagctatat ccaacagtgc tttgtttggg    39660
tgcctcacga ggtacttcag aaggaagcag ctagtgatga gtttagattc ccacgacatc    39720
ttaccttggt gtagcaatac cttgtcatta atctctgtca gcagacagct ggtttctgca    39780
aggtggggtt gaagagggag aagcagggac cctataagcc aggagacatt tcgttagac     39840 agcaccagat tccaatagca ttctgaagta ataccttgtt ctggtggttt gtaaacttgg    39900
attctgcagg acgctagaat tccttgggta gctgccaagt agttttgtgc caaggggggg    39960
gggtggggag gggagttaat gagcttctgc aggccttcat tccaggaggg aagtgatctt    40020
gagattcacg gatgttgtct tgacgagtct ttggtccccg acatggagtc ctggagggc    40080 ataggtcaga ctcctgtggg cacggctcaa agccaggatc ttaattgtgg agaaagaagg    40140
aagcccgggt atgctggggt caggggtag aagagaggac tctgggagat gttctagccc    40200
ttcttaaaga agctttggca gagaaaagtt ccagtcccga atctcactag ctaaaatcct    40260
aacgttaggg tatgtcatga aattctggaa aagcattacc ctgaaggtgg tggcgattat    40320
tctcattgtc ccaagttttt agacaactgg gggctgggtt ggggtaggag gcagtaggat    40380
atttaaccta actaaatgca agtgggattg tcatgataag aaaggcctcc tgctcttttg    40440
aatgcagaac cccaagccca gctcaagacc ccataggatc agaactcacc aaaactggac    40500
tttagaatct acatttgtca acaagctttc tcctctgctc ctttccccct ttgcttacac    40560
acagtaaaat ttgagaacaa agtatacgc tcttcattaa ttacaatgtt tttcctcctt    40620
gttaaatgga attagatagc ctggaagcgg gcttgttgct aaattaccac ctgacatcat    40680
ttttaagtaa aatgattaca ctgcccctta agcaagccat ggtctgtatg attcatcttt    40740
attagctgat ctgaggggtc aatgagtcaa agttaactta tttagcaaca tttctttggt    40800
agaaaggagc caaagaaaga agagggtggg ggtccccacc ttcctaaata gttcctgcct    40860
```

| | |
|---|---|
| gcttgtctgc aagtgaacaa gtaagcagct aaacaccagc tgcttttaaa gaaaaagaaa | 40920 |
| aacaaacaaa caaacaaact gtcctggaat gcccatagga gtttgaactt aggctgaacg | 40980 |
| aagcccacc atttccgttt ggactgtggg ccgctttctt ggctctcctg ggaatgagaa | 41040 |
| acaggagttc agaggttccc ggctgggaga cataagtact tgggttatgg gaagccttct | 41100 |
| cctgctaatg tgtatttata cttgtgagc tctgattcat ccaagcattg gaacacagat | 41160 |
| ctgcttcctg aggttcagtt tttaaataga tagtttgcaa aaacaacaat tatttttctt | 41220 |
| aaccttttt tcctaccca caagcagcta acatcctgg ctcagactat gtcagcctct | 41280 |
| aacaatgcca aaaacagct cggctaccta aggtagaagg tggcccctga ggcaggcctt | 41340 |
| ttgaggttct tgccccagaa gccttaaaaa caaagtttag aagtcattag acaatcctg | 41400 |
| ttgcatcacc aggactgcat gcagtgtttc tgggtgtact aaaaaagaat gaattttcct | 41460 |
| tggtgagcaa ctgctttctg ggggttctga gaatggcaag tgaggttgtg ggcaggtgct | 41520 |
| tgtagagtag aggctgtgtg gttgcctggc aggcagggga cctaacacct gcatggcatc | 41580 |
| ctctgagacc atgtcaaaag ggtgtggctc ccttcccttg gacctatgtt ctacctgcac | 41640 |
| tacttgctct tgcatgccag gcacaacctc tctggcagag agtgtgttcc tttcaagtcc | 41700 |
| aaagcggctt ttacaagtct caaattatgt atcattatgc acgggtccag tattaacctg | 41760 |
| tgatatgcaa gtcagggaaa ttatcttagg ggaaaggctc ttaaatccag taagaaacct | 41820 |
| ggatggaagt ctgcctgtag cctcaacaac ccactcctct gaaaatgtcc acacccaggg | 41880 |
| gaccaagggt tgaattattt atccatggag caaaaccaga tcccagcaac aggaaaggta | 41940 |
| cagctttgtg ttaaagccat gttgtcctgc agggtgtgtg gagctcctgg agagtccaga | 42000 |

<210> SEQ ID NO 2
<211> LENGTH: 5493
<212> TYPE: DNA
<213> ORGANISM: Mus musculus
<400> SEQUENCE: 2

| | |
|---|---|
| agaggtggaa gaggggggag cgcctcaaag aagcgatcag ataataaaa ggaggccggg | 60 |
| ctctttgcct tctggaacgc gcggctcttg aaagggcttt tgaaaagtag tgttgttttc | 120 |
| cagtcgtgca tgctccaatc cacggagtat attagagccg ggacgcggcg ccgcggggg | 180 |
| cagcgacgac ggcagcctcg gcgggagcac cagcgctagc agcggcggcg cgtccggag | 240 |
| tgcccgtggc gcgcggcgca gcgatgcggt ccccacggac gcgcggccgg cccgggcgcc | 300 |
| ccctgagtct tctgctcgcc ctgctctgtg ccctgcgagc caaggtgtgc ggggcctcgg | 360 |
| gtcagtttga gctggagatc ctgtccatgc agaacgtgaa tggagagcta cagaatggga | 420 |
| actgttgtgg tggagtccgg aaccctggcg accgcaagtg caccgcgac gagtgtgata | 480 |
| cgtacttcaa agtgtgcctc aaggagtatc agtcccgcgt cactgccggg ggaccctgca | 540 |
| gcttcggctc agggtctacg cctgtcatcg ggggtaacac cttcaatctc aaggccagcc | 600 |
| gtggcaacga ccgtaatcgc atcgtactgc ctttcagttt cgcctggccg aggtcctaca | 660 |
| cttgctggt ggaggcctgg gattccagta atgacactat tcaacctgat agcataattg | 720 |
| aaaaggcttc tcactcaggc atgataaacc ctagccggca atggcagaca ctgaaacaaa | 780 |
| acacagggat tgcccacttc gagtatcaga tccgagtgac ctgtgatgac cactactatg | 840 |
| gctttggctg caataagttc tgtcgtccca gagatgactt ctttggacat tatgcctgtg | 900 |
| accagaacga caacaaact tgcatggaag gctggatggg tcctgattgc aacaaagcta | 960 |
| tctgccgaca gggctgcagt cccaagcatg gtcttgtaa acttccaggt gactgcaggt | 1020 |

```
gccagtacgg ttggcagggc ctgtactgcg acaagtgcat cccgcaccca ggatgtgtcc      1080
acggcacctg caatgaaccc tggcagtgcc tctgtgagac caactggggt ggacagctct      1140
gtgacaaaga tctgaattac tgtgggactc atcagccctg tctcaaccgg gaacatgta       1200 gcaacactgg gcctgacaaa taccagtgct cctgcccaga gggctactcg ggccccaact      1260
gtgaaattgc tgagcatgct tgtctctctg acccctgcca taaccgaggc agctgcaagg      1320
agacctcctc aggctttgag tgtgagtgtt ctccaggctg gactggcccc acgtgttcca      1380
caaacatcga tgactgttct ccaaataact gttcccatgg gggcacctgc caggatctgg      1440
tgaatggatt caagtgtgtg tgcccgcccc agtggactgg caagacttgt cagttagatg      1500
caaatgagtg cgaggccaaa ccttgtgtaa atgccagatc ctgtaagaat ctgattgcca      1560
gctactactg tgattgcctt cctggctgga tgggtcagaa ctgtgacata aatatcaatg      1620
actgccttgg ccagtgtcag aatgacgcct cctgtcggga tttggttaat ggttatcgct      1680
gtatctgtcc acctggctat gcaggcgatc actgtgagag agacatcgat gagtgtgcta      1740 gcaaccctg cttgaatggg ggtcactgtc agaatgaaat caacagattc cagtgtctct       1800
gtcccactgg tttctctgga aacctctgtc agctggacat cgattactgc gagcccaacc      1860
cttgccagaa tggcgcccag tgctacaatc gtgccagtga ctatttctgc aagtgccccg      1920
aggactatga gggcaagaac tgctcacacc tgaaagacca ctgccgtacc accacctgcg      1980
aagtgattga cagctgcact gtggccatgg cctccaacga cacgcctgaa ggggtgcggt      2040
atatctcttc taacgtctgt ggtccccatg ggaagtgcaa gagccagtcg ggaggcaaat      2100
tcacctgtga ctgtaacaaa ggcttcaccg gcacctactg ccatgaaaat atcaacgact      2160
gcgagagcaa ccctgtaaa aacggtggca cctgcatcga tggcgttaac tcctacaagt       2220
gtatctgtag tgacggctgg gagggagcgc actgtgagaa caacataaat gactgtagcc      2280
agaacccttg tcactacggg ggtacatgtc gagacctggt caatgacttt tactgtgact      2340
gcaaaaatgg ctggaaagga aagacttgcc attcccgtga cagccagtgt gacgaagcca      2400
cgtgtaataa tggtggtacc tgctatgatg aagtggacac gtttaagtgc atgtgtcccg      2460
gtggctggga aggaacaacc tgtaatatag ctagaaacag tagctgcctg ccgaacccct      2520
gtcataatgg aggtacctgc gtggtcaatg gagactcctt cacctgtgtc tgcaaagaag      2580
gctgggaggg gcctatttgt actcaaaata ccaacgactg cagtccccat ccttgttaca      2640
atagcgggac ctgtgtggac ggagacaact ggtatcggtg cgaatgtgcc ccgggttttg      2700
ctgggccaga ctgcaggata acatcaatg agtgccagtc ttccccttgt gcctttgggg       2760
ccacctgtgt ggatgagatc aatggctacc agtgtatctg ccctccagga catagtggtg      2820
ccaagtgcca tgaagtttca gggcgatctt gcatcaccat ggggagagtg atacttgatg      2880
gggccaagtg ggatgatgac tgtaacacct gccagtgcct gaatggacgg gtggcctgct      2940
ccaaggtctg gtgtggcccg agaccttgca ggctccacaa aagccacaat gagtgcccca      3000
gtgggcagag ctgcatcccg gtcctggatg accagtgttt cgtgcgcccc tgcactggtg      3060
ttggcgagtg tcggtcctcc agcctccagc cagtgaagac caagtgcaca tctgactcct      3120
attaccagga taactgtgca acatcacttt tcaccttttaa caaagagatg atgtctccag      3180 gtccttaccac cgaacacatt tgcagcgaat tgaggaattt gaatatcctg aagaatgttt      3240
ctgctgaata ttcgatctac atagcctgtg agccttccct gtcagcaaac aatgaaatac      3300
acgtggccat ctctgcagaa gacatccggg atgatgggaa ccctgtcaag gaaattaccg      3360
```

| | |
|---|---|
| ataaaataat agatctcgtt agtaaacggg atggaaacag ctcacttatt gctgcggttg | 3420 |
| cagaagtcag agttcagagg cgtcctctga aaaacagaac agatttcctg gttcctctgc | 3480 |
| tgagctctgt cttaacagtg gcttgggtct gttgcttggt gacagccttc tactggtgtg | 3540 |
| taaggaagcg gcggaagccc agcagccaca ctcactccgc ccccgaggac aacaccacca | 3600 |
| acaatgtgcg ggagcagctg aaccaaatca aaaccccat cgagaaacac ggagccaaca | 3660 |
| cggtccccat taaggattac gagaacaaaa actcgaaaat gtcaaaatc aggacacaca | 3720 |
| actcggaagt ggaggaggat gacatggata acaccagca gaaagtccgc tttgccaaac | 3780 |
| agccagtgta tacgctggta gacagagagg agaaggcccc cagcggcacg ccgacaaaac | 3840 |
| acccgaactg gacaaataaa caggacaaca gagacttgga aagtgcccag agcttgaacc | 3900 |
| ggatggaata catcgtatag cagacagtgg gctgccgcca taggtagagt ttgagggcac | 3960 |
| cgcggggctt gtagtttctt taaactgttg tcctattcca gtctgaggct gttgttgact | 4020 |
| tagaatcctg tgttaattta agtttcgaca agctggcttc cactggcact ggtagtttct | 4080 |
| gtggttggct gggaaattga gtgcagcgct ctcacagcta tgcaaaaact agtgaatgtg | 4140 |
| ccctggtgtc cattcccctg ccgcagacac atcgggctcc caggagctgc ccagccctag | 4200 |
| gcctggagct tccacatctg ccagcggtcc taatggtgat ggcagcctta ggatcatagt | 4260 |
| tttatttata tttattgact cttgagttgt ttttgtatat tggttttatg atgacgttcg | 4320 |
| agtagttctg tatttgaaag tgcctttgca gctcagaacc acagcaacta tcacaaatga | 4380 |
| ctttattatt tatttttttt tattgtattt ttgttgttgg gggaggggggg atttgatgtc | 4440 |
| agcagttgct ggtaaaatga agaatttaaa gaggaaaaat gtgtcaaagt agaattttg | 4500 |
| tatagttatg taaataattc ttttttttatt aatcactgtg tatatttgat ttattaactt | 4560 |
| aataatcaag agccttaaaa catcattcct ttttatttat atgtatgtgt ttagaattga | 4620 |
| aggttttga tagtgttgta agcatatgac tcttttttt gtgaacttttt ctcataacgt | 4680 |
| gttgcctgta agccaaaatt aaggtgtttg gaaatagttt ctcttgaaag gatgggatag | 4740 |
| gcttttccc ctgggaatac tgatggaatt ttttttttt tttttttt tgtacgacgt | 4800 |
| caggtgttga aacacttcct tgatagcatc actttaagtt taagacacat tttaaggact | 4860 |
| gactgaggca gattaagaat tgctctagaa caggtttctt tctttctttt tttttttt | 4920 |
| ttcctctttc tttcctgctt tagacttgaa aagagacagg caggcgatct gctacagagc | 4980 |
| agtcagtttt aagggaacag actgagctat atgacttatg tagccagaaa gtgactggtt | 5040 |
| gaatctcatt acaaatatca aattaattgt gtgaagttgg aagcatccca atcttacttt | 5100 |
| gtaaattctg atttatttc accattcgtt atgtaatgct gaaccacttg tagacttgat | 5160 |
| ttcgttgttg ttgtctactg catttaggga gtattctcat aagctagttg aatacttgaa | 5220 |
| ccgtaaaatg tccagttaga tcactgttta gatttgccgt agagtacact gcctgcctta | 5280 |
| agtgaggaaa tcaaagtgct attaccaagc tcaagatcaa aaaaaggct tataaaacag | 5340 |
| agtgatccag gttcaccacc gggactgggg agatacttgg tgtttgttct attagtgtta | 5400 |
| tatgaacaga aaatacatct ttgatgtgtt gttcctggca ataaattttg aaaagtaata | 5460 |
| tttattaaat tttttgtatg aaaacatgga aca | 5493 |

<210> SEQ ID NO 3
<211> LENGTH: 48001
<212> TYPE: DNA
<213> ORGANISM: Mus musculus

<400> SEQUENCE: 3

-continued

```
gaacaggtgt gtcaagggag atgggagggt cctaggacaa tataatctgg ggcccttatt      60
ccttgttgaa ctcaccaccg tgttttagga tggggaggtg ttgttcgttc cagattccat     120
tgaactttaa ctgcaaaggg ataaggaagg catcttggac gcccagtgct aagcagctta     180
gcacaggatg tccaaacatc aaggtggaga taaagcatga gaggctgtgt tgacgctagc     240
agtcattgta ctggaactct gcactttccc aggccaccta agtcggacac agccagggac     300
cagtgagaag ggtgaccgtg gaacgtctag actcgggttc ctgctgggaa tcgagagcgc     360
aatctgtcca gcaaggcact agtccttggg gagttccctt agggagcccc gaactcccct     420
ctacagaggc tgcgggcgcg acgccatcat cgtttaaggt caagcgttcc ggaagtcatg     480
gctaagagtg cctggcctca atcctcctga tgcctatagc cgagaccaaa cagctcccag     540
gagtggagcc ctagggacag gacacgcgca acgctgccag ggcgccacat ttaaactcct     600
gccccaggat tcccccaaa cttgacttca gctgctcctg cccacggtcc tagacctaac     660
tccaggatgg agctggttcc ccgtgcagct ttcctttccc acaagacccg tacctcctct     720
actattgaaa tgcaaattct ggccaaatgt cgcagagggc ggctacacac aaagcctgat     780
ccttccgcag cgccagctca aacttttggt ctctgtaaac tttcgaacaa gaagtagttc     840
ctagatgccc attccataca cccctccatt cctccttgtc ttgcgaacca taagatcctt     900
agatcctggc tcgggacgcg ctccctagcc cggacaggcg cagaacccac caaagcgctg     960
ggagggacag ggtccacaag ggggtaaggg ttcgcaggaa ccaggggcgg agcccgctgg    1020
gatggggcgg ggcaggggcg ggcccccata ggggcggagc gcccgcccgc tcagagcctc    1080
actagtgcct ctgccgcggg agggagcgca ggggcgtggg gcgcagggcg cgggcgctgg    1140
gcgcgggtgc gagcgcagtg aaggaacgag cccgggtgcc ttgtagggcc cagcgccgct    1200
gagagcccag cgccgcccac ccgccaggaa agagggcatc agagggtgga cgcctgcggg    1260
accgccggtg gtgtgcgtca acgtccgatc cccgccggcc accccaagag gccgccgccc    1320
gggctgcggg cagctggcga gcaggcatgc cacggctcct gacgcccttg ctctgcctaa    1380
cgctgctgcc cgcgctcgcc gcaagaggta ggctcccgcg agcccgcaac ttcgggcgcc    1440
tttcagaaac ttctgttgcg ccctgcgcac gctttgggta gataggagta agggaccagc    1500
tgccagagtt gagagccaga gcgggtggag gggaccgtgg gacctggtgt cctggcgtgt    1560
gaggaggacc cttctctttc cagggtacc cactttctc atagcgccca aagacgctgg    1620
aagtgtggta tgggcccg gaggcccaac cctggctcgc acttgggtag acgctcctgg    1680
ggctcgccgc gggggcggac atgctgcttg cgcctctact tttcgatttg aatcgaatcg    1740
gttttggttt cctgttgctt cttgggacca tttattttca ttcttctttg cctccggccc    1800
gtgctagggc ggatgttggg gtgcagtgtg aggtcagggg cgctatactc tcgttgctta    1860
cttagagcgg ggcagagacg atgtgccctg gactcctagt atggggtttt gggatcgctg    1920
tcccctagcc ggaatcaaac tttcgaagag gggcgatgtg caggcggctt gctgcctagg    1980
gtgggcgtgg gactgactca tttcggaagt ttgaaaatcc tgtgctgatt ggaacgggag    2040
ccggagaggg gagcccttat ttcccttccg gcttcacaga acggggtact cctgttgtag    2100
taaccaactg cactcttctc ccagtaatcg aaggagagaa ctgcctgccc ttccttaaa    2160
agtggggttt tatgtgacgc tcgagctcag ccctacatcg aggcttaatt tttagagctc    2220
tttaagatgg cgtgggaggg gcttgattaa taatagcccc ttcccgagaa cggggtggaa    2280
ttccttctaa gtggggtttc taagacccc tccctgggtg cggcggggc tgcccctgga    2340
```

```
gatgcctgcg aacaggtatt gggtgtcgga gtaggcgggg caggtctccg ggtgcggccc      2400
cgctgcccca ggaggcggcc ctggcgcgac aatgggccgc tctgattccc gggccggcgc      2460
tttgttggag ggcggggtgg cgggctccgc agctgtcgct ttttcccacg atccggggag      2520
ctgagtgtgg ccaccccctc cctcctgcgg tccctcgta tcttgtgttt gaactgaggc       2580
aagggtggag gcttgtcggg gggctttgct gggcaccta  atcccctccc actttggctg      2640
tgtggttaga agtttgggag aatttgctaa gtctttctgt tgccgtccac ttcgcctcac      2700
tatgagtggg gcggtacacc tgccacctag ccagcctatc ctttccccac tagttttttga    2760 ctacaatact gtgagcagaa cattgattcg taagccgccc ccccaccgc gtcccgcacc       2820 ccctcaggac tgccaataac tctagtgcat aggcaccatg gctttaatct ccgtccacca     2880
tcaggactat aaggagttag gtgcccagaa ccaagcctga cctctctctt ctgaccttcc     2940
cccaggcttg agatgctccc agccaagtgg gacctgcctg aatggaggga ggtgcgaagt    3000
ggccaacggc actgaagcct gtgtgtgagt accgcccctg aggggacctg ttgcttttgt     3060
cagagcagag cccctgcctt ctggggacag aacactgggc tattgtcttc ggaagacagc    3120
cccgaggctg agtgcagtca cgtgctgact tttattggac aaagtctggc aattacttaa    3180
tcaccagcaa ttatgccgcg tgtggagcta ctctggcccc tggaggttgg cacactcctt    3240
cgtgggccct caggctcctg ggaattcttg gtgccctagt tcttatttaa aatgcttgag    3300
aaacagttgt tttggatgat gagcattcgt tctgggacac ttaccgagag agtctgagac    3360
ccccaccccc tgtcacctgg gatccctctt cctgagcagg agtgcactag aaggaaatt    3420 gacccgtgtt gttggtttgt gttctggttt tgttggtggt gcttttttgtt ttttttttgtt    3480 tgtttgtttt tttgtatcag gatctcacta gtagctctg gctgtcctca aactcactat      3540
atagaccttg aactcaggaa tctgcctgcc tctgcccagt gaaaagtgcc tattttaaga    3600
caagacccac ctctggactc tgtgccacgg gcccttgtcc tcaggtcacc aactgtgaaa    3660
tgggtatgac ttggggatgg gaaggtctgc tccatgttgg gaactccttt tgggaaggat    3720
cccggccagg ttgctctcaa ggactaggca gctgggggaa gtctctgctt ggcgctaggg    3780
ctagcgccct tcaacttgag ttcctccctg atgagactag caaggtgctg gaggctaagg    3840
cctcccctgg aggctggaga cagagaaggc tccagcctac atggcacgcc tcattccaa     3900 ctgctgaatg gctcatcccc ttgacaacgg gtgctgctgc ctccagtacc cagcctgtgg    3960
gctgcagccc cacctccctg gctggcccgc cctgtactga agccaattaa gcaggtctgt    4020
gagcagttta ttggacaaag ccgattgtgc ctctgtcaga cactaatgaa tgcacactac    4080 ttttttttttt tttttgcttt ttttgggggg ggccttttct ccccttgca  gaagcctcac    4140 ggacgcttga tgccctaaat cttatttcct tccattcaga ggccgacagc tgggattcag    4200
tagaagggca gcagctattg ttgggaggcg attaatgctg tgtgattaat tatgcgtggc    4260
ttcccagaat gtacaacccc cttcctcgcc tctgtgctcc ttggtctgcc tgcctcactg    4320
gcagggcggg ctgaaaggtt tcttctgctc agcacttgga ggggtcctgc cagactgggg    4380
caattgaggg tagtttcttc ttagccccgc caggaaaggg gcacagcctg gtctgctgcc    4440
tgccagtcac ttggtagagt tgtgcatggg gtacagtctg tttgctgtag tcccactaat    4500
agcttgtatc ttagtatctg tatggacacc tttcaagcca aaggcccaat ggtgctgtgc    4560
tttcttcccc acctcccaaa cttggggaag ctgcttgcaa atcccttgca ttacaagcca    4620
ggccactgaa aggctcttgg tgccaggcct tctgtcttgc actagatcct aaggcccttc    4680
ctccttggca gaaaacttgc ttcagtttgg ctcagagttc cactgagttc tatccacaga    4740
```

```
ggccccattg tgctcactcc gtaagtccag tgagatgaaa gagatatgct cacttctggt    4800
cagcagagct ggaggccaag gctacagcca ggcctggctg tgataggca caggtctggg     4860 cgcactgtgc agtttggggg gctttatagc caatccatag aggggtccag tgtcactgtg    4920
taggcttggg tgattgaggg tcccatccat tccatggtgt tgtctacttc ttcacatggc    4980
ctcaggaggc ctatccaaga gtttgccaga gcatacacag agggatccac cactcctgac    5040
tggggaaagg cagttcgctt tttcctcaaa ggaacctaaa ggagaaattg agggtagtct    5100
acaagcttgg agcctgtaga cctctgtcac acctagccat gatcctgatt gtttacggct    5160
tcttgtgctg cctactctga aagggcctg agaactatgg agtcatagga cagtgaatta    5220
gtgcttggta aagcatctct tctacccaaa cggagaacct accccgaaag ctgcggggca    5280
gggagtttca gggctcagga ttgcaaagta atcctcttgg taccaagtgc cttctcttca    5340
gtactagtac cattgaggtt tagctagcca gtgatcatat aggaaaggcc tggcttgtcc    5400
tgtagacaga gaagagtctt tgcagctgct atgctttgtg ggatatcaga ggcccttggg    5460
aggaagattt gggacccacc atgccttcct tccttgtggg cccaatttgt gctgagaggg    5520
aaggacgaca aaaggctgtc atttgaaaag ccagaaggac ctctacactt gggtaaacat    5580
gaattcactg atccaaaggg cttataagga gctgcaggcc ctgaactgag ggagctcagg    5640
gagactaagg ccaccttcac tgggagccaa gccagatgtg aggaggacat gcattttaaa    5700
tgcatttagg aatcagatga actatgccca gagaaattca gggcagtggg tgataatctt    5760
gggataccct gtgtttgaga ggtcccacct tagcttcacc atctttatta agtcagggca    5820
gaatcaggat tgatatcttg gtggtacaca ggattgagta agagctgaaa gagtacacac    5880
tgaagaacac ccgtgtcttt ttcactctct gctggtgagc tcgtgggct ggttttaaga    5940 gcttcatcct cccatattaa gttgggtgat gaatggattt gccatcccaa cagtgctctc    6000
tggtgggtct gtttgggttt ccgttaggga cgagctggct ggagctgagg atcttagcct    6060
gggacgtggc tgccgttgtc agctctttca gtttccttt ttgaaatttc tgtgtctgtg    6120
cactcagagc aggcatatgt atggaagtcc gaggacaact tctgtgagtc ggttctctcc    6180
tagtgagagg tctggggatc caaatcaggt cgtcaggctt gtgtagttca cgtctttcct    6240
ctctgagcca tctcactggt ccctcggaca cttaaagca actgctgtgc tctgcgttcc     6300
actccaggta tagcccagaa ctggactgta ctcaggagtg agcgtcatcc agcatgtatg    6360
tgacatctac atacatggta gacctgcccc accatggcct gacagggctc tcagcagatc    6420
agccaggatc aggcacaggg agagaattca gccgtgcttg ccgcggaat gtttcagctg     6480 atgccctttc ttccttccct ccagagtatg tgttatagcc acatccctga cccatcactt    6540
cctgccctcg tggtgaggcc ggaagtgatt ggtggactga ggaggaccc aacagaatgt    6600 tctatgtctt ccatctcctg gccctgctac tgttccattg agtcacatgc catcgtgggt    6660
tggtcccatc caacccagta ggagagccaa gactgtccca ggcttgcctg tctgtgcagt    6720
gccgtgtctg gccttcaagg acatgaggtt agaaaaacag gttaaaaaaa aaaacccag    6780 cctcacaact tgacgtgtca cggaatctgt ggggagatgg ccaggtacca gaacacctga    6840
gcagaggcag agtgttccat gaaggagagt gtctctgtgg gcagccctgc ctctggccag    6900
cagccaacag ttttccatt gaaggaataa taataatgct aaaggagaga gaccgagcac    6960
aagctgtgac ctcagcagga agagggtggg gtagagcaga caggagaacc gtgtttcaag    7020
gagctgagaa ggatgcagat aaccagagtg gctactggga tccccagaag ctgggtggta    7080
```

```
gaagagggt  caccacaagg  tttcatgccc  agggtcaaag  atggaagctc  cactggggaa    7140
gatggttcg  gcacttactc  ctggtccctg  tggtggggta  ctagacatca  tggtgggaca    7200
gggcccagag  ggcagcaggc  tgggctgagg  ggttgggctc  tcttgtgtgg  ggagggtatt   7260
tcatgtgtca  tctctaaata  gtgagaggat  gtggctttgt  tgtcaagtgg  catccacgtt   7320
tgctttcctg  aaaaacatga  aagcagcagc  tctcgcaggg  ctttgatcag  ctctgcaaac   7380
ttggtggcag  agggctgggt  tttcccagag  ggcctggccc  accctgcttg  tttcatctcc   7440
agtttatagg  tgggaaaaac  tgaggctaag  ggtgaagagg  ctggagggtg  ggggacctaa   7500
gggccgcttg  catcagcttt  caccttcatg  tgcaggcgta  tccagaactt  tccagacctt   7560
tcccagaggc  tgagagggaa  tcaccagctt  taacgagcgg  ctagcttcag  ggcatcgttg   7620
tgactaggtc  aggacgtgtc  tgattccccc  ttgtttccca  ggcagggcac  accctggcac   7680
ctgctggctg  gagacatgga  ccagctggtt  gtgatgagca  gtactccagt  ctcagtttac   7740
cctttgagca  tgagagagca  ccggaacctc  ctctctacta  tatctagcct  gggctgaggg   7800
ataacctaca  ggtgttaaga  gtggctgctt  ttggaggtag  cagctcctag  gactatctat   7860
gtggtagggc  cagttcttcg  agctggggca  tattttggcc  tcaggctggg  gacacctcac   7920
ctactggaga  ggggagtgat  tggcagggtg  ggagggcagt  ggatgtcttt  tctgtggcct   7980
taccccatgc  tatctagctg  taccagagac  caggagtctg  aggactgatt  tgggagatgg   8040
ggcttttggg  tggtagatta  cacactttgt  aaactatgcc  atttgagcca  tggaaagtgc   8100
acaatgcagt  gtacttaata  gaggcatgga  ttgcacaacc  tgcccaccta  tccagttcca   8160
gactccttaa  tcagcccaaa  ggcagctgct  tatcaccccc  tccctccct   ggcagccact   8220
gagctgctct  ctgtccctga  gcctttgctg  ttccatttcc  tgtgaatgga  gttacccagt   8280
ctgtggccat  tgagtgctgc  tttctgagca  cggatgatgt  cagggtctcg  cagtgccact   8340
gtgggtgcca  gctctgcact  cctgttagga  tcatttccaa  cttgtggcgc  cttcaggatg   8400
agccctgttc  tgagtcctga  caacagcacc  aagtggccag  aatgtacatc  tctggtctcg   8460
tgctgccccc  tgagaatgct  ccttaattgg  gacctgatgt  gctctcctgt  tggtcactga   8520
taatgtgccc  aaggcctta   cagtgctcag  tgcccatggc  agactcatag  ccagctatcc   8580
ttgtcttgcc  ttccaacggc  catcttgcct  cttggccttt  tacaacctga  aggaagagct   8640
agtggagtct  ttgtgcccgg  tacaggacaa  tggaagcaga  ggattttgc   tgagagcttc   8700
gtatgctttg  aagcctagga  tctagggcag  gcaaggcagc  caacccacct  aggcacccag   8760
ctatgaggag  atgggaaact  agggaagatg  ggagtcagcc  ttagtctcca  cagagtgaag   8820
cttgaggaac  cgtgtgtctg  agtgccctgg  gccttccaca  gcttggcatg  aggcccacta   8880
cagggtggca  tctacagcag  cctggatgag  gacaggcagg  gagccttagc  cagcaggagc   8940
aatggatagg  ggcagtaggg  agggaagctt  tggccctgtc  ttccataggc  ttgtgctgtg   9000
attttcccgc  cacagactag  gagatttgaa  caggtgtgcc  agtctatgaa  tagccacagg   9060
ctgttctttg  ggagggcac   caagctctgg  gagatgagag  aacccagccc  ttaccttaga   9120
ggtatagagt  atccttcagt  tgcctctgat  gctcagaggg  atgtactgtc  tcttgcagaa   9180
ctgtctccct  agccagcaca  ggtgtcccta  gcggaagagg  tagggatggc  tggatggact   9240
tggtctgaag  gggctgcttt  ctcagtgttc  ctgagatcta  caagattcta  gggctagccc   9300
ctttccagg   gacctcacct  ctagcccagg  ccttttattt  ccttgattat  tgctctcttt   9360
ttcgttttgt  gaggatcgat  gttgtctgca  tgtgtgtgtc  tgtgtgaggg  tgttgggttt   9420
tctggagctg  gagttacaga  cagtggtgaa  ccgccatgtg  ggtgctggga  attgaacctg   9480
```

```
ggtcctctgg aagagctctt aaccactgag tcatctttcc agtccgtaga ctgtgcacta    9540
ccctggactg aagtgctctg ggtagaaggc ctcccaactt taccctgtgc tcctgtcatt    9600
tacactccag agtgaattag ccagactaat tctcctcctc ctgcccgccc ctccccttt     9660 agtttctttg attggtactc acctggtgag ttatgtccaa tgctgaggca cggggaggaa    9720
tgactgtctc cagttatgga atacggccaa atgctggttc cagccttgct ctaacaggca    9780
gataagagga gttgtcattg ggcttgtgtt ggtttatcct atcacctggc ttggtgtccc    9840
tatgcaactg acatgcttgg agacctacca ttctgaacta ggtaaacgag cccctgtca    9900 tctgttgatg ctgctaattt gctgaacaaa ttctcccaca ggtagtgcca gaggccagcc    9960
tgacccaagc tccagcacag gcctgggag gcaggtcctg ccacatggac tgtcagtctt    10020
gtgtgagcaa tttgctctgt gccgtcagtt gaggattttg aaaagtggct atgtctaccc    10080
acttcttgag agttcttaga cctgagctgg aggacaaagg actgtccttc tcttaagatg    10140
atacccaggc accgaggcca tagcttggct ctgggtcacc ctgttgcctt aacaccacat    10200
gtgggtcacc ccgtatgaat cacagcccag ccacagccac agggaggccg gggagccgca    10260
ggctgcatga agccactga cttttcctaga gaaacatctg tgtttaatca agttcaggaa    10320
gaaagctggg cggcagcctg ctccctgaag caggttttcc cacggcctag aagtgtgtgt    10380
gtgtgtgtgt gtgtgtgtgt gtgtgtgtgt gtgtgtgtgt acatgcatgg aaggtgcgtg    10440
ggaaggggag gaagcaaggt tgacagtggc tttcctccac atgctccacc ttcatctttt    10500
gtggtagagt ctctcactga ccctcaagct gccaattcag ctagccagcc agccattggg    10560
cttcagagat ccttctcctg tcttctcttc tggaaggctg ggctacatgc aacatgtca    10620 gagttttacc tgggttcctt ccagaggttt gaactcaggt ccttgtactt acacagcagc    10680
tactttgcct attgagtcaa tattttgtgt gtgtttgtgt aggtgtgttc atgtctgtat    10740
acttgtatac tggggtgtgt gtggaggcca aaggtcaaca ctgggtgtct tcttttgcac    10800
cccatcttat attttataac agggtggctc acagaacctg gcactcactg cttcagctag    10860
agtggctggc tagcgagttc caagggtcct cctatgtcca cctccggcac tacgatgaca    10920
aatgtgtgtg ctgccattcc tggctcacgt gggtgctgag gactgactct aggtcctcta    10980
gcttgctcag cagtcatttt accagcggag ccagtgtgcc agtgtcctta ctttaaaagt    11040
agatttgcag atggagttct tggtgcacag catcccctac tgtagaccag atcccagaga    11100
gacccgggga ggaagcagct cacactggga tctgacttgc tctctccagg ctcccagggc    11160
tattgctctg catggggagg aatgtgggtg gtaaaggctg gaaagattgc tcaggtctga    11220
gtggcagcag ctccgcctcc caccatttcc tctctgtttc agttctgagt gagcggaaac    11280
agcacagtta ctgaaaatga gaggttgggg ggttgggggg aatggggctt ccagtgtatg    11340
tgcctggtgg ctggcgtagg ggcagatgct gcctttgtgc ctggccctct ggttcttctc    11400
ggctctgctt gctcatggct tctagaggtt gatccttcga ggtggggctt ccttccttc    11460 cttcctcctc tgagggtcag acgaggatga cctcagctct gtctcagggc ccgatagtgg    11520
aaaccaggtg gggcactgat tgtggaaca gtgttgtgac aggtcaggcc gtgactgcat    11580
cctaacttca tggctcagag tctggcctac tggtctggtg agatggactg aacaggtgt    11640 gggggcaggt gggtagcccc aggtttctaa gaagccacag tgaaggcagg atccccttc    11700 ctcacagtat actccatgcct ggcctctgag ccaggcttgt ttcccctcta accccctgtt    11760
ccagtaggct gtgcctagtc aaagctcaga taaaggatac ttccttcctc cagagctggg    11820
```

```
gctgcaacta gtctcacact tcctcttcct acgacaggac ccatatcctt ggggtgaatg    11880
gaggatccca tggggccact gtagctaaag gtgctggctg gccttactgc tggtatatgg    11940
gcttcatttg tctttggggg gggggtctc actttgagag ccatgtgtgt taccatgagg     12000
ctgcagaagg tgcccgactg acttgggcag ctcagacctg atggggcgtg tccttttcat    12060
tgtgctcagt ctcagctaag gactggagag ggcaccagga tgccagtgaa gtgatacttg    12120
aaaagaggcc aagcgtggga catcagtgtc cacggggcag aggggccagg acctgcaagc    12180
tttgagcttg tcctagaccc actggcctgg gacaccctgg gtcctataca gctccctccc    12240
cagagtacct cctcttccct ggacccctc tagagcaggg tacattcaac tggctctcct    12300
tctcattttt cctgtgtcct aaggcagaac agaagattct catggatggc cagtacactg    12360
tgagacaatt tgtgaccatt attgggatgg ggccttccta tctgctgcag tatggggacc    12420
tcccaagcag gggacttctt ccttgttgga agacatttgg ttgaagtggg ggctgctgag    12480
ttttgaggag tggggtgacc tctggggtcc cccaccaaag ctgcagtctg cacttcagca    12540
agtcattcaa agaattcact gaaagcgggt ttcctagggg gccctggaag aatgcagcca    12600
agatctgtgt cactttgtct gcccagcagc cagtgtggct ctgccccagt gggtagctgg    12660
acataggctt catcagcaca tcttcagtgc caccaactgg aaacgatagc cactggggtg    12720
gtggcaggtg accagccgct aggagggtct tgaggggttt ggtgaagctg agagttttga    12780
ggtttccctt gcagtcagtg gcaggggctt cccaattctg ggtccctcac taagaacccct    12840 gccccccttcc taggagtttt gtttcagcca aactcccta ttgtgtgtgc ctttgccctc    12900
ccgcgtcccc tcccccccca accccgagat cagataacca aagagatgag gcagtttggg    12960
atacaggaaa cttctcacat tcccaggag cctctgctac tctgtcttgc ctgtgactgt     13020
tctctgaacc aaggctgttc cactgtgggt gtcaggaatt aagcactaca gaatctggaa    13080
tgtatatgca gagcctgcta agcctctgtc ttcccatctg taaaatgggc ctagcccacc    13140
tccaggactg tagtaagagt ctagtgaggt gaagcttctg gcatccaagg gcccagttta    13200
gccaggtagg agcatgtctt ctctttgaa ctaagatggg cgggggtggg ggggtggggt    13260
gggggggagc aggggggaca gagtcgtctc tggatagctc cctctcacca tcttcacatt    13320
tatttggggg aagcagcgat ggacaggtgc tttgttgtag atctcagttt ggggcctctg    13380
gcttcatctc tctctggaca aagcttttcc ctctgcttag tgggagcagc ttcagggcca    13440
gggctaagtt ccagagtggc ctgccgttgt ccactgtggc tatttctagc cttccttggt    13500
actgctgcac acacagaggt ttgtccgcat gagtcccagg gaccactcag agtggctggc    13560
aggcattgtg gagtggaatg tgggaagaca cattcccagc cttgtttgca gcttgggact    13620
gtctgtgttt tgggatgatc aagcaggaaa ctgtccctag tggaggcagg agcttaagca    13680 ggtgttttc acaccctagc agtgaccct gcttcctggt gaccctagtt tgctggatgg    13740
tgctttcacc aatggtggaa ggggcacact gggtggagtc tcccacccct gctcccgtgg    13800
gtcaccactt cccacagacc aacttcagga aattgtttaa tgccacccc accccagga    13860 gccttttgc cccctcaga ggggccttca ccggcagcag cctggagggg agtattgttt    13920
tccctatagt gggaaaaggt ggcttcccta gagggcaggt tccaacttca actgtctccc    13980
acacaaaggg cttccctgag ccaggccagg aagcctgcgc ttttcctgag cttccttttt    14040
cagcgtattt taaaccaccc aaggatgcaa ctgtggggaa agatttgaag acaaaagagc    14100
tgagtgtgct gggagtggtt ctttgagctg gaaagctgga cactggcttc aatcctggcc    14160
agccctgcag ccacctgtcc acatgctaca cctgccctag tgtgacccat gttcctcctc    14220
```

```
tgaccactgc tttcccagtc tgaccagcag ttgatgtttg gtccaggggt gtctactttc    14280
cacagtgctg gctgtcttct cagcttcctg ccgctgtggg agccagggtc cctaaggctg    14340
ggaggagaat acagttcggt tattcctgcc tgccttccct gctggcgcag gtgaggcact    14400
gatgctggct gtaagcagca gtgttgctgt gccctctagg aacgatgctg gcagataccc    14460
acgtgcttgt gcacatctat ccacagtgag gcaggaaact gggttgaaga gggctattct    14520
cacccaatgt tctaaatgac cttcaggcaa gtgtttggat ccaggcaggt ttagtaggag    14580
agcgaggcac ttgatgctct ttgccttgag ttgtgtgggg aagagcaggg atggaactgt    14640
agtctgtagg ggtcccctgt ctcttgggct tgaatcaact gttctgaacc agggaggata    14700
ccagggagtc actcagcctg ctgtaagcac cttccttcat cgaggcacca gaatttaggg    14760
ggcttgggct agtctctgct caggttccag ggccaaggtc ccagaacctc tctcctgccc    14820
ccctccccaa gcctttgccc tggatggggc tgggtttgtt gaccctgtga aaatcctaca    14880
aggtgggctt tgagtgagag gtagccctgg ttttggaccc attgtgtgaa ggttgggtgg    14940
caggcagcaa gctttactgt atttttactg aaaagaacaa aatcaggctg gggtagggat    15000
ctgcatggaa ccatcccttg ggtacaagag aatggtcacc acttgttgag tggggagcttg    15060 cagaacaagg gcttcagcta tacttgggtg gctgcagaca caggtagagc agactaaaga    15120
aggcaagggc tccctccac caccatcact tcagtggtg ctggggacct gaggtatgca    15180
gtcatgcact gagccaccct ctgcctctgg gccctaggag ctcagatgcc tcagtgcagg    15240
cccctggtcc cagagaagaa taagcaagag ccttgatgct cagatagggg cctgtggtgc    15300
ctccagtcct cagatggggg ctttaacctg tgcaatgagt ccatttcttg agggagggac    15360
tgtacttttg tgactcaaac ctagccatgc tcagagtgag agtccctcag caccttgcat    15420
ctgctggtgc ctgctgcaag ggcctctctt caacatcccc cctcgagaca gacaggcagg    15480
cagacagaca ggcacactca cagagagaga gagagagaga tctttcttgc aaaactgagg    15540
tgccaaactg agagttccat ctcaccatgt agcagttaaa gcagtggagc tgggagggtc    15600
ctacaagacg tgtcccttct gaaagtgctt tctctcacaa ggtcttctgg cccctgggtt    15660
ctgggaagcc aatgaagggg ctccagtgtt gacaacccac cctacccct cctcaccca    15720 gctatctcaa gtttagtaaa cctactcctt tccccagccc tacttggcca taaacccacc    15780
aagggcagga gctaaagaac tcccactaca gtccctctgc cccctcctca tttgggtg    15840 gaaggagctg tcatctgtcc cctggaggtg gcagatggcc atgtagttta gaaaggaaaa    15900
cagcacttta gaattagtcc cgggtgagag gccacagcaa catctgcctc tggatgcttt    15960
ggggagtcac atttccatgg agtggcgctg ccagggaggt gggagtcagc acagtggaaa    16020
tgctgaagcc gccaacaaag cccaggcagc agttgtggga tgtcaggcac aggggccatt    16080
tgtactcctc tgagtctgca gaagccaccc cttcctgggg ccccagcctg cctgatactt    16140
acctgcagcc agccacagtg ggacaggtca caccccaggc aatggagtat gtggtacaga    16200
agaggcaaag tggagaagca ggtggcctaa ggagccctaa gaaggaagta agggagggc    16260 acacctgccg tggccgggtt cccactgtgg aggacgcccg aggagagcat tgcaggtggt    16320
tctcatctcg ttgatggctc gggctctcat cctaagcaag tcccaccttc ccattctggg    16380 aaggttttc cctacctaga caagaggtga ctcgggaagc agaggacatc ctgggtcact    16440
cggggaggct ctggttggtg ttcggggact gcccagtgag tggggcttcc catgtagggc    16500
ttccatgcct ctatgttgct cacatccact gacactgggg gattgtggcc atggctgtag    16560
```

```
cccagctgtg gcctaaatgt cccttcttag ggacatttga atgctgtgtg gagagcacat    16620
ggccaggtgt tacagaggtc agacaggtag gcggtagtca gaggagaagg gcttttgagc    16680
tgttgtctgt ctgccagccc cctgtcctag acctagaccc tgccacttgg ctccaggcat    16740
ctgagggatg atcccatcca agtggccctg ctggtcctcc agctatggaa tgctggtggt    16800
ggatggtggc ctcagccatg gtggtggacc caactaagca acatgcctgc gctatggtgt    16860
ccccaagccc agggtggcag tggggtggac aatgggcctt ctcagccacc acattccccc    16920
acggaggagc gtccctggcc accagcttcc cagctcctgc cccacccgct ggtgttggcg    16980
tctggccgcg cccagcaggg gcagctgtcc cctccacaga tgcacctgct ccctgctgcc    17040
cttttgtcca c gctgccggcg cctgatttat tggccatatt ttcccccttg ctggtccagc    17100
ggaacacagc agtgttggca agtgtgcatc ccatccaggc gggttcccca gtctctcgct    17160
gtgcttctta ttcagggtgc tgtagggaac acagcccatg gccggaggga agaggaatgt    17220
gagcaagctt ggagcctttg gttacattca gtgtctttat cctcagagac ctagcggggg    17280
ttgcttaagg actggagacc tagcatcagg cttgccccat ttttccctcc cagggaaatc    17340
ttcccgcctc ttggagcctc agtctcactg gcctagagct cccccacccc cttagcccgc    17400
aggaatgggt ggacgcagca gctccattgg cttttgaagat gaagctccct ctgtcccttta    17460 acactccctc ccccgtgact tcaccaatgg ctgggaaaga aaaaaaaaaa ccttttctcc    17520
aagtgggctg aggccaaccc tgcttgacaa agaggcattg atccagagag gagggctgct    17580
tctaggggcc agcctcagcg ggcagatccc aggctcccag cagcctctcc agcaggctag    17640
taactggatc catgagtaga aaggcaaaga ctgcctccca gcctcccaa ggtagattct    17700 accagagcct aggtgccccc agagaagcag gtgtggatct cagtggctgg ccacactggt    17760
ggggaggtgc cttccaaggc tacccccca tgcaggagga gccagatgtc ccccatcccc    17820 accccaccc ccacaccaaa cacacttccc atgctggaca ggaaccattg caaaggcttg    17880
cgttaactcc ctggggagtg ggggtgtgat ttgttttctt taagccagtt ggtttgagac    17940
ttttggcttc tggcaacaga tggtcaccag agtggccatt ttgtgtcttc catacccaag    18000
cggtagacac agatgaaagg cttcagagag gacagatgtc tcccagtact tctactgaga    18060
tacctgaccc cagaccccat gctgcctcca gcagctctta gtggggaggc ctctcctggg    18120
gccactctca cacggggtgg ggggtgggt tgattataaa tagttgttta gaagcaagtg    18180
gggactaact ggttggctgg aggtagggat tgaggcaagt tacagccaaa gcttggggtg    18240
catggcgggc tgtgtgtgtg tgtatgtgtg tgtgtgtgtc aagggggcagt ctgcatgcca    18300 gtgagcaggc tctggaaatc aggatgggct gtgtgtagcc agcacctggc tgtgaccctg    18360
ccatgggggc tgtcctgtca gctagcacgt tctgcctcag agcctttgcc tctgggaaga    18420
gcttggcttg gcggctccca gagccttctg tgggagtgtg gggccaagag gtggggcaag    18480
agtggggtca gggg tttatg gcccaagctc tgggagctag gcagacaggt ggctgaggag    18540
gctactgaga ctggggcagt ggcacacctt gagcttgtcc ccgtagggaa ccagcaaatc    18600
taagcctgga gacagcaaac cccctcacct gtctggaggt gggtcaggct ttcagcctct    18660
gtccttcaat gaatcatgtc ctcagaggac ggtgctgatg ctactgatac agagtgcgtg    18720
gtacagagtg cggggtacag agaacttgtg tctggaggtt ttatttgtcc ctgagggggt    18780
gccattttgg tttgggggta tgatatgaag aacctgtgtc tgagagcgga gttgtagaga    18840
gtgggcagca gccagcatcc tggcatagtc cccttgctac agggcaggaa ctgaagagag    18900
agaaagcaca cacagtctcc agtctgctct gcttcccgcg tccactgtgc tattgatgtt    18960
```

```
tgaaagtgga aggaaccgtg aactctttta ttacccagat gatgcatatt catgacagaa    19020
gctgggagag aaaagcagac cagcctccta aatgagagtt tcacagagtc tatgtcgaca    19080
tccccccaca gggctggggg gaggggggctc tgctgcgcct gtaggctcac ttcgagtgta   19140
gacccagatt tgaaatctgc ctggtttgaa attcaggctg gtcttgtctc tagcctggcc    19200
ccaattaaca gtcattatta tttcttttt attgaggtga ggttcactta gtatgtgaaa     19260
gtaacccctt taaagtgagc gcctccatgg catgctccag agcttacgtc atcccagaaa    19320
cctctgccca gcaagcagcc actgcacctc cattctagag cctgattcca gttgcaccca    19380
ctgcccaagg tcgggtagcc tgtggccatg agagatgagg gcggggagct gactgcccta    19440
catgtctgtc aacagctgca gcggagcctt tgtgggccaa cgatgccagg actccaatcc    19500
ttgcctcagc acccgtgta agaatgctgg aacgtgccac gttgtggacc atggtggcac     19560
tgtggattat gcctgcagct gtcccctggg tttctctggg cccctctgcc tgacacctct    19620
ggacaacgcc tgcctggcca acccctgccg caatgggggc acctgtgacc tgctcactct    19680
cacagagtac aagtgccgct gcccaccagg gtggtcaggt aagggctata ggaggttgtg    19740
aacttcacgg ttgggaccct taggcctggg cccaaggacc ctatctttgt tgacttgaca    19800
tactctggta cactaaactt tatcctctcc tggatcagag ttaagctggg atctactatc    19860
cagaaaaatc ttggggattc cttgggaact ctggtccttt tcaaccccaa actatctgat    19920
ttttggctgc cctgttccag gaccccaacc tctcactgtt tctgtgcgta aagaatgagt    19980
cctcatgtag cccgggtctt accatctcct tgtcagggtg cctcaggttt ccattgcttc    20040
tctatgtggg gtccaggaga cagctaggta caaattttag actgccattc ctactttctg    20100
tccttgagca gtcacttagt ctcttatgac ttacagtcct ctgtatgcag aaagatggcc    20160
acattctgca acagatactg agcatcatga agataacact ttagatctat ccctggttgg    20220
tacctacatg atgtccaaat ctgccctggg ttcacaggga ggccctggca acagctgacc    20280
ctcttctctg cctcccagga aaatcatgtc agcaggctga cccctgtgcc tccaacccct    20340
gtgccaatgg tggccagtgc ctgccctttg agtcttcata catctgtcgc tgcccgcctg    20400
gcttccatgg ccccacctgc aggcaagatg ttaatgagtg cagccagaac cctgggctgt    20460
gccgccatgg aggcacctgc acaatgaga tcggctccta tcgctgtgcc tgccgtgcca    20520
cccatactgg tccccactgt gaactgccct atgtgccctg cagcccctca ccctgccaga    20580
atggaggcac ctgccgtcct acaggggaca ccacccacga gtgtgcctgc ttgccaggta    20640
ggttccatct cagtatgctg gcatctagcc tggttgtcca tgtccatgcg tgttccactg    20700
tcaagcccga gggatgcaga aagagttaat accctttgaa gggagcccaa aaagaagttt    20760
agagaagggc agcagccatg gagccttagg tgtggtataa gagcaggtca ggatagggat    20820
accagaagtg aggggacact ctcagtgaca ccacacacgt ctatttctgt ctgggccatc    20880
tactgagatc cagttagttt ggtgcataac ctccaagcct tctttctgct gataagagtg    20940
ccttcccttg gtattttctt catgctgggc ctcccctgac ccatagccaa ctaataccca    21000
ccatgtcaat accctgagcc tcttagggca gggagccagc ctgcctttac agatgctcat    21060
gaactgtttg gaatccacat gtgactctct gtatgttacg ggagcaccct gtcatgggca    21120
gtccctgggg tttccccttt ctctggggat ggtaattgaa taacagggtc ttgagggcct    21180
taggggcctc acgttttca ttacttcctc tgcagtgttc ttcccactgt gctcaatgtc    21240
tctgcagggg tggggcctgc aggcacagcc ctagtccttt ctgttgctgc tctagcgatg    21300
```

```
gtaactcggt gatctaaggc agcttggagc tgccgccaac ccacttttgg caagggtggg    21360
gttggtcaac ataccaggcc gttgagagga aggaggagtg ggctcaggaa ataggaatag    21420
atttggttgc tgggggtgac ctcggaccac tccccttgca accccggggc caccctacac    21480
actgaaaaag ggaagttccc ttctgcccca agcttgcaga gccagcctca agactgcgtg    21540
cagacactgg cttatacatt tcctgaaagt cattgggcaa gctcggaggt agccgacagc    21600
tgcctacacg cttcccagcc tccctggggg ggctgggaca ggatcctcac gctcaggagg    21660
gccccagagc tgagttcagc tctgtcttgg tggccaccta agacctcagc tgttagaacc    21720
tgtgttgaga ggctagactg ggtctgtcat gcagactgag agaaagcctt gttcaaggag    21780
cttgtgaatg gagctgccac caatccacct taggcagggt ggggtgggtc aactcagagt    21840
gctggaagat gggcaggagg gaagcaagga ctgggtgggg tccctttacc ttagccggtg    21900
ggtcatccct gaagacggaa cacacactac cctgtgctgt gtggagacat gctgtttcag    21960
agtagggaga agtgaaaatt gtccacccaa attgctgttg aagggagtcc ggtctgggca    22020
cagttatacc caccatttgg gctcccaggt agctatttac caggtttcct gaagaatgta    22080
tgaactaggg tggacataaa gaactaagat gggaacagaa cttaagcctg agagctgact    22140
gggaattaaa gcgactctgg ctcctgtata tccatcctct cactctctca caagcccggt    22200
ttccctggag gaggctgtat aggcagagaa ggctttggcc aggctccaca taggacctat    22260
gatcccttct cctcgccccc agtgaaatcc ttctacacct gctcagggcc cctccaggct    22320
cgcttcttct tggaagcgtg ccctgtgcta gaataaatct ctgcacaggc agggagacaa    22380
gctatttggt cttgctgacc cctgggcggg cactaggctc caagttggtt cctccctcac    22440
ccagataagc cttttccaag cctccagctt cttgctgtgg tgcaagatgg tggggtggag    22500
gggcatcttt gaggaggagg cagacaggtg ggttctccaa gggcaggagg ggttcaaagg    22560
catccccaga gatggtgtta attagtaacc ggctgcaagt ttggctgttg ccagactcgc    22620 cttttctgggt tgatcattga cccggcagga gttgaggaga ttaatagcta actagctgct    22680
gagcaggccc tcaggaagcc acactgcagg ccacaccttg gggcccagcc acaggctaga    22740
tgggcttgta aagagagat ggttgccctg gctgtgccct gaggaaatca caggttctga    22800
ctgagcgggc ctgcctggat cccaccactc tggtttctaa cttagtgctc ccaagcccca    22860
cttttagctc cagcagtttt aggtattcgt ggctgcccca ctgattcagt gtggacaacc    22920
atagagtgca atcctctgaa actctgttag tggttttgtg gcagaacctc caaggacact    22980
atgttcctgg atccctgtct gttgagtcag ctctttacat agcgactttc tagagaagag    23040
ctgtcacctg tggacacggg agtagggatg ccacggaagg acagacagat gccttgtcca    23100
gagcagaaca ttgcaggtcc acccagaatc tgaagatacc ggagcccacc cgaggctcct    23160
cagcagactt ctgaggtcag gctaacctgc tggctggccc ctgtcccaca ggttttgctg    23220
gacagaactg tgaagaaaat gtggatgact gtccaggaaa caactgcaag aatgggggtg    23280
cctgtgtgga cggcgtgaat acctacaatt gccgctgccc accggagtgg acgggtatgt    23340
atatgggact tgtaggcagc agccttccac taacaaaact gcacaccgcg gagtggtagg    23400
aaggtctgaa ctctgttcca cgctatgaaa gcccacactg caagacccag ggtggctggt    23460
agcatggagc agcagcttct gtgcttccag ttggagtcag cacagctcag catcagatgg    23520
ttcttgtgag ctattagcag ctaacatcca gagtcaggcc ccccagcact gagccataca    23580
ggagctagca ttctgggcaa gctaccaggg atgaatacaa ggttgtcctc agccccacag    23640
cccagagcag ggagctcatc ttgtagctga ggttgatggt cctgtgaccc ctcataggtc    23700
```

```
agtactgtac agaggatgtg gacgaatgtc agctcatgcc caatgcctgc cagaatggcg  23760
gaacctgcca caacacacac ggcggctaca actgtgtgtg tgtcaatggg tggactggcg  23820
aggactgcag tgagaacatt gatgactgtg ccagtgccgc ctgtttccag ggtgccactt  23880
gccacgaccg tgtggcttcc ttctactgcg aatgtccgca tgggcgcaca ggtaagtcgg  23940
tgcaggaatg tcctgggaga agggaaactt ggttggctca ccacccctgg tggaaacacc  24000
tggggagcca tgtatgagat atatatacag atatatgtgt gtatatatat atatatatat  24060
atatcagata tagatacagc tcagatgtag atacagggct ggaaatgcag cacagttggt  24120
agagtggctg cctagcatgc acaggatact ggactcaatc cctaggacca cataaactgt  24180
gggtagtggc acgtgcctgt caagccaact cccagggaag agtgaatcca aggttaagg   24240 ccatctttag ctatatagca aacttgagtt cagcctggaa tatgtgagac cctgttttag  24300
gaaagggatg gggagagaga aagctctgtc tctttggcac ctccagcaat gacccagtaa  24360
gccttgctgg acagaggcat cctggtgatc tgaactttgt gggatgcttg agtgagtcag  24420
agagattcat tccagggtgt tgggtgagga tggccctgct gcaacaacct gttaatccca  24480
ggatagggaa aagcagcacc cactcaccgc agctgccttg tctaggtctg ctgtgccacc  24540
tcaacgatgc gtgcatcagc aacccctgca acgagggctc caactgtgac accaaccctg  24600
tcaacggcaa agccatctgc acctgccct cggggtacac agggccagcc tgcagccagg   24660
acgtggatga gtgtgctctg ggtaggtaca gatgcagtgg cacaggcagc aggaacgggc  24720
tggctgtcac atatatggga tgtgatctgt cctggagaac caccattttg atggcctggg  24780
ctggggcatt gcgggtggtc gggaggctgc aaggccagat gagccctcat ccgtgcctct  24840
ttcaccaggt gccaaccctt gtgagcacgc aggcaaatgc ctcaacacac tgggttcttt  24900
tgagtgccag tgtctacagg gctacacggg accccgctgt gagattgatg ttaatgagtg  24960
catctccaac ccatgtcaga atgatgccac ttgcctggac cagattgggg agttccaatg  25020
catatgtatg ccaggtatgt cttatgccat ttcccaccat gggggctgct aagagcaggc  25080 agcagggaa tgagtcaagg ctgcatagct tcaagtaaca tttctgtcat ggttggtagc   25140
atctgggaag ccgaggccag gataacagga caaagtggag aatgtaccca gagttgggtg  25200
catagactca gtagatatag acatgaacca cagtgggcac attaggcccg tatgagggag  25260
ggttatttct ctcccaagtc ttcagctggg gctctagaag gacctaccga agccgtcctc  25320
ggtctcacca tctcccgtcc acaggttatg aaggtgtata ctgtgaaatc aacacggatg  25380
agtgcgccag cagcccctgt ctgcacaatg ccactgcat ggacaagatc aatgagttcc   25440
aatgtcagtg ccccaaaggt gaggccacct acttaccaca ggacccgtat cctcatgatc  25500
tcttcccaga ctcctttgag ggaggacttg agttgactag ggcgttttca ggcttttcctc  25560 aaaaggtaaa ggcccacgtg agcagtggac gctgtagggg acctggcacc ggaaacccctt  25620 tactaaagga gggaaggatg ggcaggagct gcagcgctcc taagatagga gagtccacct  25680
gcttggctct gtcctcttcc tgatggtcat gggagtaagg acatagtgtg gggatctgac  25740
ctctatgcct gggaaggact tggaggaact gaagagggga ccaaagtcct gggaatctgt  25800
ctcttgccta ctccagggct ggaccaggcc ttgggccttc tgagatgtaa ataagccatc  25860
ctagacttgg tccagctagg ggagtcccat tcacagccta gtgcagctgt aaccatagca  25920
accagagtct atttaggaaa aaggcccctc tgttgggcca aggaggcagc cactgagcag  25980
tgctaaacaa ggagctgatt agaggggcag ggtgcaaggg gcaggatata agggctggtt  26040
```

```
gaagcctgga ggttagtggc ccctgttatc aaagtaccct ctagggagcc catgtgagca   26100
gacattcaac tctaaggttt gtgggtagca accaagggt taggatactg tcagatataa   26160
ccatctcgtc ttccctggcc acaggcttca acgggcacct gtgccagtat gatgtggatg   26220
agtgtgccag cacaccatgc aagaacggtg ccaagtgcct ggatgggccc aacacctata   26280
cctgcgtgtg tacagaaggt acaagaggca gtgcaagatc tgggggaggg aactcttgag   26340
gctagatagt gctgagaagg ggacaggaaa ctgggggaggc cttagtttgg ggccatataa   26400
tctgagagtc agaaacttaa ctccgcttgg actccaggca ggagtgatga aacatccct   26460 gggtatgtga tacccacat ccatcgatga ccaggcagtg atcctgggcc tgctcggtgg   26520
tttgccaagg tgtggccaac taagtgttga gggagtaact ggccctgaag ctcactaatg   26580
tccacctttc ctgccatcta ggttacacag ggacccactg cgaagtggac attgacgagt   26640
gtgaccctga cccctgccac tatggttcct gtaaggatgg tgtggccacc tttacctgcc   26700
tgtgccagcc aggctacaca ggccatcact gtgagaccaa catcaatgag tgccacagcc   26760
aaccgtgccg ccatgggggc acctgccagg accgtgacaa ctcctacctc tgcttatgcc   26820
tcaagggaac cacaggtgac tggccggagc tggcagtggg tggaaaaggg tgaggccagg   26880
cttggaagct gaccacatgt catgctgccc ctagggccca actgtgagat caacctggat   26940
gactgcgcca gcaaccctg tgactctggc acctgtctgg acaagattga tggctacgaa   27000
tgtgcctgtg aaccaggcta cacaggtgag tggctgaagg cagaggtcag ggtcatccct   27060
agagtctggg agggactgtg gggctagcca gggtccaagg gctggatgtc acaagctggg   27120
tgtcaactac ccagatcttg atctgccaac cagtagaggt atctatcata aagactgggt   27180
ggcctccata tgcctccttt cccctgtcag tgtcagccct ggccatgcca gacttaaagc   27240
cccagtagcc tgaagtgggg tggccagagc tccgaggcca ggcttttgga tatgtgttta   27300
gatctgataa aatccttagt ttctctgagc accgaggaca ttgtccacca gaggatagaa   27360
gaggatgggt ggtctcaggc tgaggtaaag ctgggctgca gagtgactca gttggtaagg   27420
tgttgaccta gcatgtgtaa accctgggtt cagtcctcct gccatgttaa ccagatgcag   27480
tggcatgcat acgttgtaac cctagcactc tgacattgga agcgagagga tcagaagttt   27540
aggtcattct cagctacatg tgagtttgtg gccagactgg atcacatgag gctcagaagc   27600
tactggcact acgtcatgt aactcatcgc tacataaggc actttactat cgctcaaagt   27660
ttcatagatt agcacaaggg gaaacttaga cccagctagg tctagctcta ggaggggtag   27720
gctctgggtg gcaggcttgg aatctgagcc ccttcccacc cacaggaagc atgtgtaacg   27780
tcaacattga cgaatgtgcg ggcagcccct gccacaacgg gggcacttgt gaggatggca   27840
tcgcgggctt cacttgccgc tgccccgagg gctaccatga ccccacgtgc ctgtccgagg   27900
tcaacgagtg caacagtaac ccctgcatcc acggagcttg ccgggatggc ctcaatgggt   27960
atggcagact gacctgggag ggactagctg tagccttggg cagacacagg ctgggtgaat   28020
gggtgctcct gtgagaccag tgatctgagg tcagccccta gtgtcttccc agcatccctg   28080
ggctgtatcc tcattggcta gcatcagctc aggatataga ctctaagcac actgtggctg   28140
ctgaaacagt tgtctgatac tgtggtgaca gcagcccttt gtcagtgtgt gggggacgag   28200
gagattacta aggtctccgt taaaactatt aaagttttat acagagggtc agcattgtca   28260
aggtggcatt gttccagtct ggaacccttg cacggtcttg gccaggtgg gtacctccag   28320 cccagtggat gatgtggcct tgtcctcaga ctggaactgt agtttagcag gagagctctg   28380
agcccaggct acagctcagg cctctccgta ggtacaagtg tgactgtgcc cctgggtgga   28440
```

```
gtggaacaaa ctgtgacatc aacaacaacg agtgtgagtc caacccttgt gtcaacggtg    28500
gcacctgcaa ggacatgacc agtggctacg tatgcacctg ccgagaaggc ttcagtggta    28560
agtgtggcgg gtgacacagc agaatgggtc ctcccttttgg tctctttctc ggtccacctg   28620
atgagctagc atttctcagg cagagatcct agttctcttg aggaaaggca tagggcagag    28680
gctctggccc acctcctctt gctcaacttc cttacaggcc ctaattgcca gaccaacatc    28740
aacgaatgtg cctccaaccc ctgcctgaac caggggacct gcattgatga tgtcgctgga    28800
tacaagtgca actgtcctct gccatataca ggtacgaaca gccagggact ggaattggct    28860
ctggtggtag ctagtggagc taagagtata tgggcttacc aggcactgaa gaaggttctg    28920
ttcctcgctg agggtcttag gtcctcagac tggaactgta gttaagcagg aaggctctga    28980
gcccaggcta cagcccaggc ctcctgggcc tgggatagt  caccagatgg gcaaacacag    29040
aggatgccta ggaggaagct ccaggccgtg tgtccgggtg tttatctggt atgtctggag    29100
tgaggtgagc actggactcc tccagagaaa gtctgggagg ctgactggta ggtactgcat    29160
ggatcagggt ccactttgcc tgtgcctctg ggggccctgg ctgccctcct ctgctggctg    29220
ggcctgggat tcctttgatg gcagcttctt tgtgtgagga gacaaggagc cctctgttag    29280
atgaacagag gcagctcctg ccatgggcac tgcctgagga atggcgagaa atagaccccc    29340
tgcaggagag atgtgcattg aacatgaaag ccgtgaccac atggcccca  accctgcagc    29400 tccaaatact gccacagagt actggtggct tcatgctgct gctgctaggt tctggacata    29460
gcaagtgggt ctgtgaaggt ggaggcccctt ccagtgttcc tatgatgcct ggcaggatgc    29520
tgttttcttt gacaaagtta aagggcctgg attttgtctc ctgtgttggt cagtgaggaa    29580
actgtcagca gccaggcaca ccccatgttc cttttggtct tgctgctatc ggggctagcg    29640
ggaggagtca agccgcgctg accagcttcc tgcttccctt tgcacaattg tcggaaactc    29700
tgtcaaagtt cctgtctgcc caggtcaccg tggaaaccga tagagagaga ggccctggag    29760
agtctcacca gtgggctggg gacatggtgg gagacaagga agataaggtt tccttgctta    29820
gctcctggag ccaaccatgg ccataaacag gaaagctaac tgggattgca aggagagtca    29880
cctgggttac tcgtggctcc cccaagcggt tatcagattt cactgcccta gtgtgaggct    29940 gcacccatg  ttccccaagt aggatatgct tggggtagcc acagtagctc tgtctcagga    30000
gtgagcctgc tgtgacctaa agcttcagaa tcagctcaag gattttcctg gaatggggag    30060
caggccaggt tcctccaggc tcaaccacct gttatagtag ggtcttgttt tgaggttttc    30120
tggttgggca aggcccaggc ttcatcgtgg agcatttggg agatgagaga tggcttccgg    30180
gactacatag atggctcatg gagaaagagt gcttgtggaa acatgaagcc tgtttcatga    30240
aaacagggta cctctaaatg cccataaccc caacatttgg gagcagagac atcttgagag    30300
ctctctggct ggccagccta gctaagatgg caaagcgtct gattcagtga gactctgtct    30360
caaaggaata gatgcggggg ttggtagagg acacctgata tccgtctctc cttctgcata    30420
cactcttaca cacctgcatg caatatacta tgctcgttaa aaaaaaaaaa aaaaagtgac    30480
ttaagagaga aacttgattc tgctttatct ctaacctcct gtcagtaatc gtcattcctc    30540
ccgggatcag agtctggctg gccaatcata cagcatctcc tatacctacc ccccgccccc    30600
ctttatggaa gaccctatgg gccaggctca ctgggttcta tcttctacaa atctttcttt    30660
ctaggagcca cgtgtgaggt ggtgttggcc ccatgtgcta ccagcccctg caaaaacagc    30720
ggggtatgca aggagtctga agactatgag agttttttcct gtgtctgtcc cacaggctgg    30780
```

```
caaggtgagg cttgcctggt cccaccaggc tgggacaagg atggtggatg ggaagtcagg   30840
ggccctggcc agcctgtggg gcagtctcga gaaaggagcc catcaatgct gagctacctg   30900
ctctgggaag ctctgggaag ctctgggagc aggagatggt ccttcccatt ccaactccat   30960
atccttctgt tgcccagagg tcaggggaga agcactggag ataaacagac cagctaggac   31020
agaggctcag agggtggggg caggtaacca aatgagtttt tgtcttcaca ggtcaaacct   31080
gcgaggttga catcaatgag tgtgtgaaaa gcccatgtcg ccatgggcc tcctgccaga    31140 acaccaatgg cagctaccgc tgcctctgcc aggccggcta tacaggtcgc aactgtgaga   31200
gtgacatcga tgactgccgc cccagtaagt ggtacccagc tctgtccatc ctatgtttcg   31260
gtgcctctgt tcctaagcac acatgacagg gagctgctga gagtctgagg tggaaaatag   31320
ccctggtgcc cggcagtcat gaaggactgt ggatagctgt gccctcagct tagtccactt   31380
gcctgtgcct taaaaagaga caggccagag gctagacagg ccaggaggag gctgttgagc   31440
atcagtgtgt gcttctcacg ggctttgctg ctagatttcc cagcccaatt gagtgatatg   31500
gagcagaggc accaggcact tcaaaatgat ggcatggggc ctagttgtat tcaaccttga   31560
cactcggccc ttgtcaggac ccattgagtt gtgtagggct ttagagatgc cctgcatcct   31620
gagtcaaagc taaaggcaga gagagattga gggaggttct gcctggcacc atcagtgtgt   31680
gtgtagggga atgggcttcc ctatgactgc cttgggcctg agggaaaaag tgtatgcgga   31740
gcagattcca ggctcagtgc tgggatgggc ccctgttgac tactgtcatc aaggcttgct   31800
gtgagcactt gccaccccat accaccttct cagcatcagg tccccgaagc atggccagtg   31860
gccacctaag gctcatcttt ctgtccctcc agacccgtgt cacaatgggg gttcctgcac   31920
cgatggcatc aacacagcct tctgcgactg cctgcccggc ttccagggtg ccttctgtga   31980
ggaggacatc aatgaatgtg ccagcaatcc ctgccaaaat ggtgccaatt gcactgactg   32040
tgtggacagc tacacatgta cctgccccgt gggcttcaat ggcatccact gcgagaacaa   32100
cacacctgac tgtactgaga ggtgggtccc agcctcagct gagacaggga agaaatggaa   32160
ctgtggaaga cacaaagtct tgacagcatg gcatctcaag ctggtgtctt gcccagaccc   32220
agtgggcata cagcactaat tgaactgaat ccagcgttgt tcattatgtt gcagtatccc   32280
tcctaaaggg gcctttgtga cctccagtga cttagaacaa ggaagtttgt gcagaggaat   32340
tgggaaacta gcctcctatc aaacaagagc tttgtaatct gtcttagttc ccctttttgcc  32400 ctggttgcca ggaagcttag agttaaatca atctcaagcc tggtttgtga tgcgcttcct   32460
atagtgttcc tattttgccc ttgatttgt ttttctcaac caccacgtgt ctatatgcta    32520
taaaatctct gctcgtgatt tgggtattgt ggccaggtag gcatggagtt gtctctcctg   32580
gcaaggacct tagggaactc ctcactcttc cctgcttctc atctgcctct agctcctgct   32640
tcaatggtgg tacctgtgtg gatggtatca actccttcac ctgtctgtgt ccacctggct   32700
tcacgggcag ctactgtcag tatgatgtca atgagtgtga ttcacggccc tgtctgcacg   32760
gtggtacctg ccaagacagc tatggtactt ataagtgtac ctgcccacag ggctacactg   32820
gtctcaactg ccaggtgagc tgaggttaca gggtatgacc cagaaggcct agggctctcc   32880
agtgcccatt gcccagccct gggccacact accttcagag ggccagggac acagaagcag   32940
agaggctccc tggtgtcatc attggttgat gagccagaat gaacccacat cctctgggaa   33000
aatgccaagt tgggtgcttc tgagggagac aggtgggcat gggtgccagc caggctcttc   33060
tgtggagtgc attatgtggc catctgtctg aagcagcctg gggcagtgct cacttctggt   33120
ggaggatgtc caaggggagg tagccagtgg gttgtggaga gccttgaaag agagcaagga   33180
```

```
agacgtggag cccaggccta tgttgttcgg agggcgggca gtgtttgtga gtcctgtgcc   33240
tgggatttct taggtgatat tctttctgag atggtggggg tggggtggg gaagtcagag     33300 cataaaatgc cttattccag tggcgctcag cctgtgggtc atgacccaa tagggtcat     33360 atatcagata tcctgcatat ttttgctaca tgacagtagc aaaattacag ttatgaagaa   33420
gcaatgaaat aattttatgg ttggaggtca ccacaacacg aggaactata ttaaaagact   33480
gcagcattag gaaggctgag aactgctgtg cttctcagag ccagccagga ccagggcagg   33540
agggtgccct agcagtcaga gttggtcagg gagaagctaa ccagcgcctg tctcctcaga   33600
accttgtgcg ctggtgcgac tcggctccct gcaagaatgg tggcaggtgc tggcagacca   33660
acacgcagta ccactgtgag tgccgcagcg gctggactgg cgtcaactgc gacgtgctca   33720
gtgtgtcctg tgaggtggct gcacagaagc gaggtaacca accggccggg cccacctgtc   33780
cttgctcagg ctcagcttag gccaggagtg ccccggtgcc tgccaggtca ggtgacaatg   33840
ggcagtagtc ccgagagctc agcccaggcc tcagctcctt cccgtcttgt ccccacaggc   33900
attgacgtca ctctcctgtg ccagcatgga gggctctgtg tggatgaggg agataaacat   33960
tactgccact gccaggcagg ctacacgggc agctactgtg aggacgaggt ggacgagtgc   34020
tcacctaacc cctgccagaa tggagctacc tgcactgact atctcggcgg cttttcctgc   34080
aaggtgtggg ccgtcatggg gtggcgggga gggtatcagc gtgagtgttg ctgcagggga   34140
gggcttttga ctgggagcta gtgcatcatg gcagactgag cacatacctg tgcaggatcc   34200
ggtcacatta cagatgtgct gaaggaggag aactatgcca agcagtggct tagggcaccc   34260 cttttcctata tggtttcatg gtacctaata cctgctccaa gacctcatcc ctggggacc    34320 aggtgttgcc ccacacacac acaccttgga cacttatttt aacttactgg ggtctactgg   34380
gtggagccct cgctgcaggg tgggacagtg tagtctaact gggtatatgg cctgcatggc   34440
aagtggagga catgatacca caaccccagc taagctgtga cctgtgccat ttctacagtg   34500
tgtggctggc taccatgggt ctaactgctc cgaggagatc aacgagtgcc tgtcccagcc   34560
ctgccagaat gggggtacct gcattgatct gaccaactcc tacaagtgtt cctgcccccg   34620
ggggacacag ggtaagggta gggacctgga tgatgggcag gatccagcca gagatcactc   34680
aggtgattga gagctgacca cggaatagga atctcagaag ggaggtgggc tccagtggca   34740
ctgtgctgcc tcccccgggc cccaggtcct aactgatttc tggactgggc tgcacaggac   34800
agagcacagt cagcatcatc cgacggtgtc tctggtcact ctgcaggtgt acactgtgag   34860
atcaatgttg atgactgcca tccccccctt gaccctgcct cccgaagccc caagtgcttc   34920
aacaatggca cctgtgtgga ccaggtgggt ggctatacct gcacctgccc accaggcttc   34980 gtcgggagc ggtgtgaggg tgatgtcaat gaatgtctct ccaaccctg tgacccacgt    35040 ggcacccaga actgtgtgca gcgtgttaat gacttccact gcgagtgccg ggctggccac   35100
actggtgcgt gccttgggca ggtggtcga acgggtgggt gggcagggtc aacagggatg    35160
gctccttact gtcccttctt cacacaggac gccgctgtga gtcagtcatc aatggctgca   35220
ggggcaaacc ttgcaagaat gggggtgtct gtgccgtggc ctccaacacc gcccgtggat   35280
tcatctgtag gtgccctgcg gtaggtgtcc ctggccctgt gcggctgcaa gggtgccagg   35340
tctgagggtg cctgaaccct gaccgactct tatggtggat ctgtcctcca cccaccctca   35400
ctgtgaatag tcagcctgaa gacctctagc agaggctagg gtccaagcca catgcttcct   35460
cgtgtccatt ccccagctcg tttataaaac ccgagcgggc acgatccata catgccttgc   35520
```

| | |
|---|---|
| tcccagtgct ctgcagcctc aggctgaaag attgccttgt atttgaggta ccttaggctt | 35580 |
| cacaacaaga ccctgtttaa aaagtttatt tcctgctgtg ctatgttggg aacctcacac | 35640 |
| atgctgggca agtgttttgc cactgtgtct tagcccaatt ttttaaatag atgtttattt | 35700 |
| tagagcggtt ttaggtttgc atgagaactt agcaagaggg ccaggtcccc accctgcagg | 35760 |
| ccgttcccta tgtttgctgc cttgcgtgga aggtgttgag ctggcactaa tatgcagtat | 35820 |
| ttgctcttgg gtgttgacat ccagggatct gtacacatac aatgtaccag catcagcctt | 35880 |
| gggtttcatg gctctaaaaa ctcctagggt tctccccatt cacctatccc tccagtttga | 35940 |
| agcccttggc aaccctgacc atcctatggt gagatgtttc aagggtcttg ttattgggc | 36000 |
| aaggccatag acacctttca caggccacag actggggcca ggtctttgct ggggtgtgca | 36060 |
| tggtgtccct gattgaatgc accatcctct ctccaccaca gggcttcgag ggtgccacat | 36120 |
| gtgagaatga tgcccgcact tgtggcagct tacgctgcct caacggtggt acatgcatct | 36180 |
| cgggcccacg tagtcccacc tgcctatgcc tgggatcctt caccggccct gagtgccagt | 36240 |
| tcccagccag cagcccctgt gtgggtagca accctgcta caatcagggc acctgtgagc | 36300 |
| ccacatccga gaacctttc taccgctgtc tatgccctgc caaattcaac gggctactgt | 36360 |
| gccacatcct ggactacagc ttcacaggtg gcgctgggcg cgacattccc ccaccgcaga | 36420 |
| ttgaggaggc ctgtgagctg cctgagtgcc aggtggatgc aggcaataag gtctgcaacc | 36480 |
| tgcagtgtaa taatcacgca tgtggctggg atggtggcga ctgctccctc aacttcaatg | 36540 |
| acccctggaa gaactgcacg cagtctctac agtgctggaa gtattttagc gacggccact | 36600 |
| gtgacagcca gtgcaactcg gccggctgcc tctttgatgg cttcgactgc cagctcaccg | 36660 |
| agggacagtg caagtaagta aggctgagtt tctttagagt cccagggctc aggatgctac | 36720 |
| gggaggacct aaccaaacac caggctcctg aagccaatgt ctatccctgc ccattgcgag | 36780 |
| tcgccaagca catttcccag atctggccta ttcaaggtat gggtttgagg tccacaggct | 36840 |
| gggatgggac tgagtgcatc ctataccctcc tcagccccct gtatgaccag tactgcaagg | 36900 |
| accacttcag tgatggccac tgcgaccagg gctgtaacag tgccgaatgt gagtgggatg | 36960 |
| gcctagactg tgctgagcat gtaccccgagc ggctggcagc cggcaccctg gtgctggtgg | 37020 |
| tgctgcttcc acccgaccag ctacggaaca actccttcca ctttctgcgg gagctcagcc | 37080 |
| acgtgctgca caccaacgtg gtcttcaagc gtgatgcgca aggccagcag atgatcttcc | 37140 |
| cgtactatgg ccacgaggaa gagctgcgca agcacccaat caagcgctct acagtgggtt | 37200 |
| gggccacctc ttcactgctt cctggtacca gtggtgggcg ccagcgcagg gagctggacc | 37260 |
| ccatggacat ccgtgggtga gtgctccagc tcctgctgtt gtgggctgtt tcccagtgtg | 37320 |
| tccctgggtt ctctaaccag cttaaccctg gaggtgtaac ctcaggggag gtagtattca | 37380 |
| ccttatttta tagtcagaaa gcacctggga tgaagagggc atccctctga tgaggacttg | 37440 |
| gcaggcctca gggtttgccc agatgtgatt ttcaggcccc actgtgtacc aggtgttgga | 37500 |
| gaccaagctg attaaagcct ccagggtgtc ccctgggggct aagtcatcct agaccaatcc | 37560 |
| tgaccctcag tcactacagc ccttatccct actacagagg aggcagtgag gggtacagaa | 37620 |
| gggcactgtt gctgagcctg gaaggctgag gagccgaggg aggcacaaat aagagcatct | 37680 |
| cctggatgct gcacagagcc atctggggat gggcagggaa gcaccagcca ggcatttgga | 37740 |
| ggttccagga gccttcgctg ttgggcatct gcctggtggc acctcagtgt ctcctgaccc | 37800 |
| cagtggttcc tggtcctggt tttcttgtcg tgggactgtg gtgaaggtca gaaattaatt | 37860 |
| gtttcctgga ggctgttaga atcctgtttc tgagaggcca gtgactgaga gttggtgact | 37920 |

```
tggctggcat gagagagctg actctctggc atctgagcct gctgtcacct caagctacac    37980 cataggagt  cacaactgca tccttgcagt tctgtggggc cccaggcact gctctcaaga    38040
gggcattgga tgcctaaaga ctattctttg aagtaaggaa aagggtgct  gtgcacctaa    38100 ggggcaaggc tagacagtgg aatgacccc  gctgagtgct aaacactggg gcagcaggga    38160
gagtgtccca ttgcggggct gtcgtctgat aagccctgtg ggtcagggtg atgggctagg    38220
gagtcagagc tggtgtgtag gcagtgtact ggggtgtatc taatctcact gtgccatgtg    38280
tgttctcagc tccattgtct acctggagat cgacaaccgg caatgtgtgc agtcatcctc    38340
gcagtgcttc cagagtgcca ccgatgtggc tgccttccta ggtgctcttg cgtcacttgg    38400
cagcctcaat attccttaca agattgaggc cgtgaagagt gagtaatcag gggctggagg    38460
gatggctcgg tggttaagag cactggctgc tcttgcagag acaagggtt  caaatcccag    38520 cacccacgca gcatcttata actatgtgtt actctaattc cagggcatcc aacactttct    38580
gacctctgca ggcaccaggc atgcacaggg tcctgacgta catgcaggca aaacacccat    38640
acacattaca tatttttaa  atgagttccc taccccgacc agccctgcct cttcagggat    38700
gggttcattg ggtggcgggt cacaggcagg cggtctctca ctccttgtgc cagctgccat    38760
tcccagctca ggaagtgctt ttctggaatt ttttccaag  gccttccctc cctgtggcta    38820
gtgggagccg taagtaaaag ctgtcccta  agatgtatac atataccaga agtatggag    38880 gagtctttct tctctcctca ttctttaccc ctgattttc  tttgttggat attatttcaa    38940
aatcattact agagttttttt tgtgtgtgtt atttttttta agagagagag agaattgatc    39000
ggtgtcatgt gaagtgttga agtttgtatc ttgaaaatcc ccctaaatcc tttgtcttaa    39060
cagctcaatg cgagcgcagt gatttgaagt tcgctaatcc tccttctcga aggggagaa    39120 gtgagcactg tctccagaca gatcagctgg tgcaggagag aatttagcga tagtttgcaa    39180
ttctgattaa tcacgtagaa aatgacctta ttttggggg  tgggatggag gagagtgggt    39240
gaggaggcac cggccgtgga gccagtcctc cgcccccgc  cagcccacag catcaccacg    39300
cctgacgagg ggtgcttgcc tgccgcccct gcccgcaggt gagccggtgg agcctccgct    39360
gccctcgcag ctgcacctca tgtacgtggc agcggccgc  ttcgtgctcc tgttctttgt    39420
gggctgtggg gtgctgctgt cccgcaagcg ccggcggcag catggccagc tctggttccc    39480
tgagggtttc aaagtgtcag aggccagcaa gaagaagcgg agagagcccc tcggcgagga    39540
ctcagtcggc ctcaagtgag tggacactgc tcccactgtg tgtgggtgag tgagtggcag    39600
ggttggtggg ggtgcttagc tccagaaggc ccatgggccc atccatccct gtccgttacc    39660 ctaagcccctt ctgcatgtag aggatgccca tatgagctgt ggcttcaggg catctcctgg    39720
agtacctgct cagtctccct accccatac  ccaggcccct gaagaatgcc tcagatggt     39780 ctctgatgga cgacaatcag aacgagtggg gagacgaaga cctggagacc aagaagttcc    39840
gggtgagtcc cgcaggctcc caagccccc  ctggtggca  cctcctgcct tggcccaag     39900 tgatgaggct ctgcttactc tgtccacact cagtttgagg agccagtagt tctccctgac    39960
ctgagtgatc agactgacca caggcagtgg acccagcagc acctggacgc tgctgacctg    40020
cgcatgtctg ccatggcccc aacaccgcct caggggagg  tggatgctga ctgcatggat    40080
gtcaatgttc gaggaccagg taaggccact ggagacacat gcacacattc cctagcatag    40140
acttaagagg ccagtaggac ttgaggaggg ctgggtcact gaagggctct gccagagcag    40200
catcctgccc tgagctgatc gtctggctcc tcctgcccac acagtatact ttttcatgaa    40260
```

| | |
|---|---|
| atgctgcttt gcaatagtca aagtgttaat ttttttttt tttttggtc tcagttttta | 40320 |
| gtatgctggg attataggtg tgtccccatg cccagctaaa gtgttgactt ttaaaattat | 40380 |
| atgcatatag gtgtatataa agatatcttt tattttatgt gcatggttct gcctacatat | 40440 |
| atgtctgtgt agtgtttaga tacccagtgc ctgtggggag cctgaagagg ccattggatc | 40500 |
| ccctgaagct gcagttacag atggtagtga gcagctatat gggtactagg gattgaactc | 40560 |
| aggtcctctg gaagagaagc cagtgctctt aaccactgag ccatctctgc agcccttatt | 40620 |
| ttatgtttta aagcatttct tcatttgagt gtaaggggca cacatgtgcc atagtacaca | 40680 |
| cgtggaggtc agaggactac ttgtatgagt gtgggttctc tccttctacc atgttggtcc | 40740 |
| cagagtgcct tccagggagg cagcactgca tccctgggga cttcatccgg ggtcccttaa | 40800 |
| actgcaggac tgcctgccag ggctatggtt gaatgttgac cctccctgag ctgacacca | 40860 |
| tccttcccac acctacccctt gtttctgtcc tctctgcaga tggcttcaca cccctcatga | 40920 |
| ttgcctcctg cagtggaggg ggccttgaga caggcaacag tgaagaagaa gaagatgcac | 40980 |
| ctgctgtcat ctctgacttc atctaccagg gcgccagctt gcacaaccag acagaccgca | 41040 |
| ccggggagac cgccttgcac ttggctgccc gatactctcg ttcagatgct gcaaagcgct | 41100 |
| tgctggaggc cagtgcagat gccaacatcc aggacaacat gggccgtact ccgttacatg | 41160 |
| cagcagtttc tgcagatgct cagggtgtct tccaggtacg cagcactgca tccttggagc | 41220 |
| cagtgacctc atcaggtctg actggcatgg accctgcaat ctctaattcc aagtgtgact | 41280 |
| gggcagggaa acttggcacc tccacactgc attttgaagg aagtccaggt acaaagggca | 41340 |
| tcaagtccca cctgtgttct ctgagcaggc tggctgaagg tggtcttgcg gaacctacaa | 41400 |
| cggtgaggca gggcctcctt actctcagta aaaccctccc aatctcaagg ctatggcctt | 41460 |
| gacttgaggt ctccacctcc gtgctaaaac ctttgcagac taaccctacc ccattcagct | 41520 |
| gtggctgcag gcatagccca tggcggcaga aagagagctt tagaggctgc tggtcctggc | 41580 |
| ctgcaaagct atctcctggc tttgcctaga agcctggagc cagcctgggt ggatttaagg | 41640 |
| atttagctgc ctgggtctgc agggaccaac cctagtagtt gctcctgcat gttgccagcc | 41700 |
| agtgacccct gctaccagac ctgtcctcta ggcggccctg gagcaaactc caatggggaa | 41760 |
| tagaccaggc atcaaaaagc ttgtcattta atcatttctt aacttgaacc acactttgtc | 41820 |
| ggtctgtaga agaaattaaa caagacaggg caatgtacac ctttatccc agcactctag | 41880 |
| aatctgagag gattgtgagc atgaggctag cctggtcttc atagaaagac cctatttcaa | 41940 |
| aatagcaaag agaggttgag accagccaca ggttatgttg actgcctggt gtacagctct | 42000 |
| ccacatggcc tgccttgctt gcatagacag atgtgtgtac gttttgtagg aatccaggca | 42060 |
| gtgctgtgaa tccttaccca ggtcaccaac ccactccctc ctctcacctt aacagttcca | 42120 |
| agtacggcta tgggccatga gcgggattcc tagcctggtt actctcccct ctctcccca | 42180 |
| tgctatgcag tttgatttcc tcaacctgga ggtagttctg gcaaccataa ccaaaagatg | 42240 |
| aggtcccagt agatccccca ctgtcactag ggactgggta agagcccag ctcttgcaca | 42300 |
| tggaatgtag ctcctgcctt cctcagggc tcagctgagc ccagtccagg cattggtttc | 42360 |
| tggagataca ggcttgcatt tagatcaccc tgcctgaacc catccctgcc ttccagatcc | 42420 |
| tgctccggaa cagggccaca gatctggatg cccgaatgca tgatggcaca actccactga | 42480 |
| tcctggctgc gcgcctggcc gtggagggca tgctggagga cctcatcaac tcacatgctg | 42540 |
| acgtcaatgc cgtggatgac ctaggtaggc ccgagctaca gcccagctac cgaggacatc | 42600 |
| agccagtgcc tggtctgctc agccccaacc cactctctcc tctctttgct tccttccag | 42660 |

```
gcaagtcggc tttgcattgg gcggccgcgg tgaacaatgt ggatgctgct gttgtgctcc    42720
tgaagaacgg agccaacaag gacatgcaga acaacaaggt aagcagacgg gctgcttaac    42780
cgcaggcgca tgatggggac tccggggcac ccatacgttg accacttaga ggtttaagag    42840
tgtctgggac aacagcagcc taaaataacc cgtgctcttg ctggagagga gctgaggcgt    42900
aagcagctgt cccatgtcac ggttacttga gccttgcctt ctgtcccctt ctgtccctgg    42960
tggctgtggt gaccctaggg gttcaggatt ggcaagggg cagggatggg gtggccctgt     43020
ctcttaaggc ctgcaaggct tctggcttgg tccaccacta ccatgctccc tcctttggga    43080
taagaaaact gctgagctgg gctgcgtgtc tccacctcgc ctcccagtgt ctctgtttgt    43140
gcagggctag ttgcttcatc aggactctgc ttagttgctc acagggcaga gtttgtgcct    43200
cccttaccag ctccactgca ggctgggaaa tggagcagga gtcaggtacc tggagttgct    43260
gttgggcaca ggttctccac agtccagggt gggccagtgg ttatagagaa tccaagcctg    43320
atagacattc tgttgtggtg tatgattatg tctgctggac agagcagacc tggaaggagc    43380
tgagatgccc tagccactgg tgacccttg gcatggtagt accttcccca tggccattca     43440
cttgccttaa aggtccctga gtcccaggat tgcagtactt gtgcctgcat tttggggagg    43500
aaagcaaagg gcacacagtt acattctgtt ttcggcagtc tgactccaca caggggaaga    43560
agccctatgt atttatccca cagatctctg ggtgtgagg tgttaaatct aggttctcta     43620 aaaaagaac tcgggaccag ccatgtgtgc gtgctagcac cgagaagctg aggcaggacg     43680
atactgagtt ccaagtacgg ctgtgggccc tgagtgagat tcctagcaac ataggaaggc    43740
cccactataa atactctctg agcctggtgg tctaggatgc ttgggtctag atagatctct    43800
ccagataaga gaagagaaag aggcagcacc tgcttcccta gccctcccc ccaggccatc     43860 catcatcaat gactcagcaa attctacacc tgcccgctcc ctcatgtacc tcctgtccgt    43920
gtcctacagg aggagactcc cctgttcctg gccgcccgtg agggcagcta tgagactgcc    43980
aaagtgttgc tggaccactt tgccaaccgg gacatcacgg atcacatgga ccgattgccg    44040
cgggacatcg cacaggagcg tatgcaccac gatatcgtgc ggcttttgga tgagtacaac    44100
ctggtgcgca gcccacagct gcatggcact gccctgggtg gcacacccac tctgtctccc    44160
acactctgct cgcccaatgg ctacctgggc aatctcaagt ctgccacaca gggcaagaag    44220
gcccgcaagc ccagcaccaa agggctggct tgtggtagca aggaagctaa ggaccctcaag   44280 gcacggagga agaagtccca ggatggcaag ggctgcctgt tggacagctc gagcatgctg    44340
tcgcctgtgg actccctcga gtcaccccat ggctacttgt cagatgtggc ctcgccaccc    44400
ctcctcccct ccccattcca gcagtctcca tccatgcctc tcagccacct gctggtatg    44460 cctgacactc acctgggcat cagccacttg aatgtgcag ccaagcctga gatgcagca     44520 ctggctggag gtagccggtt ggcctttgag ccaccccgc cacgcctctc ccacctgcct    44580
gtagcctcca gtgccagcac agtgctgagt accaatggca cggggctat gaatttcacc    44640 gtgggtgcac cggcaagctt gaatggccag tgtgagtggc ttccccggct ccagaatggc    44700
atggtgccca gccagtacaa cccactacgg ccgggtgtga cgccgggcac actgagcaca    44760
caggcagctg gcctccagca tagcatgatg gggccactac acagcagcct ctccaccaat    44820
accttgtccc cgattattta ccagggcctg cccaacacac ggctggcaac acagcctcac    44880
ctggtgcaga cccagcaggt gcagccacag aacttacagc tccagcctca gaacctgcag    44940
ccaccatcac agccacacct cagtgtgagc tcggcagcca atgggcacct gggccggagc    45000
```

```
ttcttgagtg gggagcccag tcaggcagat gtacaaccgc tgggcccccag cagtctgcct    45060
gtgcacacca ttctgcccca ggaaagccag gccctgccca catcactgcc atcctccatg    45120
gtcccaccca tgaccactac ccagttcctg acccctcctt cccagcacag ttactcctcc    45180
tcccctgtgg acaacacccc cagccaccag ctgcaggtgc cagagcaccc cttcctcacc    45240
ccatcccctg agtcccctga ccagtggtcc agctcctccc cgcattccaa catctctgat    45300
tggtccgagg gcatctccag cccgcccacc accatgccgt cccagatcac ccacattcca    45360
gaggcattta aataaacaga gatgtgggat gcaggacccc agcttccgtt cccaagccct    45420
gttgggagtc ctttccagtg cttcaggatg ctggggcgac caaggagcc ttttaaaaaa     45480
tgttttttata caaaataaga ggacaagaat ttccattttt ttttttagta tttatttatg   45540
tacttttatt ttccacagaa acactgcctt tttatttata tgtattgttt tctatggcac    45600
tagggaaaaa catatctgtt ccaagaaaat aaactagttc tcagagcctt gattttcctg    45660
gtcagggtga agttccctgt gtgtctgtaa aatatgaaca aggattcatg atttgtaaat    45720
gctgtttatt tattgattgc ttcttttccaa aatcgaaaag aaagaaaaaa gaacgtgaca    45780
ggagaaggga agctggaaac tgccatggcc agaattgccc ctccccccaca ctcactgccc   45840
ctcccccccag cgtcacctgg gatttgcaga tgtgtttaga aacacgccca gaccttgaac   45900
cttgggttca tggattagtt ttgtatctaa aacaggaaac aagtcagatg atgtggtttg    45960
tacactttct gtaaccacca gtgtggactt gaagaagtgt cctcagcatg tgcagagtct    46020
actaccccagt accagtcgtg agtctgcagg ctccagtgtt ctgtagtagt gtttatgggc   46080
cttgggagta cttctcccct gccctgcccc actgtcccct tcctgacaac ttgagccagt    46140
aagccatgca gggtgtggtg cctcctagag aaaacactgc ctggactgtt ctgtgcatcc    46200
ctccaaacag catcatccaa atccaactga ggacagacgg actgtcccgg cctgggcctg    46260
ggctcctaac acctgactgc caaagggctc caatgtgcat tgtggactcg ccagagtagc    46320
ctgcattgag actccaagaa aacagaagct atgtggcctc tgatccccaa actgcctggg    46380
gtggggacat gccttgagtg tgctggaatg tgggtggagc ctgcttctgg gccaccctc     46440
ctggttcagg gctgtgctca cagcagattc ttgcagtatc aagtatacgc ctgtggcaga    46500
ataagtatct gtaaatacat gtttaaagat ggattttgtt taaaaaatct aaaggaacaa    46560
gtgtgtcgtg tgtcaagctg atgaggactg tcagactgtg gcttagctca gtgtgaccca    46620
gaccttgtga cctgtagctg ccgaaccagt agctcctaag agcacaaccc aggatggccc    46680
atctgctgcc caccaagtcc ctttccagcc actgtgtgct gggggctttc ggggcagtt     46740
gcccacctcc tcagggcagc tctttctggc cttttggggg gcagtgtctg tgccatgcct    46800
aatagatatg accagacgca tcctaagatg ttgattctta ctgtgttgta taaaataaag    46860
tgtagtttac aaaaaaaga aacgtaaaaa aaaaaacta catgcaaaac tgtaggtaat      46920
gaaaatgatg tatttttttc atcttttttt gttaactaat ttgcaataaa aatgatactg    46980
atggttgtcc acattttgct aaacttggag tgtggtttgg ttcactttt ggggagtgtg     47040
acagagaaag ggccacccag cactgaaata accaaatcca aaccctctct tacacagaaa    47100
tacagaggtt gccataagga cacaccattt tcagaagctg cacagcgcag ggcatcaagg    47160
tgggaagaca gtttccaaaa gagttgatgc agtcctctca gggatgtgga tctgattgat    47220
gccagctgta ttcctgtgag cagcagagga gtgaaggcac cttatgttgt catagatgac    47280
tatcctctga gcccagtaac ccccaacctc ttcaaattca gccatgcctt gcaaaaggtc    47340
atcccagctg tgcttgttga ctgcttatag acccctcaa agagttggga aggtcatggg     47400
```

```
actcaaagga cccttgcctg atgatccagt cactttgttg tatgcagtcc tgccctaatt    47460
gtgcatgacc tcagggaggt actagagtat atagtctggg aagactagtg gagagactcc    47520
atctatgtgg ctgtgaggaa agccttatcc ctgctgggta aatgttgtat taatattcat    47580
ttaataaagg ctgggcgtgg tggcacacgc ctttaatcct agcactcagg aggcagaggc    47640
aggtggattt atgagttcga ggccagcctg gtctacagag tgagttccag gacagccagg    47700
gctatacaga gaaaccctgt ctcgaaaaac caaaaaaaaa aaaaaaaaaa aaaaaaaaa     47760 aattcattta ataaatcctg gcagcaggtc actatccaac tcaatggttt atgaaagaca    47820 cacaacctt ctttatattt tattatgtct tattcagcac aatagctggg tagctgccta     47880
gcctccatat tgctaagact ctgtctcccc attctgaatt cctgcttact aattctatgt    47940
tctatcgtgg ctgatctaga ccaagttggg cagccttcta ggccatgctc tcccagctcc    48000
t                                                                    48001

<210> SEQ ID NO 4
<211> LENGTH: 9497
<212> TYPE: DNA
<213> ORGANISM: Mus musculus

<400> SEQUENCE: 4
tagtgcctct gccgcgggag ggagcgcagg ggcgtggggc gcagggcgcg ggcgctgggc      60
gcgggtgcga gcgcagtgaa ggaacgagcc cgggtgcctt gtagggccca gcgccgctga    120
gagcccagcg ccgcccaccc gccaggaaag agggcatcag agggtggacg cctgcgggac    180
cgccggtggt gtgcgtcaac gtccgatccc cgccggccac cccaagaggc cgccgcccgg    240
gctgcgggca gctggcgagc aggcatgcca cggctcctga cgcccttgct ctgcctaacg    300
ctgctgcccg cgctcgccgc aagaggcttg agatgctccc agccaagtgg gacctgcctg    360
aatggaggga ggtgcgaagt ggccaacggc actgaagcct gtgtctgcag cggagccttt    420
gtgggccaac gatgccagga ctccaatcct tgcctcagca caccgtgtaa gaatgctgga    480
acgtgccacg ttgtggacca tggtggcact gtggattatg cctgcagctg tccctgggt    540 ttctctgggc ccctctgcct gacacctctg acaacgcct gctgccaa cccctgccgc    600 aatgggggca cctgtgacct gctcactctc acagagtaca agtgccgctg cccaccaggg    660
tggtcaggaa aatcatgtca gcaggctgac ccctgtgcct ccaacccctg tccaatggt    720 ggccagtgcc tgccctttga gtcttcatac atctgtcgct gccgcctgg cttccatggc    780 cccacctgca ggcaagatgt taatgagtgc agccagaacc ctgggctgtg ccgccatgga    840
ggcacctgcc acaatgagat cggctcctat cgctgtgcct gcgtgccac ccatactggt    900 ccccactgtg aactgcccta tgtgccctgc agcccctcac cctgccagaa tggaggcacc    960
tgccgtccta caggggacac cacccacgag tgtgcctgct gccaggttt tgctggacag   1020 aactgtgaag aaaatgtgga tgactgtcca ggaaacaact gcaagaatgg ggtgcctgt   1080 gtggacggcg tgaataccta caattgccgc tgcccaccgg agtggacggg tcagtactgt   1140
acagaggatg tggacgaatg tcagctcatg cccaatgcct gccagaatgg cggaacctgc   1200
cacaacacac acggcggcta aactgtgtg tgtgtcaatg ggtggactgg cgaggactgc   1260
agtgagaaca ttgatgactg tgccagtgcc gcctgtttcc agggtgccac ttgccacgac   1320
cgtgtggctt ccttctactg cgaatgtccg catgggcgca caggtctgct gtgccacctc   1380
aacgatgcgt gcatcagcaa cccctgcaac gagggctcca actgtgacac caaccctgtc   1440
```

```
aacggcaaag ccatctgcac ctgcccctcg gggtacacag ggccagcctg cagccaggac   1500
gtggatgagt gtgctctggg tgccaaccct tgtgagcacg caggcaaatg cctcaacaca   1560
ctgggttctt ttgagtgcca gtgtctacag ggctacacgg gaccccgctg tgagattgat   1620
gttaatgagt gcatctccaa cccatgtcag aatgatgcca cttgcctgga ccagattggg   1680
gagttccaat gcatatgtat gccaggttat gaaggtgtat actgtgaaat caacacggat   1740
gagtgcgcca gcagcccctg tctgcacaat ggccactgca tggacaagat caatgagttc   1800
caatgtcagt gccccaaagg cttcaacggg cacctgtgcc agtatgatgt ggatgagtgt   1860
gccagcacac catgcaagaa cggtgccaag tgcctggatg ggcccaacac ctatacctgc   1920
gtgtgtacag aaggttacac agggacccac tgcgaagtgg acattgacga gtgtgaccct   1980
gaccctgcc actatggttc ctgtaaggat ggtgtggcca cctttacctg cctgtgccag   2040
ccaggctaca caggccatca ctgtgagacc aacatcaatg agtgccacag ccaaccgtgc   2100
cgccatgggg gcacctgcca ggaccgtgac aactcctacc tctgcttatg cctcaaggga   2160
accacagggc ccaactgtga gatcaacctg gatgactgcg ccagcaaccc ctgtgactct   2220
ggcacctgtc tggacaagat tgatggctac gaatgtgcct gtgaaccagg ctacacagga   2280
agcatgtgta acgtcaacat tgacgaatgt gcgggcagcc cctgccacaa cgggggcact   2340
tgtgaggatg gcatcgcggg cttcacttgc cgctgccccg agggctacca tgacccacg    2400
tgcctgtccg aggtcaacga gtgcaacagt aacccctgca tccacggagc ttgccgggat   2460
ggcctcaatg ggtacaagtg tgactgtgcc cctgggtgga gtggaacaaa ctgtgacatc   2520
aacaacaacg agtgtgagtc caaccttgt gtcaacggtg gcacctgcaa ggacatgacc   2580
agtggctacg tatgcacctg ccgagaaggc ttcagtggcc ctaattgcca gaccaacatc   2640
aacgaatgtg cctccaaccc ctgcctgaac caggggacct gcattgatga gtcgctgga    2700
tacaagtgca actgtcctct gccatataca ggagccacgt gtgaggtggt gttggcccca   2760
tgtgctacca gccctgcaa aaacagcggg gtatgcaagg agtctgaaga ctatgagagt    2820
ttttcctgtg tctgtcccac aggctggcaa ggtcaaacct gcgaggttga catcaatgag   2880
tgtgtgaaaa gccatgtcg ccatggggcc tcctgccaga acaccaatgg cagctaccgc    2940
tgcctctgcc aggccggcta tacaggtcgc aactgtgaga gtgacatcga tgactgccgc   3000
cccaacccgt gtcacaatgg gggttcctgc accgatggca tcaacacagc cttctgcgac   3060
tgcctgcccg gcttccaggg tgccttctgt gaggaggaca tcaatgaatg tgccagcaat   3120
ccctgccaaa atggtgccaa ttgcactgac tgtgtggaca gctacacatg tacctgcccc   3180
gtgggcttca atggcatcca ctgcgagaac aacacacctg actgtactga gagctcctgc   3240
ttcaatggtg gtacctgtgt ggatggtatc aactccttca cctgtctgtg tccacctggc   3300
ttcacgggca gctactgtca gtatgatgtc aatgagtgtg attcacggcc ctgtctgcac   3360
ggtggtacct gccaagacag ctatggtact tataagtgta cctgcccaca gggctacact   3420
ggtctcaact gccagaacct tgtgcgctgg tgcgactcgg ctccctgcaa gaatggtggc   3480
aggtgctggc agaccaacac gcagtaccac tgtgagtgcc gcagcggctg gactggcgtc   3540
aactgcgacg tgctcagtgt gtcctgtgag gtggctgcac agaagcgagg cattgacgtc   3600
actctcctgt gccagcatgg agggctctgt gtggatgagg gagataaaca ttactgccac   3660
tgccaggcag gctacacggg cagctactgt gaggacgagg tggacgagtg ctcacctaac   3720
ccctgccaga atggagctac ctgcactgac tatctcggcg gcttttcctg caagtgtgtg   3780
gctggctacc atgggtctaa ctgctccgag gagatcaacg agtgcctgtc ccagccctgc   3840
```

```
cagaatgggg gtacctgcat tgatctgacc aactcctaca agtgttcctg ccccgggggg    3900
acacagggtg tacactgtga gatcaatgtt gatgactgcc atccccccct tgaccctgcc    3960
tcccgaagcc ccaagtgctt caacaatggc acctgtgtgg accaggtggg tggctatacc    4020
tgcacctgcc caccaggctt cgtcgggag cggtgtgagg gtgatgtcaa tgaatgtctc    4080
tccaacccct gtgacccacg tggcacccag aactgtgtgc agcgtgttaa tgacttccac    4140
tgcgagtgcc gggctggcca cactggacgc cgctgtgagt cagtcatcaa tggctgcagg    4200
ggcaaacctt gcaagaatgg gggtgtctgt gccgtggcct ccaacaccgc ccgtggattc    4260
atctgtaggt gccctgcggg cttcgagggt gccacatgtg agaatgatgc ccgcacttgt    4320
ggcagcttac gctgcctcaa cggtggtaca tgcatctcgg gcccacgtag tcccacctgc    4380
ctatgcctgg gatccttcac cggccctgag tgccagttcc cagccagcag ccctgtgtg    4440 ggtagcaacc cctgctacaa tcagggcacc tgtgagccca catccgagaa ccctttctac    4500
cgctgtctat gccctgccaa attcaacggg ctactgtgcc acatcctgga ctacagcttc    4560
acaggtggcg ctgggcgcga cattccccca ccgcagattg aggaggcctg tgagctgcct    4620
gagtgccagg tggatgcagg caataaggtc tgcaacctgc agtgtaataa tcacgcatgt    4680
ggctgggatg gtggcgactg ctccctcaac ttcaatgacc cctggaagaa ctgcacgcag    4740
tctctacagt gctggaagta ttttagcgac ggccactgtg acagccagtg caactcggcc    4800
ggctgcctct ttgatggctt cgactgccag ctcaccgagg gacagtgcaa cccctgtat    4860 gaccagtact gcaaggacca cttcagtgat ggccactgcg accagggctg taacagtgcc    4920
gaatgtgagt gggatggcct agactgtgct gagcatgtac ccgagcggct ggcagccggc    4980
accctggtgc tggtggtgct gcttccaccc gaccagctac ggaacaactc cttccacttt    5040
ctgcgggagc tcagccacgt gctgcacacc aacgtggtct tcaagcgtga tgcgcaaggc    5100
cagcagatga tcttcccgta ctatggccac gaggaagagc tgcgcaagca cccaatcaag    5160
cgctctacag tggggttgggc cacctcttca ctgcttcctg gtaccagtgg tgggcgccag    5220
cgcagggagc tggaccccat ggacatccgt ggctccattg tctacctgga gatcgacaac    5280
cggcaatgtg tgcagtcatc ctcgcagtgc ttccagagtg ccaccgatgt ggctgccttc    5340
ctaggtgctc ttgcgtcact tggcagcctc aatattcctt acaagattga ggccgtgaag    5400
agtgagccgc tggagcctcc gctgccctcg cagctgcacc tcatgtacgt ggcagcggcc    5460
gccttcgtgc tcctgttctt tgtgggctgt ggggtgctgc tgtcccgcaa gcgccggcgg    5520
cagcatggcc agctctggtt ccctgagggt ttcaaagtgt cagaggccag caagaagaag    5580
cggagagagc cctcggcga ggactcagtc ggcctcaagc ccctgaagaa tgcctcagat    5640
ggtgctctga tggacgacaa tcagaacgag tggggagacg aagacctgga gaccaagaag    5700
ttccggtttg aggagccagt agttctccct gacctgagtg atcagactga ccacaggcag    5760
tggacccagc agcacctgga cgctgctgac ctgcgcatgt ctgccatggc cccaacaccg    5820 cctcagggg aggtggatgc tgactgcatg gatgtcaatg ttcgaggacc agatggcttc    5880
acacccctca tgattgcctc ctgcagtgga ggggccttg agacaggcaa cagtgaagaa    5940
gaagaagatg cacctgctgt catctctgac ttcatctacc agggcgccag cttgcacaac    6000
cagacagacc gcaccgggga gaccgccttg cacttggctg cccgatactc tcgttcagat    6060
gctgcaaagc gcttgctgga ggccagtgca gatgccaaca tccaggacaa catgggccgt    6120
actccgttac atgcagcagt ttctgcagat gctcagggtg tcttccagat cctgctccgg    6180
```

```
aacagggcca cagatctgga tgcccgaatg catgatggca caactccact gatcctggct    6240
gcgcgcctgg ccgtggaggg catgctggag gacctcatca actcacatgc tgacgtcaat    6300
gccgtggatg acctaggcaa gtcggctttg cattgggcgg ccgcggtgaa caatgtggat    6360
gctgctgttg tgctcctgaa gaacggagcc aacaaggaca tgcagaacaa caaggaggag    6420
actcccctgt tcctggccgc ccgtgagggc agctatgaga ctgccaaagt gttgctggac    6480
cactttgcca accgggacat cacgatcac atggaccgat tgccgcggga catcgcacag    6540
gagcgtatgc accacgatat cgtgcggctt ttggatgagt acaacctggt gcgcagccca    6600
cagctgcatg gcactgccct gggtggcaca cccactctgt ctcccacact ctgctcgccc    6660
aatggctacc tgggcaatct caagtctgcc acacagggca agaaggcccg caagcccagc    6720
accaaagggc tggcttgtgg tagcaaggaa gctaaggacc tcaaggcacg gaggaagaag    6780
tcccaggatg gcaagggctg cctgttggac agctcgagca tgctgtcgcc tgtggactcc    6840
ctcgagtcac cccatggcta cttgtcagat gtggcctcgc cacccctcct ccctccccca    6900
ttccagcagt ctccatccat gcctctcagc cacctgcctg gtatgcctga cactcacctg    6960
ggcatcagcc acttgaatgt ggcagccaag cctgagatgg cagcactggc tggaggtagc    7020
cggttggcct ttgagccacc cccgccacgc ctctcccacc tgcctgtagc ctccagtgcc    7080
agcacagtgc tgagtaccaa tggcacgggg gctatgaatt tcaccgtggg tgcaccggca    7140
agcttgaatg ccagtgtgta gtggcttccc cggctccaga atggcatggt gcccagccag    7200
tacaacccac tacggccggg tgtgacgccg ggcacactga gcacacaggc agctggcctc    7260
cagcatagca tgatggggcc actacacagc agcctctcca ccaataccttt gtccccgatt    7320
atttaccagg gcctgcccaa cacacggctg gcaacacagc ctcacctggt gcagacccag    7380
caggtgcagc cacagaactt acagctccag cctcagaacc tgcagccacc atcacagcca    7440
cacctcagtg tgagctcggc agccaatggg cacctgggcc ggagcttctt gagtggggag    7500
cccagtcagg cagatgtaca accgctgggc cccagcagtc tgcctgtgca caccattctg    7560
ccccaggaaa gccaggccct gcccacatca ctgccatcct ccatggtccc acccatgacc    7620
actacccagt tcctgacccc tccttcccag cacagttact cctcctcccc tgtggacaac    7680
accccccagcc accagctgca ggtgccagag cacccccttcc tcacccccatc ccctgagtcc    7740
cctgaccagt ggtccagctc ctccccgcat tccaacatct ctgattggtc cgagggcatc    7800
tccagcccgc ccaccaccat gccgtcccag atcacccaca ttccagaggc atttaaataa    7860
acagagatgt gggatgcagg accccagctt ccgttcccaa gccctgttgg gagtcctttc    7920
cagtgcttca ggatgctggg gcgaccaaag gagccttta aaaaatgttt ttatacaaaa    7980
taagaggaca agaatttcca ttttttttttt tagtatttat ttatgtactt ttattttcca    8040
cagaaacact gccttttat ttatatgtat tgttttctat ggcactaggg aaaaacatat    8100
ctgttccaag aaaataaact agttctcaga gccttgattt tcctggtcag ggtgaagttc    8160
cctgtgtgtc tgtaaaatat gaacaaggat tcatgatttg taaatgctgt ttatttattg    8220
attgcttctt tccaaaatcg aaaagaaaga aaaagaacg tgacaggaga agggaagctg    8280
gaaactgcca tggccagaat tgcccctccc ccacactcac tgcccctccc ccagcgtca    8340
cctgggattt gcagatgtgt ttagaaacac gcccagacct tgaaccttgg gttcatggat    8400
tagttttgta tctaaaacag gaaacaagtc agatgatgtg gtttgtacac tttctgtaac    8460
caccagtgtg gacttgaaga agtgtcctca gcatgtgcag agtctactac ccagtaccag    8520
tcgtgagtct gcaggctcca gtgttctgta gtagtgttta tgggccttgg gagtacttct    8580
```

```
ccctgccct gccccactgt ccccttcctg acaacttgag ccagtaagcc atgcagggtg    8640
tggtgcctcc tagagaaaac actgcctgga ctgttctgtg catccctcca aacagcatca    8700
tccaaatcca actgaggaca gacggactgt cccggcctgg gcctgggctc ctaacacctg    8760
actgccaaag ggctccaatg tgcattgtgg actcgccaga gtagcctgca ttgagactcc    8820
aagaaaacag aagctatgtg gcctctgatc cccaaactgg cctgggtggg gacatgcctt    8880
gagtgtgctg gaatgtgggt ggagcctgct tctgggccac cctcctggt tcagggctgt      8940 gctcacagca gattcttgca gtatcaagta tacgcctgtg gcagaataag tatctgtaaa    9000
tacatgttta aagatggatt ttgtttaaaa aatctaaagg aacaagtgtg tcgtgtgtca    9060
agctgatgag gactgtcaga ctgtggctta gctcagtgtg acccagacct tgtgacctgt    9120
agctgccgaa ccagtagctc ctaagagcac aacccaggat ggcccatctg ctgcccacca    9180 agtcccttc cagccactgt gtgctggggg ctttcggggg cagttgccca cctcctcagg      9240
gcagctcttt ctggccttttt ggggggcagt gtctgtgcca tgcctaatag atatgaccag    9300
acgcatccta agatgttgat tcttactgtg ttgtataaaa taaagtgtag tttacaaaaa    9360
aaagaaacgt aaaaaaaaaa aactacatgc aaaactgtag gtaatgaaaa tgatgtattt    9420
ttttcatctt tttttgttaa ctaatttgca ataaaaatga tactgatggt tgtccacatt     9480
ttgctaaaca aaaaaa                                                    9497

<210> SEQ ID NO 5
<211> LENGTH: 142000
<212> TYPE: DNA
<213> ORGANISM: Mus musculus

<400> SEQUENCE: 5
gttcatcaat tatgttagat tggttgccaa caagctccaa gggccagcta gtctctgcct    60
ccttaatact tggcttttggc tttttttttt tttcttggtc aagattttgt atgtgtgtgt    120
ctgtctgtct gtctctgtgt atggtgggca ttgtgcacat atatgtgggt gcctgtgaag    180
ccagaactat tagatctcct ggaactggag ttatacgagg tcacgggcca cttgacatgg    240
gtgctgggaa ccaaactctg gttctctgga agagcagact tagcttttaa ctgctaaacc    300
attttcccca cccctctgcc tgttatggta ggggagagca agctcgggtt aaacccactg    360 gactgttttcc ccagccctga aggttattgt cttttaaagct gtcaccctga ggaacacagc    420
tacagccact tctggagctg tgcctcaggg gtgagcacct ttactctctt ttgtatgcat    480
gttggttgtg agaaatctga tctttgtagg tcaatttaaa gtttgtatcg gcaactcacg    540
atttaccctc ttacgtgagt agagattaga ctggtaacac catgggtgaa caaatgaaag    600
ttaatgttat tactcttctt taaacacatg gcacaagcaa aaattgccta gtgatttttca   660 ctaactatac tatttttaaa tttaaatttg gttttatttt atgtgtatgg gagctttgcc    720
tgcgtgtatc tctgtccatc atgtgcatgc ctggtgcctg tggagcccag gagagggaag    780
tggatccctt ggaactggag ttgcggatag acgtgaagca ccatgtggga tgtgggtgct    840
ggggattgaa cccaggttct ctacaagaac agcaaccact gagctatctc tctagtcctc    900
aattatgcta cttttgaaa agagcttcta gggtcccaat gtgaccgttt gcagtaagta    960
ctagcttctc tttcccaagg taatgtatat gtgtatgtgg tatattatta tttgtgtttg    1020
gtataaggta tatgtgtgtg acatatgctg tatgtgtgtg atatatggta tatatgtatg    1080
atatatgctg tatatgtgta tgtatatatt catgtgtgtg gaggtcagag gacatcagat    1140
```

```
atcctgttct attactctct aacttattcc ctggttgggg ggggggggat ctcttactga    1200
acctggaact gggctacctg ctaattagcc ccagagattc atttaactct actccctaca    1260
gctgtttgag gcatgtgcat agtcaaacct ggctttcact gtgagtgttg gagatttgaa    1320
ctcaggtccc cgtgcttgca cagcaagcac tctttcccgc tgatccattt cctcagactc    1380
tatagtgctt attaaactgc agttttaatg ttcacaccca tttgcacttg ctgaacggta    1440
ttctgcattc taggtcacca tctactaatt gataggcact agtgatgaag gccatgatcc    1500
tgggccataa agacttcccc gtgtagtcaa gacagaaata caaacagtcc tgtgttactt    1560
atgcaattcc tcgtagttgc caatttcgtt ctacaaatgc atttattcct aagacagatc    1620
acaccctcca ctctcccact ttggaaattg ttagtgtaat agctttatct tttaaaaact    1680
atgcacacaa acgtccatac aatgttcagt gttgtttgga acatttata tgtaaatggc    1740 attcttagag tctcgctctg cgattcgtgt tttcatcatc attttggttt tacggctgac    1800
gtatatgaag atggtatttt caattgtatt gcacttataa ttatgcatta ttcatctagt    1860
ccctaagggt ggggcattta ggttactctt cactcgcagc tattaatagg ttataaagag    1920
tattcctggt tcttctttct attttctaca cctttgacta gagtttcaag ctcctgctgt    1980
ctcttgaaag cctcccctaa attcttctag accctagagc ggacgattcc agtgtcccaa    2040
gcaccttgct acacgaagtt cactaaaaga accaaggatg ggtgggtgga tggacggatg    2100
aatgaacgaa atgcccagag catcttaagg aatgtcctct taagagtact ttggcgcctt    2160
tgccctctgc cttccgttga cagtctcgtt tttgctctcc ctcattcctc taaccagcca    2220
agaagtgtgt gggtgggtgt gtggggcatg aggtctgcct ctctctacaa gttcaggacc    2280
cgggtaaacc ctagtgtttg atgttgggcg cttcagccgc cccctttcc gagctcatgg    2340 gcgggctcgg cggtcgagcg ggcggagtac ggggtgctgc tcactcagat ccctccgcgc    2400
gcagaggacc ggcgcttctt tctgcgggaa acccctgggc gcgggcggc gacggggcg    2460 gagcctcgcg gtgggaggag gccgaggcgg aaggacacgc gggccgccca gccgcgcggc    2520
gcagccagaa actttcagcc aaacttcggg cggcggcctg gctgcgcgga gtgcaggggc    2580
ggcgcagcgg gagctccagg actcagcgag ccgcgggggc agggtagagc acgcgagagc    2640
cgggctcctg gtcgggaccc gctccccatg cggatctgct ctggctgcgg ccccgaagat    2700
gcccgctctg cgtcccgccg cgctgcgggc gctgctgtgg ctctggctgt gcggcgcggg    2760
ccccgcgcac ggtgagtacc gggcgcccgg gagaccatcc ctctctgtct ctgcgctacg    2820
gggactgcgt cttccaaact gcctcgtccg ggcctcgagt cttggcaacg cgtagcgtcc    2880
cgggttccgc gttagcgggg tctcgggcga gcagctcgcg ggccgaggtg cgagtgtggt    2940
cgggagggcg gcggggggctt gcggcgttcc cagcttttga cacccggatc ggtcggtttg    3000
tccggaggag gagttgggcg tggggcttag gtcttggata ggtggaggca gcagtggggg    3060
aactggtgtg gcagcgtgct gagccacatg attgaaaatc tcaactgctg ttattctttc    3120
cgaggcgcgg agctctgctg cggttccagt gtgcgtccag ccccaggaat gtggtgtgac    3180
gatccccaac tcctccaacc tggcagcagc ttgctgctct tttggcaccg ttgggggtgg    3240
ggcaggggca ggcgaggaaa agtggagacg ttgcttgatc cgaagtgctt gcttagaaag    3300
gcttgttatg gtgggatatt ccgtgccccc tcgctaactt ggtgggagcc aggaaaggaa    3360
atcggatcat attttaccca ctccacccac atctttagat tttacatttc tttggaatgt    3420
tgtatggaaa gaacttcggc tttggagtcc agctctgtaa tcctggattc aaatcttctg    3480
tattaactca ccaataaaat ggggatgaaa ttacccagct aataggatta attaaaagaa    3540
```

```
tgtatattaa acccgtagca cttaaaagat gttcagaaaa gttgtttcag ggcaggagca    3600
gcggtttggt ctgtgcttcc aatggggcta tgtcttgtac tggtttgaag tctgtgcttc    3660
cagtggggct atgtcttgta ctggttcgaa gtctgtgctt ccagtgggc tatgtcttgt    3720 actggtttga agtctgtgct tccagtgggg ctatgtcttg tactggtttg aagtctgtgc    3780
ttccagtggg gctatgtctt gtactggttt gttgaactgg tagggtcccc ctttactcaa    3840
gaacaattaa cttttaccag aaaaactcta gtacatttcc tcagagaagg gatgagtttc    3900
agaaaagtat ggtctttgtt cattgtaaca ggcagctgac atgccaatcg cagatgcttt    3960
gaggaagact cgattattta tcacctgcaa acagtgctgg gctgtccagc atcaaccaga    4020
tactttctgg aaaattagaa tgtcatacat tgctgggtct gtaggttttc agaagtggac    4080
caggattgaa ttcaggattg aatggttccc gaaagttttc ctcaaaactc aacgatggca    4140
ttcttgcctt gccccttttc tttgagtgaa gctgttagcc ctcagtgtag acttagtgta    4200
aagagctgta tgattagtgt ggtttttttt ctgaggatga aagtgcttgg tcccccacga    4260
cttgttttac atagtaaagt aactttagtc ttcatgacct gtgtcttttc ccatatggaa    4320
taggattcaa agcctaacta ttttttctctt gagtacttcg gggactagta cgtaaagtga    4380
ctcacaagtg ctaacgctgg caacagagat gggatgaggc tggcacacgg gctttctccc    4440
atgttgaacc ccagtgcgct gaactgatgc ccccacttct gctaatgcag gccctcgctg    4500
tcaccgatat cggttggggc gtcacactga gtgtcagtcc agctcaaatg taggcatttt    4560
gggttttgga caggtgttct ttagatgcta aactattctc atgaaagaga ttaaagagct    4620
agttgttgtt gcaaatctta aatcttccca gggtctagca gggaagcttc ctaatctatt    4680
atggtgtatt tgccaaggta ccaattataa ctctccctcc ctaagttttg agtgttcccg    4740
tgtttggctc gtggccagtt gttaatttga acatcactgg ttcctaaggc aaggagctgt    4800
caacccatct gtgtgagctt ctgaacaatt ctctggacca ccccttactc cccttacttc    4860
tggcttgctt ttggctctgc ggtgggagtg actccctggt tttgctgtca cctagacact    4920
ttctcagttg aatccctact ataaaaagaa caagtttttt ttttttttcc tttagggtgg    4980
agataaaatt caccctataa ctatttcccg tttttctttc ttggagggag gggggagtgg    5040
ttggttgcag aatctcttgt tttatggtgt ttggcatctc ttttctgcct cctctgtgga    5100
tttgtgttgc ccagaagggc agccttggct cacctggcct gtcactgatt tcaggacctt    5160
taaagaatgt ttaagcgcag tgggatatgc ttggatgctt gagagaaacc ttataataca    5220
ttttaaaaat atcacaccca cagaaatttt attttgccca cagaatttgc attgatgtag    5280
ttcccactct tccattcctg gtgaccctcc tccctgcccc ttccatgtcc tggctgcagc    5340
agacctccac tcagcaccct ggtgtcctga cacaggaggc ctgagaatct gtattattat    5400 ttttttaaa taaggcttac aaaagatttt gacaaattga ccgagtggga caatcacaga    5460
ttaattctgc cttcaagagg tgtatgagat cttgccttt agattttaat agtttccaca    5520
gtgaacccag ctttaaccag ccattccagc agttaaccct tttgactctt aaagaattca    5580
gaaattgcta acatgaaagc tgtagactgt gattggatcc ttcttgtgca caactgcttc    5640
taaaaaggct tcatgtgtga gtgataccte taccccctct gccacggatt cttcttcaaa    5700
tgttatatat acatataaat tttggattct ttataaactt ttccaggtgt gtgtgtgtgt    5760
gtgattgtgt gtgtgtgt gtgtgtgtgt gccctcaag gcatgatctg gataggaatg    5820
cattcttgtg ctgtatttac agactgtatc tgttttcttt cttgatgtct gtccggatgt    5880
```

```
ctcactgatc tgtcccctcc actcctgaac tttctggatc ctcctgctcc tgtcttctct   5940
tgctttccaa acacaccttg aaaacaagaa tgtccccccgt ctggcacttt ccctctgcac   6000
cggtccactg tatatgtagt aattgggaca agccactaag ccgggagcca gaaaaccaga   6060
aatctcctcc agctctgtta ttaattgatt tggtgacctt gcaggggagc ccatggtttg   6120
gtagttcaca ttctcatgga cttttgtcacc aatcacaggg ctggttgcag agttgggact   6180
agaatttctt tgtttaaggc ctcaggtcca gggccttgtg tatcgtccat actgcttctg   6240
tcttgtgtac agatggattt gtgtacacag aaacacatcc ttgagtgctt actgttagtg   6300
tatgctacag ggaaagaatt gtgcctctgc ttgtctgtgt tctggtaccc acatttctac   6360
cctgtacttg gcatggttcc ttggcatctc attggcatcc tgtgaagacg tgttcatttg   6420
agccagtacc tttcagtcct ttttcattgt aggccacagt ggtcctgctg gatgcctatt   6480
aagtggtgtt tgcaatgagg ctctggtgtc ttctcttccc tgacctctcc tgctccatgt   6540
ggtggtcaca ggtaacact cactgcactt tgttcacct tttctataga aggctttcat   6600
ttggggcaca gcttgggatc atttctggaa tagtatattt ttctttgggg tcagctttgt   6660
tttgctattt ttgagccttt tcatcttaaa cttgatactg caatcctgtg ccagacaacc   6720
acatgtgatt ggcctctgac acacagatcc tgctccttga gagaggtgct ctgcctcaca   6780
cacacagccc ttttctgtcc tacggatgtt cacggcatgt gtccagtgtg cagaggcacc   6840
tgagcggaac gccttggttg agcacctgtg gcttgctcag tgtgcctaca gacttatact   6900
gcctggcgcc ttttgagaca gggctttgga accttggtcc tcctgtgtca gcctctcgag   6960
tgctcgtgtt cagtgtgcac catcatgtct cacctggctt tgtgctaacc catcccctgt   7020
ttttacctaa gaggtgggtc agggttacct cttttgttgta tgtgctgatg gggactttaa   7080
agccctctgg tgcttctctc tgcccatgct agatctgatc tctacctggc aaggggcagt   7140
gtacctgtgt ttcctatcaa gaggcagtct ttgacctcta gttcttatat gcaccaagtt   7200
tctctcctct tgtttctatt cattggtatc atctctggat tttgtcctca gagtcctgag   7260
ctttgtgtgg gtgacagaag taaaaaagag caggctatgt acccttcact gaagtgacac   7320
ccacttgtcc ataaaaggag tggaacttgt gaagaacgtt atgttcttct gtctgggaag   7380
gctgttcagg tgaaccacct tagccctacg tcttcatacc tccctgtcca gataggtcca   7440
tgaagaagga aagagtttgt ccagcagctt ccctggctcc tcttacgaaa agaacacatg   7500
attgtcctgg gtagtgtgac tcagtggatc tcaagttgtg tctgggaatt tgtacgttct   7560
agttaggggt ggggatggct cagtgtgtag agtacctgtt acaagcaaga acacctgggt   7620
ttggatctcc agcaccccaca taataagcag ctgtggtggt gtttatttgt aattccatag   7680
ctggggggcag agacaggatg atcctggggc tgtaccagcc agtcactcca gatgaaacaa   7740
taaactgtat cctttcccaa aaagcaaggc agatggtgct ggagagatgg atcagggatt   7800
gtgagtgctt gctgatcttc caaggtcaca agtttgattc ccagcacctg tatcaggtgc   7860
ctcataactg cctgtaactc cagtttgggg ggggtgtctg atgcccattt ctggcttcca   7920
tgggcactga cacacacatg acttacactc acacaagcat atacataaac atagctgtat   7980
gcaatacagt gatagcttga aaaggaggcc atcacttgct ctgctggcac tgcaaggcta   8040
gtaatgttgc cttgtgcttt taaagagccg gtctgtgaag tctatatttt aggactgaca   8100
gaggtatagc gtgtgtcttt aaaggcagtc tccctccctc catcagtgtc actcggatag   8160
atcccggaat gcacggattt cacacgaagt gctgtcttta gcccgggtga ttgacgcttc   8220
ctcggaggat atctgttttg ttaacctgtg actgcctctc tgctggcagc ttttcccttg   8280
```

```
agtacaggag cacggagaga gaggaagaca acttatttca gcctgtcctg attttttgag    8340
agagggtctt actactttgt agccagaatt ggctggaact tactgtgttc gaggctggcc    8400
ttgaacttag agtgatctgt aggccttagc ttccttctta tttcgattag aggaacaagc    8460
catcattggg tggcagtact gacttgggtt gggatattct cacgtggtgc atgaggggaa    8520
gggagaatga tgagcgtgcc aaaggccccc tacatggcac gtttagcaag aagggcccag    8580
ggtcgccctg ttaccatggc acttcatgtt accgcctctg atggaaagaa agaagtggct    8640
tcagaagttg ttggctgtcc tttgggcttc ggcgggtcag actgcacagt gttccctggc    8700
agcagcagga ggtttgccgc cccttttgaa agggattctt acctgtttgc ctttaacact    8760
gtggccttca aaagcgtgaa acagagaaag agggctcttg ggagctggag tgagcaaagc    8820
aatgatcgca ttcattttt attgttactt ttggtcagtg tgttcaagaa ttcagggtca    8880
ctgctcaatt gcctgcagga ctctcaggga ctgggctcca gggcattaga agagggaccc    8940
aggccctcaa tgcctggctt gaagaccaaa gtgccagctc agccatcaaa ttggcctgca    9000
gttcaagggg tccaggcaca tttgcgtaga atcctctgaa gactgtgggc tcttagagtg    9060
atgctatgtt aaggccttgg gtgtgtcgtc aggcttaatt gtttcccttg gcatcttggg    9120
gcaggcagtg cagggaaata tagtctccag gtatgtggga attgtaccca gagtggaagt    9180
taggctcctg cccccaggac tgatagcatc actgagatga ggcagagagg tacacggtgt    9240
gtagtttgaa agccacctag ccatttattg aactctctga aagcagtttc ctgcagtctg    9300
ggtaactaag agcagtgggg ttcctgggga gtacccagga gagaagagca gccccagctc    9360
ccccaccca gggggcttg tctgctattt tgcacagtcc gctatttct tttctctgtt    9420
gtaacatagg aaaagaataa tcaacttgcc ttggtgagaa gagacaaag acccccgtct    9480
ggtggcgggt gtgagtataa cattggcaga ggttgtggtg gctattagtg gctctgtggt    9540
gagagagcac tgtgtcctca gccctgcatg gcaggcttgc tacaggacat atcagggtgg    9600
aaactgtctt cctgggaaga tcccagttct cagcggcagt ggctgaaaga cctcctcatc    9660
acaggcatgg ggtgtgtgtg gtgtggacac acccagagtc gctgctgctg gtggcattga    9720
ttaatcaacg ctgacatagc cctcaccctg ctttacttgt cttggcaaaa ccctgttctg    9780
ccagctcctc agtacttatg tggtaccagg agagatggag caaggtcctg gtggttgcgg    9840
gggcggtcac tccactgtcc tccctctgct gtctggaact gttggctgtc accttggttg    9900
accagatgac ttttctgcca ggtgtggagg acctgggtcc catcttccag tggactgaag    9960
cccagttccc tggaggcctg ccagcggaga tctctagtct ccaagtcagt tccttctaca   10020
gattgctggc aactgaatag taattctggg ttctttgaat atatcagacc aacatcatgc   10080
cagagtggac tcattgccac acaaagactg gttgggtgtg tggtgttgca gaacctgttt   10140
ctggggtaag agtgactctc ccactcacag acatgtttat tcatatgaag aaagtatgtg   10200
tgttttgtga ggccagaaaa acacgatgag aatattttga ttggagtcag atattgtctc   10260
cttaataata cgtcttcatt taacaaatag caccccctt aaatgcagcc ttgcttgcca   10320
ggtaaggtgt tgaagacaca gctgtggttg tattctaaag tatatgtcct ttttcagagg   10380
caggtgtact tttaaatggt gtggtttgct tccttttcat tttgtgttct cctccctgcc   10440
ctccctcccc tccctccctt tgagaagatt ctgcatcggg tgtaggtcac aagcgttacc   10500
tagcaggaga gagaaatctt gtctgttggg ctcacgaggt gtcccagtaa gaataaccga   10560
atgctgtcta cttaggtggt gcctgagtta actcctgcag agagaaggtg gaaaggtgct   10620
```

```
gggagccttg tgtgtttctg ggctctcgga gccttgcctt tggaagctat tcagtctcat    10680
tgaggttcca ggacaagcta tcttgcttat tcattttgta tgttttctt tgaagtgtac     10740
atggctgttc atttgctgac tcttcttta agtggcacac atttacctt agatagtaaa      10800
ttttttttt gcaacattta agacacttcc aaatctttat gaggatttaa aggcaaaagc     10860
tcaaatggtg tgcctagtgc aaggtttgtc attacgtcag caacggctgg gtggggtgtg    10920
cttacctaat tcaagaatgc tggaaactga gacaggagga ttgctgtaag gacaagcagc    10980
taggctatct tggaagaccc cctgtcctcc caaataaggc aagcaaccac ttacagtcct    11040
tgctccacat tgcctagcca ttaaggaaaa tggttgtaac taaaaacaaa cattgtaaca    11100
gtttcgctta ggtaggttta catagcaaca gaattattcc ttatgtttac acataattaa    11160
cttgtattta tactgtgttg attttccctg gcacctttac aagattttgt gtgtatatgt    11220
gcttttaaaa gcagtcacat ttggaattct ttaggtatgt gtgagcaatc agaataatat    11280
caccacacct ctgttagtgt tttggtattc atgtatgtat tttgttatat cttttttcac    11340
ccttagattt taaaagctcc tatacatttg aaagtcacac aggcagtttt ctgtttaaaa    11400
tgttttcata catttgattc tagtaattaa ataatactaa ggaatggact catatgtttt    11460
gacctctttc ttttgactgc aaatttggtt ggatccaact cccccccccc tgcccccccg    11520
ccctgtccca tgtacagata agaatcagct gcccaccaga ggaagcgttg ctctttggta    11580
ttccagcgat ttctaaacct aagagagtgg catctaaaaa aaaaaaaaa aaaaaaatc     11640
agagacaatt aacatctcca ataatcacat cgtttataag ccaaacttgt ggttaacatt    11700
ttgattgata ctttacagta ttttttccatg ctcagtgtct attataaaac tttaattggg   11760
attttaacag acatatagtt ttccactaaa aataatatga acatttcctc catatatgtt    11820
agtagccttt aagaatatga cttcaaaggc aacatactac actatcttaa gggactacta    11880
gccttcattt ttgtggaaat ccatccttag tttccaggtg tcataaatat aaagaattct    11940
gtaatgtata ttgttgctgg gactggctcg gttaagagca ctggctgctt ttccagattc    12000
ccagcaccca tctctggctg ctcgcaacca tctgtagctc tagttctaag ggcttcatac    12060
cttctgacca ctgtgggccc cacacacaca tgctgtgcag acatgcacgg agacacagca    12120
cccatactca taaaataaaa acacatcttt aaaaaaacaa atcccttact ttctaccaaa    12180
atccagaagc ttttcagcca aatggttgca ttacttttta tagagtttga cccagtcata    12240
cttttcatta gcagaatatg aggctgccag cgctgccagc caccgacagc cctgggattc    12300
atttaaataa ctcttgttat tacctggcaa atggtgaatc ctacctcatc tcttgttgcc    12360
ttttattaga gcagtataga aaaaagatc tctgtggatt cattcgtcta acgcctcttc     12420
ttccttcta tctcttttac tcaactgagt ctttaccccg tgaatttttt aatatatctg    12480
aactttagct attaaaggca ttggtacttc acctgcttaa aacatatcac agtatgcctg    12540
tcagtttaca gtacatacag gctggggctg ggatggagta catgtatgac atgcatgacg    12600
ccctgggttc aatgtccagc accaaaagca gtcagccaca cgaaaccctc tcactctgtc    12660
tgtctctgcc tcgctcagtc gaacataaag accccaaata agcaaactag aataccatac    12720
acaataccaa gttagtata agaaatgtcc tttgataagg taatagtttt tcatcttttg     12780
aattctgagt tttcgagaca gggtctgcag ccctggctgg cctagaactc agagatctgc    12840
ctgggctctg ctgggattca gggtggatgc cctcatacct tgtccttggc catttaaaaa    12900
atacatatat taagtagtat tttctatagc tactttaaat tccattttg gatgtagttc    12960
tttagttctg atttttgag agtctcatgt agcccaggct ggcctcgaac tcagtacaaa     13020
```

```
gtggaggcta gtgttgaact cttgatcttc ctgccttcat gtccctagag gggattataa   13080
gtatggattg ccattgcctg gcttggtgct ctcaaatttg gatctgactt taccacacaa   13140
cagctgcttg taagttatat gcatcaagga accgtacgtt tactatatac tgggtttaag   13200
aagagacctt gggggcaaat ggtatgtggt tccactactg tcctgttttt cggagggtgc   13260
agaaatgtgt ggagcacata acactctgaa agacaaaacc agcatcctgt cctctccact   13320
cactgggacc taactggtga gcctggacag tggtcagggc agtcagttca ggcagacaac   13380
tgggtgactg agactcccct ctctctaccc tcaccaaatt gattcgttgt gggatggagt   13440
ggcctgaagc aacctgttgt tttgcaccc tgtggacacc acctgtttct tccctttctc   13500
actccagcct cccacttgcc ggtgcagggc gagtgcacag cggagcacag cggggaagcg   13560
atcggtgttg ttgccgagga atgttgcaat aaagaggaat agattgagtt ttgcaagctt   13620
gtgtgttcct aagacgcccc actgcttttg acatggagtg ctccggctga acggctctgt   13680
gctgaagcct tgccggcccc aagcgtttgc tgcagagcaa tttcaggctg tatgaatgct   13740
taagtatcat tggaatttac tgggctggtt gtttgccagc aattaccata tttagcatga   13800
ggagacctgg ggaatgagga catttctgac caaccaaaga aggaaactct gaaggactgc   13860
aactccttcc tctctttctt tcttttcttt c tttctttctt tctttctttc tttctttctt   13920
tctttctttc tttttcttct tttaatgagg tggttaggag aacaccagcc aagctaggac   13980
tctaatttgt gacaactggt ctttgttttt gtgcccttc cacataatta atttatggac   14040
gggcaaagag atttgatagt ggagttcttt ctcaccctga cgtacaattc tgccttcggg   14100
aggaagcagg gaattactag gcctgcttcc ctgctgcctg gctcagcctg caggtgagac   14160
tgtggatcta tggctagttt ccactcttct cacttaagat gtgctagttt tcggcttttgt   14220 cctggcctga atttattttg gcctagccct tgtctccacc ctgtgtttgg agacatcggc   14280
cttcgtgctg tggcttaaca ttcctctgcc tcagttttc cagtactgga ataaccagcc   14340
aatataatta acataaacat tgttttttata aagtaagaca acctccaaca tcagtacagc   14400
cctgtgtagt tcaaagagca tctcacagga gttgctcctt taatcccttc aaacctttgc   14460
tggagcccag caccaagagg tcaggtggct ttgcactgcg tcctgttgct tcttcctaga   14520
tggtcgttgg tcgtcgaggg cagggcaggc acttaaacgc acattttgat tgtttttcttt   14580 tctttctctc tctctctttt ttaaatgttc atttccttcc caaaaaggtc tgctgcgctt   14640
ttactctgta agcatcatcc gtccagggct gtgtcgtgtg tggttcctca ttgcgctcac   14700
atgaccgtcc tttgggtaa acagtagtca ctggcgctgt agctcgagtt cggagattag   14760
aaagttaagt cagaggggca tcaggctgca tccagagccc taccagggcc tcacagctgc   14820
tgcccactcc atgacttccc tggaacacag ggcgggatgt ggagactgag gctgcagtta   14880
gtcgttggct tagtttaggt tcataaatag gcttgatccc aatgttcttc tgggttcaaa   14940
gacactgcgc acacacttta tgataggaat aactaaacat taaatcccag agtcttctgt   15000
tttgaagagc cagcctctta ggaagccttt gtaagcctca gtaaggctgg gatggctgtg   15060
tcagctgaca ggtgcagctg tggctctggc ctcccttag ctgctccact gccaggacag   15120
gcaaaaagaa ttcagggaga ttggcaggag ttcccgttag gtcaacatgg gtctctcagc   15180
tctgagctct ctcaggagga ctgctcttag gcgcaccagt ctctggctgt cctcgggaca   15240
ttccagtgtg tgtccagcct ttgtgaggaa gttgtcagct ttgtggggag aaggtggagg   15300
caccaacaag tttggttccc agcttaccag cttttttct taggacagat ttctttgtgc   15360
```

```
cttccttttg ccgtctgtgt aacgaggaga gtagtagtgt gtgatctggg ggcttgttgt    15420
gaatgttaac tggtctgtgt gagattcaca ggacagtgtc tggagtgcag tgagtgtggt    15480
aaggactcgg cactgatgtt cctttaggtc acagtgtgga cagcctgttc attcccgcag    15540
aatggaatgc ttcatccatc ttccggaatc tagtgtgagt gagtgactgc agtcctccgt    15600
gaagaaccag ggacttttca gcttcctggt caggggctgt accctgcttt cttctgactt    15660
ggggagtgtt gaagtctgtt cccttcatgg ggtggaagtc caacttggac aagttttggg    15720
ttctgctggg aaggtggtaa gattttgctt ttactttta accaggtgtg tggttatatg    15780
ttatgtcagg ccacactgaa ggtgttgatc ttagagtagt tttagattca aaactcatta    15840 ttttttaac ttgagttttc aagttttatt tgtatgtgtc tctgtgtgtg gatgttttca    15900
gaggtcagaa gaagatgtct ggtccccttg gagttacagg tggctatgca cctgaagtgc    15960
atgctggaaa ctgaacttgc ttcttcagga agagcagtct tatgcactga gccatctctc    16020
tagctccaag gttcatactt actctagact ttctgtgata tgacagatgt tcttgtctgc    16080
cattctgtac catggtgagg gatattaata aggctaggat actcaattca ttatctctgt    16140
tagacattgc aaaataatac caatgtgcga cacctctcac tacacttgca gaggcaattg    16200
gaggttctca ggctgggagc tatcctccta cttcataccc actttaaaga tggagaaact    16260
gaagcctgta gaaacagagt gtctgccaaa gggataggcg ccaggccagg gccagggcca    16320
gggccaggat ttatgctcct gatttctggt caggtggttt tttgttttgt tgttgttgtt    16380
gtttctctct gtgcttgctc ctcagaagtg tgtcagtgtg ttgactatct gggttttgag    16440
gtctgagggt tgctttcaga gccaacagca gtgacgaagt aggaaggatg tggggagggc    16500
agaggtgtag ccatcttgaa gctgtctctg aagtaaagat cttgtttcct ggggactcag    16560
gcttgtccct ttggacttct ttgtcatagt gagggtaacc agtgggcctg atgtgactga    16620
tgattcagag ttggctcatc caggactggg aagctgctgt gtcagatgga cgttaacatt    16680
tgtttcccgt ggcagcttgc ttatctcaag tcttggcagc cttggacaaa tggttgttag    16740
ggttcttttg ttttgttttg ttttaagaca agatttcaga ttctactttg cagattttgt    16800
gagccacctt ctacctacca ctcccttctg ctccctctgt aattattttt aagactttgt    16860
tttttcattg tgggaatatg aaaggtttct tttatagtct aaagatattt ataattattg    16920
gtaagcacac aattgacaga aaatgttgtg tattcatttt aacttaagat atccctaaaa    16980
cacttaaact atgttcccta aatttggat cttcctacaa aagcagttta agctactttc    17040
tgagaagact gtactaaggg gaggactatc tggatataac ctagatatgt atgaagacac    17100
tctggagaaa ctgcagtgcc tgtgtgaaag gtgacctagg acatgtcccc ttgctcataa    17160
agtaaaccag acagacacct ccgttctcat ggagcttatg tggtttccag tcatttgcat    17220
gttctgaggg cttaagtcct tagagtaagc attatgattc ctggtcacag aaaggccagg    17280
gagtggccat gcatgtgact gtcctagcca gtggatcaga gcagcggctg agcactggct    17340
tgacacgaaa gctgaccccc aaccataggg cagtctggag gaatcctgtg tcccattgat    17400
gacttagctt tgagtttaat catttatgta ctgaattgac acttggttct tagcagtatc    17460
ttcactccga ataaatacct gcatagtgtt atggaaatta ttaaaatttc cacttctact    17520
tagaagaatt ctagttcctt ctgattttt tttaactagg aaggatgtat ttatattgat    17580
agtaatgcca aagagttgtt tactggtctc gtctgtgttt tctcttgacc ctctcaaaga    17640
aactcttcag tagattggga ccaggaatga aatagtatagc ttttatattt ttattttta    17700 taataagaaa aagtttagaa agattggaaa tggtagctcg gagtcctatt tgtgttcaga    17760
```

-continued

```
aatgttttct ggcaggcttt ttggttacaa ttagctttct ctggactgtg cagttgtctt   17820
cttactgtgt ccttcaaaaa gagatgtgta aaacagattg gaatgcttca gtctctcaac   17880
actggacaca gcctgctact aaaactaccc agtactaacc tgtcctcacc agaaaccaaa   17940
actacccagt ttcaacctgc cctgcctcaa tgttagttaa aactacccat tctaacctgt   18000
cctgaccagg aagtttgaac tgtgtatggc attctgcacc tgtcgctcgc tccgggccaa   18060
gaacgaagag gccttgcctt ttccatgagc attcctcagt gtcgtctcct ctggcactga   18120
gaactagcag tcatttgcac tgctgtttgt gagaagaggg aaccccagag cacccttcct   18180
gctttgcagc gcaggcttgt cctgggcaca caattgtgca tgtgagtctt ctcagcacac   18240
ccggtttctg ccaaggactt gctgtgctcc ccaccagttg aacagtgacg gggggtgggg   18300
gggggagcag cgtaaagact gcggcagtca gcactggtca tttctcagca gccagcagga   18360
tgcttagata cgctttctgg acgcttgggg tttggaacat ggatagactt ggctttggtt   18420
cttatcagct gggaatatca gagaagccat tgaagtcttt aggtcccagg cccctcattt   18480
gtgtagtggg agtaatagta ataactaact tatggagtgc tcttaaagac tagagacatt   18540
taattatgcc tgtgtggctg tgggcacaaa ggtaggggt cccagaactt taagtgtcat   18600
taggcttatg gtaattctac attccctggg cctgtttgtt tcagtgactc ccgtttcgct   18660
ctgctctgct accaaggcaa gattctggat tacccagaat gcaggccgaa agctttacca   18720
agagtctgct actcttgttt gcagtggttt tgttcatagc atgcagcctc ttgctcctct   18780
cacctcagaa gccatcgatt catagaaaaa tactgttcag gatttcagag taaagctgca   18840
gaactctgcc agtgccaagc tacgtggttg gattatttct gtcgttaacc cccaagtcca   18900
tggtgtcagg tgccagggc tgtttccagc actgggcctc acacagacat gtgatgggac   18960
ttccactgaa acttgtgcca gagaaggctg gaggtgggtt ggggattggg gtcgggtagg   19020
gggtgggtgc ctgctcctgc ctctgactcc tgagtgtggc tgagacagca gtggaaccgt   19080
ggggaagctg ctttcagaag tggttgatgc tacatcacct aatgatgtac atgtttgtgc   19140
cctgtgggct ggggaagggg ctttcctgac ataaatcttg ttgccattta tcatttctgg   19200
cctaagttgg gggaggactt ttttttgcttc atagaacttt agactgggaa ttttgtttta   19260
atgaaacact tatattaaat aatgtttctc agtttatatt caaccctatc ttatttgagc   19320
ctcaaatcaa ctcaaccata gatgagaata atgaatattt agtaacttca gggaattctt   19380
ctaaatcatg tagttagtgt ctgacagagc caggcctggg acccacattc ttacatgtct   19440
gccagctcgc ctttatatac cacatgcttc cttcagagca cccctcatct ggattctgtt   19500
ccccatggcc tggagcactt ttctcctgtc tgactatctc tgttggctag acttcaaggg   19560
tgccttcccc aaagctgggc tgtccaggtg tggctctagt cacctgtccc tgtcccacct   19620
aagcaggatg gatccaagga gaagctggca gaaagtgtca ctgacacagc tcagccgcca   19680
cagggggcct gtgcctgctc actcagcatc acactcttcc ctgcttgttt attacccagt   19740
cttcatatgt taagcttgct ttctttccat gttgccagag caactgctcc ttaaagttcc   19800
ccaagcgtac cctggacgtg cttgtgttca ccagcagctc cagcactcag caggctgagg   19860
aagaaccatc tccgttagtt caaggccagc ctggactata tagtaacttc caagtcagcc   19920
tgggctaaac aaagcgagac cctgtctcaa acccaaaaca aaggctgaca aactgagctg   19980
actcagaaga taaaggtgct gctaagcctg gcagcccgag gttgtttgat ctctggaact   20040
caagaggttt aaaaaaaaaa aaaatcaatt tctgaaggtt gcccttttgac ctctgcatgt   20100
```

```
atgctgctgc acatgcatca tgggtacaca cacacacaca cactccacct gcctcccaaa    20160
gttacctaag gtttgtctag agtacacagc agtgaggagc cactccttag tgtaatttta    20220
agctctggct ggcaatgctt ccttccttaa tcattataac agtaaataga acccgtgctg    20280
cgcatgcaca cgggtgtgtc cgcagtgcac tgtcacttac acaagtgcac ttcaggtttc    20340
ttcttttcat caaaatgagg aaatagaaca tgttttgtta atggtgattt tacaaggaag    20400
tgtgagttca ggttctgtgg gcgtgctaag agatagagtt tagggagga aaggctgctg     20460 ctggatgtta gctgcgagat gttcaggaga gaggaaaccc acgcactcat gctgtgcact    20520
ccagatgtgc cgctcaggcc tgaggtaatg gtgatctgaa agcccttgcc tacatccatg    20580
ctgtatggac catttattca agaaaaccct cttaaaatgt gctattggtc acaggtgtga    20640
ggggctaatt aaaagtttga tatgtgagct ctcagaaaac accaaggac catcattttg     20700 actcctgcag ctgtccaggt gggtgcttgt cttggcccgt ggtcattgga gcacgtccgt    20760
gaaggctgct gcacctagct gtaccaggat ggcgctgcac tctgctctct aggaaggtgg    20820
cagctgaatc tctggtgctg taatcccag aactccgaga cagcagggtt gctccccagc     20880
aaagacggcg tttcaacatt catgtaatct tctcatagga agctggggga ctctagatgt    20940
ggttgcacac aaccctagta cttgcgaggc tgaggcagga agattgttag ttcaaggcca    21000
cctagactat gtagcaggat gagagggga gagagagg gagagggaga gagagagaat       21060
atgaatgtgt gtatgtgtct gtgagagatg taggggaac ataaattagt acctttgtta      21120
tatctcaagc aggggtgaag ttttaaatct gaaaatttgg atatctgaat tagaaattgg    21180
gcatccctaa taggttaagt tggtgtgtga gtgtgtgagt gtgtgtgtgt gtgtgtgtgt    21240
atggaggaac aatagacttt ggaacttttt tttttcagaa aggatattta tctctgtatc    21300
tcttctcagt tggcagagaa tagctatcta gagcactgct caggcctcct gaaagataga    21360
tttagggaag ttgtagctcg cttaataacc atctgtggag tgacatagat tgacacaccc    21420
aattacacaa gcctggagtc tgagaactgg tgatgtgcaa tcatctcatc cgcatctgct    21480
ggtcattatc aacagcgata atggctcagc tatttcttca gggccatgaa aaaagacagg    21540
gtagctctat caaaggttaa gtcagctctg aagagaatag cctttcccac cctcttcttc    21600
ccaaacttct cttaaacat tctctttga gaggtttga aagaattcat tttgtttctt        21660 gttttttcaaa tatatgtata tatatgaaat atatatatat gtatctatat gactatatat    21720
gaaaaacaag aaacaaaatg aatacataca tacatacata gacatgtgca tatacatatg    21780
ctgctccttc tgaaaacaga aaagatcaaa gtattgtagg ccattttctc aaattgaatt    21840
tctttgtcat gtgcaagctt ttggtgacat cacagtgctt tatttgtgtg aaggtattca    21900
ttctttctag tttatggttt tgtcacatct gctattaagt cacctgtggg caattttcta    21960
atgcaatgca tttgggtcac catgagtagg agggaaggag tcagtttaca gggatgattt    22020
gcatgtgaga acataagctg tactagtctg tccacactca caggggcatc ggtaccttt      22080 acagagactg ggcagtgtgt ctgcagatac tgaggcaggc atccgtgcga tctcaggcca    22140
gcttgctctg tgggtaccag ggtgagttag ggacaacaaa gccagctccc ctgcctgttc    22200
ctctttgtag agctggaatg ttagttggca aaagtgtggg ctcttctttt aggagatgta    22260
ctgttggctc tgggagagtg tgctaggatt cacgtcctct gtgggaagag gacacactgt    22320
tgccttatcg taaagtcat cttactgtcc ctgaaccatg catggttctg tggctatcta     22380
atggcactgc agggcttctg gctaggatgg gaaataggca gtgtcatgga aaatactgag    22440
cttctccaca gctttctgtg agaggaagtc ccatgtggta gatgatctct gatttgcca     22500
```

```
actgtagctt tggtgtttta aagtttatgt gccttgtttt tggaatgtgt ctctctctac   22560
aacacaaatg cttaatgagg tctcattgtt ttgacaaatg gtcagacaca aggggggtcag   22620 agcagtgctg ttatagctgg gactaagagt gttatgtagg cagtggtgat gggcttgttt   22680
gctgtttgag aactgctgta gaatatgagg aagcaccccg agtcgagttt ccagaagtcc   22740
aggtaatgac aatgtgagcc cagggtatgt gctagataaa aagaccaaaa aaagcaaaac   22800
tctttggagc catccatttc attcattcat tcatatatgc atgcatgact agactcattc   22860
aacaaatatt taagtgccca ccaggtgcca ggaactgaat tgctgggggt ttttgaagaa   22920
aatgctaaaa cctccatttg tggggctgca gtgagcatag gccagcactg acttgttcct   22980
gatggttagt gatgtgtaca ggtaagcctg cccttttctc ttgggctttt gtttggaatc   23040
cctgcacttt gttacagtgg cctccctgct agatacaggg tagctgatga tgcatttaat   23100
ccttagaaaa acctcagtga cttaatcagg atgtaaaaga tgatgaactt tgaagaggtc   23160
ataacttggg gctgaagagg tggctcagca gttaagagat cactggctgc tcttcctgag   23220
gtgctgggtt caattcccag cacccattgt cagcttacaa ctggctataa ctccagttct   23280
aggggatctg ataccctttt ctgacctcct tgggtattgc ttacttgtgg tacatagata   23340
tatatgcaga ttaaaaaaga cactgataaa cagaatatat atatgtgtgt gtgtgtgtgt   23400
gtgtgtgtgt gtgtgtaacc agtttgctat gtatcaaaca gcacattgta ggaaaagagt   23460
ggactcaaga gaaggtacca cagtcataag tgttgtttgg ggtgtgtatg tgtatatgtg   23520
gtataaagta tattttttacc ctaggttatt ataaaatgtc agcaagatac agcttcctta   23580
gctgtggacc cacagattgg tgttagcaga ttgtgacatt taggccttag aaaaactaag   23640
tttccaagag cacggagata gtagccacac aacacccagt cacctgctcc cttgatagtg   23700
ctgaggatgc ctgggaatca aatcttatct tctgcgtggt gctgtggatg ctttagagat   23760
gttgacagaa cctgaaaagg gaagctgacc ctcacctgct gagtaggtga aaattcggcc   23820
atggagtccc actgtttgca gataaagaca gaacatgtct ccagggaatt ctggcatgga   23880
tgatggaatg agcgtgatag ccttagtgat cagcacaggc tgcgtgtgat gtttctgtgt   23940
tagctcatgt aattgctaat tactttggca gaggggccgt agctgttggg agtgagaagg   24000
gcgcctatca gcaagcccac atttctgtac gctgccttca gttccttctt ttgtttctgc   24060
tgaggtcgga gctgttttcc tcagagcctg gctcacctgg catgcactcc ctcatttttc   24120
ttttgctgca ctatatattg cttgcttcat tagccgggtg acagtgggtc ctgtagagat   24180
gctagtgagt gagcccagtt catctctacg ttttcctggc ctgtcatatt ctctgaaggg   24240
cgtgcatatc ctaccgtgtg gagtgttggg gtgaaaactt taaaacagta taccccaaga   24300
aaaacattct tttgagcctg cctgccagtg tgtgcacagt cttaggaagg cttaatttta   24360
gaccattcta acgtttcctc cagcttccca gtggagggtc ttgcacctcc ccccataccc   24420
ttccaggata cacatacttc attttgcaga ccactgatcc agaaggtaaa ttgaagagtt   24480
taatgccaaa gctgttggct ctttcgttaa ctagattatc ttttactccc agtgttccta   24540
atgcccttct gcaaagtagc ttttgtgaat gactgcatga attgagaggc tacattttg   24600 aggtggaaaa gatgaggata gagcatgcac gtgaattaag ttgaatctgt tgttgccaga   24660
atactgtttt tgattttgga aaaggagaac caacagctct ccctgtaaca gtctgggttg   24720
gtgtttggtg tgattaagtc tctccttcat atcgtggtga ctagcctggc tcatgatcca   24780
gagttagagc ttggtaaatg tttattgaaa aaaaaaatca gcctacttga gagtaagcta   24840
```

```
gaagtgacag agtaataaaa tgggtgatac atcatctgag ggccctactg aaggctgcta   24900
gcatcgtgca acggttgtag attctccgtc ggccttcctg tgggcccaaa gtggagcagg   24960
gcataagaaa aatagacatt agaggaaaaa cttgcatttc agcgtttgga agctcagcaa   25020
tgtggggatt atcagaggcc gtgggacacc gagcagaagc aacaaaagat tattttggta   25080
ttggaagaat tttcattttt gtgatagagc aggttaccat ttgagatata aaaagcagaa   25140
tggaactggc tggctgtaag gtagaagcag acagactcac agacatgggt gcagtgtacg   25200
tagacgtttt gggcatttct tcaaccatag acatgccagt ctgttcagtg ttagggctgt   25260
ttagcttatt aatgtcactg gaaaaacgag ttagactgtg tgctgaggag gcccagtgag   25320
cagtgtccta gcctgggaca gcgcatgagc gaggtcttcc cagtgctgtg gttttcctcc   25380
agctgagtaa agacagctgc tcctcagact ggggcttggc tgcacaataa gaaggcaccc   25440
tttgcgattc ttcttggttg tcccctccca cccccaaccc ttttgtgctg atacttttca   25500
aaactctttg tttttagttt cctcagattt ttgtcattga atttcttgaa tttggtagaa   25560
catttataga gcacacacac acacacacac acacacacac acaaaaca cacacacata   25620 ctatacatgg tgtctgatac ccttacaaag gtcataacga tgggcaggaa agacagttct   25680
ctggctggta gcatgctctg ctcttttcaga gaactagaac tacatctggc tctcacaact   25740
gcctgtaact ccagtgccag gggatctgat gccagtttct agcccttgtg ggtactacta   25800
tttggagggt cgtgctcaca tgtacaaact tacactcaaa cacatataca cagaagtaaa   25860
atatttaaaa agtgccatta agaaagcaga aaagtaatat cttaaaaca tcttttaatt   25920 aagttttttt cattaaagaa actatatgtg tactgatgtt ttacctgtgt gcataatgca   25980
acatgtgtgt tcagtgcaat gtccaccgag gccaaaagga ggcgtcagat ctcctaggac   26040
tagagttata gacaattgtg agctgccatg tgggtgctgg gaattgaacc tgtgtcctct   26100
ggaagatcag ccagtgctct taagtcctac gacatctccc cagcccctat tttatacagt   26160
tttaaagtag tgcagacatg aaataaggtg acactttggg gacaacatat gaaaatgtaa   26220
tgtacttttg tctttggaag actagggtct ggggtctgag ccatgtggaa agaatgagct   26280
aacgactctt gcagcaccga gggcatgcgg cagaattgct tatttcctgc cttgggaagt   26340
taggctgctc tctgctgtct ctgttgattc ttttaattgg acagaagctg agcagatgaa   26400
gaaaatcccc agcttcctat ggccttttgg ttcaccgcat cagtcattac ccaccctcta   26460
cagagcatgc cacgcttttt cctggtgagt gctccgtctt cattagcttc gtttgcagat   26520 gtgttttta ttttggaggt atttctatct aactgtttga actgtggatt cttttgtccca   26580 gtgagggtga ctgtccccgt cactaggctc accatctgta agagtaaatt cctgtcaaag   26640
tgaggtgtgg tcagtcgttc ctgagttcca gttctgactc ctgggtgttc tcttccttcc   26700
ccatgctgtt ctgttattga aagaaatgc tgtctagcta cagtctgatt atcaacaact   26760
tcagcctctc ccctgctgct ttcaactcca tatagtaccc tgttttgttt tgtttcccag   26820
gctggaaagc ctgggattgc tgtggaggtc ggtgatggtg aagtgtgtgt cttcataggg   26880
cttgactgtc cagggtgggt ctggaacaca gcactgtagc ctctcctgtc ctaggagctc   26940
aggcctactt tcacaagcat gtgggctttg cagaggtgtc tcttcatatg catggctaat   27000
atgtaagtgg ctgtctattt gacgagactg ttgtatcgca aatggtatta atgcaagttt   27060
gttgttgttg ttttgtatct aatacaggat tggtagatta acaaaacaaa acaaatctaa   27120
aatactgcat tctagccttg gtttggagtc tccatctgta tggctatagg caagtctgtt   27180 attttttaaaa ttcttccctc ttttgcaaag tggagctaat atcaatttgt atgccttgcc   27240
```

```
aggttgtagg gattaaagga tttgtatgaa gacacctagc tggccgagac agtactttat   27300
tgtagccgtg catttctaga gctggtggga gagtccttgc ctgtgaggag ctgggccgtc   27360
cgtcgtaaat actctgtaca gggctgctgt ctatggtctg tgttgctccc tggtgctcag   27420
tcaacgccag cttcagctgt tgttggagtg ggtgcctttg accctctagc tatatggctt   27480
gggatgcagt tagatcattt ctgaagttca tgtcctcaga gttcctccct gagacctcca   27540
gtagcagggt tgggattgtt ttctgctcag atccgtgaga taggctggag cccaccgtgc   27600
tcaaaagtca taatcttgcc aacattataa atttagcagg ccgaaaacca ggccacattg   27660
caggggcagg taggagctag agacttggtt tgaattttt ttttttttt aactataaaa   27720 cgtagagtat ttgagacttt ccacggagac atactcgggc gcatagccaa agtggttaca   27780
ataccctggt tttaatattg tcggtgaggt aatcgtgtgt tgggagaggg gatgcttgtt   27840
tcctctctgg cactccacca aaccccacca ctgactcctt tgtcccttga acctaggctt   27900
acttgtacca gtaccggctt ttccaaagga tttgaccctg gtaatgagat gaggtgatgg   27960
gaaggcaggc cccagccctg ggcatggact ggtgtaactg gtaaactccc tcttaaatcc   28020
ctctgttcaa caggcctctc gctcccatgt cctcagtggg gtgaattgtt ctcgaggaga   28080
gaattttaag agtgataaac aagagggatt aaaatgtccc ctccaccagg tctctgtgtc   28140
cttataaaag gctataataa actgtcattt tgcaggtttt ccttgtgctt tgtgggcaat   28200
taaggccttg tttatcattc tcttggtggg agatagaaaa ttactggtct ctccattcct   28260
tgggcagtcc agcttagcaa ccatttccca agcattgatt gtatgtgtgc ctgtcctcac   28320
agctgagctg agtgatgtag gtggagcaga aagggcttgt gtttgttgcc ttagtcctag   28380
aacccacaag cttctggaac tctcttcagc tccgaataga aggaatgcca aggaagatga   28440
atgggagttg accccgagtt cactcttctg gatccttgag ctccctcagg acttgttaat   28500
gacgagcggg gggggggggg gggaggtagg ggggtgatgg atgggtggga ggggcaacac   28560
ctcacacaga acttaccctc aggtcttagt ttagtaatct agagtttgca ctgtcactgg   28620
cggcctttct gagacctcca ggctgagcta ctcttgacct ctctagactt gagaatgctg   28680
ccaagggcat cgtggccctc tgtgtttgtg agttgacttt gttttttgg aagcctaggg   28740 tttgatgaag gagctccctg gctgcgggga tcagtggcag ccatcagtgt cgcctgcttc   28800
tctctgccct cgtgttgata tgagttgatt tctgtgtgag gaaacagctg aggagaactg   28860
agaagtaaga ctagggatgg aagggccggg ctgtgcccct tgcaccatct tcatgtgcac   28920
tacagagtgg gtgtctgcct gctggctccc tctggtcccc agatttgggc cctgggtgta   28980
ctgtgcatcc cccatctcca cggttacttt tctgactgca agtctctgtg ctgatttgga   29040
gtgtcagata taggcaggcc agggacttag gacctttgga ggttcttgga cttagacaat   29100
tctcagtgac gtgtgcagga atgctgggct tgaataccat gcacgggtga gtggggttca   29160
tttggtgccg taggtatcga gcatctggga ccgagatgac catgtagctg ccgacttgca   29220
cacttcagag catatcgttg aactctgtgg tgtcaccatt tgcacagcag ctgcggtatt   29280
ccggtgactc ctgcccagcc tggttcttgt gaatagcccc tgttcctacc acacaagggt   29340 gttttgaaa aagaccatga ggatggacgc tggtcaggaa atctgagact agtctctgga   29400 tttccctgc ttggttttgg gaagttgcca tattttgtga tagcatttaa caatcacagg   29460
attttgtttt gttttgtttt gttttttttc ctttttaata taacattgtg tcttagactt   29520
ttttgaaatc tacctctgga tgaacaaaca ctagacattg tcttcttcac ttaaaaagca   29580
```

```
ccaagaagtt taagctaaaa gacattctgc ttcttttggg gggagggtag caagaaaatt    29640
atatatactt ataatttttt ccagtaaggg tacttaaaag cttctattta aaattatggg    29700
gtttaaaaac tttaagttgt acttaaaata cttttttttt taaatatctt ttaatagaga    29760
gggcttacta aaagaacagg gaattgttgg caggcagaat ttgtcttgat aagaggacag    29820
atagaggtag tacgacagat cagctagaag gctggcccett tgagcctttg gatgggaatt    29880
cttcctctac ctgaggcttt agcacactga gccatgggct tgtaagcccc gcgtctgtct    29940
ttgttagtgc catttcttcc ccagatggat gtccatgctg aggaaataca ctggggcttc    30000
ttggaaccat actggcacct actgaccagt ggatgtgcca ggagcaaaag tgcttactgc    30060
gagaggagag caggcatgca tcctccctca ctgcgagagg agagcaggca tgcgtcctcc    30120
ctcactgtga gaggagagca ggcatgcgtc cttgctcaag tttcctggac agtttccttt    30180
tgaggagttt gtttttgcat ttgttggtta gttgcacatg attttgcttt tgtccaactt    30240
cttcagtcag tctcccctcc ttgatacaca tggctaaagg tgcacagggg ttgggtcgga    30300
gggaatatca tcatgcacac aaattttcct ttattttaaa gacttatttt agttatatgt    30360
gcatgtgcca cgtgcacatg agtgcaggta cacaccgaag tcagaagagg gcactgtgtg    30420
ggtgctagga ggagctgtgt ggcctctcag ccacttgccg tctccccagc ccagctcat    30480 gcgtattta agacagaaga aacattgaaa ggtgttttag ttttgccgag atcagaaatg    30540
tacaattcta ctttctcaga cttttattct tgttaaaggc taagatgtgt ctaactgtgt    30600
tcctctgttt attttacttc tcctgacaaa cgtaaaatct gtgttagagt ctcatttcag    30660
tgtctccatg ctcagtaaaa tggaaacctt tgaacatttt aatcacggga gctggtggtt    30720
gagtctgaca gtaggttttt gtcttagctg tttagtttgt tgaatgtcag tgactatgca    30780
ccttccgtgg ttcatacaca tggagatgag ccatctctgt tgtcaacacc actgcctttc    30840
aagaactttg ctagacgtga gggtgagagt atgatacacc tgcccaagcc atagtggaag    30900
cacgtggaag caaatgattc ggaatgcaag taggaattag caagctagag aggggtcgca    30960
tcgttcagtg ccgtctagag ggacagcatg cagtggtgcc attaatagac tgacatgtcc    31020
tggttcttct gtgggttttc aaaccatatg ttgtatatag tgtaatcttt aacatgcaag    31080
ggctgaaact tacctagttg aactcatttg cttcagctca caattggggt ctagttgttt    31140
tttctataat cccgataaga gaaaagcaga ggaggaggag aagaaggagg gggaggagga    31200 ggaggggggaa gaagaagaag gaggagaagg agaaggagaa ggagaagaag gagaccacca    31260
tcaccaccac caccaccacc attgtatagt aaactctggt gttacatagt acattgatga    31320
gttcaggttt tagaatcaag gattaatatt tcatagaaat gaatttctgt ataaaatgaa    31380
aatcctagat gctgggcatg gtgactcacc tgagaggcag gcaagagctt tgccaggagt    31440
tcaagggcag cctggatcac acagtcagtt tccggccagt ctgggccgga gtgaaaccct    31500
gttgcttctg ttttttcccaa accacagcag gtttcatttt tgggaaagca gctgggacgg    31560
ggagccctct agatgtcctg tctgcatcag gaatcggcat attttaggtc agaaatattt    31620
tctactggtg atctctgaag aacgcagaga tccttgacat attaggggag gcataaaaat    31680
ccgtgtctcc ctggttgctt ttctccttttc ttttaaccaa gactgatttc aggagggaga    31740
caactactcc cacgttgctt ctgtttaaat gtgagcttct gtgcttctgt ttgtttgtat    31800
ttttttttca tggctgacac gcccctccccc ctcggcggct gcccccccaaa aatggaataa    31860 aaaacaaagt ggaagctttg ttgtttgaaa ttgaagggtg ctgtgagaat cactgcaaat    31920
ccctgctgtc tccgcctgcc ctcagttctc ctattttggg tagtagtgca agcagtcatt    31980
```

```
ttagaaaaca tggccgtgtc cactggacgg cactccttcc agaggccctg tgccagaagc    32040
aacagaggga cacacagcca agtcccagcc agcaacccag acttcagctc tcaaattctg    32100
ctacttgaaa tttgcataaa cgttgaaggg agaaaagaag cgccctgtgt ctgtcactct    32160
tctactttag gctctgcagc cattcagagc attaaacctc gtctgagggt gcagcggatg    32220
agcgcgctgc aggcagaagg agcagggtat gaaaagagtc atgtgagtca gacaacagac    32280
agaggcttat ttgaagaggc tacaaagcaa caagtattgc caatttaaaa cattgcttgt    32340
cagagcaagg agtgaaacac attgtaggct gctcagatta caccgtctgg ggtaccagac    32400
ttaattactc atgtttgaga ttcttaaaac aaagggaggc ttttaagcct gtgatacata    32460
gctggcacgg cccaaaaagc tccggaaagc ctagaaaatt gtgatgggga ctccatcaag    32520
cctggatacc ttcagtctgt cttttcgaag ataaattcct ggtgcgttgg acctggtaaa    32580
gatcactgac tgatatgtac cttgttgtct gcagtgtttg tatacagtgg aggctaataa    32640
atgtgaatat gaagcctcgt ctggactgaa tggcttcaag ggtctgtgct gttttcgtag    32700
ttctttgtag agaggttttg acagtgagtt ttaagagggt atactgaagg catccaataa    32760
aagccatttt tgctgtgttt gtattttttct ggagtcattt ggctaggtcc ctttctctct    32820
gttccatctg tcccttccct gtaggctgag aggatggtgt atccagagac tggttcattc    32880
atggttggtt ggtctctgtg tattgctggt tgagcgccat gctcgtgtat ggagtggccc    32940
tttgctcaag tatagtactg gctgtacatt tagtgaatca tttcttttt attgccctt     33000 taggaggata gcagtaagct ctgcgtggct tgtgtgtttt attagagggc tggtgatggc    33060
atctgggagg aattaatccc atttattgat atcatactct atattaaatt gtgtcatttt    33120
cctttgaagt tgatgtgctt aaacagggca gtttgttccc ctcccacttg aaggagcagc    33180
tgtgacctga ccaggccttt ggtgacttat cccatcctag cctccatggc cttttcttg    33240 tgactattgt ttaatttgcg atctcaatcc ccaaatgtat gttagttttc tgtgcctggg    33300
ttcctgctca agtgggcttt tcttatctct acctgagaac ttttttcgtt gcttggtttt    33360 gtttttttt ctagaacata ccactgtcta aagaggcttt atttacattt tgtttgttgt    33420
tgcctgtttt cccctaagag aagcagagtt tgtgagagtt tgctgactac agtgtccctg    33480
acatcagggc cctgcatctg catgctttgt agatgtgctg tgttctgaat gggtttcagc    33540
tgagggtggt ggcacccacc tttgatgtct gcactgagga ggccgagcta gatggtgctc    33600
tgtgaatttt gaagctagcc tgctctacat agtgagttcc aggataacca gagctacagt    33660
gagaccctat ctcaaaactc cgaaaaaaga aaaattctag aagctttctt ctacgttttg    33720
tgtcacactg ccaagtgacc gggcaatgag acacaagtcc actttcttgt gtttgctttt    33780 cctttttattg tggggtacat gtccagaaat acagaccgtg gtctgaaaga ttgatcttcc    33840
tctgctactg tgtgcagcct gagaagaaaa gttgggctgg tgtctcagac tccatccact    33900
cttggatttg attggggctg gagagccagt ccaggtactg atttaacagg cgcctctgat    33960
gcatattgaa gtttgaaaac tgtgactggg gaaatgttaa aggttcaagg tagtagaatc    34020
ccagaaacca gccaagtggc attaattatt agcctggggt gcccacccttt tttttttttt    34080 ttttttttgg tcactgactt ggattggttc tctaaagcaa ggctgtaaag ttatttgcta    34140
ggtagatagg cacatattga ctctaggttg tgtgtattct atgaatctgt cactgtgatt    34200
atttgccagg acacctagta ggaacaggct gtgattttt tttttttcct ctccctgccc    34260
acagctgagt catgggtggc tggggtcctt ctgctctcct ggataaattt ctctttgtat    34320
```

```
tctgcctatt tttatgtact tgttaaaact tggtgtattt cgtgtcgcac gcctttaatc   34380
tcagcacttg ggagctagag gcaagcagat ttctgagttc aaggccagcc tggtctacag   34440
agtgagttcc aggacagcca gggctttaca gagaaaccct gtctcgccaa acaaaaaaaa   34500
caaaaaacaa acaaacaaac aaaaaaaaac caaacaaaaa caaaaacaaa acccaaccc   34560 ccccaaaaca aaacaaaacc aaaaaaccctt ggtatatttc ttaacacatt atccctgtgt   34620
gtggtgtaat gcttatgcat ttgtgtgtgg tacgtgcact gagtgtggag gtgagtgacc   34680
ttgtgtgcac acgccaggtt cagaggggga gctgctgcct ccctctgctt ctctttccct   34740
cactgtcttg agacagggtg ttaatctgag ctgaagctgg cttttgggat tagcctggcc   34800
atgcagtgag ctcttgggcg ctgcccccat ccccctcttc aggttgagat cccaggcgtg   34860
cacagccatg tctgactctt tgcgtgggtg cctggggggg tagtgggggg gttgatctca   34920
tctcttcact cttgcacagc tagcgctctc cagctgagcc tctgcagcct cttttatgga   34980
gtgccactcc ctgctggatt acaggggact ctggggcgg tcaacctaga ttagttcaca   35040
ggtagggaat ggagcccagt gaggctgtct tgcctgaggt taccagctag gtacaggagg   35100
caggactcat gatggctttt gcctgttgga attcttgtag gggactgagc tggaacgctc   35160
tgtgctggtg gtacagtcct ttcctgagct gttttccttt tttaaataag aggaagagga   35220
aaaggcaacc agaagagagc taataaaagt gtctcaagag gatgaaaaca tgagtttgag   35280
cgctgcagta tggaggaaat aacctgacat tactgtttta attatggtag ttgcattgga   35340
gcttatcagt gtgggaagag ggagcgctta tgccttacag ggaagtgggc cgtggatgag   35400
aagatgtgcc tggctgtgcc tgttgagtgc acagcccagc gggtgcttct gtgatgccaa   35460
cagctgtcgc agagatggc cgggcttagc gagaggcctg gctctcaggc tcagtgctgc   35520
caccagatag gatctgatac ctcatgagga agccacttaa cctctctggc cctcactttc   35580
cagcacgtgg tcataataac acccgcccag ccatggtagt gggaagtagc ctgtctctgt   35640
gcataaggac agtctctggg cctggtcacc ccaggccagt gttgtatctg gctctggctc   35700
actgtgatga tctcacaggc tgcctgccta cgctgcttct tcagctatga cgtagggtgt   35760
gatgaaatga accatttcag ggttgttgtc aaagctgaat tagttcccgt gtgtacagtg   35820
cctgataaat aaacacttct aagaggggtt tgaatgtctt gaatgttaga ataggttcta   35880
tcttgccttc ctagtagtcc ttaggagtct tgatgtatct ttggtgatga aaattccact   35940
tctaaaagct gaacatttgg atgctgaaag cacctgagct gggtagacat cctcctttcc   36000
tggctgaaat cagtgcaagt tttggggtat ggccattccc ctaccacgc tgagtcggct   36060 gctttgggga gccttttcctg ctaaagtctt ccttgtcgcg caaggggctt ctgtgtgtcc   36120
gtaaatacga agttagtttc tactttgttt acttagtccc ttctcccacc gtctccattg   36180
accaccttct ccttgctttt ttgtgagtcc ttgaaatgag aggttattgt agtcccttct   36240
ccacagatgt ggtttctcct ttttctggg tcctgttagt ggatgttgat gcttttggct   36300
gcttactaaa gtgcccatt ttattaaatc gtaacctgaa gccaagcagc tcctcctata   36360
gtcaaccgct gtccactcag atcttaagta gtcagtggtg gactcttgtg tgctttgctg   36420
aagtgtctaa atcctgaaag gcccacagcc tgttatggtt ggtacggctt taacgatctc   36480
attgtcacta ggacatgtgt ctgccagaca catggaggca cagagaacga agggcataca   36540
agaccatgag aggagactgt gaggtgaact gtgttcctgt gacttgggag ccaaacactg   36600
gctagtcagt gaagtctcaa gggacgtgca ggggtgctaa gaaaggcttt ctctttggat   36660
cccactttgc cgtcaaaggg ctgtgactgg tgcctgattt ctgattccac tttgtctttt   36720
```

```
atttcagctt tgcagtgtcg aggtggtcaa gagccctgtg taaatgaagg gacctgtgtt    36780
acctaccaca acggcacagg cttctgccgg taagttcttc tgtaatcatc tctctgacag    36840
taggccctgg gcaaggtgtg cttgggcttt ttaaaatttc aatgcttctg tgaagtgttg    36900
ctggctctta gatcttctga tgtagttttt gtgggtggtg aggatggaag ggcgggctgg    36960
ttgttagtga aatggttgag gagagtaagt cactatcctg ccattatctt tatcattgtg    37020
aaagggtttt agtgagtggc tagtaatatc tattgagtat ttcttttatt tttcagtgta    37080
agagatagcc ttttttttct ccctcaaata ccagatatga tcatgttttt aagtcatacc    37140
aagtagatac actctaaatg aatgtcaagt agtcattgga aaactttaat ccccctgttt    37200
aaaaagtcca gttctgaatg cgagactatg gagcaagatg tatatgagct tgtaggatgg    37260
aggaggggcc ggtctatggg tggagcacat gggtgggagg ggatcggacc tggaaacttt    37320
cagtacctct tgattcaaga acacttcctt tctgtttttc caatggtcta atctagccta    37380
atttttttgt ttgagacaag ctgtgagata atttcataca cagcttttc cccacttctt    37440 ctatgtatta ttttcttatt ttaaagacag ggtcccacta tctagccttg gctgcttaga    37500 actcccttg tagacaaggt tggccttgaa ctcacagaga tatgcctgct tctgctcaga    37560
gtccttggat taaaggcttg catcaccaaa ccaagctacc tttcttactg atgtcatatg    37620
ttttttacct cagaagtttt agtgctaagg cagctccatt ctctttacac cagggaaata    37680
agatgtggat aggaaattgc tggtccttt tcttttgacc ttgtgacaac taccccctaga    37740 ttctgacctt acgatctgca ttctttaatg tcataagatt ttcagaaaga tggtcagaaa    37800
cagttttctt caacaaagtg aaaatatttt aaactgtgat gacagtcaaa tttaacattg    37860
gtttgtttgg gttggaatta agatagcatc agaaatggaa gattatataa ctgattgtgg    37920
ctactcactt gagtcttagc caggaaaact acccgacgtg gtacactctc ctccacttgg    37980
aagatactaa gggagggagt tcaataccctc aacagtttgt ctctcgcagc atctgctgtg    38040
tggttggtta ctctgttcta actggctcaa tgtgattacc tgctgagcct cttcttagta    38100
ccggactctg gcattttttg catagctaat acctagcatg gtgcctgcta tgtagagact    38160
gtagagcaaa gtgtcttgtg ccttcttcaa cagcagcagg tctcagcctt cctagtactg    38220
ccaccctcta atatagttcc tcatgtgtgg tgacccccct cccaccataa aatcatttca    38280
tagctgtaat tttgctactg ttatgaatca taatgtaaat atctatgttt tccaatggcc    38340
ttaggcgatc cctatgaaag ggtcgttcaa ccccaaaggg gtcacaaccc acaggttgag    38400
aactgctgtt ctaggatgct gtcaacagac acctatttac ctcaagtggg gcactgaaaa    38460
tggaaccaag aattgatgcc acttaagtct agctagtcca ctggggttcc ttattggagc    38520
acaggccact aaaaggccag ctgccacact gaaaagccca ccagcatgtg acaaaatcta    38580
gagagcctta actcacacaa ctcgcaggac gtgagcctgc tccccccacc agctgatggt    38640
tgtttttgta accctggagc agggcttgc agatcctctg ggtcccaagc ttcttatgcc    38700
ttgtgagttt cattagctgc atcttaccag cccctcctac cttgcagaa taaatgtttc    38760 aattgggagg aaacagccac acaggatcct tgagtaaaaa ggtccataca cacagatttc    38820
agcacatgta atcatttcca tgtctcttat ctgtttatct ttcaagattg attttcccct    38880
gggaatttta cttgctttgt gtggcattgg cctggtggag aggcaagctg gttgggtata    38940
attggactta atgagttatg caggggggagt ttcacataca tgctgatctg cgcatggtct    39000
gatgtgagag gggaggcatc agggagaaca gtgtctgagt actggagagg acacagaagt    39060
```

```
tcacctttaa aaaaaaaga tttatttatt gtttattcta tatgtaagta cactgtagct    39120
gtcttcagac acaccgggag agggagtcag atgtcattaa ggatggttgt gagccaccat    39180
gtggttgctg ggatttgaac tcagaacctt cggaagagca gtcagtgctc ttaaccgctg    39240
agccgtctct ccagcccaga agttcacttt tagagaaagg cagttgctag cctcagactt    39300
gaccagggag gcatggttgt accgacttca ggaagaagcc ccgcatagtg acgtgcatgc    39360
tagaagtggt gtcagcctgg gactctctgt ggtgagtact gtttgtccca gtacttgaca    39420
gaaggcatat taagggtgat ctgtgtgggt tcaagatcag cctgatttac atagtgagtt    39480
tcaggccagc cagggtcaca cagcaaagaa agtaggtttg gaaaaggagg cctaagtgcg    39540
aaagttggca gagccatcct tttgggagac cagcaagaag cctgggcaga gtgctctcct    39600
ctcccatgtg tccaccgtgt cctcaggaga ggtcgtgggc gtgactgacc acggagagt    39660 ggcagtgcag cctaggctga gcacattgct ctctggctcc tcagcatcat cttaagtaac    39720
aatggtgtgt actcacggca cttgtcagca tccttcacca cccccgaccc gagggataag    39780
gtatgcgagt ttgttcagta aatattttca caacatagta agtaagtatt ccaacactta    39840
gaggattatg aaaattacat cagatgtgca gggcatgtga ttgtcttttt atttttttc    39900 cctgaggttg cttagtggat taaggaaaca gagttgaagc caagttcctt ctgtaggggg    39960
tagggtggga attgggagaa aactgttta gagtggaagg tatcccagaa cctgctaagg    40020
tggccttatc ctgctgattc agccaaaacc taatgattgt ttatagaaat tatagaaacc    40080
ctcgataaga tcacattgac agatgcggat aagtactttc aaagataggt tttgtgcaca    40140
gctcaactgt gtggttattc ccccccccc cccttcacac tgtgatgagc tcaaggaccc    40200
tgtcagactg tgatgccagg caaggggaac ctgtgcaatc ttgcatgaaa ctcaattact    40260
gctgctaaat agtcgctgtc agctcttaat aaagtcctct cagtacttaa agttaagaca    40320
ttttattctc tccctgtcct actgggaggt gtaaatatat aattacgttt ggatgtaatt    40380
aatcactttc gagttgtttg ttccaagctt tcaagtataa accacgcaaa tcccatttg    40440 attaaaaatc acgggcagtg catgtttgct agcctggcgg gtgtaggtga ggtcatgagt    40500
tacccagtcg ggacgttcac tctaaggacg tatttatcct gttacatacg gtctgcccgc    40560
tgctccttgt cttcactttg ggctcacgtt tgctttcctt cactctttga aatgactgcc    40620
tggacactgg atgatgcatt cggagtgttt atcccagcag agcttcgtgg gagtgggtct    40680
gttccatccc tgacggatca cttttgatccc actgaggcta tgttacatgg ctttgcttct    40740
gtttcaccct tactgctggg agatggccca catggccaaa tgtgacccct cagaggactg    40800
ctgtggagcg tggggggggg ggggggttg accgagcctg ggatgttctt aacaggccct    40860
ctgttctggc cgacttgagt tctaaggagg aactaactgc ctgcgcagtc tttacagcca    40920
tccaactctt tctcttgggt cctgtgttct cctcttctgc acagtcagaa gccattgaag    40980
gggaagtatt ttcagagttg tgttcagacg ttgcgctcct cctcccaggt cttttctaag    41040
gttttgcctt tcaaattctg tttacctcca tggctcctgg tgccccgcc ctgccctgtc    41100 tctgttagag agatgtccat ggccacttgc tgtctctgtt agagagatgt ccatggccac    41160
ttgctttttt tctgtagcgc tgcaggacct tcatgtagag cagcttgcag agggaaagca    41220
gctaactgtg ggattctcac agtttgcgtc tgtcctgtgt cccttgtagt tttctctagt    41280
gcctttaata tttcatcctg agttgataat tgttatgaac aagagagttg ttctgatgtg    41340
attgttgctg ttcgtgaggg tgcagattgg ggtcgtgaag ggtccttcac cctcgcctgc    41400 cggggttgagg tgcctagcac agtactggga aagggaggaa aggatacatg caaagccaca    41460
```

```
caattgcaga gtccctgagg atggggcttt actcctggga aactccagtt tgtatctaag    41520
aattacattt ttaagtgcat gatgatggat gcaaaatgtt ataaaatata agctgtgtca    41580
cattttatcc aaaccttgtt gctagctgca gtaaacatta gcaactaagt attttctttg    41640
ccaggattag gagtgatgtt ggtggtccag gcatctgaaa tccatccaag aaagctgggc    41700
gggttgcctt cattgtcctc ctaacacgtt aggtatcaca gcagagagca gaggagctag    41760
actcccccag aactcagctc tggatggagg ccctagccta gtgcttgtgc cgcggtggtg    41820
gtctcagaag ggtgtgtgcc actgtggcca gctcagcctt agtccctttt gtcaccttct    41880
cctgagcgca tgcgttgctg tgaggggttgc tgaggatcag ggccatggag tggactgtcc    41940
actgccaatt gctcgcttgc ttccctgcca agctggtcct gccagcctgg tcccttcatg    42000
ttgggtgccc aggttaccag aacatcgtgc gtgcttacgc tctctggaag gtgatagcag    42060
agttagccat acctctgagt gccttcatct tccttttttct tagcgtcttg cagatcttaa    42120
gtgaagagtg gtagctttgc cttcacagg gtaatgtttc ttttcttctt ctgagagtgg    42180
tgcctaagaa tgattaactc ccagagttac ttattgtgca gacagcgatg gctccgtggt    42240
taaaagcacc tgctgctctt gcagaggatc caggtttggt ttcaagcacc cacatggtgg    42300
ctcacaacca tctgtatgta actccagtct agggcacctg aagtcacctt gggcctctga    42360
ggccaccagg cttgcaggtg gtacacagat acgtagacgc aaaacacccc tacacataac    42420
gtaaaaaata aacacatctt gaaaaaccta agagtgactt actgcagtct gtgtgtacca    42480
caggcagcac cccatgcacc gctcaagtcc gtggtagcag ttgcaattaa ttgatgttgt    42540
tctattattt cattcttctt cgggagtcac cagccttttcc cagtccactg gatgacttac    42600
agcagtcccg agaagccctg cagggctctt gtgaggacgg gcgagaaata agttaggca    42660
ggaaacaact gaatctcgta tggtctgttc agagcgagct ggggctacgg tgagtgggga    42720
gagccacagc ctcaggtgtg gaagtcaggg cactgcctga aaactcactc atcagtcggg    42780
gataccttgg ttcaaaaata tcaaagttaa tgcaaaaaat ggtgaaaaat cctaacattc    42840
taaataagga gattagcaat acccattact gccttagccc caggctccag tgtggctcag    42900
cctagtgctt gtgagtggat taagtcttgg aagagtcctg tctggtaaca tgcagagaac    42960
atagatttct atgccagata gactgagtct gagtctactt cctgctagca atcagatctt    43020
tggcagtgta acggctcagt gctagctgat tgttctggac caactctgac atcagttcag    43080
ctgtttatat gaaatgcatg ctaaattctt gttttatcag tcagtatatg gatgctcaga    43140
gagtttagat aatttgccca agatcttaaa actttctatt ttaactgatt caagaggaat    43200
tcttgaaaaa tgtgctgtct ttgtctcagt ttacctatca ataaaatgga accaaattgt    43260
gtattaaact gaaagctcaa acaagactgc cccaaaaaga aactgtgaca cttgaaaaca    43320
tataattact agaatacgat taaatctctg cttttattag ctaaaagtta tgtatatatt    43380
tacttacttt tatgtgtggg cacgcatgtg ctgtggcatg cacactgaga tgagagcaca    43440
gtttgcagat gccagttctc tcccatcatg tgggtcccag ggcctcagcg caggctgtca    43500
ggcttggccg caagcacctt tatctgatgt gcctatcttc tggccttttta gtgcttgctt    43560
tgaaagtaga agtagtggtt ttaggtaggc ctcagcatct cacttaacca tttattactg    43620
gcttttagct agcttaggtt acatgggtga gcctgtacta gtgcctgttg ccattatgta    43680
gatgaaatat aaagagaaag gcagtggaat gtggggtgga aaatattgtt tgtgactgag    43740
cttttcagta gagaaagcaa atgaacaaaa ccttgaacct ccccatttcc tgactgggga    43800
```

```
ctggcaggtc cagaaccgtt ttacacagcc atgaatgaca ctgagatgga cgaagccccg   43860
tgactgcttg gatgttgctg ccaacacaga actacttgtt aaacatggca cttggtgctt   43920
gcacatgaat tacctatgta cgttggtatt tccatcaagg ctgtaccttg tctaactgcc   43980
attccaaagg gagttttatt cacatggtcc tttcagagtc ctttaagctg tgagtctgtc   44040
tgaagagtct tccattacgg tcttgatcac cagtttctta tcagcgcatg gtaagagagt   44100
ccccgtgcgc tatctaagtc ccctttatgc ttttggctga atcagtcagt aaccattgtt   44160
tgatagggaa gtagagtgcc atccgtaggc tctgcctgaa ttctgctgcc tgtcttgggt   44220
agctgccaat aaattaaatc aattaatttt ggctcacaaa gctggcatta atagattgga   44280
atttagctca gcttctttga acacggcctc caggttaacc ataatcctgg gtgaagttgc   44340
ttattgttca atcgtagctt gtcagcgcca tcacttcatg taggagcccc cctgactccc   44400
cacttctctt ccctggggag aagaatgaga aatatttctc ttctggagaa gcttaattaa   44460
attcttcatt ttagttttgc ctatatttgc ccttagtcac aactgaatgg aaatatagtt   44520
attcagagat ttccaagctt attttgataa aatagcataa atatgtgggc atgatggacc   44580
ctttcctcag tgctcagggg ttggaattcc caggaaagaa ggagtgtctc gtctcccct   44640 tgttgcatgc acacatatgc aggaatgagc gtgcacgcgt gtgcacatgt attaggaaac   44700
tgtgttgttt ccaggttttt gtataatttg agttctattt tatatctcac gaaatgtaag   44760
gcaaattaat attcctcttc aatttcacta tactttctag atcatatcga ctgttagtga   44820
cctccctgaa gacgcaggca gccatctggg tctaaggtcc ttggatagga acatccggct   44880
tccccttctg atgccgcagc ttctgtttaa tatctccttc cagaaatagt ccacatggtc   44940
tttatgagaa gggctttagg aaagaggagc gaaggcaagg gcagtggtga tagctggcat   45000
tgctcaatga ctacagaatc acaccctccc acccgcttcc cctcctgtag gaagagaaag   45060
ttcatgagaa cattgcctgc cttggagtct ccgtggtagc agaagcctct aattccacct   45120
cctgttccac cgaggcgctt cctctgcttg actcttcgta cttctcggga tctgtcaccc   45180
aaggcagcta cagactgttt tattcaaata ggaacacccc atgttcccct taggatggca   45240
aggactcgga ggactgcagc cacacatgcc agaggcttct caggcctttc tgtgctgggt   45300
cgtgtgaata gacccaaaag ccccaaatat gtctccatct tggctgcttt ttctgtctaa   45360
attctagttc atgtaatgtt tcactgaacc agtgtgtgga ccagtcaggt ttcaagcgac   45420
agttaagtgg tttggacaaa catcccttga gcacatgtta gcaatgagcg tgtggaggtg   45480
gagtggccag cgtgagaggc tggggaaagg gcccaggcac aggaagagag ggcagctggc   45540
agcaattacc ttccttccct ggactttctg actcattgtg ttgctagaca gagtagccag   45600
gtagcttgtg gctggaaact cggagttcaa gaatctcaga agccaagaaa aagtttgggt   45660
agagggagtg aaacaagagc agagacagtg cctgggcgct atgcgcgggc tccctctgtt   45720
agccaagagg ctaggtatct cacagtcatg tcttctgccc agcatctcac tggccaggtt   45780
caattcatct taggaattcg gagtgagtgg gtatctgtta gccaagtctt gggttacccc   45840
aaattagctc atgtccttta ctgcttgttt cctctaatta tatagtacat atccaaaccc   45900
ccaattatcc agaatagacc aggctgcctg ctccgcgtgg aaaacatttg acagtggtta   45960
tgattttctt gcctagacct tggcagtgcc ttcgtccctc aacctcctgg cccctttaaga   46020 ttgtgaaacc ctggtgcttg tgtaagtcag gcacatctcc ttgaggaatt tcttcactgg   46080
gcagcttgcc ccttttgaaac cttagtcatt ctgagcagta cccaaagaac cttctcgact   46140
ctaatttttc tgccacggcc ctatttgtat ataatatttg tggtgtctga ctcttggtct   46200
```

```
cttattgccg aaacttatgg ttgtgaatgt ctaggtcact ccttaaaacc ggacagccct    46260
tgattactaa agaaaggtga ctcatttcct tccaggcaaa gactggcact gactgtcaga    46320
gtcctaagtt tgtatctaca cacagttcag tgatgcgctt cacatagccc ttctaagttg    46380
ttattggtgg tggtttgttt tagagacaag atctctctcc ttaaccttct ctctccttaa    46440
ccttgcctgg aacttactat gtagagtaag caggctttga actcaaagag atccatctgt    46500
ttctgcctct gctgggatta aaggcttgta ccaccacacc tggctcctcc ggttttattg    46560
gaggtaatga caacatcact gtgacctggg gagggagcag gagaggccct catgctgagt    46620
tgaagggatg tctgaaaatg agttctggag aaaggccttc cccagattta cctaagggtt    46680
gattccctgt gaggggttct tcccagacca ctgtctctcg cacacatgtc agccattaaa    46740
atgtctcctg taacttacct gtaaggcttg agatgtctgc tgccgtgtca ttctgtgctg    46800
aagaaagcag gctgccacgc tggcatgggg gtttgggaa gatgctaagg cctggaaggg    46860
gacagaggtc cctggtctct ggatttcctc ctggtgccct gatggtttgt tagttctgtt    46920
ttgctcggtc ttggcctcct tgcttcctgt gagggcttag ctcaaggtga cacctttagca   46980 acagttcatc tacataagca tccacaggcc ctttggaggg actgctagac tccatgaggg    47040
gtgtgattct tgcccaagga gtgggacttg gagttcttac atcctggggt tgaagggtgc    47100
tgaaggagtt aagtgtcact attgaagtca cctcatttag gaggagggta aagcacactt    47160
agagtccttc ctactcattg tgatgtatat atgacaagct gacacagaat acaaccgagt    47220
gagttcctct gtgttcctct gtgtatccga ctgactggaa tatagacagg attcagttag    47280
ttctcttgac ctcattagga agaaagctgg acatcttatc ttatttttt ctttatggta    47340 gcaaccctt aagagctggt gtgggtagac atatgtgtta tcatggaagc agaccttaaa    47400
aacaaaagat ttgggttttt gtgaagcagt ttgaaagaat aggcattttc attttttaaa    47460
agtccagtga atccaagcaa tggggagatc acagctctcg gtgaggcgtg tgtccctgtg    47520
actccagggc tctgaacaga actgagggca cctgtacaat ttcagagcaa ctgttggaga    47580
ttgtttggtc cagcatctta cttttagaaa atgcttgggg ctcttggaag gccagaagag    47640
cgcatcagag tccctgaagg cagagttaca gagggttgtg agctgccagg tgagttccag    47700
gaactgaatt ctggtcctct gcttgaacag caagtgctca taaccaccga gccctctgcc    47760
cagaaccaag catcttcttt ttaacacaag ggagactgag gatcagagag gtaaagtgat    47820
ttgttcaagg taacatgtcc agcagcagag ccaaggctag gctgaggaaa gggctgtggg    47880
tcagcaactt taccagagag atctggggcc atcctggagc ccttggccaa acattgtaaa    47940
aactttaata ttcatttaga tagacaaaag gtcacaaccg ttggacacac atggctatgt    48000
acgtttgcac acatgtttta tatgtgacag acttggattg tgagtgttta cccacacgtg    48060
tatacacttg tgaatgcacc catgccctca gagtctccca tagaaccgtc ctgaaggctg    48120
ctgggcagtc tgaggagag tgtgggtcca tctgtagtgg cttttgcccac atctctagtc    48180 agtgaagcac cttttccagaa atgatgtaga atgtctgtgg catggaccat gatagttcct    48240
gctgtagact gtcttttgctt acacttgtga ccttggcctt gggctccatc tggaagcaca    48300
gatcagcctg ggccggtcag ctctggcttt gctgtgcttt ctgctactgc cccacaagtg    48360
tctctgcact tcccttttgcc ttcgcttttgg gcacagtgga gtggtaagtt cagcgtgtct    48420
gttggatgtt tagtttctgt agtatgaaag gccacagacc actataaagt ctcagataag    48480
ttttactccc aagaattgat cttcctccct ccccctgata ggcaatgact ctgttttttaa    48540
```

```
gaggagtagt taggaaccat aattattttg cagatgtcta ctgttttagg tatttattta    48600
tttatttatt taggtgttgg caaccaatct ggagtcttgc tgttgtcaaa tgctctacct    48660
ctgagctatg ctcccagtct tgttttttct ctatacagat ggtgtggcat tgggctgtct    48720
ttctgaaatt aagcatactt cataataact gcttctcaag tggcctggtt tctataaccc    48780
tgttttgttt tttgttttg ttttgtttt tgtttttttt ttgtttgttt gttttgtttt      48840
tctccttctc tttcttttgc tctggtcttg ggagttaaac ctaggactc acacagggga     48900
ctcgagggtt ctaccagctg agcattatta tctcttgcag aaatggcctt atttgcagtg    48960
aacaagagtt cacctaaaact gtaagccttt tgcctttatg atgtcagtgg tgtcctgccc   49020
tcgagcaagt gtcagcaaac ttccttaaaa atgctagata tcacatcttt taggccaaga   49080
gtcaagctga cagttctgtg tcactttatg cccatttaaa atgccaccag tgacagttcc   49140
tgagctgatg atccaaacat agatggtgga gtgtgccagc ccaccttagg gctcaggagc   49200
cattggaaag cttcctgttt ccccagaagt gccagatgcc agaaagccac tgtttctgct   49260
gtttgttctt gatttaatgt gcaatgatgt tcttgaagca gaggagctga gatcacaaca   49320
gtgaactacc cttgatccct ctgctgcccg cttttggtcg atgccatctc tggctgaggt   49380
gatgtgtgct agttacagcc agggtttcta ctaaattaac gaggaacatc attcaaagaa   49440
gtgaacacca ctcattttc tttggcaatt aattgttctc attaccatca aagtaataaa    49500
tgttagttgg tgtaaatgcc ataaaagtta tcttttgtgt ggacaagttt tggggttggg   49560
tgttgtgaca gtggtggttt aatagtcatg tttgctctta agagcatctt gagaggcttg   49620
caggtaaatc tggcagagct ggtgctgcct ggtgtctgct tctgggcaca gcaatgcagt   49680
gtgagcctct tacatgggca ctgcaatcaa tttctgttgt atgtgacagt cagagggttt   49740
atgtgcagca gatatgcact ctgaaagctg agtaacacac acacacacac acacacacac   49800
acacacacac acacacatat atattaggaa aatgtgattt aaagaaatct attccatatg   49860
gggtagggca gctttgaata gccttgggtt tatgaaggtt aagaggtagg tgctttgtgt   49920
atcaagaatc ttaattagct taaagatcct ttaggtaaac agctcaaccc agtggttccc   49980
aaacttccag tgtaattgaa gtctggagcc tttaagttgt aaagattatg tggacccttg   50040
catcttgccc tttggcatcc gttaagaatt tgaacagctg aatggcttcc atatgctagt   50100
cactgtgttt ggcacatagg gtatagtaga gaataactct tgtctattag agaagataaa   50160
taattgtagt aaaggttaat gcactgtgtc agatttatgg gaacataaag tggggatgtc   50220
ccttccaaac cttctctttc cctttctctc ctccctcttc ccctttcttc tccttcctgt   50280
atcttcccct cctctccttc ttttgggggt ggggacaggg tcttattgcc tgagcctctc   50340
gagtgtgctt acaggcagca tgaggctgcc agcaggaaat aacgtttagg cagaggcttg   50400
gaggaatttt agggcatggt tgtgacagag ggtggagaga gtggggggctt tgtgactgac  50460
gtgtgcacag gtctggcagg aggcgtgttg gattgtagca tgttctttga gctgaggaa    50520
gctgagcaca gagaacgtac agtgcatgaa gaaaagctac attgaaaccg ttgtttcaac   50580
acaatgcacc aggtcaaagt ctacaaggaa ttcaggcatc ttcccagggc ttgggaatga   50640
tgcacagtgc aggagcaagg tctgcctcca tcagcagtaa tatggaagtc acccagatag   50700
accgttaggt taatcgtaac agcatcttat atacattcaa atgtggacca gatagaactt   50760
agtggtgtaa ggagtgcttg tcaggattac agccctggc atgctgctgc aacacaacac    50820
ttagagcacg catctccttc tctcagacag tttgtctgtt atggtgaagg gtgtgataag   50880
agccgctctg tgatgttttta gtcacattct aatatttttc agggttcagg gcacatggta   50940
```

```
aaggactgat tatttcttct gctacatcaa ggacacaagc ctcagcactg tctgtgtgtc   51000
ccggttccat cattcaaggc tgctgaagag cctgggcact ccgcttgttc tcagagctct   51060
gatgaatgcg ctgagactct ctgctggaag ataagggcgc tcacgacatt ccattgtaaa   51120
taaagcatgt gttcccatct cctcactcct tataccagcc tcctacagag ggtcgagttg   51180
ctgtgaatga gtgggtctga ggtcgtgcct cttcagcctc ttcagtctgg atgtgttagc   51240
atcagtgtgc ttgttgcttt attcagatga ggggtggaa  aaacctgagc acctgtgaac   51300
caagcgaggt ggggctccag aagacgagcc ctggcctccc ggctcccatg tcggtttttt   51360
cctgtgggaa acttttaatt tggaagcatt cagctaatgt gggaatcaag attaacattt   51420
tctgaaatac ttgtacaaga aaggcagaaa cgtgctgtcc aggaagcaga tttacatagt   51480
agaaaaaaat gcctgccttg cagggtttgg tagtctttgt gtgtcagatg tgagtgtgtg   51540
tgtgtgtgtg tgtgagagag agagagagag agagagagag agaatgtgtg tgtgagagag   51600
agtgtgtgtc tctctgtgtg tgtgtgtgtg tgtgtgtgtg tgtgtgtgag agagagagag   51660
agaaagagag agagagagag tgtgtgtgtg tctgtgtgta gggttgatta tatacaggtc   51720
tttgtttcct ttacatcaaa ccaagaaggc cctagaaagc atgttttacc acaaacagcc   51780
tgtttggggc tccactctgc acaccagcgc ttccccttct tactaaggaa ggtgtactgt   51840
ttctttctct ggttttcttt atttcccttt catttctgga agtagcagtg gggaatgagt   51900
gggagtggga acatgggaag atgcatgtga tatgatatgc agcttccatt ttctctaatt   51960
actaggatgt taactaagtc tgtgcttaaa acaaaacaaa acaaacaaaa aacaaaccac   52020
agcaacaaca aaacagtcag cagtgagcac aacccattta gtttcttttg catagagtca   52080
cagagttaag aggctgaagg tctagtgaga tgtggggctg aagttcttga atgaggggcc   52140
atgtcaggtt gcccagtggc ctgggctatt gagtacagca ggggcatttt aggctggagt   52200
ctgaatgctt tggggcatct agatgttttc agcctggctt tgggaaagtt aaaagggaac   52260
tttcactggt tacgctagct tcgcctgtta gcaattaatt ttatctactt taacagggga   52320
acaggaacag ggtaggggtg ggtggcggtg gcaggaaacc tggctggcat catggtcaca   52380
ggaaagaaca gactgatttg gggcccttca aactgtagac ctttgttact gaccagtgtt   52440
taatttggtt tgtgggttct gttagctccc accccattca ccttaatggc tgtctccgtc   52500
ctgggctcag cagaggctgg ctgctgctgt agagtggagg gctgagaggc ccagggcaag   52560
aagaaagtgg gctgaaagct gcgttctgtt taaagaattt tctgctggaa accagcccag   52620
agggagtcaa gaggagcttt aatgaggagc agctgcgctg cgatcagccc acaggagaca   52680 ttttcccctcc atcccacatt ctgcacaggt tttgaaaact caggattttg aaattgctgt   52740
tgtgtgaaga atgcccctcc ctcttgcgtg tggtgggct  tttctttgtt gttgttttta   52800
atgaccagat cctcaccaaa agtaaaaata aaactcctaa aaacaaaacc aaaagggttg   52860
cagtagagcc tggcacaat  ttgggctcac cctgctgctg aacatttggt ggggaaagtg   52920
ggggagcaag ccctggggtt tagttggaag agacgttgtt tccttctcag acttcacccg   52980
tgttggagct gacagagcct ctcactgctc ttggcgtttc tctcgatggg tggctattca   53040
cgtgggaaag ttttctgccc tgtattactg gggagacagc tattgcagat agactatagg   53100
tgggaactgc cattcacgtc cctgcctcat gtcaagaatg caggcctgtg agaggcaggg   53160
gctgtttcag cgagggggc  tgtactgaaa tcctttcgga tggaatcttt tctactgcgt   53220
ttctctcttt cctgccttca ccctgttcca ccatgtgcat gtgaaatgaa cagtaggttc   53280
```

```
ttttgtgtca tcaacagtag acttttaaga actaggtaat ggatgtagcc gtggggacca    53340
ggcagcaagc acctgcctgt gtctgtggcc ttgcctgctg tgctcatctc taaggacaga    53400
ataagacccg tggctgcctg gttctgctgt cttttactta gcataatatt tccagtgttg    53460
taggatgtga caggagtcta tctcttttca cagacaaata atattttatt gtgtggatat    53520
aatggctttt atttctctac tcatcagatg gtgggcattc gggctatttc taccttcagc    53580
tattatgagt catgctggca tggacatatg gacgaacttt ttttttttt aatgaagagt     53640
gctagtatga acatatactt ttagttactg tggtgtgtgt gtgggggggt gggggggca     53700
gaattttaga gaaagatgta tcttataatg gaaagaccaa agaatgttaa agcagcaagc    53760
cagtagtttt acttaaaaag tacatttgct acatagtgtt ctcagtgctg tgatgatgtg    53820
aagaccccag gagggcaggc actcatactg agtctgtgtc aaagagaggg ggccagtgct    53880
gtgctcccga atccatggtg agccagctct gcagtccagg cggctggttc tggggcacag    53940
gctcagcagc accaagtgac cacttagtaa tggaagtgta gtcaacatag taaaggcctg    54000
ccacgggcgt gtgttggtgc aagcagggcc tggtgattgc ctcttcggaa tattttagaa    54060
atgcttatgg cattcgatag aaatcacctt aaggtgcctt aaggttctgc tattcaggga    54120
tgcgtggagg tgggaaaaga gccagtaaca agatgtctgg cctgaggctt taaagatgat    54180
ctgaattgct atcaagaggg aaactgtgaa catgagtgat aagcgttaca ggaattcggt    54240
taacaagact tgtcagacac agcaattata taaacttca agggattaaa taaagtcga    54300
attatgaccc ctagaaaatt ggaagagctg aagtttcatg gaaaaatgat gttttcctaa    54360
tgtttgtctt taagtcattg gcaggacata gtatgatagg tgaatggttt agaaagctaa    54420
actggtgccc tagagtggtg tcctttggca tcttttgtgt ttaaatcatt gtaaaatgac    54480
aaacattaaa tgtatagtag agagaagagc agtgtggccc agagttgaat tgaaaatgac    54540
catgatggaa gaggaaagag gtagactaac tttgccaggt cttgtgagag acatggtcac    54600
attccagatg gtgcgggaag tgacccgcac agcttccagt gggaatgggg actcacttat    54660
agtgagcaga gaagtgtcag ctaagcctga ccaagtcgga actctcagaa ggtgatcatg    54720
gagcctgctg ggctgcaggc tgtgttctga gaactgcgga cggtgtggat ggagagaaag    54780
aggactgtct gcccagcgtc cgagaagcct gtttgtgcac aggatgcctc catagaagga    54840
aagggcagag ggacttagtt gaaaaggtaa gttagaagag acctgcatat attttaagct    54900
aaacacaaag acacagagga atggtaaact caggacattt taattaggaa attggatctt    54960
caccaataag aaagtctagt ttcatataaa gcgaggtggt tctgcccatg ggctttagag    55020
gcctcttttt tttgtttgtt tccatttat ttgatgtttc caaacgtaaa aaagaaagtc     55080
aagattctta caattcttac aacagttcga atacaaccct ctcagatgag accatgcaaa    55140
gcaattcttg tacacatacc cttttctctc cttcaccttt gctgcttcat acggtgtgac    55200
tgacaactgg atggcttgtc cttggtggga aaatgccatt tctttacacc accacccaac    55260
aatttctact tttctgcaag tcaatttta acaagttact ttgctgtttt cttttaaaca    55320
ttaggaggca catggaactg ctgtgtgtca tcccaaggat tctggagaac cctgaccctg    55380
cacctcgact aagggcttca tgtccttgcc agcttgcagc ttccctccgt cgttactcct    55440
tatgccctta ggtgtggcag tacagggtcc cttgccgctc cttggctaag ctagggttgc    55500
ttccatcctt aggaccttgg tgcttggtgc tctgtgtccc tttgcctcac acactttccc    55560
ctcagtcagc agcctcgggt aaaaggtaca ttaggcagaa ggaaagctaa atcaggaagt    55620
ggtgtggggc tggagcaatg tctcagtagc tgagagcaca ggctgcattt gtcatggacc    55680
```

```
tgggctattc cctagcaccc acagagtggc tcataactac tgtaacccca gttccaggaa    55740
ctcatcacca cactctgggg aaccctgacc ctgcaccacg actaaggcct cattgccttt    55800
gtctctgcta gactttacat ctatgagcac agaggttttt ccagcacagt tgttcctcaa    55860
atcagctggg cattggctcc aggaatccca cagtctttgg ataaagttac acagtctttt    55920
tttttttttt ttagaattat ttctttattt tatgtatata agttcgttgt acctaccttc    55980
aggtgcacca gaagagggca tctggtccca ttacagatgg ttgtgagtca ccatgtggtt    56040
gctggcaatt gaactcagga cctctggaag aacagtcagt gttcctaatt gctgagccat    56100
ttcttcagcc cgacatagtt tttttttatt caacctgtgc ataaactccc acattaaacc    56160
atctgcatat tacttttaat gcttaatata atgttagcac tgtgtaaata gctgccatga    56220
tatatatttg gggaatggca aagcaactga acatggctag tgcagatgcc atcttgccca    56280
tttttgacct atggttggtc gagtccttgg atgcggaacc tatgtgtatc catgactact    56340
aggaaaaaaa aataaaaaac aaaaaacgcc tggcacacag tcagtatttg ctaagcgttt    56400
gctctaacag ttaatgaatg ggtttaatat tttttgtact aaactagtat tcttcatcat    56460
cattaatgtc atgattaata agcatattgg atgctattaa taggctccat gtcttctcta    56520
ctgaggaatt ggcaaacttc tgcaaagttc cagggactaa atattttgt gggccatgtg     56580 gtctcgctgt aaatactcta ctctgttgtt gtggcagcca tggccatctg caaatgagca    56640
agcctggcag atctccaacg tgactattta tggatgcgga aatgggaatt tatatatttt    56700
ccaagtacca caaatatga tttttttaaaa gtttttcaag catctacaaa tgtaaagacc     56760
actcatggtt tataggccat acagaaacag acccctaaac accagacccc taaggactcc    56820
ttgcttcttc tccactgtgg ccagcttctt aaacaccatc tacttagtgg aagcttatct    56880
tctgtacttg gtagggaatg gctatttgga ttaaacccta gaaattcatc tcggaggtcc    56940
cagaactttc ctgctgatcg tttctgggtt cctggggacc ttgttctcat tgtatgttca    57000
tgatgttgac atttaaatga ctttgcattt tctcagccga tgacacatgg cagcgctggg    57060
ggtggcgcaa cagtcgagga gcagagctgg gcagagccca cccgggttta caggcacgcc    57120
attcttcaca cggtgcatgg ttcccaccct ggaagatcaa caggcctgat gcccagaggc    57180
ctgtagctgt gagtgggagg tgggatacag cttcttagca tcttccacaa cacatttctt    57240
gaataagccg caagtgcttt taataatccc ttgcagggtt aattttagcc atgccacact    57300
ggtgttctca gtgcctctat ttaagaaaaa gaaatccagc gaagcctcac agcctattgt    57360
caaagcaagc tgtgatttgg ataaggcaac atattttcct cagcacgcat gaagagaaaa    57420
atggttttta tttgctgagc attttaatgc ttataatttt ttttccaca tacttgagtt     57480 tgcctggttc tcacacaatc ccacagtgta agtggccttt ttaactattt aagatgtcag    57540
tgaggagaag cagttagccc aaagcctgga ctcttcttaa aattaagtaa cttagtttc     57600 attctctgtc tgtgcatatc tgtgtgtggg tgtgtgcgtg tgagtgtgtc tgtgcatatc    57660
tgtgtgtggg tgtgtgcgtg tgagtgtgtg tctgtgcata tctgtgtgtg ggtgtgtgag    57720
tgtgtgtctg tgcatatctg tgtgtgggtg tgtgcgtgtg agtgtgtctg tgcatatctg    57780
tgtgtgggtg tgtgcgtgtg agtgtgtgtc tgtgcatatc tgtgtgggg tgtgtgcgtg    57840 tgagtgtgtg tctgtgcatatc tgtgtgtggg tgtgtgcgtg tgagtgtgtg tctgtgcata    57900
tctgtgtgtg ggtgtgtgcg tgtgagtgtg tctgtgcata tctgtgtgtg ggtgtgtgcg    57960
tgtgagtgtg tgtctgtgca tatctgtgtg tgggtgtgtg cgtgtgagtg tgtgtctgtg    58020
```

```
catatctgtg tgtgggtgtg tgcgtgtgag tgtgtgtctg tgcatatctg tgtgtgggtg    58080
tgtgcgtgtg agtgcagggc aggaagccag aggcatcagc ttctcctgga gctggagtca    58140
caggctcgtg agttgtctgc tgtgcggtgc tggggaccaa acttggatcc tttcaagaac    58200
agaatgctct taactactga gccatctctc agccctgacg cctggactct tgacaagacc    58260
tgtgcccttc tgaagtgcac tccctgtcca cagccagtct gttggtttca tcactgtgaa    58320
ctctgctcct tgcctatctg gagagtgact tactgatgaa gaagctcaag agtcctgtcc    58380
tctctccccc tcccccacca ccgtatagag ttctgggaag gggcaggagg ccttcgctga    58440
tgacctcaca caccgtccct gtttaccagc tactttcccc accagtcgtt atagctactg    58500
cgcaattctt ctgagcatgt tgtcttagtt ccccagtttc atgccttcct catatttttc    58560
aaaaaccttc tggctaatga ggtgtctttg gtgtgcttgg taaaagcagg aaggaattca    58620
gtgcttccag tcatcaggga agacatgaca ggagctgggt ctgtgggtga aggcttggtt    58680
taaagatgtt ttaggtagga gtggaacagg cttctatgtc attctcctgt cctccaaaaa    58740
gtaaaattga caagtagatc actcaggtat ctggggttcc agccaaacag cgcacattat    58800
agtgagaagc acagtcttta aatgtgttct tgttacgtag tcgttagtgg tctcgattaa    58860
acaacttcac atccttcctg aggctgttta gagaacattt ctgtaagtga ttcctgtgtc    58920 tatgggtgt ctatgtgtct tacagacgag aggaacaact tctcaatgaa ctaattggaa    58980
aatgtgggag aaagttgttt tgaagcaggt tctcatacag ttctggctgc ccttgatttc    59040
agtgtgtggc ctaggctggc cttgaacctc ccaaaccctg ggttgcagg tgtgtgtcat    59100 cacgctcagc tagagtgttg ttcttgaatt agttccctgc tatacacagc tgtttacgtg    59160
ttacttgaga ttttctatgc attcttcatt atacccagtt tttcatttgc ttagttatca    59220
acatttatga tgtctctttg aacccctcct gaaccttcct ttcctcctct gtgtcggtct    59280
tagctacctg aatgtaatcc agcgaggcaa gtgcagaaca gagagagaga gagagagaga    59340
gagagagaga gagagagaga cctaccatgt cctagcactc agttgtgaag agcccatga    59400 tggcagctat atgttaactg ggaggtctgg agggctcagt gtacttgtta tcatgaaagc    59460
gtcatagtcc tgtccactgc ctcgccagca tgagaaagtt acggccacaa aggaggcagg    59520
tcttcatagc actgtataag gagaccatct cagcctgtgc tgatggacag atgtggtggg    59580
tatattttac ctctgaggaa gggtcgtgct gcctggctgt agttgaccct gctgggtcac    59640
ccgtctggta ttttgttacc tgccaggact cacagggact tggagatata gtaaattctc    59700
tgagtgccac ttccgcagtc agggagtttg tagattgtac ctttacacgt ctttgtttac    59760
acttgaatat tttcttgcat gtacaacatc gttttctggt ctttggactc acaagaaatc    59820
aggtggtttt catggatttt tccttcttc ttaatacaga tgtccagagg gcttcttggg    59880
agaatattgc caacatcgag acccctgtga gaaaaccgc tgtcagaatg gtggtacttg    59940
tgtgccgcag ggcatgttgg ggaaagctac ctgccgatgt gctccaggat tcacaggaga    60000
ggactgccaa tactccacct ctcaccctg ctttgtgtcc cgcccttgtc agaatggggg    60060
tacctgtcac atgctcagcc gggacaccta cgagtgcacc tgccaagtcg cttcacagg    60120 taatgggttc agccagagca cgtgcttttcc ggtctccgtg gtgacctgta ctgtgcacgt    60180
ctagtcctca gtgccttacc ctgtgttagc tacttctcac tgctgtcata gaacacttcg    60240 atcacacgcag ctcagagcac cacagctcca agaagagttt gttttctgtt agttctagag    60300
gaaggataca tagtatctag ggaaggtatg ggggtgggt gggaggtggg ggctgcaccc    60360
tgtcagaaag ttggctggtc aggtttcaac cccagatagg aagcagctca gctcacagcc    60420
```

| | | | | |
|---|---|---|---|---|
| tgcccttgtc | tctgggcttc | ctgcagtagg | ggctccccag | gcagcagtgc cagctgttag | 60480 |
| ataccagcct | gggagggatg | tttctcattc | aaactcccac | acccgggtcc cccaactcca | 60540 |
| gtgcacgttt | agcgttataa | tacaagttgg | aatatgggga | aaaggctcag ggacacttaa | 60600 |
| aaaaatctgt | taatagataa | atgttagcta | ttttaaacaa | gtaaaaggtt aaaaatatgg | 60660 |
| ttaagaggac | ataaaatatg | tgagatcttt | tatatagtat | agaaagaaaa taattcaaga | 60720 |
| acattctaaa | acatctttta | tattgaggca | ctgagaatct | tctaatttgt cagatgagca | 60780 |
| gtcagtgcgt | cctctacctt | tggagagttt | gaagggatag | aggggagaa aggaaaaagg | 60840 |
| tcagacacct | tgaagtttct | gcttagacac | tggcttttct | ggcttctcca actcttcttc | 60900 |
| tccctacaac | ttactgacaa | aaggagaatt | gtttgtcatt | ttggtccctg ctggagacac | 60960 |
| taaaccaatg | gttctataaa | tctataagcc | aaaatgaaca | gggtgttcaa aaaattagac | 61020 |
| ttcctctctt | gtgcttgaag | aagcatggtc | ttgtttctct | aagaagtgct caactcggca | 61080 |
| accatcagca | gacatgactg | agagctgtgg | ggtctcagct | ttgttgctgt ggtggctggc | 61140 |
| atgggtggaa | ggacacagca | ttgggtgggc | attgagggca | gtttgaagag gtggcagctg | 61200 |
| ttgggcagag | tggtcaacag | ccagtaaaca | agaggcgttc | ccagctgaga agcagcttaa | 61260 |
| cagcggacct | ggagctagga | gagcgatgga | tcctgacccc | gggctgcagg actaatggac | 61320 |
| tcctgccggc | ctggcttcat | gtagccaaca | ctcagtcccc | tcaggtgccc tgtcccctga | 61380 |
| gtctttgagt | ctcaccttaa | ggcctcagcc | tctgaaaaac | accatttgtc tgaagatctt | 61440 |
| caggtgacac | tgctatgcgc | tgtagaatcc | aaagtctagg | ggtctccatg taaggtcttg | 61500 |
| ttgttcgctg | gctgggagac | agagctgctg | agtgtggggc | tggctcccett tgcgagtggt | 61560 |
| actaagttct | gttaccccttc | ctttagggaa | gcagtgtcag | tggacagatg cctgtctatc | 61620 |
| tcatccctgc | gaaaatggaa | gcacctgtac | atctgtggcc | agccagttct cctgcaaatg | 61680 |
| ccctgcaggc | ctcacagggc | agaagtgtga | agctgatatc | aatgagtgtg acattccagg | 61740 |
| acgctgccaa | catggtggca | cctgcctcaa | ccttcctggt | tcctacagat gccaatgtcc | 61800 |
| tcagggcttc | acaggccagc | actgtgacag | cccttatgtg | ccctgtgcac cctcgccctg | 61860 |
| cgtcaacgga | ggcacctgtc | gtcagactgg | cgacttcact | ttcgaatgca actgcctgcc | 61920 |
| aggtgaggag | ctctctcttg | gctatggagg | tgggggtaaa | ccaacctcag gatgaaggtg | 61980 |
| gagggtgtac | ttcccagagc | ctcctttagg | aagcaaagca | gggggaagga gaagtgagag | 62040 |
| ctttgtgtgg | ggtgggttgc | tggcgaggga | ggggttttat | gggctcactg tggtccataa | 62100 |
| gtagagcagg | gggtaatttta | acatgtcaag | agtttatgac | gatgagtgct tagaaaattg | 62160 |
| tttattgtcc | cttttggaga | aacagttcta | agaaacggcc | aggaagatct ggagtgggga | 62220 |
| agacggtgag | aaccacacac | tctgtgtgtg | tgtgtgtgtg | tgtgtgtgtg tgtgtgtgtg | 62280 |
| tgtgtgtgtg | tagtaagcac | tgtaagccaa | agtgacacca | agacgggagg atcagctccc | 62340 |
| ttttatgctt | ccgcaccccc | accccacac | agaatagtta | cctctcttgc gtcccttcct | 62400 |
| tgacttgggg | agagggtagc | ccttcccacc | ttgatatagt | agttaaccct ttcaccttga | 62460 |
| catgggagtg | gcccttccca | ccttcaagct | gtggagactt | gaaagaagct cttctgttaa | 62520 |
| ccaaggcatt | ttctgacaag | ctctggttga | catcgtggga | gaaactaatc acgacacaac | 62580 |
| actttgccat | tctcttggct | gctcagggtc | ctaggtacac | acacaaccca actctgacac | 62640 |
| acagaggagt | tgtgtttggg | ggcccagagt | ctggtgatcc | ttagagggag aaaggcgcaa | 62700 |
| gcctggccag | ctcacttcac | tccatataaa | agtaatgagg | atgctgaaaa gcaagaattt | 62760 |

```
tgattgggaa cagagcacaa gcagctggag cagatgaatt actaagcaac aaagattctg   62820
tttttataca aataccctta gcacaaaaac aaaagagaaa actgtgtgtg gggtgtgggg   62880
tgtgtgtgta atgtgcaaaa taagcaggat tgcctcaaaa agaagttgtt cagccactct   62940
tcgagtggga gtcctagact ccggtgttga gtctaggact caacacataa tcggtttgtg   63000
tgtgtcatct ttaggggctt aaaggtcata ggtcaatcct tagtagaaaa ccaaatggca   63060
atttatttga aactcttttg gtttgtttat tttatgttta agagtgtttt gactacatgt   63120
atgtctgtac actacatgtg tacctagtag ccaaggaggt cagaagaggg cattgtagtc   63180
cctgaaaccg gagttacagg tagttgtgag ccaccatgtg ggtgctggga actgaacctg   63240
gatccgcacc cagaccagca aatgctctta atcactaagc cctctcttta gagcactgat   63300
tttcaacttc ctaatgctgt gacccttag tacagttcct catgttgtgg tgaccccaac   63360
cgtagaatta ttttgttgct acttcataac tgtaactttg ctagttatga actgtaatgt   63420
aaatacccga tgtgcacagt atctggcccg tgttgcagta agcggcatgt cagaacccta   63480
agtcaagctg gtcacttagc caagacagaa ggaggtacat ttaatcatac tgctttagtt   63540
tctctttcaa tcaagaataa ataaccatca ttctacatgc taaataaaca tttagtaaga   63600
attgctgtca cctatattat catgtagaag gagagactat gatatctttc tttatatttg   63660
catttgtttg catttttagga cttaaaaaca gaaagagaaa tataaacaac ttcctttgta   63720
gatattttaa tattgcagac attctaataa cctaatgtaa tggcccaagt ggctcataat   63780
tgaagttagt gtgatttatg ctgggggct gtgcgccatt ttcagtttca agaaaattgc   63840
ttttaatagt tgcctagaac aagaggctgt ttggcagcaa gatattgacc ggaagttaga   63900
gaggtcaata aaggaagtct ttagctgggg agtgattatt cacccgcatt gttctgcatt   63960
gttatccact aggcacgata aagcacctca gggaattctg agagaggtca ggaaaggctt   64020
gtcaaatgag aatggctgct cctccttgag aaaggaaata accagggatt ccacagccag   64080
cggactgcca gggctggagt ggtggagtaa ggaggtttgc ctgaattcca tgctgtgctt   64140
ggtgtgtgtg tgtgtgtgtg tgtgtttgtc tattcgtgtg tatgcacatg catgcatgtg   64200
tgtgcacaca tctctaatac tttggaggta ggtattattg tttgagtttc tcagaggaa   64260 gtgtctagag tctggcatgt taagtcactt aatgagccac agctgatcct tcctatagaa   64320
gcagagccct ggaacccagg caggtcattt ccaaagccag cacctggtgt acctggtggc   64380
cgtcacactg ctcatctgct tctgaggcca ctttggcgtg tttgacatct cattaaatgt   64440
cttgagcagt ttggattaaa attaaacgta gtttacatat gaggaaaaga agacacttcc   64500
attataagca attagtgttt gttttgcatt agcccaggtg tactgcacac agcacagagg   64560
gctcactgga ctagtgcttg tcttttggga tcacctgatc tgaggcagat gactgccttc   64620
tgtgtgtata gaaggagtgg gtggtgcaca gcactgtgag caagttaggc ttttccagag   64680
tgtggaaggc tcatgctcta ttctatccca ggagaggccc gggcagtgtt cttgcaggcc   64740
tcctagactt tctttttcac agttctttct tactgtagtt cccttctcac tccccttcct   64800
tgttcctgct ctggacaggg gattgagatg ctgctagaat aggaatctct atgtgttggc   64860
acacccagcc taacagaatt gtcatttctg ttgtcacagt ggggaaactg agtcagcggg   64920
gcacaaggcc tcctgcatcc cctgcactgc tgtttcctgc tacagtgcag gtctttgcat   64980
ttcatataca tacatatata tatatatttt tttttttgg ttaggtattt tcctcatta   65040 catttccaat gctatcccaa atagtccccc atactctccc cgctcactcc cctacccacc   65100
cactcccact ttttggccct ggcgttctcc tgtactgggg catataaagt ttgcaagtcc   65160
```

| | | | | |
|---|---|---|---|---|
| aatgggcctc | tctttccagt | gatggctgac | taggccatct | tttgatacat atgcagctag | 65220 |
| agtcaagagc | tccggggtac | tggttagttc | ataatgttgt | tccacctaca ggggttgcaga | 65280 |
| tccctttagc | tccttgggta | ctttctctag | cttctccatt | ggggaccctg tgatccatcc | 65340 |
| aatagctgac | tgtgagcatc | cacttctgtg | tttgctaggc | cccggcatag tctcacaaga | 65400 |
| gacagctata | tctgggtctt | tgcatttcta | atcgtactct | gaccactcta tttaaaatta | 65460 |
| tagccatccc | ctccatcccc | ataattactg | gccctggcct | cagtctttgt tttctttttc | 65520 |
| tgtgacactt | agagtcctac | tgtatgatcg | gtaccctgtc | atttcctcca ttatacctgt | 65580 |
| tggttttttgc | cagttgtccc | ccagatcgac | tgaaggtcag | gacccttgtt tttgtttatt | 65640 |
| gatcactgtc | ccaaacacct | gaaaacaggg | cccttgtgga | acaggcccac agatgcttgc | 65700 |
| caggatggtg | gggtgactgg | tgtcatttcc | tgtctggaat | cctgcatctc aggattggcc | 65760 |
| gcttttgtcc | aaggacactc | taatactgga | taaaagtgat | tttgagtgtt ttcagttctg | 65820 |
| aaagttgggg | agtaggacat | gttagtgatt | ctgtttgcat | ggttaaggtg caggttttct | 65880 |
| gcaaagagca | ctgtagttac | tgtgttgacc | caggaagaag | gaattcatac cacaaaagtc | 65940 |
| attcaagttt | gtacaacatt | gagagaaatg | ttcacaattg | gcatggacag tcctggaagg | 66000 |
| tactggcttt | tttttctcta | ctctctatat | ggtgacttct | cagaatgcca cctggtctgc | 66060 |
| ccattgctgt | cagtgaaagc | ctgttcttgt | aaagtgcaag | ggcctgtatg ctgtgcaggc | 66120 |
| tgagtgtgtg | tcatctcctg | gcaggaaagg | ccttgtactt | gtgtgtcttc tgagctctgt | 66180 |
| tgttggtgag | cagaagtaca | accagcagtg | gttctctcta | ccatttccac gctcaggagt | 66240 |
| gtgtgctctt | gtcttgcaca | ttctgatcac | accctacagc | ttcacctttg tgagatttct | 66300 |
| ttccaggaaa | aactgccact | gaggtctctc | agtctgcctg | agaggcttct cctctcctgc | 66360 |
| cagcagctct | ccaccctcat | tgaaagggcc | tgaagacagg | ccgacagcag ctctcctgag | 66420 |
| agacctgctc | tctgcatggg | aggacatgcc | ccttactgaa | tgttgctcag cagggtggcc | 66480 |
| cacagtttcc | taaaggcaca | gtcttaaaat | ggcccttctg | agtttaatttt tccccttttg | 66540 |
| gcctttaag | gatgggagtt | ggctttgagc | agtggactcc | ttgcgagctc ttctgtgact | 66600 |
| gacgcatcta | ccttcccgta | catctgatct | gcgtgctact | cctccgacag acttgaaatg | 66660 |
| ttttcaagaa | gcgatggctg | taacttcctg | tcccacccctc | actttttggat ggagagtttc | 66720 |
| tttcaagaat | ttgctagccc | ttttcagaaa | gatttctaga | ttttttagtta ttttaatgtg | 66780 |
| attatttgtg | tctgcatctc | tattttttaaa | gtgtcaatca | tgccttattg gggaggaatg | 66840 |
| gatgtggctt | gagtttgctc | agatctgggg | acttttaacc | tatgctctgt ttttcaggtt | 66900 |
| gttgtagggc | aggcagctct | ggggtctcat | aaaacaggct | ggtgaatact gagtggtgct | 66960 |
| ctggttccct | cctggatgct | gcccactagc | cttgcaattc | tgggctagtg agcccagccc | 67020 |
| aattaccctc | agcttccgca | tttataatat | aagaggctta | aggagatga tccccagcgg | 67080 |
| atgctctaat | ccccttgctg | caaaatggta | tgagctcata | cgtttaagaa ccttcccctg | 67140 |
| gactaacagg | tttattgaga | tataaatttac | acaccatcca | gtttcctctt atagatgtac | 67200 |
| agtagctcct | acttgctaga | cttacggatt | tgtgtcgtca | tctccacagt caggttgtaa | 67260 |
| tgttctcacg | ctgcagaaga | accacatact | gtctgtttat | atcccgccca tgcttcctaa | 67320 |
| ctccctctag | tactgggtga | ccatgatgga | cttcgtgact | ctctttgcct actgtgggta | 67380 |
| ttgtatatag | atggaaacac | ataccgtgtg | gcccctattc | actcagtgtg acttggatgc | 67440 |
| gctacaacat | gcatggtaga | atgcactgcc | ataccttttcc | ttttctcgat gcccaatagt | 67500 |

```
ctctggcaca gtcttgccac cgtgtatttc tcaggggggtg acattttgac tctgagttct    67560
gtccagtggg tctttacctg ggagaggagt cgctgagtca tatggtaacg ctaacttcca    67620
ggcgtggcca gactcacaag gtagtcacac tgcactatgc tccgaccagt agccaaatag    67680
tattccagtt cccacctccg tggcggcatt gttgccgtct gccattttga ttataacagt    67740
ccagagggat gtgacattat ccatctcttt gtttcgattt gtgcttccct gatggcttgc    67800
agcgacaaga cctggtcctt atgcttattg tttatgtgct tgtttgggga gtgtccactg    67860
agagccttta tcatttagtg attgggttat ttgtattttt tgttaagctg tgtaagttct    67920
aaaaaaatac atcctagatc caagtcttat tgtatgtgtg actcacaggc actctctccc    67980
attctgtggc tgccccccttc cttccccctc actgtttaga tgtcccgagg agatctattt    68040
tttccctgc ttgagctttt ggccatattt aagcaagctt tgcttagctc aagttagaaa    68100
agatccactc ctattttagc acctttatct agggccaatg gttctcagcc ttcctaatgc    68160
tgtgactctt taatacagtt cctcatgttg tgctgacccc caaccataca gttatttctt    68220
tgctacttca taactaattt tgttactgtt atgaatctta atgtaaatat ctgatatgca    68280
ggatttctga tatgtgaccc cctctaagga tcctgaccca caggttgagg acctctgatc    68340
taggcctctt acaagtcttt gaatgaattt ttatgtgtat gtgagtccac gttcacccctt    68400
gtactcatgg acatctgatt ggttaattta agtgttcttt acatggaact catttatgtt    68460
tggagccagg tcctgggaat cctagcagca atgtaggtgg ggatgctgtg ctgggttctc    68520
ctcagtgact gcgagtctga ccttggaacc tatgttttta acaaagcaaa ttcacgttct    68580
ttctccattt cctttttcccc tacttaccca ttgatgagaa agaactatct tgaaaattat    68640
cagctatgaa aactgtcttt cttgcttcct atggttttga tgaagtgttg ctgtttctta    68700
atttgtacat gattggtaaa ttcaatgagt tgtaacacta gctagtacaa tgtcaaggtc    68760
ccagttaaca ttccttttgg ctgagctaca agggcactgc cactagcctg ctaccttatt    68820
cttcactatt tagccttagt catgtgagac taagttaggg agatgatgtt tttcttaggg    68880
tttctgttgc tgtggtgaca cagcatcacc aaaagtcaat ggggaggagc ggtttatttg    68940
gtttatactc ccacatcagt gtctgtcatc aaagaagggt ggggctggga cctgagcaca    69000
gacctggagc agaggctgcc gagggaagct actcactggc tgcatggtag aggtgtagtc    69060
agaagcctcc ctttatcact acttaggggt gtgctttagc agttctacat cttcttgtgc    69120
actggcccat ttgtaagact ttcatgtaat agacagaaat agaagtaatt tgataatttt    69180
aaaaaatgta aatgtatgct tccacagctt ttaattattt ctgtcttcta aaggtgatt    69240
tttggttttg tctacttggt ttatactcat ttatatgact gtcacaacat cagtcactgt    69300
gccatggttc agcacagcaa atcggatgta gagtccatag tagcttgtgg ttaggaaaga    69360
agagagcaag gcatgattga agtctgtacc caacaaatag ggcatctgcc tatcactctg    69420
tggtaccccca ggatgtagtg taaatagaat gaggaaagct gtaagagata cgttggggaa    69480
tgcaaatgtt tggtcacaca gtgcttcaaa tacgtgctca ctggccactc ttcttagagc    69540
tgacagggct tctcttcttt aattcagaaa tttggtcaca caggaaggaa agaaacttag    69600
tgacagtgac agagaaccac cccacaggga cttagggtga gcctagtatt ttagagttgc    69660
agacgtgtgg aagacaagcc atgaagcctt cacatggaga gaggagcagg aagtttggaa    69720
cactggcagt tctagtcact accagtgcca cctctcccaa agcctgtgtt actgtggagg    69780
actcttcctg atgtggcact taccagtcca gaaaggcagg ctgggcaggt gtgttcagac    69840
tccctaccaa atgaccgacg ctgactcaga gtttgtaatg ctgtgcagtg aacagcttca    69900
```

```
ggtggggacg ctgtgactca gctctgctct tcctacctca agctcagtgt ctcccctgtg   69960
tcctcccacc caagtcacct gtgtagtttt ggaatcctct gacctgttgt ccaagaaaaa   70020
aaaagagaga gacttaaatc ttgttgttac aacactgttt tctcctccag tttatttgtt   70080
cattaaaaca ttttcttgg gttaggtaaa atttaagtcc ttgaagtatt ttcattcctt   70140
cttaaaatta gcgtgtgaaa gtgtgggttc ctttttctat ttcatttggt tgatcttctc   70200
cccatgtgcc ccttacccgc ctcccctatg tgaccctgac tggccttcca tgcttgcccc   70260
caacctgcca tttcttctca cttgcatgct tttaggtcca gtgctcctcc tttaggtcca   70320
gtgctcctcc tttaggtcca gtactcctcc tttagctcca gtgctcctcc ttccccttct   70380
cagaaatgtc cggtttccct ctctccctct cttttctccc tcttccttcc ctctcattcc   70440
cagcttcctc cctctcttcc ctccaatctc tctctgtcct tttttttgtg gaactggggc   70500
ctatgtcctc tagacaagca ctctaccacc aagctctatg tgcagcctca aagacttaat   70560
taatcattga ttgattgagc tgttctttt agtaatctag acaggagctt cggaaaatcc   70620
aataccctgg tgtttggaac cagttaatgg ttgtccaagt atacatttgt cttctctgat   70680
tttatttcac agaaatgaat gtgaggtaac tatgaacgca agaggcatac tgaatgactt   70740
tcattgtcta gctgtgctta aggccaaaga gtagaggact gggtatttct tgtgcagcag   70800
ttgctgggat atgcactgaa attgcaaagc aggtctgtcc tgtgaccatg tcctgctagt   70860
gagagcagaa cactgtgttg tgagatcctc attgtctttt gttcttcttt gatcaggttt   70920
tgaagggagc acctgtgagc ggaatatcga cgactgcccc aaccacaagt gtcagaatgg   70980
aggagtttgt gtggatggtg tcaataccta caattgccgc tgtcccccta gtggactgg   71040 taggttcagg gtagagtacg gcacgtggca gacgaaactc ttagcaaagt gggtattgtg   71100
ttcatgttac cataggatgc ttagctgtca gagtgtgtag cctggcttca attcccaggc   71160
cttgagtggg actctcccgt gattctttgc ccactctgaa gtgtgttcac aggcacccct   71220
gggcaagaag agctctgagc tcagagctgg gacaagcact gttctgggtt ggagagcaga   71280
gcttagcatc tgtcagcctg tggtctggac acagaacgtg ctctgtaggt atttgagagg   71340 gaaaaaatt gtactttgat gcacaacaaa ctgtgcatat cttaagaacc cagagcttac   71400
ggtttatctt ggacagacag ctgtcctttc acaatgccag gggcaatggg cagggactct   71460
tggtgacatc atttctacta tgtctttctc cttttttgta tctttttgc acagtggttt   71520 aaagtaagtt ttttccctac cactgacatg agtaggtcag ttgtgcttaa atccttagcc   71580
gttttgaagt ttcttgtgtt tcttaggttt gtaacccatt tttaaaagg tgagtgatct   71640 tatgtaggta tttgtctta gattctgctc atgttgacct gtttatgact gacacagaga   71700
taagtagaaa ctggttaaga aatgaagagc tgaataaata gtctttaagt taattatgtc   71760
cagatggtgg tacacagttt taaccccagc acttgggagg cagaggtggg tagatgtttg   71820
tgagtttgag ccagctggtc tcatagcatg ttccagggca tccataatgg cacagtgaaa   71880
ctctgtcctg ccccggccat caagtttcta tttgtgtaca tgtgtgtgtg tgtgtgtgtg   71940
tgcatgtgcc ttcatgtgag cacacatatg tatgtgtgtg tgtgtatgta tatatgtatg   72000
tttgtgtatg tatgtggggg tgcatatgcc atagcatcat ctggaggtca gaggacacat   72060
cctggttgtg tctttatgct ctcttttcac catgtgtctc ccggggattg aactctggac   72120
acggcttgtg caacaggaac ctttcttctc tgcactgtct caatggtcta cactgacctt   72180
gttttgaaag aagttgattg gcttaatgcg gaagagggag gagtgagtta atgtgaccag   72240
```

| | |
|---|---|
| agaaacctga actatctcct tcaggaaaca gccagggctc taggtctctg aaatgtataa | 72300 |
| ttatttagag tgcctcagta ctatagacta tggatagaaa agtctaaaga ggatttaaaa | 72360 |
| cttagtgctg tgattgtttt ctggaagagc ccgtaattct acttctaatc cccgttcttc | 72420 |
| tgagtgcttt cccacaggtc tagagttgga cttctgcagt ttcttcatga cgccctggtc | 72480 |
| ccgggacatc attcctaaca cctcctgaca ggttttcttc tctctagctt ttaccactcc | 72540 |
| tgtggcacat ttttcagaa actgttttct cttccagctt agaaatttat cagaaagtta | 72600 |
| attacatgag aaatagtcac tgctaatatt ggaccttatt cttctgaaga tgcagtatac | 72660 |
| agggttggga gaaatgcttg ccagctgtgg ctctgttcta acctctgctt gttctgtgga | 72720 |
| gtgtgatgca taggcattag gctgctgtcg ccagggctca gtaactggtg gtgtaacttc | 72780 |
| ataactgact cttctgatgc tgcatcaggc tgcctgctct aaccttggtt aacctggaag | 72840 |
| tgtcatgtta gggaagggtt ctctgagaac cagtgtttaa ccctggtgta caggcagtgc | 72900 |
| tttcctgcaa tagcggtctt ctatttggag tgccattctc ccagttcctt gtgtctgtag | 72960 |
| aaagggcagc agaggtcatg gagaagtttc ctcaggcaga gtttatttct gctgatcact | 73020 |
| gtcatgctat gaccctcagc ctctcgcttg cctcctcctt cactcagacc agttctttga | 73080 |
| tttccaatga cgaggctgtg tctgtcctta gatgaaaatc caagctcttc cttggttgtg | 73140 |
| tgaagcacca cgccttgtgt ctgtctggtt tctagtctcc gcatgcgtgt gtcagctctt | 73200 |
| ctcaccctag caattctgcc caacagtcct gtctgcacaa gcaagcttcc acatccggtc | 73260 |
| ctcagccaac ttccccttcc tcaggtctcc cctctgttcc tctccctgcc tcactcaggt | 73320 |
| gctctcctcc caggaagcct tccctcct ccgtccaggc tgagtgaggc tcttgctccc | 73380 |
| ctctggctgc ctttcatttg gatgtgtcta tatagctgtg gaagcatgct gtggtggaga | 73440 |
| ggtggagtca caggggttg agccgctgtg gcagacattg gtagctgcat ttaatggctg | 73500 |
| ccttctgctg atgctgagaa ggcagaggta gttgtgtttc ccaggagccc tgtttttatt | 73560 |
| gctgctagtg ctctgagctc tacataattg acaggaatga gcagagcttc aactcacgac | 73620 |
| ttagatgtgt cagcatctta atgtgctaat tgcatatttt ctattagcgg tataacctat | 73680 |
| tgagtatcct tcttattaga tgatgatgat gcacaatgca tacctaaaag aattaaatta | 73740 |
| tctgcccttg gtaaataaat cgtgattggg ttcatgtttt aatctagatt tattgagttt | 73800 |
| caaatctgtg gtctcttttt ttctgtatca agagggctct gtgaggtggc cttttatttt | 73860 |
| ttatctttta cggataaaga ccattgaagt gcctttaatg ctcaaaaatt caatttctga | 73920 |
| tttcattatt ctaggatttc atgatttgtt ttcccttctt gggaacctca ccggtgactc | 73980 |
| tgaggttagg agttcacacc gcgtgaaggg ttcattgcca gtgcgctgcc tcttgcctgt | 74040 |
| acctaagagc ctgctgcaac tgatcataac cccctcggc tcccagctgt agttgaagtc | 74100 |
| tgcgctgctt ggcctgcgtt tgataggcaa agagggctgt acgggactag tgggagagga | 74160 |
| gaggaggttt ctagcctgcc ccaggagagt ggcagaggtt acttggtaga aggaaccggc | 74220 |
| atgggtttgc acatccatgg ggaaatcggg aggttgcctc gtccttcgtg aggacagcag | 74280 |
| gacagttttg ctccataagt gggttagcag gaaacaccac ccttctcggc tctagacctc | 74340 |
| caggtgaata gaagcatctc cagttcggtt catcgttgat ttgcagtgaa gagtttcttt | 74400 |
| ttcttgggct ttgtttatgg cctgttatac cccgtgtatg ttacgtactc tgtggggtc | 74460 |
| ttgacaatca gggtgcagca gtaggtcttg tagcctttgt gtttcttcag cagcatcagt | 74520 |
| tatgatgaac actctggagc aatttgttat gatagctgct agtcatgtgc ctgagagagt | 74580 |
| ctgacgtgtg acatgtctga attcaggggt gttgtaagtg ctgcacaata cctgatttct | 74640 |

```
gaggaggttg ataggaaaag gttaaatatt ccatttggga atgtttagag attaagtctc   74700
acagttacag tgttttagat gtattgagtt tgaagggtta atttcacttt ttttttaaa    74760 gtggctgtta ggagttttag aagcacccgt gtgcatctct gttgtttctg tgtgagaggt   74820
gctgctacag cttcagggc tgtgcagagc tggctgctgc tggcccctcg cttagggca    74880 gagcaactct gcctctgggt actccatggt gagcaagcca gcctccttct gaccttgttt   74940
ggcggtagct cctcccagg ggctgggtgg ggctgttgta gctcagtaca gagcttttca   75000
tcttcagtca ctagtgaggg tttcccaag tctacaggcc cccagaacta ggcagctctg   75060
ctcacgtgtg ttgggggtgg gttgactgat ggagaaagtg aatatgcaga tattccttag   75120
gcaggaaagt acagagggtt ggtgcaggct cagcacagtt gcatttatta tgcagccgtt   75180
gttggactcc tgccttctta tcaggatagc tctactctgg caaatgtcca cggaagggaa   75240
gaactttaaa aagccccaaa tttatgaggg cagtgtagat taatgttttg tctacataga   75300
tggttatttg aattttcttc ttaaaggttc atttccttca gaattaaagt tgactctaag   75360
ctcaactcac aaattcctct gtgtggctgc ttttggtttt gagttcattc ccagggcaga   75420
tgtgattgat tttcctgctc tcattattaa tccagaaatg taatttcaac ttgggcttgg   75480
aacactgctt tgggacacga agcagaggca agcaatgaaa gttaggtaaa tttgagtcaa   75540
tcaagtggac cacatcttct cttcactctc ctatataata aaggcagtga gccttcagtg   75600
ggggttagga ttgctcttgc tctggtttca gaaagaacat ctggcctgaa tttgagtgct   75660
tgtgccagag gtgggccgcg agctccaggg ttttcgagca gagtctgtgt gctggagttt   75720
ggatgctgag tgaggtggtt ctgctttggt cactctgatt ggtgagttgc cctggaaaca   75780
ctcaccaccc tgtgtgtgtg tgtgtgtgtg tgtgtgtgtg tgtgtgtgtg aagactatag   75840
ggatggagcg ggaacatatc ttaggctgag acactctgtc tgagaagatg ggaaaacact   75900
cctcacactt caccttcttt gttcaccggt tgttacaact tgacctccag cccaccttct   75960
ggaatgctgc cttcccaccc ccagttttgg tttcctgtca gttgacagat cacccgggtg   76020
atcacctgaa gcatccacat cctagaggcc cctttacagc tgataggaag ccatgtgggt   76080
ggaaacagct gcgaaggcat gggctagacc aggaaggcct cctgcccgtg gttccttatt   76140
catatctagc ttgggcctca ctataggcca gcagtgtatt ccaggttttt aagcccttac   76200
ggaatgacag tgaggaaact cagaagcaga cacctactga acaactcaca gtccagggcg   76260
ctctgtgagt ctataaagag cacaaagcta agacaagtcc taccttgtaa gttttgtcaa   76320
aagaagatgc aaccctgcat ggaatcacta taagagatag aaagcatgaa caagacagag   76380
tcagaaagag gtgcggtgtg ggttagaatt aacacaccca gtgaggactg agaaggcaaa   76440
cctatgcttt gactctctga tgttgacttt gaattaagtt ttcagaaaac attagcagaa   76500
tagaggaata gaggcaggta gagggagata gaggcggatg aggtaggtag agacaggccc   76560
agagcctcag atctagagtt gttttatttt ggggggggg gcagtgagtt ttcatgagaa    76620
tctattacgt ctgtgaggca aacactgtcc agtgagtaaa acaagattga agccagaact   76680
gtgacaagtg ttcagactga agaaaatgga ggaggaagtt ggaatgaagg aggaagttgg   76740
tgcagagaag gaagctaaga aacggggatg gaagagattg gaagagagct ttgtctgagg   76800
caccactgag tcacaggcta tcccacaaga aggcttcacc tgctcacctc tgcctgcctc   76860
tgctgcagcc tctgcggtac tctgtctgct ccatctggct tataggttca gcttacctgg   76920
tagatcactg gtcttactat atgtagcaca ctcctgggac cattttaat aagtgacagc    76980
```

```
tcctggatga gtgagtgaaa accaggagag gcaagagtga caagatccca ctctcttttg    77040
ttgttgttgt taagaaaacc gatatgtggg tatgtgcaca ggagtgtatg tgcatgcgag    77100
gggcagttgc ctacagagtc cagaggtgta cgatactcgt gttgctggag ccgcctatgt    77160
gggtgctggg acttgaactc aggtgctctg gaagactaat atgtgagctt aacaactgct    77220
gtctctccag ctctgatcac atgtattctt tacatggttg aatcatggtc tgtgatgtgc    77280
acatagcata tttttgtatg cattgtccgt tgatagaagc tttcgttgtc tctgtctcct    77340
gactgatgtg aatagtactt cagtaaacat ggaaacagat gtctccagga tgtattggct    77400
tcttttcccc atatgggatt gtgtgtgtgt gtgtgtgtgt gtgtgtgtat gtgtatgttc    77460
catgtgcatg cagtgcccat agaggccaaa agaaagcatc gaataccctg gagctggagt    77520
ttcaggtggt tgtgagtcac catgtaagtg ctgggatttg aacccagttc ctctggaaga    77580
gcagccagtg ctctttaact actgagcggt ttctcccgcc cctggtagtt ctgttttcaa    77640
actgtgagca gcttccatcc tgataggcat tcctatcaac agggtgtagg agcccacttt    77700
tccctcatct ccacattata gtcagcgttt gctattggtg tgttttgat ggagcagctc    77760 ttctggggtg agagtatctc ctggctctgg ttcacctttc ctgctctcat gggttttcca    77820
tttgtaatct gggttgtaaa aattcacttt atagtgtagt tatgactttt gaaatcttag    77880
tgcatcttaa tgccttgggc tgtgagtgca gctttggtgc aacacatcag ttataccaca    77940
ggcatctcat gtgtgtggct tcttcatctt ggctgagttt cagtcaatta ggtaactgtg    78000
agtgatgtga cgtcttcagg gatgcactct ggtagccatc gggagctgga agctcttgga    78060
taggctgtct tcatgtgtga aagcattttg ctggtataga attcttgggt ctccagtgta    78120
agctgggatt ttaggcatgt ctcctttgca tctggtgatg agtcctgggt gggatgtttc    78180
ttcctccttg atggtcagca tcactgctct tgatgttctc cctgtaatct cttgaaggcc    78240
atccttccct cccacagagc gcagctcctc tcccttgcta tttcagcctg tcttcctttt    78300
cctttacatc ttaggagaac atttatagtt ccttgtcttc tgttctgtcc ttcacagcct    78360
gtgaccctga gttttatttg cagagcattt ttgttttctt gtgacacaca gttatctcca    78420
tccttcctgt ctcttctgct gcttctcagc cccttccact gacccctgctg ttcagtgttg    78480 ttttagaacc cgagtttgtt agtgtcttga gagcggagaa ccaactcttt ctcagtgtgc    78540
tagttcctgg caatggatat ttttacagtg tgttctttat ctgatcgtat gtggcacaca    78600
tccatacttt atattgcaga acctataat agccccatgg tggagttttc cactctactc    78660
attctgcaca aagtaactac ttgtctgtga atagagaaat tctgggctgt ttggatcccc    78720
tcaccctgaa cctccctgtg aggtgagggc tctcccgtgt caattggctt agaagtgagg    78780
agcctaaaga agtgggtatg gagccaacac atgggccttc cagaggcgag agtgaagctt    78840
ggcattacct tcctctctgg agaagcctct gtgccagggg tcagcttcct gaatgccagc    78900
tttggctcag ctctccacag aggccaagcc cggctgtgct ttggtgctgt tgcatccgga    78960
gtttgcccca gatgcaccac agactctctt gttgctatag tggccacagt ggccttcagc    79020
tcctctgtgc tttaaattgc tgttgacctg gaggggtgag gtggagttca gcgcattctt    79080
cctgtagctg ggcaggcttt ctgaaacaca atcgcatgt gctgtttctt tccttaaatg    79140
ctttggtggt gagtccttgg tttgggatgg agttgcagag tgctgcatgg aaccagctct    79200
ctgcatctcc ccactaccca tgcacgcctt gcaattcagc tgcaccctct gcttctcatt    79260
gcctcaagtg agccatggtc cttccttattc gaagtgcgta ctccatgtca ttctttgaga    79320
aatgttctcc acgccttctt tccacccaca catacactcg tagacagcct gccctgccca    79380
```

```
tgtgtccctc gggctttcat ttcccagttt tgttctctag ctctctgttc tcctgaggca   79440
acaggtaccc attaaaatac ttgacaccct gtattatcgt tgtttgtgtg ggatacccac   79500
tatttgccta aacgtctaca gggtaaaaac cagggctgct tgttcatgg gtaatcccag    79560 tacaaatagt ccagacatga cacagcatgt gtgcgtgtgt gcgtgtgtgc gtgagtgcgt   79620
gagtgtgtgt gtgtgtgtgt gtgtgtgtgt gtgtgtgtgt gtgtgtgtgg tgaggcaatg   79680
aatgaatagg gaaattagat tttctggtgt ttctcatgcc atttccccc tggattcttt     79740 gttgagaacg tttgtaaatt gagctcacct cttggaaaga tgatgtttgg cagtaaatgg   79800
aaagagctta cagagatgtc tggcatctag aaataattta atgcatccat ttttactgtt   79860
ggaggtcagt aattgtgaga cgggacctct cttagtgcac ccttacaaag atgacggtgc    79920
tcttaggagg actgcaggac tctactgcag gccgctgtct tggaagatgt ctttagggat   79980
ggggtagact tcagttagga agaaaattgt catcgctgca tggattggtc ttagatctag   80040
tgaagtagat taggacagag gcaaggggaa cttggtgtca cattgagatg tcgtttagca   80100
aacagggtaa gggacttgga tgaggagttc ctgagctgat tggtggatgt agataaggac   80160
agaaggagac tgaggaatgg acagaatcga taccctctgt tgctgttgga aaagtaaggt   80220
tgctattcta ttgagattat gataataaga gaagacagat caatcactta cttaataaat   80280
taacattcct ggatattatt agctgggttt tttgctaagc tgtggggatt cagcaatgag   80340
gtagatggct gccatcattt ctctataagg tttaaagtcc tgaattaaac aatagtgaga   80400
aataataatc tatgtataaa atctgatctg tagggaatgg cttgcaaggt tagtagaggg   80460
tgagaggagg tctattaatg gggaaaacta attttgtttt ggcagaaaag gtctctgggg   80520
gaagatgaca tttcagatgt agactgtgag taagagttat gtggggaagg cagggtaaga   80580
atgtccccag gcacagggaa ccacgtgtcc taacgtcaag gtgaaggacc tcgaccactt   80640
tgaggtatgg acaaagaagt ggagaagctg gtacagaaag caggacaagt ggcggaatcg   80700
tatcccacca gagacaccat cagagggctc agagaagagg tggctcaatc cggtttatat   80760
gttaagatca ttctggaagc tctctagaaa atggcattgg tcatgatgta ggaaacaagg   80820
ttttgaggag tcctgaagga gatggtggta tggaattagc tctgtgaact tcccttcttc   80880
cttcatacct tagccactcc caccctccta gggagcaggt acttgggctt ccatcaagtg   80940
catgtacact gcaaaggact agttcaatca ccaggagtcc tgcaggcctg tacagccata   81000
tggcttttcc tctgctcttt aacttgagaa ataaactaga gtctgcatag agaaagtcta   81060
tagaataaaa ctggagaaat gctctctgtg gcctggactc gagtgattgc gggcgggaag   81120
gatgtgtcag aggtgaattt accatagaaa ggaagggaac agggtcaggg acagtctaac   81180
taaactttat gcttcttgtg tggggattat tgtcaagatg tgtgttgact cttaatgtgc   81240
ttgaatatta agagtcaaaa tattccctgc agaccttgaa gtccacagat tggggggggg   81300 gcggggggc gaggcatatt cagagctcag gtctctgttt ccctgagtgg cctcccgatc    81360
tctcatccca tcttgtaact ccaagtcaga gagatgtttt ttgtgtggtg cattgagaag   81420
taccctggcc tgttatagtt gctaaatgtt ttttgtgtta atggactgtg gctcatttgg   81480
catggcccaa ctcttacaaa cccagtgtag ggccttattt acaaatggtg ggctggtgct   81540
gtcttcacct gcaaccctgc tgagctctct tccgagcttc tcaatccttg ctgtccctca   81600
ggagtcagct cagattcctt tcccattctg aaagttgact tctgtagcag tctgtcagtc   81660
ccaccctttt aagcacatat ttccattttg aatctgtgtt tctagttctt ctgtaaagag   81720
```

```
ctattcacag ttgggcaggt tagcatactt ctctggccct actcctcatc tcgagcataa   81780
ttggatttgt tgctgtctaa agtctgtttt tccaccaacc ccaagtgtat ctggcatacc   81840
ttctgaagca gatggtagat ccagaccctc tccttgtgaa acctgtagcc taatgggagg   81900
agggatgaga gtcgtgggat aaagtccagc tctgccagat tccaggacag atgactggaa   81960
cagtggcagt ggtgagtctc cgggagatgg gcatgtagag gtatggctga gtcacaagca   82020
acgtctgagg gatggtgagt agctaaccct gcaattggaa ggggtagaga gcataggatg   82080
tgcggagccc tgccatagga aaaaaaccca gcattagatg agctgccaga agctgttgtt   82140
ggtcagagaa gatgtctgaa ggggagggct agtcttgtgt gacgtacagg gacaagccag   82200
aaagttttcg gtagcttcag ctggtgtccg tgtttagagt atctgccagc tgcagactgg   82260
tgagtgtgat gtctcagacc aaatggatca gggcccctg tgactgtgtt agaaagacaa    82320
gccctactct tttccttctg cccgagggag tcggagaggg cctgagcagc ccattgctct   82380
ggtcccaagg ttaagtggtg gcagcctgca gcatctccaa gtgaaaatta ctacgaggtg   82440
attattgtcc tctgaagact tgcctcactg aactctgcag tctactcagg gagttcacag   82500
cgtggtttgt gttgacccag atgacagggt tgccaagacc ggggccgggc aacaacacaa   82560
gtctcccttc ccaccgcaca cttttgatttg ctaggtagct caggacttag tattctccct  82620
ctcttcctgc taagcatcac ttgtccttgc cctccctgta ttcacagatg atttactgtc   82680
aatcatgtct tcccccaact gttctttacc tgttacatca agtccagagt tcatattcaa   82740
atttaaagtc ttaaaccatc tctggccttt taaatctcca gtaggagagt acaccgcatt   82800
catttgctgt cttctagacc tgcctgtgtt gggtctttct tctgaagtaa gcctccttcc   82860
tcccacaaag gcaagcactg tgttcctgag gggaacgaga aaagtcgaat gagcagagag   82920
catgcaccca gtgtcctttg agtgccgaat tttcccatcc taatctctcc tgacctctgc   82980
tctgctgcct tcactaggat ggtctttatc tcagacagct gcgccttctc actggacttt   83040
aggaactggg ggcagggatg aagatgtagc tgagaggtag agcatttact tagcatgtgc   83100
aaggtgctgg gttcaattcc ctggtactgc cacagaagcc cctgggctgg gggaggggct   83160
ggggtttaga gttggcatgg taacggtttt ggtgacagcg ctccctgagc ttgggaagct   83220
tccttgatgc tgaaccccc cccccccccc actgtgggct tctttctgcc tgggttttct   83280
cctgctcaaa gcagatgtgg acacgaagtg tggtatccta ggaaacgtct tttgaagtt    83340 ttggagcaag gggttgtagt aactacccag gctaccgttt tcagcatctt tgaccataga   83400
gcttggtgac agacttgtat gagggagagg gaaagaacta tcagaaagga gtctaggagg   83460
ttcttgttct acaacctaag agaaaaatga tgtggtttgc agaaaatcac ttctaagctg   83520
gggtgtcctt agctgtctgt ttttgtgtct agcagtgtca aatggacata tagatgcagc   83580
ctcattgaag cagccgtgag ctgcccaccc ctcaagcatg tttccatttc aggcagtgca   83640
ttgctgctgt aagttccccc taatccagca gagtgactca tggccttggt cttcacatcc   83700 caccccacc ccatccctgc caccccatct cagcccaccc caccctac gccaccccct       83760 gcatgcctgt gcccttggaa agatgcagcc tgtagcgctg gtccgatcct gtccgactca   83820
caccacgagt ctgtgttaag tttagtgcaa ggtggaccag ttacagtccc agcttccctg   83880
cccttgctgc ctgccagtga ctcctctgag cccgttgttc agttacaaat gacatggttt   83940
gggtggcagc tcacaatgtc tgcttcattg tagacaatcc agctattact atcgtttccc   84000
aggagtgtca ggtttctttc ccaaggaaat attattttac ctactttta tttcttactc    84060 agtctctctt acgatagtat gtataaagta tattttaaa cacaacagtg tctcataccc    84120
```

```
agatttatct cagggcctca ctaaagaatg gtgacacgga ccatgctagc attccacacg   84180
tcagggaggt tcaggggcag cacagccgac tgtgttagtg taagtgcaat ggctagactc   84240
agcaattacc caggttacaa cagctcttta cctactttgt ggtcatgtat ttatttctca   84300
gccccgcctg aatcctaata acacagctgt cattctttga agtagcattt ttgctagaag   84360
cgtaagggag caaatgtttt gtaccgaatg acgtcatcta tcctggggtg ggtgtttgca   84420
ctctgagctc ttcagccttc gatctgttgc ccgctctctc tctctctctc tctctctctc   84480
tctctctcct ttactcagct cctcctccct tcattctcta caccttccat cttctctcct   84540
ctccctccct cctctcccct cccttcatca cttcctcctt cccttcttc  cttagtcatt   84600 cactccttca atctttcagc acgttgctta ccacctcact cattcacccc atcactcact   84660
caccctatca ttcattcacc ccatcattca ttcaccccat cattcattcg ctcactcact   84720
cattcattgc ttttctcttt cactcgttag ccccttact  ccctcccttc tcaattagtc   84780
tggctggagt cattgatact tctggtagca atcggtagaa cctcctttca gatcaagaag   84840
cttgctgtac accgagagcc tgctcagaac tgtgtgctga tgggtgggct cccagccagc   84900
ttctcaggag tgacaggagc cagtagtctt agtgctgtga tgatagtcta ctttgctcta   84960
cactttacca tttccctgca gaccagcctt agccagtcag tcctgtggca gggtggtttc   85020
agtccaataa tggaaagaga cacagtgatg taacttggat tggatgccat cctgcatcca   85080
gcagtagggc tagatcatgg tagtcatatg cattctctca gaggccctgc aagtgaagca   85140 agggaggaa  caggaaggtc tcttagggga gaccccaaac atccacatct atcctgtcag   85200
gcaaggtaat ggcctctgct gcaacgacac agaagcccca gacagattgt ttgcagcgag   85260
ggagcaggag aagaatatgt aactaagcaa gtgacagtta tattgcttct atagtagaga   85320
ggctgaaggc caaaccaggc tgaagtgtgg gtggtcagac tcatttagca caagcatgaa   85380
gggaagcggc cacagctggg cacagtatgg gccttctgta gatatatgac ttaggaggta   85440
ttccggggac tgtggggagc tttagtattt tttaattcat taaaattaat ctaataaatt   85500
aataaattag cttggagac  agggtttctc tgtgtaatag ccctggctgt cctgggctcg   85560
cttttgtgac caggctggcc tcaaactccc agaaatctgc ctgcctctgc ctcccaagtg   85620
gtggaattaa aggcctgtgc caccaggacc aactggcttt agtattttta aaattcaagc   85680
agtctatgct tttttttttca taagtagatt cctaatcaga atgcccttc  aattgatcat   85740 tgacggttta tttatttact tacaaagggg gaatgaatga cttttttgttg ttgtttggtt   85800 ttagaatttg ttatggttta gagaatttag atagtctaat tttaatagcc tttgaagaaa   85860
aagctggttt taaaatagtt ccaagaagac ctgcttatta atttgtttat aatccaggtg   85920
gtctgagacc aaactgcttt tgtggatcat gaactccttg ttgtaaggag cacaaaacat   85980
cccctctttc tgtgcccagg acccttccag cagttcagtc cccatggtag ccagcactca   86040
tagctcatct gtaggagcac ataccccagca gtggtccttc agtgctctgt cggacgacac   86100
agtgggcctc actcagctcc tgtggcattg ggtggaccgt gcccctgggg tgagacactt   86160
gggtgaactg tgccccttgg gtgagacact tgggtggact gtgccctgg  ggtgagacac   86220 ctgggtggac cgtgccctg  gggtgaaaca tctgggtgga ccgtgccct  ggggtgagac   86280 acttgggtgg accgtgtccc tggggtgaga cgctgtgctc cattttcatt ctttgtggct   86340
ttttctttca catctgtact ttatggaggc ttttgtttat tcttgctcat ccacacttt   86400 aaaattgtta tagtctgttt tgggagaatt catgagagat accggggacc ctttcctagt   86460
```

```
ggtctttgct atgtgaggtg tgtgtaccgt gtggaagcca gggcactgac acaagcacca    86520
tccatgtctc tccttgctct gtccactttc aattgcttac ctgcttgcat tctttccttc    86580
ctctctcctt tccttcttcc ttccttccct ccctccttcc ttctttcctc tctttttatg    86640
tgtatgtttg catgtatgtc tgtgcaccac atgtaaaccc tcagaggcca gccagaagag    86700
ggcatcagac tccctggaac tgagttacac acagctgtga agtgggtgct gggatcaaac    86760
cctggtctct cagagagcgc agtgagtgct ctgaatgcct gagcagcctc tctagcccta    86820
cttttctatt tcttggccca agaaattggc taagacaagg cacctacaga gtttggctag    86880
ttggataggt tttcatgttg ccagagcttc gagaaaggcc atttctgttc tgataagtgt    86940
tatttggata actcagggtc accttaaatt tcataagagg acacagattg ctgtaggtac    87000
catttacatc aggctcaggc agctcagtga agggctgtta gggtgccagt catttatgac    87060
ctaagggtcc taacccagca tctttccccc cacagggcag ttctgcacag aagatgtgga    87120
cgagtgtctg ttgcagccca acgcttgtca gaatggaggc acctgcacca accgaaacgg    87180
aggctatggc tgcgtgtgtg tgaacggctg gagcggagat gactgcagcg agaatatcga    87240
tgactgtgcc tatgcttcct gcacgccagg gtccacctgc attgaccgcg tggcctcctt    87300
ctcctgcctg tgtccggagg gaaaggcggg taagaccaac agcacagctg agctagaggt    87360
ggcggaggcc ggagtgtgca cactctggcc ttctcttccc tgtggcacct ctgaggacca    87420
ttctggaatg cagtctggta gtaaagggca gtcatcttcc ctagacattc tgttccagta    87480
gaattcccca agactctggc cggagaaatc cagactagat ggccaatccg tggactcagg    87540
gagacagttt aaatgaaata cccatttatt cagaagagtg tgcctctagg agtctcttag    87600
gaagaactct ttagagggca caggtcacct tgttttctgg acagcatcta gttttaggag    87660
tggcggagca ctgcaggcaa acccactaga agaagatagc tcagtcaaga aacctgtacc    87720
tggcagtctt gagacatcct tgtgtttctg ccttttcccaa agccacacct ctagctttgt    87780
ggaagaagtc ttggccaatt gcagactgga aaatccggtt cccaccagaa ctctgcagag    87840
cagggagcct gatgcctccc tgcttggctt cctcatgcct gggcacttgg caggtcccca    87900
ccccctccc cctggcacct gatccaggaa tgtgctgatg tgattccttg ggtgctggag    87960
aacagacagg tggtgctcag ctctgaggct cgtgagatgc cagcgagccg tgctcactag    88020
ggagtgtgac actggagaag gaagatgctg ggtcaaactc tggaagcacg gagtatttga    88080
cacatactta catgaacact taccagaaat ccagatttaa ctggacacct gcaattttg    88140
tttgctaatg ctggtactct ccacaggata gctccatttt cccgtgttcc tccacaaata    88200
catgcccggc cctgagagct ctggcccaga gtgctcacct atgcccaggt tgtcagcggc    88260
agctgagggc tgtggcatgt ccctagtgta gaatcaggtg aaggcaatgt tgcctctggg    88320
tcttaattgg tttgtttggt tctgcttttg acaagaaaaa gcatttctct aagagagatt    88380
ttgtgtgtgt gtgtgtgttt tctctcgctc taccctgaga caggtctcct gtgccatctg    88440
gatgatgcct gtatcagcaa cccttgtcac aagggggcgc tgtgtgacac caacccctg    88500
aacgggcagt acatttgcac ctgcccacag ggctacaagg gcgctgactg cacagaagac    88560
gtggatgagt gtgctatggg tgagtgtctg gcatctcttc tagacttgga ggtgtgtcgt    88620
gtcggctcag aaagtgctgc agcgggagtg ttctgtacgt tagcgactgc tacacccaaa    88680
cctgaatttc tgtttcctgt tctacacacg taatttacaa tcaaccttta ctgtacatgc    88740
attctgggaa ttcagtgcaa cggcaagtct agacttgatt attaatagac gctcctgagc    88800
tgggatgatg gctcagctgt taattatgta ctacgtttgt agaggatcca agttcaattc    88860
```

```
ctagcaccca catcaggcag ctcacaattc cgtgcaactc cagctccagg gaatatgacc    88920
tcattttctg gtttcagaca tatatacatg cacatagcta aaaataaata aataaaatga    88980
atataaagtc ctacctcagt aagagtttaa aaaaacagca cacatttgga gaccactctt    89040
gtcatttctt cttataagtt aacaaataaa cctgaaaaca gagtgatctt gtttaaagtg    89100
gggccttggg ttgtagattc ctgactgccc tgtgttatct gtctttgtgg gaactctggc    89160
aagcgctcgg tcctggtaac tggttcttat gtgttacagc caacagtaac ccttgtgagc    89220
atgcaggaaa gtgtgtgaat acagatggcg ccttccactg tgagtgtctg aagggctacg    89280
cagggcctcg ctgtgagatg gacatcaacg agtgtcattc agaccctgc cagaacgacg     89340 ccacctgcct ggataagatc ggaggcttca cctgtctgtg catgccaggt aaggagggct    89400
ggtcagctgc tgacaggact cactgactcc atgcactgag ccagcgcggg gttcccagc     89460 tgactaagag agctgagccc gggacccctg caagccccat gattgcagag aaagtaggag    89520
acaactgggg tggtcagagc agagcagacc aagtcagaca ggagctccac ctcaggctcc    89580
agcttcacac agtgggaagc tccggagcc gtttcccacc ggaaccctct aaacatggag      89640
tgtcctgatg ctctgaagga tcccgtgtgc catcccatct cacttacaga gctagtcgtt    89700
agccacactt aatgcaggca tctgctgctt acccagaatg agccctagc tcagttgtgt     89760 tctggagcga ctcctcagtg gacaaaaaca gaacgacgac gtgacagcac aggtcagctg    89820
ttctgttaat gactgaagcc agcgctatag cctcggcagg agctccccct agtcctgacc    89880
ggcaccccaa gttgcaccac ttcagttggt cttaggaagg cagtggggaa ggggtccaga    89940
aactagaagt tatccaaaat gtgggagtct tggtttgcat gctgtgtcct ggggtgtacc    90000
cttgcattgg cctttttct tgtcgctgtg gtgatgtacc tgacagaacg aattaaagtc      90060
ccacaggcaa gtcagtccat cgtggcagag gaagacatgg ggcagggcat gtggctgcag    90120
ctcctcatat tttggtgggt tgggaagcag agataacaga aacaaaagca aagctattgt    90180
cctaaggtcc cattgccagt ctaccatcta ggccccgtct ctctcccaca gctgtcctcg    90240
ccgccaccag ctgggactgg gtgttcaagc acacgagcct gggagggat ttcacacctg      90300 taccatacca accctgcctc ttcctcacat tggcaaaaat gtcttacggc atctatgttt    90360
tgtccactac agcgactact ctatcatagt gaagactcgc tttctttgga gagctgctca    90420
tgcttgcgga ggttttagc tctctctgca cattttgct tccttggctg gaatgcccct       90480
ttatttctgt ctgaaccgca tgtgtggtcc atttgtgcag gtttcaaagg tgtgcattgt    90540
gagctggagg taaatgaatg ccagagcaac ccgtgtgtga acaacgggca gtgtgtggac    90600
aaagtcaacc gcttccagtg tctgtgtccc cctggtaagc gcctgccacc tgcccctgtg    90660
ctctccaaaa ccccaagcca gccaaccaca ggaaggggag gggagcgag tgcgtgtggg      90720 ccgagcatga ggaagtcatt aaagtggcta cttgggaaga ctttgtgt atgctgaggt       90780 ggggaactgt ttcagccagc atgtcttcca agacttttgt ggcctgaagt ccaagtctgt    90840
tctcgaacgg ccctgacct ccctgtctgt gtgtatattt cagagtgctc acacctcaca      90900
gaagcgcagg attttatttt ttcctcatga gtcatattcc taaatcccaa gacatttat      90960 tccattaagt ccaggccggc accacacatc agatttttt ccaaggtcct gtgcctctgc      91020
tgatgttgaa ggcctgccag ctgtctgctg tggacggtgg cttttctact taatctccaa    91080
agagaagatc ctttcagtct ggggatacag ttactggttt gagactccat cttcagtagt    91140
gtctcagttc ctcttgcttt ccctggagat ggacctgaga gtcaggggta gaaccccagt    91200
```

```
acctctgacc tccgagcttt gccttggtga cccttggca tacactctgc cagtgattca    91260
accactgttt cagtaaagga agatgggtca gtctctgata tgtgtcacct cggtgcctct    91320
tccaggcttc acaggaccag tgtgccagat cgacattgat gactgctcca gtactccctg    91380
cctgaatggg gccaagtgca tcgatcaccc gaatggctat gaatgccagt gtgccacagg    91440
taagtgtcag cccctcccat ccctttgagg cccctctgtg ggcaaggcga ctgtcttccc    91500
ctagctgctc ggaggtagag cataaagggt gctgccctcc tctaacagcc aggggctggc    91560
tcatgctttc gctgcagacc tcctactgct gcagacctcc tgctgctctt acagtcctta    91620
cctgtagccc ctggctcatt gtcaccacac agtagttctg cccacatgtt cagctggtgt    91680
ctgtgtgttt atggaaaggg tttgggcagc agtgagcttc tagcttgctt ccctggtacc    91740
ttgggaatag gagaattcta gaagaaagct gttcttcact gaggctctct acagggtctc    91800
tgtgtctctg agtccaacct tgtgcagtg tagatacaga tgtccttgag agttggctgt    91860
gtctctctag gaaggtgctc cctgcatgat ctgattctgt attctgagaa actttggtaa    91920
cacatttctg ggtcttggac catatttctc acatgggaat gggctttatt gagctgaatg    91980
actacagcac acttgctgtg cagatgcatg gctcatcaat atggagaaag ccttaaacta    92040
ttcaaaaagg aaacctcttc cttatgtgat tctgagatag aagctatagg gagagaggc    92100
tggagcaaga gcatttgctg ctcacgcaga ggacctgggc ttggttctca gcacccacat    92160
agcaggttcc aaccatctgt aactccagtc tcagggaatc tgacaccctc ttgtggcctc    92220
tgtgggcatc acacacacac acacacacac acacacac acacagag ttcgcatgca    92280
tacatatagg caggcagact ctcaaagtca tgagtaatgt cagagcataa gttagaaaca    92340
ggtttttagc atgtaggcct tgtgcctctg atttctctca ggtctcagga agcacactc    92400
tgttcccata gtggtgcaga gctgatgtct gttgtaggtg tggactctgc tgagctgcct    92460
tttcctcgta ggaacgttgc ctcctgttgg agatgctcca gacgtttcta gcctgcttct    92520
gtggagcgtg acttcacagc agtgaggttt aagtcctaga tctcatgttt aagggacagg    92580
agggtgctga ggtgctcagt gggtactaac acctgccgca caccctaaa aacatgaatt    92640
cgactcccag acctcgggga gcaaggaggg aacctactcc caaaagttgt cccctgactt    92700
caacatgtac acacccacac cacccatttg aaaaataata atttaaaaaa taagtttaaa    92760
caataaaagg gaggaaagac ctccttggac cctttttagg aagaggtggg acatggatca    92820
agttacacct cagttgtggg atgcttactt ctctcattgt ctttcagaga gtcacaagtg    92880
gatcattcat tttatttaat gaataccat ttagaaatta gtagcataac actcttggac    92940
gggctctgag actctgttct ccagactcag atctgtaaga cggaatatgt gaagtcatag    93000
tcagtgcctg tgtgctggga ggagagctgc tcagaggcag catgcaagga ggaagtgtgg    93060
agtgccttcc ttccctgcag gccaggaagc aagcacactg agaagagagc agcagacccc    93120
aggctcaggc acaggggcat atccgttctg cagactcctc caagaatctg tgagcacggg    93180
gtccccaagc tcgaattata aatcagacag gcaaggccac tgctcaaagc cacctgtgaa    93240
gattgctcca gacgtggggc atgcagggcg gctgggcagg ccgcctttgg gtgtagactc    93300
agcgtgctcc ctggtttcaa aggctcctca ctaaaattct ttctgcaggt ttcactggca    93360
tattgtgtga tgagaacatc gacaactgtg acccagatcc ttgccaccat ggccagtgcc    93420
aggatgggat cgactcctac acctgcatct gcaaccctgg gtacatggga gccatctgta    93480
gtgaccagat tgatgaatgc tacagcagcc cttgcttgaa cgatgggcgc tgcattgacc    93540
tggtgaatgg ttaccagtgc aactgccaac caggcacatc aggtaggaca gtccctcctt    93600
```

```
ctctcagtcc ctccatccag ggcctgctct ttggcattgt cagctaaaag tgacagcttt    93660
cttcctgctc tgtgtctggt ggggcctcag gaatttcagg caaaggtaag accttggtag    93720
tttcgaagtc aaatgcctca ggctcctcac aggccacctg agcctagagg gaggctgctt    93780
gctagacgag ggcctgctct gtcctattag gagttctgga gctagttcac tgggcagcta    93840
catttcccag atttcccaga attccatttt acctgtgaga ggaacgatct tggacacagc    93900
tttagctgga gacagaggga tactgtgaga gatcaaaggg aaatgtctga gtggaagatt    93960
aaccagtgtg agccttgcgg agcagagggc ctactggata cacggggtga tttgtagggg    94020
ctcatcctgg acttaaggaa gtcggcctat ggagggggca gaggcagggg agtggggagc    94080
tgccctgatt tcattgtgtt acttcaaatc catttcttca aacttgtcaa aggtcctggt    94140
cttcatccag ggcctcacac atgccaagtt tgaaaacaaa gtcctttttg aattgctcaa    94200
gcatacgaaa aacatcccat gccttcacag ctgagaatgt gggtcccctc cccacattta    94260
gataactccc tcaaaggact gaataggact ttgtgaaacc ttccaaaagc aatttgcttc    94320
cgggctggtc cccagacatg agaaattgca gtacgaagga aaagtgagag atttacaagc    94380
agttgaatag gggcctttag aatggagggg ctgtgttagg cttgctgtct ccctcattgt    94440
aacaaacacg ctggaaacct ggcgagtggt gggttggcaa gaacttattt tcctctggga    94500
ttatatcctt gtgccagagt gtatcaggta tactttcctt cagggacaga ggcaagaagt    94560
taatattcat ggtttgcagc aggcagcatg cagagagagg ccagacccat tgctgcagct    94620
gtttgaagag ttagagcaaa gagctgcagg caacatacag acttgctggt ctgtgttcag    94680
tagaaaggag ctggcaggtg ctgccggcct ggctggaaag tccatttagg ggacagtgtg    94740
gatagactgt cacggagtca cgatttctga tcgatccagg tatcatgcag tctctgttgg    94800
tagtttgatg tttggaagga aggaatcatc atagcttgct caccgttcct gtggtttcca    94860
ctgtctgggt gctcaaaggg agagacacgc tcactgttag ggtcttctct catctgtcct    94920
ttataatgat aaactcttgg aataattagt tctcttgagt ttcaagtcac ctaaaatggc    94980
ttgatctagc ataaggaaga gaaaacagaa aagcagccaa ttcagcaaca gcatagaagt    95040
ctcctcgggc tctaagaaac agtagaaccc cagaccttgt cagaggagag ctgcagacct    95100
gaggccccag agggctgctc tgccagtgta gacgcttgtg ggcagctcag ctgaaccagg    95160
acctcagggt ctggagctgt actggcatgc taggacttca tggactgggg gccggaggct    95220
aaaaggccca cccctgcata caggaatatg gaagcttgtc tctcattaat ggtcattgtg    95280
gttagcctca gcgacatagg agggctgcat gacattctgg agctagcata gaggtggtaa    95340
ttattaacaa atgtctgatc acttacagat aggacggttg gtgagtgact caaatggtga    95400
catttggtct aggagcttta tctgtattct tacatgagat tttactttta cacttttttat    95460 accacaaaac agtctatgga ccccacatag cttgcttaga tgcactttaa tgattgcagt    95520
atgttttctt gttttgtttg ttttgtttta gttaaaatgg gattctagaa cggtaggctg    95580
ccgctgtttc agttcatggt tcaggccatg gctgctcctc ctggctgtga tgctctctca    95640
acctgagggc tgagagttaa caagttacac agtgacagat tttattgtcc tcaccaaagc    95700
catgaagcgg gcatgtgttt gttttggctgt gggtatgtag atatgtgtcc atctggttgg    95760
ggcctgcagc ctggatcctg gcagagatgc tgacagtttt gcctatattg cctttgtacc    95820
gtttccatga caacagagta gaagggacaa atcatggcta agtatgagta atccagtcct    95880
cttggcttct cagttctggc ttctgtggac tgtacttggc gatgcgtcgc tttgttctga    95940
```

```
tcggatggcc tggatcccct acagacttct gactgagtag caccacaggc ggaagtgctg    96000
acattcctgt ggtaacacag aatcatttct ctgggtctct ttacaggcct taattgtgaa    96060
attaattttg atgactgtgc cagcaaccct tgtatgcacg gagtctgtgt ggacggcatc    96120
aatcgctaca gctgtgtgtg ctctccggga ttcacaggta acactccttg tctttggagg    96180
gggcctcctt tagcccatc aagctgggaa aggggtccct cagtgaaaat cacttttttca    96240 cctgttcct gtttctcatc gtctctggaa ggtttgcagt ctgctctgta cttctcttc    96300 tgttccagac cttcctaagt ggaaacacag cctttccttt agcgtttcag gccacgcgtg    96360
tcttgctccc tgagacttcc tagcagatgg taacttttcca tccccgtgct tgggttaatg    96420
cctgcaaagc cacctttgct tccccacagg cagaggccag tgccttctgt aaggctgtgt    96480
ccaaggtaaa cgtgcatgga aacactggct gctcaccctg gggtctcgcc tctcccggga    96540
gcctgtttgg ggagggcata acttgaggag accaccacat agtttgtcta cagtgagcaa    96600
gatctttttg cccatgaaaa gaaagtagat tagaattatt ctgcattgtg actcttcctt    96660
aggtatgaac ctctagagag tttgcacatg tgcccatagg tgaagtataa tccacacatt    96720
ctctcttctt ccttttcctt gttaacatta actttgtcat ttatgtttct ggaaaaatta    96780
tcgtagaggc tccagaggaa gcctgggccc tcactgatac ctcatatcgg tgacagtccc    96840
attgttagga tacactgtgt gttctgcttt ttctggacat taccacacat gtgcagacat    96900
atataatatt acccttagt aactgccta tggtcatctg ctccccaggt gtgtagccca    96960
cttcagagct tttggcagag cctaaggaca gtcagagcca ggtgaagaga gtgctaggta    97020
cccagttcct ctatgccagc ggtatgcat gtcaggaact tttgtggctt tggtggatct    97080
cagttcttcc tggtgactga gacgccagtg tggtgaaggt ttcatgccct gacccactga    97140
ggtagcccga tgaatttggg catcctgaaa actgttctct caaatacgtg ggagctgact    97200
aaatacacag acctgttaag tgtaacagga agaaaatgcc caatttgtat gaacggctta    97260
ttctgagcta ggaaccaaag atgctgtctc acctcactta gttgggatag atgctactgt    97320
tcctgtggta ctgaggagag ggcagagagc gagagacgca gggtgatgtt cccagtgccc    97380
tgcaatcagg gtcttttccca ggcgtctacg ccagagccca ggctcattcc cattacatgg    97440 ccaagggga gcctgttacg gtttcttctg ggatttatgt aaggcttctc accggttta    97500 gttttttaa atgtcaggga atcatattct gtctgttttt aacatttagc aaatcaacgg    97560
ggtcaaagag ggggcacata ggctaaaaat actctaaaat aaacataagg tgtagcatga    97620
aaccacataa ccaagagatg gaatgttttg gttgctgggt ggtgccccct tcttgggaac    97680
tgttttctgg tccaagaggc tgttttgtaa atcggttgct ggaaatgtct aagagtcatg    97740
agccataact gtgaagtatt tggggctttt ccttctattt tattttaatc atttcccctg    97800 ctgtttttcat aggagcttta gaatatccga gggaggcctt tgtctcttct cttcctaagg    97860
ctgttcttta ttctcacagg agctctacat gttctgatta catgggagaa agtcaggcat    97920
catgtgatcc tataaactcc ttttcatttt ctaaagcccc tggtggtgtt tgggttacag    97980
cctggtggca gacacccata atcctagctg ttgtagaagc tcatgcagga tggccacaag    98040
tccaaggtct gcctggacca cggactgaat tcaagtcagc tgcccaactt agtaagagct    98100
tgtttcagaa tgaaaagtga aaaggcaaac aacaaaagca acaacaaga acggggcaga    98160 gaggccaagc gcagtagtag agtgcttacc cagcatgcat gaggccctgg gttccaaccc    98220
aagtaccaaa aactaaaccc aaactacaag aacaacagaa cccaaaaagt aaaacaaacc    98280
aaaaacaaac taagtcttcc agaaaacaaa caaaaagccc agcctacccc agatctactg    98340
```

```
tcttcctaca tttcctcacc atccataaat ggagttgtgc agtgctcagt taacgaatat   98400
ggctgcagag atggtgctgg ataagccagt gagctacaga gagcccatgc actcttccca   98460
gggctgggac cctctttctc atcctttggc agtagttatc gcaggagaag ttctcaggac   98520
acattggcaa atgaatagac aacttctgct gtccagccta gacccgtggt ccacactgca   98580
gcatgctgtc atatccagcc tagaacccga ggtccacact gcagcacgct ggcatctatt   98640
atacactaac taatttactg taaatagtaa gaaacatgca gtaattctca tgttgatcaa   98700
cgcttagccc cacaaggtgc agagctgaca ctagccattt ctgatacccca gtggacactg   98760
tgtgacaact atagaagaac actacagaag tagctgccaa cctacacaca ggctgcacaa   98820
gtagggatgg tgcaaatgca catgaaaatg gcttaaaact ttatctttga aattgtttaa   98880
aggcaaatga ggagctggga agagtgcttg cagatcctaa gttttatccc agtaccacaa   98940
caaaagaaa  agaaacaga  aaaaaaaaa  aagataaaaa agaatgaggt ggctcatgtt   99000
gaacacttgg aagactgagg caagacatac agaggaaaat ggcagctatc ccagactgtg   99060
ggtctttacc acaggagcca ccagagatgg ttcactgtgc atggaggctg gcagcctgct   99120
aatgccttac tttaaagggt gtgtctcttt tatttggaac ttttgaact  aaataaatat   99180
agtgttattc tttcttaaat taattttaga aaaagacttt taaacctgat ttagaacact   99240
gtgtccttga agttcataaa ttccttcata atagttgcta gatttcactc ccaatactat   99300
agggagaatg ttaattctca actattagaa atataaaaag acatctgtat gcttagtcta   99360
tatacatata cagcataaga caacggtgat gaaggctata gcagacaggc cttcaaaatt   99420
tagccgcagg tgtgttctgg caagatcacg tccacttcga tttcaggtac tgccaggacc   99480
tatattttta gagactctgg tgtctgaacc acataaatcg tatgaaatgt ggttggcagg   99540
ccaggccatc atagtctatg gcaatgcggc ctagaaattt gttgtcactg tttcaaaaaa   99600
acatacattt attcattcat ttatttattt gtttgtttat ttatttattt atttatttat   99660
ttatttattt atttatttct ggtgcctacg aaggccagaa gaggacattg gatttcctga   99720
gctggagctg agcacttttg agccatctaa catgggtgct gggcgctgaa ctctggtcct   99780
cagtatgaac agtcagcatt cttaaccact ggaccataaa accacatttc aaagagacgt   99840
tcttacagta aagtttgaaa accactggtc tggactggga gtcaccaaag tgttttctca   99900
gtttctggag ggcagtaaat tcttgcttac agactactta cggaggaaga aagtgagtgg   99960
gctctgttct aaggatgaaa ccaaagtgtc tattttttaa aatcagttta acattaaact  100020
agcagtccat tcatatccca gctaattgcg attaactaga gatagaaacg taaaaccttg  100080
actgaggaaa agtgacagaa cacgtgtgag gcagagctct gcacacatac atggcagtgc  100140
caggaggggc agcagtctct ggtgacagaa cacgtgtgac agaaacagaa aagtgacaga  100200
acacatgtga ggcagagctc tccacgcaca cacggcagtg ccaggagggg cagctgtctc  100260
tggtgacatc tggtgttctc cttaatgcct gtgaagttct gaagttctaa gctagatgca  100320
gtctacccga gagtgccgtg gcttcgatct gctgtcatta gtaacttccc ttccttatta  100380
atagcaagtg ctcctcgagc cttccttgca tggtgtgaca tgcttctccg tgttagtcct  100440
tgaaccttac agcctgcctc cgtgaagtgt ctgcatatgc gtctcatcgt tctaaccccg  100500
tcccttgaga atttaagttt gagtgacatg gccctgacc  cctctacagg ccagaggtgc  100560
aatattgaca ttgatgagtg tgcctccaac ccctgtcgca agggtgcgac gtgcatcaat  100620
gatgtgaatg gtttccggtg tatatgcccc gagggaccgc atcatcctag ctgctactca  100680
```

```
caggtgaacg agtgcctgag caatccctgc atccacggaa actgtactgg aggtctcagt    100740
gggtgagtag ctaccctgtg ctagctagta gttactgatt ggcccagttg gcctttaaaa    100800
ccaactgaag gaaacactaa cacaatagct tcagtttgtc ggttgggaac ttgacctgat    100860
atttaggtaa aggttttgaa ggtctgtgtc aaagtctttc aaatcaccgc tctgtctcta    100920
gaagctggcc tgtctcctag gactgagagc ttacttgaga aataaacact gtctccttta    100980
catgagtaat caatgaggac cccacaggag ggtccaggaa ttcatacatg tagcagttgt    101040
gttttacact acaggattga gatctgacga gtgttctaga gccacgggca ccttaacacc    101100
gtctattcct gttctgtcat ggagcctggg ataatgcatt tgcagcctgc atgccctcag    101160
agttgtgcag catgtgatgg ttttagaaca agagtgtctt agacactatg aggggcatgg    101220
ccatgcctca agcctaaaag aatggagagt gtgttagata acttcctttt cttactggct    101280
taagctagat ttctgatcca gaacatgatg atctttaaag caccctttca cggctctccc    101340
ctcctccact ctctctccat ccttccccca cttcccagct ccccttctct gcctgatctg    101400
atattatact tacgtactaa tgatgttgaa gtcagatatt atatgtgttg cagatatctt    101460
cagcttttg gcttttttg gtctgaagaa agtgtgactg acctgttaag actccagtca    101520
atcctcagca ggcttaagtg gcttattttc tgatgtctac tttgtactag cgattctgag    101580
cttTgttcat gttcatgttt ccttcagatt gccccagtat atttgacaag ccatagcttg    101640
tgcttgcaat tcatcagctt cctcatgatc cagggaagca ctgtgtaggt ctcccatctg    101700
aacatactag atggattcat gactcttacc atgtggtgat gattccagta tagatccata    101760
ggaatataga aatgagctaa ttcctgtaat cttTgtacta gggaggctta agcaggagga    101820
ttaccatgag tttgcagcaa gccaagacca catagtggtt ctaggccagc ctgggcaaca    101880
gagtgagact ctgtcctcaa aataccagac aaaaggaaag gtgaaactgg cttTcaccta    101940
tctcttatgt gtctcttatg actcagttgt acctttggac cacatagtca cacctctctc    102000
ttcttgcagc tataagtgcc tctgcgatgc aggctgggtt ggtgtcaact gtgaggtgga    102060
caaaaatgag tgtctttcta acccatgcca gaatggagga acgtgcaata acctggtgaa    102120
tggctacagg tgtacctgca agaaggggtt caaggtgaa gtgaagtctc ggcttgttat    102180
acccgctgtt tgtcttccct tgtggtacac ccctccacat cttggtttcc atttcttttt    102240
gttgtagttt actaatacag taccatgctg agcagttagt atgtctgaga tatgtgggga    102300
ataaaaacaa gagtagatat cttTctactt tcagcttagc agagaggtaa attgttggga    102360
caataatact taaacagtta agactcgact taggggcgtg tgggtaaaag tgcgtgctgc    102420
ctgacaacct aagttccagt gtttgtgtaa ttgtaagctt cctggccaag gcttgattct    102480
ataataagct tctcagaagt gagatgagag tgttgtactt actggatcga gcccTgtgct    102540
atgctcagga cctttccagc aaatcctcac acatgagcta ttctggacac tcagtttcct    102600
gtgctctttt gggaaaatac atagtagagg aacatgtctc aacaatattt tacagtcagt    102660
tttccccgag ttgggctgtt tgacactttg gcatcttTta gaactactca ttttgattgc    102720
aggttgagta tccctaactc caaacatgga gtcttccaaa atcgggaact ttttgaatat    102780
cagcatgaag tgcaaggtcg tgacgctcta tttcttgtac agtattactc taacagattg    102840
cattaagtca ccctcagttg tgtgcaggag gataactgga gagagacaca atgacatcct    102900
tcaagtagct tgttatttat ttgtaagaat cctcactctg tcctacccct aaaaaatcct    102960
aaacagataa aacaccatga ccaaaagcaa gctgggagg aaagggttta tttagcttac    103020
acttccacat cactgttcat cattgaacga agtcaggacc ggaactcaaa cagggcagga    103080
```

```
acccagggc   aggaactgat  gcagaggcca  tggagagtcc  tgccttgcct  cccatggctt  103140
cctcggcctt  tcttcggcct  ttttagagac  cccaggacca  ccagcccagg  gatggcacca  103200
cctataatga  ctgggccctc  tgtcatcaat  cactaattaa  gaagtgctct  gtaggcttgc  103260
ccacatttat  ttattgaggt  tccatctgtc  agatggcttt  agtgtgtatc  acagtaacat  103320
aactgtccag  gacacatgct  aagtatgtca  gagaaaggag  attttttttc  ccaagacgac  103380
accagacaga  cttagaaagt  ctctacatca  gatactaatg  ttattacatt  ttctaggaaa  103440
cttgtagatt  caaaagctct  tttcttttct  ttcctctcct  ctcctctcta  ctcccctgcc  103500
cctcccctct  tctccccctc  ccctcccct   ccctcccct   ccatttttta  aaatctcact  103560
gtaacttacc  atttatctca  tgggaaatga  gaatatacaa  tcaaacccg   tttgttcagt  103620
gagctatgag  cccctctgag  cccgccatct  ccctgctccc  ttctgctaac  agtgctctgg  103680
ctttgccatc  tttatggtcc  ttgttgggtc  acattggagg  tgcaaagaca  ggtggattct  103740
ggtcttgcct  tagtcccact  ctgttctttt  tcttttttgat cttttagtgg  gaataaattt  103800
tctgccttga  aataggagaa  ctatttttaa  ggctttggaa  cctagctcac  tgatagcaga  103860
gactataccg  gtggaagagt  gggcaggcac  ttcagggctt  ttcttcatga  gtttgccctt  103920
tttctgacga  accagagact  tctcttaaag  ggtgcatgtt  taggtagagc  agcatgcttt  103980
tcagcatagc  gagtgctcag  ttcattatgc  agaatccagt  tccataagga  ggagcgttag  104040
gcctgagtca  ggccctccct  cacagttttg  gccaaccgtc  aaactaaaat  gaatgagcag  104100
gtgctcccat  gacccaaaga  aatgagtgtc  agtctgtgac  ttctaatttt  cacaaccacc  104160
aggagagctg  gtgagtaact  gaggctgaca  gtttgagtgt  gtatgtgttt  ctcctcctcc  104220
tcctcctcca  ggctacaact  gccaggtgaa  tatagatgag  tgtgcctcca  acccgtgtct  104280
gaaccaagga  acctgctttg  atgacgtcag  tggctacact  tgccactgca  tgttgcctta  104340
cacaggtggg  tactgcaggt  gccagcatgg  ctggggggg   ggggggtgtgc  cctgtgactt  104400
gggtaagtga  cgatactctg  aggactcagt  ttggtgtcac  tcgtggtctc  caaggcttcc  104460
ttcctttatg  cttttttagtg tttggggttt  tgtttgttgg  tttttctggt  gctgggggtt  104520
gatcccaggg  ccttgcatct  ccttagtatt  gttttgttgt  tgttgttttc  atttttttac  104580
ttattcttct  ctcagcagtt  gcccccttcct cctctcctgt  aagttgttca  gtgagcttca  104640
ggggcgcagc  tctcctgagt  caccacccat  gttggggtga  acttttagat  gacatagcca  104700
tgctattgtg  ggtcatcctc  aagggctctg  tgactgacct  ccaccccag   ccctgtgttt  104760
tactctttgg  ggttttaaat  ttatgtatga  tatttagaac  cagatgccta  cttggtccag  104820
aggcatctat  ccttttgaca  ttgtaacata  aaattattga  gaaaattcat  ggtaatgtgt  104880
ttttctttct  atatacaaag  ttttaagatg  actgttaaag  ttgactttgt  tgtcacttga  104940
ctttagaaac  aactcaatat  cctgtaaact  tcctcagtaa  gtaaaagcat  ttgccaccaa  105000
tcctaagaac  tggagcattg  agtctgcaat  tcaccttctc  aaaaactaat  gtgttttaaa  105060
acataccttg  atcctttttt  tagtggaatc  attttttaatt ttaattttc   tctaagtgtg  105120
aattcagtat  tctaaggcag  gaagcaccca  ctagcaggca  gctgttagca  cctggtgata  105180
gcagtagaga  ttgcctggca  acagagatgc  aggtatagag  ccggcccag   tgatagcagg  105240
ggaggaagca  gccagcagag  agactgagtt  cactaggtgc  tagacaggac  ttagagtgtg  105300
cttcccactt  agtccgcaga  aatcctccct  gaggacaggc  tagggaagtc  tcagggagat  105360
aaatgagctg  cccacggtca  ccagattagc  tgcagtgggc  caatattgga  aggagcaggt  105420
```

```
gtggttatgt gcatatcaga taccctgcac atcagatatt tacattagga ctcataacag    105480
tagcaaaatc acagttacaa agtagcaatg gaaataattt tatggttggg gtcacctcag    105540
catgaggaac taactgtact aaagggtcat ggcaccacca agctagaacc tctcagttgc    105600
tgctgtagcc tgggattctg agcacacctg tgtttgcagt cttgggacgc catcttttcc    105660
tcggttgatt ctttatcaca gactgtcatt tgttttccag gcaagaactg tcaaacagtg    105720
ttggctccct gttccccaaa cccgtgtgag aatgctgctg tttgtaaaga ggcacccaat    105780
tttgagagct tcagctgctt gtgtgctcct ggctggcaag gtaatgatgc tggatgcatc    105840
ctgcacttta aacaaagcca tcggccctca gatgacatgg gagaccatgc tgacacctgt    105900
aatctctgta gggagcgact agctggaagg gctcataaca ccttctcaga ttccatcttt    105960
atagtcctca agtagctgag accctccaac ccaagtgttt caagctgtga gtagcagttg    106020
ggaggagttt ccgaaggacc tcctgcatcg gaccaatcag gtggcctcct gcaccaaaac    106080
accctaagct cacagtggac tgaaactcac acccacctaa gcttacaccc tgccttgatt    106140
tctatgggaa ttttcttcca aggactggct gttcattctc ctgtcttcat aggtaaacga    106200
tgtacagttg acgttgatga gtgtatctcc aagccgtgta tgaacaatgg tgtctgccac    106260
aacactcagg gcagctacgt gtgtgagtgt cctcccggct tcagtgggat ggactgtgaa    106320
gaggacatca atgattgcct tgccagtgag tacacctgcc ctcagggtcc cagagagaga    106380
gggccacgtt ccctacactg acatcgatgt cccacactcc aggatcttta agtcttcctt    106440
ctgaagctac tgtctttaga aatcaaaata gtagaatctg tcttgagcat ctctctacag    106500
catcttaaat gctgacaaac tacgacagt gctgtggtag ctttgtgaga acatagattt    106560
ttgaaaggca gtaaacagac aaaagctaca agtattttaa tacctggtag aattcatcca    106620
attttggcaa aatgatagag aaaaccatca accatcatga atgttcctct aaaagtcgct    106680
tcgtagcttt acctgttcta cttccttgtc tcacgccagc acagaccagc ctctgccacc    106740
atagataaat taatacttta tatagatgca tctatatagg catgctcttg tcagtaatat    106800
ttcaggctgg ttcatgtcca tatcaccact agggtcttcc gtcttattgc tgagtggtct    106860
ccactctggt tgtgcacatt gagcatgctc agccctgaag gacactcacc cgttccaggc    106920
cttttggttt tagagtattc acatcttagg gatgtgaccc aagtgggagc atgaggtgtg    106980
ttcatgcttt catatgtacc gtgcatgagt aggccgaagg taacttgatg caattctttc    107040
aatgcatctg aatgctgact gtgcaatgaa ttttagttgt tcttgtgaca tggtgctgac    107100
cctcataggg tttcagactt tggagagctt tgcattttag acttttggat tattttgacc    107160
tgtgctattg ttacttgttt gcttttccag ttttaggca ttatagataa aaatgttatg    107220
ataggagttt gccttctctt ccttcttaaa gatattgtgc ataatgggtg tatactcctc    107280
ccaaacagca agaaatggac tctttatcat cgtcatcatc atcattgcca agttttaaat    107340
cttttttaag atttactctt tttgagtctt aacttttgac tattttagtt tggtttggat    107400
tgagctttgg tgaaatgtgt ttcagagatt ccatctgtct tagttaagtt tctagtgctc    107460
tgatgaacac tgtgactgaa agtgatgtgg gagagaagga ttcatttcat cgtactacta    107520
tagtcgttac tgtggaagtc agggcaggaa cctggaggca ggagctgatg cagaggccat    107580
ggaggggtgc tgcttactgg cttgctcccc atggcttgct cagtcttcct tccttccttc    107640
cttccttcct tccttccttc cttccttcct tccttcctte cttccttcct tccttctcat    107700
aatgaaaatc cttatcccac attatttttt attattattt tattgataga ttgtgagttt    107760
cacatcatgt actccaaccc tgcttctctc catcccttca tattcacccc attacccttg    107820
```

```
caacctccttt cctaaaataa aacacacaca cacacaaatg aaaaaccaag gcatagaaaa   107880
catctccttg tggaaaccgt agtgtgtcac agtgtgtccc acagtatacc cacccctttg   107940
tccacacgtc tttacttgca aatgttcatt acagtcagtc attggtctgg tttgaggcct   108000
ccagcttctg tgacatcaat aatattgtat cctcgcctgg acttctcctg gttaacctgt   108060
tgttgcgcag ggtcatggag gtcctgcagc tttggttcaa cagaactggc ccctttttg    108120
tgtccctgcg attcacagat gatatagatt ttgttgtagg ccaactcagg ccctggatct   108180
gggcctgggt ggtagctgag ctggttagcc tacaggctct cccttatcct catcactggg   108240
gcgagctctt cagcactact ttggctgggc cacctatgtc tctatctgca ggaggcaggg   108300
tcacctctcc tgcactgaac tcagctcctt tgtgcttcct aggcaaggtg cagggtgcgc   108360
tcccctaaat gctgtagcca ctgaggggc agggctagct ctcctgctct ctcccatgcc    108420
ctcctgccag ctcactctgc gagctctcct gactaactaa ctgcaggtgg ctgggaggta   108480
aggaggcagg gtatcacact cacacccaca ccctagggg ctggctcacc tgctttacca    108540
ccaccagggt cagatctgct gtttagcctg cttctcata gaatccagga tccccagtag    108600
gctgggtcc tcccatgtta atcattaata aagaaaacgc caacacagac ttgcctacag    108660
gaaaatctga taatggcgtt ttctccagtg actgtggttt gtgttgagtc gaccgaacaa   108720
aacatgaaaa caagaaaaac atgcatggca cattacctaa ctgacttatt ttcaattttt   108780
tggcacaggt tcattaataa taagtcttat tttaccctga atagctatga gatgtatgct   108840
aattttccct cttggatctg gtagggacca tttcttcctt ctctcttgga gaagaatctg   108900
ggtagaattc agtccctcat tctcagggct cagcctgccc tgggagtccc tgtgcagccg   108960
gtgctggcct cgaacttatg gcagttttcc cgccatttaa atgctgggct acagtgtga   109020
agcaccaagg ctgactcttt tcttcttgaa catgttttgg agtgtgttaa atggctctct   109080
gataaagcag agcgcacttg acctttcaat tcactgctta aattttcatt tcatatttgt   109140
gatggtttct gccactataa cttaacactc tgaatgccag cagcaatgtc acggttttct   109200
tgatttagcc cctttgtcat tagattgtgt gaggccctgc tgtgattata actcaggacc   109260
tgttgacatt tctccgactg aagcaattta caaaaaaaag aaagtaagag agaagtacag   109320
gaaagtcgat tgatttatgc agtgttcttg gaacagactg agtttataac ctgacccctc   109380
agcctccaca aacatgtttt gaaaatactt accaatattc ccaatattgt atgtgttagg   109440
ccacataatt gatttacgta tacgtggagg atcaatggaa gttttatgac tattaatgtt   109500
ataaaatagt gttaatatag attagattgg tcttgatttt caaacagata aaaaatctca   109560
ggcaaacgat aactgaatta attttcatga tagggttcat gtcaggataa atgaaagggg   109620
tcaaatgtgg gggatggaat gcgcttctta agggtgtggc ttggcctggg tcatctgcct   109680
tcacagtgct gctgtcctga gtcccacttc ttttgtcctg tctcagaccc ctgccagaac   109740
ggaggctcct gtgtggacca tgtgaatacc ttctcctgcc agtgccatcc tggcttcata   109800
ggggacaagt gccagacaga catgaatgag tgtctgagcg agccctgtaa gaatgggggg   109860
acctgctccg actatgtcaa cagttacacc tgcacatgcc ctgcgggctt ccacggagtc   109920
cactgtgaaa acaacattga cgagtgcact gagaggtgag cagggtgggc ctgggcacca   109980
gtagctcaca ggacggggag gcaggggagg taacatcaca gcatatcaca atacaatgcc   110040
aggattgtag ggcaaggatg aaccgcactt gaggcccttt cttccacag tcctctctca    110100
ttgctcagtt tttgaaagac atgtaattgg aaggtcaaag gtcagaggtt gaaaggcttt   110160
```

```
agtgggatag actgaataga cagcatcgct tctttcttgc catggagcag aggagccctc    110220
agttctgttc tgttgccctg tctctttgtt ccagctgtaa gatttctctt tctttgtaga    110280
tctgttacca ctgtctaagt agttttaga aggtttgttt gatttctttt tattattta    110340 gcaatgtgtt tattcccttt cataaagaaa tctagagtga aaagctattt aggacttttc    110400
ctgtaaggct gattgattta atgataaaat aatgttatgg aaaacaactc tcttcaggat    110460
tctaggcaga tctgtctttc aaatgctcct aagatggata ttgggaagga agttgatact    110520
gcaatctctg acctccagtc tagtttagaa gactttaaaa cttactgggc acaggcattg    110580
gagtctcaga ggtgtttgtc cagttaaatc ctctatttct ctgctttttt ttttttaagat    110640 ctatttattt tatgtatatg agtacactat agctattagc agacacacca gaagagggca    110700
tcggatccca ttacagatgg ttgtgagcca ccatgtgatt gctgggaatt gaattcagaa    110760
actctggaag aggtcagtca gtgttcttaa ccgctgaatc atctctccag ccccgacatc    110820
ctacatttca gcagccagac tttacagtag cagctcaggg cctcagctca cacagctgat    110880
gttgtctctc atttgctcct cagctcctgc ttcaatggcg gcacgtgtgt tgatggaatc    110940
aactctttct cttgcttgtg ccccgtgggt ttcactggtc ccttctgcct ccatgatatc    111000
aatgagtgca gctctaaccc gtgcctgaat gctggaacgt gtgttgatgg tctgggtacc    111060
taccgatgca tctgtccctt gggctacacc gggaaaaact gtcaggtaat cagcctccct    111120
cccgttcacc cgctcacctg gctccccaca gtagccgagg actctgtcta gtttccaggt    111180
ggggtgaacc atttgagaag agagaacagc atctcaggtg gtccctgagg tggctgggtc    111240
accttcttga tagctagaag agtccagact ggtgacacca gcaatgccat atgggctaac    111300
aagcttctgt ggaaactgtg actgacagtg agcacgtaca caccttcaca gtgcatatgc    111360
aggaagaatg gatgtgagct tttcattgct aacctaaaaa acaaaacaac agcaacttaa    111420
taggaggttg gtttgggttt gtggttttag agattttagg cttcactggc ttcttttgtt    111480 tatgacctg agacaagagt aagtgtcatt gggacagagc cggtgtagaa ctcttcatgg    111540
tggcctgaag cagagaggga caggagaaga ggaggggag ggaagggaaa agacaaagga    111600
agagagggag agaggaggca ggacagacag atgaggtagg gaaagccaag aacgagatgt    111660
agctccccca gacatgtacc cagtgagccc tgtttccagc tggcatttcc tctagttctc    111720
agaattgttc agaagtaata ccatctttga gaactaaacc actagtgcac gagcctctga    111780
ggacatttca tattcaaaca caggacagaa caatcgaagt caaatcagta ataccaggg    111840 agagccacca gggtactgct ttacagtgtt ataacatagc catcaccaaa ctgtgtattc    111900
ttaaaactca aatatagaaa tatgaatctg ttataatctt aggatggaag aagccatcat    111960
aggaaactga ctttcaattc atggaggaga aacagcctcc accttgtccc cagaaaggat    112020 agttttaaa ctatccaagg tcacatacaa attgtaattt gtgccgcttt acatcttctg    112080
taagagtgac ggaactcaga gctcatgaat acgagactaa ttagagacca cattggatga    112140
cactggaccc agaagcagcc accccagccc cgctccccac atgaagcagc ttggtcttgc    112200
cccatcctcc actgaccatc tctcagccag cagcagtctg tgtcaggaag caggcccct    112260 ctctgcctca tgttatttgt gatcctggag ttgaaaatac ggttgtggac cgtttaggct    112320
tttgagttgg atcatttcac ccatctcccc ccataggcag gagcggtcaa ggcatatgtg    112380
gtcctgcggg gttaacatag gaagcatggg cccaggcagc agctatagct cttgccagcc    112440
ttgcaaggag gccacatatg ctcacatagt catgactaat gctctgggga taacagctta    112500
ctgagcctct agagtggtta ggttcctgag gtaagggctt ttaaaatgac actggccaga    112560
```

```
caaacgaggc tataaagtga cagagtgtgt ctaggacagg gtgcccagtg aaggcttctg  112620
tgaaggcgtc cctttctttc taaaaccagt cctttccttt gacatctcgt gacacactgt  112680
aacttagaga cttcatttat ggcatctggg ttttgatgca tgtacaccct tgcctccgct  112740
tcagaccctg gtgaacctct gcagccggtc tccgtgtaaa aacaaaggaa cttgtgttca  112800
ggaaaaggca aggccccact gtctgtgtcc gcctggatgg gatggtgcat actgtgatgt  112860
gctcaacgtg tcctgtaagg cggcagcctt gcagaaaggt gagctctgcc ccaagcatca  112920
ggtactgaca tataggccat catcttaggg cacagtactg aaaggacaag ggtctgaaga  112980
aaggctagag gaacatttag agatcccaaa gagaaaggtg gttgaaatga agaactagac  113040
acagatgaag caaaccctag agcagccacc agccaggctc acttgctttt gggttgaacc  113100
tgccgtgggc cgcactctct gatgcttctc tctccacctg gtgcccagga gtacctgttg  113160
aacacttgtg ccagcactcg ggcatctgta tcaatgctgg caacacccat cactgccagt  113220
gcccctggg ctacacgggg agctactgcg aggagcagct tgatgagtgt gcatccaatc  113280
catgccagca cggtgccacc tgcaatgact tcatcggagg atacagatgt gaggtgagga  113340
gatggcttag cccagagggc tccaatgacg tagtgccggt gttaaaaaca ctggctactg  113400
agttcatccg tctgtgtcct acagagtatg aatgtctact cgtccttatc atagtgtttg  113460
cagccagcat ttttattttc agccatgctt tcccatagct ctggtaagat gtcttcatag  113520
agtctggacc atccctcctt aactggcttg ctctttgtgt tggcatcctg caggctcacc  113580
tagtacagta gtccccttgc ttcctgaaga gcaacacagt tcatcagcca atgagtaatt  113640
ctctcacacc aaaaaaaaaa aataaaataa aagtgtggtc tcacctgcta tgccacagca  113700
ccatgctcag ggttactgta atgtttaaga atgtgtcttt tgctggatgg tggtggcgca  113760
cacctttaat cccagcactt gggaggcaga ggcaggcgga tttctgagtt cgaggccagc  113820
ctgatctaca aagtaagtgc caggacagcc agggctacac agaaaaaccc tgtctggaaa  113880
aaaaccaaaa aaaaaaaaaa aaaaaaaaaa agaatgtgtc ttttttcagc gtctgggctg  113940
atagatgtta gagccagtgt tagacaaaca ccagaatggg aacccgaaac ccaccagacc  114000
accgagcaac aacagaaggc ttctctcctg ctgcctccgt tgtttatctc cgagcaggcc  114060
actctcggag caggtcgcag tctgttagtt caaaagcctg ccgctgctga actcaaactt  114120
ctccacagct gactttttt aatagccaaa atgagcagaa ttatagccat ttaatatcgc  114180
ttgcctcatg tggcctgcaa agagacacac agtgagtgta tcctaggtag tcaactctgg  114240
aggccaagga gcctaaactc ccccgggagc tccctcaccg taagactggt gttgctgggt  114300
cactgaatgt caccacacac agttttaagc tatggtatcc cctctttcaa agtttgcttc  114360
tcctcttact ctgtcgtctt gtgctgtgag ggacttcctc tgcaggcact gttggggtag  114420
cagtgtctaa atgaaacttc ccccacagtt gtctgtttcc ttatcaagac ttgtttcttc  114480
caattcctcc attgcccacc accctccatt tccccccca cctgctctcc atctccccc  114540
accttccatt gcccactacc ctccattgcc cccacccctc tatctccccc caccttccat  114600
tgcccactac cctccattgc ccccaccct ctatctcccc ccaccttcca ttgtccacca  114660
ccctccatag tctcccctg ccctccgtcg cccactgcct tcagcctcat tgtccattca  114720
cacaatcctg caatgggcac agcctctta ctcctgcatg cacgtgcggc ttgagcctta  114780
ggctacacat catgtgtgaa ggggtgcgca ctacatggat gaggaaatcc ttacctgaa  114840
gttttgcttg ggggatgcca tgaaaatgac cctcagaaca tacagtcctc actttccttt  114900
```

```
aaagtggctt tgggggcga aggggctaga agaggaatag gtaaccgtga ccctgcacca    114960
ggaagcagca gagaatgcag tggttataga ggggcggata cacagttgct tagtgggatg    115020
gaagcaaagt catggtaacc tgacctctcg cttggccctg tggtcggtct gcagcagtga    115080
cccctttctc cgtgtccttc tatcctgaca gtgtgttcca ggatatcagg gtgtcaactg    115140
tgagtatgaa gtggacgagt gccagaacca accctgccag aatggaggca cctgcatcga    115200
ccttgtgaac catttcaagt gttcgtgtcc cccaggcacc cggggtatgc agtcttcagt    115260
cttcgttact cttteccacca gggacattcc ctctaggcat acattcttag tgctgaagca    115320
acttttaaaa tctgagacaa tttaaagaag actagcttca ttggagccac ttactcagtt    115380
atctgctctc actctgatct cctgccagct tccattcagg tttggttgtt tcttagctta    115440
tgttcaggaa aacagaatgc agaatgaaca taacccctaga taaccaggtt ttttttggtgc   115500
ttcaagtgaa atcaactgtc aaccttttaa aggaagcgaa tccacatagg cctgcttttt    115560
aattgtttaa gctagccaag tctgtccata gaacgaggga atctatgaga tgtgtttggc    115620
tgctgtcctg ggaggcagca gacaggaggc tgtgctcctg cacctgcacc tactacaccc    115680
ctggactgtg gaccacagag catcagtgtg ctctgggaat tgccacttgc tccagactgc    115740
ctcctggaga gagcattgct tgctaacatt gcttgttagg gacatctggt gctgaaggaa    115800
atgcgtagcc tgtgagcaac atggcaaaga tagcagtcgt gcgtttaggc agcaatcaaa    115860
cagaggagac cctcatagct ggctttgtgt ttacgtagac ttttgtgcca gtgcatttga    115920
ataccttctt tttcctagag atcaaatttg gctaaattga ggcagaagaa tactccatta    115980
ataggtatgt aatacagaat gagtcttagg gaagggaaag ctgaagacta gcctacaact    116040
aactgtttta aaattcatta catggtttct agtctagaaa taggaaattc catggtgcaa    116100
agttccaggt gcttactagt gtattccttt gtatttaccc atccatctac ctgtccgtcc    116160
atccgtctat ccatccatct atccatctac ctgtccgtcc gtccatcctt ccatccattc    116220
atctatccat ccatccatcc atccatccat ccatccatcc atccatccat ccatccatcc    116280
atcttttgtg acagggcatt tttgagtagt aaagctaaat gcataaggta agaagcaaat    116340
tgattctctg tcttctcctt tgggaggttc atagccatcc ccaccccat ctgatctccc     116400
cttctctccc ccaccccatc tctctttgtc tccctctgtc ttctactctc tccctcttcc    116460
cctctcccctt tctacatccc ccactccatc tctctccttc tctctttctc cagtcccctag  116520
tcccatctcc ctcttttcct ctctatcttt tcccatccct cctcctttct cccctcagtc    116580
cctctcccta tctcttcctc cccttttcct cccccctctt gttcccgctc tcttcccttc    116640
tccctatgt cttctcctct ctttcatccc tcttctctct tcttacctct tccctcctc      116700
tctttctgtt cccagaattc caagtagcct cagcctcaaa ttcactatag gcatgtacta    116760
ccatgcccga gtggttaatg cctttaaata atggtattgg ttagaacaag ctacaattct    116820
agtggtagct aattatatat atcaagtctc agatagcaca atagtggttt tgttggggtt    116880
ttttgtttgc tgttttggca ctcagacttg cacaggtgtt gggttgctgc ctttctttct    116940
ctgtgctttg gggctgcagg ctccaaggca gccacagcaa aggtggagaa actgcatagg    117000
gctgtgcagg ggcttttact cagtgtggag gtgacacaca tcacgctccc agaggtgtgt    117060
cagaaccact cattactgtt cttccaaggc ctgtggaggc tgagaaccca ggaaagggca    117120
tgcgtttgta ctgtaccaca gactaccaca tagacataga tgcatccagt cccagagtgg    117180
aacatctcct aagccaatga gattttttgtc ttttctcaat caatcaatca atcaatcaat    117240
caatcaactg atcaatcaat ctcttttct ctcccctcc ttctcgtcta tttcctcctc      117300
```

```
ttcctcctcc ttcttttcct ttgttttgt tgttgttgta ttgagacaga gtttctctgt 117360
atatccctgg cttttctgga tcttgttcta tagaccaggc tggccttgaa ctcagggatc 117420
tgcctgcctc ttcctcctga gtgctgggat taaagccttg tgccactgct tggctcctaa 117480
atacttcttt gtggtagctt agaataataa tctagtatat ctattgatct gttgactgtt 117540
tctgagccag ctcctcagat gtgtcttctc gctgatgttc ctgccgtggt cttcaccgag 117600
aacttagcag ttagtcttac tgatggtctc tcacgatacc tggctctcct ttgcagtgtt 117660
tccaagattg ccttttaatg gtctgttata gtgtggttct cttccagtgt ggtctgtttg 117720
aatgtttgtt ggattatatc ctgtgtgctg atctttccag gtgcctgaca tagtgtatat 117780
ttgttctgac ttttcctctc tggccatcca ccctgtccac ctgtgactgc tcccagcgac 117840
tctggagttc tcttacagta cagtgagtta ttccagtgct tgttctcagc actgtactcc 117900
caggccttgg atgttgcctg cgcatacctc ctgctcccag tgcataggct aacctagaac 117960
acttctgtca tcctgtgttt gcttcaggct aagaatgagg tcacgctcac atgataagct 118020
gtgcatcact gatagttccg tctacatgga agctttatgc ttatttact cctcatgcca 118080 aacaccaagt atcctgtgag actgggagca cgtcctggct tgtttgctt ccactttctg 118140 gttcccattt taatctaatc tgtgagtaga taaggtgata tgtgcatgtg gacagggtaa 118200
acatgtccac atatgcatgg aaagacatgc agtaaagaca cactcccac tgtactcacc 118260 cccagcaccg cgccctccct ctcccctcac actgcagaca gcctcttgtg tgtttctaga 118320
ggagttaaaa ggctatcttt cagaattgca ttatgtatgt aggagccaaa ttcaaagata 118380
gttttacccc ctccattttt aactctaaag atgtatcaaa gatgctgttt ttctcttgac 118440 cttttttactt aattggaata ttttcatatc aaaatagga acttcttcag tattttctca 118500
tagcttcaga attcccctt atgacaacat tatgtattgt gcttaactgg tcctctagtg 118560
atagacattg gtgttttttt ttttaaagga cacatataag tgcacgttac agaatgtgtt 118620
ttcagaaata gagtctgctg ggccactata ccgaggttaa gtgtcatta agtggcaatg 118680 ctggctgcat cctctctatg taattcatca tctagcatat ttacaagttc ctgttttccc 118740
actgggattt atcccttcct ccttctgta gatgctgtct gtccttacta tgtgcagaag 118800
ttgtttgtct ttgctgtgtg atgtggatat ttcctgatg tactgggtt gcaatctttc 118860 agacgtctta ttctgaggtc ggaatctttc agatgtctct ggggatttt tacatgcaga 118920 ttatttctaa tcatattgaa tttatccatc ttttttatgg ctgcttgcat ctgagtggta 118980
gttgatttta tcctccatgc ttcaagattt ataaagacat tcttctgtgt ttttatcctg 119040
gactagaatc ctgaagtggc tttcccatgt gactggatgg ttgatgttt ctacaatgac 119100 ttgagatgga actttgatca aattctaagc tccggtgtgc atttgggctg ttgttctgtc 119160
cgtcgattca caacaaactt ttaaccatga aggactcttt ttcatgctct cctggctgtg 119220
atttggtttt tctatatcat tttttagtca gtttgccatt aaaaagtatt gctgatatct 119280
ttttgagatc atattacctt catatataat acagtgagca tgccttttca tggagtcgca 119340
taatcagata atgtatgtct tccatctgtc cacgtctcct ctgtctgtcc ttcagagcac 119400
ttgcctgcaa ggccacacag cttgctctga tgctctcagc catttgcctt tgacactgc 119460 tgctgacagt gaggtacatc tgtgtctcct tcccttttta tgtcttgctt ctcttaaagt 119520
ataccaaagt gctatagaag tatcttcatt tttaacctt tcaaattacc ttgtggagta 119580
gtcattgatt ttgttgtttc taaacgtgtt cacagatatt ttaactagat ggctcctaga 119640
```

```
tcttcagtgt gttacttagc cagaataatc ttcaaattct tagcaagata tttccactct   119700
gttgttgtct taaataaaag atattagtgt acctatcctc ttttaaagaa aaaaaaagtc   119760
agtgtttata aaacataaaa tactattgcc caaaatctaa ccccagcata gcctatgtag   119820
tgattagatg tgctccctgt tgaactgttt cacagtttga tgggagttga taaggggtgg   119880
aaaactccca cagtctcctg agctttgact cccgtgtgct tgcgatggcg cagttgtccc   119940
tgctgctctg gattgggtga aacacaagtg gagcctcagg gtgcaacttc ctctcctgtt   120000
gctccccggg aagcagctgc acgagctgca tgcagctggc atgggctaag aatatttttt   120060
gccttgccca atttaaaagc tcccactgta gattaaggat tatactcaaa ttaatctcta   120120
aagcccacaa gggcatttat cccttgctaa tggcgggttc agtggatttt tgtaattctg   120180
tctttcttct ctcataggcc tgctgtgtga agagaacatc gatgaatgtg ctgggggccc   120240
ccactgcctt aacggtggcc agtgcgtgga ccggattgga ggctacactt gtcgctgttt   120300
gcctggcttt gctggggagc ggtgtgaggg ggacatcaac gaatgcctgt ccaacccttg   120360
cagctcagag ggcagcctgg actgcgttca gctcaaaaat aactcaaact gtatctgccg   120420
cagcgccttc acgggtgaga acctctcagc ccttgctagt ctgatgtgca ggagtcttga   120480
gtaagcaaac catgatctct atggaaatgt ctgacctcct gcagcaagcc aagaccagct   120540
tagggcaagg acgcagggcc caggtttcct taagtcttta taccatgggc atcataacta   120600
ggctcatctt tacctttgct tttctgagag actcttttgt ggtatatgga ttatatcatg   120660
cttggcaaga atatgaaaaa taatctgttg gggtacaggg caaaattaac atttttcaat   120720
tgagataaat taaacaagac ataaaatctg ccatctttat catattaagc ttgttgtgca   120780
ataactttca gcactgcagt gaccacagta gcattcagca cccccccact gcagtgactg   120840
cagtagcatt cagcacaccc acactgcaat gatgcagtag cattcagcac ccccactg   120900
cagtgactgc agtagcattc agcacactca cactgcaatg atgcagtagc attcagcaca   120960
cccccactgc agtgactgca gtagcattca gcacacccac actgcagtga ctgcagtagc   121020
attcagcaca ccccactgc agtgactgca gtagcattca gctcaccccc actgcagtga   121080
ccgcagtagc attcagcaca ccccactgc agtgaccgca gtagcattca gcacaccccc   121140
actgcaatga tgcagtagca ttcagcacac ccacactgag tactacagag atcactgtat   121200
actctcaaac ttttatgtga caatacaagg gctggcaaga tggctcagtc aataagagca   121260
ctgactgctc ctgaggtcct gagttcaaat cccagcaacc acatggtggc tcacaaccac   121320
atgtaatggg atctgacgcc ctcttctggt gtttctgaag acagctacca tgtacttgga   121380
tatattaata aatctttggg cctcagtgag cagggactga gtgagcgggc caaccagagt   121440
gagcgaggtt aactgagcg agcagaggtc ctaaattcaa ttcccaacaa ccacatgaag   121500
gctcacaact gtctgtacag ctacagtgtg cttatataca tttataaaat aaatatataa   121560
atcttaaaga gagaaagaga aagaaacaaa gaaaagaaa atacaagacg tttatcttca   121620
ggagccgtat atctgagtct gggtggaccc actaccctgc accttttgac actctgtgct   121680
gagttacttt gctgtgtctg tgcctgtcat cttttctaact ctgggaggcc tgttaaaaga   121740
tcaggtccaa aaagcagccg atgcgaaccc caggaagct gcagtaagca tggtcctcct   121800
gcatgactaa ggcttggctg tgcgccgagc ctgctcttca tagatggcgt gaagagagca   121860
agcgctgcct cggaacagga gctctgtagg ccacctagtc acttatggtg acatttggag   121920
ctaaagtagt tgcccgtaca gagatgtgtc atggtcatag gctttgaaat ctgtcttgtg   121980
cttttctggaa cctgcttgga cttcttatgc tgggtgtgtc ctcacattct agaagcctgg   122040
```

```
gaacagcaca gtcctctaac taactggtaa tttccagtgt ggatgctggt ccatgctgag 122100
cccctgtcca gcctgcatgc cttccgtctc ttttctctcc caccccccac cccttccttc 122160
ttttcagtct gaaatacatg ccaccettaa aatgcttgga attctacaga gaatggatgg 122220
gatttcacag tgtgaaagct gcctcagtgc agtaactccc aacaagaaac tgttcttttcc 122280
agctgttata gacgctgggg cagtgtgggc tctgaggatg ctcatatgtc aaacgctgac 122340
cagaacttaa aaaggagaa aaaggcagag gggcaggaca gggcgaggca aggtgtgggg 122400
acacctgagt gagtttccca aagtcaggaa atgctgtctg ctcgtgccca tgttggaagt 122460
ggtccactga gctgtgctct gagatgtccc ctctaatggt cagcggggc tcttgatgct 122520
gctgtcccca tcagccgttt caccttagtg tctgcctctg tgatctgaga catttcatat 122580
tcttgtttct caattctgaa tggcaaaagc attgcacttt aaagcttttg ttagtttaaa 122640
tcttcaaatg gccacagggc agatgggacc cttttctac gatttgtcaa gagacccag 122700
cagagcccca cattccctct gtgattccaa gcacctgtcc agtgtatcag ggagaagcag 122760
ccagcaggtg tcctctgcct tagagctggg tttagagtag atgagctctg ggcaaagtca 122820
gatgtattgt aaagcaattt ggccagagta gctaagacaa gatgaaaatt ctctccaaaa 122880
ttctctccaa actatcagtc ccggttgggt gcatgctttg gcctaatgtt gctgcttctg 122940
tgaggtagct gaacaaaatg ctaacaatag tcttcaactt aaaaacaaga cgcgtactaa 123000
agctgaggtg taacctccct ttgcctgaga ggatttaggt tttttttttt tttttttttt 123060
tggtgttttg ttttgttttg ttttgttttg ttttgttttg ttttgttttg ttttctgaga 123120
cagggtttct ctttgtagcc ctggctgtcc tggaactcac tctgtagacc aggctgacct 123180
cgagctcaga aatccacctg cctctgtctc ccaagtgctg ggattaaagg cttgtgccac 123240
cactgcccgg ctagttttttg ttttattgg agtttgtttc acttttctgc ctgtcacttt 123300
gggggtcagg ctgggataga tagttcttgt gtgcttgctg tcttagcaag acacttgagg 123360
gactcgtctg agtagagatg ggccctttgt gttgaggtcc acagagtgtc ctctcgctat 123420
cctgtaggct tagaactgcc ctgccctgcc ctgcctcttg ctgcctctga ggctgcttcc 123480
tatcccttag ggtagtgttt agtgtctctg agttaatagt tataccttgt aaatctgctg 123540
ttcatgttct ctcctaaggc cggcactgtg aaaccttcct agatgtgtgt ccccagaagc 123600
cttgcctgaa cggagggact tgtgccgtgg ctagcaacat gcccgatggc ttcatctgtc 123660
gttgtcccccc agtaagtggc ctgctgctga cataagggat gcaccgcctt ccatatgctc 123720
tagggagctg agattgagcc tgtgttttcg tgccccagga aggatgctaa ggtgttagtg 123780
tcttgaaggt ggtctgggtc ttccctggct ctagttgttc cgctgcgctc agcaactaag 123840
cttcccagtg aagcctgtca gccttcagag cattaagtgg gaaccacaag tggtctgctg 123900
tcccctgaa atggggccag cgcccttggc ttcccagcct agccctggtg ctgtggcatg 123960
gcggcctccc tgccccgcta ggtgagcgcc attctgctgc tcctgtcctt tagcagtggc 124020
cattggcaag taagcgcttc tcaaacgaga aggaagcttg atgcagtttt tgctgtgcag 124080
aggcctttgc cagtgccaaa ggccagaagt cccctcacac agagagtgcc atgtagggcg 124140
atactcagag gacacctgtc tagttaggac cttaaagtga cagcctgcca cattcatccc 124200
gtgagccatc agccctcacc tgttgactga tctgaagagg ttatttctag aacactggtg 124260
aatattaccc gtgggcaagc tcttaagccc ttctgccatc ctcattttcct tgccgtgtca 124320
tacagggggtt ctctggggcg agatgccaga gcagctgtgg acaagtgaag tgcaggagag 124380
```

```
gggagcagtg tatccacact gactcgggac ctcgctgctt ctgcctgaac cccaaggact   124440
gcgagtcagg atgtgccagt aacccctgcc agcatggggg cacctgctat cctcagcgcc   124500
agcctcctca ctattcctgc cgctgccctc cgtcgttcgg gggcagccac tgcgaactct   124560
acacagcccc caccagcacc cctcctgcta cctgtcagag tcagtactgc gccgacaagg   124620
ctcgggatgg catctgtgac gaggcctgca atagtcatgc ctgccagtgg gatggaggtg   124680
actgttccct cactatggag gacccctggg ccaactgcac ctccactctt cgctgctggg   124740
aatacatcaa caaccagtgt gatgagcagt gcaacaccgc agagtgcctg tttgacaact   124800
ttgagtgcca gaggaatagc aagacgtgca agtaagagcc ccgggcctca gaggccgagg   124860
ggggctgtca ctaacacact cagtctcctg ttcttgctcc taactgctcg ggtgcttcgg   124920
cccaagccgc ctctgccttt cagatggtgc cagccttgtc ccggtgcacg ctgcccttg    124980 ctgacagagg gctgggactg ctcactgcat aacatcccct ctctctgcct atctctgcct   125040
tctcacatgc tgctcttgcg accgtggggg aaataatctt ggaagtggcg ttgccactct   125100
caggcagcct ccagcctagc ctgctgcagg atggatggaa aggtctgtac cactgtctcc   125160
ctgctcattt ctttccttaa gactagcttt cccatctagt taagaagcgt gaacttaggg   125220
tgagctcggg cctcttggct ctctctcctt gtcgtcagtg ttgtagacag agtccttgtg   125280
gacgttccta ttaactattg cacttcaccc caagagagtc tcagcagctc tgtgagctta   125340
ggtgttgtta gtgatcttcc ctggaaggta agaacttgc cacgaacata cacagctgtt   125400
ggagttgcct ggttttagtc aagcagatgg caagaaaagc cctccaaata acaaaggtct   125460
ggggtggcag aaggaggagg agagagaatc agtcatgcct caggggggacc tttgcagttc   125520 tcattctttt gcctgacatg ttagtggtag ttgtgtatat acacaacact gtgtgtgtgt   125580
gtgggtgtgg gtgtgggtgt gagtgggtgt gtgttgtgag gcagggttcc atacagcaga   125640
agctggccct aaactcctga gtctagaact tctgatcatc ctcctgcctt cccaagtgct   125700
gacgttatag gcatgcacca ccacacccag attttctta gcatttgaaa gagagtaaat    125760
gagctagatc tcacaccctg tatgaacatc tctctgcccc ttaccttctg taattgtctt   125820
actccagaaa gagaaagaaa cagacagttt tggcacactc ttctgaatag cacttagata   125880
gttggaggtc tgggacaagc ttggactcct tctgtttcta gaacccttg ctctgactga    125940 gtcagtgggg agagggaagt gtgagccaca ttgactttgg cttcagatat gcattcttat   126000
acaaaattct gcccttgtag tatgattagt tcagtgggac ctactaaaca catgcaggat   126060
gatgggtata acaatattcc ccattccagg gataacgtcg agtgccatag ctgtatagcc   126120
catggtgttg gagtgcatga tttatgggaa gtttctctag acattgatgt gctgaaaatg   126180
agccagaaaa gatgggtagg aaagtgctcg gtcattctga gtggaagccg aggctgcagt   126240
gtgttctgat gccctcctcc tctctcctga ctaggtatga caaatactgt gcagaccact   126300
tcaaagacaa ccactgtgat cagggatgca acagcgagga gtgtggctgg gatgggctgg   126360
actgcgcttc ggaccagcct gagaacctgg cagagggcac cctgatcatc gtggtgctcc   126420
tgccccctga acagctgctg caggattcgc gaagcttctt gagggccctg gcaccctgc    126480 tccacaccaa cttgcgcatt aaacaagatt ctcaggcgc tctcatggtg taccccta      126540 ttggggagaa gtcagctgcc atgaagaagc agaagatgac acgcaggtct cttcctgagg   126600
agcaggagca ggagcaggag gtgataggg  aggtttgtgt ttctggactt agaagttccc   126660
aaaggaccag catttccagg ccagttcata cagctgggca ctttgatccc tagtacagat   126720
actcagccca tccaaatgaa aagctcaagt agagtacccc tcatttaaaa cacacatctt   126780
```

```
ggcctcttaa atctaaggat acagatctgc cttgactgag gggtcctaaa gatcagctaa    126840
gcaagaaaga tgcaggtatg agaaaggact cctcagatct gagattcgta atgtttctcc    126900
agagttgccg agaaccacat tcataatgtg tcttttgggt tcattattgc ctcattttca    126960
aggccccct  tcacgcctgt gcttgacccg agcagtaatc ctcagtgggt gggcctgtcg    127020
ttcacgcccc actgtgtgtt gatgctctgt aactttcagc cttttccttg ctgagatatg    127080
agtgtagaca cataggagaa caagggggca ccaatctgcg ctgagcaggc ggggctgggg    127140
gagcactagg accgcttccc cagttacttg ttatgtgtca cccagccagg ggcttatgtc    127200
agctggacat gagccctccc aggcaggagt ccatgttcag catctgaagc atcctgcttt    127260
ctgagttctt tctcccgaag gtggaaagct tgatgctgaa ggaggggagg gtggaccacg    127320
tgagcctttc tgaccgagcc tgccagacct gaccttcgt  ttcttccccc cattctccct    127380
ctaagctcta agatatttct ggagatcgac aaccgacagt gtgttcaaga ttcagaccag    127440
tgcttcaaaa acacagatgc ggcagctgct ctcctggctt tcatgccat  ccaagggacc    127500
ctatcctacc ctctagtgtc tgttttcagt gagtggcatt agtgctggag tggggctggg    127560
aagggccttc actggggctc acccttctgg taggaagagg ttgctgtttc tacatcactg    127620
tccctatgtc tgaactctca ggtgaactgg agagtccaag aaacgcccag cttctctatc    127680
tgctcgcggt cgctgttgtc atcatcctgt tcttcatcct gctgggggtc atcatggcca    127740
agcggaagcg caagcatggc ttcctctggc tgccggaagg gttcaccctc cgccgagact    127800
ctagcaatca aagcgccgt  gaacctgtgg gacaggatgc cgtggggctg aagtaagagg    127860
gctttacaat aagacacagt tcacagggag aagcagagat gagcagatgg gcatattact    127920
gaatcataat ctcaaattct aaattcacct ttagtcacct tgaccacagc tcctaatggc    127980
ttgtctaggt ctttgagtat ggccgcctct ttctgtgcac acctgacgaa gtgccgctca    128040
atgtttgagt gggagaacac tcaaaagaca tggtcttta  gtgagaagag aaagaatgag    128100
tgctcagaag tgtcacatct cacattgccc atcagagttg gtgtggtggc cctgtaggtg    128160
aaagtgcccc cgccacgtct gctgacctga gtgtgatccc cagtgcccat aagctagaag    128220
gacggaagtg acttcctcat gttgtgctgt gagtgtgtaa tataattaga gggctggagg    128280
gatacttcag tagtcaagaa aggaactgac ctgggttcag tgcccagcac ccatgctggg    128340
cagcttacag cccctgtgat tccagctgcc acgggatctg tagacacctg aactcacatg    128400
ctcagataca cacagacata gacacttaat tttgaaaaat gttaatataa ttttgaaaaa    128460
gtgctgtgca tcctatcccg ttggacagag tgagaggatg tgtgggagtg ctggtgaagt    128520
gcagaaagct actgcgtttg cccagctgta acctctcctc ttgtttctcc cctgaatatc    128580
atcagaaatc tctccgtgca agtgtcagag gctaacctga ttggttctgg gacaagtgaa    128640
cattgggttg atgatgaagg accccagcca agaaagcca  aggtaagctg tcttaggaag    128700
ccatgttact agcagtcatg tgaccacatt ctcagtgtgt gtctttcctg gagcccccatc   128760
atcggcaggg gcccgtagag cacagtcttt gtggctcatg tatgttcttc aggaagacct    128820
tttaaatagt aaagccagcc tgccttctgg ctcaagtgtc acacttgtgt ttactgagtc    128880
aggactggtg gtgtagatgc tcacagttcc atttatgggg gcttctctga tacttctata    128940
agaggagatg gagttatccc gtgaagaaag ccaagaccat taacttctgg ggaggtcact    129000
gagcatgatg gtcaagaatg ttgctttaaa ccaccattct agaggctgtg tcaagggaat    129060
ccaagtttaa ggccaacctg agctacctct aaaaccaaat aaaataaaca aatgaaaaca    129120
```

```
tatacagata acattgtaca aactgagcag gttgtattta gggatatata agcatttaac   129180
aacaactgat aataaaagaa acctggattt gaaggagagc aaagaggggt atatgggagg   129240
acttggagag aggaaagaga agggagaaat ggtgtaatta taatctccaa aaaaatggaa   129300
gtggtaaaag caacaggaag cattgctcta gtcaggctac ttgattgcag ctactttgta   129360
tttaaattaa acctttgtat ttaatattcc ttgcctataa gatagcaata ataataacaa   129420
cagtgatagc tcttttctcg ctgagttgcc agagtacctc tggcctatct gctttcacag   129480
atagagtcaa gtaaagggca gatgctgatc tctcgtcctc tccgcggtgc tcccctgagc   129540
actgtcccac agagtttatt ccccttctca agaaccttcc agttgaaaga gaaatagtgt   129600
gtgccttctc tcatgtgcag agtctgtatt taactatgga gacggacagg acagagacag   129660
tacacacaag gggctgttag gatggaggac aggaaagggg tgtgaggtga atgtaccagc   129720
aaggtacaat gatttgtaaa aacccattgt ttggggctgg agagatggct cagcagttaa   129780
cagcactgac tgctcttcca gaggtcctga gttcaattcc cagcaaccac atggtggtcc   129840
acaaccatct gtaatgggat ctgatgccct cttctggtgt gtctgaagac aactacagtg   129900
tacttaagat gaatagatga atgaatgaat gaatgaatga atgaatgaat gaatgaatga   129960
atcttttta aaaacacca ttgttttgca tactaaactc tttgaaagga aggaaggaag   130020
gaaggaagga aggaaggaag gaaggaagga aggaaggggg aaaggggaaa ggggaaaggg   130080
gaaagggaa aggggaaagg gaaaagggga aaggggaaag gggaaagggg aaaggggaaa   130140
ggggaaaggg gaaaggggaa agggaaggaa aggaaggaa aggaaaggaa aggaaaggaa   130200
aagaagctag caaccatggt tgacaggtga tgcagtgcca ggtagcacat accacacggt   130260
cagctgagaa gagagaaacc acttattaaa gtcaacaaga ttaaaatttc atttgaagag   130320
caaataggag tcagccaaac aaggtggagg ggaccatcac aggcaggtta gaagagatgg   130380
gaggagaccc tgccattcct cagccttgtc tgcagctcct ggagggctca ggttaatgag   130440
gggaacctttt cttccctctc caggctgagg atgaggcttt gctgtcggaa gatgacccca   130500
tcgatcgacg gccctggaca cagcagcacc ttgaagctgc agacatccgc cacactccat   130560
ccctggcact cactcctcct caggcagaac aggaggtgga cgtgctggac gtgaatgtcc   130620
gaggcccagg tcagtagcgg tccctgccct ccatggttct ggctggtcgg tgagcgtttc   130680
tccccctggc cagctgcccc tgccaattgc agacctcgag gaagctcgag ggaatgaata   130740
tgtgagaaac attgtcatgc ggaaattatg aacctggac aatgacactg gtggctcatg   130800
ggtaaaagta tttaccatga aagcctgacc acctgagttc aagcctcagc gtccatgtca   130860
aagttggaca gagtcgtcct ctggcctcca catacgtgtt atggacatgc acacgcacgc   130920
acatgtgctc atacatacca taccagtaat ttatgtgcta aggcatatgt gcacatatca   130980
tatacataca ataagataaa taaatattta agtgatttta aattatgggc tggagagatg   131040
ctcagtggta agagcacttg ttgctcttac agaggacctg cacccacatg gtgccttact   131100
acctcagtgc caggggctcc aacaccattt tctggcctgt atgagcactg tatgctcatg   131160
gttcaaaaat acatgtaggc aaaacactcg tactcattaa ataaatcctt aagttttttt   131220
caactgaaaa tgcagatttc aaagaaaagg aaggattttg cagtgcttca tatacagcat   131280
actgagaaaa ttaaacaaat tggatttag ggggatagaa aaatagtatc tgtcttagtc   131340
actggtctga tgttgtgaag agacactgtg gcagagagag atagagagac agacagacag   131400
atagacagac agagacagac tgggcctggc atgggatttt gaaacctcaa aatgcatccc   131460
ccagtgacac acttcctcca ataagaacca cctcctaatc cttctcaaat agtgtcgctt   131520
```

```
cctgttaact aagcattcaa atctacgagt tggtggggc cattcttatt cgaaccacca  131580
cagtatccga cagcagactg tggggaacta ctataattcc tgtcttacag gcagattaaa  131640
atattgtctg tctagtttga gatgtcataa ttgcacttaa actcaagcag aaaagtttgt  131700
cagtttgagg aagagcctca gggcagaagg cagctgcttc cctacactct tcacatagct  131760
ggtgctgtca tgtaaaacct gtcatagttc tacaagcacg gagagtccac agcccacagc  131820
atgatggcgg tcagcagaac tgttcctgta atgggttaat ttgaatgtgt ttgcaatatt  131880
ccctccctac agatgggtgt actccactga tgctggcttc tctccgagga ggcagctcag  131940
acctgagtga tgaagacgaa gatgctgagg actcttctgc caacatcatc acagacttgg  132000
tctaccaagg tgccagcctt caagcacaga cagaccgcac tggcgagatg gccctgcacc  132060
ttgcagcccg ctattcgaga gctgatgctg ccaaacgcct cctggatgct ggtgcggatg  132120
caaatgccca ggacaacatg ggccgatgtc ctcttcacgc tgcggtggca gcagacgccc  132180
aaggtgtctt tcaggtaaag agccaagagt tggtttgaat ctgaaagatg aggtggctca  132240
gtgggtaagg tgtatcgtgg taaatcacca tgtttacggc aacttataat agagcaagtc  132300
tagtggagcc tatgctttca gaagatcaga gtccatcatg gcagagtgag aacaccgggc  132360
tgggggaagg tgtgggggct gtgggggcca ggaacagctg agagctcaca tcttgaacca  132420
caaatgggag gcggagagct actgggagtg gcacacattt tatttcaaac ctcaaagtac  132480
gtccctgtga catacctcct ccaacaaggc catacatctt tcccaaatgg ccaccagtct  132540
aaatcaaatg cccaagactt aactggggac atctcattca aaacaccaca ggtgtttgcc  132600
accaatcccg agaacccaag gacctaggac cttcagcccc taggacccac atagtaaaaa  132660
gagagaactg atccctgaag gttgttccca aacctctgtg tgtgtaccat tgcacagaca  132720
tgcctgcaca cgcacaaaat aaaataacta ttacaggcct gtggtggttc agcttaacta  132780
acacacttac ccgctcattg aattcattca gaacttctga atgagtgtta tgcgggacag  132840
aaaagggggg aaggccagct gacctactgt gagtagccag agaaaagggg gaaggccagc  132900
tgacctactg tgagtagcca gagaatgatt cagtcagcaa cagggttctg aatctaatca  132960
gcaatatttt gatgtgcagt gatgcctcgc agatggcggt catatgggag tagtaaatga  133020
cccaactcct tggattactg ttaactctct ggatagctct gcctgtctgt gggcccacgg  133080
ctcatccctg acatgagtgg gcagtgtgtt ccttgatact cgtatttaa cctgaagagg  133140
aaattggaaa cattctagct gtatgcatga ttgaagttgt gacacctgta cataccttc  133200
cctatatagt ggttcattca cttattcagc aaatgcctaa tgattagcca ttatagctcc  133260
tagggcatag aatagcctgc ctcccaggga cacctcattt ggagtgctct tatttcattc  133320
tttttcctta tctaagggac acttctctgc ttctcttcta gattctgatc cgcaaccgtg  133380
taaccgatct ggatgccaga atgaacgatg gtactacccc cctgatcctg gctgcccgcc  133440
tggctgtgga aggaatggtg gcagagttga tcaattgcca agcagatgtc aatgcagtgg  133500
atgaccatgg taggacaag gatgtggctc catctgcaga gagcgtctct acacaagaga  133560
cttgctaccc ttctgagagg actttctcag atctgaaact ggacagtccc ttgtccttcc  133620
ccatcatttg cacatccttc agtctgcggg gctcagagac tgaggtgata ggagcccac  133680
attaagatga gagggggctt tagttgtagt ttttttcagt aagagggttc ttggacctca  133740
aagaatgttc ttgaaaagtt tgcctgtggg ttcctagtca taatcactct tactgtggga  133800
gtggattcac tgggggttat gagatatcct caatatgtac ttggtgtata gtagcatgtt  133860
```

```
tgctatcttc agtttgtgaa gcttgggcat gtggagggca tggatgtccc acaccaggga    133920
tcctgttagc tagaggctcc cagcctgtgc caaaatattc tgagaacaca aggaaaggaa    133980
aatacaagtg tgctttcctg tgggctctct tggcccctga cctcatgctg ctctctgggg    134040
agttcaaggt tcttgaaaa aaacaaaaca acagcacagc actttcctta gtgtcttact     134100
tacaaaatgt ttcccctgca ggaaaatctg ccctccactg ggcagctgct gtcaataatg    134160
tggaggcgac tcttctgctg ttgaagaatg gggccaacag agatatgcag gacaataagg    134220
tacagctctt agctcagagc ctgagtatgc tcacagcagt gtctctctca cttaggagga    134280
caaatgggga agcttgtgcg ggagctgggt ccagagagcc tgagggaggg aggatgcagg    134340
ccttgttggg aggcagcccc tggttgtccg gtgctcactg cactgccctg ggaatcactt    134400
ggcgcactcc ttcctgcctt tttccttcag cagtctgtct gctctgggag gtgcttaccg    134460
acctctctca cgttcctccc ttctctctgt gcggtagttt gtttctctgt tcttggatac    134520
cgaggtacac ttgtgtttga gctgcctgtc gtggccccgt ggccccgctc ttgttgtggc    134580 tccctcctc tccttacccc tcctgttgtg ccccctcct ttcctcaccc ctcctttatt      134640
cctcttgcac ttactgtttt ccttcttctc ctcaagcccc accccaccc cgcgcccctg     134700 ccatctcatg ttctgaattc tttgtacact ttggcttccc cctctttct tattggtagc     134760 ccagtttccc cttggcactt cgtgttgaca gcccatctc ttttcagtga ggctttggct     134820
ctgaggctgt ctaaaagct ggtggtcctg ggagcagact gggttctttg aatagagaa      134880 gatcgctgtg gaagtcaaag atacacaata tgtagaaaat gatactgtct gtctgtggca    134940 tttttatagag gaagcactta ggaaaagcac taaaaaggtt ataaaagagt aaaggttaga   135000
aacaatcctg tgttctctgg gtattaaaat gtattctacg gtctttcttc aggaagagac    135060
acctttgttt cttgctgccc gagagggaag ttatgaagcg gccaaaatcc tgttagacca   135120
ttttgccaac cgggacatca ctgaccacat ggaccgcctt ccccgggatg tggctcggga    135180
ccgcatgcac catgacatcg ttcgcctcct ggacgagtat aacgtgactc ccagccctcc    135240
gggaacggtc ttgacttctg cgctctcacc tgtcctctgt gggcccaaca ggtctttcct    135300
cagtctgaag cacaccccaa tgggtaagaa ggctaggcgg cccaacacca agagcaccat    135360
gcccacgagc ctgcctaacc ttgccaagga ggccaaggat gccaagggca gcaggaggaa    135420
gaagtgtctg aacgagaagg tccagctgtc cgagagctca gtgactctat ccccgtcga    135480 ttcgctcgag tctcctcaca cgtatgtctc cgatgccaca tcctctccca tgatcacatc    135540
ccctggaatc ttacaggcct cgcccacccc cctgctggct gctgccgcc cggctgcccc     135600 agtgcacaca cagcatgcgc tgtctttctc taaccttcat gacatgcagc ctttggctcc    135660
tggagccagc accgtgctcc cctcggtcag ccagctgcta tcccaccacc acatcgcgcc    135720
cccaggtagt agcagtgcag gaagcttggg caggttacat ccagttcctg tcccagcaga    135780
ctggatgaac cgtgtggaga tgaacgagac ccagtacagt gaaatgtttg gcatggtcct    135840
ggctcctgca gagggagccc accctggcat agcagctccc cagagcagac ctccggaagg    135900
gaagcacatg tccacccagc gggagccctt gcctcccatc gtgactttcc agcttatccc    135960
aaaaggcagc attgcccagg cagcggagc tccccagacg cagtccagtt gcctccagc     136020 tgttgcaggc cccttgccct ctatgtacca gatcccagag atgcccgtt tgcccagtgt     136080 ggctttccca cctaccatga tgccccagca ggaggggcag gtagctcaga ccattgtgcc    136140
aacctatcat cctttcccag cctctgtggg caagtacccc acaccccctt cccaacacag    136200
ttacgcctcc tcaaatgctg ctgagcgaac ccccagtcat ggtggtcacc tccagggcga   136260
```

```
gcacccatac ctgacaccat ccccagagtc tcctgaccaa tggtcaagct cttcaccaca 136320
ctctgcatct gactggtcag atgtgaccac cagcccaact cctggaggtg gtggaggcgg 136380
tcagcgggga cccggaacac acatgtccga gccaccacac agcaacatgc aggtgtatgc 136440
atgaagagtc tgcctcagcc ttagagatgg aagtgcctat cacacatact gctgagggggc 136500
gagtgaaggt tatccggaga gaaatgaaga gacgtcccgt ccgtgaccat ctttcggagg 136560
caggagagag aggctccaaa cctgaggcaa gcgtgagaag ccttctctcc atcttccctc 136620
gctctctgtg cagttttagg ggaggacgca gctcctactg accttacccc atcctgcaag 136680
ttcatggaga tgcaagatga gtgacaagcc ttgagacccc ttgctctctt ttaatttgga 136740
gaataccgtg gatgcctttt atcgcccaga cattctcgca gcctgagtaa cattttaagc 136800
cccgggggctt ctgactgagt gccccgggac tctgtccagg ctgacgtgtc cagtcttctc 136860
agccctggaa gtggccttga cgtcactcgg tgctttcctc tctgcgcccg tctgtggttg 136920
atccccgtca gtgtgtcata agcgagatgt ctgtgctctt aatcattcct gacctggaaa 136980
ccgacttcag cctcctgttc ccacattccc ggcacctcac aggtgcctca cagggtttac 137040
tctggccatg ggtctcagcc ctggcctctg aagtatgctt ctatggaaaa tgcacacact 137100
agtcttcatg tcttattcct agaaggaaag aggaagcaaa atatttgggg actagaagcc 137160
tccttctgaa cctgcacctt aatttctctc ccctgcatgt ggggcccccat atacactcat 137220
caggggggaag gatctgaatt gttcttctgt cagttggcct agtcagtata aaattgaact 137280
ctaggaggct taggtactgt gatattcctc tcattttgtt gtaaagtagg aaaagtgggg 137340
gagtgttgga atgtccaaga aataagctaa cttgctcaag aagcaatcgc cccctccag 137400
gccctccatt gactgccact gtgaagcaca tttatcaccct gatcttagga ctcattgatc 137460
cagcagatga aggtactctt ggctgctgca ctgctcctca tagatgcccg cagaagaaaa 137520
tgcctctcca tttgcccttg ccatttagga cagaacttgc ctggggcaca ggggacccag 137580
tgactgccaa cttccttagg accactttgc tttccgatca gaagccagtt tctttccaca 137640
gcgtgtgatc tgagagactg gtgcacacac agtaggttct cagtgaagac gtggagtctg 137700
tatttggggtt ccagatgtgg agaagggaca gtctcctgag ctcacgaggc agcctttgct 137760
agtcgatgct gcattctctt ccttccctag agtcccttc cgatgatgac ggctccccat 137820
tgtccttgtg ttcagattaa gattgtacct catccgaacc tgcttcctgc agtgtggtct 137880
cagtgacttc tcagactctc aagagcagaa acattttttat ctgtggtaat ctaggatgat 137940
agttttctcc tcagtcatag ggctaataat tgccccctatg gccatgccat cagtcactgc 138000
ttcctggtgc catggcaccc aggacacagg aaaatgagtt ctgctggagc atttgtgtat 138060
attattaggg ggaccacctg ggggtgtttg ttttatgggt tttgttgttg ttgttttaat 138120
aatagtcttt attcctgtga tagttaaaat aagtgcccctt cgcctcattc atcagtttgt 138180
gaacttagta agtctgtgta tctgttacac agcagtctat aaacaagtga ggattttagt 138240
cccattcaag ttcactgaat caacaaaaat aatttgttct gtcctggtct atggcagatt 138300
aagtttgatc atttgacttt attctcatgt ggtgacatca tcttaccagc ccctttcatg 138360
gaatagagac attttattgc cctaaatggt gactgtctgc cctaaagctc tagtgccact 138420
gcctgcgaac agtaaccaag aatccagcca ctgggtctgg tcactggacc taccccagac 138480
acagagaaga acaaacttgc tgtttctcct tcaaggatcc ctcaaagagg atcctttggg 138540
atttaggagg agggatgtga aaactgccgt gacagacaac agactacaga gatgaagaag 138600
```

```
acaacactgc cagtcataca tctatctgat cagtcccttR ggtgttagaa ttcttgacct  138660
gtgtagtgtc caggaaaaga aagggggatg ggcagtccct tactccggga cctgagtcaa  138720
gaggccgagg ttgtatgagg cacatccttt attccataca cagagccctg ttttgggctt  138780
tttttttttt tttttttttt attcctatga aatcttcctt tgacttttac ctgcctttaa  138840
ggatatttt tttttaatttg ttcttttttg ttttaagcat aattttctga cttatgcgat  138900
ggtgggggga ttgaaggaaa gaaagactga gttaaagatt ttcaagaaag ccgtcagcac  138960
gagttggtta tatcattttg ttaaacttgg ccacttgaag tcttgcatag aaatgaacca  139020
aaggtgttca gtgttcacgt gtgatttcag gacccggact ttaaccagcg cgttgaatgt  139080
acgaggactg tttggaagga cacgtgtcta tgtcctgagg cccccaccct taactgtttt  139140
ggtactatgg caacttcctc gtgtatattt ccctgaaaag tgacattata tctgtttgta  139200
tgagaaactc agtaaccaga aaatgacttc gtgttcctga ctaaatatag gaaggaatat  139260
gcacactgtt tttacttttt aaagtttcat tctaaaagta gattaagatg aaatttatat  139320
gaaaacattt ttatcacaaa ataaaaaagg ttccatgtca aagctcagtg atagcctact  139380
gtgcccttcc ccattgctgg ggccctggtt ccacagtgat cacctcgtga cgtcacagtt  139440
ggcgagagag acttaaatcc tcctcatccc gaatcttcag cccagtcctg ggcttcttcc  139500
attttcttgt ctagtttgat cacaaataaa tgctgctgag gggaaagttt tcatccattc  139560
agaaatgcca aatacaggg tcattcctct cacccctgac cgtaggatgt gaccaacaga  139620
cagctgcttg ggaccaggtg cccccccacag acgtggggaa tgtgtgctgg ggcaaggatt  139680
gggatagaaa cacttactgg ttcatttgcc cgagcactgc tagtctgtgt gggcttgtgt  139740
aggatataat ttacaatagg attatatggt aatatcgggg tatagatttg aaacaggtgc  139800
attagtttat agaggcaatc aatgagagta tgcacacaag tccctggggt tggcacagaa  139860
cgatgccagc agtaacacag caaccgaacc atctagctta ttttcacttc ctggtgtttt  139920
atagacactt ctagatcgag tgtgcataat tacaaaaaga taacagttcg ttttttctcc  139980
cgaaatgact tgatttcaaa tcttgggaga tgctttggtt aagtcgggac ttcacagctc  140040
attcgcacac atcagttagt cctcaggttt tataattgta cataagacat gtcggcctcc  140100
acgtgggttt tttaattggt gtgtgaagat cataagagcc tcagagggat gccccaccgg  140160
gccgttctcg gagctggagt tgcttcttgc aaacgtttgt ggtgctgaat cttgcttgga  140220
ggacacttcc ttccatggat gtaggctgaa ggtcaccggt ctgttgatct cctgcccttg  140280
cacctgaaag ccttgcagcc ttgctctcaa gtgtgcactg ctgtagatca gcaggaccgg  140340
atactgccca caatcatgga ggaaagggag tgaattgtct ccctcagcca agcatcagtc  140400
aagcctcaca gcctaagagc tgggaactgg cttacatcag gttggaatga ataaaataga  140460
acagtctcct atagtaccag ctttccagga tgtggggtgc ctgggatctg tgagctgatc  140520
actgccttta gtgcctctgt catggagagg gtgaggaata aagaatacaa tgttctcttc  140580
ggtatagaat agttaacaac aaaactacca ggtgacagta ttcccaggac ttgggaatga  140640
agtcatgtgg atcccaaatt ttaagattat cttcatttac atagttcaag atcagctagg  140700
gttagacaag actgtgtttc aatagcggag tggatgcgtg agtgttagaa acacaacatg  140760
gagtgcagag acccccctccc cccctgagta gcattgacca gtctattaat ttttaggaca  140820
aaggaatgga agccaagagg agttactgga acctggaaag aaaactacct agcacaggtt  140880
tcctatcaag gcaaaccata aaccttgctt gtctcacccc accctgagag atagctcaga  140940
gtcctgggcc agagtttgaa tggggaggag ggtgtatttg aaggcacagg tcttcctcaa  141000
```

```
tcgttgttgt ccaaccacat tttgggggaa acttccactg tcactgatgt gttagtccag    141060
gggacacaaa gtaaaaggga ttctgtgtta attgtgacaa aactgctgct cctggcctgc    141120
tgctgggttt ccttagctgt gatggcacaa cctggagaca gtccagcagc aggatagaaa    141180
atggaaactc ttcaagccct ataaagatga aatggctcaa tgggtgaagt cacttgccac    141240
caaaactgac aacctgagtt ccattccagg dacccacatg gtaagacaaa gagaaccaac    141300
tcctcaagtt gtcctgtgac ctccacatgt gtgccgtaaa ggaaaacatg aagaaaatta    141360
tagattcatc ttacttctag atacacaaat ctaaatcagc tgttaccaaa ctaaaactac    141420
agtgctgatg tgttttgccc cctatcaccg tggtaaactc cataatcaaa agcaactcga    141480
ggagggaagg attgatttct gcttacaatt catgaaggga gggagagcag gacagaactc    141540
tggcggcagc aactgaagca gaggacatgg gcaaacactg ctgactggct tgatgtttgt    141600
ggcttgccag ggcggcacca tccatggtga gatgggtctt ctcacatgtc atcaatcaat    141660
caaggaaatg acccataaac ttgcctacag gagaatccgg tgggggaggg tcttgtttgt    141720
ttgttttgtt ttgttgttgt ttttttttcac ttaagtttct tctctgatga ctttagcttg    141780
tgtcaggtag taacccaaat tggcacaagt gggtattata acattccatc tcctaaggaa    141840
acaactgcaa agaagtgtat tgaaaggact gaagagatgc ttggtggtta agatcacgtg    141900
ttcttccaga gaaactggat ttagaatcca gcatctgcat agtgggtggc tcacagtgct    141960
ctgaaactcc agttccaggg gatctaatgc cctcttgtag                          142000

<210> SEQ ID NO 6
<211> LENGTH: 10506
<212> TYPE: DNA
<213> ORGANISM: Mus musculus

<400> SEQUENCE: 6
gccaaacttc gggcggcggc ctggctgcgc ggagtgcagg ggcggcgcag cgggagctcc       60
aggactcagc gagccgcggg ggcagggtag agcacgcgag agccgggctc ctggtcggga      120
cccgctcccc atgcggatct gctctggctg cggccccgaa gatgcccgct ctgcgtcccg      180
ccgcgctgcg ggcgctgctg tggctctggc tgtgcgcgcg gggccccgcg cacgctttgc      240
agtgtcgagg tggtcaagag ccctgtgtaa atgaagggac ctgtgttacc taccacaacg      300
gcacaggctt ctgccgatgt ccagagggct tcttgggaga atattgccaa catcgagacc      360
cctgtgagaa aaaccgctgt cagaatggtg gtacttgtgt gccgcagggc atgttgggga      420
aagctacctg ccgatgtgct ccaggattca caggagagga ctgccaatac tccacctctc      480
accctgcttt tgtgtcccgc ccttgtcaga atggggtac ctgtcacatg ctcagccggg      540
acacctacga gtgcacctgc caagtcggct tcacagggaa gcagtgtcag tggacagatg      600
cctgtctatc tcatccctgc gaaaatggaa gcacctgtac atctgtggcc agccagttct      660
cctgcaaatg ccctgcaggc ctcacagggc agaagtgtga agctgatatc aatgagtgtg      720
acattccagg acgctgccaa catggtggca cctgcctcaa ccttcctggt tcctacagat      780
gccaatgtcc tcagggcttc acaggccagc actgtgacag cccttatgtg ccctgtgcac      840
cctcgccctg cgtcaacgga ggcacctgtc gtcagactgg cgacttcact ttcgaatgca      900
actgcctgcc aggttttgaa gggagcacct gtgagcggaa tatcgacgac tgccccaacc      960
acaagtgtca gaatggagga gtttgtgtgg atggtgtcaa tacctacaat tgccgctgtc     1020
cccctcagtg gactgggcag ttctgcacag aagatgtgga cgagtgtctg ttgcagccca     1080
```

```
acgcttgtca gaatggaggc acctgcacca accgaaacgg aggctatggc tgcgtgtgtg   1140
tgaacggctg gagcggagat gactgcagcg agaatatcga tgactgtgcc tatgcttcct   1200
gcacgccagg gtccacctgc attgaccgcg tggcctcctt ctcctgcctg tgtccggagg   1260
gaaaggcggg tctcctgtgc catctggatg atgcctgtat cagcaaccct tgtcacaagg   1320
gggcgctgtg tgacaccaac cccctgaacg ggcagtacat ttgcacctgc ccacagggct   1380
acaagggcgc tgactgcaca gaagacgtgg atgagtgtgc tatggccaac agtaacccctt  1440 gtgagcatgc aggaaagtgt gtgaatacag atggcgcctt ccactgtgag tgtctgaagg   1500
gctacgcagg gcctcgctgt gagatggaca tcaacgagtg tcattcagac ccctgccaga   1560
acgacgccac ctgcctggat aagatcggag gcttcacctg tctgtgcatg ccaggtttca   1620
aaggtgtgca ttgtgagctg gaggtaaatg aatgccagag caacccgtgt gtgaacaacg   1680
ggcagtgtgt ggacaaagtc aaccgcttcc agtgtctgtg tcccccctggc ttcacaggac   1740 cagtgtgcca gatcgacatt gatgactgct ccagtactcc ctgcctgaat ggggccaagt   1800
gcatcgatca cccgaatggc tatgaatgcc agtgtgccac aggtttcact ggcatattgt   1860
gtgatgagaa catcgacaac tgtgaccag atccttgcca ccatggccag tgccaggatg   1920
ggatcgactc ctacacctgc atctgcaacc ctgggtacat gggagccatc tgtagtgacc   1980
agattgatga atgctacagc agcccttgct tgaacgatgg gcgctgcatt gacctggtga   2040
atggttacca gtgcaactgc caaccaggca catcaggcct taattgtgaa attaattttg   2100
atgactgtgc cagcaaccct tgtatgcacg gagtctgtgt ggacggcatc aatcgctaca   2160
gctgtgtgtg ctctccggga ttcacaggcc agaggtgcaa tattgacatt gatgagtgtg   2220
cctccaaccc ctgtcgcaag ggtgcgacgt gcatcaatga tgtgaatggt tccggtgta   2280 tatgccccga gggaccgcat catcctagct gctactcaca ggtgaacgag tgcctgagca   2340
atccctgcat ccacggaaac tgtactggag gtctcagtgg ctataagtgc ctctgcgatg   2400
caggctgggt tggtgtcaac tgtgaggtgg acaaaaatga gtgtctttct aacccatgcc   2460
agaatggagg aacgtgcaat aacctggtga atggctacag gtgtacctgc aagaagggt   2520 tcaaaggcta caactgccag gtgaatatag atgagtgtgc ctccaacccg tgtctgaacc   2580
aaggaacctg ctttgatgac gtcagtggct acacttgcca ctgcatgttg ccttacacag   2640
gcaagaactg tcaaacagtg ttggctccct gttccccaaa cccgtgtgag aatgctgctg   2700
tttgtaaaga ggcacccaat tttgagagct tcagctgctt gtgtgctcct ggctggcaag   2760
gtaaacgatg tacagttgac gttgatgagt gtatctccaa gccgtgtatg aacaatggtg   2820
tctgccacaa cactcagggc agctacgtgt gtgagtgtcc tcccggcttc agtgggatgg   2880
actgtgaaga ggacatcaat gattgccttg ccaaccctg ccagaacgga ggctcctgtg   2940
tggaccatgt gaataccttc tcctgccagt gccatcctgg cttcataggg gacaagtgcc   3000
agacagacat gaatgagtgt ctgagcgagc cctgtaagaa tggggggacc tgctccgact   3060
atgtcaacag ttacacctgc acatgccctg cgggcttcca cggagtccac tgtgaaaaca   3120
acattgacga gtgcactgag agctcctgct tcaatggcgg cacgtgtgtt gatggaatca   3180
actctttctc ttgcttgtgc cccgtgggtt tcactggtcc cttctgcctc catgatatca   3240
atgagtgcag ctctaacccg tgcctgaatg ctggaacgtg tgttgatggt ctgggtacct   3300
accgatgcat ctgtccccttg ggctacaccg ggaaaactg tcagaccctg gtgaacctct   3360
gcagccggtc tccgtgtaaa aacaaaggaa cttgtgttca ggaaaaggca aggcccact   3420 gtctgtgtcc gcctggatgg gatggtgcat actgtgatgt gctcaacgtg tcctgtaagg   3480
```

-continued

```
cggcagcctt gcagaaagga gtacctgttg aacacttgtg ccagcactcg ggcatctgta    3540
tcaatgctgg caacacccat cactgccagt gcccccctggg ctacacgggg agctactgcg   3600
aggagcagct tgatgagtgt gcatccaatc catgccagca cggtgccacc tgcaatgact    3660
tcatcggagg atacagatgt gagtgtgttc caggatatca gggtgtcaac tgtgagtatg    3720
aagtggacga gtgccagaac caaccctgcc agaatggagg cacctgcatc gaccttgtga    3780
accatttcaa gtgttcgtgt cccccaggca cccggggcct gctgtgtgaa gagaacatcg    3840
atgaatgtgc tgggggcccc cactgcctta acggtggcca gtgcgtggac cggattggag    3900
gctacacttg tcgctgtttg cctggctttg ctggggagcg gtgtgagggg acatcaacg     3960 aatgcctgtc caacccttgc agctcagagg gcagcctgga ctgcgttcag ctcaaaaata    4020
actacaactg tatctgccgc agcgccttca cgggccggca ctgtgaaacc ttcctagatg    4080
tgtgtcccca gaagccttgc ctgaacggag ggacttgtgc cgtggctagc aacatgcccg    4140
atggcttcat ctgtcgttgt cccccagggt tctctggggc gagatgccag agcagctgtg    4200
gacaagtgaa gtgcaggaga ggggagcagt gtatccacac tgactcggga cctcgctgct    4260
tctgcctgaa ccccaaggac tgcgagtcag gatgtgccag taaccctgc cagcatgggg     4320 gcacctgcta tcctcagcgc cagcctcctc actattcctg ccgctgccct ccgtcgttcg    4380
ggggcagcca ctgcgaactc tacacagccc ccaccagcac ccctcctgct acctgtcaga    4440
gtcagtactg cgccgacaag gctcgggatg gcatctgtga cgaggcctgc aatagtcatg    4500
cctgccagtg ggatggaggt gactgttccc tcactatgga ggaccctggg ccaactgca    4560 cctccactct tcgctgctgg gaatacatca acaaccagtg tgatgagcag tgcaacaccg    4620
cagagtgcct gtttgacaac tttgagtgcc agaggaatag caagacgtgc aagtatgaca    4680 atactgtgc agaccacttc aaagacaacc actgtgatca gggatgcaac agcgaggagt     4740
gtggctggga tgggctggac tgcgcttcgg accagcctga gaacctggca gagggcaccc    4800
tgatcatcgt ggtgctcctg ccccctgaac agctgctgca ggattcgcga agcttcttga    4860
gggccctggg caccctgctc cacaccaact gcgcattaa acaagattct cagggcgctc     4920
tcatggtgta ccctctctttt ggggagaagt cagctgccat gaagaagcag aagatgacac    4980
gcaggtctct tcctgaggag caggagcagg agcaggaggt gataggctct aagatatttc    5040
tggagatcga caaccgacag tgtgttcaag attcagacca gtgcttcaaa acacagatg     5100 cggcagctgc tctcctggct tctcatgcca tccaagggac cctatcctac cctctagtgt    5160
ctgttttcag tgaactggag agtccaagaa acgcccagct tctctatctg ctcgcggtcg    5220
ctgttgtcat catcctgttc ttcatcctgc tgggggtcat catggccaag cggaagcgca    5280
agcatggctt cctctggctg ccggaagggt tcaccctccg ccgagactct agcaatcaca    5340
agcgccgtga acctgtggga caggatgccg tggggctgaa aaatctctcc gtgcaagtgt    5400
cagaggctaa cctgattggt tctgggacaa gtgaacattg ggttgatgat gaaggacccc    5460
agccaaagaa agccaaggct gaggatgagg ctttgctgtc ggaagatgac cccatcgatc    5520 gacggcctg gacacagcag caccttgaag ctgcagacat ccgccacact ccatccctgg     5580
cactcactcc tcctcaggca gaacaggagg tggacgtgct ggacgtgaat gtccgaggcc    5640
cagatgggtg tactccactg atgctggctt ctctccgagg aggcagctca gacctgagtg    5700
atgaagacga gatgctgag gactcttctg ccaacatcat cacagacttg gtctaccaag     5760
gtgccagcct tcaagcacag acagaccgca ctggcgagat ggccctgcac cttgcagccc    5820
```

-continued

```
gctattcgag agctgatgct gccaaacgcc tcctggatgc tggtgcggat gcaaatgccc    5880
aggacaacat gggccgatgt cctcttcacg ctgcggtggc agcagacgcc caaggtgtct    5940
ttcagattct gatccgcaac cgtgtaaccg atctggatgc cagaatgaac gatggtacta    6000
cccccctgat cctggctgcc cgcctggctg tggaaggaat ggtggcagag ttgatcaatt    6060
gccaagcaga tgtcaatgca gtggatgacc atggaaaatc tgccctccac tgggcagctg    6120
ctgtcaataa tgtggaggcg actcttctgc tgttgaagaa tggggccaac agagatatgc    6180
aggacaataa ggaagagaca cctttgtttc ttgctgcccg agagggaagt tatgaagcgg    6240
ccaaaatcct gttagaccat tttgccaacc gggacatcac tgaccacatg gaccgccttc    6300
cccgggatgt ggctcgggac cgcatgcacc atgacatcgt tcgcctcctg gacgagtata    6360
acgtgactcc cagccctccg ggaacggtct tgacttctgc gctctcacct gtcctctgtg    6420
ggcccaacag gtctttcctc agtctgaagc acaccccaat gggtaagaag ctaggcggc    6480 ccaacaccaa gagcaccatg cccacgagcc tgcctaacct tgccaaggag gccaaggatg    6540
ccaagggcag caggaggaag aagtgtctga acgagaaggt ccagctgtcc gagagctcag    6600
tgactctatc ccccgtcgat tcgctcgagt ctcctcacac gtatgtctcc gatgccacat    6660
cctctcccat gatcacatcc cctggaatct tacaggcctc gcccacccccc ctgctggctg    6720 ctgccgcccc ggctgcccca gtgcacacac agcatgcgct gtctttctct aaccttcatg    6780
acatgcagcc tttggctcct ggagccagca ccgtgctccc ctcggtcagc cagctgctat    6840
cccaccacca catcgcgccc caggtagta gcagtgcagg aagcttgggc aggttacatc    6900
cagttcctgt cccagcagac tggatgaacc gtgtggagat gaacgagacc cagtacagtg    6960
aaatgtttgg catggtcctg gctcctgcag agggagccca ccctggcata gcagctcccc    7020
agagcagacc tccggaaggg aagcacatgt ccacccagcg ggagcccttg cctcccatcg    7080
tgactttcca gcttatccca aaaggcagca ttgcccaggc agccggagct ccccagacgc    7140
agtccagttg ccctccagct gttgcaggcc ccttgccctc tatgtaccag atcccagaga    7200
tgccccgttt gcccagtgtg gctttcccac ctaccatgat gccccagcag gaggggcagg    7260
tagctcagac cattgtgcca acctatcatc cttttcccagc ctctgtgggc aagtaccccca    7320 caccccttc ccaacacagt tacgcctcct caaatgctgc tgagcgaacc cccagtcatg    7380
gtggtcacct ccagggcgag cacccatacc tgacaccatc cccagagtct cctgaccaat    7440
ggtcaagctc ttcaccacac tctgcatctg actggtcaga tgtgaccacc agcccaactc    7500
ctggaggtgg tggaggcggt cagcggggac ccggaacaca catgtccgag ccaccacaca    7560
gcaacatgca ggtgtatgca tgaagagtct gcctcagcct tagagatgga agtgcctatc    7620
acacatactg ctgaggggcg agtgaaggtt atccggagag aaatgaagag acgtcccgtc    7680
cgtgaccatc tttcggaggc aggagagaga ggctccaaac ctgaggcaag cgtgagaagc    7740
cttctctcca tcttccctcg ctctctgtgc agttttaggg gaggacgcag ctcctactga    7800
ccttcaccca tcctgcaagt tcatggagat gcaagatgag tgacaagcct tgagacccct    7860
tgctctcttt taatttggag aataccgtgg atgcctttta tcgcccagac attctcgcag    7920
cctgagtaac attttaagcc ccggggcttc tgactgagtg ccccgggact ctgtccaggc    7980
tgacgtgtcc agtcttctca gccctggaag tggccttgac gtcactcggt gctttcctct    8040
ctgcgcccgt ctgtggttga tccccgtcag tgtgtcataa gcgagatgtc tgtgctctta    8100
atcattcctg acctgaaac cgacttcagc ctcctgttcc cacattcccg gcacctcaca    8160
ggtgcctcac agggtttact ctggccatgg gtctcagccc tggcctctga agtatgcttc    8220
```

-continued

```
tatggaaaat gcacacacta gtcttcatgt cttattccta gaaggaaaga ggaagcaaaa    8280
tatttgggga ctagaagcct ccttctgaac ctgcacctta atttctctcc cctgcatgtg    8340 gggcccccata tacactcatc aggggggaagg atctgaattg ttcttctgtc agttggccta    8400
gtcagtataa aattgaactc taggaggctt aggtactgtg atattcctct cattttgttg    8460
taaagtagga aaagtgggtg agtgttggaa tgtccaagaa ataagctaac ttgctcaaga    8520
agcaatcgcc cccctccagg ccctccattg actgccactg tgaagcacat ttatcacctg    8580
atcttaggac tcattgatcc agcagatgaa ggtactcttg gctgctgcac tgctcctcat    8640
agatgcccgc agaagaaaat gcctctccat ttgcccttgc catttaggac agaacttgcc    8700
tggggcacag gggacccagt gactgccaac ttccttagga ccactttgct ttccgatcag    8760
aagccagttt ctttccacag cgtgtgatct gagagactgg tgcacacaca gtaggttctc    8820
agtgaagacg tggagtctgt atttgggttc cagatgtgga aagggacag tctcctgagc    8880 tcacgaggca gcctttgcta gtcgatgctg cattctcttc cttccctaga gtcccctcc    8940 gatgatgacg gctccccatt gtccttgtgt tcagattaag attgtacctc atccgaacct    9000
gcttcctgca gtgtggtctc agtgacttct cagactctca agagcagaaa cattttatc    9060 tgtggtaatc taggatgata gttttctcct cagtcatagg gctaataatt gccctatgg    9120 ccatgccatc agtcactgct tcctggtgcc atggcaccca ggacacagga aaatgagttc    9180
tgctggagca tttgtgtata ttattagggg gaccacctgg gggtgtttgt tttatgggtt    9240
ttgttgttgt tgttttaata atagtcttta ttcctgtgat agttaaaata agtgcccttc    9300
gcctcattca tcagtttgtg aacttagtaa gtctgtgtat ctgttacaca gcagtctata    9360
aacaagtgag gattttagtc ccattcaagt tcactgaatc aacaaaaata atttgttctg    9420
tcctggtcta tggcagatta agtttgatca tttgacttta ttctcatgtg gtgacatcat    9480
cttaccagcc ccttttcatgg aatagagaca ttttattgcc ctaaatggtg actgtctgcc    9540
ctaaagctct agtgccactg cctgcgaaca gtaaccaaga atccagccac tgggtctggt    9600
cactggacct accccagaca cagagaagaa caaacttgct gtttctcctt caaggatccc    9660
tcaaagagga tcctttggga tttaggagga gggatgtgaa aactgccgtg acagacaaca    9720
gactacagag atgaagaaga caacactgcc agtcatacat ctatctgatc agtcccttag    9780
gtgttagaat tcttgacctg tgtagtgtcc aggaaaagaa aggggggatgg gcagtccctt    9840 actccgggac ctgagtcaag aggccgaggt tgtatgaggc acatcccttta ttccatacac    9900 agagccctgt tttgggcttt ttttttttttt tttttttttta ttcctatgaa atcttccttt    9960
gacttttacc tgcctttaag gatattttttt tttaatttgt tcttttttgt tttaagcata    10020
attttctgac ttatgcgatg gtggggggat tgaaggaaag aaagactgag ttaaagattt    10080
tcaagaaagc cgtcagcacg agttggttat atcatttttgt taaacttggc cacttgaagt    10140
cttgcataga aatgaaccaa aggtgttcag tgttcacgtg tgatttcagg acccggactt    10200
taaccagcgc gttgaatgta cgaggactgt ttggaaggac acgtgtctat gtcctgaggc    10260 ccccacccctt aactgtttttg gtactatggc aacttcctcg tgtatatttc cctgaaaagt    10320
gacattatat ctgtttgtat gagaaactca gtaaccagaa aatgacttcg tgttcctgac    10380
taaatatagg aaggaatatg cacactgttt ttacttttta aagtttcatt ctaaaagtag    10440
attaagatga aatttatatg aaaacatttt tatcacaaaa taaaaaaggt tccatgtcaa    10500
agctca                                                              10506
```

<210> SEQ ID NO 7
<211> LENGTH: 52000
<212> TYPE: DNA
<213> ORGANISM: Mus musculus

<400> SEQUENCE: 7

| | | | | | |
|---|---|---|---|---|---|
| ttgcagtgac | tcagcctacc | tccttcttac | gcaacatttt | tttttctttg | tccaacctttt | 60 |
| actccttcct | tatttctccc | ctgcaataca | cagggccagg | agtctcctag | acccagttc | 120 |
| aaatctgagc | tctaaatgcc | tacacagtga | gttccaggcc | actcaagggt | acatactgag | 180 |
| accttgtctc | aacatacacc | ctcataaaaa | gagaagacag | ccacaggatt | ctatttatat | 240 |
| ggaatactat | actgagggct | gagagagatg | gcacacagcc | aagcctgatg | acttgagttt | 300 |
| gattccaaac | ccacgtggta | gaggggaaga | actgactcct | acaagtggtc | ctctgacccc | 360 |
| cgcacagatg | ctgtgcatgc | cccacaaccc | taggaacaaa | tacaatcata | gaaaataaat | 420 |
| gtccagagca | agcaaagcca | caaatgcagg | gagctggtgg | cagggatatt | aacaagatcc | 480 |
| cttttccagg | ataatggaat | gtcttggagc | tagagaggtc | ataactgaga | atatattaag | 540 |
| tggcactgaa | ttgcaaacat | caaaatctca | aatatgtaca | tttatataat | ataaattata | 600 |
| cctcaactta | aaaataatca | agaatcaggt | gtggtggtgc | acagtgcatg | agcataggag | 660 |
| acctcaaaaa | tggccccaca | gtgacacact | tcctcaaacc | aacaaggcca | catctcctaa | 720 |
| tggtgccact | ccttatgaac | caaacactca | atacatgaa | taggaagcta | ttcctattca | 780 |
| agccaccaca | ctgcgcttgg | cagcacatgc | ctacagtctc | agtattaggg | agttggaggt | 840 |
| atattcaaga | tctcaaggtc | agtccggact | acactgtgag | ttcaagggga | gtccgagctg | 900 |
| cattcaaaga | ccctgtgtca | aaacaagggg | agtggctgat | ttggtagagt | agttggtcaa | 960 |
| catgctcaag | gccctaggca | tcatcacagc | actgcaaaat | aaataaacag | aatattgaga | 1020 |
| taagaggaag | aaaacgtcac | caactcagcc | taagccgtga | agtttaata | ccaccgatac | 1080 |
| taggaaaaga | tggcaggtac | cctgataata | tgccctggga | aggatacggg | gattctgcca | 1140 |
| aagacgcata | aagttaatct | tgtagaactc | gcaggtcatt | gcaggtccaa | gaggcactct | 1200 |
| ttcaaacaac | tgacctcaaa | ctaaggctga | ggtgaagatc | tgggatccag | tcttcggtcc | 1260 |
| acaaagaagc | tataagggat | gttattcgga | ataaccataa | aactttgagt | agaaacttgg | 1320 |
| gtgaggactg | gagatgtggt | tacatggtag | agtgtctccc | ttacacactg | gaaacccag | 1380 |
| gttctggccc | cagcatcaca | aaaatcaggc | atggaagctc | ataccttaa | tcctagcact | 1440 |
| gggaggcaaa | gccaggaaga | ctgggacttc | taggtcattc | tggtttcagt | aagttcaagg | 1500 |
| ccagtctggg | ttgcacgaga | ctctgcctga | aaggagaag | cccccaaagt | aggacaacaa | 1560 |
| cgaagtgggc | ctgaaagact | gttcagttgt | taagagagca | gcagcagcag | caggaggatc | 1620 |
| tgatttcaga | ttccagttgt | ctcatgtaac | aagctggcta | ttccacaaat | gaccataact | 1680 |
| ccagctttga | ggggtgcagt | gccttccctg | gtctctgcat | atgcaggtac | tcacactagt | 1740 |
| gcacacacac | acacacacac | acacacacac | acacacacac | acacacacag | agaaacacac | 1800 |
| acacacaaat | aaatctttaa | aaagtgtatc | cgtgactgtc | ctggaatttg | ctaggtagac | 1860 |
| caggctggct | ttgaattcac | agatctatct | gcctttgcct | ctggagaccg | tgtgaaccat | 1920 |
| gacatcttcc | ccaattaaca | aaaatacact | tatttattat | gtagccagtt | gggggggggg | 1980 |
| gcgcggcagg | gagggggagat | gggccctcta | caatgtagag | atcagaggac | aacttgtgga | 2040 |
| agttgttctc | tcctcccact | acaggagtgt | ctgtgtatgc | ccttccagga | ttatatgggt | 2100 |
| cctctgtttc | agtcctttgg | tctcctagtg | atggagatgt | tcaagaacgg | caccctttcac | 2160 |

```
ccgactcctg agatttcccc tgaatgcacc tctagagctt ccattctcac ttcacacaga   2220
gggagtgttc agagcctttg caggtctcct ggatgtaaaa ctcagtgaat ggcaacgaaa   2280
tgataggcct catggtaaaa ccatgtagag tgtgggatgt gctaggagct ggtgtggatt   2340
ttttttacaa agtattttat cttatttctt gcgcacataa gcgtgtgtgt gtgtgtgtgt   2400
gtgtgtgtgt gtgcgcgcgc gtgcgtgcaa gcattcgagc acagtgtgtg taggagtgca   2460
tgtgtatcac ggggtacatg tggcagtcag aagacaatgt atgtgttggt tttttattt   2520 tagcatggga ggcccaggaa ttgaactcgg gtgtctgtga ttggcagcaa gcacctttcc   2580
ctcttcggta gacctttgtg atcttcacat tgtaggagag ctgcacacag gtacatgaga   2640
ctcatatcca cgaaacccct ggccagattg taaatgctgc ccgcccgggt tgtggcgca    2700 gttggagcct gagttttgag gtgattgatg tttagtgtcc ccatgaaact tctatatggt   2760
ttgcatgggt gcggctactt tgttcattg gcctctctac acccaggttt agagggtttg    2820
gagtcagggg tgtttgcgtt tgtgtcatga ctgtgtgtgt gagccctggc tttggttgtg   2880
tgctggagga taaggatgga tgtgctcacg agctggatac ctgtcacgtc acgcaggtta   2940
agcccgcatc tcttgtggca gacctgagtg taccgaggtc tgcaagtccc aggcttggcg   3000
ggtagaaggg tcggacccca ggaggccggg caggggggcgg gggcgctcag agccggcccc   3060
ggggcggggc gagccgccca ggctggggg cgggcagcc cgacagcctc acttcggcga     3120
agttggcggc gcggaggctg gcccgggacg tgcccggagc cctgggaaag agggaggagg   3180
gaggagggag ggtcgtggcc ggccgccatg gggctggggg cccggggccg ccgccgccgt   3240
cgtcgcctga tggccttgcc accgccacca ccgcccatgc gggcgctgcc cctgctgctg   3300
ctgctagcgg ggctggggc tgcaggtgag ggatcaggga ctcggagggt gggactgggg    3360
ttgcaggggc ggggaagcaa aaaaaaaaaa gtatatatat atatatatat attctcctaa   3420
gtttggaatt tagaggacct gccccccag gattaaagcc ggggcagaga tgcagcagct    3480
gggggtgtgt atcagtcatg gggttcgcac agattcatga tgggaaggca ggatcctaga   3540
ggcccaagga atcgagaccc ttgaatgaat caagagtcca agagtaggag ctggagttgt   3600
gggaatctgg ggctgaaatt cggaagcgag gtgtaccaaa agtttcaggc tcaccccatc   3660
ctacttctgc ctggagtcct gggaaggtta ggatgggggc tcaaggaccc cccaaggcct   3720
aggacccctt gcacaaaagc gcctcccta tcccggcgg gccgtgaagg ggggggggg     3780 acaaggaggg ggcgcggagt tctcggagct ctgaactcgg agaaacgtc tcatgttgga    3840 gagctgcaag acccggcgct ggagcgcgag aagcaggagc tggagccctt gcgaagcccg   3900
cgccccctcc ccgcgtgcc gcccgatccc tcttcaggcc gccgggatcc cgtagtctcg    3960
ggaccccgtc tctgtgccgg gaggagaagg ggcgaggtcc acgtgctcat ctccagcttc   4020 tgggcccca tccctgtggc cgcagcccct ccccagcatg cctgggcccc cctcccctct   4080
tcctccactc tgagctcccc tccccgctc gggacaatgg cttcgccgtc tagacacccc   4140 ctcccccgg ccggcctcac gctttctttg ccagacaaag cgggacccac gaagggccag    4200
agcggggact gaggggggcgc ccccacccct gccccgggag gcctgatcag cgggggaggg  4260
gcataggcag ttggctgtgg ccaggggttc tagggctcct atggtgggac tcagtgctgg   4320
gccgggtgag agttgcatag agagtggctt agcctctagg ctctactagg caggactggg   4380
caggagccac cgccccgcg gggccagtgc agactcatgg cctgtcacac atagaaaggg    4440
aaaaaaatgc atgtgcacag gtttagtaca gccatagatg cacacttggc acacacaaga   4500
```

-continued

```
cacacctatg tgtttgctgc tcacatgttg atgtgcattc aggcataggt cacccaagac   4560
ctgctaggca ttcatgttca aggtcacatt tatagctgcc aatccatgac ccagacaagc   4620
acaccagtgg ccacacagct gtatgcttga atactgctgt tcatatagat ggatgcacag   4680
tgcatgcagc tcgtgtgcac atggtgtaca aggctatgct gtttgaagat accagcatgg   4740
taccaagcac atgcactatt agtcactatt agtaatatag tggcctaata cacagactgt   4800
cacacaaact cacaggcata tgtacacaca cacacacaca cacacagagc tcacatggtt   4860
gtgttctccc ccccccccat acagcttcta gtgtgatgtc acaaaattga ataggtcctt   4920
cattcttaac tcatccttt actgtctctg ttttttttt ttttttttt tttttttt   4980
ttttggttgg tttctccttt cagtttctgt ctgtccctat ttctcaattc tcccccaatc   5040
tcctttcctt ctctctctga ggaacaaaac ttctacaggg gcccacacct gtctgagcac   5100
ataattctcc accagctcag acctggccac acctctcacc atctggcaag actgccacac   5160
ccaaagtggg atacaaccct gagggatggg gacactggac agggcagcac atatcttgca   5220
ccagttctct cccttacact ccatagccta tccatctagt acccaaaacc acctctctat   5280
ggctgctgtt ggttcctcct aggtgtacgc tttgcctact ctttcaagag ctagcaggga   5340
ctacagtaga cacaggctca acactgcctg ccttctccat ctacccaaga catgggcttg   5400
aagctgcaga tccccttta cactcagcat ctttacttcc tactctgtgc cttttctctg   5460
ttgtgcacat cctagtcaag gcaacttcct gagcccacac atctggcaca agtcaactcc   5520
tccttctcac ccctgccttg tggttcccag ggcttgagct ggcagggaca gctgcagccc   5580
caacagctgg ggctggggtg gggggccgtg ggaactgtag ataggggcc tcttagtacc   5640
cacacagata ccctcctagc ccagtgcagc tgttgcctgg cagacaggag gggagggtct   5700
gatttggggt tctgtgtgcc tgtctgacct ccccaccttc ttttgccccc acacagcacc   5760
cccttgtctg gatggaagcc catgtgcaaa tggaggtcgg tgcacccacc agcagccctc   5820
cctggaggct gcttgcctgt gagtgtctgg cccagcgcca tcagtgggcc ctgtgtgggg   5880
agggaatagg tcctctgcct ctgagtctcc tgggggatgc tggtatcact tcctccatgt   5940
gtgtggcttc ggtaacctct tgtgtttccc cataggggaat cagacagctt taagagcaga   6000
agctctggtg tctctctggc ttgggttcaa atcccgcatc atcttgctaa gtgtctgaga   6060
cttaaccagt tcgttaagtc acagtgctct ggaataaaag attgatttcc aaggccaatg   6120
acagtggctt gacagtgaca aggacgtcca tgccctccca tatgtcagaa tacaggaggc   6180
acccaggaga cctatttag agccctgttt tattttgttc tagtttgtat gacctttggt   6240
tagtcatttc tcttttctga acctcacggc atctgtgaag caggagtgct ttccctggcc   6300
tgtgactgtg caggaaggga cccaagaatt atttgggaaa tgcagaaagt tagagaagag   6360
gaggagggtt tgggagctac cagaggcagg cagaactcta gattctggga catctcgagc   6420
aagtgctggg gaccttccca gccacttttg catctacaat ggcttttctt tcatgaggtt   6480
gactgtaaag atttgaaaag gacctttaac tgggcttacg cttgtatttc ccagcagaag   6540
caggaggtca ttccgtacag ttccagggca gtctgggctc tcacagagtg agcttgtctc   6600
aatgttttgt tttctaaagg gggctgggc agctgagagc ttagtaggta aaggcacttg   6660
ctgccaaact ggacaacctg agttaagtcc tggggaccca aaagatggaa agagagaact   6720
aatctcggca agttgttctc tggcctctgc atgaatacat acacacacag ataatgtaat   6780
aaaaatcaaa actatattaa aaataagaga aacttttgaa acctttgac gactggagat   6840
ttcaatggtg tttgcccagt acatacaaag ccctgggttg gagggaaagg acctcaaggt   6900
```

```
ctgtgggctt attggttttg ttttcttttt aatagtaata gcattccatt cagcagctat    6960
taattagttc gttcatcagt gtgttcattt cctcaatact gtgtgggcta gccagtggat    7020
cagcctcaag ctaggtgggg ccaggatgac ttccgatata gaaaaacaaa aacctttaaa    7080
attcaatggc tggaatctca tttagcttta ttggggtca ctggccgagg gcatcctga     7140 ggctgagggt tgggagggtc cttacttgga agcagtcgct tggaagggag gctgaggcgt    7200
ggggcggggc gcctgcgcag tagaactaca cgcctggaca gctgccgaca ggtgaatacg    7260
cctgaggctg ccccgcccct cgacaggtga atcaccggct cacgcggcct ccgggagccc    7320
ggatcgcgcg gagtggagct cgcttaaggc tccagaatag agatttgggg gggacctcag    7380
cctatgttct tctcatccca acccactctt tcaggcttct caaatcctgc tgtctcctta    7440
ggagtgaccg ccccctcccc aatgacactt tctcccccac ttctcccag tcttccgacc     7500 gggagaaggc ttcggagttc tccgtcgctt ggtccttgtc tgtcttgcta gtccgttccc    7560
tccttggaag ctgctccccc gcccccctcc cgctccgcta cgtctcccct aaagctaagg    7620
cggcgaggcg ggtccggggc tggaaccggc cggaccggtc ggcggggggcg cgaggtgcag    7680 agcgtgggaa cccgcccgcg cgcagggag ggtgccgcgc ccagcttggc gatgataccc     7740
gtggtcccca gtgctctgca cgcagcgccc cctcctggcg tgtcatcgtc gccgccttgc    7800
aggactgggt aggggttga gagcatcacc tccaaggttc gaatgtccac cacacccttg     7860
cagggttgag cttcgacagg gttgagcttc gacacgttta tctaggaacg gaattcgggg    7920
tgggggtatt gtagggtgac gctaagaaat gagtcacctg ctttgagttc tgcccttggt    7980
gtttgagaca agactgagct aggggatcct cgctgggagc cggaagggta gggtagagga    8040
gaggagggtt gaggtagggg tgatgtacgt tgtgtcattg catagttgca tagccaggat    8100
tgtttgacta ctccagtccc cttccttagc cctcctcacc tctgtccgta gaaaggttac    8160
aaacttaagt cgtctttag tttttattt ctagcactca ggactagat tttttcgaga       8220 cagggtttct ctgtgtagcc ctggctgttc tggaactcac tctatagacc aggctggcct    8280
cgaactcaga aacccgcctg cctctgcctc ccaagtgctg ggattaaagg cgtgtggcac    8340
ccctgtccca ctactcagga ctatcttgat gggtttgggg aaggggccgc aggccttggt    8400
ccagattgag ggctgaggtg cccatgccaa gccccaccga tccatgagag gaggattgca    8460
tgctcttggg agaaaggagt ttatgatttg tggctatctt cctgcctctc catatgagtg    8520
agagtttccc atattcgtgt gggaggctgt ggcttcttgt ctgtgtatgc caggccagta    8580
tgcccagttg tatgtgtctg tgcggtttct gggtcttctt gggtgtgtct gcctcctgga    8640
gtctgaggct tttcatttgt tgttcccagt acctggaatg cccttcccca catcaccctt    8700
tggctcaccc atttttttgc cgtttttgt tgtttgaaaa tataacaccc actcattcta    8760
tcacccttag gctgcttgtg agtttcctgt ggttgctgta ccagattacc acaaacaggg    8820
tggcttaaaa caacagaaat gtactctgga aaatcctgga ggccgaagt ctgaaattaa     8880 ggcgttgcca gaactggctt tctttactga ccatccaggg ggagaagact ttcttatgtc    8940
ttgtccagtt tctgattggc tcaggcttat ggctgcccca ccctactctc tgcctttgtc    9000
tgcacatgac ctttcttctc tctttagttt ctatctgtct ctctcccgtg tcctgggaaa    9060
ggaacctagg cccctgcaca taccatacaa gaactaccac tgtgtcatgt ccctggcttt    9120
tctcttgtaa agatactgtg tgttgggct ggtggcacga ctcagtagtt tagagcagag     9180
tttggtcccc agctctcatt ggttactcac ctgtaactcc agctccaggg gttttggcct    9240
```

```
ctgaggaagg acactgtact caggtgcaca catactcaca cacaaccaca catgcataca    9300
ataaataggg gctgaaaatg gctccacagt taagagcgtg tattattttc tcagaggact    9360
tggatttgat ccctggaatc cgcatgataa ctcataacca tccttaatgc caacgccctc    9420
ttcagacctc catgggcatc aggcacgcac agcatgcacg tacatacatg cgtggaaaac    9480
acttatccac atcaaagtaa aataaatctt ttaaaaattg gcttgaaata caaagtgaac    9540
ttgtcttggt attcttcaca attacattgg caaaaattct tcttcccttt cttttcttg     9600 tgctgagaat tgaatctagg gctttatgca tcctaggcaa gtgcagtacc actgagctat    9660
attccaaatc ctcttgttat ttgtttaaaa tatatgtatt gatcttgaga cagcgtctca    9720
tgcagtcaag gctagcctca aacttgctat gtggccaagg ctgaccttga actcctcatc    9780
ctcctgcttt ttcctcggaa tgccaggttt gtgtgaacca ccttgcctgg cacatctcct    9840
ttaaaaagaa ataaagtgat agtcacagct tctgggacat gggcgtgttc ttcagtgtac    9900
cacgtccttt gtgagcttgt ggcatgtaca agctgttttt ggtatgttcg tattaatgtg    9960
ttacctgtct atgttttctt tgcctgacct ggctatgagg accaaaaggg taagagtcac    10020
ttttattttg cttgctgctg tgttttagta tgtagtaggt gtcaataata tttgttgtca    10080
gaataaatga ggatggctgg gaatggtggc acttgccttt aaacccagtg ctagaggcag    10140
agaggcagag gggcagaggg gcagaggcag aagagaggca gagaggcaga gaggcagaga    10200
ggcagagagg cagaggcaga ggcagagaga ggcagagagg cagagaggca gagaggcaga    10260
ggcagaagag aggcagagag gcagagaggc agaggcagaa gagaggcaga ggcagaggca    10320
gaggggcaga ggcagagagg cagaggggca gagggacaga ggcagaggca gagaggcaga    10380
gaggcagagg cagagaggca ggcagagaga ggcagagagg cagagaggca gaggcagagg    10440
cagaggggca gaggcagaga ggcagagagg cagaggcaga ggcagagggg cagaggcaga    10500
gaggcagagg ggcagagagg cagaggcaga ggcagaggca aaagagaggc agaggcagag    10560
aggcagaggg acagagaggc agaggcagag aggcagagag gcagaggcag aggcagaggg    10620
gcagaggcag aagagaggca gagaggcaga ggcagaggca gaggcagaga ggcagagagg    10680
cagagaggca gagaggcaga gaggcagaga ggcagagagg cagaggggca gaggcagagg    10740
aagagaggca gagaggcaga gaggcagaga agcagagagg cagaggcaga gacagagaga    10800
cagaggcagg taaattactg tgaattccag tctagccagc gatatgtagt gagaccctgc    10860
ctaaaatata ttaaaaaaaa aaaaaaaag ggaaggaaga gtaaatggat ttgtctgata     10920
gtctgtctgg cacgagtgtt gtttgataaa cgcatcttgt gttatctgtc tggcattgcc    10980
atgcttttat accgtcccga ccacacatct tcccacaggt gcctgccagg ctgggtgggt    11040
gagcggtgcc agctggaaga cccttgccac tcaggccctt gtgctggccg aggcgtttgc    11100
cagagttcag tggtggcggg caccgcccga ttctcctgtc gttgtctccg tggcttccaa    11160
ggtgaagggg tgtgtctgga cgggaaccct tggtaggcga gaatgtagtc agacccaagc    11220
tcaccctctc ctggttcttc caggcccaga ctgctcccag ccagacccct gcgtcagcag    11280
gccctgtgtt catggtgccc cctgctcagt ggggccggat ggccgatttg cctgtgcctg    11340
cccacctggc taccagggtc aaagctgcca aagtgacata gatgagtgcc gatctggtac    11400
aacttgccgt catggtggta cctgtctcaa tacacctgga tccttccgct gccagtgtcc    11460
tcttggttat acagggctgc tgtgtgagaa ccccgtagtg ccctgtgccc cttccccgtg    11520
tcgtaatggt ggcacctgta ggcagagcag tgatgtcaca tatgactgtg cttgccttcc    11580
tggtaagtaa gttgtgccca gggaaggcag ctggggacaa taggctagcc tcttagtgac    11640
```

```
cattgtcacc ttgtcctccc ctacgaggct tcgagggcca gaactgtgaa gtcaacgtgg    11700
atgactgtcc tggacatcgg tgtctcaatg ggggaacgtg tgtagacggt gtcaatactt    11760
acaactgcca gtgccctccg gagtggacag gtgggcatca gggctgcaga gaaccagggt    11820
ggctgacctc aggtgggcac acgggcaact tagactagca catctttgtg ccctaggcca    11880
gttctgtaca gaagatgtgg atgagtgtca gctgcagccc aatgcctgcc acaatggggg    11940
tacctgcttc aacctactgg gtggccacag ctgtgtatgt gtcaatggct ggacgggtga    12000
gagctgcagt cagaatatcg atgactgtgc tacagccgtg tgtttccatg gggccacctg    12060
ccatgaccgt gtggcctctt tctactgtgc ctgccctatg gggaagacag gtgagtggcc    12120
cttttctttg taggcaacag aatggtttca gcatgaaagg taaaaacaga ctctgagttg    12180
agcgttagaa agattggggg ctgggatgt ttcttcctgg cagagtgtgt gcttagtgtg    12240
cacaggctct gagtttaatc cttagcgtga aggaagacaa gaaggaggag gaaggtgga    12300 agaaagaaag gaaagaggga ggaagggttt gctggaccct gggtttggaa agaagcctga    12360
gcctctgtcc tatgaggtgc atagtccaag gcagagactg ttggaattgg ggaactattg    12420
agaggtctaa ctgggaaaaa ggcaggaact atggaagtca caaggtctg tttgtcccctt    12480 acatcttatt ttggtggggg gtggtcagac tctggttgtc aggctaggtg gcaagtacct    12540
tgagtttatt gttgttgttg atgcgttgag acatggtgtc actatttgta catcaggcta    12600
gcctcaaact tgcaagaaag gatccttggg cttctgtgtt ctgagtggtg ggattaagga    12660
attttgttgc tatgcctgaa tagggtcttg atttatcatc ttttaaaata ttaaaaaaag    12720
tgtgtgtgtg tgtgttttgg ctgcatttat gtatgttata ttatgtcatg ctacacgcat    12780
gactggtacg ctgagaggcc agaaaaattc atcagctctc ctgagattgg agttactgat    12840
ggtggtgagc tgccgtgtag gtgtgttggg aatgaaacgt aggtcttctg gaagagcagc    12900
caggattctt agccgctgag cacctctttg ggccccggtg ccttgtttgt aaaatgtttc    12960
taagttattt tcaaatggta tcgaagaagc agattaacag ataatactga accaatattc    13020
caatgtgaaa cgtcctgaat gtttcactgt ttcataataa atggcttttc caggacagcc    13080
agggctatac agagaaaccc tgtctcgaaa aaaaccaat aataaataa ataaataaat    13140 aaataaataa aataatatta atagatggct taaaaaaata agaacagata ctaatacagt    13200
gctggttaat atacataaga aacaggaggc aagggccacc ccaaagggtg ctcagggcgt    13260
aaaggcactc gctgagttgg cctggcaagc ctacttctat caagggaatc cactggtaga    13320
aggagaaaac caaccaagtt tcctctggct tctacacatg cactatgaca tgcacacact    13380
ccccagataa gtacattagg aatgatgatg gtgatgatgg tgatgataat gcaaggagct    13440
ggaagcgtag ctgagtgatg gtattcattc gttgtatgct catggtcctg gggatccatt    13500
accagtacca gtcttcttcc tcaaacgcta ggtctggggg aactttgggc caccccgagg    13560
atcagcgctt catttctgct taccttttct caggcctctt gtgtcatctg gatgatgcat    13620
gtgtcagcaa cccctgccat gaggatgcta tctgtgacac aaaccctgtg agtggccggg    13680
ccatctgcac ctgcccacct ggcttcactg gaggggcatg tgaccaggat gtggatgagt    13740
gctcgattgg tgagaagagt accttctgga aaggagcctg aaaacggagg ggtggggcca    13800
tggctggcca cgcccacact ggctgtgtct tctcccccat attccccctt cttgcaggtg    13860
ccaacccctg tgaacatttg ggtcggtgtg tgaatacaca gggctcattc ttgtgccaat    13920
gtggccgtgg ctatactgga cctcgctgtg agactgatgt caatgagtgt ctctccgggc    13980
```

```
cctgccgcaa ccaggccacg tgtcttgacc gaattggcca gtttacttgc atctgcatgg    14040
caggtgggtg gtgggtatgg cttgggtggg tcatgaaggc tggggcctgg ggtaaaactt    14100
ggtttattgt tatttacttg aagaaaaaat gctgggcata gagacacatg actgaaatcc    14160
cagcacttgt gaggcagaga taggctcatc tctgtgagtt cgaggccagt ttggtctaca    14220
gggtgagttc taggatggct aggattataa agtgagactc tgtctcaaaa taaataaaat    14280
aaataaaaat aaaataaaac aaaacaaaat aaaaagggga tagagagata gcttagtggt    14340
taagagtcct ccctgctttc tagagggctg agtttggttc tcagtaccca tatggggcag    14400
tgcacaacta tctagctcca ggagatctac aatgctcttt tggcctctga agatacccat    14460
gtgtttggga cacacacaca cacacacaca cacacatgca tgcaaataaa caaaattaaa    14520
caaacaaata aacaaaagac atttcaaaag agctgaagtg gcacagtaag acggtctgga    14580
actcactgtg tagaccaggc tggccttgag ctcacagaga tccacctgcc tctgcttccc    14640
aaatactgga tcgaatggca tgtgcctctc ggcctagtgc actttaacca tgagggttcc    14700
aaattgtcag gcttggcagc aagcatcctt atttgagcca tcttgcttgc ccatgactga    14760
gtttaaagtg aagcttcctg gctggagaaa gagagagaga gttatgtgtg tttaggatga    14820
aaccttgaaa actcgataag gtaggtgcag ggtcagagcg gattttacca gataacatca    14880
aaggggagct tcataaacct tagtccatga ggggccacag ctgggtgagg gtccagcttg    14940
tttgaaacta aatctaagcc tgaaagtgtc gtgcacgcct gttatcccag cacttgagca    15000
gctgaggcag gagcatcatt agtttgaggc cagcctcaag gccatagtaa gaatttatct    15060
caacaaaccc acaaccaaat caaagtcccc aaaccaagtg aagaggcctt ctgagggaac    15120
tttctgggcc ctcataccat tcccttcagg cttcacaggg acctactgtg aggtggacat    15180
cgacgaatgt cagagcagcc catgtgtcaa tggtggtgtc tgcaaggaca gagtcaatgg    15240
cttcagctgc acctgcccat caggtgagga ccctgggaca aggagcctgg tgtgtcaggt    15300
tatgacaatg tggaacttaa aaaaaaaagt aattagttac ttaactcttt tgtgtgtggg    15360
ggttctctcc ttccactatg ttatgtacat tttgggaatt gaactcaggt ggtcaagctt    15420
ggctggcaag catgttttatc ttctgagcca tctctctggg ctagtctgta ttgaaattaa    15480
tttaaaacaa agccaagggg gtttcccact caaataaggc aggctgcctg ctttaactgt    15540
ttgtgtcacc tttcatccac tactcacttc caggattcag tgggtccatg tgtcagctgg    15600
atgtggatga gtgtgcaagc actccctgcc ggaatggtgc caagtgtgtg gaccagcctg    15660
acggctatga gtgtcgctgt gcagagggtg agggcggacc gtgagactgt ggcaagagcc    15720
agaaggtggg ctggtgggcc aatgggtgtc aaggaccaat aacagacttg gggatggcct    15780
cagctaggcc aggtcagggc cagtgacgct gatgatggag gtaggcagag gtcttggcaa    15840
gattcagggt gcagctagca gtgagattta aagtgggcgt ttctgggtca ggaacagagc    15900
ttggagctgg gcagaatgga agggagaagg ggtgaggtct gagagctgag ctggaattgg    15960
gctgagatta cagccatgga gaagtgggca gaccctcacc tcccgttctt gcaggctttg    16020
agggcacttt gtgtgagcga aacgtggatg actgctctcc ggatccctgc caccacgggc    16080
gctgtgtcga tggcattgct agcttctcgt gtgcttgtgc cccaggctat acgggcatac    16140
gctgtgagag ccaggtggat gagtgccgca gccagccctg tcgatatggg gcaaatgtc    16200 tagacttggt ggacaagtac ctctgccgtt gtcctcccgg aaccacaggt ggggcctggg    16260
gctgggctat aacagtacgt gggggtgtgt ggggtctgt gatgaatttg taactggtgc    16320
ttgacaatag taggtactct tgccatactt cttccctccc tgtaggtgtg aactgtgaag    16380
```

```
tcaacattga tgactgtgcc agtaacccct gtacctttgg agtttgccgt gatggcatca    16440
accgttatga ctgtgtctgt cagcctggat tcacaggtgg gtaggtggct gccatgtagt    16500
gggggggggg gggcttgtaa gatagggatt aagacacaag tctcttgggt gtccccactt    16560
tattttttta aaaaggaaa tattacattt catttatttt gtgtatgtct ggaggtcaga    16620
gggcatctgg ggggagtcag ttctctccgt aaaggtctca gggacccac tcatgtcatc    16680 aggcttgggg acacgtgtgc tttcccccca gttaagtccc tttcttccct ttatcaagat    16740
tatctccaat actcagaagg ccaaggttgg aggattagtg catgtttgaa gctagtctga    16800
gcatcatagt gagcactagg ccagccaggg ctgcatagca agatcatgtc tcaaaataaa    16860
acaatatata gagagggctg gagagataga tggctcagca gtttcaagca cttgctcttg    16920
cagacgactc gggtttagtt cctagcatta acacgctggc tcacaagtgc atagttttgt    16980
ttttgttttt gttttttaaa taataaagta aaataagata aacaaagca aaaaaaaaa    17040 aaaaaaaaac acatcagaaa tggacaaaac aaaacaaaat caggagggaa aagagcccag    17100
gagaagacac aagaatcgga aactcattca ttcacacact caggagtccc acaaaaacac    17160
caaactggaa actataatgt ataggcagag ggtctgggga gggcctggca ggctccgtgc    17220
atactgcccc agtcttggtg agattgtctg agctttgata atgttgattt agagggcctt    17280
attttcttga ttttctccat cccctctggc tcccagtctc cttctgcctc ttcttcatcg    17340
gaaaagggat ttgaaggaga cacccccta gttttcttagt ctctcactct ctgtgtacag    17400
tctaggagtg ggtctttgta tttgttccca tcagctgcag gaggaagcgt ctgtaatgat    17460
ggctgaacaa ggcactggtc tgtgaggtat taggagtcat tttagcctta cctttttcc    17520 ccttaaggct ggttctaccc ttgccctctg ggctatctag ccgcaggttc ttggtcactg    17580
aagcaatatt gggtatgggt tctgtcttgt ggagtgggcc ttaagtcaca cagatattgg    17640
ttggttactc ctgcaagctc tgtgccacca cagcactagc agatctagag gcaggacacc    17700
actgtagatc aaagggttg tggttgggtt ggtgtttatg tttctctagc atgcagaaaa    17760
cctttctgta ccaaagaccc tagaatatag aaggctctat gtaggcataa gtttgacttc    17820
tccatgttca gtgagtctca caactgctta taactccaga gtaaacttat aattccagga    17880
atctgacatt ctctgctggc tttcatgggc accaggaatg caccatgatg cactaacata    17940
catccaagca ctcatataaa ataaataaat aaataaataa ataaataatc tttttaaaag    18000
cagagagaga aagaggagag agatggagag agggagggag ggagggagat aggtgcacac    18060
ctgtgcacac acacacacac acacacacac acacacacac acacaaagtt gggggcgggg    18120 ggggggaaacc accttggact atcctgagct tgtttcctca gtggcatggg gctgtcgttc    18180
tgtcagcaga gtgaggtcag gatcagctgt gtgatagaga acaggacgtc cctttccttc    18240
agttggcacc actgtcttcg ttctggaatg aagttgcctg tatgctcccc agggcccctc    18300
tgcaacgtgg agatcaatga gtgtgcatcc agcccatgtg gagagggtgg ctcctgtgtg    18360 gatgggaaa atggcttcca ctgcctctgt ccacctggct ccctgcctcc actttgccta    18420
cctgcgaacc atccctgtgc ccacaagccc tgtagtcatg gagtctgcca tgatgcacca    18480
ggcgggtgag gccctttccc aactcccgac ccctcttctg ctgtctccag ccacctgtca    18540
cacctcactg cctcccccac caggttccgc tgtgtttgtg agcccgggtg gagtggccct    18600
cgctgtagcc agagcctggc tccagatgcc tgtgagtccc agcccgccaa ggctggtggc    18660
acctgcacca gtgatggaat aggctttcgc tgcacctgtg cccctggatt ccagggtgtg    18720
```

```
tgaccccata ttcctccccc agggcacccg acacccttgt ttcttatgtt tctttcctgc  18780 ttttttttgtt tttaaagctt tgcttagtac cttttgttct gtgtgtctct gttacatatg  18840
tctgtgtgtg gagaccagaa ccagaagaag gcatgtgtcg tcttttatca ctctctaccc  18900
attcctctga ggtgtgcagg gtctctccct gaccctgggg tttgtgcttt ctcggatagg  18960
ctggaagcta ctgagtccct gggatgcccc tgttttttctt tcaacttgca gctggggtta  19020
cttgttatag aggtgggagg gtctgagttc tggtcctcat gattgggcct gaggtgctct  19080
taactgctga accatccttc cagccccatc tgcatttcct tccttccttc cttccttcct  19140
tgcttgcttg cttccttcct tccttcttca ttcctttaat ttctctcttt tttgtctttt  19200
ctaaatatca gggtggggac tccagggatg ggggaattgg gagcagtgag tttcaaaact  19260
atctaaacta tctgcttcta acaggccatc agtgtgaggt gctgtccccc tgtactccaa  19320
gcctctgtga gcacggaggc cactgtgagt ctgaccctga ccggctgact gtctgttcct  19380
gtcccccagg ctggcaaggt acactaatat cctcctcttc ttctcgtctc ccttctctct  19440
tctttctctt cctcttcctc ttcccctctt tctcctcttc tgcactttgc tccatgttgg  19500
gcaatgccag ggagcccaga gaggactcag tcctgccctg cctttgaagt tgtttctttc  19560
tgggaaaaga cagctggatc cagacattca cagcccagga gtcagctcag gagaagaggg  19620
aagccatatg gagctgagga cactgggata cctgagattt gatgacattt ttgatcgggt  19680
gacttcagag tgtgtattca acatctaaag agataggcag aatatatttc aggagtggca  19740
tgtgccaaac gcccagggat agcggctggt ctttgctttc cttgactcca ccagcgggtt  19800
cttgagctgc aggcatcctc agacccctttt ttacccctgt aacctcaatt gcttcccctc  19860
tcacctccag gcccacgatg ccagcaggat gtggatgaat gtgccggtgc ctcaccctgc  19920
ggcccccatg gtacctgcac caacctgcca gggaatttca ggtgcatctg ccacagggga  19980
tacactggcc ccttctgtga tcaagacatt gacgactgtg accccagtaa gtgcagggat  20040
ctttggggcg cttccttccc cagggaaccc acccatcaag tcataccatg tcctggcact  20100
gtgttgctgt ttcctgactc tcctgacaac tattactccc ctcattcatg agggtcttac  20160
ttccatccca gcaccactgt agaaatgggc aatgggctgc tgggatgact ctgcaggag  20220 aggcactgcc tctaaacctg atgaacctag gtcagtccta caagttgtct tctgatctct  20280
acatgcctgc tatgcacaca cacacacaca cacacacaca cacacacaca cacacacaca  20340
cagagagaga aagaggggc gggagagaga gaaaaaaata acaataataa cccaaaatag  20400
aataaaaagt taaaaatatg ttttatttaa gccaatatag aaaatatttt catttcacat  20460
ataagccttc aaaaatttaa attttgctaa atgtatttta catttgcagc ttgtctcatt  20520
tggcctggca gtgagatcac gggcctatta acctcatgtg gctagtagta gctacactgg  20580
tcaccacagg ctgtgctgag cgtatgaatc agagcaggca gtggcactac aagtattcct  20640
tggttctttg aggttgttcc cacagcctcc atggattaca gactctatgg gtgtttaagt  20700
cccttattgt caaatggctt aatgtttgca aatagcctct gcatctcctc ccagattatt  20760
taaatcatct ccaaataact ttttatttta aaatgtttac atttacctgt tattgtgtgc  20820
atgtgtgtga gcgtgtatgt accacgtgtg gaggtcatag gacagtatag tccttctacc  20880
ttgtgggatc tggtgttcca actcagggtg ttgggtttgg tggctttact caggctgagt  20940
cctatcatca acccagactt catttttaat tgaactggaa ggagggaggg gggagggagg  21000
gagggaaggt gagagagaag gggggggtgt ggaatgcaaa catgctacat tagattgtgg  21060
aggccagagg acagcttgca ggagttgatt ttcttcttcc accatgaggg ttgcagggat  21120
```

```
tgagctcaga caggcagtcc tgggtgggca agcacccttta cctactaaag tcatcttgcc   21180
ggtccctcta gatggcttga cacaccaagt acgatggaca tagcatgtat atgtttgcta   21240
tactctattg tttagaaaat aacaagaaaa tagtgtgcat gttctgccct tgggtaatct   21300
ctgattttcc ctattgtcca tctactggtt gaacccacag attctgaact tcagaatagg   21360
tagggccagt tctatagctc aaagggtttt gttttttgttt ttgttttttgt ttttgttttt   21420
tgttttttcga cagggtttt ctctgtatag tcctggctgt cctggaactc acttttgtaga   21480
ccaggctggc ctcaaaactca gaaattcgcc tgcctctgcc tcccgagtgc tgggattaaa   21540
ggcgtgcgcc accatgcccg gcactcaaag gggcttttttt taaaaggata tttttaaaat   21600
gtatttattt gtctatgtgt tgcatgacac atttgtctac gtgagccatg acattcacgt   21660
ggtggtcaga ggacatctta tagagggggg ttgaccacaa aaggggacta actttgatct   21720
ctgaccaaga gtgtctcttg tagtctggga tacacacacg tttaatttct gcacttagaa   21780
ggcagagtgc aggctcatct ctgaactatt caaggccagc ctcatctaca tattgaactc   21840
caggctagtc ttggctacat agtaaaacta tttcaaaaac aagcaagcaa acaaaaagga   21900
ctgtccctc tggcttcttc ctgagtcttc ctgtgtgtaa agcatagctg agtcaggcca   21960
ggctgatgtg ggcataggca ctgaccagat tattttcctg ctcactgcag acccgtgcct   22020
ccatggtggc cctgccagg atggcgtggg ctccttttccc tgttcttgcc tcgacggctt   22080
tgctggtcct cgctgtgccc gagatgtgga cgaatgtctg agcagcccct gtggccctgg   22140
cacctgtact gatcacgtgg cctccttcac ctgtgcctgt ccacctggtt atggaggctt   22200
ccactgtgag attgacttgc cggactgcag ccccaggtgg gtggagcatg ggctggagac   22260
tcaggggcca gagagggcat cctggactcg gcatctgtta gagggctgga atgatgctgg   22320
cacatggctg aggaatgggc aaggctgctt ggaagtcaca gactccagtt ctttggaggc   22380
ctagactgag gcagcgtccg taggcgaagg agccaggtta gatcttcata gtgctatggc   22440
ttgttgagga tagcaagggt ccgaaattgg gaagtactta gttctagaag gattggggtg   22500
gtctttaagg tcttgaactt cttgtcctgt tctccagttc ctgcttcaat ggagggacct   22560
gtgtggatgg cgtgagctcc ttcagctgtc tgtgtcgccc cggctacaca ggcacacact   22620
gccaatacga ggctgacccc tgcttttccc ggccctgtct gcacgggggc atctgcaacc   22680
ccacccaccc aggatttgaa tgcacctgcc gggagggctt cactgggagt cagtgtcagg   22740
tgggtggtgt ctgaggtcct tggtggaaga gtccagaaat gagggggggac ccgtgggggg   22800
catcctgaag ggataaggcc atctggtttc tagggtctct cccagcactg atcttgaaga   22860
tttcttttgc agaacccagt ggactggtgc agccaggcac cctgtcagaa tgggggtcgc   22920
tgtgtccaga ctgggcttta ctgcatttgt ccacctggat ggagtggccg cctgtgcgac   22980
atacaaagcc tgccctgcac ggaggccgca gcccagatgg gtgagggaag catgtggtgc   23040
gtgcgtgtgg ggctgaaggg tggtggtgca tccctcttgc tggcatgagc caaatgagag   23100
cgccatacaa catatgggac taatgaggtg tgtggctcag tatgtgtgtg actggaataa   23160
ctggccagag tgtgactata tctgtcacag tgagacagct gggtgtgtgt gtgactaagc   23220
tgatagagtc atcaaagtgg tgctgtggaa agagaccagg ttagctgaca agtggcctga   23280
cagcttttgg atgtgggtga gacactaggg attgatggca gtgggatgt tagatgaatg   23340
tgtgatgtgg ccgaataggg aaaggtggca tggccacctc tgagtctgat gtcaccctct   23400
gcttttcagg ggtgaggttg gagcagctgt gtcaggaagg tggaaagtgc atagacaagg   23460
```

```
gccgctccca ctactgtgtg tgtccagagg gccgtacggg tagtcactgt gaacacgagg    23520
tggatccctg cacggcccag ccttgccagc acggggcac  ttgccgtggt tacatggggg    23580
gctatgtgtg tgaggtaagt gcgtctcagg gagagggaag agaagtcagt catgcttgcc    23640
tgtgtttctg tgtcctggtg tgggtccttc ccctcccccg tcggtgggag agcagggatg    23700
tttcatgtgt agtaggtaag cactctgtat cactcagctt catccagagt cagcatggct    23760
gctatagaat tttttattt  tattttattt ttttttttt  ttggttagat ttttgagaca    23820
tggtctcgtt atgaagctct ggctgtcctg gaatttgcta tgtagtccaa gctggcttcc    23880
aagtcacagc aatccttctg cctctggctc tatatgagtg ctagataaca gtcatgcgcc    23940
ataatacttg tctgcgtgtc ttttctttcc tccttttctt tatcttttcc tttcccttct    24000
ttccttctct ttctttcttt  ctttcttcct ttcttcttt  cttctttct  ttctttcttt    24060 ctttctttct ttctttctat tttgagacag agtctcacta tgtagctctg gtgggcttaa    24120
actattagag atctacctac ctcagcctcg tgggtgctag gattaaagga atgagcaacc    24180
aggcctggcc tagcagtcct tttatgggta tatgtctgtg tgtgtgtgtg cacaggagtg    24240
taaatgcaga ggtcaggggc agacatcagg tgtcccctct atcactgtac tttgttcgcc    24300
tgcggttctc tcactgaacc tcaagttagg ctgtagatgg tgagcccag  tgatcctcct    24360 gcctccccca ccccacacct gggtgacaca catagaagac cacacctagc tttttaagta    24420
ggtactgagg atttgaactc aaatcttcac gtgtgtgcag caagcgctct tacccactga    24480
accatctctg cagctcctta accctcatgc acttgtggat ggacttgggg catgtgagtt    24540
tctgtctcca gttctgtgtc tctctctggg tatgagtgac ttaccattgt gtctggacat    24600
gtggtctggg gtacctgggt atttttcctg cgtgttctca tcagcctatc tccctctgta    24660
ctgagtgtgc tggtggcctt cccagtctca ccctgaccaa tagcaacttg agggaggaga    24720
ggatttactt cagcttacag gttactgtcc atcattgagg gaggctgtga agaagcccaa    24780
aggcagggaa ccatcgtcca gaactgaagc agagaccata gaattgtgtt gctttcccgg    24840
agcggtctgg gtcttcccac atcaatcagc actcaagaaa atgcccccac agacatgcta    24900
taggccaatc tgaaggaggc agtttctcaa gcaagattcc ctcttcccag ataggtctag    24960
gtttggttca agttcatgca cacacacaga taacaagtgt gggcacagtg tgtttccttg    25020
tactgggtaa gtctgccccc tacactggct ttgtgttgga tgtctatgtg tgtccttttg    25080
tggtgagatt ctgtgtgctc acaggtatgc cgaggcacgt ctgtgtccct cggggctgag    25140
tgaattcctt tcttgcctca atacagtgtc cagctggcta tgctggtgac agttgtgagg    25200
ataatataga tgagtgtgct tcccagccct gccagaacgg aggctcctgt atcgatcttg    25260
tggcccgcta tctctgttcc tgtcccctg  gcacactggg tatgttaagg ccagggttgg    25320
gggcaggata agaggatgag tttctagcct ccactgacca tgctcctata ccctaggagt    25380
tctctgtgag atcaatgagg acgactgtga cctaggccca tccttggact caggcgttca    25440
gtgcctacac aatggcacct gtgtggacct ggtgggtggc ttccgctgta actgtccccc    25500
aggatacaca ggtctgcact gtgaggcaga catcaatgag tgtcgcccgg gtgcctgcca    25560
tgcagcgcat actcgggact gcctacaaga tccaggtggg catttccgct gcgtctgcca    25620
tcctggcttc acaggtaaga atggcagaga gcctggccag aaacctgatg tggttctgct    25680
tctgtagttg atcctcctgc atctgtttgt tcagggcctc gctgtcagat tgctctgtcc    25740
ccctgtgagt cccagccatg tcagcatgga ggccagtgcc gtcacagcct aggccgtgga    25800
ggtgggctga ccttcacctg tcactgtgtc ccggtaggtg tgattggtag gggttggaac    25860
```

```
ccttggggaa agaaaaggcc tgtggcttta gggaagcata ggtctatacg ggaaaagtag    25920
aaggaaagga ggttctgaaa ttatgaaatt atgaaattat ggtttggagt gtaacttagt    25980
gaaattgtga cttggctttg ttgcctcctg gggaggtatg gcttatcttc aaaatgaggt    26040
cagtagagga aaggttgctg gaattggagg ggtgggggtg gggtgtcagc atttctcaag    26100
tcttgacctc cattcttttc tctcttttcc actctcctgt ttcttctcac taccaatttt    26160
ttctctttct gtctcctcac ttcaccatta gccattctgg ggtctgcgtt gtgagcgggt    26220
ggcacgctct tgccgagagc tgcagtgccc agtgggtatc ccatgccagc agacagcccg    26280
tggaccacgc tgcgcttgtc ctccggggct gtccgggccc tcctgccggg tttctagggc    26340
gtcaccctca ggagctacta acgccagctg cgcctctgcc ccttgtctgc atgggggctc    26400
atgcctacct gtacagagtg tccctttctt ccgctgtgtg tgcgctccgg gctggggcgg    26460
cccgcgttgt gagacccctt ccgcagcccc tgaggtcccc gaggagccac ggtgcccgcg    26520
agcggcttgc caggccaagc gaggggacca gaactgcgat cgtgagtgca acaccccagg    26580
ctgtggctgg gatggcggtg actgctcact gaacgtggac gaccctgga ggcagtgtga     26640 ggcactgcag tgctggcgtc tcttcaacaa cagccggtgt gacccggcct gcagctctcc    26700
agcctgcctc tatgacaact ttgactgcta ctctggtggc cgcgaccgca cctgcaagtg    26760 agcccctga ctctgtcctt ctgtctatct atatgttgca ctgtcagtga gccacatctg      26820
tcccagtttg tctgtcagtc tgttttggc tcgtctgatg ggctgtccct tccagctgct      26880
accaccaggg cactggtggt ttcatccgcc tgtttccacc catgtgcctc atctctgcct    26940
atttatattt ttacctatat atcttgccca tttgcttctg tctgcctgca gttacacatc    27000
ccatctgtcc acacttagga cttgttcatt tgtctttctt aaaattttaa aattaaact     27060 gggtctagtt gctcacacat tttaatgcca gcatttcaga ggcatagaca gcaggtctct    27120
gtagggattc aaggccagca tgatctacat agtgagttct aggccagcca aggccacaca    27180
gtgataccct gtctcaaaac aaaaacaaac aaacaaacaa acaaagcaaa acaggagccc    27240
acagcaggtg ctcattcaag agcatacaat agtgatactg gttgagcatc ccaaatccca    27300
aacctgaatc cctgagccat gtggggcatg ggcatgatgc cacagtggaa aattccatcc    27360
tttgccccaa tgataagtta cagtcaaaat tcagacacag gttggtctgt agtggcagag    27420
caccttccta gatggcatgt ggcccttggt tcaatccccg cccagcatgg aaataaaaca    27480
accaccaaag gcaggcacac taaaaatata tagttacttt tgggtatgtg tattttgtc     27540 tttagacttg ggcctcatcc cagaggtgcc ttatataaat tatgtataga gggctgggga    27600
tgtagctcac ttgatggaat gcttgcctaa catccacaga gccaggcttg ggtcccagc     27660 accacctaaa ctgtgagagg tgctgtgtgc ttgtaatctt ggctctcagc aggtggatca    27720
ggaggataat aagttcaaga tcaccctcag caacatagtt ttgttttctt tgttaaaaat    27780
aaggcttcag ccaggtgtgg tggcgcatgc ctttaattcc agcacttggg aggcagaagc    27840
aagtggatat ctgagttcaa agccagcctg gtctacaaag tgagttccag acagccaga    27900 gctacacaga gaaaccctgt ctcgaaaaac caaaataaat aaataaaata aataaataaa    27960
taaataataa aaataaaaat agggcctcac aattcctggc tggaattggc tgtgtaaatc    28020
aggctggccc tgaacacaca gagatatcct tgtctctgcc tctggagtac tggaattaaa    28080
ggtatatgcc agcctgtctg actaacatag ggagtttgag gccagcttga gatacatgag    28140
atcttatctt aaaatattta tagaaagata tctcattgca tttatttgca tatataatat    28200
```

-continued

```
ttaagcatat gtgtaaatat tctaaaacta taatttgaac tctgaaatag ttttagtccc  28260
aattatttca aattaggaac acagaacttg tgcttatgca gccaacgact gcatttgcag  28320
aaagcatatg caagaacatt tcccaccacc accatcccca accccatacc agcactgtcc  28380
actactgcta ttctctgtgt gtgcatttag gtgacccgaa gaatctctga gtttgtgttc  28440
tctgtcccca gccctgttta tgagaagtac tgcgccgacc actttgcaga tggccgttgt  28500
gaccagggct gcaacactga ggaatgcggc tgggatgggc tggactgtgc cagcgaggtc  28560
ccggcccttt tggcccgagg ggttctggtc ctcacagttc ttctgcctcc tgaagagttg  28620
ctgcgctcca gtgccgactt tctgcagcga ctcagcgcta ttctgcgcac ctcactgcgc  28680
ttccgcttgg acgcacgtgg ccaggccatg gtcttcccct atcaccggcc aagccctggc  28740
tctgaatccc gggtccgtcg tgagctgggt cctgaggtga tcgggtgagt gactgtggct  28800
cagggctggg tacagcggtt agggcacccg tggtccagac cgtctgtttc acgcttctta  28860
gttgagagct ctcttggcaa ggcgtcttcc acaggttttt ccgtgtctgt cgggttgaca  28920
tctttgctat gggggggggg ggggttcatc ctctgtacac tacagggagc ctcgctgcag  28980
cgctgagatt ttactcttca aatgcaggtg acagcacctt cttgtgtgca tgatgtgtgt  29040
gtgtaggtcc ccaagtgcca tgacgacgca tgcctgtaga ggttagagga caacagtgtg  29100
aagtcagttc tctcttctca tcaggatgtc aggcttgcat gatgagcatg ttgcctgtga  29160
gccatttcgc tggcttgttt gttgttttct tctcgttgtt tgctttgttt gtgttttata  29220
ggcactaacc tgaaattcaa tctgtagccc aggttggctt tgaactcatg gttctcctac  29280
tcagcccttc caagtactag gattgcaggc atacaatatc gcccccgaca ctcactctct  29340
ttcctcccca ctctcttcat tcccctttcc cctcatctca caaagttgt agaacttgct   29400 cactggtgac ctggtagggg gaacctgaag tgggagaggc attttttga gggtggacca   29460 gggcctgaag attgggccct gacaaggaaa ggagagctga actttagaga tgctgtggtt  29520
tgtgggttct gattggatgc aggcagaagt caagtagatg ggtgaggtga cacatggccc  29580 cttctcttggc taaagtggct tagtgatgag gacatagggc taagcagggg ccaccttgga  29640
acttgctatt cttagggggt cttgaggtat ggggaggaac cccaggagat gactgagggc  29700
tgaagatgca tacaagacaa ctgggtattg gaggccattg gagggaaaga agggagaatc  29760
aaggaagcag gagagaagga aatgaagaag gaatctaagg actctcagag acctaagaat  29820
tgggggacag tagaggacgt ggctcagtgg tagagaacct accttgtata ttcaaggccc  29880
caagttcatc tccaatacca caagaaagga taaaggagaa aaagcaagct tttagagaaa  29940
ctgacatggt acactgtccc agcaaagggc gacaccaaca gactctacca gggcgaatga  30000
agacattatt gaattcacag cttttgagaca ctgtgaccaa taagatctgt tgggagagac  30060
agtggagttg gatgccagct gagagctggg tgggtggtag agacatggag agtggagacg  30120
gatgtggctc tctgaggtcg ggtgtctagg atgctgtaga caagtgttga gcctttgggt  30180
ccctctgctc tgttcccaca gctctgtggt gatgctggaa attgacaacc ggctctgtct  30240
gcagtcagct gagaatgacc actgcttccc tgatgcccag agtgctgctg actacctggg  30300
agccttgtca gcagtggagc gacttgattt cccataccca cttcgggatg tgcgaggtga  30360
gctgggaaga agagagggta gtacattaga gcgtgtagcc ccagagatgg ttgaatccta  30420
tagtatggtt gaagccctgt gagtaaagcc ccatcttctg gctgaagctg tcccatagct  30480
aagccaaccc catgggtaag agccacttaa aattgaaacc ttacttgtag tcctgctcca  30540
cggctacagc cctgcttata gctgagtatc gcccatggct gaaatctgct cactcgttcc  30600
```

```
tgccctgata cttggctgaa ggctcatctg ctgcttccat cctacaggag agccgctgga   30660
ggccccagag cagagcgtgc cactgctgcc actgctggtg gcaggggctg tctttctact   30720
catcatcttc atcctgggtg tcatggttgc caggcgaaag cgagaacaca gcaccctctg   30780
gttccctgag ggttttgcat tacacaagga catagctgct ggccacaagg gccggaggga   30840
gcctgtggga caagatgcac tgggaatgaa gtaagaacct cacatgctct acatccccaa   30900
ctgtgggtcc cttgtaagct ctagaccata ctcacctcgg tcatattcca acctctgacc   30960
ccagcctaac cttaactaca gactccatct gggccttcag tgttaatcct cttgacctat   31020
gaccccatga tccctgagga ttgccccaac ccctatccct tgacgtgatt ttctatttct   31080
atacatttcc tgactcatat cttttccctga cgccatcctg aactaacctc acaaaattca   31140
ttcttatgac tgctaacctc aagactttttg tcatttcaac ctgtccctga ccacgactgt   31200
atccttgatg actcctgaat catctctggc ttcaacccac ctgtacccttt gacctcacct   31260 cagacccctg tttctaccca atcctgtgtt aattcccttg tgatcctcaa tcccaagcct   31320
tcaacttgac ttattcctca acaccaatag ccatattctg accttaaccc ttccctatga   31380
caccataact cctgactcct catcctgatg tttcaagcct ggctatcccg tttgtcacaa   31440
gagagtaact cctcttccat gagctttgat aactcccttta tcaaagttat gagaggaaac   31500
ttcctttgcc cctgcagttt gtctcatcta tcctcatgca tccatgttcc attgtgtgtg   31560
ccactcttga ctctgagttc accttatgag tctggccacc tcagatgtga ggtgtggagc   31620
aggtataaag accgttgttt ggatccctag aacctgtata aatgccataa aatccttaag   31680
tgctcagtgg gcccggcagc ctgacttgga agatggagtc ctggtcccta gagcaagctg   31740
actagtgagt ctagtcatat ccgtgagctc ttggtttgat tgagggaccc ttcctcgatg   31800
accaagactg aggagagatt cctctttatc aacctcagac ctgtgcaccc aaaacacaca   31860
cctgcactca cagatggaaa gagaaaacat tttgattgcc acctgacatg cttcctgcaa   31920
cttcatctct atcctcctat ccatcattgg aatctttgtc aacgacccag gaccccctcct   31980 cagttcctga cccttacct acctctatga cctctgcctg aaccaaaccc taaaccctct   32040
tcccaggcca gagttctcta gtgtactttc tcacgtcttt tcttcttgt tttccccaag   32100 gaacatggcc aagggtgaga gtctgatggg ggaggtggtc acagacttga atgactcaga   32160
atgtccagag gccaagagac tgaaggtatt aacctgcttc tctgactctt tccttcaggg   32220
ttccaagttg ggatcccta acagctggag agcccaggga agtctctctt ctcccgattg   32280
cctcagcccc agacaatttc cacatctgtg tggacctcac ttttcccttta atgtgattct   32340 gttgctgtgt tgggaggaac agagatttac catgggttcc ctgggtgggt ggggcttccc   32400
cttcttcata tggttcctcc tcacacaggt tcctgctccc aggtctgcct agggtcaccc   32460
tagagcagca gctcttaacc tgtgggttgt gaacctattt gggctgcgct cttcagtttc   32520
agatggctca gtcggtaaag aaagaaaaga aagccaggcg tcttgtggta cacaggtagt   32580
cccagtgaac aacctttcca cagaggttac ctaagaccat tgaaaaacac aggttttttac   32640 attatgattc ataatagtag caaaattaca gttatgaagt agcagtgaaa ataatttttat   32700 ggctggggggg tcatcacaac atgaggaact atattaaagg gtggcagcat taagaagagt   32760
gagaaccaat gccctagagg gaacacccta gtccacagag tgattgtttt ctgttccttg   32820
tctagcatcc ccagcctgaa agtgtcccca gctgctctag ggttccatct atctttagga   32880
accacaccca tttatttggg ctgtgctctt cagtttcaga tggctcagtc gctaaagaaa   32940
```

| | |
|---|---|
| aaaaaaaaaa aagaaagcca ggcgcttgtg gtacacaggt agtcccagtg ctggtgaggt | 33000 |
| ggcaagagca aactcctggc tggttaacta gcctagcctt cttggcaagt tcttagaaga | 33060 |
| accctgtctc ataaaggaag atggatcgtg ccagagagtg gtggcacaca cctttaaccc | 33120 |
| cagcactcgg gaggcagagg caggtgtttc tctgagtttg aggccagcct ggtctacaaa | 33180 |
| gtgagttcca gtacaaccag ggctacacag agaaaccctg tctcaaaaaa tgacacaata | 33240 |
| acaacagtaa caaaagagg gacagtgcta cagagcaatg catagggagg cggttctttg | 33300 |
| gcttccatac acacagacac actcgtgtgc acacacacac aagcttgcac actcatgcaa | 33360 |
| cctgagggct gggtaatgta tgaaggaaag gtctttctgc ctcagcttct ccagtagctg | 33420 |
| ggactgcagg tttgagtcac aacatccagc ctccatattt cttttaccag ggatctgaag | 33480 |
| tatccagggt tggaggacta catttaattt tttaaaattt caaatatttt gctcttttta | 33540 |
| tttatttata tttattttta aaaattggag actagagaga tgactcaaca gttaaatgct | 33600 |
| ggctgctctt ccagaggacc tgtgtttgat tcccagtacc cacacagtgg cttacaaatg | 33660 |
| tctgtaactt cagttcctat agatgtttga cgtcttctgg tctcccacca ggcatgcatg | 33720 |
| acaggagtgt gccaccgtga cagctgtagt ttgttaattt aaaaatttgc attcacttat | 33780 |
| tatttattta ttttgtgtgt gggccgtgtg agctacatta tgggggaggg aggtcagaga | 33840 |
| acaactgtgg gcgttattct ctttccactg tgtgaattcc agagatcaaa ctcaggtcat | 33900 |
| tgggcttggt gacaagttat ctcttgtttt gataatttaa ataaaaatat ccttttctct | 33960 |
| ttaaaaaaat attaatttgt ttttttttt gagacaggat ttctctgtgt agccttggct | 34020 |
| gcccaggaac tcactctgta gaccaagctg gcctcgaact cagaaatccg cctgcctctg | 34080 |
| cctcccaagt gctgggatta aaggcgtgcg ccaccaccac ccggcttaga tctacctatt | 34140 |
| tctgtctctt gagtcctggg attaaagatg tcccccactg ccacccagct aaatatttat | 34200 |
| ttttgtgtat atgtgtacac attggtgtgt gtgccatggc aatgtgtgga gaagcacatt | 34260 |
| taatctgcaa gtacgtttac ctgctgagca ctctccccaa ctctgtttta tttttttgag | 34320 |
| acagcaggtt gcttttggtc tcctacacct gatacagctt tatcagcagc actggtggga | 34380 |
| atgcccaccc ttttttgtta ctgccttcc cacagcaaat gagaggtgag cgcctgtatc | 34440 |
| tgtgtccctc caggtagagg agccgggcat gggtgcagag gagcctgagg actgtcgcca | 34500 |
| gtggacccaa caccacctgg ttgctgctga tatccgtgtg gcaccagcca cagcgctgac | 34560 |
| tcctcctcag ggagatgcag atgcagacgg agtggatgtc aacgtccgag ggcctggtga | 34620 |
| gtgccctccc aaagaggccc tcattggtcc tacctgctgg atcccatgca ggggttctgg | 34680 |
| gagcgtctgg gcctctgggc ctctgggcct ctgggcctct gggcctgctg cgtgtgttgt | 34740 |
| attctaagtg attggaacgc catgcaaggt gaagcagaag gtgggctggc tgcaactgag | 34800 |
| aaccctgagg ctgtgtggac cctggactct ttcttttatg agattaaaat ttccttcttt | 34860 |
| tcttttcttt tcttttcttt tcttttcttt tctttatttt tcttttcttt ttttctttat | 34920 |
| tttttctttt ttttgttttt ctttttttag atttatttat tattatatct aagtacactg | 34980 |
| ttgctctcct cagacacacc agaagagggt gtcagatctc attatgagtg gttgtgagcc | 35040 |
| accatgtggt tgctgggatt tgaactcagg accttcagaa gagcagtcag tgcccttacc | 35100 |
| agctgagcca tctcaccagc cctctctttt tgttttcaa gacagggttc tctgtgtagc | 35160 |
| cctggctgtc ctggaactca ctctgtaaac caagctggcc tctgaactct gagatccacc | 35220 |
| tgcctctgcc tcttgagtgc tggggttgaa ggtgtttgct cccccaaccc cagctctttc | 35280 |
| ttcctgtgta gccctggctg tcctggaact tactctgtag accaggctgg ctccaaaccc | 35340 |

```
atagagctcc acttacctca tcctcccgag tactgggatt aaaggcttgt tccagcacca    35400
ccactgcctg gctcttgctc ttgctctttc tctctttctc tctttctctc tttctctctt    35460
tctctctttc tttctctttc tctttctttc cctttctttc tctctctctc tctctttctc    35520
cttcttcttc ctcctcctct gcctcctctt cctcttccct ctcctcttct tcctcttcct    35580
cttcctcctc ctctttcttg ttatactttt atataagatt tcactatata gctctggcta    35640
tcctggaact cataatgtag atcaagttgt tgtgaagtca cagagatcct cctgcctctg    35700
tcccccaagt gctggaatta aatgtgtatg ccatcatatc cagctgggat ttatttaaaa    35760
atcacactta tttgtgtgta ttcgtgtact cggaagtcag aggacacctt actggagttg    35820
attatctcct atctcggtcc aagagatctc attcacgctg tccagtttct ctgtagcttc    35880
tctatccatc aagctcctgg atgttcaatc cctccttacc cctctagccc ccttagcttc    35940
agccatacag cttgtcagga gagtctcgga ttagttctga cagggtgaac tagaaccacg    36000
tacttattcc tgggccaatg aatgtggcta gggcctataa tatgcagata agccagtccc    36060
catctggtct aagtagggct tgctattagg gaattcgtga ggagaactag ggaaaaggtg    36120
gttcccttcc cctttattcc aagtgctcgg cttcctggaa tcgcttttgc ggtccatcat    36180
gtaatcttcg tggggtggct ttgcagttgg gagaatttac ctctgtctgt ggcgctgtgt    36240
gtcacagtgc ccctgacatt tgccccagga agacccctat gcctgtgaca cactactggt    36300
tcctgcagat ggcttcaccc cactcatgct ggcctccttc tgtgggggag ccctggagcc    36360
gatgccagct gaggaggatg aggcggatga cacatcagcc agcattatct cagatctgat    36420
ctgtcaaggg gcccagctcg gggcacggac tgaccgcact ggcgagaccg ccctgcattt    36480
ggctgcccgc tatgctagag cggatgcagc caagcgtctc ctggatgctg gggcggacac    36540
caacgcccag gatcattcgg gccgcacccc cctgcacacc gcagtgacag ctgatgccca    36600
gggtgtcttc caggtgagac aggcctgtct cttcagactg cagagctgct gggaggggat    36660
cagacacacc tagattggag ccccggtctg tcttgcaagg cttttgtcat ttggaaatag    36720
gaataggtag tatctcacct agatttcccg ccggcccccc cccccccccc ccaggacagg    36780
gtttctgtat agtcctggct gtgctagaac tcactccaat aaaccaggct ggcctcgaac    36840
tcagaaagat ccacttgcct ctgcctctgg agtgctagga ttaaaggcat gcaccactaa    36900
cactggatag aattttttc ttttttaatt ttattaatat atgtaagtac actgtagctg    36960
tcttcagaca ctccagaaga gggagtcaga acttgttgca gatggttgta agccaccatg    37020
tggttgctgg gatttgaact ctggaccttc ggaagagcag tcgggtgctc ttacccactg    37080
agccatctca ccagccctgg atagaatttt ttaaaaagta tcattaaaat tacatttatt    37140
tggtgtgtgt gtgtatgtta tgctgattgg tttgtgtttg tttgtgtggc atatgtgtac    37200
ctgggtatgt acattgccca gcttgctgaa gctagaggag gctgttgatt gttctgctct    37260
atcgtgctcc acccaatctt ttgagacaga gcccatcagc gagcctggag ttgagctggt    37320
gtccagaaag ctctcttgat cctcttgtct tcttccccac agccctgggg cacacatgac    37380
caagactggc tttttaggtg gactttgggc tctgacgtca ggtgcttgtc ccctgagcca    37440
tctccctgtc cttccatatc atactgttac ttaaatccat tttgaatgag catatttttt    37500
gatttataat gtgcttagca ggaatagcac ctcatttaa gtcaggagat atctgtagct    37560
cctgggttcc aaagctgtgg catttggggt tcagggtgtg gtatactcct cccttggcat    37620
aatgtcctgc catggctttt gtcgtcgtta gattctcatc aggaaccgct ccactgacct    37680
```

```
ggatgcccga atggcagatg gctctactgc actgatcctg gcagcccgcc tggcagtgga   37740
gggcatggtg gaagagctca tcgccagcca tgccgatgtc aatgcagtgg atgagcttgg   37800
taagtgctgc ggaggggatg gggaggggct gtggtgccac tgccctctta atgtgaagtc   37860
acacctacgt tgacagcaag gtgtgcacgc cagggctccc aaacggatgg aacaggaccc   37920
acagagtgtt ctggttcaga aaagatgtag actcccttct cctcccctcc cttcccttTt   37980
tcttccactc ccttccTTtc ccctccccca tctcctagac cccatccccc actTtcacat   38040
tatgatactc ctcttcctcc ccttcctccc gggcttcctt ctagagtcca aatcgttgat   38100
caaacccaaa gtgcttgtct ttgagtctga cttatTtcac ttactgtgat gatctccagt   38160
tctattcatt tcttgaagat tgtTtaatTt ggctccccCg actTttgaga cagggtctca   38220
tgcaagctag gctcgcctcc aacttactgt gtagtcaacg accttgaaat ctggaccctc   38280
ctgcctctgt tcccaagtt aggcattcgt catcacatcc agcccaatTt ctttcttTgt   38340
tttggttgag tagcattctg ttgtatgcag tgtgggtggg cacctaggct gagcaactcc   38400
attgtatgca gtgtgggtgg gcacttaggc tgactccata gtgtaccggc ttcgaatagc   38460
aatgtggatg ccacagttcg catgggcatg cagacatctc ttattgtatg ctgactcagc   38520
cctcaagtat agacccaggg gcacaggagt gccatacctg aacctagggt agttcttttt   38580
tttttttTtt aagaattatt tattTattat atgcaagtac actgtagctg tcttcacaca   38640
ctctagaaga gcgcgtcaga tctcattacg gatggttgtg agccatcatg tggttgctag   38700
gatTtgaact caggaccttt ggaagagcag ttactgctct taaccactga gccatctctc   38760
cagcccccta gggtagttct acattTagtt ttTtgaggac cctccatagc atTctctata   38820
cTtactactT agcatactTa gtTactTtat cattaatagg gcatgaagat cccttTctct   38880
agtgtttgta ttcttTctTt ctTtTtccct tttTtggctg ttTtcatgat tgaagccatt   38940
ctggtagcat ctaagtacag ttttTgtctg ttTttatTtt tTtgtTttgt tTtgtTttca   39000
gacagggtta ctctgtgtag ccctggctgg ccatggaact cacactgtag accaggctgg   39060
ccTtgaactc agaaatctgc ctgcctctgc ctcctgagtg ctgggatcaa aggccgggat   39120
caccaccacg cccggctgag accctctttt tctgccaggc acagaaaggc caccttTtgc   39180
cttcctgccc agctataggc tattcagctc ttTatTtaac caatcaggag acgatggaga   39240
acatTgtttt acaaaatacc aagtTagacc aaagtctgga ctgtaaccag atctctggga   39300
acagaaatca gcatctgaat acacagtgca caaaccacc ccccaacggg acttcatcgc   39360
caactggggg taaacgctca tgctTtgccc acactgacca agcacacgag cttgcttctt   39420
agtgtgctgt ctagatgctt tgttaaggaa acggactctc ctgctacctg ctagacagtg   39480
ggataaactt gcatgtggtg atctgtgggg gcagctgcct ggtagtggcc tgcttggctt   39540
gggtatgtca tgagcaaggg tcacagcaag ggttcttgta ttcacaggcc gcacagctgt   39600
agacactcta agacacttac acacatTtgt ttgacgtacc cttggttctc aacttcatca   39660
gcatTgacat ctatggtTgg gtaatTctTg gtctgcgtgt tggatgaagg tctgggctgt   39720
gcactccggc ctgtggggca gcatcccacc aggagcatcc catctctaca atgtTactga   39780
gtatagtggg ctTcttccct gggtgggcct tgtTtcaac aacaaaagga tttagaaatg   39840
gtctcagaag gaagctcaaa cacagtTaga ctagagtTtg atagcaaagc aacagatcaa   39900
gcaagctgtc agtctctctg gaatagagag atggagaaga tgcattcatg tctTttgagc   39960
tgtggctgga aagccgcagc ctggtgggag ctggggagga ggtgagcttc cgaggacaag   40020
tgcgagctca tgtcctggct ttagccagga tctgaaagaa aaggaattga gaagaaagaa   40080
```

```
aaggggtgcg gtggccaatg catttgctat gccagggcga agacctgagt ttggatcttc    40140
agaaacctat gtaaatgcta agtgggtgtg atggccacct gtaattccag acacacacac    40200
acacacacac acacacacac acacataccc catgtataca cagaaaaaga aaaaaatatt    40260
cagaaaagct ggcagggtgc ataatggtgg ctccaatgtg ctgcctgcct gatggatgtc    40320
ctgcaagtag ctgctttgag ggagaggctc ctaggaaggg aaaatacaat atgtcattaa    40380
ggggataatt agtccttccc tgtcaatagc atgtctttag gtgactcaga gttttttggcg   40440 ggacaaaggc agactcttgg acagataatt gacagactct attgggatac ctttaaaaat    40500
agtctattta tgtttacttt atgtgtaggg tgtttcgcct gcatgtatgt ctgtgcaccc    40560
cgtgcatgca gtgcccacac aggccagaag aggagagggc atcagatcct ctggaactgg    40620
agttacagac cgttgtgaac tgttatgtgg gtgctgggaa ctgaacctgg gtcttctaga    40680
agatcagcca gtactcttaa ccactgaacc atctcccagc tccccgaatt aactcttaaa    40740
aggagacagt cataagtagc atgttgggtt ccaccaagga ttggaactag aactcagatt    40800
ctatttaaga agcagctttg cattaagtgg gcctcaacaa actcagacac tcccagcttt    40860
ttatggcaag ttgatgtctc tcctaagtag tcttagtcct gtaagactac tgtaacaggc    40920
aaatgacctg gggtgggg tggggggagg gcagtcattc atggttgata ttagctaact     40980 tttaaaggc aacaatagag gggccaaagg tagagagaaa aagacttgat tgtggatgcc     41040
aaaatgccta caggggaaga tgggatgtgc ctcttataag ggaggactcc tgtagtccac    41100
aaggaaagct gggaagtgta gtccttcagc aggaaactcg gtcccaattc tgagaggata    41160
ttaaaaagac gcagggcagg atgtcatagc ttttctttt ctttccccgg aggagagtct     41220
ttatcagagg ggttagttct gggtccagta aagggaaact ctctggccat gttgtatgct    41280
agagtcttga ttagctgtga tggatcaggc cattgtcatt ccgcattcct gaggagagct    41340
gggaaaatat ttattagaag gccacaagca gatgatttgg ttatagagta gagctgagag    41400
atttctgggg aaggttgagg gaggggagg agcaggagcc taggcagaag agacaagagt     41460
gagacaaagt gggcagaggc tggtcccagg gtgacagtga ctggtcccat tgccaggact    41520
gctagaaaaa tgagctagca gaagcagcag agggctacaa agcagcagag gacgggaaga    41580
ggggtcaata aagggttaat gtgaagaact gtatctggcc tgtggtggaa gagatcacgg    41640
tcccttttct attcagcacc taaacaattg ttgtttaggt gctgaataga aattgttgtt    41700
gtttctcaga tgtgtcagga acaaatggag ctgttgtggg atgagagcca ctgagagagc    41760
tcgaatggga aattctgcgt gggttcagta agcaaaacat ttaaagacac ggtaaaaatg    41820
taggtattaa gataaagaag ggagaaagcg tgaggcaggg gaagagacag agtgggggga    41880
agccaggagg aactttgtc tggtccctgt gcctttaggc cccatttcaa accaggcagc      41940
atttgttggc gtggtagcag ccctgatcaa ggagggcagc agtcagagct agtccttttg    42000
agttgtagag taccgcgtcc gtcaaggagt tgacctgctc ctagagggtg tcacgctgat    42060
ctgagctggt gacacagagt tcactgatgc agcgaaggct tcagcccagc tgtgacacag    42120
agaagttcac tgaaggtgtc agtccagctg tttcagtcca gagtggcaag aagagggtg     42180 gcttggctca ttcatggtcc atcatcccct cttagatgtc gtccaaactg ctcttagggg    42240
cctggggtgt tggtctccct gtgacttctt taaggctggc agaagtggga cgaggggagc    42300
agccgtcaga gtgcctcaga agagggtcca tccaagggga catgatagaa cttaagagtt    42360
ggcaaagatc cagaacataa gtcccagggt gataacacac agctgaatgg agacaaagtt    42420
```

-continued

| | | | | | |
|---|---|---|---|---|---|
| acagaaggaa | aactttgaca | accagttgaa | tacaactgga | caactgactg | caccagaagg | 42480 |
| atacggtagc | tgtaagtagc | tctttgtgtg | cattagaatc | ctgccagcta | agaatgactg | 42540 |
| tggctcagtg | ctggacacta | gagctttctc | tgaggattgg | aaggaatatt | tgttggccca | 42600 |
| gtctgttttg | gctgctactg | gcctcttgtg | gctgatggcc | acttgaaaac | tggcttggac | 42660 |
| caatgaagag | ctgttttctt | tagttcatcc | aatgtttaca | atattgggcc | agggatatag | 42720 |
| ctcagttggt | gaagtaatcc | tgctaggtcc | attctctact | accacataaa | atcaggcgtg | 42780 |
| ttaatcttag | gcaggcccag | gatcccaggg | ctcaggaccc | atctgcagcc | aggaggatca | 42840 |
| gaagttcgtc | ttcaggtgca | cagtgagtta | caggccagcc | taggatactt | gagtccttgt | 42900 |
| gtttgttttg | tttttaacta | tttaaaaaaa | tatttatttt | atgtgtatga | gtataccata | 42960 |
| gctgtcctca | aacacaccag | aagagggcat | tacagatgtt | tgtgagccac | catgtggttc | 43020 |
| ctgggaattg | aactcaggac | ctctggcaga | ggataacctt | ttaaccgctg | agccatttct | 43080 |
| ccagcccctg | agaccttgtc | tcaacaacaa | caacaacaac | aacaacaaca | acaacaacaa | 43140 |
| cagttaaacg | cacatagtgt | tcttgcagag | gacctgacag | gggttcttac | cacctaagtt | 43200 |
| gggctcccca | caaccatctg | taactctagt | tccagggaat | ctgatgccct | cttctggacg | 43260 |
| ctgcagatac | ctgcacccat | atgcacctcc | cctgtgcaaa | cacacatata | cacataatta | 43320 |
| aaaactataa | aaataaatac | atcttaaaag | gaaaagccca | ccctgaacag | gcaatctaga | 43380 |
| atataaagac | tgaaatcata | tcgacaactg | cctaaagctt | gggatgggag | gagactgatc | 43440 |
| aatgatgagt | aattaaagtg | atggaaatgt | tgtaaaacct | gattaattgt | aaattatgac | 43500 |
| tcaacaaaaa | tatagtcttg | tatatataca | agaaaagata | ttaaaaacaa | aaattttgag | 43560 |
| acatcgtctt | agcgttaact | gtcaacttga | catagcctag | agtctctgag | aagtgtgtct | 43620 |
| cggatcagtg | tgattgtctt | gattgttaac | tgatatagga | gggttcagcc | cactgtgggc | 43680 |
| agcagtgttc | tgggccgtgt | gatcctgagc | tatacaggaa | ggttagctaa | ggatgaacct | 43740 |
| gcaagtgagc | tggcggcacc | accatcctgc | acggtttctg | ctgtgctttg | gctgggaagt | 43800 |
| gagctcctta | gttggagcta | atgctgtcaa | acctgccttc | aggttattgc | cttacttcac | 43860 |
| tcagtgatgg | attgtgatct | aagagtgcaa | gccaaatagg | tcccaagtgc | tgtgtgtgcc | 43920 |
| accacaacgg | aggtgctagg | gattaaaccc | acacctccgt | gcatgccagg | caagcacgct | 43980 |
| actgacttat | cgacaagccc | agcacatgtt | ctaaatattc | tatattttaa | aaagctttat | 44040 |
| tatataaaaa | accatgcaag | taaatgaaag | taccacatat | catgctggag | acatggctca | 44100 |
| gtagttaaga | gcactaactg | ctcttagaga | ggacctgagt | tcaggtccca | gcatacacag | 44160 |
| agtggtttat | aacttcctgt | agctccagat | ccagaaagac | atgatgtccc | ctctggcctc | 44220 |
| cttgggcact | acagtcacat | gcacataccc | ccacacgtac | atataaataa | taaagaaaaa | 44280 |
| aattttaagg | gttggagaga | tggctcagca | gttaagaata | ctgtctgctc | ttccagaggt | 44340 |
| cctgagttca | atccctagga | accacatggt | ggctcacagc | catctgtaat | gggatctgat | 44400 |
| gccctcttct | ggcacgcagg | tgtacatgca | gatagagcac | tcatatataa | aataaatatt | 44460 |
| ttaaaaaatc | atatatccaa | attaaccaga | cccaaagtct | atataacgta | ataaatttat | 44520 |
| atacagttag | aattggcctt | ctggcagaag | ctatgaaact | tcacattaaa | ttttatattt | 44580 |
| ttagtactga | acaaatttta | gattcttttt | tttttttttc | tttttctttt | tgttttttc | 44640 |
| gagacagagt | ttctctgtgt | agccctggct | gtcgtggaac | acactttgta | gaccaggctg | 44700 |
| gcctcgaact | cagaaatccg | cctgcctctg | cctcccgagt | gctgggatta | aaggcgtgtg | 44760 |
| ccaccacgcc | cggctatttt | aggttcttag | gttcttatcc | accaccaacc | ccaaaagacc | 44820 |

```
atggcaaatc agaactagaa cacctaagtt tttgtcgtca ttcacaaatg cctcgtgcct   44880
gcacttagtc tttcctcctc ccatacattt agcctttctt gttctcttct ctctgtgttg   44940
tgctgtaccc acatgaacat gtgtggcttt agcttgcatt tccctcatgg gaaatgaacc   45000
tggctaactt ttcacctgat cattggtcgt acgtagatct tccttgagga ataattatt    45060 tggaatttat tttggtggtg ctggagatca aacgcaggct cttctagatg ctactcagcg   45120
ttccagggct cagctgcaca cctaagcacc gagattatca tttctcactg ttattagact   45180
tcatatatat gttagaattg tatatgtgag ccggcagtgg tgacgcacgc ctttaatccc   45240
agcacttggg aggcagaggc aggtggattt ctgagttcaa ggccagcttg gtctacagag   45300
tgagttccag gatagccagg actgcacaga gaaaccctgt ctcgaaaaac caattaaaaa   45360
aaaaagaatt gtgtgtgtgt gtgtgtgtgt gtgtgtgtgt gtgtgtgtgt gtgtgtacac   45420
atacacagat cccattacag atggttgtga gccaccatgt ggttgctggg atttgaactc   45480
aggacctctg gaagagcagt cagtgctctt aactgctgag ccacctctct agtccttgcc   45540
aggccatttt ctacacattt ctgcctgttc tgtaatggag aacctgacat gagcctgaca   45600
ctgatgttta tctccttaca gggaaatctg ccttacactg ggctgcagct gtgaacaacg   45660
tggaggctac cttggctctg ctgaaaaatg gagccaacaa ggacatgcag acagcaagg    45720 tgagccactg ggggcctaca gtgctacagc ccctgaatgt gacaaagcag agtcagggag   45780
gaataagcct gttaggggca tccatcttgc ttgcagtcag ctctcaggag tgggattctg   45840
gcctgaaggc tgtgagagca aactgttgaa gtcgctgtgt gacatcgaac gcagttgtcc   45900
ccattgtgac aggggaagca gcagcatgag ctgctgagct tgaacaagcc tactttctct   45960
ccttccttct ttctttcttt ttgagactaa cttcctacct caggttggcc ttgaactcac   46020
aattctcata tttctactaa ctaaatgctg gtatatgctc tcatgcctgg cttttcttt    46080 tttcaatgat atatttatt tttaaatagt gtgtgcgtgt aagtatgtgg acatgagttg    46140
cagatatcct tgaagcaaga agagggtgtt gaatccccct agagctgaat ctataggcag   46200
ttgtgaactg cccgtgtgga taccagggat ggcactgaag tcaccaggct gagtgacaag   46260
tgtggttacc cactgtgccg tcttgccgtc ttgccagtct ttacattgtt tccttctctt   46320
ttggagatca tgtcttactg gttaatttag caaaagctga cctcaaactc ttggtgagtc   46380
ttctgcctta gcctctcaag tgctggggtc ataggctcag gttctctctc tgtctgtctc   46440
catctctgtc tttccctccc ttccttcctt ccttcctcc ttccttcctt ccttccttcc    46500
ttccttcctt ctttctttct ttctttcttt ctttctttct ttctttcttt ctttctttct   46560
ttctttcttt ctttctttct aagacaagga ctcactttgt agaccaggct agcctagaac   46620
tcagagaccc ttttgccttt gtgtcctgga tggtaggact gaaggtgtac aggaccacca   46680 gaacccaac aactcacttt ttaatctttt gttttttgg ttttttcaaga tagggtttct    46740 ctgtatagtc ctggctgtcc tggacctcac tttgtagacc aggacaaaga aactggtaga   46800
actcagaaat ctgcctgcct ctgcctcccg agtgctggga ttaaaggcgt gcttttaat    46860 cttttataac tcttttaaa acttttataa catcaccatg cagtttattt tgatgactgg    46920
aagttttgat gcccctttaa attttgtgcc taaggtaagt cctggccaga tgtgcctgct   46980
acagagagag cttgtttctt caacagagct ggaatccaaa ctcaggtcca tctatttcca   47040
gggtatcaac tcttagttct caggctgccc tagagattag aaagctaggt gttggccaga   47100
gtgactgacc tccgtgggtt ctgccctcc cccgcctcag gaagagacgc cgctgttctt    47160
```

```
ggccgctcgg gagggcagct atgaggctgc caagctgctg ctggatcatc tcgccaaccg   47220
ggagatcaca gatcacttgg acaggctgcc ccgggacgtg gcccaggagc ggctgcacca   47280
ggacattgtg cggttgctgg accagcccag tggacctcga agtccctctg gtccccatgg   47340
cttagggcca ttgctctgcc caccaggggc cttccttcct ggcctcaaag cggtgcagtc   47400
tgggaccaag aagagcagga ggccacctgg caagaccggg ctggggccac agggaactcg   47460 tggtcgggc aagaagctga cactagcctg tccaggacct ctggcagaca gctctgtcac   47520
actgtcaccg gtggactctc tggactcacc acggcctttc agtgggcccc ctgcttcccc   47580
tggaggcttc cccttggagg gcccctatgc caccacggcc accgcggtgt ccttggcaca   47640
gctaggcgca agtagggcgg gtcctctggg cgccagcct cctgggggct gtgtgctcag    47700
ctttggtctg ctcaatcctg tagctgttcc cctcgactgg gccaggctgc ctccacctgc   47760
ccctccaggg ccctcattcc tgctgcccct ggctccggga ccccagttgc tcaacccagg   47820
agccccagtt tctccccaag agcggccccc accctacctg gctgctccag gacatggaga   47880
ggaatatcct gcagcaggaa cccgcagtag ccccaccaag gcccgcttcc tgcgggttcc   47940
cagcgagcat ccttatttga ccccgtctcc tgagtcccca gagcactggg ccagcccatc   48000
ccccccatcc ctctcagact ggtctgactc aacacctagc ccagcaactg ctaccaatgc   48060
cacagcctct ggagccctgc ctgctcagcc acaccccata tctgttccct ccctccctca   48120
gtcccagact cagctgggac cccaaccaga agttacccc aagaggcagg tgatggccta   48180
agttcttgga tttgagggt gctgaagtga cactcctcta tgacttcttt cttcctcctt    48240
tttaatctta ctctcatccc tttctctctg tcccagcctt cctgcacctc tctgtcttgt   48300
agtgtgacca agttggtcac cagcccagac ccccagtctt cctttattta taatgggtag   48360
gggctgacct tccaccacct tggcccccta agggatctgg gacctccttt tgatccctct   48420
ccctgcctca acttcctccc cccctctttt ctgcttctca ttgtctcaca ctctgacaag   48480
agtgagttat tattttttc ttttttacat tttgtataga acaaaattca tttaaacaaa     48540
cttattatta ttattattt ttacaaaata tatatggaa gttgctccct tcccccgct       48600 gcaaattcct ccagcgcccc cgtggggctg agtctgtggg cccgttttggc caatccggac   48660 tctgtgtact gagtacacag atatgactag ggctccacgt actgagtatg tggccctcgt   48720
atgtaccaag tagccagcct tgggcacacc ctccctggg gtcagggac atttgggagc     48780 ctccttcccc tccccattcc ccttcctcac ttcactgcat tccagataag acgtgtagac   48840
tcactgggaa aggggtcttg tctgctcaaa gcctcaactc caggctcacc tcccagagcc   48900
tggctcacct tttagggcct ggggtggggg ggcacgtcag gggagatgta ttttgtatgc   48960
attccacttc taattgtaaa tacagggcag aaggtgggag tggctctccc tcttcctgtt   49020
gttctcttgg ctcagcctgc ctaatagaaa tgttttttagg ctgttttttgt aatatggcac  49080 ctggtcacag tcctttgtag ctgaattccc aggtcctgca ctgtacaacc ctcaccttct   49140
cagttccctt accacctaat aaaggaatag ttaatacca agtgtctggt ttctgtgcaa    49200
ggtccaaagt gggggtttct gggcctcttc ctccacaggg ctaacttgaa ctcccatctt   49260
ggggcagagc catgtgcttt gtcagtccac ctttgactcc ttttggtca ggtatctagc    49320 ttcatttctg ttgctttaag caaataccta acagaaaaga aacttaaggg acagagggac   49380
tttttcctaa ctaaatattc caggttacag tccaacattg tgaagaagag gcaggaactt   49440
aaaatagttc accacatcac accacagtca agagcagaga gaaagaagtg agtggatgca   49500
tgcttgcttc cttgtgtcgg gctgaatcat tacactctta aacagtttag aaacccttgt    49560
```

-continued

```
ttggggaatg atgccaccca cagtaggcag tgtcttccca cattaatttg acttaattac   49620
gacaatctcc taaagacatt ctttcaggtc aactcgatgt agacaacttc tgttcccagg   49680
tgatttgtaa gttctgtcat tgtgacaaaa ctgatcatca tatcaggtgg tttcaattt    49740 tgaatcttgg gttggaacca ataaagggac tcaaaacaaa aacaggcaaa caaaccaaaa   49800
ggaaaaaaaa aaaacctaca aaactcaata gtgttatttt gagaacttac ttttttcttt   49860
aaaaatttta ttattattat tatcattgtt gttgtttttt tttgtttgtt tgttttttga   49920
gacagggttt ctctgtgtag ccttagttgt cctggaactc acaaaagaaa acacacaaaa   49980
taacaccaaa cccagtacac aggaagcagg cctggctcac ctgcagaact gcccgaacaa   50040
ggcaagacag cctatgggac agcaaaacag ggcacaaaga atgagagccc aggagagaga   50100
gcaacagaca gaagagacaa acccctaggc gccaccagag aatgattgcc ctggagggga   50160
gaaggtggag tactgggtgc tgggaacacg ccacacacac acactctgtg tgctggtgtt   50220
tgctttgtgc taagccactg agctcaagtg cttgcggttt gcatccagaa actcatccag   50280
ttgagccagt attaccccca gagcaatgtg atggaaatca gcagtggttt gaatccagaa   50340
atataaaaac ggcacttttt ttgctcacct atctattcta gacttctgtg cactgatata   50400
ggttccaggg tctcaaatcc cttaaaattc taatcaactg tgatgggcca ggctggaagc   50460
agcgatgaca cgcgtcctgg aaaccctgcc aagctgtcct gtaccgctgc ttctgcgtgt   50520
gttgataatt aatccttcgg agcgggcgca cgaatgtgag aaattggcta ttttccgctt   50580
ctgaatgatg gctctgagcc actacggcag cttttccatt tcaaatctga ctgtcaaaag   50640
tggtgcatta atcagtattt cgttagtttc aacatttcca gaatccgcct ccccaagtgc   50700
acatacaaag tgcagccatc ctcagccgag aaggcaaggg cggggccttg cttcaggtga   50760
cgactctttc tttctctttg caccactcca tcctctgaga ggctatggct gtgactccgg   50820
agctcacttc cctgcaaagt agtggctctt ggctgagtac ttccaacagg agacagaac   50880 aggaccggag ggtggcagac ggtgcctcta tccaatggcc ccctgggtga cttccccaga   50940
agcactttat tattattatt attattatta ttattattat tattattatt attattggtg   51000
tggttagttg ttttgagaca ggattgctct ttgtagccca ggctggccgt gaactcagaa   51060
gtccacctgc ctctgcatct ggtgtgctga ttctgatgtc accaccagat gtgagcctcc   51120
accatcagac tcacatccac tacagacgac ctgaatgtct cagccaagct gtatactaga   51180
gaaagtggct actgttacaa aactcagtgg agacacagct ctagcagatg taggtctggc   51240
tgaccacata agcactgact agtgctggag acacactggt actgagcgac agctgtgctg   51300
agaaccatat ctggctgagg tgctgcttgg gtcaacctct cagagtgtcc agcaggaggc   51360
agggcttcca gacctactga tggatgagtc tggggggctgg gcaaactgga cagcattatt   51420
ctgtggagaa gccttagact gtcccccaaa gtaaaagcac cccaaccagc ctgttatact   51480
tcctccctcc cactgtcagg gccaccaacg cccaagagtg caaaaggcac ccaggaaaga   51540
gaaagttaaa aaaacaaggg aaggttgatt ttcctacttc ctgctgcccc taactgccag   51600
acgaggcttc tcccctgcc cctcaagcaa ccctcagact ccgcccatgt ccgtgccccg   51660 cccctcctc tccaacagtg acgcgtgctg tgctggcatg gctgccggtg ggcaggtgat   51720
gcacatccca ggaacatttt gcccgcccca actgcttcat caccaagcct ccagcaaaga   51780
ggctcaggca gcctgaagcc tcgctgcctg gcatagcgca tttagagtaa cagctcagct   51840
aatctcttcc aagggaggca gagctgctca gcacagcagg agtggggcga gctctggaat   51900
```

```
attccagtgt ggttctccca caggcatcta gggacagaga ggagtgtggg ggtgggggac    51960
aagctgagcc tcacaggtgt tcctaggctg atgcttaagt                          52000

<210> SEQ ID NO 8
<211> LENGTH: 7943
<212> TYPE: DNA
<213> ORGANISM: Mus musculus

<400> SEQUENCE: 8
cgtgcccgga gccctgggaa agagggagga gggaggaggg agggtcgtgg ccggccgcca      60
tggggctggg ggcccgggc cgccgccgcc gtcgtcgcct gatggccttg ccaccgccac     120
caccgcccat gcgggcgctg cccctgctgc tgctgctagc ggggctgggg gctgcagcac     180
ccccttgtct ggatggaagc ccatgtgcaa atggaggtcg gtgcacccac cagcagccct     240
ccctggaggc tgcttgcctg tgcctgccag gctgggtggg tgagcggtgc cagctggaag     300
acccttgcca ctcaggccct tgtgctggcc gaggcgtttg ccagagttca gtggtggcgg     360
gcaccgcccg attctcctgt cgttgtctcc gtggcttcca aggcccagac tgctcccagc     420 cagaccctg cgtcagcagg ccctgtgttc atggtgcccc ctgctcagtg gggccggatg     480
gccgatttgc ctgtgcctgc ccacctggct accagggtca aagctgccaa agtgacatag     540
atgagtgccg atctggtaca acttgccgtc atggtggtac ctgtctcaat acacctggat     600
ccttccgctg ccagtgtcct cttggttata cagggctgct gtgtgagaac cccgtagtgc     660
cctgtgcccc ttccccgtgt cgtaatggtg gcacctgtag gcagagcagt gatgtcacat     720
atgactgtgc ttgccttcct ggcttcgagg gccagaactg tgaagtcaac gtggatgact     780
gtcctggaca tcggtgtctc aatggggaa cgtgtgtaga cggtgtcaat acttacaact     840
gccagtgccc tccggagtgg acaggccagt tctgtacaga agatgtggat gagtgtcagc     900
tgcagcccaa tgcctgccac aatggggta cctgcttcaa cctactgggt ggccacagct     960
gtgtatgtgt caatgctgg acgggtgaga gctgcagtca gaatatcgat gactgtgcta    1020
cagccgtgtg tttccatggg gccacctgcc atgaccgtgt ggcctctttc tactgtgcct    1080
gcccctatgg gaagacaggc ctcttgtgtc atctggatga tgcatgtgtc agcaacccct    1140
gccatgagga tgctatctgt gacacaaacc ctgtgagtgg ccgggccatc tgcacctgcc    1200
cacctggctt cactgagggg gcatgtgacc aggatgtgga tgagtgctcg attggtgcca    1260 accctgtga acatttgggt cggtgtgtga atacacaggg ctcattcttg tgccaatgtg    1320
gccgtggcta tactgaccct cgctgtgaga ctgatgtcaa tgagtgtctc tccgggccct    1380
gccgcaacca ggccacgtgt cttgaccgaa ttggccagtt tacttgcatc tgcatggcag    1440
gcttcacagg gacctactgt gaggtggaca tcgacgaatg tcagagcagc catgtgtca    1500 atggtggtgt ctgcaaggac agagtcaatg gcttcagctg cacctgccca tcaggattca    1560
gtgggtccat gtgtcagctg gatgtggatg agtgtcaag cactccctgc cggaatggtg    1620
ccaagtgtgt ggaccagcct gacggctatg agtgtcgctg tgcagagggc tttgagggca    1680
ctttgtgtga gcgaaacgtg gatgactgct ctccggatcc ctgccaccac gggcgctgtg    1740
tcgatggcat tgctagcttc tcgtgtgctt gtgcccagg ctatacgggc atacgctgtg    1800
agagccaggt ggatgagtgc cgcagccagc cctgtcgata tgggggcaaa tgtctagact    1860
tggtggacaa gtacctctgc cgttgtcctc ccggaaccac aggtgtgaac tgtgaagtca    1920
acattgatga ctgtgccagt aaccctgta cctttgagagt ttgccgtgat ggcatcaacc    1980
gttatgactg tgtctgtcag cctggattca caggggcccct ctgcaacgtg gagatcaatg    2040
```

```
agtgtgcatc cagcccatgt ggagagggtg gctcctgtgt ggatgggaa  aatggcttcc   2100 actgcctctg tccacctggc tccctgcctc cactttgcct acctgcgaac catccctgtg   2160
cccacaagcc ctgtagtcat ggagtctgcc atgatgcacc aggcgggttc cgctgtgttt   2220
gtgagcccgg gtggagtggc cctcgctgta gccagagcct ggctccagat gcctgtgagt   2280
cccagccctg ccaggctggt ggacctgcca ccagtgatgg aataggcttt cgctgcacct   2340
gtgcccctgg attccagggc catcagtgtg aggtgctgtc ccctgtact  ccaagcctct   2400 gtgagcacgg aggccactgt gagtctgacc ctgaccggct gactgtctgt tcctgtcccc   2460
caggctggca aggcccacga tgccagcagg atgtggatga atgtgccggt gcctcaccct   2520
gcggccccca tggtacctgc accaacctgc cagggaattt caggtgcatc tgccacaggg   2580
gatacactgg cccccttctgt gatcaagaca ttgacgactg taccccaac  ccgtgcctcc   2640 atggtggctc ctgccaggat ggcgtgggct ccttttcctg ttcttgcctc gacggctttg   2700
ctggtcctcg ctgtgcccga gatgtggacg aatgtctgag cagcccctgt ggccctggca   2760
cctgtactga tcacgtggcc tccttcacct gtgcctgtcc acctggttat ggaggcttcc   2820
actgtgagat tgacttgccg gactgcagcc ccagttcctg cttcaatgga gggacctgtg   2880
tggatggcgt gagctccttc agctgtctgt gtcgccccgg ctacacaggc acacactgcc   2940
aatacgaggc tgacccctgc ttttccggc  cctgtctgca cggggcatc  tgcaacccca   3000 cccacccagg atttgaatgc acctgccggg agggcttcac tgggagtcag tgtcagaacc   3060
cagtggactg tgtcagccag gcaccctgtc agaatggggg tcgctgtgtc cagactgggg   3120
cttactgcat ttgtccacct ggatggagtg gccgcctgtg cgacatacaa agcctgccct   3180
gcacggaggc cgcagcccag atgggggtga ggttggagca gctgtgtcag gaaggtggaa   3240
agtgcataga caagggccgc tcccactact gtgtgtgtcc agagggccgt acgggtagtc   3300
actgtgaaca cgaggtggat ccctgcacgg cccagccttg ccagcacggg ggcacttgcc   3360
gtggttacat gggggggctat gtgtgtgagt gtccagctgg ctatgctggt gacagttgtg   3420
aggataatat agatgagtgt gcttcccagc cctgccagaa cggaggctcc tgtatcgatc   3480
ttgtggcccg ctatctctgt tcctgtcccc ctggcacact gggagttctc tgtgagatca   3540
atgaggacga ctgtgaccta ggcccatcct tggactcagg cgttcagtgc ctacacaatg   3600
gcacctgtgt ggacctggtg ggtggcttcc gctgtaactg tccccagga  tacacaggtc   3660 tgcactgtga ggcagacatc aatgagtgtc gcccgggtgc ctgccatgca gcgcatactc   3720
gggactgcct acaagatcca ggtgggcatt tccgctgcgt ctgccatcct ggcttcacag   3780
ggcctcgctg tcagattgct ctgtcccct  gtgagtccca gccatgtcag catggaggcc   3840
agtgccgtca cagcctaggc cgtggaggtg ggctgacctt cacctgtcac tgtgtcccgc   3900
cattctgggg tctgcgttgt gagcgggtgg cacgctcttg ccgagagctg cagtgcccag   3960
tgggtatccc atgccagcag acagcccgtg gaccacgctg cgcttgtcct ccgggctgt   4020 ccgggccctc ctgccgggtt tctagggcgt caccctcagg agctactaac gccagctgcg   4080
cctctgcccc ttgtctgcat gggggctcat gcctacctgt acagagtgtc cctttcttcc   4140
gctgtgtgtg cgctccggc  tggggcggcc cgcgttgtga ccccttcc   gcagcccctg   4200 aggtccccga ggagccacgg tgcccgcgag cggcttgcca ggccaagcga gggaccagta   4260
actgcgatcg tgagtgcaac accccaggct gtggctggga tggcggtgac tgctcactga   4320
acgtggacga cccctggagg cagtgtgagg cactgcagtg ctggcgtctc ttcaacaaca   4380
```

```
gccggtgtga cccggcctgc agctctccag cctgcctcta tgacaacttt gactgctact    4440
ctggtggccg cgaccgcacc tgcaaccctg tttatgagaa gtactgcgcc gaccactttg    4500
cagatggccg ttgtgaccag ggctgcaaca ctgaggaatg cggctgggat gggctggact    4560
gtgccagcga ggtcccggcc cttttggccc gaggggttct ggtcctcaca gttcttctgc    4620
ctcctgaaga gttgctgcgc tccagtgccg actttctgca gcgactcagc gctattctgc    4680
gcacctcact gcgcttccgc ttggacgcac gtggccaggc catggtcttc ccctatcacc    4740
ggccaagccc tggctctgaa tcccgggtcc gtcgtgagct gggtcctgag gtgatcggct    4800
ctgtggtgat gctggagatt gacaaccggc tctgtctgca gtcagctgag aatgaccact    4860
gcttccctga tgcccagagt gctgctgact acctgggagc cttgtcagca gtggagcgac    4920
ttgatttccc ataccacctt cgggatgtgc gaggagagcc gctggaggcc ccagagcaga    4980
gcgtgccact gctgccactg ctggtggcag ggctgtcttt ctactcatc atcttcatcc     5040
tgggtgtcat ggttgccagg cgaaagcgag aacacagcac cctctggttc cctgagggtt    5100
ttgcattaca caaggacata gctgctggcc acaagggccg gagggagcct gtgggacaag    5160
atgcactggg aatgaagaac atggccaagg gtgagagtct gatggggag gtggtcacag     5220
acttgaatga ctcagaatgt ccagaggcca agagactgaa ggtagaggag ccgggcatgg    5280
gtgcagagga gcctgaggac tgtcgccagt ggacccaaca ccacctggtt gctgctgata    5340
tccgtgtggc accagccaca cgcgctgactc ctcctcaggg agatgcagat gcagacggag    5400
tggatgtcaa cgtccgaggg cctgatggct tcaccccact tatgctggcc tccttctgtg    5460
ggggagccct ggagccgatg ccagctgagg aggatgaggc ggatgacaca tcagccagca    5520
ttatctcaga tctgatctgt caaggggccc agctcggggc acggactgac cgcactggcg    5580
agaccgccct gcatttggct gcccgctatg ctagagcgga tgcagccaag cgtctcctgg    5640
atgctggggc ggacaccaac gcccaggatc attcgggccg cacccccctg cacaccgcag    5700
tgacagctga tgcccagggt gtcttccaga ttctcatcag gaaccgctcc actgacctgg    5760
atgcccgaat ggcagatggc tctactgcac tgatcctggc agcccgcctg cagtggagg     5820
gcatggtgga agagctcatc gccagccatg ccgatgtcaa tgcagtggat gagcttggga    5880
aatctgcctt acactgggct gcagctgtga caacgtgga ggctaccttg gctctgctga    5940
aaaatggagc caacaaggac atgcaggaca gcaaggaaga gacgccgctg ttcttggccg    6000
ctcgggaggg cagctatgag gctgccaagc tgctgctgga tcatctcgcc aaccgggaga    6060
tcacagatca cttggacagg ctgccccggg acgtggccca ggagcggctg caccaggaca    6120
ttgtgcggtt gctggaccag cccagtggac ctcgaagtcc ctctggtccc catggcttag    6180
ggccattgct ctgcccacca ggggccttcc ttcctggcct caaagcggtg cagtctggga    6240
ccaagaagag caggaggcca cctggcaaga ccgggctggg gccacaggga actcgtggtc    6300
ggggcaagaa gctgacacta gcctgtccag gacctctggc agacagctct gtcacactgt    6360
caccggtgga ctctctggac tcaccacggc ctttcagtgg gccccctgct tcccctggag    6420
gcttcccctt ggagggcccc tatgccacca cggccaccgc ggtgtccttg gcacagctag    6480
gcgcaagtag ggcgggtcct ctgggcgccc agcctcctgg gggctgtgtg ctcagctttg    6540
gtctgctcaa tcctgtagct gttccctcg actgggccag gctgcctcca cctgcccctc     6600
cagggccctc attcctgctg cccctggctc cgggaccccca gttgctcaac ccaggagccc    6660
cagtttctcc ccaagagcgg cccccacccct acctggctgc tccaggacat ggagaggaat    6720
atcctgcagc aggaacccgc agtagcccca ccaaggcccg cttcctgcgg gttcccagcg    6780
```

```
agcatcctta tttgaccccg tctcctgagt ccccagagca ctgggccagc ccatccccccc    6840
catccctctc agactggtct gactcaacac ctagcccagc aactgctacc aatgccacag    6900
cctctggagc cctgcctgct cagccacacc ccatatctgt tccctccctc cctcagtccc    6960
agactcagct gggaccccaa ccagaagtta cccccaagag gcaggtgatg gcctaagttc    7020
ttggatttga ggggtgctga agtgacactc ctctatgact tctttcttcc tccttttaa    7080
tcttactctc atcccttct ctctgtccca gccttcctgc acctctctgt cttgtagtgt    7140
gaccaagttg gtcaccagcc cagaccccca gtcttccttt atttataatg ggtaggggct    7200
gaccttccac caccttggcc ccctaaggga tctgggacct cctttgatc cctctccctg    7260
cctcaacttc ctcccccccc tctttctgct tctcattgtc tcacactctg acaagagtga    7320
gttattattt ttttctttt tacatttgt atagagacaa attcatttaa acaaacttat    7380
tattattatt atttttaca aaatatat atggagttgc tccctcccc ccgctgcaaa    7440
ttcctccagc gccccgtgg ggctgagtct gtgggcccgt ttggccaatc cggactctgt    7500
gtactgagta cacagatatg actagggctc cacgtactga gtatgtggcc ctcgtatgta    7560
ccaagtagcc agccttgggc acccctccc ctggggtcag gggacatttg ggagcctcct    7620
tcccctcccc attccccttc ctcacttcac tgcattccag ataagacgtg tagactcact    7680
gggaaagggg tcttgtctgc tcaaagcctc aactccaggc tcacctccca gagcctggct    7740
cacctttag ggcctggggt gggggggcac gtcaggggag atgtattttg tatgcattcc    7800
acttctaatt gtaaatacag ggcagaaggt gggagtggct ctccctcttc ctgttgttct    7860
cttggctcag cctgcctaat agaaatgttt ttaggctgtt tttgtaatat ggcacctggt    7920
cacagtcctt tgtagctgaa ttc                                          7943
```

<210> SEQ ID NO 9
<211> LENGTH: 28000
<212> TYPE: DNA
<213> ORGANISM: Mus musculus

<400> SEQUENCE: 9

```
tggtggcctg aaggatgggt taggagtcag ggcacctggg tttgggcaga gtccagtccc      60
tcactcagat ctgcagcctg acgggcaggt cagcaggcac cactcctggg cctaatggag     120
ctggcatcga tttcccggct tggggtgggg gggctgtaac cggaaactcc cctccctgga     180
cgctatattt agcatcacag acatgggcg gaagcatagc tcactccaga gtccagccag     240
ctctgtccaa atcctgggct gcttcatcct tcagtctggt cctgaggccc ctctgggcct     300
ctccagctca agctaagcac ccattcagaa aaggtcctga ccccagtgct gggggtctta     360
gagcgagcta ccatgcggga gaccaaaggg tgctgtgccc agcgggtgat gcaggccttc     420
ctgaaaagac agaacatctg acccacagg gtcaggtcag ggatcctgag cccccaagta     480
cagcatgaag gaaagcacga ggtttgacgg gtgtccatgg cagttctgcc cgagggctgc     540
agaactctgt gcaggaggg gattcccatg ggaggggacc tctcaatgca agtaaccacc     600
ttcacatctt gagcgtttcc tggtcaccat caggcaaggt tgtggctccc agaggacagg     660
aggaagaaga agaggaaggg gaggaggtgg aagaggagga ggaagaagag gagggagaag     720
aagaggaaaa ggaggaggga gaagaaaagg aggaagagga agaagaagag gaagggagg     780
aggaggagga ggaagaagag gaggaggaag aagaggagga ggaggaagaa gaggaggagg     840
ctattaccat tgtgggatga cacctggaca tagcaggtgc agcccagata ttgaatattc     900
```

```
tgctgtcgtg atacttgcca gctgttctcc ctcacaaagt gcctggatag acaggagagg    960
cggactacat ctccccgctt tccaaggtat gctggtggca tgtccacctt gagccagtgt   1020
ataaggtgac ccccgtgtct cggccagata ggaagaatcc ccccctgggc cactgcaccc   1080
acagctctga gctgggaggc agggcaggta ggctgagtca ggcagccaca cagaagtcct   1140
tgtcagcgta ccctggctct gcctgctggc ctgcccccca ccccatcccc ccacagctgg   1200
ctgacagcag ggaaacagag gtacacaggg aggggctgca gcttcatgct aaactccctc   1260
tcctcagccc ctgcaccgtt agtcattgtc ctgactatgc ttgtgcctcc caacagcacc   1320
acatcaccct gacctcctaa gtcatggtgt ggcacttccc agccctggtc tttgtgacat   1380
ctcattgatt tcagtaggaa gactgactgc aggattgcca cctgcttttg gttgggctat   1440
cttgtcctca caagctcttg tcaggttctc tcagccccag aactttggca tgttgttcct   1500
tctcctcacc ttgctggccc taccatcggg gtctcatgcc cccccacccc cggtttggat   1560
gctcatggtt tgctggtcta cagtatatgt ctaagccatc atccatcttt agacagaggc   1620
ccctgcaggt aggccagggc tgtggctgcc tagttcaaag attggctgag tgcctcagag   1680
gtggtggtga acttaggtga ctggaagct cagactctct gtcctctgtg atctcctgtc   1740
tccaagcaag agggacaggg aagctgaatt tgctaagggg atgtcactta aaggatgcaa   1800
acaacagaaa gattcttaat atgcaccaat tcccttattt ggtgtggagg aggggaggct   1860
ctgtgtgtag ccaggcctgg cttgtgtctg ccctatcacc taccctacct gcgtgtgggc   1920
tccctgggcg agtgctccac tccttggagt gggagcagtt tgagacagag ccaggtatgc   1980
tgcaagtatg ggggatactg gttcacccct tcaggcctac tgcttctgca ggagatcctg   2040
gacggccatt cacagtggta gggcaggcaa actggatcaa ggcttttcga tggcctggct   2100
ccctgtgtag gctgcctggc actgccctga cccaagttcc ttctactgtg gctctgattc   2160
accggtatca gaacttctcc ctctctgcgg aaatcctggc tggcagtgac ttggactaga   2220
aagggagact agagtgagga gccttcggga gacttttgta agggcagagt agcacatcac   2280
caatcatgga ggctaaccac tggaattgca aagggccctg ctgagtggga gagaggcagc   2340
ttgtagacaa agaaccccttg gtgttgacgt gtggaagagg aaatgatcac ctaggaacag   2400
ggtcaagaaa tggtaatgga gggttgggac acccaggctc tgtgacttaa tactcccaga   2460
ctgttggaaa gtcctcttcc ggtagctctc ttgacatggt ccactatcct ttatgcccgt   2520
ttcttttccc ctaaatttga acctcaggcc ggcacgttcc ttgaagataa gagaatgtag   2580
cgatggccac cacctcagtt tggaattggg aacagcctgc aggaaggagc atttgttgac   2640
tggctactca acctgtgcgc ttggaggaag ggagggctga gcgccggagg ggagtagcgc   2700
cccctgtagc cggcgtgaaa gtaacaggag gctgcggagt tgggggggaaa ttcctggggg   2760
aagggggcgc accaggagtt gggctcactc aagtctcagt gccccacccg ctctgcgtgg   2820
gggcaaaatc ctgatgtgtg cagcaggcag tatctcccct gggaccaaga gcagcgcgag   2880
agtggctgcg ctctgatggg aggggaccaa ggcagtgacc tcaggggcg ccccactcac   2940
tcccaggctg ttaacccggg cgagaattct ggagcagaaa aggccccacc tcagtgagcc   3000
tgggcgcagg agaagccaca gctcggtggc ccgcgcccc gccgcccgc gcatagaccg   3060
caccctcgcc tcctttaaag ctcggggtgc ccccaacacc ccccacggcc ccaccccacc   3120
gcgaggcccc gccccctcat gcatatgcag gtgcgcgggt gacgaatggg cgagcgagct   3180
gtcagtctcg tcccgaactt gttggctgcg gtgccgggag cgcgggcgcg cagagccgag   3240
gccaggaccc gccgccgccg tcgccgccgc cgccgggtgg gagccgggcc ggccgccgga   3300
```

```
gagcggctgc agtaagccgg agccgccgcc tccctgcac gcccgccgcg cagcccgcgc    3360
gcactgctcg accccgcccg cgccgcctgt gcggccgccg ccgcctgtgc gccgccgggc    3420
tcggagggcg ggcgggcgtt ggaggccggc gcggcggcta tagcgggcgc gggcggcggc    3480
ggcggcggcg gggccgcggg cggggtcgag gcggcgatgc gggcacgcgg ctggggacgc    3540
ctgcctcggc ggctgctgct gctactggtt ctgtgcgtgc aggtgagcgg ggcgcgcggt    3600
ggcgacgggc gcggacgggg cgcaccgggc cgggccgctc ctccgggcca ggcggcgcac    3660
aaacggccgc ggtccggagc cctaggaacg gcgcaagggt gggggcgggg cggaggctcg    3720
gcgaccccgg cccgcgcctc cctgcactct gcgctgcctt atttttaggc gacgcggccc    3780
atgggctatt tcgagctgca gctgagcgcg ctgcggaacg tgaacgggga gctgctgagc    3840
ggcgcctgct gtgacggcga cggccggacg acgcgcgcgg ggggctgcgg ccgcgacgag    3900
tgcgacacgt acgtgcgcgt gtgccttaag gagtaccagg ccaaggtgac gcccacgggg    3960
ccctgcagct acggctacgg cgccacgccc gtgctgggtg caactccttc tacctgccg     4020
ccggcgggcg ctgcggggga ccgagcgcgc gcgcggtctc ggaccggcgg ccaccaggac    4080
ccgggcctcg tcgtcattcc ctttcagttc gcctggccgg tacgtgcgcc cctcccccgc    4140
actctgcttc cctgcgcgct cggcgcccgc cgcggtccct tcagcacctg cggccgcgcg    4200
ggtgcgggcc gcgcgcgccc agacggggcg gggccggcag ggggcgccgc gccgcgggcg    4260
ggcctggggc gcgtgctctt gcggccaggt tcgcgcctgg ccacgtgggc gcgcggggtt    4320
cccaagggcc gacaggcttg gggtcgcggc ggggctggga ggccaaggtc cgcgtgcacg    4380
gcggccctcg gagtgtgcct acgtcgccct gcgcgtgtca gtgcgtgggg aggtgcgagg    4440
cgcctgcggc ccggtaggct gtgcaggcat gtgcgctgcg cgtgctgggg ctggtccggg    4500
gcaggccctg gcggagccgt ccgggcccgc ggccagcctg ctcctgccct gcagtttcct    4560
ggatgcccgg gggcacggac aggcgcctgg gacctgcgcg gggatggcct gattgtgtgt    4620
gttggcagaa gctgctagag atgggaagac ccctcctccg aaagggaaga gacactaaca    4680
aggctccaag ttgtaaccct ctgtggcact gctgtttgcg gatgtttat tgtgcttctt     4740
agtttctgga attgggaagc accctgtctg cttaggggtg gtcaggtcag gcaagaaccc    4800
gagtctgggc atgctgggaa gaagggtcat ggggatccag cttttgggga gacaggtagc    4860
atgcctgtgt tataaaggcc tgggatcagg aagtcttatg gtgcttgctt ttattcactt    4920
tctggacctg gcttgtaccg gcacctgatt gtctgcaggt gtgaagctag ttaggtgcag    4980
atgtgaatat ggacatagtc ttgagtgtga gattaaaaac agctggtaaa ggtgggtctg    5040
gaggcctgag actagcgagt agagggggg tatcaagcaa tggcccaagg gctttcctga    5100
ctgagggctt gcggttggtt cagataccaa gagccatggg aatgggtctg cctggtacct    5160
tggtcctgaa agagactttt ggttaggggg tcaggcatgg gtgggcaggg tttgccctgc    5220
tctgctcttg ctctgagccc tggacaatta tttcttccaa ggccaccag cttgtgcctc     5280
catctttacc tttccctagg ctcctgctcc atacgtaggg agggataccc ttgcctagcc    5340
aggtagcctt gaccctgggg gcttgtgata ggaagtttat ccctgagacg gaaaaaggca    5400
ggggcaggca tgggagaggc cctaggcagt tactattggc cctgccccc tcgcccccac     5460
agcagcacag caggcaggtc tgagcagggc cgacagcctg tcatctgcac ttgggcccaa    5520
gccagcgtgg ctccaaatcg ctacctgagg atgtgttttc tgctcgagtt ggcagcggtg    5580
ggtgtggggg gcagggaggg cctggaggaa tgtggcgggc caacgcgtgt cccttgtggc    5640
```

```
tctttgcccc gctggccagc cggttggtgt ggaacgggat gggacaggcc cttgccttcc    5700
ttcgactctt ggtacttggt cttggggaca ctttagcttt ctgttcccag atgctttccc    5760
aagatgcctc aggggtaggg aagtttctag catggatgga agtttggagg ttgaagggta    5820
ccttgtgttt gggggcaggt ctggttctcc cgtctcccat cttgctgcgt gtcctggctg    5880
ccaggcatgg agctggtgct gtgatgccag taccttggta tttccgctct ttggcaacag    5940
ccctgcggcc atgctgcttg atctgccaca agttcatctc tgtcccgtga gccagggtac    6000
attgggaatc caggcgccca ctggagcatt tggtacctgg ggacagcaag aaccagctgg    6060
gacttgggtt ccttggggttg gtggagggcc ctgtggaaag atgggacggt gttagaaggt    6120
ggacaagagc aggcacgggc ttctcacaac tcctgtgcct gcaccgaggt agctgtggct    6180
tcgaatccat ctcagagcct cttgagtgg attcttcgat gcagaaagcc gcagcaaccc    6240
ccgccaggct gtgcatgttg cagatgtcct cgggagatgt acgttttccc tggagtggct    6300
ctggtgcctg tctgtaccca gcagcgggga ggcctcgttc accacgcatg cttgagatcc    6360
gtggcccgag caggtggttg atggagagtt ctgaggaaag cggaggcttt tctttggggt    6420
ctggtggctg gtgtatttag gaggtccctg ttggctaaat gaggaacaag gtggtcgctg    6480
gcctgtctag tggggctgtg cttgggaaag gatgccaaaa gagaagaggt ctctactaca    6540
ggccctctgt ctgaccagct tgccttttga gcccagggtg cagccctgtt ccggtctctt    6600
tccttggtgg tgcttctggg gtcatgagtg atagagagag aggcaggtct gaggcggcgg    6660
acctggtttc taaggctgga agagctgagc tagcagtcct gtaacctgct tcccctctcc    6720
tgagacggat gcaaggcctt ttccactagg attcctgaag ctagctgagg ctgtagggtg    6780
cccagcatgt cccctactga actccccaat gtagctttct cctgcttaag ttcttcctct    6840
ccccctgctg gctgtccagc acatggccat gtgtgtactt gagggaggga ggtaaggcaa    6900
ggtggtcagg gaggactgtc ccataggaca gaggactgac ggttgttgta aggttgttcc    6960
agcgtaagag ggtgctggaa cagatccggg agcacaggca gagagggcct gacccaagtg    7020
ggctattcta aaatgtgtgc cctgcatgta catcaaagga ccccgctgcc ctccgggcct    7080
tttgggactg ggatgagcac cagtctcttc atcacaaccc acgctgaggc acatgcctcc    7140
cacagcatcc ccataagacc aagagtcctc cttggctgga gctaggggca ggtgctatt    7200 cattctgtac ccgaccgtct ccctcatagg ttgggtgtct tgatccaggc cacatagtat    7260
gtgttatggt agggctctct gtagccagca acacgggggg gggggcggc ggggactgag    7320 gcagaaagtg ctaacttggg ccagtggagg attcagacgt ggaagtggat ctggcccttg    7380
tccctgggcc cacaggagtg aatgggaaac cgagctgtag tgagatgggc gaggggtggg    7440
tgctgtacct gtgggttggc aggaaaggta ctatcatggt gtctggacag aataggaaat    7500
gggctggtcc actgagagtt gctggggagc caggcaaagg ctctgatcca tctgcccatc    7560
cacccatcct gaactagatg tcgcataccc attctgatcc tgggctagct gcagtagacg    7620
atgaggcatg ctagggggcca cacaggctgc tgctcccctc ttcacggtgg agcctgggt    7680 ttcccagcag tgggtgagcg gcgcacctag gctaggcctc agctggtctc tgatgtgggg    7740
tgcacctgtc caaccctagc atgggctaac ctactgtctc ttcctgtgac ccagagacct    7800
ggagtcttaa gagggttatc ccttgggtga caatggcgac agaggcctag gcctctccaa    7860
agctctggtt tcaggaaata tgtctgtgct tagggctccg gacattggca gcaagtgctg    7920
agctctgtca ggggccaaga aaggcagcta gagagtagaa caagccttgt acctgaggct    7980
aggctgtgag taaccctggc tatggggcca gggggcacac ctgtcccttg gtctgccttt    8040
```

```
cccatggtcc tctgctgtcc ttttagctct gtctaagggc tagattgggg gggggaatta   8100
cagttagact tggagtttga ccagacggtg atggacttgg ctgggggtgt gtctgggcc    8160 aggctttggg ccgaggctgt aggatataga actccagagt ctgacaggca ggtggcccag   8220
gaggactgcc ctaggaggag ggaccaggat tttctctctt gcttctggga aacctgggca   8280
ggtggtagct ctctgtctca cccatggtcc tccagctttc cagcccca  tccactctaa    8340 aagcccaag atcctacagg cttccagccc agtcgccttt gtccctctgt caaccagtag    8400
gatttggctt cccaggaagg ggtgcacaga gctatttgta gtgagggata tggtactgga   8460
agctggggga agggaggagc tggggggcca ctgtggcagg tggggagaag ccacaggtgc   8520
cgcctgcctg ctggctcagg ttctccctgg atgacttcct gccatccagg tgtagggagc   8580
ccagctggcg ggcgacaggc cctctcgggc gagcgggcgg gccacgtccc tgcgggagca   8640
ggtaaccgga gcccagggct caggctgagg tggtggtaac cctacctgtg cgcctgggt   8700 gggtttcctg ggagtgttcc tggatcatcc gaagcgcagg tgtgtgcagg gaatcttacc   8760
gcctgccctg tggctactgc ctccgaacct tgctggtggg cttggcctgt agtgatggtg   8820
gcagagatct taagcccagc ctagccttgt cctctcacag cccgtcagct ccttgttcct   8880
atgtagcagc tgagcgagta taaaacctga tagcctcaga tcttactggt cacttgtttt   8940
gatgggaacc agtgatgatt ccaccgtggg gtgggggtc  ctctggtgcc ctgtgctatg   9000
gtcccctctg ttctgcattc ctcgatctct tagccctgtt tggtcttctt tctgactcct   9060
cctcctcctc ctcttcctcc tccctgcttc ttttttcctc ctcctcctcc tcctcttttt   9120
cctcttcccc tcttcttcct cctcttcttc cacttcttcc tcctcctcct catagtgctt   9180
cctcccttgg gctaaagcct atttctcctg gggctatgtg acctgggcct gtccctcact   9240
ttctctggct ccatctgttg atgcagggc  tgtaggcagt ctgaactctg ttctgcacta   9300
taatgagtgg gcgggtaaag aactgaaggg gcagggaagg gactgcctgg aagggactg    9360 gggaccctgc ctgtcaccag ggagctagcc ttggacaaat ggaggctctg aggagtgctt   9420
tgcaggtggt tagggtggta tggagagggc ccccagatag gctctgcacc caggcacatg   9480
agggtagcac agtggggatt tcttaggcct ctaagcccta tgcttgccga gagaccaggg   9540
agaggagcag tcagggtggg aaggggagc  aggggagcga acgaggaaga ggatctaaag   9600
ggggatttag atggcaataa aggtgggctg gagagatggc ttagcggtta agagcactga   9660
ctgctcttcc agaggtcctg agttcaattc ccagcaccta cttggtagct cacagccatc   9720
tgtaatggga tctgagtccc ccttctggta tgtttgaaga gagtacttt  atatacataa   9780 atatgttttt aaaaaagaa  gaagaaaga  aaaaggaaa  cctggtagtg gcttcatgga   9840
gccaggggac cagtggccct ctgctttttgg cctggctcac atggcatggg ccctatgtgt   9900
gacgacaggt gctcagagga ggtaccagag tagggagtga gagtgttcat gctgagctgc   9960
caacagatag gaaaaggaca gggtctccta acacgaggtc ccgtgaggct gggtatggca   10020
gtgggataag ttctagaaag cccaggttag atggggctcc agtgagtctg gagggagggc   10080
tctgagggct gaggaatggc tggtgctctc agccatccag gaaaacatga ggtttcctca   10140
gcatagtcga gctgcagagg aagggtgcc  tgaggtcacg gtgagctcag gctgccctat   10200
tataggggca ggccttatgt tgccaaggta acagctcaca gcagcactca tcgccatggc   10260
ctggggcagg agggacagat ggtgagggct ggccatgatt acagactgag gctgtgccta   10320
gcacagcagc tcttgggcct cagtgtcccc cacctgtaca gcaagagacc tccatcagcc   10380
```

| | |
|---|---|
| ttgtcctggg ggatagttag gaggctgact gtatgctctt tgatggtaag cacttctgtg | 10440 |
| tgactggtag aatgactgct gagtagccag gacgcagccc tgtcaagtgg gcttcaagta | 10500 |
| tatatatagt gccacataat cttcaacttc agctcagccc tctgaggtgc agggatgtat | 10560 |
| tcccaacgga agtgctctgc ccacagatgc ctgaacccct cccttcaccc tttgctgact | 10620 |
| tcaggagctt gcacagggtg gagctgaact gggccttggg gaccccaaga gcaaggagcc | 10680 |
| aaaacttcct gagaggtgca gccagggata attatcctcc atttccgagt tgggatatat | 10740 |
| ggggtctgta gaggagatgg gccagtgttg gggacacgga tggggaaggg agggtaccac | 10800 |
| aaagccgtgg agcagagttc tctataaggc ctgagcatcc cagagacaca caggccaggg | 10860 |
| ccatgcaccc tgcccccatc ctgaatagca gcaggtggga gggagcccca ggcacctgac | 10920 |
| cagctctcct cctgtgtctg cagcgttctt tcaccctcat cgtggaggcc tgggactggg | 10980 |
| acaatgacac cactccagat ggtgagtatg ccctgtactg ggggaagtgg gtgggtggag | 11040 |
| ggaggctgcc agcaagaatt tctggtcccc tgggccagag tgcttgtggc caggcccatg | 11100 |
| gccctctgtc tgctgggggc gatggctcgt atgactagaa ggtcttattc tggtgaaaga | 11160 |
| ggctctccac gcacgcctgt ggctttgcag agctgctcat actattcctt cactcctggt | 11220 |
| gtcgtcagtg cattcttctg aggcccatgt tggtgacacc atggaatgag ataccctcaa | 11280 |
| gtggctctct ctggctttgt gacgttctcg ctatcttaga acatgaagct cgagggtcac | 11340 |
| cacttcaaag ccagccgttc tgtgtacagt ctgtgtgtgt ggcgggggtc atctcagcct | 11400 |
| tctagcggag aggcagagct ttttctgtag acaaacggag aagccccttg agcagagagt | 11460 |
| gaaggatcca agctagtatc tgaggttctg ggtggaggtc ttgtgactgg gagacgaagc | 11520 |
| agtcagcgag gcttggttca ggccgagcaa gctcctgggc ccgggaggat gccggcttct | 11580 |
| tcctggggat gcattgccct ggctgccctg tggacagagt ttgcaaggcc gaaacaaagg | 11640 |
| ccaacaaaga gggtgctgct tgcatcaaga caaagaggct gagacaggca gcttgagggg | 11700 |
| ctaaggagtt ctggctattc tcaaaaggta gagatgcggg gtggctgatg gatcagaccc | 11760 |
| caggttatga ttagacgtaa cccttgagat cttacagagc aatgcaccgt gatcaggatg | 11820 |
| aaccccgagt cctggcgatg tcgccaagga taggcgaaaa ggggagagca ggaagctcag | 11880 |
| agtagagggt cagccagggt ccaaggaagg caatcggggg ccttaccaaa acgcaaagcc | 11940 |
| cagggcactg ggtgcccagt tgggcctgta ctaatgcaac aggaagaaaa agtgaggcag | 12000 |
| caggactgta tgcccagctg ccatagaaaa ccccaaacag cagtggtggg tgctgtgcag | 12060 |
| cccgctcagg tagcctgctt cagtgcgctg ctccccaccc ccccatggga cagtccatcc | 12120 |
| tggggtccca gaattttgtt ttaaggtgga tcagtaggga gggtgcttct gagagccaga | 12180 |
| ggcagaagga ggaggaggag gagagaatgg tggcccatgg gtggtgtggt gcctgtgaat | 12240 |
| gtggaaggaa gcttagagca tatggccctc gtgacccttt gtgggagagg agcagtggtg | 12300 |
| ccagcttaca gggttcaagc atcctgctta gagcttctgc ccagccttct cgtgggccc | 12360 |
| tggacagtgt ccgctccgcc cctggctcct gcagggctgg cagccttcct ctgcctggct | 12420 |
| gccctgttgc ccctgaagct gcctggtagg gcccgcgtgg caccccctggg ggactgacgg | 12480 |
| gtagctgctg ccgccagcta actcggctgc tcccaaagag gagctgctga ttgagcgggt | 12540 |
| gtcgcacgct ggcatgatca accccgagga ccgctggaag agcctgcact tcagcggcca | 12600 |
| cgtggcacac ctggagctgc agatccgagt acgctgtgat gagaactact acagtgccac | 12660 |
| ctgcaacaag ttctgccggc cccgcaacga cttctttggc cactatacct gcgaccagta | 12720 |
| cggcaacaag gcctgcatgg atggctggat gggcaaagaa tgcaaagaag gtgaggggtc | 12780 |

```
tgtctcccag tgtggggctg ggcacgggca ccgggcaggg ctagcatggc tggctgcagc    12840
tgtgcctctc tctgcccctc tgttccagcc gtgtgtaaac aaggatgtaa tttgctccac    12900
gggggatgca ctgtgcctgg ggagtgcagg tgagcaccat gcctgccctt cccttcctca    12960
cccgagctgc tgtagagcct gcagcagctg gggcaccctg cgggctttag taggccacga    13020
agtaggtgct tcatgccagg tgcccaccat gcagggaatc agatgctata gagttggaat    13080
ggaaccctgc ccttacaaag cttgtggcca cgaagagggc agtgctgtcc tgagcatgtg    13140
gcatgtccag tgacattttc tccatgggac agctagaagg ggacaaggga aggtggccag    13200
gtagtcacat caccaagaag caaaggctaa ggggtatgtg tgtgcgtgca tgcttgtgca    13260
agtgtgtgtg catgcaagcg tgtgtgtgtg tgtgtgtgtg tgtgtgtgtg tgtgtgtgtg    13320
tggtatgcat acatatgagc actacataaa tgtgaggaat ctggtgccca ggtgaacaca    13380
gtaggaagtc accgtggcgt gctagtggga gaaactgaca tgattctgca gagagaggct    13440
tagggggaag aggagcccta tcaagagagg ctgaggagaa ccacacagcg tggcagtgag    13500
gaagaagaga gcaatgggcc agtggggtgg aggggtggga tggacctgca gacgttctga    13560
ggaataggaa tttgatgatg agtttggttt aggaggaggg gggtgcagtc aagcaggagc    13620
tgtaaacctg ctagcttgag ccactaaacc atggatttgt ggtggctgag gtagggatga    13680
ttgtcagaga ggcgggctag tgtgtgccaa gcagggcgca ttggacaggc ctggccttaa    13740
ggcagcacag agtcaggtgg agaggagggg ctgggaatgg cttggcctgc agcacttgga    13800
ggcatgtaga cagacaggtg aggaggacag agaggggatc ctgcagccca gagcagagta    13860
gaagccattg gggctcatga aggtgatgga ggtgatgagg ctaagttagg ggtagaggat    13920
agagagaggc aaaggtcggc accctgggat gtgtgagttg ggaacgtggg ggcccagggg    13980
gttggagggt gtaggaaaag agttagagat gagcatctta gactcagggg agccacagca    14040
gtaggcctgc caaggccctc ctgccatcct ggttctcact gtccctgggt gccctctgag    14100
cagtgggtat acctcgtgtg ttttcggatg aggacgatgg ggacgtgtac tgtttggtcg    14160
ggagaggctg gccagggagt tggggagttg agatgggctg ggggagggggt tgtatagtgg    14220 cattagtgat gtgttcagca gctaggctgg tccctgggca gaaagagatg ggtgtgcagt    14280
ggagacatcc caggtgccac ttgcacacag tgtggtttca gacagtcttg gcaggactca    14340
aggcagtgca aggagcacct gtctcaggat gggctggctt cttactccag gagccacatc    14400
caaggaggga gatgggggggt gggacaggca gcagaaatcg tccatccaca cagccctctg    14460
ccccagtgca gtctttcaca gcccggctct gagcagtgtg ctggagttgg gcgtgggttc    14520
tgggcagatg tgccccactg gtggtaaaca caggagccta ctcttaaccc cacactcact    14580
ctgtagccca aggtatatta cggtatcttg gcggctatac cagcagcatc ccaaagtggt    14640
cagtgctgga gggagatgaa agatgaggca acgtccctcc gtccctccgt gcagaaaggc    14700
tgtgggtagc acacaggcag gagccctggg gaggaaagca agggtagggg gtggtaggtg    14760
agtgccaccc tctccctggg ccagagggtg aggccaagtg gcctcctgct gtccagagct    14820
caggtttcag cagaggacac ccctccccag ccggatgcta ctgcggagat ggccgtgctt    14880
tcctgccacc ctccccaggc cctggaacgg ctggcaggaa agccacaagg tggggtctgg    14940
tgtgggatgg cccgcccagg gtggagaacc tgcccttggg gctcacgggg tctgggctca    15000
aagctagcct tggtgttccc tggtgaatga cccaaggcta gtcccagccc tctctgcccc    15060
tcgactcccc gtatcacctg gagagaagac tcccaagtag agacagggga ggcctactgt    15120
```

```
ggacctgcct tggacgttcc gggctggacc ctggagccag cctcagtttc cctatgtgag    15180
cctgggtgag ccgggctgat aagtgcctgt gtgcgtggct ccagggcagc tcaggaaggg    15240
ctgtggtttt tccttctata aaataactc ctgtggcggg tgtcagcgtg aagtgacgt     15300 ggcctgcacg tcattcctgc cccacaggac cttagccttt aaggaagggg cccccagagt    15360
cttgtccagg gcccagaggg cagccctact ggagccctgt actctcgcac ctgctggttc    15420
tgtgctggcc acctacttac atcctgaggg actcccagaa ggctacacta gtccccagtg    15480
tggtcagagc caggtcgtaa gattacggcc tctgacgagg tcttcgggtc tatgtgttgg    15540
gttcagcccc actcagtgtg cgctcccat agggctggct gggcagccac tgggttggac    15600
tgtcctagga gtcagagaaa cctctgccct tgagtagcag tgaggatatg ggcggcaccc    15660
aaggtcacag agcccttgga ccagggtagc taggatctct cctgatgcct cttcatccct    15720
ctcagatccc agttgctgct gtgtcccagc agcacctggt gagcagcacc tggcactgta    15780
cccctgggcc tccccggct gggccttcct tccaggcgcc tggctcagag ctgagtccta    15840
gaatagctca gggggagtga cgggacagct gggctgacca tctcggccag tggccgggaa    15900
tgcctgtgac agcagactg gccggcaggc cgtaacccct gcttggttca gagctgttct    15960
ctgggaccac cacccagtag gggtagcctg cacttctgtg cctgcctccc atgcccttc    16020 ctcatctgcc cggctgatgg cctcgtcgct cggtccccca ggtgcagcta cggctggcag    16080
ggcaagttct gtgacgagtg tgtccctac cctggctgcg tgcatggcag ctgtgtggag    16140
ccctggcact gtgactgtga ccaactggg ggtggcctgc tctgtgacaa aggtagagag    16200
atggtgggca gtgggcaggg ccaggcctta agctctgaca ctgggcccat ccctgagagc    16260
cctacccttg tgcccagacc tgaactactg tggcagccac cacccctgtg tcaacggggg    16320
tacctgcatc aatgctgagc ctgaccaata cctctgcgcc tgcccagatg ctacttggg    16380 caagaactgc gagcggggta ggttggaatg ctgtctctcg gggagcctgg ctgaggcctt    16440
tcttcactgc cttgtacagt gggctgtacc cctgtgaact ctgggtctgg tgggctcggg    16500
gaagcgtgct caagttcagt gggcatcgct ccactcatgt tctggttctg cagctgagca    16560
cgcctgtgcc tccaacccgt gtgccaatgg gggctcttgc cacgaagtgc catctggctt    16620
tgaatgccac tgtccgtcag gatggaacgg acccacctgt gcgctcggtg agtgtctggg    16680
ggcttcacaa ggtaggagtg ggtagcactt cggggtgtgg acagagtggt tgaatccgct    16740
gcacagcaga cactgcagcc aaacaatcgg ttcctgctgc tttacatggg actgtgactc    16800
cctgctgcag actgagaccc cgtgtactgt gtccctactc actgaccaca ccccatgtcc    16860
tctgtccatg ggtctacact aactagacac gatcccacgt tcactggcca tagtctgtac    16920
ccgttgactt cgtcctctca tttgctggcc acacccttac ctacctacct ctttttcatt    16980
ctctctcttc ctcctccccc actgcagaca ttgatgagtg tgcctctaac ccatgtgcag    17040
cgggtggtac ctgcgtggat caggtggacg gcttcgagtg catctgcccg gagcagtggg    17100 tggggggctac ttgccagctg ggtaagggct ccctgggggg gactgtctgt gcatgggttg    17160
tgtgctgtgc atgtggctgc tgctgctgct gctgctggca ctgctggggc tgcggcgtc    17220 aggtgcaggg cccagtgggt gagtgggggcc cgagccccac agctcccttg tctcattcac    17280
agacgccaat gagtgtgaag ggaagccgtg ccttaatgct tttttcttgca aaacctgat    17340 tggcggctat tactgtgatt gcctcccggg ctggaagggc atcaactgcc aaatcagtca    17400
gtatgggtgg gcggcgccgg tgggcgggc tgggagcac agagggcccc cctgacccca    17460
cccgcatgcc cttctgcctc cagacatcaa cgattgccat gggcagtgtc agcatggggg    17520
```

```
cacctgcaag gtaaggggc tgccaagtct gggagggtgg aatgtggctg gaggaggcag    17580
gcagggttgt atgaggttcg ctcacccacc cacctgtcca cacacctagg acctggtcaa    17640
tgggtaccag tgtgtgtgcc cgcggggctt tggaggtcgc cattgcgaac tagagtacga    17700
caagtgtgcc agcagcccct gccgccgggg tggcatctgt gaggacctgg tggatggctt    17760
ccgctgccac tgcccacggg gcctctctgg gctgcactgt gaggtaataa cctagagggg    17820
ctttggtggg agccctgtct aggagggtca ccaaagccag gcttgtccct tgtctcaaca    17880
atcttatatg cttcactccc tgtatgggac cgtgcagagg ggaagcctgc aagaaggacc    17940
cccaaaggca gaattgcata ttttatgtgt ggacatcatg ggtcaagggt gggcctggga    18000
agaaacgggt gattttccac acggctgcta ccctgacccc tgttgggtga tctcccttgt    18060
cctgagctac acatggtttt gctctggcct tgtgggcttc ttagtggccc gtggcagagg    18120
cctctgactt cgggtcccca gagcatggtg gtgctggctg taggaaggac ctctcttggc    18180
tctgagggca gcctggcaac atgggggtca gaagctggcc ttcctgccgg cgggaggagc    18240
caaaaccgga tgctgtctgt gggaggcaga ggaagcttgg ctgctgtgga ggcgagggcg    18300
gcaggagggg gctggtggcc cacaggtgtt tccgtccagc tgacggtgct cagacattct    18360
tgggtgggtg ggagcttcaa gctcagcttg gcaccgctgg gtctaaggca gagaggcctg    18420
gttgtctata cgaaacagtg cttctatata gagctggata ctcacaaata catccccac     18480 tccttacctg caggtggaca tggatctctg tgaaccaagc ccctgcctca acggtgctcg    18540
ctgctacaac cttgagggtg actactactg cgcctgccca gaagactttg gtggcaagaa    18600
ctgctcagtg cccagggaca catgccctgg cggggcatgt agaggtacat gatgcaaccc    18660
ttcaggctgg gtgggtaccc cggtggagat gggtctgacc cctgtccatc tctttgccac    18720
agtgatcgat ggctgcgggt tcgaggcagg gtccagggca cgcggtgtcg caccctctgg    18780
tatatgtggc cctcacgggc actgcgttag cctgcctggg ggaaacttct cctgcatctg    18840
tgacagcggc ttcacaggca cctactgcca tgaaagtgag tggtgtgcag agttggtggg    18900
gtggggcaag ctggccagcc acagggacag ctcacccatc ctctccctca gacattgacg    18960
actgcatggg ccagccctgc cgcaacgggg gcacgtgcat tgacgaagtg gactccttcc    19020
gctgcttctg ccccagtggc tgggaaggag aactctgtga catcagtgag tttgcaccct    19080
tgccttaccc ggaccgcccc cactggctaa ggcctggctc caccccctatg tcctactcag    19140 cactgtgtac atgggcctga agtcatgggg tggaatccca ggctcccatg tgcttgggcc    19200
cagctcttgc tcttctccgt gaagccctcc ccagcgccgg tgaccccgc tgaccggcgt    19260 cctccccca gatcccaacg actgcctccc cgaccctgc cacagccgcg ccgctgcta     19320 tgacctggtc aatgacttct actgtgcctg tgacgatggc tggaagggca agacctgcca    19380
ctcacgtaag tgccccgggg tccctgcaaa tgagcaagcg agcgagtgga ggggctgctt    19440
gccaggaccc tgctgggggtc aatatggccc gcccactgag cggccatgtg cttgcaggcg    19500
agttccagtg tgacgcctac acctgcagca acggtggcac atgctatgac agcggcgaca    19560
ccttccgctg cgccgtgccct ccgggctgga agggcagcac ctgcaccatc ggtgagcacc    19620
ctacccagcc tggctgcctc ccctagccct gggctgccga ccccagccat gttgtggtct    19680
gccccaggca tctcaatcct ccccctccc tccctgcagc caagaacagc agctgtgtgc    19740
ccaatccctg tgtgaatgga ggcacctgcg tgggcagcgg agactctttc tcctgcatct    19800
gccgggatgg ctgggagggc cgcacctgca cacatagtga gctggagggg cttcaggtgg    19860
```

```
gggaggcctg tgggttctgc ttaacttcac ccagccccac ccccatccct tcttccaact   19920
tccaggaaga accactcttc cacctgccta cctcacacat ccacactctt gagacctgct   19980
ctgccacttt gtaattcagt ccctgtgcca tatctgcagg gtccttctac ctaccctgat   20040
ccaccactct gcaggcttgg gctcctgcta agacataggt cccattccaa ctatagctcc   20100
caccccatgg aggcttccct tggggtcctg agccttcctc gtacttctcc actggctgtg   20160
ccaggctggt atggacagga tagtgtctac ccacgagcct cagacacaga gatgctgctgc  20220 agaggtgttc tgggcaagag tgtgctgaaa taaccaccct gtctttcccc ttaaatccag   20280
acaccaatga ctgcaaccct ctgccctggt gagtggcggc ccaggaggct ggtgggggc    20340 agggcccatc ctaggggacc ctttatggcc accctctccc ttgcagctat aacggaggca   20400
tctgtgttga tggcgtcaac tggttccgct gcgagtgtgc cctggctttt gcgggtcctg   20460
actgccgtat cagtaagcag cctaggtgga tggaaggggc tggggttggg ggcttcgtct   20520
ggggccctct cctgacaatc tcagtatcga aagccgggag gcataaacat ccacatcctg   20580
acagggacat ggccgcagcc ttcccttgcc tcccatgagc atgtctgcat cctatgagag   20640
cctagttcct tcctgaagag ccagttgcat cttgggaaga gggagagggg ctacaggggtg  20700 gaatgctcct gcccctcag gctgtgagga tgcctctgtg tacatggcca cctcagagag    20760
agaggagcac agaggtccct gagtgctcac agcacagagg cagtagagga gggcgaggga   20820
ctgagagtta gaaggcttca gatggacaga gacacagaca gcctaggtag ctgtgcgaca   20880
ggtggactga ggtactgcct tccagccctc tgcctcgccc acacgctggt ccctgggtgg   20940
ggtgcacacc cctaagaaca cagccgctct ccttgcagac attgatgagt gccagtcctc   21000
gccctgtgcc tacggagcca cgtgtgtgga tgagatcaac gggtaccgct gcagctgccc   21060
accaggtcgt tctggcccca ggtgccagga aggtaggctg tctgtgcccg tggtcagggc   21120
gtgggccaga tccaccctcc agcgcttgga cactctgttg agcctcctcc ttcttaccac   21180
agtggtcata ttcacgaggc cctgctggtc cggggaatg tccttcccgc atgggagttc    21240
ctggatggaa gactgcaaca gctgccgctg cctggatggc caccgggatt gtagcaaggt   21300
ggggccagcc cctcctccgc ccctcttgca ctgtgaccct gagtaatctt gagcctttag   21360
gctcactcag ctatcaagag gctgatgcag gggtgggggt gtgggttgat aaggctgccc   21420
acttctgagg gccatcctaa ggggatgagc tgggaggggc cttgggcctg cctctcttct   21480
ctgtccattc ccaggctctg cctagttctt tctgttttgg cagaaagttc tctctggact   21540
ggagttttgc ctgcttccct agggcccctg ggtgttagag acattgactt gaaacttact   21600
ccttgatgtc ttctctctgt gctgcctgac tgtgcgctgt gtgctgtctg actgtgctcc   21660
cgctcccatg tgtctcctgc gcgtctctcc caggtatggt gcggatggaa gccttgcctg   21720
ctctctggtc agcccagcga tccgagtgcc cagtgccccc cagggcagca atgtcaggag   21780
aaggccgtgg gtcagtgctt gcagccaccc tgtgagaact gggggagtg tacagcggag    21840 gagcctctgc cacccagcac cccctgtcag ccacggagca gtcatttgga caacaactgt   21900
gcccgactca cactgcgctt caaccgtgat caagtgcctc aggtgagtgc tcctggggga   21960
cccaggattc ccaggtttac ccctagagtg atagtccgct tgctcgctct ctcaaggctc   22020
agctcacgta ggtccagaag cccgtggctg tgcagatagg tggatcacac gagaaagcac   22080
tgagccgagg cgttgttggg caagagagag tgggtccagg ctgggctgct aacgtgccca   22140
gtgttcctgg ggcctagact gcaggggtgc tgcgggccac cctactttgg attgacatgc   22200
aaaggatagt tcccgtttct gatgtgtccc atcctcaccc tctggatgtt ccgaactagc   22260
```

```
ctacccgttc cccagaacag gggctcgaac tcaacggtgg ccgttccaag ctcctcccat    22320
tgcctcagac agactgggtt aagagcaggg taggctcctt gtcagcagag acatggcctc    22380
agatcttggc cctaaacccc gctaacctgt tgcttatctg cccagggcac caccgtgggc    22440
gctatctgct ctggaatccg agccttgcct gccacgaggg cggcggcaca cgaccgcctc    22500
ctcctgctgc tttgtgatcg agcatcctcg ggggccagtg ctgtggaggt ggctgtggtg    22560
agtgtgggtg gtgacctgaa ctgagcaggc ctctagaccc tcagcggcag tgacactctg    22620
gcatcccgcg gggcagtggc agagttgaag atgacgggga ggcacttaca tggtggaatg    22680
gagacccggg gcagtgggaa ctgagatagg agccagatct ggcatccctc tgggcacctc    22740
cacagctggg tgcggctggg tggggaagct gtatccacgt ggactgcgtg cggcaggcgg    22800
gtaggggcca gagctataag agaagaacat caggctgtcg aggtggtcac tgacagtccg    22860
tagggtcagc tgctcgatgg gaaggcaaca aggatgtgag tttgggtttt atcgtgagga    22920
aatggcctgg gtgcaggtcg ggtcccagca cgcaagaaga gagagagttc tggggttggt    22980
attgtttggt attgtccagc ggtccccata caggatgcag gggtttgaca ggggcagggc    23040
caggccctta tctatctggc gggtgcatcc tctacatcaa gatccaaccg cactgagctt    23100
cccgtctctt ggtctccaag ccctgtcagg tcctggccgt gtgtagcaca gcactgattc    23160
agttctaccc atggcagccc tctgtacatc tggctaggac ccgatcagag tttgggcagt    23220
ggctataaca ggctcctggg atgtaggaag ggtacctttg ggccgtcccc cagtgtcatc    23280
ctctgccaca gtctttcagc cctgcaaggg acctgcctga cagcagcctg atccagagca    23340
cagcccacgc catcgtggct gctatcactc agagaggaaa tagctcactg ctgctggctg    23400
tcaccgaggt caaggtggaa acagttgtta tgggtggctc ttccacaggt aagctggggt    23460 gatagggct cccagactca agaccagtgg gaatctgctg tggatgttgc tcagagggaa    23520
gaggtgtctg ctgctaccca gcttcattct ggaaaccaga agagtccctg cttggcccat    23580
gtggacgcag gatgtttacc tcttcttcta cccaggtctg ttggtgcccg tgctgtgcag    23640
cgtgttcagt gtgctgtggc tcgcctgtgt ggttatctgc gtatggtgga cacgaaagcg    23700
caggaaagaa cgtgagagga gccggctacc acgggatgag agcgccaaca accagtgggc    23760
cccgctcaat cccatccgca accccattga gcggccaggc ggcagcggtc tgggaactgg    23820
gggccacaag gacatactct accagtgcaa aaacttcaca ccgccgcccc gcagggcagg    23880
cgaggcactg cccgggccag ctggccatgg ggctggtggg gaggacgagg aggatgaaga    23940
gctgagccgt ggagatgggg actccccaga ggcagagaag ttcatctcac acaagttcac    24000
caaagacccc agctgctccc tcggaaggcc agcccgctgg gctccagggc ccaaagtgga    24060
caaccgcgcc gtcagaagta ccaaggacgt gcgccgtgct ggcagggaat agccagccac    24120
caggctggca cccagaaccc ttgctggcac cacgctgcct gccggaccat aggaggccaa    24180
ggccgtgtgc atagtttctt tattttgtgt aaaaaacaaa accaaaacca aaaacaaat    24240 gtttattttt tacgtttctt taaccttgta taaattattc aacggctgtc aggcggaaaa    24300
caacggagta ttctcggatc attgctattt ttgtaaagtt tccgcgtccg cacgcactgt    24360
ggcaggagag cagggcgtgt gtatgtgtgt gtgtgtgtgt gtgtcctcac caaatcgtat    24420
aatgtttgtt accacaggcc gtcgctgttt acagaatctt cttttttatt cctcatttgg    24480
gtttctctct agctcgaggc ccaaaagccc acgagacctg tgggctgggc tgtggctctc    24540
agtgagatct gtggctttca gtgtggcccg tggctctcag tgggacctgt ggctgacagc    24600
```

-continued

```
atggcccgag gctgtcagtg ggactgtggc tgttgtctta gctgtagctc tcagtgggac    24660
ctgtggctgt ccatggtacc catggcaatt ggcccagcct gtggatgtca gtgggacctg    24720
tggctgtcag tggcactggc tgctgggctg gcgtactgtc agtgggaccc gtggtggccc    24780
gtgtgatgcc ggttacatag ctgttggtgg cgcctgtggt tgtcagtggg gttggaggtc    24840
actggtgtgg cctaaggctg gcacgtaaac ctggcccatg ccttggctag cccctccagc    24900
ctgctgtcct tgcttcctcc tgcccagaac tctccagaga tctccaactg tgctttcaga    24960
agtgcccttc ccaactgctc ggtttccctc ccgggacggc ggcagtattg aagcttgtga    25020
caagtgcctt cacacagacc ccctcccagc tgtcagcgtt tgccgtgggc accaggccgc    25080
tgcccacctg ccggccccgg ccaccctcct tgtgaaagtg catttctgta aatatgtaca    25140
tattaaatga atcactctgt atatttgatt taataactta aacgttttgg cctccctgtt    25200
ctttgggttc tgttcctttt ctccatgtgc agttgggaca taggtggaag tgggacatgg    25260
cctgagggtt gggtcatgtt gatgtggggt cttaagaggt caggtggttc tgttgacctc    25320
agcgcagtgg gtgacttggg cctcaggcac tgctggagtc ctactgtagt agttgacacc    25380
cgtttagtgg aaccctcctg gggagtaagg tttggggaat gtgtgtacct ggcctcctaa    25440
ctaaagagag ggctttatga aatgggacag tgctcagcaa aaatgaattc acagtctaag    25500 agacccaag tttgagagaa ggaagcccaa ggatgccaca gacttctagc cagtgccctc    25560
ttgtcttttt ttttttttt tttttttgg tttttcaaga cagggtttct ctgtgtagat    25620
ctggctgtcc tagaactcac tctataccag gctggcctcg aactcaagaa atccacctgc    25680
ctctgcctcc caagagctgg gattaaaggc atgcgccacc accgcccggc cctcttgtct    25740
ttatatctaa agtagaaact ataaggacta agcagtggtg gcctcggggc tgggcgttgg    25800
gagccaatcc tggagccaac tgccagcagt gcacagggtc tttgccctct ctggcagagg    25860
ctggcagacg gtacatagca aggccagcat ccacagctta ggagagcaga aagaatgctt    25920
ggctcttgag aggagggga ctcactatac ttcttgctgg gtaaaaagct ggtctggttc    25980
ctgccagggt tgtttctgga gatgccttgt gctgtttctc taatactgca gtgtgtgatg    26040
agtcttccca ccaggctctt cagagaagtg ctagaccagc agcaacactc gcaggcactg    26100
ggcagtcccg tcgcaagcct gccgaggagg cgtggtcttc atcctgactc ggtaataaga    26160
tttgaaagtt acgttcccgc cattatgctg gctaaaaaac accccctagg cttcaagttt    26220
cttcctaatt gataatttga ggccctcaag ggcatgatgg gaatgaatat caccctcccc    26280
tgttctagaa tgctacccac tggtctctta aatgacttta tatggtcctt gagcagacta    26340
cagccaagac cctcagagtg acgggaagcc cggcctgtga gcagcagcct gaagaacgga    26400
ctgcagagag gcctgcatgc agacgttagg attctcagtc accatccata gagcgaggct    26460
gctcaccgcg cccaaagcag atgcctcctc agaagcactg gcagccagag aagccgcaga    26520
aaggaagata tgtggaccgc aaatgaaaca gtgcaactag aagatgaccc tcaggagatg    26580
gccagcactt gaagagagag agcccagttg gtacggcgct tgctgcagaa gcacgggaga    26640
tgagttcagc cctggcagtt acggaccaag agaccctgcc tcaaactaaa ggtggatggc    26700
ttcagagaaa tgctctgcaa ggttaagctc aggcttccgt atgtattcac agtgcgcatg    26760
cacctacaca cacccataca tctctctcca cgtgagcaca catacacagt ccagatatag    26820
ctagggacaa cagataggaa tggcaacagc agccaagagt cctgggttga gggcctgtca    26880
cggtagtcct gctaccatga gaacacagtc ttaggacaag cagaggggtg tgtttgtgtg    26940
tgtgtatgtg tctatgtgtg tctgtgtgct cctgtgtgtg tgtgtgtgcc tgtgtgtgtg    27000
```

-continued

| | |
|---|---|
| tgtgtgtctg tctgtgtgtc tgtgtttgtg tctgtgtggg tgtgtaggta tgtctgtgtg | 27060 |
| tgtgcctgtg tctgtgtgag agtgtgtgtg tgtgtgcctg tgtgtatgta tctgtgtgca | 27120 |
| tgcctgtgtg tgtgtgtctg tgtgagtgtg tgtgtgtgcc tgtgtctgtc tgtctctgtc | 27180 |
| tgtgtatgtc tgtgtgtgtg tctatgtgtg tgcctgtggt gcgtctgtgt ctgctgctag | 27240 |
| atctttccta aagggtgtgt atggaatgct catgcatgga tggtgccagg aaggcccca | 27300 |
| tagaccaggt ggggctcata ggataaagtc ttaccatctg cctgtccaag gtaaggtgct | 27360 |
| gctggaggct gaagtgggag tggcacacgt gtgaggtgtg caccaagtgc atgagtagag | 27420 |
| ctggcgtctc tagaggccca catgcacaca tgctgcaggc ctgcacctcc cgccacatct | 27480 |
| actgtccagt gtctcaagtc cattgcaggt tccaggcttc tctggcaaac tataccctcc | 27540 |
| tcaagcttgg catggtcagt aactgagaat tagtcttcac tcaggtaacc tgctacccag | 27600 |
| caggaatggg gacagactgg ctacagctag cccatgctga tagcaatact aaacaggccc | 27660 |
| agattccctt gctcactcca cagtcccctc tgtctggagt ccctactggg tcataaatgc | 27720 |
| tggcccact ttcgttgtgg ccactgactg taggggaata taggccattc agctgacacc | 27780 |
| agggttccca tgggcaaggg ttcaacccag ggccaccctg ttcctatact agctcgccca | 27840 |
| ctctgcagag ctggacagtc agatgcacag aggctcatcc ctcaggaagg ccagccagat | 27900 |
| gtggtcagcc agatgtggct agctatctgc atgcactgtc acccggaggc tgttactggc | 27960 |
| cttgggtttt ctttccctgg ccgagtgaag agaaatccgt | 28000 |

<210> SEQ ID NO 10
<211> LENGTH: 4054
<212> TYPE: DNA
<213> ORGANISM: Mus musculus

<400> SEQUENCE: 10

| | |
|---|---|
| tcgaggcggc gatgcgggca cgcggctggg gacgcctgcc tcggcggctg ctgctgctac | 60 |
| tggttctgtg cgtgcaggcg acgcggccca tgggctattt cgagctgcag ctgagcgcgc | 120 |
| tgcggaacgt gaacggggag ctgctgagcg gcgcctgctg tgacggcgac ggccggacga | 180 |
| cgcgcgcggg gggctgcggc cgcgacgagt gcgacacgta cgtgcgcgtg tgccttaagg | 240 |
| agtaccaggc caaggtgacg cccacggggc cctgcagcta cggctacggc gccacgcccg | 300 |
| tgctgggtgg caactccttc tacctgccgc cggcgggcgc tgcgggggac cgagcgcgcg | 360 |
| cgcggtctcg gaccggcggc caccaggacc cgggcctcgt cgtcattccc tttcagttcg | 420 |
| cctggccgcg ttctttcacc ctcatcgtgg aggcctggga ctgggacaat gacaccactc | 480 |
| cagatgagga gctgctgatt gagcgggtgt cgcacgctgg catgatcaac cccgaggacc | 540 |
| gctggaagag cctgcacttc agcggccacg tggcacacct ggagctgcag atccgagtac | 600 |
| gctgtgatga gaactactac agtgccacct gcaacaagtt ctgccggccc cgcaacgact | 660 |
| tctttggcca ctatacctgc gaccagtacg gcaacaaggc ctgcatggat ggctggatgg | 720 |
| gcaaagaatg caaagaagcc gtgtgtaaac aaggatgtaa tttgctccac gggggatgca | 780 |
| ctgtgcctgg ggagtgcagg tgcagctacg gctggcaggg caagttctgt gacgagtgtg | 840 |
| tccctaccc tggctgcgtg catggcagct gtgtggagcc ctggcactgt gactgtgaga | 900 |
| ccaactgggg tggcctgctc tgtgacaaag acctgaacta ctgtggcagc caccaccct | 960 |
| gtgtcaacgg gggtacctgc atcaatgctg agcctgacca ataccctctgc gcctgcccag | 1020 |
| atggctactt gggcaagaac tgcgagcggg ctgagcacgc ctgtgcctcc aacccgtgtg | 1080 |

-continued

```
ccaatggggg ctcttgccac gaagtgccat ctggctttga atgccactgt ccgtcaggat   1140
ggaacggacc cacctgtgcg ctcgacattg atgagtgtgc ctctaaccca tgtgcagcgg   1200
gtggtacctg cgtggatcag gtggacggct tcgagtgcat ctgcccggag cagtgggtgg   1260
gggctacttg ccagctggac gccaatgagt gtgaagggaa gccgtgcctt aatgcttttt   1320
cttgcaaaaa cctgattggc ggctattact gtgattgcct cccgggctgg aagggcatca   1380
actgccaaat caacatcaac gattgccatg ggcagtgtca gcatggggc acctgcaagg    1440 acctggtcaa tgggtaccag tgtgtgtgcc cgcggggctt tggaggtcgc cattgcgaac   1500
tagagtacga caagtgtgcc agcagcccct gccgccgggg tggcatctgt gaggacctgg   1560
tggatggctt ccgctgccac tgcccacggg gcctctctgg gctgcactgt gaggtggaca   1620
tggatctctg tgaaccaagc ccctgcctca acggtgctcg ctgctacaac cttgagggtg   1680
actactactg cgcctgccca aagactttg gtggcaagaa ctgctcagtg cccagggaca    1740
catgccctgg cggggcatgt agagtgatca atggctgcgg gttcgaggca gggtccaggg   1800
cacgcggtgt cgcaccctct ggtatatgtg cccctcacgg gcactgcgtt agcctgcctg   1860
ggggaaactt ctcctgcatc tgtgacagcg gcttcacagg cacctactgc catgaaaaca   1920
ttgacgactg catgggccag ccctgccgca acggggcac gtgcattgac gaagtggact    1980
ccttccgctg cttctgcccc agtggctggg aaggagaact ctgtgacatc aatcccaacg   2040
actgcctccc cgacccctgc cacagccgcg gccgctgcta tgacctggtc aatgacttct   2100
actgtgcctg tgacgatggc tggaagggca agacctgcca ctcacgcgag ttccagtgtg   2160
acgcctacac ctgcagcaac ggtggcacat gctatgacag cggcgacacc ttccgctgcg   2220
cgtgccctcc gggctggaag ggcagcacct gcaccatcgc caagaacagc agctgtgtgc   2280
ccaatccctg tgtgaatgga ggcacctgcg tgggcagcgg agactctttc tcctgcatct   2340
gccgggatgg ctgggagggc cgcacctgca cacataacac caatgactgc aaccctctgc   2400
cctgctataa cggaggcatc tgtgttgatg gcgtcaactg gttccgctgc gagtgtgcgc   2460
ctggctttgc gggtcctgac tgccgtatca acattgatga gtgccagtcc tcgcccctgtg   2520 cctacggagc cacgtgtgtg gatgagatca acgggtaccg ctgcagctgc ccaccaggtc   2580
gttctggccc caggtgccag gaagtggtca tattcacgag gccctgctgg tcccggggaa   2640
tgtccttccc gcatgggagt tcctggatgg aagactgcaa cagctgccgc tgcctggatg   2700
gccaccggga ttgtagcaag gtatggtgcg gatggaagcc ttgcctgctc tctggtcagc   2760
ccagcgatcc gagtgcccag tgccccccag ggcagcaatg tcaggagaag gccgtgggtc   2820
agtgcttgca gccacccctgt gagaactggg gggagtgtac agcggaggag cctctgccac   2880
ccagcacccc ctgtcagcca cggagcagtc atttggacaa caactgtgcc cgactcacac   2940
tgcgcttcaa ccgtgatcaa gtgcctcagg gcaccaccgt gggcgctatc tgctctggaa   3000
tccgagcctt gcctgccacg agggcggcg cacacgaccg cctcctcctg ctgctttgtg    3060
atcgagcatc ctcgggggcc agtgctgtgg aggtggctgt gtctttcagc cctgcaaggg   3120
acctgcctga cagcagcctg atccagagca cagcccacgc catcgtggct gctatcactc   3180
agagaggaaa tagctcactg ctgctggctg tcaccgaggt caaggtggaa acagttgtta   3240
tgggtggctc ttccacaggt ctgttggtgc ccgtgctgtg cagcgtgttc agtgtgctgt   3300
ggctcgcctg tgtggttatc tgcgtatggt ggacacgaaa gcgcaggaaa gaacgtgaga   3360
ggagccggct accacgggat gagagcgcca acaaccagtg ggccccgctc aatcccatcc   3420
gcaaccccat tgagcggcca ggcggcagcg gtctgggaac tgggggccac aaggacatac   3480
```

| | |
|---|---|
| tctaccagtg caaaaacttc acaccgccgc cccgcagggc aggcgaggca ctgcccgggc | 3540 |
| cagctggcca tggggctggt ggggaggacg aggaggatga agagctgagc cgtggagatg | 3600 |
| gggactcccc agaggcagag aagttcatct cacacaagtt caccaaagac cccagctgct | 3660 |
| ccctcggaag gccagcccgc tgggctccag ggcccaaagt ggacaaccgc gccgtcagaa | 3720 |
| gtaccaagga cgtgcgccgt gctggcaggg aatagccagc caccaggctg cacccagaa | 3780 |
| cccttgctgg caccacgctg cctgccggac cataggaggc caaggccgtg tgcatagttt | 3840 |
| ctttattttg tgtaaaaaac aaaaccaaaa ccaaaaaaca aatgtttatt ttttacgttt | 3900 |
| ctttaacctt gtataaatta ttcaacggct gtcaggcgga aaacaacgga gtattctcgg | 3960 |
| atcattgcta tttttgtaaa gtttccgcgt ccgcacgcac tgtggcagga gagcagggcg | 4020 |
| tgtgtatgtg tgtgtgtgtg tgtgtgtcct cacc | 4054 |

<210> SEQ ID NO 11
<211> LENGTH: 16000
<212> TYPE: DNA
<213> ORGANISM: Mus musculus

<400> SEQUENCE: 11

| | |
|---|---|
| ctcgaggcca atgctaagtc atcatcttcc tctctcctcc ctcagcctca ggcctattct | 60 |
| ctggggaatc cactctgacc ccgggcaaaa actccaagta cgcagtttct ccaaggggca | 120 |
| gtagggaaaa gtgcgccgcg ccgcggggcg ctgcttgcta agcgggaaac cggttcctaa | 180 |
| ccgctggcgc ccctcgaggg gaggggagag ggcggaggtg cttctgcggc ggcatctgtc | 240 |
| cgaggcgggc gggaagctgc tgcattaaat tgtaaaatcg atttattgac cggcaggtgc | 300 |
| gagcagcggc agatggagag cagcgctgcc ggggcgcatc tgcggggagc ggcggcatcg | 360 |
| atcctggccc ccctctcaaa ccgttcgtct tgttcctttc tgtcggttca ctcctaaatg | 420 |
| cggggccaag gtccgagaat ctgcggcgcc ttagtggcta gagaagttga ttttccttcc | 480 |
| cctaccccc tcccagcctc taggccagag ctgcgccccc acggctgcca ggctctgcca | 540 |
| gccccactgc cccagttggc acgcggaggg ccagcctgac gcgtggcagc gccctgcggc | 600 |
| agatgaggca cgcgccggcc tcatttcaat gtgaatggat cgaatgaagc agccatgtgg | 660 |
| cagcaacagt ttgcaaatct cccccgcctt ctgtgcagctc cccggccgcg gctcgcagca | 720 |
| cgtggcccct tctccgcagc gaccgcagca gtgtctctca aggcttaagt gccccgcccc | 780 |
| gggcaggcct tcttccccgc ccccagcctg tcctgcgggc gcagtagctc agaccccacc | 840 |
| tcgcctctac ccgggtgcag tgtgccaggt ccagatcgtt gtcccctggg aagggtagcc | 900 |
| ggtgagagtt gagataacac cgcgctggag gtctccgagc tgcgctggtg gccctgggga | 960 |
| gcgcttgtag gcttctagct aagaaggagg cccgaagccg caccccagta acctgcagcc | 1020 |
| agtttgggga caccgctgaa agacagcttt ggcgttttg ttttgtttt tcagttccgg | 1080 |
| gggctggttc tgcataatgg gagaaactga aaaatagcgt gcacagtggc caagaggagg | 1140 |
| gaacagtaga agcaggagac ttgtagggag aaaggcttcg cctggcctcc ctgctactcg | 1200 |
| ggcttcaggg ctgggaaatg ttgaggactc tgtagagtcg aaaagctgta ggcccaagaa | 1260 |
| agagctgtag tttatgggaa cccaggtcgt atggcttaga gacctagggg ccatctacat | 1320 |
| cagggtcaga gccagatggc cctgactaga ggcctgctat gagcctcaca accttccatt | 1380 |
| cctttgagta accagaaggg tgttgtcttt cttccactag agagttggtt ctactaatta | 1440 |
| cggagtgaca gagaaggact ccagctgtgt ggtctggaga gacactgggc accacagctt | 1500 |

```
gagcccttgg tgcctagcaa tgtgggtaaa gattgatacc agcagatggg aactctagca   1560
gggacccaag gctaagggtg gtgttccgaa gaggaatatt gtaataggtg cttctggtaa   1620
aaagagagag agaaaaaatg aacactttt ccttcttagg tcagaaattt tataagtggg    1680
tgatttgtcc atttctgagg aaaatggtga ttccaacttt tgtttggccc ttcactattt   1740
gccaaatatt ttggcatact aatgtgtatg agggtaggcc acttccaaaa taatagatat   1800
cccgtgtggg agtctccctt gagagtcaag caagtgcccg cgttagagtt tctactaact   1860
cccaggctag gattttgaga tgaaaactgt tagatgaaaa ccattagagt caggtggggt   1920
tgcaagccca gctccaagga gagagggga gcaccctctg gcactccagg caggtctacg    1980
gtgcaaagag gatgcagaca gagaggattt ggaagtccac ttgccaggac cgccgggagg   2040
tacgccccga gctccccgtc cctcgggcct gggactcggc ttgcccataa cctacattaa   2100
ctcgctagtg cagcctgggc ccatctgccg gcccccgcct cacctcggtt ccccacgcca   2160
acccgctcgc gccagatggt ggctgggagg ggtggccgtg cgtggggac cccggagcct    2220
gtcgcctcac ctcaccccac ccccaccccc acgctcacaa cctcatgttt cttacccccc   2280
cccaattctc catcaccacc acccaagtca aaatatcaga ccatgttcgt cattggcagc   2340
tgttgggttc cacttccccc taccacggcc tccctggggc tggagccgcg tccctgctcc   2400
cctcaacccc cgcccgcact gatcttatcg tccgaccata gccagcaatc accacgcggg   2460
agggctgaca gctgaagcca cagggccccc accgctctca ctgtaggaga gagagagaga   2520
gagagagaga gagagagaga gagagagaga gagagagaga gagagagaga gagagagaga   2580
gagagagaga gagagagaga gagaaatcta gcaccccca aaactgggag aagccagccc    2640
tccccggtct gcagcctcgg gggagcacga cgggttctgg gaaagcagct gcagggtttg   2700
cgctcggagg ccacccggga gaggcgcgcg tgtgacatgg gtgaaaccac ccgaaactca   2760
aacaactcta tgcgcctcca gttccaccct acatcctgcc ctatgcagag agatctagac   2820
ctgatcagcc tcaagctctc tcaccttgcc tctcaagtgg cccaaggaaa ttctggaatt   2880
aagaaagttt cctccctact ccagcggagc taggggacgc gggtggggc caggatgagg    2940
atatggagac caagcgcgac ccaggtgaga taggcactga gggaaaagac tagaacctca   3000
ttaccataca gctgaggacc cccccccac ttcgagaacc acgcccccca cctctctttc    3060
gaacctctag tcctggctct agcacgagcc aggaggagt gggggtgggg acaaagaga     3120
gaaggcacgc gctgggcacg ccctgctgct tgaggtgaca cgcctaccag gtgcagagaa   3180
gaccagagtc ctagacgctt ggcccttgc cttgcttgga atagcagggg aaaggttaag    3240
gcgtcggatg gcttccctgc ggtgctgggg acgcgtggag ggtgggcaca cataggctgg   3300
aggccagcga ggcaggagct acctaaagtc tggaaggaa agggagatcc aaatcccctg    3360
gtcctgcttt ttgctttcct agtttaagct ttccccacct gctagaggac tgtaggtatc   3420
taatgcctgg atcaggtgca ccgcctacgg ggaccccta gagtttccac cccctggacc    3480
attcgggaac cacctcacct cccgccgcat cactgggcta ccctcctatc ctctggtggc   3540
gagggtctca gcctttaagc agacgatctc taaggactgc tcgccgggca cgcgcagagc   3600
tggaagccca gaagttggaa gaggggcggg gacctgcgcc ctactggctg gctgacaggg   3660
ggagcggcgg gggcggaggc cccctccggt gggtgctggg actgtagcca ctagaggcct   3720
ggaggggagg ggagagtgac cgtgagtctg tctgactgac aggctgcgaa gagcagccaa   3780
tatatataag aaaaggctctg gagcaagcag gtttcagtag cggcgctgct cgcaggctag   3840
gaacccgagg ccaagagctg cagccaaagt cacttgggtg cagtgtactc cctcactagc   3900
```

```
ccgctcgaga ccctaggatt tgctccagga cacgtactta gagcagccac cgcccagtcg    3960
ccctcacctg gattacctac cgaggcatcg agcagcggag tttttgagaa ggcgacaagg    4020
gagcagcgtc ccgaggggaa tcagcttttc aggaactcgg ctggcagacg ggacttgcgg    4080
gagagcgaca tccctaacaa gcagattcgg agtcccggag tggagaggac accccaaggg    4140
atgacgcctg cgtcccggag cgcctgtcgc tgggcgctac tgctgctggc ggtactgtgg    4200
ccgcaggtaa tgtctcacgt cctctccgcc ccctcccgca gcgctccggg cttgcgcccc    4260
ggccccggct gagcctgacc gctctcctcc ctccttctct cggtccctgt gcagcagcgc    4320
gctgcgggct ccggcatctt ccagctgcgg ctgcaggagt tcgtcaacca gcgcggtatg    4380
ctggccaatg ggcagtcctg cgaaccgggc tgccggactt tcttccgcat ctgccttaag    4440
cacttccagg caaccttctc cgagggaccc tgcacctttg caatgtctc cacgccggta    4500 ttgggcacca actccttcgt cgtcagggac aagaatagcg gcagtggtcg caaccctctg    4560
cagttgccct tcaatttcac ctggccggta agcacaactt aaatgcaccg ggagataacc    4620
gaagggaaag aagggagcgc cgggacacca gagctccttt ccaaagcgct ctctggagag    4680
ccccaagggc tctttctctt ctgccccgc cccctgttc tctcatagga tcatcccgga    4740
gaggctttgg ttagtctttc ctcccagttt cttccctttc cttctcccca attcttggga    4800
tacgaatttc attaccaaac ccccaacgcg gcgccgccg cccaccccc ggctctcact    4860 tacactcccg catccctcat ccctcccctg ccttctcagc tcgcgcgcag cgctgcgcga    4920
acaccagtta tgttgagccg agctccgtaa ctatatcctg caattagatt aattaaacag    4980
gctgctgcga ggcaccccct cctttccctc cctgctgata tcgctatctc taatgtcccc    5040
caccccccct tttgcttccc agggaacctt ctcactcaac atccaagctt ggcacacacc    5100
gggagacgac ctgcggccag gtgagtatct aacttctcgg ccacagggg gcgacatcac    5160 acagcgccga aagagttaac cagttatagg cggggtggg ggttggggac gcaggcttgg    5220
ggggtggggg ccaggacgct tagcttggcc ggagctgcgc cccgcgctgg acgctcggat    5280
tccgctcgct gcctggactc agagcacaat tgcgtttcct gcgggttatt tttggcgtgg    5340
gaacgcgggg agcacggcgg tgagaaaggc cgaggctgcc agcgccgctg acgggcctct    5400
tcctgtattt tacacctttt gcgaattccg ctcctttgga aagggaataa tggctttggg    5460
atgttgttct gacacagagg aaaaggatat ttcaccagca caacaattct cactttgaaa    5520
aggaaaaaga aaaccatta cctacgtcta gaacagaacc ccttgctccc agttctcgaa    5580
ccagaaaact tcccccttta aattttttct ttttttccat tttgacctct tttcctcttt    5640
cccctccgta tctgcctcca caaccctagg atatcttaac atccgtccat tgtacccttt    5700
tttgaatgct atcaagcccc ctgcacatgc acacacccag ggagactaag tagcaagatt    5760
ctgggaccct ctggcctgtg cttacttgca ggtagagtta atctagataa ttagagtgtg    5820
aactgaccac catagtcaca actaaagaga gagttggcag cagtcaactc tctctgaatc    5880
aggttggctt tctgaatcag gttctctgac caaagcctct ttctgcagag acttcgccag    5940
gaaactctct catcagccaa atcatcatcc aaggctctct tgctgtgggt aagatttggc    6000
gaacagacga gcaaaatgac accctcacca gactgagcta ctcttaccgg gtcatctgca    6060
gtgacaacta ctatggagag agctgttctc gcctatgcaa gaagcgcgat gaccacttcg    6120
gacattatga gtgccagcca gatggcagcc tgtcctgcct gccgggctgg actgggaagt    6180
actgtgacca gcgtaagtag ccaggccccc tgtgagaata gaagggatgg gattttccca    6240
```

-continued

```
agaaagcact cagaatgggt ctgtgctggg tctcaggacc agctggggat gctgtactgt    6300
acccttagtc tcagagcctc ctccgcagtg cttaagccta cagggtcctt attcttcatc    6360
ccatgcagtg tgatgttctc ccaccccctc gtccctggt cccctttaag ataaccatgg     6420
ctcctcttgg aggccaagag caggaagtga gcccagggga gcaggagagg aggttgaagc    6480
ttcagagtcc atggtaccac aacctcatcc agcccaattt cttttcctta gctatatgtc    6540
tttctggctg tcatgagcag aatggttact gcagcaagcc agatgagtgc atgtaagtgg    6600
ggacaggaaa cgggagtagg ggggctctcc cttgtgagca ggtctcccat cttacactgg    6660
gctcccctct tgtcttaaca gctgccgtcc aggttggcag ggtcgcctgt gcaatgaatg    6720
tatcccccac aatggctgtc gtcatggcac ctgcagcatc ccctggcagt gtgcctgcga    6780
tgagggatgg ggaggtctgt tttgtgacca aggtgagtaa gggaaggaga gatggggtgg    6840
cagggcctga aactagagat ggtgactgga caccttctt ggtggtcagt aactgacttt     6900
cctattattc tattattgtt caaggacaag tctcaggact tgtctatgtg cacatgtgtg    6960
tgtgtggtgt gtgtgtgtgt gtgtgaggta ttaggaatgg aactcagggt ctctaacata    7020
ctaggcaagc actccacctg tgagctctac cccagtccac tcactgcttt taaaggctct    7080
ttacaactga cctaaaatgg gatggtggga cattcttctc cacatcctaa agagccagga    7140
tgactaaaga ggccaggggt aacagcttgg cagcctgcag ctcatactca taaattctag    7200
caagactaaa gagaaaggga aggttagcgc tgttcctctt tctgccttgt agttacctat    7260
taacccctg agtgtttgct caccttccaa ggctctcccc taaacagctg tctggtgggg     7320
tgtgcccact ggctgccctg ggctgtagcc aatccaggcc tttggataga gggaacatgt    7380
aactgccttt ttagtgtggc cacagccacc tgcctttctc cagtgacact tgccaggcag    7440
ctgcctgagc tcacacagtc tctacctgac atttgagggt tgccactctt ttgcccacat    7500
aggagtcttt gagctccagt cttatagaga gggaatcttt tcttttacat ccctgtagcc    7560
agctgcatcc tcccatttc agggtcaagt actgtgcctg ctgccatggc aacaccacac     7620
gggcctggag aggatgggga gtgggtttgc caagctggaa aaagcttgcc taggtcctga    7680
cttattgcca gaatggaatt cagtccttgt atgtttcccc ccttctttcc cctcactcct    7740
ctcctcctcc ccccgcatc tctctctc tctgacacac agaacttctc ttctttattt       7800
ctgatcccaa cacacacaca cacacacaca cacatacata cacacacaca cacatataca    7860
cacccacac acacacacca cacacacaca cacatataca tacacacaca cacacatata    7920
cacccacac acaccaca ccacacacac atacacacat acatacacac acgtacacac       7980
acacacacca caccacacac accataccac acacacatac acacacacac acacccttc     8040
tgccgtccac atttgctccc aggtgacagt cgtttactca ctgtatgcaa acacaaccct    8100
tccaaccct ctgtttgctt tgtctggctc tccctccttg ttcttctcca acaagaaaac     8160
aaatagctat cattcaaaat acactttcaa cacctccttt agaagatgcc ggtcctgcct    8220
gtagtggctc ttatgccccc tcactctttc cacctgttga attttactc ttccttctag     8280
tccttccagg catgcacctc ctctatgaag ccttcctga cttcctcatt ggctaagggc     8340
ctcttcttca tcttgctctg gctggaaatg tttgtgagca tacccagcag gatgctggcc    8400
aattgtgctt tgtctcccac ttttggtata cgtatacagt ttagatgtag tttcaggcga    8460
gtgaatgctc aggatttcac aggcagagaa aggagggatg cctgggcctg gaaaacttat    8520
gagtttaaac ttctttgggc caaatacagg gtgatcttga gtgaggtgg gagagttcct    8580
ggtcccactc agctggtttt ttcctgtctc cacagatctc aactactgta ctcaccactc    8640
```

-continued

```
tccgtgcaag aatggatcaa cgtgttccaa cagtgggcca aagggttata cctgcacctg   8700
tctcccaggc tacactggtg agcactgtga gctgggactc agcaagtgtg ccagcaaccc   8760
ctgtcgaaat ggtggcagct gtaaggtgag acccacatca gctcaggaag gcacaggtct   8820
aaccaggtag catccagtca gtgtggttgt atatgcatgc atggatgggc actctggaca   8880
agtagaggct aggcaccaac ctcatacatc cttgtcccat cccccgggcc caactttagc   8940
ctgtttatat tctctctcca ggaccaggag aatagctacc actgcctgtg tccccaggc    9000 tactatggcc agcactgtga gcatagtacc ttgacctgcg cggactcacc ctgcttcaat   9060
gggggctctt gccgggagcg caaccagggg tccagttatg cctgcgaatg ccccccaac    9120 tttaccggct ctaactgtga aagaaagta  gacaggtgta ccagcaaccc gtgtgccaat   9180
ggtaagctct tctgtcacct taccaacctg ctgaagtggc ccggggcca  gagagcctga   9240 gaaaatcgtg aggagagaga cctgtctgct attgtggtca ggctgactga aacaggctcc   9300
tctttggttt ggagggtgaa gaactttatg cattatggag agtagggctt ggagaagaa    9360 ggtcatcgat aggctgtagg tgagggtagt gcccatctgt atgacctctg ttcttattcc   9420
atgggtgagc ctctgcctga caaggctagc ttgtgccctc ctcaggaagc cttgaattag   9480
aaaaaaggat gttggaggct tcacattccc ttttcaaggg aggctggtga tagagctctg   9540
taccttgaag cctcatcttc cccgacattc acctagaaca agtgtagcac aaagaatctg   9600
gaatacccag tgcttttga  tacacagaac acgttggtag gtgatggtct aagaggcagg   9660
caggcaggca ggcaaccatt caggagctga caaggccctg ggagtggcaa tgtgatctat   9720
tcgcactctc ctgtgcgtgg tctatactat tctaccttgc gtcttcccta ctgatcctca   9780
gggctacctg tgaaaggatc aaattctcca gtttagcagg tgaggaaacc aagactaagg   9840
gatcaggtga agctacaggt gtcagatccc ctgccagaga gatcaagcca agcatatctg   9900
tctgacccta aattctggaa gacgccagta actattatcc aatagcccac tgtggcatag   9960
agaaccagga ttaccccaga ggccaggact ttggagtctt tgtacagttc tctgtagaga  10020
gctctctgtc cacgcaggct gaacacacg  tggtagaaga gcttaagctc gtgggggaga  10080
cctcattccc ttcacccggg aatccacagg ctattgctga tgcgggtcct gtgcccttac  10140
aggaggccag tgccagaaca gaggtccaag ccgaacctgc cgctgccggc ctggattcac  10200
aggcacccac tgtgaactgc acatcagcga ttgtgcccga agtccctgtg cccacggggg  10260
cacttgccac gatctggaga atgggcctgt gtgcacctgc cccgctggct tctctggaag  10320
gcgctgcgag gtgcggataa cccacgatgc ctgtgcctcc ggaccctgct tcaatggggc  10380
cacctgctac actggcctct ccccaaacaa cttcgtctgc aactgtcctt atggctttgt  10440
gggcagccgc tgcgagtttc ccgtgggctt gccacccagc ttcccctggg tagctgtctc  10500
gctgggcgtg gggctagtgg tactgctggt gctcctggtc atggtggtag tggctgtgcg  10560
gcagctgcgg cttcggaggc ccgatgacga gagcagggaa gccatgaaca atctgtcaga  10620
cttccagaag gacaacctaa tccctgccgc ccagctcaaa aacacaaacc agaagaagga  10680
gctggaagtg gactgtggtc tggacaagtc caattgtggc aaaactgcaga accacacatt  10740 ggactacaat ctagccccgg gactcctagg acggggcggc atgcctggga agtatcctca  10800
cagtgacaag agcttaggag agaaggtgcc acttcggtta cacaggtaag ccacacctgg  10860
aagcccatag cttggtcaca gacccttcca tagtttgaca ggatctccta ggctgagtgg  10920
gaggctggca tcaggccttg gcaacttttta atcaagtaag attgtagtac tgacaagaag 10980
```

```
acactctagt tacatttatt ttttttttgtg gggggtgggg tggggttttt tgagacaaag    11040
tttctctgtg tagccctagc tgtcctggaa ctcactttgt agaccaggct ggcctccaac    11100
tcagaaattc acctgcctct gcctcccgag tgctgggatt aaaggcgtgc gtcaccacgc    11160
caggcttcta gttacatttc tatagggacc caggcacagt ggcacagact ttgtagccct    11220
acctacttag gctaagacag gaggattgct agtttgatgc tagcctgggt aacatagcag    11280
cagatcatgt ctcaaaaaca ttgagatggc tcagagagta aaggcacctg ctgccaagcc    11340
tggtgactga atctgacctc caggacctac atattagaag tcctttaact tctgagacgg    11400
tgcagtcaca cacacacaca cacacacaca cacacacaca cacacacaca cacacacaca    11460
cactaatttt taagaattct gctaggtggc cgggtgtggt ggcgcatgcc tttaatccca    11520
gcactcggga ggcagaggca ggcggatttc tgagttcgag gccagcctgg tctacaaagt    11580
gaattccagg acagccaggg ctacacagag aaaccctgtt tcaaaaaacc aaaaaaccaa    11640
aaaaaaaaaa aaaaaaaga attctgctag gaatctttta ctagggaagt ccctctcatt    11700
cattcattca ttcattcatt cattcattca ttcagtctta actcccaaat accaagtgtc    11760
cacagtatat ctctcgtggt ttccatcttc ccacagtagg gcttgtctct agtggcaata    11820
ctggcttttt tctggtttgg tcggctcctg tagctcccct agaggcctat tctaaccccc    11880
tgcccctgaa ggccagcact gagcatcctc cccgatgccc tccccgaacc cctccggacc    11940
cctgcagcac atccctaaa ggggatctct gggatctaga ctgacagctc cttgcttgtc    12000
ccctccctat tccttccttc ttacctccct gtcttctgtt ccttcagtga aagccagag    12060
tgtcgaatat cagccatttg ctctcccagg gactctatgt accaatcagt gtgtttgata    12120
tcagaagaga ggaacgagtg tgtgattgcc acagaggtga gttcttccct ctaagcatgt    12180
cccctcctgc tttgtgtggt gggaaaaaaa tgtcctgttc actagcaatc tcattcctga    12240
aggggtgggt cagagatctc ttctttggtg tgtagtggct cttgggtgcc ctgctggccc    12300
cattgccaca gagggagtga tactggagcc aggtggtatg cctgacttgg cagctgtgcc    12360
agggaaaggg acatagtcaa ggagcaggag aaggctcagg cagagctttc aggaactatt    12420
tcccacttgc ctttgggtga agacacaggg ttacctgtgt ctgcttcctc cattgaactc    12480
ctcttgtgtg tcttagagca ggaggctgag ggtactaact ccctcagtgg tgtctcctag    12540
agaggtccag agcacctctg gatcattgca taccgcccccc cccacccccc ggtataacca    12600
ttttcccatt ttgtatgtga tccccaggta taaggcagga gcctactcag acacccagct    12660
ccggcccagc agctgggcct tccttctgca ttgtttacat tgcatcctgt atgggacatc    12720
tttagtatgc acagtgctgc tctgcggagg aggaggaaat ggcatgaact gaacagactg    12780
tgaacccgcc aagagtcgca ccggctctgc acacctccag gagtctgcct ggcttcagat    12840
gggcagcccc gccaagggaa cagagttgag gagttagagg agcatcagtt gagctgatat    12900
ctaaggtgcc tctcgaactt ggacttgctc tgccaacagt ggtcatcatg gagctcttga    12960
ctgttctcca gagagtggca gtggccctag tgggtcttgg cgctgctgta gctcctgtgg    13020
gcatctgtat ttccaaagtg cctttgccca gactccatcc tcacagctgg gcccaaatga    13080
gaaagcagag aggaggcttg caaaggatag gcctcccgca ggcagaacag ccttggagtt    13140
tggcattaag caggagctac tctgcaggtg aggaaagccc gaggagggga cacgtgtgac    13200
tcctgcctcc aaccccagta ggtggagtgc cacctgtagc ctctaggcaa gagttggtcc    13260
ttcccctggt cctggtgcct ctgggctcat gtgaacagat gggcttaggg cacgcccctt    13320
ttgccagcca ggggtacagg cctcactggg gagctcaggg ccttcatgct aaactcccaa    13380
```

```
taagggagat ggggggaagg gggctgtggc ctaggccctt ccctccctca cacccatttc   13440
tgggcccttg agcctgggct ccaccagtgc ccactgctgc cccgagacca accttgaagc   13500
cgatcttcaa aaatcaataa tatgaggttt tgttttgtag tttatttttgg aatctagtat   13560 tttgataatt taagaatcag aagcactggc ctttctacat ttataacat tattttgtat    13620 ataatgtgta tttataatat gaaacagatg tgtacaggaa tttattactt cttgggtcct   13680
atctgtgtaa tagcagagtg gggatctttt tcctgcctcc ctatcccaaa ttcaaagccc   13740
cttatcttct cactgtggag tggctctgcg ggaacccccag ggcctgtgta tgcttgggtt  13800
tgccatgttg tgtagaaggg tggtctttgg gtagcctggc cttggcctcc tgtgcctggt   13860
gactttaagc ctgggtgttc ctactccact ttaagttcca tggggctatt ttcccctgcc   13920
ttgattttct cccattgagg aagagcctct cattacttat tcaaaagtgc tcttttatta   13980
gatcatgagt gtcgtcccct cgggtacttc ctcctgccac tgggggcattt gggttgtact  14040 ggcacctgca cttctggtac tagtgtggaa ctggtctggg ttgaggaagg ggaggggatc   14100
tgccctagat ttatcttttt cgaagttggg cagagctgaa gggatggctg aggctacaag   14160
gggagggtca gagccttccc cgagtctgtt gctcaggctg agacactgat gagggagttt   14220
ccagtctact ccatgcccag cttcctctaa ggcacaggat actcccctgg gtgctgattc    14280
tctctctgca gccaccaatg tcaccccatg tcaagcaaat tgagagaaac agcagcaacc   14340
accacccaaa gccagtgaga agctatgcag aggctcctag tcagtccaca gtaaagcaaa   14400
agcagaccca acagatgcct ttctcttagt ggaatccaac ttcaggaggc aaactactcc   14460
ccaaccccgg ctccagtatg gtggacagga gctgggtgcc cactggactc ctcatgtccc   14520
aggagtgtgc atatgctcca tccacggctt ggtcatcatt ccctgttgct ctcctgcaca   14580
cacagggtat caaacaggaa aacattcagg gaaccgttcc cacagcctga gccgacagca   14640 ggggaagaa caacaagacc tcactcttcc tgcccaaaat gaaacaggaa agcggcttct    14700
aggctctggg gggcggggga ggctgggctg ggacagaagt cgagatgacg aggctcccat   14760 gtggggaca ggtaggacac ccgcaggcct gcacgtccac accacccggc taggctatat    14820
tgccagatgg tcagagaaga gccctggagg ggtcctggtg gctctctcaa tccattttac   14880
cacctctgat accctagcca aggagctgag agagagccca acatatgaac actgccttct   14940
ggtgcaagtt ggaactcaga gcaagggact tagtgtggaa tgcttgtagg ggctccaacc   15000
tgcgcccacg ccacaccctc ttcccagcaa ctcagatgtg ggcccagttt ttacatggag   15060
tgtgaacaaa atatattctt ttcccagaa attcccgaag gtctctcctt gagaggccac    15120 acaccccat cacagaggta gggtacttaa tggtctcttg atcactccaa gagtccagga    15180
gacttggcat tcaaacaata ttagattata gctctagaag cattgtaaag cattctcaag   15240
agcctggcaa atgctcttct ttgaatattt tataatagaa ttagagttta gcagttcctc   15300
agtaacttgg agttacagtc ctgtctaaag aattagtctg acctcctggt gaccttcggg   15360
cctgaggaca gctgctttc cagagcttgt tggctggtga ccacctggag atccttgtcc    15420
tctaggttgg gagggccgc agtcatgcct ctcttggcta gccctggcac agttgatctc    15480
aactgggggc aaatgagtgt ataacggttc cgacccgctt cgactcaggc tagttgaggc   15540
cactagactc aagcaaggtg tacagtgttt cgcctctgcc agggtcccta cagggccctc   15600 cttttggctcc ctcttcccct ccctatgtta tctccacgtg gtctgcacc atctgtgggc   15660 ccaacccctcc gccccgtgt gacctgctgc attccgggaa ggagatggaa gtgattcagt   15720
```

```
caggaactg tgactgtccc ttcccgggga ggggatgctc ctgggagacc ccagaggtct    15780
ttccccaggg gccgcgccca cgaccccacg cgtcccaggg tggcctggac tgggttgggc    15840
agaggaagag gcaggtgcgt cgccggcccg tcggggtcag ctctccacct gccgccaccg    15900
ccgggcgccc gagagcgctg cggctccccg ccctctgctc tttgttacag cctgacttcc    15960
tgtttgtggt cgccgacccc ggcttacttc ccgggccggg                          16000

<210> SEQ ID NO 12
<211> LENGTH: 3451
<212> TYPE: DNA
<213> ORGANISM: Mus musculus

<400> SEQUENCE: 12
atataagaaa ggctctggag caagcaggtt tcagtagcgg cgctgctcgc aggctaggaa      60
cccgaggcca agagctgcag ccaaagtcac ttgggtgcag tgtactccct cactagcccg     120
ctcgagaccc taggatttgc tccaggacac gtacttagag cagccaccgc ccagtcgccc     180
tcacctggat tacctaccga ggcatcgagc agcggagttt ttgagaaggc gacaagggag     240
cagcgtcccg aggggaatca gcttttcagg aactcggctg gcagacggga cttgcgggag     300
agcgacatcc ctaacaagca gattcggagt cccgagtgg agaggacacc caagggatg      360 acgcctgcgt cccggagcgc ctgtcgctgg gcgctactgc tgctggcggt actgtggccg     420
cagcagcgcg ctgcgggctc cggcatcttc agctgcggc tgcaggagtt cgtcaaccag     480
cgcggtatgc tggccaatgg gcagtcctgc gaaccgggct gccggacttt cttccgcatc     540
tgccttaagc acttccaggc aaccttctcc gagggaccct gcacctttgg caatgtctcc     600
acgccggtat tgggcaccaa ctccttcgtc gtcagggaca gaatagcgg cagtggtcgc     660 aaccctctgc agttgccctt caatttcacc tggccgggaa ccttctcact caacatccaa     720
gcttggcaca caccgggaga cgacctgcgg ccagagactt cgccaggaaa ctctctcatc     780
agccaaatca tcatccaagg ctctcttgct gtgggtaaga tttggcgaac agacgagcaa     840
aatgacaccc tcaccagact gagctactct taccgggtca tctgcagtga caactactat     900
ggagagagct gttctcgcct atgcaagaag cgcgatgacc acttcggaca ttatgagtgc     960
cagccagatg gcagcctgtc ctgcctgccg ggctggactg ggaagtactg tgaccagcct    1020
atatgtcttt ctggctgtca tgagcagaat ggttactgca gcaagccaga tgagtgcatc    1080
tgccgtccag gttggcaggg tcgcctgtgc aatgaatgta tcccccacaa tggctgtcgt    1140 catggcaccct gcagcatccc ctggcagtgt gcctgcgatg agggatgggg aggtctgttt    1200
tgtgaccaag atctcaacta ctgtactcac cactctccgt gcaagaatgg atcaacgtgt    1260
tccaacagtg ggccaaaggg ttatacctgc acctgtctcc caggctacac tggtgagcac    1320
tgtgagctgg gactcagcaa gtgtgccagc aaccctgtc gaaatggtgg cagctgtaag    1380
gaccaggaga atagctacca ctgcctgtgt cccccaggct actatggcca gcactgtgag    1440
catagtacct tgacctgcgc ggactcaccc tgcttcaatg ggggctcttg ccgggagcgc    1500 aaccagggggt ccagttatgc ctgcgaatgc ccccccaact ttaccggctc taactgtgag    1560
aagaaagtag acaggtgtac cagcaacccg tgtgccaatg gaggccagtg ccagaacaga    1620
ggtccaagcc gaacctgccg ctgccggcct ggattcacag gcacccactg tgaactgcac    1680
atcagcgatt gtgcccgaag tccctgtgcc cacggggca cttgccacga tctggagaat    1740
gggcctgtgt gcacctgccc cgctggcttc tctggaaggc gctgcgaggt gcggataacc    1800
cacgatgcct gtgcctccgg accctgcttc aatggggcca cctgctacac tggcctctcc    1860
```

-continued

```
ccaaacaact tcgtctgcaa ctgtccttat ggctttgtgg gcagccgctg cgagtttccc    1920
gtgggcttgc cacccagctt ccctgggta gctgtctcgc tgggcgtggg gctagtggta     1980
ctgctggtgc tcctggtcat ggtggtagtg gctgtgcggc agctgcggct tcggaggccc    2040
gatgacgaga gcagggaagc catgaacaat ctgtcagact tccagaagga caacctaatc    2100
cctgccgccc agctcaaaaa cacaaaccag aagaaggagc tggaagtgga ctgtggtctg    2160
gacaagtcca attgtggcaa actgcagaac cacacattgg actacaatct agccccggga    2220
ctcctaggac ggggcggcat gcctgggaag tatcctcaca gtgacaagag cttaggagag    2280
aaggtgccac ttcggttaca cagtgagaag ccagagtgtc gaatatcagc catttgctct    2340
cccagggact ctatgtacca atcagtgtgt ttgatatcag aagagaggaa cgagtgtgtg    2400
attgccacag aggtataagg caggagccta ctcagacacc cagctccggc ccagcagctg    2460
ggccttcctt ctgcattgtt tacattgcat cctgtatggg acatctttag tatgcacagt    2520
gctgctctgc ggaggaggag gaaatggcat gaactgaaca gactgtgaac ccgccaagag    2580
tcgcaccggc tctgcacacc tccaggagtc tgcctggctt cagatgggca gccccgccaa    2640
gggaacagag ttgaggagtt agaggagcat cagttgagct gatatctaag gtgcctctcg    2700
aacttggact tgctctgcca acagtggtca tcatggagct cttgactgtt ctccagagag    2760
tggcagtggc cctagtgggt cttggcgctg ctgtagctcc tgtgggcatc tgtatttcca    2820
aagtgccttt gcccagactc catcctcaca gctgggccca atgagaaag cagagaggag     2880 gcttgcaaag gataggcctc ccgcaggcag aacagcttg gagtttggca ttaagcagga     2940
gctactctgc aggtgaggaa agcccgagga ggggacacgt gtgactcctg cctccaaccc    3000
cagtaggtgg agtgccacct gtagcctcta ggcaagagtt ggtccttccc ctggtcctgg    3060
tgcctctggg ctcatgtgaa cagatgggct tagggcacgc ccctttgcc agccaggggt     3120 acaggcctca ctggggagct cagggccttc atgctaaact cccaataagg gagatggggg    3180 gaaggggct gtggcctagg cccttccctc cctcacaccc atttctgggc ccttgagcct     3240
gggctccacc agtgcccact gctgccccga gaccaacctt gaagccgatc ttcaaaaatc    3300
aataatatga ggttttgttt tgtagtttat tttggaatct agtattttga taatttaaga   3360
atcagaagca ctggcctttc tcattttat aacattattt tgtatataat gtgtatttat    3420
aatatgaaac agatgtgtac aggaatttat t                                   3451
```

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
accgtaatcg catcgtactg                                                   20

<210> SEQ ID NO 14
<211> LENGTH: 23
<212> TYPE: DNA
<213> ORGANISM: Artificial sequence
<220> FEATURE:
<223> OTHER INFORMATION: Primer

<400> SEQUENCE: 14
tgctatcagg ttgaatagtg tca                                               23

<210> SEQ ID NO 15
<211> LENGTH: 23
<212> TYPE: DNA
<213> ORGANISM: Artificial sequence
<220> FEATURE:
<223> OTHER INFORMATION: Probe

<400> SEQUENCE: 15
cctggccgag gtcctacact ttg                                              23

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
cgtggtcttc aagcgtgatg                                                  20

<210> SEQ ID NO 17
<211> LENGTH: 18
<212> TYPE: DNA
<213> ORGANISM: Artificial sequence
<220> FEATURE:
<223> OTHER INFORMATION: Primer

<400> SEQUENCE: 17
ggtgcttgcg cagctctt                                                    18

<210> SEQ ID NO 18
<211> LENGTH: 26
<212> TYPE: DNA
<213> ORGANISM: Artificial sequence
<220> FEATURE:
<223> OTHER INFORMATION: Probe

<400> SEQUENCE: 18
ccagcagatg atcttcccgt actatg                                           26

<210> SEQ ID NO 19
<211> LENGTH: 22
<212> TYPE: DNA
<213> ORGANISM: Artificial sequence
<220> FEATURE:
<223> OTHER INFORMATION: Primer

<400> SEQUENCE: 19
cgacttcact ttcgaatgca ac                                               22

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
caccatccac acaaactcct                                                  20

<210> SEQ ID NO 21
<211> LENGTH: 24
<212> TYPE: DNA
<213> ORGANISM: Artificial sequence
<220> FEATURE:
<223> OTHER INFORMATION: Probe

<400> SEQUENCE: 21
aatatcgacg actgccccaa ccac                                              24

<210> SEQ ID NO 22
<211> LENGTH: 20
<212> TYPE: DNA
<213> ORGANISM: Artificial sequence
<220> FEATURE:
<223> OTHER INFORMATION: Primer

<400> SEQUENCE: 22
ctttggagtt tgccgtgatg                                                   20

<210> SEQ ID NO 23
<211> LENGTH: 21
<212> TYPE: DNA
<213> ORGANISM: Artificial sequence
<220> FEATURE:
<223> OTHER INFORMATION: Primer

<400> SEQUENCE: 23
tcattgatct ccacgttgca g                                                 21

<210> SEQ ID NO 24
<211> LENGTH: 25
<212> TYPE: DNA
<213> ORGANISM: Artificial sequence
<220> FEATURE:
<223> OTHER INFORMATION: Probe

<400> SEQUENCE: 24
accgttatga ctgtgtctgt cagcc                                             25

<210> SEQ ID NO 25
<211> LENGTH: 21
<212> TYPE: DNA
<213> ORGANISM: Artificial sequence
<220> FEATURE:
<223> OTHER INFORMATION: Primer

<400> SEQUENCE: 25
ctgactgccg tatcaacatt g                                                 21

<210> SEQ ID NO 26
<211> LENGTH: 21
<212> TYPE: DNA
<213> ORGANISM: Artificial sequence
<220> FEATURE:
<223> OTHER INFORMATION: Primer

<400> SEQUENCE: 26
gcctcgtgaa tatgaccact t                                                 21

<210> SEQ ID NO 27
<211> LENGTH: 21
<212> TYPE: DNA
<213> ORGANISM: Artificial sequence
<220> FEATURE:
<223> OTHER INFORMATION: Probe

<400> SEQUENCE: 27
cagtcctcgc cctgtgccta c                                                 21

<210> SEQ ID NO 28

```
<211> LENGTH: 23
<212> TYPE: DNA
<213> ORGANISM: Artificial sequence
<220> FEATURE:
<223> OTHER INFORMATION: Primer

<400> SEQUENCE: 28
gccttccttc tgcattgttt aca                                              23

<210> SEQ ID NO 29
<211> LENGTH: 19
<212> TYPE: DNA
<213> ORGANISM: Artificial sequence
<220> FEATURE:
<223> OTHER INFORMATION: Primer

<400> SEQUENCE: 29
ctccgcagag cagcactgt                                                   19

<210> SEQ ID NO 30
<211> LENGTH: 23
<212> TYPE: DNA
<213> ORGANISM: Artificial sequence
<220> FEATURE:
<223> OTHER INFORMATION: Probe

<400> SEQUENCE: 30
tgcatcctgt atgggacatc ttt                                              23

<210> SEQ ID NO 31
<211> LENGTH: 20
<212> TYPE: DNA
<213> ORGANISM: Artificial sequence
<220> FEATURE:
<223> OTHER INFORMATION: Primer

<400> SEQUENCE: 31
caaccagtgt gatgagcagt                                                  20

<210> SEQ ID NO 32
<211> LENGTH: 21
<212> TYPE: DNA
<213> ORGANISM: Artificial sequence
<220> FEATURE:
<223> OTHER INFORMATION: Primer

<400> SEQUENCE: 32
gttgtctttg aagtggtctg c                                                21

<210> SEQ ID NO 33
<211> LENGTH: 29
<212> TYPE: DNA
<213> ORGANISM: Artificial sequence
<220> FEATURE:
<223> OTHER INFORMATION: Probe

<400> SEQUENCE: 33
ttgtcatact tgcacgtctt gctattcct                                        29

<210> SEQ ID NO 34
<211> LENGTH: 15
<212> TYPE: DNA
<213> ORGANISM: Artificial sequence
<220> FEATURE:
<223> OTHER INFORMATION: Primer

<400> SEQUENCE: 34
```
tcgccgcttg ctgca                                                    15

<210> SEQ ID NO 35
<211> LENGTH: 17
<212> TYPE: DNA
<213> ORGANISM: Artificial sequence
<220> FEATURE:
<223> OTHER INFORMATION: Primer

<400> SEQUENCE: 35
atcggccgtg atgtcga                                                  17

<210> SEQ ID NO 36
<211> LENGTH: 23
<212> TYPE: DNA
<213> ORGANISM: Artificial sequence
<220> FEATURE:
<223> OTHER INFORMATION: Probe

<400> SEQUENCE: 36
ccatggtcaa ccccaccgtg ttc                                           23

<210> SEQ ID NO 37
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 37
aagtatcact ctcccc                                                   16

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 38
ggcacattca ctagtt                                                   16

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 39
gtaatgagat tcaacc                                                   16

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 40
gtaagattgg gatgct                                                   16

<210> SEQ ID NO 41
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 41
cagcattaca taacga                                                    16

<210> SEQ ID NO 42
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 42
gcaatatagg gctcgg                                                    16

<210> SEQ ID NO 43
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 43
atgtacttgg cccagc                                                    16

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 44
gcgaatgaag ctgtgc                                                    16

<210> SEQ ID NO 45
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 45
gcttatgtgg ctatga                                                    16

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
gcgatactga gatggc                                                    16

<210> SEQ ID NO 47
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 47
gtgtgacacg ggttca                                                    16

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 48
cagcataatc ataccc                                                    16

<210> SEQ ID NO 49
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 49
ggattaccaa gctggc                                                    16

<210> SEQ ID NO 50
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 50
agaataccag ggagcc                                                    16

<210> SEQ ID NO 51
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 51
tgcattggag ttccag                                                    16

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
cacaatgaga cagcgc                                                    16

<210> SEQ ID NO 53
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 53 agttttgca aataga                                                     16

<210> SEQ ID NO 54
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 54
gagtttttgc aaatag                                                         16

<210> SEQ ID NO 55
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 55
tgtgatccgt atcctt                                                         16

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
cagtattgtc cctgga                                                         16

<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 57
ctgttcaagc aatgac                                                         16

<210> SEQ ID NO 58
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 58
tgtcatgtgt caagca                                                         16

<210> SEQ ID NO 59
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 59
ccagactagc ggttcc                                                         16

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
tggacaatgg cttggc                                                         16

```
<210> SEQ ID NO 61
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 61
accacaacag ttctga                                                    16

<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 62
actcaaaggg caggca                                                    16

<210> SEQ ID NO 63
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 63
atacaccttc ataacc                                                    16

<210> SEQ ID NO 64
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 64
gtaggagttg tcacgg                                                    16

<210> SEQ ID NO 65
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 65
ctcgcagtgg atgcca                                                    16

<210> SEQ ID NO 66
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 66
ctcaatctgc ggtggg                                                    16

<210> SEQ ID NO 67
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 67
cgattttgga aagaag                                                   16

<210> SEQ ID NO 68
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 68
aagttgtcag gaaggg                                                   16

<210> SEQ ID NO 69
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 69
acacttgttc ctttag                                                   16

<210> SEQ ID NO 70
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 70
caaggtctgg gtcaca                                                   16

<210> SEQ ID NO 71
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 71
aacatcttag gatgcg                                                   16

<210> SEQ ID NO 72
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 72
caagactgac agtcca                                                   16

<210> SEQ ID NO 73
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 73
gcaagaaaga tctctc                                                   16

<210> SEQ ID NO 74
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 74
atgtcaagtc aacaaa                                                     16

<210> SEQ ID NO 75
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 75
cttcatgttt ccacaa                                                     16

<210> SEQ ID NO 76
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 76
gatcaattct ctctct                                                     16

<210> SEQ ID NO 77
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 77
gacaaaggat ttaggg                                                     16

<210> SEQ ID NO 78
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 78
ctgcgctcgc attgag                                                     16

<210> SEQ ID NO 79
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 79
ggacgcagag cgggca                                                     16

<210> SEQ ID NO 80
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 80
```
gtctgaatga cactcg 16

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
gtcgatccca tcctgg 16

<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 82
gcgattgatg ccgtcc 16

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
catacacggc ttggag 16

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
tgtattccca gcagcg 16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
ggttacacgg ttgcgg 16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
gggcaactgg actgcg 16

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
tggtacatag agggca                                                    16

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 88
aggtatgggt gctcgc                                                    16

<210> SEQ ID NO 89
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
caggaagcag gttcgg                                                    16

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
gactgatggc atggcc                                                    16

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 91
ggttactgtt cgcagg                                                    16

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
acaagacata gcccca                                                    16

<210> SEQ ID NO 93
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 93
tacaagacat agcccc                                                    16

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
gtacaagaca tagccc                                                    16

<210> SEQ ID NO 95
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 95
agtacaagac atagcc                                                    16

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
tgagtctagt catgca                                                    16

<210> SEQ ID NO 97
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 97
gttatataat cttcca                                                    16

<210> SEQ ID NO 98
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 98
tgcaagattg cacagg                                                    16

<210> SEQ ID NO 99
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 99
taatataggt gacagc                                                    16

<210> SEQ ID NO 100
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 100
gataatatag gtgaca                                                    16

<210> SEQ ID NO 101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 101
tcagtatgcc tcttgc                                                    16

<210> SEQ ID NO 102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 102
gtgtctcacc ccaggg                                                    16

<210> SEQ ID NO 103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 103
agtgtctcac cccagg                                                    16

<210> SEQ ID NO 104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 104
atagttgtca cacagt                                                    16

<210> SEQ ID NO 105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 105
agcgatatta aatggc                                                    16

<210> SEQ ID NO 106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 106
ggtgtgctga atgcta                                                    16

<210> SEQ ID NO 107
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 107
gctactgcgg tcactg                                                 16

<210> SEQ ID NO 108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 108
tgctactgcg gtcact                                                 16

<210> SEQ ID NO 109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 109
aatgctactg cggtca                                                 16

<210> SEQ ID NO 110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 110
gaatgctact gcggtc                                                 16

<210> SEQ ID NO 111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 111
ctgaatgcta ctgcgg                                                 16

<210> SEQ ID NO 112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 112
gctgaatgct actgcg                                                 16

<210> SEQ ID NO 113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 113
```
gcacataaat tactgg                                           16

<210> SEQ ID NO 114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 114
atctatgtca ctttgg                                           16

<210> SEQ ID NO 115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 115
ccagatcggc actcat                                           16

<210> SEQ ID NO 116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 116
ctgcacagcg acactc                                           16

<210> SEQ ID NO 117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 117
tgccatcgac acagcg                                           16

<210> SEQ ID NO 118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 118
ggcacaagca cacgag                                           16

<210> SEQ ID NO 119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 119
ccgcagggtg aggcac                                           16

<210> SEQ ID NO 120
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 120
gcacaggcgg ccactc                                                     16

<210> SEQ ID NO 121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 121
tgtatgtcgc acaggc                                                     16

<210> SEQ ID NO 122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 122
tgtctatgca ctttcc                                                     16

<210> SEQ ID NO 123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 123
cgcagcggaa atgccc                                                     16

<210> SEQ ID NO 124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 124
gtgttctcgc tttcgc                                                     16

<210> SEQ ID NO 125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 125
tcaagtctgt gaccac                                                     16

<210> SEQ ID NO 126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 126
caggattgag cagacc                                                     16
```

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 127
gtcttatctg gaatgc                                                    16

<210> SEQ ID NO 128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 128
agcaagatga tgcggg                                                    16

<210> SEQ ID NO 129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 129
tcactctgtg agagcc                                                    16

<210> SEQ ID NO 130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 130
tcgaagctca accctg                                                    16

<210> SEQ ID NO 131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 131
gtcgaagctc aaccct                                                    16

<210> SEQ ID NO 132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 132
tgtcgaagct caaccc                                                    16

<210> SEQ ID NO 133
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 133
tgcaactatg caatga                                                    16

<210> SEQ ID NO 134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 134
gtagtcaaac aatcct                                                    16

<210> SEQ ID NO 135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 135
tcctctcatg gatcgg                                                    16

<210> SEQ ID NO 136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 136
tcagtattat ctgtta                                                    16

<210> SEQ ID NO 137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 137
gaatattggt tcagta                                                    16

<210> SEQ ID NO 138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 138
ggaatattgg ttcagt                                                    16

<210> SEQ ID NO 139
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 139
gtgatctcac tgccag                                                    16

```
<210> SEQ ID NO 140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 140
tgtagtgcca ctgcct                                                       16

<210> SEQ ID NO 141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 141
acaattctat ggtctc                                                       16

<210> SEQ ID NO 142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 142
ctacctgtgt accaca                                                       16

<210> SEQ ID NO 143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 143
actacctgtg taccac                                                       16

<210> SEQ ID NO 144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 144
acttagatgc taccag                                                       16

<210> SEQ ID NO 145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 145
gcaactcatg tccaca                                                       16

<210> SEQ ID NO 146
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 146
taccacccgc tgcaca                                                   16

<210> SEQ ID NO 147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 147
ctctagttcg caatgg                                                   16

<210> SEQ ID NO 148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 148
cgtactctag ttcgca                                                   16

<210> SEQ ID NO 149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 149
gtagtagtca ccctca                                                   16

<210> SEQ ID NO 150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 150
tctacatgcc ccgcca                                                   16

<210> SEQ ID NO 151
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 151
tcgaacccgc agccat                                                   16

<210> SEQ ID NO 152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 152
gtccaccata cgcaga                                                   16

<210> SEQ ID NO 153
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 153
cagtacgcca gcccag                                                     16

<210> SEQ ID NO 154
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 154
agtagttcag gtctgg                                                     16

<210> SEQ ID NO 155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 155
tgttagtgtc tcttcc                                                     16

<210> SEQ ID NO 156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 156
acaataaaac atccgc                                                     16

<210> SEQ ID NO 157
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 157
caccataaga cttcct                                                     16

<210> SEQ ID NO 158
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 158
gcttgatacc cccct                                                      16

<210> SEQ ID NO 159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 159
```
ctaaccaaaa gtctct                                                      16

<210> SEQ ID NO 160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 160
agaacttaag caggag                                                      16

<210> SEQ ID NO 161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 161
gttactcaca gcctag                                                      16

<210> SEQ ID NO 162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 162
cgcttcggat gatcca                                                      16

<210> SEQ ID NO 163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 163
tttatactcg ctcagc                                                      16

<210> SEQ ID NO 164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 164
tgccatctaa atcccc                                                      16

<210> SEQ ID NO 165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 165
tataagtact ctctct                                                      16

<210> SEQ ID NO 166
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 166
tcctatctgt tggcag                                                     16

<210> SEQ ID NO 167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 167
aacttatccc actgcc                                                     16

<210> SEQ ID NO 168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 168
gataattatc cctggc                                                     16

<210> SEQ ID NO 169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 169
gtatgagcag ctctgc                                                     16

<210> SEQ ID NO 170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 170
cacttgaggg tatctc                                                     16

<210> SEQ ID NO 171
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 171
tactagcttg gatcct                                                     16

<210> SEQ ID NO 172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 172
gagaatagcc agaact                                                     16
```

<210> SEQ ID NO 173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 173
tcctactgtg ttcacc                                                   16

<210> SEQ ID NO 174
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 174
tgcagaatca tgtcag                                                   16

<210> SEQ ID NO 175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 175
gacaatcatc cctacc                                                   16

<210> SEQ ID NO 176
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 176
acacatcact aatgcc                                                   16

<210> SEQ ID NO 177
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 177
gtggatggac gatttc                                                   16

<210> SEQ ID NO 178
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 178
gtaagtaggt ggccag                                                   16

<210> SEQ ID NO 179
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 179
aagttaagca gaaccc                                                      16

<210> SEQ ID NO 180
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 180
gttggaatgg gaccta                                                      16

<210> SEQ ID NO 181
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 181
agaagtacga ggaagg                                                      16

<210> SEQ ID NO 182
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 182
gttatagcca ctgccc                                                      16

<210> SEQ ID NO 183
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 183
gctcacagtg ctcaccagtg                                                  20

<210> SEQ ID NO 184
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 184
gcaaatccta gggtct                                                      16

<210> SEQ ID NO 185
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 185
gctcgatgcc tcggta                                                      16

<210> SEQ ID NO 186
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 186
agggatgtcg ctctcc                                                   16

<210> SEQ ID NO 187
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 187
cgctgctgcg gccaca                                                   16

<210> SEQ ID NO 188
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 188
ggcaactgca gagggt                                                   16

<210> SEQ ID NO 189
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 189
gtccagcccg gcaggc                                                   16

<210> SEQ ID NO 190
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 190
ggatacattc attgca                                                   16

<210> SEQ ID NO 191
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 191
tcacagtgct caccag                                                   16

<210> SEQ ID NO 192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 192
```
ggtactatgc tcacag 16

<210> SEQ ID NO 193
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 193
ccattggcac acgggt 16

<210> SEQ ID NO 194
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 194
ctccattggc acacgg 16

<210> SEQ ID NO 195
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 195
cgctgatgtg cagttc 16

<210> SEQ ID NO 196
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 196
gtccggaggc acaggc 16

<210> SEQ ID NO 197
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 197
gcatgccgcc ccgtcc 16

<210> SEQ ID NO 198
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 198
ggctgatatt cgacac 16

<210> SEQ ID NO 199
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 199
ggcaatcaca cactcg                                                    16

<210> SEQ ID NO 200
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 200
tctgagtagg ctcctg                                                    16

<210> SEQ ID NO 201
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 201
gttcatgcca tttcct                                                    16

<210> SEQ ID NO 202
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 202
tcgagaggca ccttag                                                    16

<210> SEQ ID NO 203
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 203
tccaagttcg agaggc                                                    16

<210> SEQ ID NO 204
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 204
gccaagaccc actagg                                                    16

<210> SEQ ID NO 205
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 205
ctcatttggg cccagc                                                    16
```

<210> SEQ ID NO 206
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 206
cttaatgcca aactcc                                                     16

<210> SEQ ID NO 207
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 207
tagcatgaag gccctg                                                     16

<210> SEQ ID NO 208
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 208
gaagatcggc ttcaag                                                     16

<210> SEQ ID NO 209
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 209
gatttttgaa gatcgg                                                     16

<210> SEQ ID NO 210
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 210
ggtgttcgcg cagcgc                                                     16

<210> SEQ ID NO 211
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 211
tggcaagtgt cactgg                                                     16

<210> SEQ ID NO 212
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 212
gcacagtact tgaccc                                                    16

<210> SEQ ID NO 213
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 213
accattggca cacggg                                                    16

<210> SEQ ID NO 214
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 214
agcactgggt attcca                                                    16

<210> SEQ ID NO 215
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 215
ggcttgatct ctctgg                                                    16

<210> SEQ ID NO 216
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 216
tgtgactgca ccgtct                                                    16

<210> SEQ ID NO 217
<211> LENGTH: 5440
<212> TYPE: DNA
<213> ORGANISM: Mus musculus

<400> SEQUENCE: 217
ggctgggggt gggggtggc gatgggggt ggggacgggg aagggggccc acgaattccc        60
cgatcgccac ccttgggcgt gcgctccctg cccggaagga ttgaccttgg ccggggcggg     120
ggaagggagg ccagcgcggg ggctcagctt tcggccgcc gccccgcgg attcctggct      180 cgcccgggcc ggaggagggg gccccggaca cacggacgca cgcacacacc ccacacgcag    240
cgcgcgccaa tgagccctgg ccaggcgcag ggggcgggt tttcccaggc tcgagcacag    300
cagctgctat ttaccttctt ggcttctccc ggggaccaga ggcggccccc gctccctccc    360
ggccggccgc cgccggcccc cgcctccctg ccccgggggc gcgcgcacac acactcacac    420
acgcacgcac acacacacat cctctgggcc ccggccgcag ccgcggcggc aataaaacat    480
cctggcacgt gctccgactc caggcgcgcc ctcgccggcc ggctgatgtc aaactgcagc    540

-continued

```
tcggctggtg gagctcttaa agggctcgcg cgcggggcgc cgaggccgcc ttggccgccc      600
gcggggtgag gaggggagag ccccgactcc cttgcccgcc gtctatccgt attgccaact      660
gggagcctgc ggggagaaag gtagagagag tggcggagga acgagcgcgc ccctcctgtc      720
gcattgctat caaagccccc cttgttcatt tttttttcg tttgaaattc catttccttt       780
ctgcccagta ggaaattatt ctgattgttt tctggagaag cgtgaggtcc aaggttgcaa      840
ttccaagaga ggaatgaatg ggctagaggg agacaagcat ccaaaagaca ccttgctccg      900
aaaaccctgg ctgtgaaggc atttgggggg acggtaaggg catgtttagc gtgtggggtt      960
tagtatctcc ccaacctcat gagcagtttt gactccccta acatacaga gttcgagcgg      1020
gaattccgga agacattaga gtaacacatc ctctttacct tgttccctcc ttttttcaat     1080
cactaaattt tgtcttggcc tatatctgtt caaaatattt ttcaaatgaa cttattatac     1140
aaagtagtta tattgcatgc agcaagaaca ataaaaacca aaggcctggc cacaaaagaa     1200
atagactaga ctaaaactaa gcaaagccca gaggaaagag ttagcaaagg gttaaaatcc     1260
ttttgattga cgttgtagcc tccggtgccc cgggctcagg cgcgcgccat tggccgccag     1320
accttgtgcc tagcggccaa tgggggggcg cagtccacga gcggtgccgc gtgtctcttc     1380
ctcccattgg ctgaaagtta ctgtgggaaa gaaagtttgg gaagtttcac acgagccgtt     1440
cgcgtgcagt cccagatata tatagaggcc gccaggggct gcggatcaca caggatctgg     1500
agctggtgct gataacagcg gaatccctg tctacctctc tccttggtcc tggaatagtg      1560
ctaccgatca ctaagtagcc ctaagacata ataaaccttc aactgctcag tagttttct     1620
tatgaaagtc aagtaaaagg acgtaagcaa aaaaaaatta ttttttttt gcgtgaagga     1680
ttccaaaaat aaaattctct ggggactgag aagaaaaaa aaaaaaaac gaaaatgcca     1740
gctgatataa tggagaaaaa ttcctcctcc ccggtggctg ctaccccagc cagtgtcaac     1800
acgacaccgg acaaaccaaa gacggcctct gagcacagaa aggtaagaca gtacctgcgt     1860
ctagaaatta agtgggttgt gcacagcggg actccttta cttttctctt aaaacctcgg     1920
ggtgaaatgg cagatcccgt gggaactcag gacctctttt ctcccccttt gcagtcatca     1980
aagcctatca tggagaagag gcgaagggca agaataaatg aaagtctaag ccaactgaaa     2040
acactgattt tggatgcact taagaaagat gtaagtgagc aatgcttttt tttatttta     2100
attacgaatg gaatggcatt tcccaggcac aaagaactaa gctcttagcc tgctgcatgt     2160
ggatcttacc ccgccagcac tacgttccca ctggcgggag agaggccgcc gggccctggg     2220
atgtgggaca tgcgggcggg gaccttcaga actcggaggc agctgacaag gaggactgac     2280
tttcatccct tgttttttct gcgcagagct cccggcattc caagctagag aaggcagaca     2340
ttctggaaat gactgtgaag cacctccgga acctgcagcg ggcgcagatg accggtaagg     2400
accgcgcgtg cgtcccctct ctgcgggtgt ccctctcggc ccgcggtgat tcttccaga     2460
cttccgcccg cggttgtgag aggcattcag ctacatttta ctgccttggc tcactccgcg     2520
ttcccacggt ctgggtctta tttatagcca cagctcccaa gttgttactg ctccggaaat     2580
ggagggagag gctgtagccg agaagggtgg tgggcagctt ggctgtggta gaagccggtg     2640
agggcgaaag gacgtaagac tgaggaagtt tggggctgga tagaaggtag gggtcagtgg     2700
tttagcaccg gtccaacccc tgccgcagga ggggaagtgg ggtttggaag gcgccttggg     2760
tggcattgtc caaggtcagg tcgcgcgcgg gactaggggt ggcagatctg gagctgagat     2820
cggtttagat ggagggagtg tcctggctta tgtccccaac ctagggagaa ggagctggct     2880
```

```
gttcttagcc tacccaaccc tcccaacccc aggtggttcc ggaggcgcgc tgcgggggacc    2940
tcccagggcg ggaggctgta tggctccggg gccaggctt  ttcggtgacc catcttttct    3000
ccttctggcc tgcagccgcg ctcagcacag acccgagcgt gttggggaaa taccgcgccg    3060
gcttcagcga gtgcatgaac gaggtgaccc gcttcctgtc cacgtgtgag ggcgttaaca    3120
ccgaggtgcg cactcggctg ctgggccacc tggccaactg catgacccag atcaacgcca    3180
tgacctaccc cgggcaggcg caccccgcct gcaggcgcc  gccgccgccg ccccgtcag     3240
gacctgccgg tccccagcac gcgccattcg cgccgccgcc gccgccgctt gtgcccatcc    3300
ccggggggcgc ggcgccccct ccggcagcg caccctgcaa gttgggcagc caggctggag    3360
aggctgccaa ggttttggc  ggcttccaag tggtgccggc tcctgacggc caatttgcct    3420
ttctcatccc caacgggccc ttcgctcaca gcggcccgt  catcccggtc tacaccagca    3480
acagtgggac ctcggtgggt cctaacgcag tgtcaccttc cagtggctcc tcgctcactt    3540
cggactccat gtggagaccg tggcggaact gagagcctca ggccactgct acccgtaaag    3600
tccctagccc acctctctct tctgacggac actaaaaacg aacttggatt ttaggagaga    3660
cttttataat ttggtggtta ttttgttgct ttttttaatt ctaaaaagtt acttttttgta   3720
gagagctgta ttaagtgact gaccatgcac tgcatttgta tatatttat  atgttcatat    3780
tggattgcgc ctttgtatta taaaagttga gatgacattt cgttttttac acgagatttc    3840
tttttttatg tgatgccaaa gatgtttgaa aatgctctta aaatatcttc ctttggggaa    3900
gtttatttga gaaatataa  taaaagagtg aaggctttta tgtcttagaa ctgattattt    3960
caaaatttgt aaaaaaaaaa aagtggtggg gcttgaaatt catgtagttt ggcaattcag    4020
aaataggatg tatttttaa  agttttaaac aggaaccatc aaacctttca gcaacactca    4080
atgatctaag aagacctaat ttatgagaat tcatttgatg gggctttcct gataaacagt    4140
ccttattttt ttaccttcca aagggcggct cccaactcac tccctgtagt agccactggc    4200
ctcctaaagt aaaagcgcgc tcaagccaca ttgcagccct ccagcattgg gaccttcatt    4260
tgtctgtcct tactcaggcg tagctaggca tcccctggca cccgtatcac aaagtttgaa    4320
atgcctctct tcaccctctt caagcaagct gaaaaggtca acagattctc tctgccaggg    4380
tacaactagt tagactccca agtggagccc gggccagatg attaacagca gacatatgtt    4440
tctgataagt ttctgcgctt gactttaatg gagaaagcat gtgggggttg cgctggcagg    4500
cacacgggcc gttttttcccc ttttaataca aacagcaagc gacccccttcg catggtcatg   4560
ccccatttcc aggcaagatg tgggctccag atagaagcaa aagggttgtc tcgggtttca    4620
gctcacacaa ccctccttaa caagtcctaa ctcaaagcgg acagctttaa actgtgccag    4680
gatctgcagg gaatttcttc caaatccat  cacaaaggct tgtcagattt tctcagattt    4740
ggccaggtgt ttgactgcat ccaggtgttg gggaaatgaa aaccacgagc cctgcgagac    4800
cagacacatc agccgcgctg tgggtctggc cggcgcgccc ttcctccccc acagccggcc    4860
agtcctccgc ccagccccg  ctcctcccgc ccgcctctca accccctacc cccttttccct    4920
tacagcggcg gcttctggga ggagaaggat gaggcgggag agatcaatct tgaagctt     4980
cctaacaaag ataaagccaa cgattttctg tcttgtttca aaagccttac ctctccccg     5040
cctggctgta gccttttccca caggccagcg ccgagtgcgg ctctatcaca ggaatgatct    5100
agcagacagc agccggttct ttccaggacc ttcagcttcg accccggag  agagaggttt    5160
aaaagattgt tttgttttgt tttgtttaat tggctcctat ttgccttatt ttctgccaa     5220
gaaaggtatt caacgcatac tttgtcattc cattttttcc tggttttcct ttttgtttat    5280
```

| acataaacat agtaacaatt actccattaa gacacatccc aaatttagat attaaagtcc | 5340 |
| tctgtttcca ccaagaattc ctagcttctg tagtagaaat aatcaagaca tcaggaactc | 5400 |
| aattttataa aagtaattcc ttttacatct atggaggagg | 5440 |

<210> SEQ ID NO 218
<211> LENGTH: 1487
<212> TYPE: DNA
<213> ORGANISM: Mus musculus

<400> SEQUENCE: 218

| agctggtgct gataacagcg gaatccctg tctacctctc tccttggtcc tggaatagtg | 60 |
| ctaccgatca ctaagtagcc ctaagacata ataaaccttc aactgctcag tagttttct | 120 |
| tatgaaagtc aagtaaaagg acgtaagcaa aaaaaaatta tttttttttt gcgtgaagga | 180 |
| ttccaaaaat aaaattctct ggggactgag aagaaaaaa aaaaaaaaac gaaaatgcca | 240 |
| gctgatataa tggagaaaaa ttcctcctcc ccggtggctg ctaccccagc cagtgtcaac | 300 |
| acgacaccgg acaaaccaaa gacggcctct gagcacagaa agtcatcaaa gcctatcatg | 360 |
| gagaagaggc gaagggcaag aataaatgaa agtctaagcc aactgaaaac actgattttg | 420 |
| gatgcactta agaaagatag ctcccggcat tccaagctag agaaggcaga cattctggaa | 480 |
| atgactgtga agcacctccg gaacctgcag cgggcgcaga tgaccgccgc gctcagcaca | 540 |
| gacccgagcg tgttggggaa ataccgcgcc ggcttcagcg agtgcatgaa cgaggtgacc | 600 |
| cgcttcctgt ccacgtgtga gggcgttaac accgaggtgc gcactcggct gctgggccac | 660 |
| ctggccaact gcatgaccca gatcaacgcc atgacctacc ccgggcaggc gcaccccgcc | 720 |
| ttgcaggcgc cgccgccgcc gccccgtca ggacctgccg gtcccagca cgcgccattc | 780 |
| gcgccgccgc cgccgccgct tgtgcccatc cccggggcg cggcgccccc tcccggcagc | 840 |
| gcacctgca agttgggcag ccaggctgga gaggctgcca aggttttgg cggcttccaa | 900 |
| gtggtgccgg ctcctgacgg ccaatttgcc tttctcatcc ccaacgggc cttcgctcac | 960 |
| agcggcccgg tcatcccggt ctacaccagc aacagtggga cctcggtggg tcctaacgca | 1020 |
| gtgtcacctt ccagtggctc ctcgctcact tcggactcca tgtggagacc gtggcggaac | 1080 |
| tgagagcctc aggccactgc tacccgtaaa gtccctagcc cacctctctc ttctgacgga | 1140 |
| cactaaaaac gaacttggat tttaggagag acttttataa tttggtggtt attttgttgc | 1200 |
| ttttttaat tctaaaaagt tacttttgt agagagctgt attaagtgac tgaccatgca | 1260 |
| ctgcatttgt atatatttta tatgttcata ttggattgcg cctttgtatt ataaagttg | 1320 |
| agatgacatt tcgtttttta cacgagattt ctttttttat gtgatgccaa agatgtttga | 1380 |
| aaatgctctt aaaatatctt cctttgggga agtttatttg agaaaatata ataaaagagt | 1440 |
| gaaggctttt aaaaaaaaaa aaaaaaaaa aaaaaaaaa aaaaaaa | 1487 |

<210> SEQ ID NO 219
<211> LENGTH: 21
<212> TYPE: DNA
<213> ORGANISM: Artificial sequence
<220> FEATURE:
<223> OTHER INFORMATION: Primer

<400> SEQUENCE: 219

| gcacagaaag tcatcaaagc c | 21 |

<210> SEQ ID NO 220

```
<211> LENGTH: 21
<212> TYPE: DNA
<213> ORGANISM: Artificial sequence
<220> FEATURE:
<223> OTHER INFORMATION: Primer

<400> SEQUENCE: 220
atgtctgcct tctctagctt g                                           21

<210> SEQ ID NO 221
<211> LENGTH: 24
<212> TYPE: DNA
<213> ORGANISM: Artificial sequence
<220> FEATURE:
<223> OTHER INFORMATION: Probe

<400> SEQUENCE: 221
attcttgccc ttcgcctctt ctcc                                        24

<210> SEQ ID NO 222
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 222
cactattcca ggacca                                                 16

<210> SEQ ID NO 223
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 223
agcactattc caggac                                                 16

<210> SEQ ID NO 224
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 224
atcggtagca ctattc                                                 16

<210> SEQ ID NO 225
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 225
gatcggtagc actatt                                                 16

<210> SEQ ID NO 226
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 226
```
gtgatcggta gcacta                                                        16

<210> SEQ ID NO 227
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 227
ctacttagtg atcggt                                                        16

<210> SEQ ID NO 228
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 228
gctacttagt gatcgg                                                        16

<210> SEQ ID NO 229
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 229
ttattatgtc ttaggg                                                        16

<210> SEQ ID NO 230
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 230
tttattatgt cttagg                                                        16

<210> SEQ ID NO 231
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 231
ggtttattat gtctta                                                        16

<210> SEQ ID NO 232
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 232
aggtttatta tgtctt                                                        16

<210> SEQ ID NO 233
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 233
gcagttgaag gtttat                                                      16

<210> SEQ ID NO 234
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 234
agcagttgaa ggttta                                                      16

<210> SEQ ID NO 235
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 235
tttttggaat ccttca                                                      16

<210> SEQ ID NO 236
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 236
ggactttacg ggtagc                                                      16

<210> SEQ ID NO 237
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 237 cgttttagt gtccgt                                                       16

<210> SEQ ID NO 238
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 238
agagcttagt tctttg                                                      16

<210> SEQ ID NO 239
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 239
gtaagatcca catgca                                                      16
```

<210> SEQ ID NO 240
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 240
ggtaagatcc acatgc                                              16

<210> SEQ ID NO 241
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 241
cagtcctcct tgtcag                                              16

<210> SEQ ID NO 242
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 242
ggaatgccgg gagctc                                              16

<210> SEQ ID NO 243
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 243
ggcagtaaaa tgtagc                                              16

<210> SEQ ID NO 244
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 244
ggctataaat aagacc                                              16

<210> SEQ ID NO 245
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 245
gtaacaactt gggagc                                              16

<210> SEQ ID NO 246
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 246
agtaacaact tgggag                                                         16

<210> SEQ ID NO 247
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 247
cttctcggct acagcc                                                         16

<210> SEQ ID NO 248
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 248
accggcttct accaca                                                         16

<210> SEQ ID NO 249
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 249
gtgctaaacc actgac                                                         16

<210> SEQ ID NO 250
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 250
ttctccctag gttggg                                                         16
```

MODULATION OF THE NOTCH SIGNALING PATHWAY FOR TREATMENT OF RESPIRATORY DISORDERS

SEQUENCE LISTING

The present application is being filed along with a Sequence Listing in electronic format. The Sequence Listing is provided as a file entitled BIOL0319USASEQ_ST25.txt, created on Feb. 10, 2020 which is 524 KB in size. The information in the electronic format of the sequence listing is incorporated herein by reference in its entirety.

BACKGROUND

The Notch signaling pathway is a highly conserved pathway that is involved in a large variety of developmental processes, diseases, and other biological functions and processes. (See, e.g., Bray, S. *Nat. Rev. Mol. Cell Biol.* 17, 723 (2016).) Ligands of the Notch signaling pathway activate Notch receptors, which ultimately leads to activation of target gene transcription.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics or affinity for a target nucleic acid.

SUMMARY

Provided herein are compositions, compounds and methods for modulating expression of the Notch signaling pathway. In certain embodiments, one or more members of the Notch signaling pathway is modulated. In certain embodiments, the Notch signaling pathway is modulated by a compound comprising or consisting of a modified oligonucleotide complementary to a transcript encoding a member of the Notch signaling pathway. In certain embodiments, the Notch signaling pathway member transcript is a Notch1, Notch2, Notch3, Notch4, Jagged1 (hereinafter referred to as JAG1 signaling pathway), Jagged2 (hereinafter referred to as JAG2), Delta-like 1 (hereinafter referred to as DLL1), Delta-like3 (hereinafter referred to as DLL3), Delta-like4 (hereinafter referred to as DLL4), or Hes family bHLH transcription factor 1 (hereinafter referred to as Hes-1) transcript. In certain such embodiments, the compound decreases expression or activity of one or more members of the Notch signaling pathway. In certain embodiments, the modified oligonucleotide of the compound can be single-stranded or part of a duplex.

Certain embodiments are directed to compounds useful for inhibiting the Notch signaling pathway, which can be useful for treating, ameliorating, or slowing progression of a respiratory disorder associated with excessive mucus production. Certain embodiments relate to the novel findings of antisense inhibition of the Notch signaling pathway resulting in improvement of symptoms or endpoints associated with such respiratory disorders and/or lung function. Certain embodiments are directed to compounds useful in improving trans-differentiation from club cells or goblet cells to ciliated cells, decreased mucus in the lungs, and increased lung function.

Provided herein are embodiments including but not limited to:

1. A method of treating, preventing, delaying the onset, slowing the progression, or ameliorating a respiratory disorder associated with excessive mucus production in an individual having, or at risk of having, a respiratory disorder associated with excessive mucus production comprising administering a compound comprising a Notch signaling pathway inhibitor to the individual, thereby treating, preventing, delaying the onset, slowing the progression, or ameliorating the respiratory disorder associated with excessive mucus production in the individual.
2. The method of embodiment 1, wherein the respiratory disorder associated with excessive mucus production is asthma, chronic obstructive pulmonary disorder (COPD), idiopathic pulmonary fibrosis (IPF), or cystic fibrosis (CF).
3. The method of embodiment 2, wherein the respiratory disorder associated with excessive mucus production is asthma.
4. The method of embodiment 2, wherein the respiratory disorder associated with excessive mucus production is COPD.
5. The method of embodiment 2, wherein the respiratory disorder associated with excessive mucus production is IPF.
6. The method of embodiment 2, wherein the respiratory disorder associated with excessive mucus production is CF.
7. The method of any of embodiments 1-6, wherein the compound increases trans-differentiation from club cells or goblet cells to ciliated cells, decreases mucus in the lungs, and/or increases lung function.
8. The method of embodiment 7, wherein the compound decreases mucus in the lungs.
9. The method of embodiment 7, wherein the compound increases lung function.
10. A method of inhibiting expression or activity of the Notch signaling pathway in a cell comprising contacting the cell with a compound comprising a Notch signaling pathway inhibitor, thereby inhibiting expression or activity of at least one member of the Notch signaling pathway in the cell.
11. The method of embodiment 10, wherein the cell is a lung cell.
12. The method of embodiment 11, wherein the cell is in an individual.
13. The method of embodiment 12, wherein the individual has, or is at risk of having asthma, COPD, IPF, or CF.
14. The method of any of embodiments 1-9 or 12-13, wherein the individual is human.
15. The method of any of embodiments 1-14, comprising administering to the individual or contacting the cell with no more than one compound comprising a Notch signaling pathway inhibitor.
16. The method of any of embodiments 1-15, wherein the compound inhibits the expression of at least one Notch signaling pathway member transcript.
17. The method of any of embodiments 1-16, wherein the compound inhibits the expression of at least two Notch signaling pathway members.
18. The method of any of embodiments 1-17, wherein the Notch signaling pathway inhibitor is a modified oligonucleotide complementary to a Notch signaling pathway member transcript.

19. The method of any of embodiments 1-17, wherein the compound comprises a modified oligonucleotide complementary to a member of the Notch signaling pathway.
20. The method of embodiment 18 or 19, wherein the modified oligonucleotide is single-stranded.
21. The method of embodiment 18 or 19, wherein the modified oligonucleotide is part of a double-stranded duplex.
22. The method of any of embodiments 18-21, wherein the modified oligonucleotide is 12 to 30 linked nucleosides in length.
23. The method of any of embodiments 18-22, wherein the modified oligonucleotide comprises at least one modified internucleoside linkage.
24. The method of embodiment 23, wherein the at least one modified internucleoside linkage is a phosphorothioate internucleoside linkage.
25. The method of any of embodiments 18-24, wherein the modified oligonucleotide comprises at least one modified sugar moiety.
26. The method of embodiment 25, wherein the at least one modified sugar moiety is a bicyclic sugar or 2'-O-methyoxyethyl modified sugar moiety.
27. The method of embodiment 26, wherein the at least one modified sugar is a cEt, LNA, or ENA.
28. The method of any of embodiments 18-27, wherein the modified oligonucleotide comprises at least one 5-methylcytosine modified nucleobase.
29. The method of any of embodiments 24-28, wherein each modified internucleoside linkage is a phosphorothioate linkage.
30. The method of any of embodiments 18-29, wherein each cytosine nucleobase is a 5-methylcytosine.
31. The method of any one of embodiments 18-30, wherein the modified oligonucleotide comprises:
    a gap segment consisting of 7-11 linked 2'-deoxynucleosides;
    a 5' wing segment consisting of 1-7 linked nucleosides;
    a 3' wing segment consisting of 1-7 linked nucleosides;
    wherein the gap segment is positioned immediately adjacent to and between the 5' wing segment and the 3' wing segment and wherein the nucleoside of each wing segment that is immediately adjacent to the gap segment each comprises a modified sugar.
32. The method of any of embodiments 18-31, wherein the modified oligonucleotide is at least 90% complementary to a Notch signaling pathway member nucleic acid.
33. The method of any of embodiments 18-31, wherein the modified oligonucleotide is 100% complementary to a Notch signaling pathway member nucleic acid.
34. The method of embodiments 32 or 33, wherein the Notch signaling pathway member nucleic acid is a Notch signaling pathway member transcript.
35. The method of embodiment 34, wherein the Notch signaling pathway member transcript is a Notch signaling pathway member pre-mRNA.
36. The method of embodiment 34, wherein the Notch signaling pathway member transcript is a Notch signaling pathway member mRNA.
37. The method of any of embodiments 32-36, wherein the Notch signaling pathway member is a Notch receptor, ligand of a Notch receptor, or intracellular protein that transmits the Notch signal to or within the nucleus of a cell.
38. The method of embodiment 37, wherein the Notch signaling pathway member is a Notch receptor or a ligand of a Notch receptor.
39. The method of embodiment 38, wherein the Notch signaling pathway member is a Notch receptor.
40. The method of embodiment 39, wherein the Notch receptor is Notch1, Notch2, Notch 3, or Notch4.
41. The method of embodiment 40, wherein the Notch receptor is Notch1, Notch2, or Notch3.
42. The method of embodiment 41, wherein the Notch receptor is Notch1.
43. The method of embodiment 41, wherein the Notch receptor is Notch2.
44. The method of embodiment 41, wherein the Notch receptor is Notch3.
45. The method of embodiment 38, wherein the Notch signaling pathway member is a ligand of a Notch receptor.
46. The method of embodiment 45, wherein the ligand is DLL1, DLL3, DLL4, JAG1, or JAG2.
47. The method of embodiment 46, wherein the ligand is DLL4, JAG1, or JAG2.
48. The method of embodiment 47, wherein the ligand is DLL4.
49. The method of embodiment 47, wherein the ligand is JAG1.
50. The method of embodiment 47, wherein the ligand is JAG2.
51. The method of embodiment 37, wherein the Notch signaling pathway member is an intracellular protein that transmits the Notch signal to or within the nucleus of a cell.
52. The method of embodiment 51, wherein the intracellular protein that transmits the Notch signal to or within in the nucleus of a cell is Hes-1.
53. The method of any of embodiments 16-52, wherein the at least one Notch signaling pathway member that is inhibited is the target transcript.
54. The method of any of embodiments 17-53, wherein the expression or activity of at least one Notch signaling pathway member that is not the target transcript is inhibited.
55. The method of any of embodiments 1-9 or 12-54, wherein the compound is administered parenterally.
56. The method of embodiment 55, wherein the compound is administered parenterally by subcutaneous administration.
57. The method of any of embodiments 1-9 or 12-54, wherein the compound is administered via inhalation.
58. The method of any of the preceding embodiments, comprising co-administering the compound and at least one additional therapy, wherein the additional therapy is not a Notch signaling pathway inhibitor.
59. The method of embodiment 58, wherein the compound and the additional therapy are administered concomitantly.
60. The method of embodiment 58, wherein the compound and the additional therapy are administered consecutively.
61. Use of a compound comprising a modified oligonucleotide complementary to a Notch signaling pathway member transcript for the manufacture or preparation of a medicament for treating a respiratory disorder associated with excessive mucus production.
62. Use of a compound comprising a modified oligonucleotide complementary to a Notch signaling pathway member transcript for the treatment of a respiratory disorder associated with excessive mucus production.
63. The use of embodiment 61 or 62, wherein the respiratory disorder associated with excessive mucus production is asthma, COPD, IPF, or CF.

64. The use of any one of embodiments 61-63, wherein the compound is capable of increasing trans-differentiation from club cells or goblet cells to ciliated cells, decreasing mucus in the lungs, and/or increasing lung function.
65. The use of any one of embodiments 61-64, wherein the modified oligonucleotide is at least 90% complementary to the Notch signaling pathway member transcript.
66. The use of embodiment 65, wherein the modified oligonucleotide is at least 100% complementary to the Notch signaling pathway member transcript.
67. The use of any one of embodiments 61-66, wherein the Notch signaling pathway member transcript is a Notch receptor transcript, a transcript of a ligand of a Notch receptor, or a transcript of an intracellular protein that transmits the Notch signal to or within the nucleus of a cell.
68. The use of embodiment 67, wherein the Notch signaling pathway member transcript is a Notch receptor transcript or a transcript of a ligand of a Notch receptor.
69. The use of embodiment 68, wherein the Notch signaling pathway member transcript is a Notch1, Notch2, Notch3, or Notch4 transcript.
70. The use of embodiment 69, wherein the Notch signaling pathway member transcript is a Notch1, Notch2, or Notch3 transcript.
71. The use of embodiment 70, wherein the Notch signaling pathway member transcript is a Notch1 transcript. 72. The use of embodiment 70, wherein the Notch signaling pathway member transcript is a Notch2 transcript.
73. The use of embodiment 70, wherein the Notch signaling pathway member transcript is a Notch3 transcript.
74. The use of embodiment 68, wherein the Notch signaling pathway member transcript is a DLL1, DLL3, DLL4, JAG1, or JAG2 transcript.
75. The use of embodiment 74, wherein the Notch signaling pathway member transcript is a DLL4, JAG1, or JAG2 transcript.
76. The use of embodiment 75, wherein the Notch signaling pathway member transcript is a DLL4 transcript.
77. The use of embodiment 75, wherein the Notch signaling pathway member transcript is a JAG1 transcript.
78. The use of embodiment 75, wherein the Notch signaling pathway member transcript is a JAG2 transcript.
79. The use of embodiment 67, wherein the Notch signaling pathway member transcript is a transcript of an intracellular protein that transmits the Notch signal to or within the nucleus of a cell.
80. The use of embodiment 79, wherein the transcript of an intracellular protein that transmits the Notch signal to or within in the nucleus of a cell is a Hes-1 transcript.
81. The use of any one of embodiments 61-80, wherein the modified oligonucleotide is single-stranded.
82. The use of any one of embodiments 61-80, wherein the modified oligonucleotide is part of a double-stranded duplex.
83. The use of any one of embodiments 61-82, wherein the modified oligonucleotide is 12 to 30 linked nucleosides in length.
84. The use of any one of embodiments 61-83, wherein the modified oligonucleotide comprises at least one phosphorothioate internucleoside linkage, at least one bicyclic sugar moiety or 2'-O-methoxyethyl modified sugar moiety, and at least one 5-methylcytosine modified nucleobase.
85. The use of embodiment 84, wherein at least one modified sugar is a cEt, LNA, or ENA.
86. The use of any of embodiments 61-85, wherein each modified internucleoside linkage of the modified oligonucleotide is a phosphorothioate linkage.
87. The use of any one of embodiments 61-86, wherein each cytosine nucleobase of the modified oligonucleotide is a 5-methylcytosine.
88. The use of any one of embodiments 61-87, wherein the modified oligonucleotide comprises:
a gap segment consisting of 7-11 linked 2'-deoxynucleosides;
a 5' wing segment consisting of 1-7 linked nucleosides;
a 3' wing segment consisting of 1-7 linked nucleosides;
wherein the gap segment is positioned immediately adjacent to and between the 5' wing segment and the 3' wing segment and wherein the nucleoside of each wing segment that is immediately adjacent to the gap segment comprises a modified sugar moiety.

DETAILED DESCRIPTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase.

As used herein, "2'-deoxynucleoside" means a nucleoside comprising 2'-H(H) deoxyribosyl sugar moiety, as found in naturally occurring deoxyribonucleic acids (DNA). In certain embodiments, a 2'-deoxynucleoside may comprise a modified nucleobase or may comprise an RNA nucleobase (uracil).

As used herein, "2'-substituted nucleoside" or "2'-modified nucleoside" means a nucleoside comprising a 2'-substituted or 2'-modified ribosyl sugar moiety. As used herein, "2'-substituted" or "2-modified" in reference to a sugar moiety means a ribosyl sugar moiety comprising at least one 2'-substituent group other than H or OH.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means a compound comprising an antisense oligonucleotide and optionally one or more additional features, such as a conjugate group or terminal group.

As used herein, "antisense oligonucleotide" means an oligonucleotide having a nucleobase sequence that is complementary to a target nucleic acid.

As used herein, "ameliorate" refers to an improvement or lessening of at least one indicator, sign, or symptom of an associated disease, disorder, or condition. In certain embodiments, amelioration includes a decrease in severity and/or a delay or slowing in the progression of one or more symptoms or indicators of a condition or disease. The severity or progression of symptoms or indicators may be determined by subjective or objective measures, which are known to those skilled in the art.

As used herein, "animal" refers to a human or non-human animal, including, but not limited to, mice, rats, rabbits, dogs, cats, pigs, and non-human primates, including, but not limited to, monkeys and chimpanzees.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "cEt" or "constrained ethyl" means a β-D ribosyl bicyclic sugar moiety wherein the second ring of the bicyclic sugar is formed via a bridge connecting the 4'-carbon and the 2'-carbon of the β-D ribosyl sugar moiety, wherein the bridge has the formula 4'-CH(CH$_3$)—O-2', and wherein the methyl group of the bridge is in the S configuration.

As used herein, "cleavable moiety" means a bond or group of atoms that is cleaved under physiological conditions, for example, inside a cell, an animal, and/or a human.

As used herein, "complementary" in reference to an oligonucleotide or region thereof means that at least 70% of the nucleobases of such oligonucleotide or region thereof and the nucleobases of another nucleic acid or one or more regions thereof are capable of hydrogen bonding with one another when the nucleobase sequences of the oligonucleotide and the other nucleic acid are aligned in opposing directions. Complementary nucleobases means nucleobases that are capable of forming hydrogen bonds with one another. Complementary nucleobase pairs include adenine (A) and thymine (T), adenine (A) and uracil (U), cytosine (C) and guanine (G), and 5-methyl cytosine ($^m$C) and guanine (G). Complementary oligonucleotides and/or nucleic acids need not have nucleobase complementarity at each nucleoside. Rather, some mismatches are tolerated. In contrast, "fully complementary" or "100% complementary" in reference to an oligonucleotides means that such oligonucleotide is complementary to another nucleic acid at each nucleoside of the oligonucleotide.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "conjugate linker" means a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "double-stranded antisense compound" means an antisense compound comprising two oligomeric compounds that are complementary to each other and form a duplex, and wherein one of the two said oligomeric compounds comprises an antisense oligonucleotide.

As used herein, "expression" means the formation of the structures into which a gene's coded information is converted in a cell, including the products of transcription and translation.

As used herein, "gapmer" means an oligonucleotide comprising an internal region having a plurality of nucleosides that support RNase H cleavage positioned between external regions having one or more nucleosides, wherein the nucleosides comprising the internal region are chemically distinct from at least one of the nucleoside or nucleosides comprising each of the external regions. The internal region may be referred to as the "gap" and the external regions may be referred to as the "wings."

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "inhibiting the expression or activity" refers to a reduction or blockade of the expression or activity relative to the expression or activity in an untreated or control sample or relative to the expression or activity prior to the onset of inhibition. Such inhibition does not necessarily indicate a total elimination of expression or activity.

As used herein, the term "internucleoside linkage" means a group or bond that forms a covalent linkage between adjacent nucleosides in an oligonucleotide. As used herein "modified internucleoside linkage" means any internucleoside linkage other than a naturally occurring, phosphate internucleoside linkage. Non-phosphate linkages are referred to herein as modified internucleoside linkages. "Phosphorothioate linkage" means a modified phosphate linkage in which one of the non-bridging oxygen atoms is replaced with a sulfur atom. A phosphorothioate internucleoside linkage is a modified internucleoside linkage.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "linked nucleosides" are nucleosides that are connected in a continuous sequence (i.e. no additional nucleosides are present between those that are linked). Linked nucleosides are linked together by internucleoside linkages.

As used herein, "lung cell" means any cell found within the lungs or the airways leading to and inside of the lungs. As described herein, lung cells include but are not limited to cells of the trachea, bronchi, bronchioles, and alveoli.

As used herein, "mismatch" means a nucleobase of a first oligonucleotide that is not complementary with the corresponding nucleobase of a second oligonucleotide or target nucleic acid when the first and second oligomeric compound are aligned.

As used herein, "modulating" refers to changing a feature in a cell, tissue, organ or organism. For example, modulating the Notch signaling pathway can mean increasing or decreasing the level of at least one member of the Notch signaling pathway in a cell, tissue, organ or organism. A "modulator" effects the change in the cell, tissue, organ or organism. For example, a compound can be a modulator of the Notch signaling pathway that decreases the amount of at least one Notch signaling pathway member transcript in a cell, tissue, organ or organism.

As used herein, "MOE" means methoxyethyl. "2'-MOE" means a 2'-OCH$_2$CH$_2$OCH$_3$ group in place of the 2'-OH group of a ribosyl sugar moiety.

As used herein, "motif" means the pattern of unmodified and/or modified sugar moieties, nucleobases, and/or internucleoside linkages, in an oligonucleotide.

As used herein, "naturally occurring" means found in nature.

As used herein, "non-bicyclic modified sugar" or "non-bicyclic modified sugar moiety" means a modified sugar moiety that comprises a modification, such as a substituent, that does not form a bridge between two atoms of the sugar to form a second ring.

As used herein, "Notch signaling pathway" or "Notch signaling pathway members" means the Notch receptors, ligands of the Notch receptors, and intracellular proteins that transmit the Notch signal to or within the nucleus of a cell, as well as the nucleic acids encoding said Notch signaling pathway members. Notch signaling pathway members include the DNA sequences encoding Notch signaling pathway members and the RNA transcripts transcribed from said DNA sequences.

As used herein, "Notch signaling pathway inhibitor" refers to any agent that binds to a member of the Notch signaling pathway and is capable of inhibiting expression and/or activity of at least one member of the Notch signaling pathway.

As used herein, "nucleobase" means a naturally occurring nucleobase or a modified nucleobase. As used herein a "naturally occurring nucleobase" is adenine (A), thymine (T), cytosine (C), uracil (U), and guanine (G). As used herein, a modified nucleobase is a group of atoms capable of pairing with at least one naturally occurring nucleobase. A universal base is a nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety.

As used herein, "oligomeric compound" means a compound consisting of an oligonucleotide and optionally one or more additional features, such as a conjugate group or terminal group.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-80 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering a compound or composition to an animal. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water; sterile saline; or sterile buffer solution.

As used herein "pharmaceutically acceptable carrier or diluent" means any substance suitable for use in administering to an individual. For example, a pharmaceutically acceptable carrier can be a sterile aqueous solution, such as PBS or water-for-injection.

As used herein "pharmaceutical composition" means a mixture of substances suitable for administering to a subject. For example, a pharmaceutical composition may comprise an antisense compound and a sterile aqueous solution.

As used herein, "phosphorus moiety" means a group of atoms comprising a phosphorus atom. In certain embodiments, a phosphorus moiety comprises a mono-, di-, or tri-phosphate, or phosphorothioate.

As used herein "prodrug" means a therapeutic agent in a form outside the body that is converted to a different form within the body or cells thereof. Typically conversion of a prodrug within the body is facilitated by the action of an enzymes (e.g., endogenous or viral enzyme) or chemicals present in cells or tissues and/or by physiologic conditions.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense oligonucleotides that act through RNase H.

As used herein, the term "single-stranded" in reference to an antisense compound, oligomeric compound, or oligonucleotide means that the compound or oligonucleotide is not paired with a second compound or oligonucleotide to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound.

As used herein, "sugar moiety" means an unmodified sugar moiety or a modified sugar moiety. As used herein, "unmodified sugar moiety" means a 2'-OH(H) ribosyl moiety, as found in RNA (an "unmodified RNA sugar moiety"), or a 2'-H(H) deoxyribosyl moiety, as found in DNA (an "unmodified DNA sugar moiety"). As used herein, "modified sugar moiety" or "modified sugar" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars. As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "target nucleic acid," "target RNA," "target transcript" and "nucleic acid target" mean a nucleic acid that an antisense compound is designed to affect.

As used herein, "target region" means a portion of a target nucleic acid to which an antisense compound is complementary.

As used herein, "terminal group" means a chemical group or group of atoms that is covalently linked to a terminus of an oligonucleotide.

As used herein, "therapeutically effective amount" means an amount of a compound, pharmaceutical agent, or composition that provides a therapeutic benefit to an individual.

CERTAIN EMBODIMENTS

Certain embodiments provide methods, compounds, and compositions for treating a respiratory disorder associated with excessive mucus production, or a symptom thereof, in an individual by administering the compound or composition to the individual, wherein the compound or composition comprises a Notch signaling pathway modulator. Modulation of one member of the Notch signaling pathway can lead to a decrease of the level or expression of one or more Notch signaling pathway members in order to treat, prevent, ameliorate or delay a respiratory disorder associated with excessive mucus production, or a symptom thereof. In certain embodiments, the Notch signaling pathway modulator is a compound comprising or consisting of a modified oligonucleotide complementary to a transcript encoding a member of the Notch signaling pathway. In certain embodiments, the Notch signaling pathway member transcript is a Notch1, Notch2, Notch3, Notch4, JAG1, JAG2, DLL1, DLL3, DLL4, or Hes-1 transcript. In certain embodiments, the Notch signaling pathway member transcript is a JAG1 transcript. In certain embodiments, the compound decreases expression or activity of one or more members of the Notch signaling pathway. In certain embodiments, the individual is human. In certain embodiments, no more than one compound comprising a Notch signaling pathway modulator is administered. In certain such embodiments, one compound comprising a Notch signaling pathway modulator is administered, and a second agent that does not comprise a Notch signaling pathway modulator is administered.

Certain embodiments disclosed herein provide compounds or compositions comprising a Notch signaling pathway modulator. Such compounds or compositions are useful to treat, prevent, ameliorate or delay a respiratory disorder associated with excessive mucus production, or a symptom thereof. In certain embodiments, the compound or composition comprises no more than one Notch signaling pathway inhibitor. In certain embodiments, the compound comprises a modified oligonucleotide complementary to a Notch signaling pathway member transcript. In certain embodiments, the Notch signaling pathway member transcript is a Notch1, Notch2, Notch3, Notch4, JAG1, JAG2, DLL1, DLL3, DLL4, or Hes-1 transcript. In certain embodiments, the Notch signaling pathway member transcript is a JAG1 transcript. In certain embodiments, the modified oligonucleotide is single-stranded. In certain embodiments, the modified oligonucleotide is part of a duplex. In certain such embodiments, the compound or composition comprises an antisense compound. In any of the foregoing embodiments, the compound or composition comprises an oligomeric compound. In certain embodiments, the compound comprises 2'-deoxyribonucleotides. In certain embodiments, the composition is double-stranded and comprises two oligomeric compounds that comprise ribonucleotides.

In any of the foregoing embodiments, the compound can comprise a modified oligonucleotide consisting of 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides.

In certain embodiments, at least one internucleoside linkage of said modified oligonucleotide is a modified internucleoside linkage. In certain embodiments, at least one internucleoside linkage is a phosphorothioate internucleoside linkage. In certain embodiments, the internucleoside linkages are phosphorothioate linkages and phosphate linkages.

In certain embodiments, any of the foregoing oligonucleotides comprises at least one modified sugar. In certain embodiments, at least one modified sugar comprises a 2'-O-methoxyethyl ("2'-MOE") group. In certain embodiments, at least one modified sugar is a bicyclic sugar, such as a 4'-CH(CH$_3$)—O-2' ("cEt") group, a 4'-CH$_2$—O-2' ("LNA") group, or a 4'-(CH$_2$)$_2$—O-2'("ENA") group.

In certain embodiments, at least one nucleoside of said modified oligonucleotide comprises a modified nucleobase. In certain embodiments, the modified nucleobase is a 5-methylcytosine.

In certain embodiments, a compound or composition comprises a modified oligonucleotide comprising: a) a gap segment consisting of linked 2'-deoxynucleosides; b) a 5' wing segment consisting of linked nucleosides; and c) a 3' wing segment consisting of linked nucleosides. The gap segment is positioned between the 5' wing segment and the 3' wing segment. In certain embodiments, each nucleoside of each wing segment comprises a modified sugar moiety. In certain embodiments, the nucleosides immediately adjacent to the gap each comprise a modified sugar moiety, and at least one wing comprises an unmodified sugar moiety. In certain embodiments, at least one internucleoside linkage is a phosphorothioate linkage. In certain embodiments, at least one cytosine is a 5-methylcytosine.

In certain embodiments, a compound comprises a modified oligonucleotide 12 to 80 linked nucleosides in length and having a nucleobase sequence complementary to a Notch signaling pathway member transcript. In certain embodiments, the Notch signaling pathway member transcript is a Notch1, Notch2, Notch3, Notch4, JAG1, JAG2, DLL1, DLL3, DLL4, or Hes-1 transcript. In certain embodiments, the Notch signaling pathway member transcript is a JAG1 transcript. In certain embodiments, the compound is an antisense compound or oligomeric compound. In certain embodiments, the compound is single-stranded. In certain embodiments, the compound is part of a double-stranded duplex. In certain embodiments, the modified oligonucleotide is 12 to 30 linked nucleosides in length.

In certain embodiments, the compounds or compositions disclosed herein comprise a pharmaceutically acceptable carrier or diluent.

In certain embodiments, the compound or composition is co-administered with a second agent. In certain embodiments, the compound or composition and the second agent are administered concomitantly. In certain embodiments, the second agent is not an inhibitor of a Notch signaling pathway member.

In certain embodiments, compounds and compositions described herein targeting the Notch signaling pathway can be used in methods of inhibiting expression of the Notch signaling pathway in a cell. In certain embodiments, compounds and compositions described herein targeting the Notch signaling pathway can be used in methods of treating, preventing, delaying or ameliorating a respiratory disease or disorder associated with excessive mucus production, including, but not limited to, asthma, chronic obstructive pulmonary disorder (COPD), idiopathic pulmonary fibrosis (IPF), and cystic fibrosis (CF).

Certain Indications

Certain embodiments provided herein relate to methods of inhibiting the expression or activity of at least one member of Notch signaling pathway, which can be useful for treating, preventing, or ameliorating a disease or disorder associated with the Notch signaling pathway in an individual, by administration of one compound or composition that targets a member of the Notch signaling pathway. In certain embodiments, such a compound or composition comprises a modified oligonucleotide complementary to a Notch signaling pathway member transcript. In certain embodiments, the Notch signaling pathway member transcript is a Notch1, Notch2, Notch3, Notch4, JAG1, JAG2, DLL1, DLL3, DLL4, or Hes-1 transcript. In certain embodiments, the Notch signaling pathway member transcript is a JAG1 transcript. In certain embodiments, the compound comprises or consists of an antisense compound or an oligomeric compound targeted to the Notch signaling pathway.

In certain embodiments, a method of inhibiting expression or activity of at least one member of the Notch signaling pathway in a cell comprises contacting the cell with a compound or composition comprising a modified oligonucleotide complementary to a Notch signaling pathway member transcript, thereby inhibiting expression or activity of the Notch signaling pathway in the cell. In certain embodiments, the Notch signaling pathway member transcript is a Notch1, Notch2, Notch3, Notch4, JAG1, JAG2, DLL1, DLL3, DLL4, or Hes-1 transcript. In certain embodiments, the Notch signaling pathway member transcript is a JAG1 transcript. In certain embodiments, the cell is a lung cell. In certain embodiments, the cell is in the lung. In certain embodiments, the cell is in the lung of an individual who has, or is at risk of having a respiratory disease, disorder, condition, symptom, or physiological marker associated with excessive mucus production. In certain embodiments, the respiratory disorder associated with excessive mucus production is asthma, COPD, IPF, or CF. In certain embodiments, the Notch signaling pathway inhibitor is an antisense compound or an oligomeric compound targeted to the Notch signaling pathway. In certain embodiments, the Notch signaling pathway inhibitor is an oligonucleotide complementary to a member of the Notch signaling pathway. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be part of a double-stranded duplex.

In certain embodiments, a method of treating, preventing, delaying the onset, slowing the progression, or ameliorating one or more diseases, disorders, conditions, symptoms or physiological markers associated with the Notch signaling pathway comprises administering to the individual a compound or composition comprising a Notch signaling pathway inhibitor, wherein the Notch signaling pathway inhibitor comprises a modified oligonucleotide complementary to a Notch signaling pathway member transcript. In certain embodiments, the Notch signaling pathway member transcript is a Notch1, Notch2, Notch3, Notch4, JAG1, JAG2, DLL1, DLL3, DLL4, or Hes-1 transcript. In certain embodiments, the Notch signaling pathway member transcript is a JAG1 transcript. In certain embodiments, a method of treating, preventing, delaying the onset, slowing the progression, or ameliorating a respiratory disease, disorder, condition, symptom, or physiological marker associated with excessive mucus production in an individual comprises administering to the individual a compound or composition comprising one Notch signaling pathway inhibitor, thereby treating, preventing, delaying the onset, slowing the progression, or ameliorating the disease. In certain embodiments, the individual is identified as having, or at risk of having, the disease, disorder, condition, symptom or physiological marker. In certain embodiments, the respiratory disorder associated with excessive mucus production is asthma, COPD, IPF, or CF. In certain embodiments, the Notch signaling pathway inhibitor is administered to the individual via inhalation. In certain embodiments, the individual is human. In certain embodiments, the Notch signaling pathway inhibitor is an antisense compound or an oligomeric compound comprising a modified oligonucleotide complementary to a Notch signaling pathway member transcript. In certain embodiments, the Notch signaling pathway member transcript is a Notch1, Notch2, Notch3, Notch4, JAG1, JAG2, DLL1, DLL3, DLL4, or Hes-1 transcript. In certain embodiments, the Notch signaling pathway member transcript is a JAG1 transcript. In certain embodiments, the modified oligonucleotide is 8 to 80 linked nucleosides in length. In certain embodiments, the modified oligonucleotide is 10 to 30 linked nucleosides in length. In certain embodiments, the modified oligonucleotide can be single-stranded. In certain embodiments, the modified oligonucleotide can be part of a double-stranded duplex. In certain embodiments, a method of reducing, improving, or regulating trans-differentiation from club cells or goblet cells to ciliated cells, decreased mucus in the lungs, and increased lung function, or a combination thereof, in an individual comprises administering to the individual a compound or composition comprising one Notch signaling pathway inhibitor. In certain embodiments, administering the compound or composition reduces, improves, or regulates increased lung function in the individual. In certain embodiments, the individual is identified as having, or at risk of having a respiratory disease, disorder, condition, symptom, or physiological marker associated with excessive mucus production. In certain embodiments, the respiratory disorder associated with excessive mucus production is asthma, COPD, IPF, or CF. In certain embodiments, the Notch signaling pathway inhibitor is administered to the individual via inhalation. In certain embodiments, the individual is human. In certain embodiments, the Notch signaling pathway inhibitor is an antisense compound or an oligomeric compound targeted to the Notch signaling pathway. In certain embodiments, the Notch signaling pathway inhibitor comprises or consists of a modified oligonucleotide complementary to a Notch signaling pathway member transcript. In certain embodiments, the Notch signaling pathway member transcript is a Notch1, Notch2, Notch3, Notch4, JAG1, JAG2, DLL1, DLL3, DLL4, or Hes-1 transcript. In certain embodiments, the Notch signaling pathway member transcript is a JAG1 transcript. In certain embodiments, the modified oligonucleotide is 8 to 80 linked nucleosides in length. In certain embodiments, the modified oligonucleotide is 10 to 30 linked nucleosides in length. In certain embodiments, the compound comprising or consisting of the modified oligonucleotide can be single-stranded. In certain embodiments, the compound can be part of a duplex that is double-stranded.

In certain embodiments, lung function is increased by at least 5%, at least 10%, at least 20%, at least 30%, at least 35%, at least 40%, at least 45% or at least 50%.

Certain embodiments are drawn to compounds and compositions described herein for use in therapy. Certain embodiments are drawn to a compound or composition comprising a Notch signaling pathway inhibitor for use in treating, preventing, delaying the onset, slowing the progression, or ameliorating one or more diseases, disorders, conditions, symptoms or physiological markers associated with the Notch signaling pathway. Certain embodiments are drawn to a compound or composition for use in treating, preventing, delaying the onset, slowing the progression, or ameliorating a respiratory disorder associated with excessive mucus production, or a symptom or physiological marker thereof. In certain embodiments, the respiratory disorder associated with excessive mucus production is asthma, COPD, IPF, or CF. In certain embodiments, the Notch signaling pathway inhibitor is an antisense compound or an oligomeric compound targeted to the Notch signaling pathway. In certain embodiments, the Notch signaling pathway inhibitor is a compound comprising or consisting of a modified oligonucleotide complementary to a Notch signaling pathway member transcript. In certain embodiments, the Notch signaling pathway member transcript is a Notch1, Notch2, Notch3, Notch4, JAG1, JAG2, DLL1, DLL3, DLL4, or Hes-1 transcript. In certain embodiments, the Notch signaling pathway member transcript is a JAG1 transcript. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be part of a double-stranded duplex.

Certain embodiments are drawn to a compound or composition comprising a Notch signaling pathway inhibitor for use in reducing, improving, or regulating trans-differentiation from club cells or goblet cells to ciliated cells, decreased mucus in the lungs, and increased lung function, or a combination thereof, in an individual. In certain embodiments, the compound or composition is provided for use in improving and/or increasing lung function in the individual. In certain embodiments, the individual is identified as having, or at risk of having a respiratory disease, disorder, condition, symptom, or physiological marker associated with excessive mucus production. In certain embodiments, the respiratory disorder associated with excessive mucus production is asthma, COPD, IPF, or CF. In certain embodiments, the individual is human. In certain embodiments, the Notch signaling pathway inhibitor is an antisense compound or an oligomeric compound targeted to the Notch signaling pathway. In certain embodiments, the Notch signaling pathway inhibitor comprises or consists of a modified oligonucleotide complementary to a Notch signaling pathway member transcript. In certain embodiments, the Notch signaling pathway member transcript is a Notch1, Notch2, Notch3, Notch4, JAG1, JAG2, DLL1, DLL3, DLL4, or Hes-1 transcript. In certain embodiments, the Notch signaling pathway member transcript is a JAG1 transcript. In certain embodiments, the modified oligonucleotide is 8 to 80 linked nucleosides in length. In certain embodiments, the modified oligonucleotide is 10 to 30 linked nucleosides in length. In certain embodiments, the compound comprising or consisting of the modified oligonucleotide can be single-stranded. In certain embodiments, the compound comprising or consisting of the modified oligonucleotide can be part of a double-stranded duplex.

Certain embodiments are drawn to use of compounds or compositions described herein for the manufacture or preparation of a medicament for therapy. Certain embodiments are drawn to the use of one compound or composition as described herein in the manufacture or preparation of a medicament for treating, preventing, delaying the onset, slowing the progression, or ameliorating one or more diseases, disorders, conditions, symptoms or physiological markers associated with the Notch signaling pathway. In certain embodiments, a compound or composition as described herein is used in the manufacture or preparation of a medicament for treating, ameliorating, delaying or preventing a respiratory disorder associated with excessive mucus production, or a symptom or physiological marker thereof. In certain embodiments, the respiratory disorder associated with excessive mucus production is asthma, COPD, IPF, or CF. In certain embodiments, the compound or composition comprises an antisense compound or an oligomeric compound targeted to the Notch signaling pathway. In certain embodiments, the compound or composition comprises or consists of a modified oligonucleotide complementary to a Notch signaling pathway member transcript. In certain embodiments, the Notch signaling pathway member transcript is a Notch1, Notch2, Notch3, Notch4, JAG1, JAG2, DLL1, DLL3, DLL4, or Hes-1 transcript. In certain embodiments, the Notch signaling pathway member transcript is a JAG1 transcript. In certain embodiments, the modified oligonucleotide is 8 to 80 linked nucleosides in length. In certain embodiments, the modified oligonucleotide is 10 to 30 linked nucleosides in length. In certain embodiments, the compound or composition comprising or consisting of the modified oligonucleotide can be single-stranded. In certain embodiments, the compound or composition comprising or consisting of the modified oligonucleotide can be part of a duplex that is double-stranded.

Certain embodiments are drawn to the use of a compound or composition for the manufacture or preparation of a medicament for reducing, improving, or regulating trans-differentiation from club cells or goblet cells to ciliated cells, decreased mucus in the lungs, and increased lung function, or a combination thereof, in an individual having or at risk of having a respiratory disorder associated with excessive mucus production. Certain embodiments are drawn to use of one compound or composition in the manufacture or preparation of a medicament for reducing, improving, or regulating increased lung function in the individual. In certain embodiments, the compound or composition comprises one antisense compound or an oligomeric compound targeted to the Notch signaling pathway. In certain embodiments, the compound or composition comprises or consists of a modified oligonucleotide complementary to a Notch signaling pathway member transcript. In certain embodiments, the Notch signaling pathway member transcript is a Notch1, Notch2, Notch3, Notch4, JAG1, JAG2, DLL1, DLL3, DLL4, or Hes-1 transcript. In certain embodiments, the Notch signaling pathway member transcript is a JAG1 transcript. In certain embodiments, the modified oligonucleotide is 8 to 80 linked nucleosides in length. In certain embodiments, the modified oligonucleotide is 10 to 30 linked nucleosides in length. In certain embodiments, the compound or composition comprising the modified oligonucleotide can be single-stranded. In certain embodiments, the compound or composition comprising the modified oligonucleotide can be part of a duplex that is double-stranded.

In any of the foregoing methods or uses, the compound or composition can comprise an antisense compound targeted to the Notch signaling pathway. In certain embodiments, the compound comprises a modified oligonucleotide, for example a modified oligonucleotide consisting of 8 to 80 linked nucleosides, 10 to 30 linked nucleosides, 12 to 30 linked nucleosides, or 20 linked nucleosides. In certain embodiments, the modified oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked 2'-deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein the nucleoside of each wing segment immediately adjacent to the gap segment comprises a modified sugar. In certain embodiments, the compound can comprise a modified oligonucleotide 12 to 80 linked nucleosides in length and having a nucleobase sequence complementary to a Notch signaling pathway member transcript. In certain embodiments, the Notch signaling pathway member transcript is a Notch1, Notch2, Notch3, Notch4, JAG1, JAG2, DLL1, DLL3, DLL4, or Hes-1 transcript. In certain embodiments, the Notch signaling pathway member transcript is a JAG1 transcript. In certain embodiments, the compound is an antisense compound or oligomeric compound. In certain embodiments, the compound is single-stranded. In certain embodiments, the compound is part of a duplex that is double-stranded. In certain embodiments, the modified oligonucleotide is 12 to 30 linked nucleosides in length. In certain embodiments, the compounds or compositions disclosed herein comprise a pharmaceutically acceptable carrier or diluent.

In any of the foregoing methods or uses, the compound or composition comprises or consists of a modified oligonucleotide 12 to 30 linked nucleosides in length, wherein the modified oligonucleotide comprises:
a gap segment consisting of linked 2'-deoxynucleosides;
a 5' wing segment consisting of linked nucleosides; and
a 3' wing segment consisting of linked nucleosides;
wherein the gap segment is positioned between the 5' wing segment and the 3' wing segment and wherein the nucleoside of each wing segment that is immediately adjacent to the gap segment each comprises a modified sugar.

In any of the foregoing methods or uses, the compound or composition can be administered via inhalation, parenterally, or non-parenterally. Parenteral administration includes subcutaneous administration, intravenous administration, intramuscular administration, intraarterial administration, intraperitoneal administration, or intracranial administration. In certain embodiments, the administration is via inhalation. In certain embodiments, the compound or composition is co-administered with a second agent that is not a Notch signaling pathway modulator. In certain embodiments, the compound or composition and the second agent are administered concomitantly.

Certain Compounds

In certain embodiments, compounds described herein are antisense compounds. In certain embodiments, the antisense compound comprises or consists of an oligomeric compound. In certain embodiments, the oligomeric compound or antisense compound comprises a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of a modified oligonucleotide. In certain embodiments, the modified oligonucleotide is an antisense oligonucleotide.

In certain embodiments, antisense compounds are double-stranded. Such double-stranded compounds comprise a first oligomeric compound comprising or consisting of a modified oligonucleotide having a region complementary to a target nucleic acid and a second oligomeric compound comprising or consisting of a modified oligonucleotide having a region complementary to the first modified oligonucleotide. In certain embodiments, the modified oligonucleotide is an RNA oligonucleotide. In certain embodiments, the thymine nucleobase in the modified oligonucleotide is replaced by a uracil nucleobase. In certain embodiments, the compound comprises a conjugate group. In certain embodiments, each modified oligonucleotide is 12-30 linked nucleosides in length. The oligomeric compounds of double-stranded compounds may include non-complementary overhanging nucleosides.

Examples of single-stranded and double-stranded compounds include but are not limited to oligonucleotides, siRNAs, microRNA targeting oligonucleotides, and single-stranded RNAi compounds, such as small hairpin RNAs (shRNAs), single-stranded siRNAs (ssRNAs), and microRNA mimics. In certain embodiments, a compound described herein has a nucleobase sequence that, when written in the 5' to 3' direction, comprises the reverse complement of the target segment of a target nucleic acid to which it is complementary.

In certain embodiments, a compounds described herein comprise a modified oligonucleotide 12 to 30 linked nucleosides in length. In certain embodiments, compounds described herein comprise a modified oligonucleotide 12 to 22 linked nucleosides in length. In certain embodiments, compounds described herein comprise a modified oligonucleotide 14 to 30 linked nucleosides in length. In certain embodiments, compounds described herein comprise a modified oligonucleotide 14 to 20 linked nucleosides in length. In certain embodiments, compounds described herein comprise a modified oligonucleotide 15 to 30 linked nucleosides in length. In certain embodiments, compounds described herein comprise a modified oligonucleotide 15 to 20 linked nucleosides in length. In certain embodiments, compounds described herein comprise a modified oligonucleotide 16 to 30 linked nucleosides in length. In certain embodiments, compounds described herein comprise a modified oligonucleotide 16 to 20 linked nucleosides in length. In other words, such modified oligonucleotides are from 12 to 30 linked nucleosides, 12 to 22 linked nucleosides, 14 to 30 linked nucleosides, 14 to 20 nucleosides, 15 to 30 nucleosides, 15 to 20 nucleosides, 16 to 30 nucleosides, or 16 to 20 nucleosides, respectively. In certain embodiments, a compound described herein comprises a modified oligonucleotide 16 linked nucleosides in length. In certain embodiments, a compound described herein comprises a modified oligonucleotide 17 linked nucleosides in length. In certain embodiments, compound described herein comprises a modified oligonucleotide 18 linked nucleosides in length. In certain embodiments, a compound described herein comprises a modified oligonucleotide 19 linked nucleosides in length. In certain embodiments, a compound described herein comprises a modified oligonucleotide 20 linked nucleosides in length. In other embodiments, a compound described herein comprises a modified oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides. In certain such embodiments, the compound described herein comprises a modified oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleosides in length, or a range defined by any two of the above values.

In certain embodiments, compounds described herein are interfering RNA compounds (RNAi), which include double-stranded RNA duplexes (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics.

In certain embodiments, a double-stranded compound or duplex comprises a first oligomeric compound comprising the nucleobase sequence complementary to a target region of a Notch signaling pathway nucleic acid and a second oligomeric compound. In certain such embodiments, the double-stranded duplex comprises ribonucleotides in which the first strand has uracil (U) in place of thymine (T) and is complementary to a target region. In certain embodiments, the double-stranded duplex comprises one or more modified nucleosides comprising a 2'-F modified sugar moiety or 2'-O-alkyl modified sugar moiety (such as a methoxy group; 2'-OMe). In certain embodiments, the double-stranded duplex comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along an oligomeric compound of the duplex. In certain embodiments, the double-stranded duplex comprises one or more linkages between adjacent nucleosides other than a phosphodiester linkage. Examples of such linkages include phosphoramide, phosphorothioate, and phosphorodithioate linkages. The double-stranded duplexes may also be chemically modified nucleic acid molecules as taught in U.S. Pat. No. 6,673,661. In other embodiments, the duplex contains one or two capped oligomeric compounds, as disclosed, for example, by WO 00/63364, filed Apr. 19, 2000. In certain embodiments, the first oligomeric compound of the double-stranded duplex is an siRNA guide strand and the second oligomeric compound of the double-stranded duplex is an siRNA passenger strand. In certain embodiments, the second oligomeric compound of the double-stranded duplex is complementary to the first oligomeric compound. In certain embodiments, each oligomeric compound of the double-stranded duplex consists of 16, 17, 18, 19, 20, 21, 22, or 23 linked nucleosides. In certain embodiments, one oligomeric compound of the duplex comprises a conjugate group. In certain embodiments, both oligomeric compounds of the duplex each comprise a conjugate group.

Further description of the compounds herein is provided below:

I. Certain Oligonucleotides

In certain embodiments, compounds described herein comprise oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified furanosyl sugar moieties comprising one or more acyclic substituent, including but not limited to substituents at the 2', 4', and/or 5' positions. In certain embodiments, the furanosyl sugar moiety is a ribosyl sugar moiety. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, $CF_3$, $OCF_3$, O—$C_1$-$C_{10}$ alkoxy, O—$C_1$-$C_{10}$ substituted alkoxy, O—$C_1$-$C_{10}$ alkyl, O—$C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$ $SCH_3$, O($CH_2$)$_2$ON($R_m$)($R_n$) or $OCH_2$C(=O)—N($R_m$)($R_n$), where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859, 221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836).

In certain embodiments, a 2'-substituted nucleoside or 2'-non-bicyclic modified nucleoside comprises a sugar moiety comprising a non-bridging 2'-substituent group selected from: F, $NH_2$, $N_3$, $OCF_3$, $OCH_3$, O($CH_2$)$_3NH_2$, $CH_2CH=CH_2$, $OCH_2CH=CH_2$, $OCH_2CH_2OCH_3$, O($CH_2$)$_2$ $SCH_3$, O($CH_2$)$_2$ON($R_m$)($R_n$), O($CH_2$)$_2$O($CH_2$)$_2$N($CH_3$)$_2$, and N-substituted acetamide ($OCH_2$C(=O)—N($R_m$)($R_n$)), where each $R_m$ and $R_n$ is, independently, H, an amino protecting group, or substituted or unsubstituted $C_1$-$C_{10}$ alkyl.

In certain embodiments, a 2'-substituted nucleoside or 2'-non-bicyclic modified nucleoside comprises a sugar moiety comprising a non-bridging 2'-substituent group selected from: F, $OCF_3$, $OCH_3$, $OCH_2CH_2OCH_3$, O($CH_2$)$_2SCH_3$, O($CH_2$)$_2$ON($CH_3$)$_2$, O($CH_2$)$_2$O($CH_2$)$_2$N($CH_3$)$_2$, and $OCH_2$C(=O)—N(H)$CH_3$ ("NMA").

In certain embodiments, a 2'-substituted nucleoside or 2'-non-bicyclic modified nucleoside comprises a sugar moiety comprising a non-bridging 2'-substituent group selected from: F, $OCH_3$, and $OCH_2CH_2OCH_3$.

Nucleosides comprising modified sugar moieties, such as non-bicyclic modified sugar moieties, may be referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. In certain such embodiments, the furanose ring is a ribose ring. Examples of such 4' to 2' bridging sugar substituents include but are not limited to: 4'-$CH_2$-2', 4'-($CH_2$)$_2$-2', 4'-($CH_2$)$_3$-2', 4'-$CH_2$—O-2' ("LNA"), 4'-$CH_2$—S-2', 4'-($CH_2$)$_2$—O-2' ("ENA"), 4'-CH($CH_3$)—O-2' (referred to as "constrained ethyl" or "cEt" when in the S configuration), 4'-$CH_2$—O—$CH_2$-2', 4'-$CH_2$—N(R)-2', 4'-CH($CH_2OCH_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C($CH_3$)($CH_3$)—O-2' and analogs thereof (see, e.g., Seth et al., U.S. Pat. No. 8,278,283), 4'-$CH_2$—N($OCH_3$)-2' and analogs thereof (see, e.g., Prakash et al., U.S. Pat. No. 8,278,425), 4'-$CH_2$—O—N($CH_3$)-2' (see, e.g., Allerson et al., U.S. Pat. No. 7,696,345 and Allerson et al., U.S. Pat. No. 8,124,745), 4'-$CH_2$—C(H)($CH_3$)-2' (see, e.g., Zhou, et al., *J. Org. Chem.*, 2009, 74, 118-134), 4'-$CH_2$—C(=$CH_2$)-2' and analogs thereof (see e.g., Seth et al., U.S. Pat. No. 8,278,426), 4'-C($R_aR_b$)—N(R)—O-2', 4'-C($R_aR_b$)—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —[C($R_a$)($R_b$)]$_n$—, —[C($R_n$)($R_b$)]$_a$—O—, —C($R_n$)=C($R_b$)—, —C($R_a$)=N—, —C(=$NR_a$)—, —C(=O)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 20017, 129, 8362-8379; Elayadi et al.; Wengel et al., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

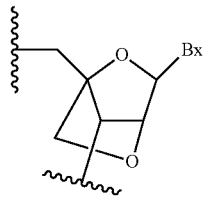
LNA (β-D-configuration)
bridge = 4'-CH$_2$-O-2'

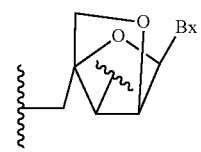
α-L-LNA (α-L-configuration)
bridge = 4'-CH$_2$-O-2'

α-L-methyleneoxy (4'-CH$_2$—O-2') or α-L-LNA bicyclic nucleosides have been incorporated into antisense oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

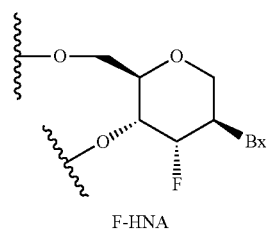
F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

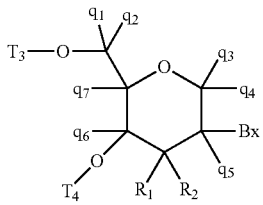

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

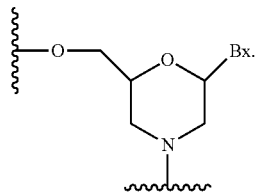

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides).

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further modified nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

B. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS-P=S"). Representative non-phosphorus containing internucleoside linking groups include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

C. Certain Motifs

In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain such embodiments, each nucleoside to the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

D. Certain Lengths

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides E. Certain Modified Oligonucleotides In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists if of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 70%, at least 80%, at least 90%, at least 95%, or 100% complementary to the second oligonucleotide or nucleic acid, such as a target nucleic acid.

As an example, a compound in which 18 of 20 nucleobases of the compound are complementary to a target region would represent 90 percent complementarity to the target region. In this example, the remaining non-complementary nucleobases may be clustered or interspersed with complementary nucleobases and need not be contiguous to each other or to complementary nucleobases. Percent complementarity of a compound with a region of a target nucleic acid can be determined routinely using BLAST programs (basic local alignment search tools) and Power-BLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein also include those which are complementary to a portion of a target nucleic acid. In certain embodiments, the compounds are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

In certain embodiments, compounds herein comprise oligonucleotides that are complementary to the target nucleic acid over the entire length of the oligonucleotide. In certain embodiments, such oligonucleotides are 99% complementary to the target nucleic acid. In certain embodiments, such oligonucleotides are 95% complementary to the target nucleic acid. In certain embodiments, such oligonucleotides are 90% complementary to the target nucleic acid. In certain embodiments, such oligonucleotides are 85% complementary to the target nucleic acid. In certain embodiments, such oligonucleotides are 80% complementary to the target nucleic acid. In certain embodiments, antisense oligonucleotides are at least 80% complementary to the target nucleic acid over the entire length of the oligonucleotide and comprise a region that is 100% or fully complementary to a target nucleic acid. In certain such embodiments, the region of full complementarity is from 6 to 20 nucleobases in length. In certain such embodiments, the region of full complementarity is from 10 to 18 nucleobases in length. In certain such embodiments, the region of full complementarity is from 18 to 20 nucleobases in length.

In certain embodiments, compounds comprising an oligonucleotide comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the antisense compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region.

II. Certain Oligomeric Compounds

In certain embodiments, the invention provides oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, abasic nucleosides, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., Bioorg. Med. Chem. Lett., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Lett., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO 1, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid a palmityl moiety (Mishra et al., Biochim. Biophys. Acta, 1995, 1264, 229-237), an octadecylamine or hexylamino-carbonyl-oxycholesterol moiety (Crooke et al., J. Pharmacol. Exp. Ther., 1996, 277, 923-937), a tocopherol group (Nishina et al., Molecular Therapy Nucleic Acids, 2015, 4, e220; and Nishina et al., Molecular Therapy, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain oligomeric compounds, a conjugate moiety is attached to an oligonucleotide via a more complex conjugate linker comprising one or more conjugate linker moieties, which are sub-units making up a conjugate linker. In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

III. Certain Antisense Compounds

In certain embodiments, the present invention provides antisense compounds, which comprise or consist of an oligomeric compound comprising an antisense oligonucleotide, having a nucleobase sequences complementary to that of a target nucleic acid. In certain embodiments, antisense compounds are single-stranded. Such single-stranded antisense compounds typically comprise or consist of an oligomeric compound that comprises or consists of a modified oligonucleotide and optionally a conjugate group. In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of a modified oligonucleotide and optionally a conjugate group. The oligonucleotide of the second oligomeric compound of such double-stranded antisense compound may be modified or unmodified. Either or both oligomeric compounds of a double-stranded antisense compound may comprise a conjugate group. The oligomeric compounds of double-stranded antisense compounds may include non-complementary overhanging nucleosides.

In certain embodiments, oligomeric compounds of antisense compounds are capable of hybridizing to a target nucleic acid, resulting in at least one antisense activity. In certain embodiments, antisense compounds selectively affect one or more target nucleic acid. Such selective antisense compounds comprises a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, the invention provides antisense compounds that are sufficiently "DNA-like" to elicit RNase H activity. Further, in certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain such embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain such embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

IV. Target Nucleic Acids

In certain embodiments, compounds described herein comprise or consist of an oligonucleotide that is complementary to a target nucleic acid. In certain embodiments, the target nucleic acid is an endogenous RNA transcript. In certain such embodiments, the target transcript is selected from: an mRNA and a pre-mRNA, including intronic, exonic and untranslated regions. In certain embodiments, the target transcript is a mRNA. In certain embodiments, the target transcript is a pre-mRNA. In certain such embodiments, the target region of the target transcript is entirely within an intron. In certain embodiments, the target region spans an intron/exon junction. In certain embodiments, the target region is entirely within an exon. In certain embodiments, the target transcript is a Notch signaling pathway member transcript. In certain embodiments, the target transcript is a Notch1, Notch2, Notch3, Notch4, JAG1, JAG2, DLL1, DLL3, DLL4, or Hes-1 transcript. In certain embodiments, the target transcript is a JAG1 transcript.

In certain embodiments, a compound comprising a Notch signaling pathway inhibitor inhibits the expression or activity of multiple members of the Notch signaling pathway but targets only one member of the Notch signaling pathway. In certain such embodiments, the Notch signaling pathway inhibitor is a modified oligonucleotide complementary to a Notch signaling pathway member. In such embodiments, the target nucleic acid or target transcript of the Notch signaling pathway inhibitor is the nucleic acid or transcript of the Notch signaling pathway to which the modified oligonucleotide has the greatest complementarity. In certain embodiments, the target Notch signaling pathway transcript is inhibited and at least one Notch signaling pathway member that is not the target transcript is also inhibited.

Nucleobase sequences of Notch signaling pathway member transcripts include, without limitation, SEQ ID Numbers 1, 2, 3, 4, 5, 6, 7, 8, 9, 10, 11, and 12.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

In certain embodiments, the present invention provides pharmaceutical compositions comprising one or more compounds or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compound and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

A compound described herein comprising a Notch signaling pathway member inhibitor can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a Notch signaling pathway member inhibitor and a pharmaceutically acceptable diluent. In certain embodiments, the pharmaceutically acceptable diluent is water. In certain embodiments, the compound comprises or consists of a modified oligonucleotide provided herein.

Certain embodiments provide pharmaceutical compositions suitable for aerosolization and/or dispersal by a nebulizer or inhaler. Such devices are well known in the art. In certain such embodiments, the pharmaceutical composition is a solid comprising particles of compounds that are of respirable size. A solid particulate composition can optionally contain a dispersant which serves to facilitate the formation of an aerosol, e.g., lactose. Solid pharmaceutical compositions comprising a modified oligonucleotide can also be aerosolized using any solid particulate medicament aerosol generator known in the art, e.g., a dry powder inhaler. In certain embodiments, the powder employed in the inhaler consists of the compound comprising the active compound or of a powder blend comprising the active compound, a suitable powder diluent, and an optional surfactant.

In certain embodiments, the pharmaceutical composition is a liquid. In certain such embodiments, the liquid is administered as an aerosol that is produced by any suitable means, such as with a nebulizer or inhaler. See, e.g., U.S. Pat. No. 4,501,729. Nebulizers are devices that transform solutions or suspensions into an aerosol mist and are well known in the art. Suitable nebulizers include jet nebulizers, ultrasonic nebulizers, electronic mesh nebulizers, and vibrating mesh nebulizers. Companies such as PARI and Vectura sell some types of such suitable nebulziers. In certain embodiments, the aerosol is produced by a metered dose inhaler, which typically contains a suspension or solution formulation of the active compound in a liquefied propellant. Inhalers suitable for dispensing liquid aerosol also include certain inhalers sold by Respimat (See, e.g., Anderson, *Int J Chron Obstruct Pulmon Dis.* 1, 251 (2006).) Pharmaceutical compositions suitable for aerosolization can comprise propellants, surfactants, co-solvents, dispersants, preservatives, and/or other additives or excipients.

A compound described herein complementary to a Notch signaling pathway member nucleic acid can be utilized in pharmaceutical compositions by combining the compound with a suitable pharmaceutically acceptable diluent or carrier and/or additional components such that the pharmaceutical composition is suitable for aerosolization by a nebulizer. In certain embodiments, a pharmaceutically acceptable diluent is phosphate buffered saline. Accordingly, in one embodiment, employed in the methods described herein is a pharmaceutical composition comprising a compound complementary to a Notch signaling pathway member nucleic acid and a pharmaceutically acceptable diluent. In certain embodiments, the pharmaceutically acceptable diluent is phosphate buffered saline. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an individual, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound.

In certain embodiments, the compounds or compositions further comprise a pharmaceutically acceptable carrier or diluent.

Certain Combinations and Combination Therapies

In certain embodiments, a first agent comprising the compound described herein is co-administered with one or more additional agents. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, one or more compounds or compositions provided herein are co-administered with one or more secondary agents. In certain embodiments, a method of treating an individual suffering from a respiratory disorder associated with excessive mucus production comprises administering a compound or composition provided herein and and one or more secondary agents. In certain embodiments, one or more compounds or compositions provided herein and one or more secondary agents are administered at different times. In certain embodiments, one or more compounds or compositions provided herein and one or more secondary agents are prepared together in a single formulation. In certain embodiments, one or more compounds or compositions provided herein and one or more secondary agents are prepared separately.

Certain embodiments are directed to the use of a compound comprising a Notch signaling pathway inhibitor as described herein in combination with a secondary agent. Certain embodiments are directed to use of a compound comprising a Notch signaling pathway inhibitor as described herein and a secondary agent in the preparation or manufacture of a medicament for treating a respiratory disorder associated with excessive mucus production. In certain embodiments the respiratory disorder associated with excessive mucus production is selected from: asthma, COPD, IPF, and CF.

Certain embodiments are drawn to a combination comprising a compound comprising a Notch signaling pathway inhibitor as described herein and a secondary agent. In such embodiments, the secondary agent is not a Notch signaling pathway inhibitor. In certain embodiments, such a combination is useful for increasing trans-differentiation from club cells or goblet to ciliated cells, decreasing mucus in the lungs, or increasing lung function, or a combination thereof and/or treating a respiratory disorder associated with excessive mucus production. In certain embodiments the respiratory disorder associated with excessive mucus production is selected from: asthma, COPD, IPF, and CF.

In certain embodiments, the compound comprising a Notch signaling pathway inhibitor, as described herein and the secondary agent are used in combination treatment by administering the two agents simultaneously, separately or sequentially. In certain embodiments, the two agents are formulated as a fixed dose combination product. In other embodiments, the two agents are provided to the patient as separate units which can then either be taken simultaneously or serially (sequentially).

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β, such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their racemic and optically pure forms. All tautomeric forms of the compounds provided herein are included unless otherwise indicated.

The compounds described herein include variations in which one or more atoms are replaced with a non-radioactive isotope or radioactive isotope of the indicated element. For example, compounds provided herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

Example 1: Inhibition of the Notch Signaling Pathway by Modified Oligonucleotides Complementary to JAG1

Modified oligonucleotides 100% complementary to mouse JAG1 were tested at various doses in HEPA1-6 (mouse hepatoma) cells. The cells were plated at a density of 20,000 cells per well and transfected using electroporation with 0.22 μM, 0.66 μM, 2 μM, or 6 μM modified oligonucleotide, as specified in the tables below. After a treatment period of approximately 24 hours, total RNA was isolated from the cells and JAG1 mRNA levels were measured by RT-qPCR. Mouse JAG1 primer probe set RTS35952 (Forward sequence: ACCGTAATCG-CATCGTACTG (SEQ ID No: 13) Reverse sequence: TGC-TATCAGGTTGAATAGTGTCA (SEQ ID No: 14) Probe sequence: CCTGGCCGAGGTCCTACACTTTG (SEQ ID No: 15) was used to measure mRNA levels. JAG1 mRNA levels were adjusted according to total RNA content as measured by RIBOGREEN. Results are presented as the percent level of JAG1 mRNA, relative to that of the untreated control cells. As illustrated in the tables below, JAG1 mRNA transcript levels were reduced in a dose-dependent manner in cells treated with modified oligonucleotides complementary to JAG1.

The modified oligonucleotides in the tables below are gapmers, wherein the central gap segment consists of ten 2'-deoxynucleosides linked via phosphorothioate internucleoside linkages, and each wing segment consists of three cEt nucleosides linked via phosphorothioate internucleoside linkages. All cytosine residues throughout each gapmer are 5-methylcytosines. The internucleoside linkages throughout each gapmer are phosphorothioate linkages. In the tables below, "start Site" indicates the 5'-most nucleoside to which the gapmer is complementary in the mouse nucleic acid target sequence. "Stop Site" indicates the 3'-most nucleoside to which the gapmer is complementary in the mouse nucleic acid target sequence. The modified oligo-nucleotides are 100% complementary to the pre-mRNA sequence of mouse JAG1 (the complement of GENBANK No. NC_000068.7 truncated from 137078001 to Ser. No. 13/712,000, herein referred to as SEQ ID No. 1) and/or the mRNA sequence of mouse JAG1 (NM_013822.5, herein referred to as SEQ ID No. 2). An entry of "N/A" in the table below indicates that the modified oligonucleotide is not 100% complementary to the corresponding nucleic acid.

TABLE 1

Modified oligonucleotides complementary to JAG1

| Compound Number | Sequence | SEQ ID 1 start site | SEQ ID 1 stop site | SEQ ID 2 start site | SEQ ID 2 stop site | SEQ ID NO. |
|---|---|---|---|---|---|---|
| 897215 | AAGTATCACTCTCCCC | 34671 | 34686 | 2861 | 2876 | 37 |
| 897272 | GGCACATTCACTAGTT | 37184 | 37199 | 4127 | 4142 | 38 |
| 897316 | GTAATGAGATTCAACC | 38094 | 38109 | 5037 | 5052 | 39 |
| 897317 | GTAAGATTGGGATGCT | 38139 | 38154 | 5082 | 5097 | 40 |
| 897319 | CAGCATTACATAACGA | 38183 | 38198 | 5126 | 5141 | 41 |
| 897353 | GCAATATAGGGCTCGG | 4635 | 4650 | N/A | N/A | 42 |
| 897363 | ATGTACTTGGCCCAGC | 6521 | 6536 | N/A | N/A | 43 |
| 897367 | GCGAATGAAGCTGTGC | 6883 | 6898 | N/A | N/A | 44 |
| 897368 | GCTTATGTGGCTATGA | 7133 | 7148 | N/A | N/A | 45 |
| 897372 | GCGATACTGAGATGGC | 7390 | 7405 | N/A | N/A | 46 |
| 897375 | GTGTGACACGGGTTCA | 7919 | 7934 | N/A | N/A | 47 |
| 897376 | CAGCATAATCATACCC | 8019 | 8034 | N/A | N/A | 48 |
| 897382 | GGATTACCAAGCTGGC | 8854 | 8869 | N/A | N/A | 49 |
| 897386 | AGAATACCAGGGAGCC | 9368 | 9383 | N/A | N/A | 50 |
| 897393 | TGCATTGGAGTTCCAG | 11088 | 11103 | N/A | N/A | 51 |
| 897417 | CACAATGAGACAGCGC | 14223 | 14238 | N/A | N/A | 52 |
| 897426 | AGTTTTTGCAAATAGA | 15634 | 15649 | N/A | N/A | 53 |
| 897427 | GAGTTTTTGCAAATAG | 15635 | 15650 | N/A | N/A | 54 |
| 897439 | TGTGATCCGTATCCTT | 17410 | 17425 | N/A | N/A | 55 |
| 897454 | CAGTATTGTCCCTGGA | 20564 | 20579 | N/A | N/A | 56 |
| 897498 | CTGTTCAAGCAATGAC | 28083 | 28098 | N/A | N/A | 57 |
| 897505 | TGTCATGTGTCAAGCA | 28105 | 28120 | N/A | N/A | 58 |
| 897506 | CCAGACTAGCGGTTCC | 28243 | 28258 | N/A | N/A | 59 |
| 897530 | TGGACAATGGCTTGGC | 33218 | 33233 | N/A | N/A | 60 |
| 897533 | ACCACAACAGTTCTGA | 33811 | 33826 | N/A | N/A | 61 |

TABLE 2

Dose Response

| Compound Number | JAG1 mRNA (% control) | | | |
|---|---|---|---|---|
| | 222 nM | 666 nM | 2,000 nM | 6,000 nM |
| 897272 | 92 | 66 | 37 | 19 |
| 897316 | 77 | 52 | 25 | 12 |
| 897353 | 72 | 52 | 20 | 4 |
| 897363 | 77 | 63 | 32 | 6 |
| 897375 | 69 | 41 | 15 | 4 |
| 897376 | 81 | 79 | 30 | 7 |
| 897382 | 79 | 50 | 16 | 5 |
| 897393 | 84 | 50 | 27 | 6 |
| 897417 | 92 | 74 | 41 | 11 |
| 897454 | 103 | 66 | 38 | 9 |
| 897533 | 88 | 74 | 36 | 11 |

TABLE 3

Dose Response

| Compound Number | JAG1 mRNA (% control) | | | |
|---|---|---|---|---|
| | 222 nM | 666 nM | 2,000 nM | 6,000 nM |
| 897215 | 83 | 60 | 40 | 12 |
| 897317 | 66 | 45 | 22 | 17 |
| 897319 | 79 | 69 | 28 | 15 |
| 897367 | 81 | 45 | 18 | 5 |
| 897368 | 64 | 54 | 19 | 5 |
| 897372 | 45 | 16 | 4 | 3 |
| 897386 | 67 | 49 | 24 | 12 |
| 897426 | 98 | 81 | 52 | 19 |
| 897427 | 83 | 48 | 19 | 7 |
| 897439 | 79 | 57 | 26 | 8 |
| 897498 | 90 | 72 | 40 | 17 |
| 897505 | 64 | 45 | 18 | 8 |

TABLE 3-continued

| | Dose Response | | | |
|---|---|---|---|---|
| Compound | JAG1 mRNA (% control) | | | |
| Number | 222 nM | 666 nM | 2,000 nM | 6,000 nM |
| 897506 | 79 | 55 | 27 | 17 |
| 897530 | 82 | 69 | 27 | 9 |

Example 2: Inhibition of the Notch Signaling Pathway by Modified Oligonucleotides Complementary to Notch1

Modified oligonucleotides 100% complementary to mouse Notch1 were tested at various doses in b.END cells. Cells were plated at a density of 20,000 cells per well and transfected using electroporation with 0.37 µM, 1.1 µM, 3.3 µM, or 10 µM modified oligonucleotide, as specified in the tables below. After a treatment period of approximately 24 hours, total RNA was isolated from the cells and Notch1 mRNA levels were measured by RT-qPCR. Mouse Notch1 primer probe set RTS1458 (Forward sequence: CGTGGTCTTCAAGCGTGATG (SEQ ID No: 16) Reverse sequence: GGTGCTTGCGCAGCTCTT (SEQ ID No: 17) Probe sequence: CCAGCAGATGATCTTCCCGTACTATG (SEQ ID No: 18) was used to measure Notch1 mRNA levels. The resulting Notch1 mRNA levels were adjusted according to total RNA content as measured by RIBOGREEN. Results are presented as the percent level of Notch1 mRNA transcript, relative to that of the untreated control cells. As illustrated in the tables below, Notch1 mRNA levels were reduced in a dose-dependent manner in cells treated with modified oligonucleotides complementary to Notch 1.

The modified oligonucleotides in the tables below are cEt gapmers (as described in Example 1). The nucleobase sequences of the modified oligonucleotides, shown in the tables below, are 100% complementary to mouse Notch1 pre-mRNA (the complement of GENBANK No. NW_000174.1_truncated from 3935000 to 3983000, herein referred to as SEQ ID No. 3), and/or to mouse Notch1 mRNA (Genbank No. NM_008714.3, herein referred to as SEQ ID: 4). An entry of "N/A" in the table below indicates that the modified oligonucleotide is not 100% complementary to the corresponding nucleic acid.

TABLE 4

Modified oligonucleotides complementary to Notch1

| Compound Number | Sequence | SEQ ID 3 start site | SEQ ID 3 stop site | SEQ ID 4 start site | SEQ ID 4 stop site | SEQ ID NO |
|---|---|---|---|---|---|---|
| 784187 | ACTCAAAGGGCAGGCA | 20358 | 20373 | 727 | 742 | 62 |
| 784217 | ATACACCTTCATAACC | 25344 | 25359 | 1705 | 1720 | 63 |
| 784227 | GTAGGAGTTGTCACGG | 26792 | 26807 | 2124 | 2139 | 64 |
| 784255 | CTCGCAGTGGATGCCA | 32080 | 32095 | 3192 | 3207 | 65 |
| 784303 | CTCAATCTGCGGTGGG | 36410 | 36425 | 4587 | 4602 | 66 |
| 784421 | CGATTTTGGAAAGAAG | 45740 | 45755 | 8225 | 8240 | 67 |
| 784432 | AAGTTGTCAGGAAGGG | 46117 | 46132 | 8602 | 8617 | 68 |
| 784446 | ACACTTGTTCCTTTAG | 46549 | 46564 | 9034 | 9049 | 69 |
| 784448 | CAAGGTCTGGGTCACA | 46612 | 46627 | 9097 | 9112 | 70 |
| 784455 | AACATCTTAGGATGCG | 46817 | 46832 | 9302 | 9317 | 71 |
| 784496 | CAAGACTGACAGTCCA | 10006 | 10021 | N/A | N/A | 72 |
| 784511 | GCAAGAAAGATCTCTC | 15515 | 15530 | N/A | N/A | 73 |
| 784527 | ATGTCAAGTCAACAAA | 19786 | 19801 | N/A | N/A | 74 |
| 784563 | CTTCATGTTTCCACAA | 30213 | 30228 | N/A | N/A | 75 |
| 784585 | GATCAATTCTCTCTCT | 38985 | 39000 | N/A | N/A | 76 |
| 784596 | GACAAAGGATTTAGGG | 39041 | 39056 | N/A | N/A | 77 |
| 784600 | CTGCGCTCGCATTGAG | 39064 | 39079 | N/A | N/A | 78 |

TABLE 5

| | Dose response | | | | |
|---|---|---|---|---|---|
| Compound | Notch1 mRNA (% control) | | | | IC$_{50}$ |
| Number | 370 nM | 1111 nM | 3333 nM | 10,000 nM | (µM) |
| 784511 | 62 | 44 | 23 | 14 | 0.7 |
| 784600 | 92 | 76 | 51 | 29 | 3.6 |
| 784187 | 84 | 66 | 49 | 40 | 4.0 |
| 784455 | 68 | 46 | 38 | 34 | 1.3 |
| 784421 | 75 | 50 | 40 | 20 | 1.5 |
| 784227 | 79 | 58 | 46 | 25 | 2.2 |

TABLE 5-continued

| Compound | Dose response | | | | |
|---|---|---|---|---|---|
| | Notch1 mRNA (% control) | | | | IC$_{50}$ |
| Number | 370 nM | 1111 nM | 3333 nM | 10,000 nM | (µM) |
| 784563 | 67 | 55 | 34 | 22 | 1.3 |
| 784527 | 78 | 61 | 49 | 17 | 2.1 |
| 784217 | 76 | 62 | 42 | 24 | 2.1 |
| 784432 | 63 | 56 | 38 | 27 | 1.4 |
| 784446 | 61 | 48 | 30 | 27 | 0.9 |

TABLE 6

| Compound | Dose response | | | | |
|---|---|---|---|---|---|
| | Notch 1 mRNA (% control) | | | | IC$_{50}$ |
| Number | 370 nM | 1111 nM | 3333 nM | 10,000 nM | (µM) |
| 784255 | 114 | 92 | 82 | 46 | >10 |
| 784585 | 103 | 87 | 71 | 36 | 6.5 |
| 784303 | 100 | 83 | 64 | 45 | 7.5 |
| 784448 | 88 | 55 | 44 | 27 | 2.3 |
| 784496 | 65 | 50 | 38 | 16 | 1.1 |

Example 3: Inhibition of the Notch Signaling Pathway by Modified Oligonucleotides Complementary to Notch2

Modified oligonucleotides 100% complementary to mouse Notch2 were tested at various doses in HEPA1-6 cells. Cells were plated at a density of 20,000 cells per well and transfected using electroporation with 0.33 µM, 1.0 µM, 3.0 µM, or 9.0 µM modified oligonucleotide, as specified in the tables below. After a treatment period of approximately 24 hours, total RNA was isolated from the cells and Notch2 mRNA levels were measured by RT-qPCR. Mouse Notch2 primer probe set RTS36985 (Forward sequence: CGACTT-CACTTTCGAATGCAAC (SEQ ID No: 19) Reverse sequence: CACCATCCACACAAACTCCT (SEQ ID No: 20) Probe sequence: AATATCGACGACTGCCCCAAC-CAC (SEQ ID No: 21) was used to measure Notch2 mRNA levels. The resulting Notch2 mRNA levels were adjusted according to total RNA content as measured by RIBOGREEN. Results are presented as the percent level of Notch2 mRNA transcript, relative to that of the untreated control cells. As illustrated in the tables below, Notch2 mRNA levels were reduced in a dose-dependent manner in cells treated with modified oligonucleotides complementary to Notch2.

The modified oligonucleotides in the tables below are cEt gapmers (as described in Example 1). The nucleobase sequences of the modified oligonucleotides, shown in the tables below, are 100% complementary to mouse Notch2 pre-mRNA (GENBANK No. NC_000069.6 truncated from 98011001 to 98153000, SEQ ID No. 5) and/or to Notch2 mRNA (GENBANK No. NM_010928.2, SEQ ID No 6). An entry of "N/A" in the table below indicates that the modified oligonucleotide is not 100% complementary to the corresponding nucleic acid.

TABLE 7

| Modified oligonucleotides complementary to Notch2 | | | | | |
|---|---|---|---|---|---|
| Compound Number | Sequence | SEQ ID 5 start site | SEQ ID 5 stop site | SEQ ID 6 start site | SEQ ID 6 stop site | SEQ ID No. |
| 977277 | GGACGCAGAGCGGGCA | 2700 | 2715 | 163 | 178 | 79 |
| 977296 | GTCTGAATGACACTCG | 89309 | 89324 | 1535 | 1550 | 80 |
| 977302 | GTCGATCCCATCCTGG | 93419 | 93434 | 1913 | 1928 | 81 |
| 977306 | GCGATTGATGCCGTCC | 96111 | 96126 | 2141 | 2156 | 82 |
| 977313 | CATACACGGCTTGGAG | 106227 | 106242 | 2795 | 2810 | 83 |
| 977338 | TGTATTCCCAGCAGCG | 124731 | 124746 | 4572 | 4587 | 84 |
| 977359 | GGTTACACGGTTGCGG | 133370 | 133385 | 5954 | 5969 | 85 |
| 977375 | GGGCAACTGGACTGCG | 135999 | 136014 | 7138 | 7153 | 86 |
| 977376 | TGGTACATAGAGGGCA | 136035 | 136050 | 7174 | 7189 | 87 |
| 977380 | AGGTATGGGTGCTCGC | 136257 | 136272 | 7396 | 7411 | 88 |
| 977406 | CAGGAAGCAGGTTCGG | 137854 | 137869 | 8993 | 9008 | 89 |
| 977408 | GACTGATGGCATGGCC | 137980 | 137995 | 9119 | 9134 | 90 |
| 977413 | GGTTACTGTTCGCAGG | 138422 | 138437 | 9561 | 9576 | 91 |
| 977428 | ACAAGACATAGCCCCA | 3623 | 3638 | N/A | N/A | |
| | | 3664 | 3679 | N/A | N/A | |
| | | 3705 | 3720 | N/A | N/A | 92 |
| | | 3746 | 3761 | N/A | N/A | |
| | | 3787 | 3802 | N/A | N/A | |
| 977429 | TACAAGACATAGCCCC | 3624 | 3639 | N/A | N/A | |
| | | 3665 | 3680 | N/A | N/A | 93 |

TABLE 7-continued

Modified oligonucleotides complementary to Notch2

| Compound Number | Sequence | SEQ ID 5 start site | SEQ ID 5 stop site | SEQ ID 6 start site | SEQ ID 6 stop site | SEQ ID No. |
|---|---|---|---|---|---|---|
| | | 3706 | 3721 | N/A | N/A | |
| | | 3747 | 3762 | N/A | N/A | |
| | | 3788 | 3803 | N/A | N/A | |
| 977430 | GTACAAGACATAGCCC | 3625 | 3640 | N/A | N/A | |
| | | 3666 | 3681 | N/A | N/A | |
| | | 3707 | 3722 | N/A | N/A | 94 |
| | | 3748 | 3763 | N/A | N/A | |
| | | 3789 | 3804 | N/A | N/A | |
| 977431 | AGTACAAGACATAGCC | 3626 | 3641 | N/A | N/A | |
| | | 3667 | 3682 | N/A | N/A | |
| | | 3708 | 3723 | N/A | N/A | 95 |
| | | 3749 | 3764 | N/A | N/A | |
| | | 3790 | 3805 | N/A | N/A | |
| 977454 | TGAGTCTAGTCATGCA | 22842 | 22857 | N/A | N/A | 96 |
| 977472 | GTTATATAATCTTCCA | 37896 | 37911 | N/A | N/A | 97 |
| 977474 | TGCAAGATTGCACAGG | 40230 | 40245 | N/A | N/A | 98 |
| 977499 | TAATATAGGTGACAGC | 63604 | 63619 | N/A | N/A | 99 |
| 977500 | GATAATATAGGTGACA | 63606 | 63621 | N/A | N/A | 100 |
| 977515 | TCAGTATGCCTCTTGC | 70718 | 70733 | N/A | N/A | 101 |
| 977525 | GTGTCTCACCCCAGGG | 86267 | 86282 | N/A | N/A | 102 |
| 977526 | AGTGTCTCACCCCAGG | 86268 | 86283 | N/A | N/A | 103 |
| 977539 | ATAGTTGTCACACAGT | 98757 | 98772 | N/A | N/A | 104 |
| 977545 | AGCGATATTAAATGGC | 114166 | 114181 | N/A | N/A | 105 |
| 977557 | GGTGTGCTGAATGCTA | 121156 | 121171 | N/A | N/A | 106 |
| 977568 | GCTACTGCGGTCACTG | 121110 | 121125 | N/A | N/A | 107 |
| 977569 | TGCTACTGCGGTCACT | 121111 | 121126 | N/A | N/A | 108 |
| 977571 | AATGCTACTGCGGTCA | 121113 | 121128 | N/A | N/A | 109 |
| 977572 | GAATGCTACTGCGGTC | 121114 | 121129 | N/A | N/A | 110 |
| 977574 | CTGAATGCTACTGCGG | 121116 | 121131 | N/A | N/A | 111 |
| 977575 | GCTGAATGCTACTGCG | 121117 | 121132 | N/A | N/A | 112 |
| 977581 | GCACATAAATTACTGG | 130943 | 130958 | N/A | N/A | 113 |

TABLE 8

Dose response

| Compound Number | Notch2 mRNA (% control) | | | | $IC_{50}$ (µM) |
|---|---|---|---|---|---|
| | 333 nM | 1000 nM | 3000 nM | 9000 nM | |
| 977499 | 40 | 16 | 6 | 4 | 0.1 |
| 977431 | 83 | 52 | 16 | 5 | 1.1 |
| 977515 | 92 | 58 | 13 | 8 | 1.3 |
| 977375 | 71 | 34 | 15 | 8 | 0.7 |
| 977571 | 112 | 49 | 20 | 15 | 1.7 |
| 977539 | 105 | 63 | 28 | 6 | 1.8 |
| 977575 | 100 | 76 | 29 | 17 | 2.1 |
| 977359 | 55 | 33 | 20 | 15 | 0.4 |
| 977472 | 51 | 27 | 5 | 4 | 0.3 |
| 977428 | 77 | 41 | 15 | 2 | 0.8 |
| 977500 | 84 | 43 | 17 | 3 | 1.0 |
| 977572 | 74 | 48 | 18 | 10 | 0.9 |
| 977296 | 99 | 69 | 38 | 9 | 2.0 |
| 977380 | 87 | 62 | 32 | 23 | 1.8 |
| 977408 | 89 | 59 | 34 | 28 | 2.0 |
| 977568 | 117 | 82 | 39 | 18 | 2.7 |
| 977376 | 112 | 75 | 44 | 17 | 2.6 |

TABLE 9

Notch2 Expression

| Compound Number | Notch2 mRNA (% control) | | | | IC50 (μM) |
|---|---|---|---|---|---|
| | 333 nM | 1000 nM | 3000 nM | 9000 nM | |
| 977557 | 42 | 24 | 18 | 11 | 0.1 |
| 977525 | 63 | 36 | 23 | 20 | 0.6 |
| 977545 | 71 | 41 | 23 | 10 | 0.8 |
| 977413 | 76 | 51 | 24 | 17 | 1.1 |
| 977313 | 100 | 63 | 26 | 21 | 1.9 |
| 977569 | 123 | 80 | 44 | 18 | 2.9 |
| 977581 | 128 | 90 | 55 | 20 | 3.5 |
| 977429 | 101 | 59 | 21 | 7 | 1.6 |
| 977277 | 68 | 49 | 26 | 11 | 0.9 |
| 977574 | 46 | 24 | 14 | 8 | 0.2 |
| 977474 | 72 | 36 | 11 | 2 | 0.7 |
| 977526 | 79 | 44 | 14 | n.d. | 0.9 |
| 977454 | 85 | 52 | 13 | 3 | 1.1 |
| 977306 | 94 | 51 | 34 | 9 | 1.5 |
| 977406 | 80 | 59 | 28 | 18 | 1.4 |
| 977338 | 99 | 73 | 33 | 19 | 2.2 |
| 977430 | 118 | 81 | 20 | 12 | 2.1 |
| 977302 | 102 | 70 | 31 | 15 | 2.0 |

Example 4: Inhibition of the Notch Signaling Pathway by Modified Oligonucleotides Complementary to Notch3

Modified oligonucleotides 100% complementary to mouse Notch3 were tested at various doses in C2C12 (mouse myoblast) cells. Cells were plated at a density of 20,000 cells per well and transfected using electroporation with 0.259 μM, 0.778 μM, 2.33 μM, and 7.0 μM modified oligonucleotide, as specified in the tables below. After a treatment period of approximately 24 hours, RNA was isolated from the cells and Notch3 mRNA levels were measured by RT-qPCR. Mouse Notch3 primer probe set RTS36974 (Forward sequence: CTTTGGAGTTTGCCGT-GATG (SEQ ID No: 22) Reverse sequence: TCATT-GATCTCCACGTTGCAG (SEQ ID No: 23) Probe sequence: ACCGTTATGACTGTGTCTGTCAGCC (SEQ ID No: 24)) was used to measure Notch3 mRNA levels. The resulting Notch3 mRNA levels were adjusted according to total RNA content as measured by RIBOGREEN. Results are presented as the percent level of Notch3 mRNA transcript, relative to that of the untreated control cells. As illustrated in the tables below, Notch3 mRNA levels were reduced in a dose-dependent manner in cells treated with modified oligonucleotides complementary to Notch3.

The modified oligonucleotides in the tables below are cEt gapmers (as described in Example 1). The nucleobase sequences of the modified oligonucleotides, shown in the tables below, are 100% complementary to mouse Notch3 pre-mRNA (the complement of GENBANK No. NC_000083.6 truncated from 32118001 to 32170000, SEQ ID No. 7), and/or to mouse Notch3 mRNA NM_008716.2, SEQ ID 8). An entry of "N/A" in the table below indicates that the modified oligonucleotide is not 100% complementary to the corresponding nucleic acid.

TABLE 10

Modified oligonucleotides complementary to Notch3

| Compound Number | Sequence | Start Site SEQ ID 7 | Stop Site SEQ ID 7 | Start Site SEQ ID 8 | Stop Site SEQ ID 8 | SEQ ID No. |
|---|---|---|---|---|---|---|
| 976941 | ATCTATGTCACTTTGG | 11368 | 11383 | 527 | 542 | 114 |
| 976942 | CCAGATCGGCACTCAT | 11382 | 11397 | 541 | 556 | 115 |
| 976960 | CTGCACAGCGACACTC | 15669 | 15684 | 1650 | 1665 | 116 |
| 976963 | TGCCATCGACACAGCG | 16080 | 16095 | 1734 | 1749 | 117 |
| 976964 | GGCACAAGCACACGAG | 16106 | 16121 | 1760 | 1775 | 118 |
| 976977 | CCGCAGGGTGAGGCAC | 19907 | 19922 | 2509 | 2524 | 119 |
| 976989 | GCACAGGCGGCCACTC | 22962 | 22977 | 3146 | 3161 | 120 |
| 976990 | TGTATGTCGCACAGGC | 22970 | 22985 | 3154 | 3169 | 121 |
| 976992 | TGTCTATGCACTTTCC | 23442 | 23457 | 3237 | 3252 | 122 |
| 977008 | CGCAGCGGAAATGCCC | 25598 | 25613 | 3744 | 3759 | 123 |
| 977032 | GTGTTCTCGCTTTCGC | 30754 | 30769 | 5060 | 5075 | 124 |
| 977034 | TCAAGTCTGTGACCAC | 32135 | 32150 | 5211 | 5226 | 125 |
| 977057 | CAGGATTGAGCAGACC | 47705 | 47720 | 6540 | 6555 | 126 |
| 977081 | GTCTTATCTGGAATGC | 48817 | 48832 | 7652 | 7667 | 127 |
| 977103 | AGCAAGATGATGCGGG | 6033 | 6048 | N/A | N/A | 128 |
| 977107 | TCACTCTGTGAGAGCC | 6576 | 6591 | N/A | N/A | 129 |
| 977113 | TCGAAGCTCAACCCTG | 7861 | 7876 | N/A | N/A | 130 |
| | | 7877 | 7892 | N/A | N/A | |

TABLE 10-continued

Modified oligonucleotides complementary to Notch3

| Compound Number | Sequence | Start Site SEQ ID 7 | Stop Site SEQ ID 7 | Start Site SEQ ID 8 | Stop Site SEQ ID 8 | SEQ ID No. |
|---|---|---|---|---|---|---|
| 977114 | GTCGAAGCTCAACCCT | 7862<br>7878 | 7877<br>7893 | N/A<br>N/A | N/A<br>N/A | 131 |
| 977115 | TGTCGAAGCTCAACCC | 7863<br>7879 | 7878<br>7894 | N/A<br>N/A | N/A<br>N/A | 132 |
| 977116 | TGCAACTATGCAATGA | 8075 | 8090 | N/A | N/A | 133 |
| 977117 | GTAGTCAAACAATCCT | 8096 | 8111 | N/A | N/A | 134 |
| 977119 | TCCTCTCATGGATCGG | 8437 | 8452 | N/A | N/A | 135 |
| 977129 | TCAGTATTATCTGTTA | 12995 | 13010 | N/A | N/A | 136 |
| 977130 | GAATATTGGTTCAGTA | 13005 | 13020 | N/A | N/A | 137 |
| 977131 | GGAATATTGGTTCAGT | 13006 | 13021 | N/A | N/A | 138 |
| 977154 | GTGATCTCACTGCCAG | 20525 | 20540 | N/A | N/A | 139 |
| 977156 | TGTAGTGCCACTGCCT | 20616 | 20631 | N/A | N/A | 140 |
| 977170 | ACAATTCTATGGTCTC | 24812 | 24827 | N/A | N/A | 141 |
| 977191 | CTACCTGTGTACCACA | 32564<br>32967 | 32579<br>32982 | N/A<br>N/A | N/A<br>N/A | 142 |
| 977192 | ACTACCTGTGTACCAC | 32565<br>32968 | 32580<br>32983 | N/A<br>N/A | N/A<br>N/A | 143 |
| 977213 | ACTTAGATGCTACCAG | 38941 | 38956 | N/A | N/A | 144 |
| 977234 | GCAACTCATGTCCACA | 46126 | 46141 | N/A | N/A | 145 |

TABLE 11

Dose response

| Compound Number | Notch3 mRNA (% control) | | | | IC$_{50}$ (μM) |
|---|---|---|---|---|---|
| | 259 nM | 778 nM | 2333 nM | 7000 nM | |
| 977131 | 40 | 18 | 9 | 2 | 0.07 |
| 977119 | 41 | 13 | 19 | 4 | 0.05 |
| 977107 | 69 | 38 | 16 | 4 | 0.54 |
| 977103 | 72 | 40 | 9 | 5 | 0.57 |
| 976963 | 115 | 61 | 18 | 6 | 1.35 |
| 977115 | 79 | 50 | 16 | 8 | 0.80 |
| 977191 | 45 | 27 | 9 | 4 | 0.14 |
| 977156 | 45 | 15 | 3 | 1 | 0.10 |
| 976992 | 57 | 28 | 7 | 7 | 0.27 |
| 977032 | 36 | 12 | 13 | 4 | 0.03 |
| 977116 | 81 | 41 | 13 | 2 | 0.70 |
| 977192 | 65 | 33 | 12 | 4 | 0.42 |
| 977008 | 78 | 38 | 14 | 6 | 0.65 |
| 976964 | 63 | 34 | 9 | 11 | 0.39 |
| 976960 | 89 | 46 | 44 | 13 | 1.21 |

TABLE 12

Dose response

| Compound Number | Notch3 mRNA (% control) | | | | IC50 (μM) |
|---|---|---|---|---|---|
| | 259 nM | 778 nM | 2333 nM | 7000 nM | |
| 977117 | 35 | 14 | 6 | 5 | 0.02 |
| 977057 | 55 | 27 | 19 | 10 | 0.24 |
| 977129 | 30 | 14 | 4 | 1 | 0.02 |
| 976941 | 62 | 28 | 17 | 6 | 0.36 |
| 977113 | 61 | 31 | 12 | 7 | 0.35 |
| 976989 | 100 | 55 | 38 | 15 | 1.44 |
| 977213 | 98 | 54 | 36 | 10 | 1.32 |
| 977081 | 64 | 22 | 16 | 7 | 0.32 |
| 976977 | 58 | 53 | 26 | 16 | 0.57 |
| 977114 | 36 | 14 | 2 | 7 | 0.03 |
| 977170 | 46 | 22 | 6 | 3 | 0.13 |
| 977130 | 68 | 37 | 16 | 5 | 0.52 |
| 976990 | 41 | 18 | 7 | 4 | 0.07 |
| 976942 | 80 | 34 | 14 | 5 | 0.64 |
| 977034 | 71 | 46 | 15 | 8 | 0.65 |
| 977154 | 125 | 56 | 15 | 5 | 1.36 |
| 977234 | 79 | 59 | 18 | 10 | 0.92 |

Example 5: Inhibition of the Notch Signaling Pathway by Modified Oligonucleotides Complementary to JAG2

Modified oligonucleotides 100% complementary to mouse JAG2 were tested at various doses in primary mouse embryonic cortical neuron. Cells were plated at a density of 60,000 cells per well and treated via free uptake with 0.313 μM, 1.25 μM, 5.0 μM, or 20.0 μM modified oligonucleotide, as specified in the tables below. After a treatment period of approximately 24 hours, total RNA was isolated from the cells and JAG2 mRNA levels were measured by RT-qPCR using primer probe set RTS35955 (Forward sequence: CTGACTGCCGTATCAACATTG (SEQ ID No: 25) Reverse sequence: GCCTCGTGAATATGACCACTT (SEQ ID No: 26) Probe sequence: CAGTCCTCGCCCTGTGCCTAC (SEQ ID No: 27)) was used to measure JAG2 mRNA levels. The resulting JAG2 mRNA levels were adjusted according to total RNA content as measured by RIBOGREEN. Results are presented as the percent level of JAG2 mRNA transcript, relative to that of the untreated control cells. As illustrated in the tables below, JAG2 mRNA levels were reduced in a dose-dependent manner in cells treated with modified oligonucleotides complementary to JAG2.

The modified oligonucleotides in the tables below are cEt gapmers (as described in Example 1). The nucleobase sequences of the modified oligonucleotides, shown in the tables below, are 100% complementary to mouse JAG2 pre-mRNA (the complement of GENBANK No. NC_000078.6 truncated from 112905001 to 112933000, SEQ ID No. 9), and/or to mouse Jagged2 mRNA (GENBANK No. NM_010588.2, SEQ ID 10). An entry of "N/A" in the table below indicates that the modified oligonucleotide is not 100% complementary to the corresponding nucleic acid.

TABLE 13

Modified oligonucleotides complementary to JAG2

| Compound Number | Sequence | Start Site SEQ ID 9 | Stop Site SEQ ID 9 | Start Site SEQ ID 10 | Stop Site SEQ ID 10 | SEQ ID No. |
|---|---|---|---|---|---|---|
| 897605 | TACCACCCGCTGCACA | 17034 | 17049 | 1191 | 1206 | 146 |
| 897613 | CTCTAGTTCGCAATGG | 17680 | 17695 | 1490 | 1505 | 147 |
| 897614 | CGTACTCTAGTTCGCA | 17684 | 17699 | 1494 | 1509 | 148 |
| 897619 | GTAGTAGTCACCCTCA | 18553 | 18568 | 1673 | 1688 | 149 |
| 897621 | TCTACATGCCCCGCCA | 18628 | 18643 | 1748 | 1763 | 150 |
| 897622 | TCGAACCCGCAGCCAT | 18729 | 18744 | 1771 | 1786 | 151 |
| 897664 | GTCCACCATACGCAGA | 23676 | 23691 | 3319 | 3334 | 152 |
| 897695 | CAGTACGCCAGCCCAG | 24743 | 24758 | N/A | N/A | 153 |
| 897718 | AGTAGTTCAGGTCTGG | 16274 | 16289 | N/A | N/A | 154 |
| 897720 | TGTTAGTGTCTCTTCC | 4665 | 4680 | N/A | N/A | 155 |
| 897721 | ACAATAAAACATCCGC | 4718 | 4733 | N/A | N/A | 156 |
| 897724 | CACCATAAGACTTCCT | 4888 | 4903 | N/A | N/A | 157 |
| 897727 | GCTTGATACCCCCCCT | 5063 | 5078 | N/A | N/A | 158 |
| 897728 | CTAACCAAAAGTCTCT | 5171 | 5186 | N/A | N/A | 159 |
| 897742 | AGAACTTAAGCAGGAG | 6819 | 6834 | N/A | N/A | 160 |
| 897751 | GTTACTCACAGCCTAG | 7979 | 7994 | N/A | N/A | 161 |
| 897756 | CGCTTCGGATGATCCA | 8721 | 8736 | N/A | N/A | 162 |
| 897758 | TTTATACTCGCTCAGC | 8889 | 8904 | N/A | N/A | 163 |
| 897762 | TGCCATCTAAATCCCC | 9601 | 9616 | N/A | N/A | 164 |
| 897763 | TATAAGTACTCTCTCT | 9758 | 9773 | N/A | N/A | 165 |
| 897764 | TCCTATCTGTTGGCAG | 9957 | 9972 | N/A | N/A | 166 |
| 897765 | AACTTATCCCACTGCC | 10017 | 10032 | N/A | N/A | 167 |
| 897771 | GATAATTATCCCTGGC | 10701 | 10716 | N/A | N/A | 168 |
| 897775 | GTATGAGCAGCTCTGC | 11187 | 11202 | N/A | N/A | 169 |
| 897776 | CACTTGAGGGTATCTC | 11268 | 11283 | N/A | N/A | 170 |
| 897777 | TACTAGCTTGGATCCT | 11463 | 11478 | N/A | N/A | 171 |
| 897780 | GAGAATAGCCAGAACT | 11707 | 11722 | N/A | N/A | 172 |

TABLE 13-continued

Modified oligonucleotides complementary to JAG2

| Compound Number | Sequence | Start Site SEQ ID 9 | Stop Site SEQ ID 9 | Start Site SEQ ID 10 | Stop Site SEQ ID 10 | SEQ ID No. |
|---|---|---|---|---|---|---|
| 897794 | TCCTACTGTGTTCACC | 13371 | 13386 | N/A | N/A | 173 |
| 897795 | TGCAGAATCATGTCAG | 13415 | 13430 | N/A | N/A | 174 |
| 897798 | GACAATCATCCCTACC | 13670 | 13685 | N/A | N/A | 175 |
| 897803 | ACACATCACTAATGCC | 14219 | 14234 | N/A | N/A | 176 |
| 897805 | GTGGATGGACGATTTC | 14434 | 14449 | N/A | N/A | 177 |
| 897813 | GTAAGTAGGTGGCCAG | 15425 | 15440 | N/A | N/A | 178 |
| 897833 | AAGTTAAGCAGAACCC | 19872 | 19887 | N/A | N/A | 179 |
| 897835 | GTTGGAATGGGACCTA | 20076 | 20091 | N/A | N/A | 180 |
| 897836 | AGAAGTACGAGGAAGG | 20133 | 20148 | N/A | N/A | 181 |
| 897862 | GTTATAGCCACTGCCC | 23214 | 23229 | N/A | N/A | 182 |

TABLE 14

Dose response

| | JAG2 mRNA (% control) | | | | |
|---|---|---|---|---|---|
| Compound Number | 312.5 nM | 1250.0 nM | 5000.0 nM | 20000.0 nM | $IC_{50}$ (µM) |
| 897836 | 28 | 10 | 8 | 6 | <0.3 |
| 897780 | 22 | 14 | 10 | 6 | <0.3 |
| 897728 | 65 | 40 | 21 | 7 | 0.74 |
| 897756 | 47 | 33 | 20 | 16 | <0.3 |
| 897720 | 85 | 50 | 20 | 6 | 1.50 |
| 897724 | 83 | 52 | 27 | 15 | 1.78 |
| 897764 | 97 | 77 | 43 | 21 | 4.17 |
| 897776 | 71 | 56 | 39 | 27 | 2.10 |
| 897664 | 72 | 47 | 32 | 15 | 1.33 |
| 897775 | 42 | 25 | 13 | 7 | <0.3 |
| 897803 | 52 | 33 | 12 | 5 | <0.3 |
| 897763 | 68 | 44 | 20 | 6 | 0.90 |
| 897751 | 72 | 47 | 20 | 12 | 1.08 |
| 897619 | 45 | 29 | 17 | 12 | <0.3 |
| 897835 | 75 | 44 | 19 | 8 | 1.10 |
| 897795 | 63 | 47 | 23 | 9 | 0.84 |
| 897727 | 84 | 57 | 36 | 18 | 2.33 |
| 897695 | 67 | 52 | 28 | 20 | 1.24 |
| 897771 | 92 | 68 | 41 | 20 | 3.38 |

TABLE 15

Dose response

| | JAG2 mRNA (% control) | | | | |
|---|---|---|---|---|---|
| Compound Number | 312.5 nM | 1250.0 nM | 5000.0 nM | 20000.0 nM | IC50 (µM) |
| 897836 | 31 | 17 | 8 | 6 | <0.3 |
| 897721 | 53 | 41 | 22 | 5 | 0.46 |
| 897805 | 40 | 25 | 13 | 15 | <0.3 |
| 897605 | 51 | 38 | 23 | 15 | 0.32 |
| 897813 | 46 | 40 | 20 | 16 | <0.3 |
| 897777 | 61 | 48 | 29 | 14 | 0.91 |
| 897621 | 67 | 44 | 28 | 31 | 1.07 |
| 897765 | 85 | 75 | 37 | 16 | 2.97 |
| 897833 | 74 | 53 | 21 | 7 | 1.28 |
| 897613 | 77 | 40 | 19 | 11 | 1.06 |
| 897758 | 63 | 44 | 14 | 5 | 0.70 |
| 897798 | 63 | 41 | 15 | 9 | 0.67 |
| 897742 | 48 | 30 | 13 | 6 | <0.3 |
| 897862 | 67 | 50 | 19 | 9 | 1.00 |
| 897762 | 87 | 53 | 25 | 9 | 1.77 |
| 897794 | 94 | 36 | 23 | 11 | 1.55 |
| 897614 | 72 | 50 | 22 | 11 | 1.21 |
| 897622 | 73 | 58 | 26 | 18 | 1.63 |

Example 6: Inhibition of the Notch Signaling Pathway by Modified Oligonucleotides Complementary to DLL4

Modified oligonucleotides 100% complementary to mouse DLL4 were tested at various doses in b.END1 cells. Compound 380876 was included as a comparison in all experiments. Cells were plated at a density of 20,000 cells per well and transfected using electroporation with 0.74 µM, 2.2 µM, 6.7 µM, and 20 µM modified oligonucleotide, as specified in the tables below. After a treatment period of approximately 24 hours, total RNA was isolated from the cells and DLL4 mRNA levels were measured by RT-qPCR. Mouse DLL4 primer probe set RTS2518 (Forward sequence: GCCTTCCTTCTGCATTGTTTACA (SEQ ID No: 28) Reverse sequence: CTCCGCAGAGCAGCACTGT (SEQ ID No: 29) Probe sequence: TGCATCCTGTATGGGACATCTTT (SEQ ID No: 30)) was used to measure DLL4 mRNA levels. The resulting DLL4 mRNA levels were adjusted according to total RNA content as measured by RIBOGREEN. Results are presented as the percent level of DLL4 mRNA transcript, relative to that of the untreated control cells. As illustrated in the tables below, DLL4 mRNA levels were reduced in a dose-dependent manner in cells treated with modified oligonucleotides complementary to DLL4.

The modified oligonucleotides in the tables below are cEt gapmers (as described in Example 1). The nucleobase sequences of the modified oligonucleotides, shown in the tables below, are 100% complementary to mouse DLL4 pre-mRNA (GENBANK No. NC_000068.7 truncated from 119322001 to 119338000, SEQ ID No. 11), and/or to mouse DLL4 mRNA (GENBANK No. NM_019454.3, SEQ ID: 12). An entry of "N/A" in the table below indicates that the modified oligonucleotide is not 100% complementary to the corresponding nucleic acid.

TABLE 16

Modified oligonucleotides complementary to DLL4

| Compound Number | Sequence | SEQ ID 11 start site | SEQ ID 11 stop site | SEQ ID 12 start site | SEQ ID 12 stop site | SEQ ID No. |
|---|---|---|---|---|---|---|
| 380876 | GCTCACAGTGCTCACCAGTG | 8713 | 8732 | 1308 | 1327 | 183 |
| 797555 | GCAAATCCTAGGGTCT | 3908 | 3923 | 125 | 140 | 184 |
| 797562 | GCTCGATGCCTCGGTA | 3978 | 3993 | 195 | 210 | 185 |
| 797569 | AGGGATGTCGCTCTCC | 4080 | 4095 | 297 | 312 | 186 |
| 797580 | CGCTGCTGCGGCCACA | N/A | N/A | 413 | 428 | 187 |
| 797619 | GGCAACTGCAGAGGGT | 4553 | 4568 | 662 | 677 | 188 |
| 797656 | GTCCAGCCCGGCAGGC | 6157 | 6172 | 983 | 998 | 189 |
| 797676 | GGATACATTCATTGCA | 6710 | 6725 | 1108 | 1123 | 190 |
| 797700 | TCACAGTGCTCACCAG | 8715 | 8730 | 1310 | 1325 | 191 |
| 797710 | GGTACTATGCTCACAG | 9015 | 9030 | 1434 | 1449 | 192 |
| 797730 | CCATTGGCACACGGGT | 9167 | 9182 | 1586 | 1601 | 193 |
| 797731 | CTCCATTGGCACACGG | N/A | N/A | 1588 | 1603 | 194 |
| 797738 | CGCTGATGTGCAGTTC | 10214 | 10229 | 1672 | 1687 | 195 |
| 797750 | GTCCGGAGGCACAGGC | 10349 | 10364 | 1807 | 1822 | 196 |
| 797793 | GCATGCCGCCCCGTCC | 10769 | 10784 | 2227 | 2242 | 197 |
| 797801 | GGCTGATATTCGACAC | 12060 | 12075 | 2316 | 2331 | 198 |
| 797811 | GGCAATCACACACTCG | 12135 | 12150 | 2391 | 2406 | 199 |
| 797813 | TCTGAGTAGGCTCCTG | 12636 | 12651 | 2421 | 2436 | 200 |
| 797822 | GTTCATGCCATTTCCT | 12754 | 12769 | 2539 | 2554 | 201 |
| 797835 | TCGAGAGGCACCTTAG | 12901 | 12916 | 2686 | 2701 | 202 |
| 797836 | TCCAAGTTCGAGAGGC | 12908 | 12923 | 2693 | 2708 | 203 |
| 797843 | GCCAAGACCCACTAGG | 12986 | 13001 | 2771 | 2786 | 204 |
| 797844 | CTCATTTGGGCCCAGC | 13066 | 13081 | 2851 | 2866 | 205 |
| 797847 | CTTAATGCCAAACTCC | 13135 | 13150 | 2920 | 2935 | 206 |
| 797860 | TAGCATGAAGGCCCTG | 13356 | 13371 | 3141 | 3156 | 207 |
| 797868 | GAAGATCGGCTTCAAG | 13493 | 13508 | 3278 | 3293 | 208 |
| 797871 | GATTTTTGAAGATCGG | 13500 | 13515 | 3285 | 3300 | 209 |
| 797941 | GGTGTTCGCGCAGCGC | 4910 | 4925 | N/A | N/A | 210 |
| 797964 | TGGCAAGTGTCACTGG | 7420 | 7435 | N/A | N/A | 211 |
| 797966 | GCACAGTACTTGACCC | 7582 | 7597 | N/A | N/A | 212 |
| 797978 | ACCATTGGCACACGGG | 9168 | 9183 | N/A | N/A | 213 |
| 797983 | AGCACTGGGTATTCCA | 9599 | 9614 | N/A | N/A | 214 |

TABLE 16-continued

Modified oligonucleotides complementary to DLL4

| Compound Number | Sequence | SEQ ID 11 start site | SEQ ID 11 stop site | SEQ ID 12 start site | SEQ ID 12 stop site | SEQ ID No. |
|---|---|---|---|---|---|---|
| 797987 | GGCTTGATCTCTCTGG | 9874 | 9889 | N/A | N/A | 215 |
| 797992 | TGTGACTGCACCGTCT | 11395 | 11410 | N/A | N/A | 216 |

TABLE 17

Dose response

| Compound | DLL4 mRNA (% control) | | | | IC50 |
|---|---|---|---|---|---|
| Number | 740.5 nM | 2222 nM | 6667 nM | 20,000 nM | (µM) |
| 380876 | 112 | 88 | 92 | 69 | >20 |
| 797656 | 74 | 106 | 43 | 40 | 5.9 |
| 797844 | 78 | 52 | 46 | 25 | 3.9 |
| 797759 | 96 | 94 | 33 | 28 | 6.6 |
| 797868 | 85 | 55 | 28 | 29 | 3.7 |
| 797843 | 87 | 125 | 49 | 53 | 15.8 |
| 797700 | 76 | 65 | 54 | 19 | 4.8 |
| 797801 | 78 | 128 | 56 | 49 | 13.1 |
| 797730 | 65 | 65 | 41 | 23 | 3.4 |
| 797987 | 124 | 157 | 84 | 42 | 18.3 |
| 797676 | 58 | 36 | 31 | 23 | 1.1 |
| 797580 | 77 | 76 | 62 | 40 | 13.1 |
| 797813 | 170 | 141 | 69 | 60 | 16.0 |
| 797941 | 86 | 64 | 37 | 35 | 5.3 |
| 797731 | 85 | 70 | 52 | 57 | >20 |
| 797964 | 62 | 114 | 31 | 25 | 2.5 |
| 797983 | 67 | 71 | 36 | 39 | 5.2 |
| 797555 | 115 | 138 | 21 | 15 | 4.6 |
| 797562 | 97 | 71 | 46 | 30 | 6.6 |

TABLE 18

Dose response

| Compound | DLL4 mRNA (% control) | | | | IC50 |
|---|---|---|---|---|---|
| Number | 740.5 nM | 2222 nM | 6667 nM | 20,000 nM | (µM) |
| 380876 | 152 | 140 | 127 | 66 | >20 |
| 797978 | 18 | 16 | 11 | 6 | <0.74 |
| 797966 | 67 | 43 | 76 | 30 | 6.7 |
| 797793 | 61 | 40 | 38 | 28 | 1.6 |
| 797569 | 63 | 39 | 43 | 17 | 2.3 |
| 797847 | 81 | 50 | 47 | 41 | 5.8 |
| 797750 | 88 | 55 | 47 | 30 | 5.1 |
| 797835 | 79 | 46 | 41 | 30 | 3.6 |
| 797822 | 57 | 53 | 51 | 42 | 4.7 |
| 797710 | 74 | 46 | 27 | 23 | 2.4 |
| 797860 | 102 | 66 | 62 | 60 | >20 |
| 797738 | 59 | 62 | 54 | 39 | 6.8 |
| 797836 | 99 | 80 | 73 | 55 | >20 |
| 797871 | 117 | 85 | 78 | 34 | 13.2 |
| 797992 | 87 | 63 | 57 | 41 | 9.4 |
| 797811 | 115 | 66 | 62 | 62 | >20 |
| 797619 | 82 | 81 | 72 | 53 | >20 |

Example 7: Inhibition of the Notch Signaling Pathway In Vivo by Modified Oligonucleotides Complementary to Notch1

Groups of 6 week old female BALB/c mice were administered 50 mg/kg of a modified oligonucleotide on study days 1, 6, and 12, via intraperitoneal (IP) delivery. Compound 549144 is control oligonucleotide. It is a cEt gapmer, as described in Example 1, with a nucleobase sequence that is not 100% complementary to any known mouse transcript. Each group contained 4 mice. One group of male mice was administered a saline control via IP delivery. Mice were sacrificed 48 hours after the last dose, and liver tissue was harvested. Total RNA was isolated from the liver tissue, and mRNA levels of Notch1 were measured RT-qPCR using primer probe set RTS1458 described above and normalized to Ribogreen.

TABLE 19 mRNA levels

| Compound Number | Notch1 (% control) |
|---|---|
| Saline | 100 |
| 549144 | 94 |
| 784192 | 54 |
| 784421 | 64 |
| 784432 | 83 |
| 784446 | 51 |
| 784496 | 57 |
| 784511 | 48 |
| 784563 | 28 |
| 784586 | 35 |

Example 8: Inhibition of the Notch Signaling Pathway In Vivo by Modified Oligonucleotides Complementary to Notch1

Groups of 6 week old female BALB/c mice were administered 6.25, 12.5, 25, or 50 mg/kg of a modified oligonucleotide described above once per week for 6 weeks via subcutaneous delivery. Each group contained 4 mice. One group of male BALB/c mice was administered a saline control via subcutaneous delivery. Mice were sacrificed 48 hours after the last dose, and liver tissue was harvested. Total RNA was isolated from the liver tissue and, mRNA levels of Notch1 were measured by RT-qPCR using primer probe set RTS1458 described above, normalized to Ribogreen. Results are presented as the average percent level of Notch1 mRNA transcript for each treatment group, relative to that of the saline treated group. As illustrated in the tables below, Notch1 mRNA levels were reduced in animals treated with a modified oligonucleotide complementary to Notch 1.

TABLE 20

Dose response

| Compound No./Dose (mg/kg) | | Notch 1 mRNA (% control) |
|---|---|---|
| Saline | | 100 |
| 549144 | 50 | 107 |
| 784563 | 6.25 | 45 |
| | 12.5 | 27 |

TABLE 20-continued

Dose response

| Compound No./Dose (mg/kg) | Notch 1 mRNA (% control) |
|---|---|
| 25 | 27 |
| 50 | 29 |

Example 9: Inhibition of the Notch Signaling Pathway In Vivo by Modified Oligonucleotides Complementary to Notch2 or Notch3

Groups of 6 week old male BALB/c mice were administered 50 mg/kg of a modified oligonucleotide described above once per week for 4 weeks via subcutaneous delivery. Each group contained 4 mice. One group of male mice was administered a saline (PBS) control via subcutaneous delivery. Mice were sacrificed 24 hours after the last dose, and liver and lung tissues were harvested. Total RNA was isolated from the tissues, and mRNA levels of Notch2 or Notch3 were measured with RT-qPCR using primer probe set RTS36982 (forward sequence CAACCAGTGTGAT-GAGCAGT, designated herein as SEQ ID NO: 31; reverse sequence GTTGTCTTTGAAGTGGTCTGC, designated herein as SEQ ID NO: 32; probe sequence TTGTCAT-ACTTGCACGTCTTGCTATTCCT, designated herein as SEQ ID: 33) for Notch2, or primer probe set RTS36974 for Notch3, described above. The resulting mRNA levels were normalized to cyclophilin A levels. Results are presented as the average percent level of Notch2 mRNA transcript or Notch3 mRNA transcript for each treatment group, relative to that of the saline treated group. An entry of "n.d." means that the corresponding data was not analyzed.

TABLE 21 mRNA levels (% PBS control)

| Compound No. | Target transcript | Notch2, liver | Notch2, lung | Notch3, lung |
|---|---|---|---|---|
| PBS | None | 106 | 100 | 101 |
| 549144 | None | 89 | 89 | 88 |
| 977277 | Notch2 | 54 | 93 | n.d. |
| 977359 | Notch2 | 13 | 71 | n.d. |
| 977375 | Notch2 | 21 | 84 | n.d. |
| 977406 | Notch2 | 16 | 79 | n.d. |
| 977413 | Notch2 | 11 | 51 | n.d. |
| 977431 | Notch2 | 6 | 60 | n.d. |
| 977472 | Notch2 | 3 | 41 | n.d. |
| 977474 | Notch2 | 23 | 68 | n.d. |
| 977499 | Notch2 | 6 | 54 | n.d. |
| 977500 | Notch2 | 12 | 70 | n.d. |
| 977545 | Notch2 | 16 | 71 | n.d. |
| 977572 | Notch2 | 2 | 43 | n.d. |
| 977574 | Notch2 | 2 | 52 | n.d. |
| 976941 | Notch3 | n.d. | n.d. | 27 |
| 976944 | Notch3 | n.d. | n.d. | 64 |
| 976990 | Notch3 | n.d. | n.d. | 18 |
| 977057 | Notch3 | n.d. | n.d. | 32 |
| 977081 | Notch3 | n.d. | n.d. | 23 |
| 977103 | Notch3 | n.d. | n.d. | 74 |
| 977113 | Notch3 | n.d. | n.d. | 49 |
| 977114 | Notch3 | n.d. | n.d. | 25 |
| 977117 | Notch3 | n.d. | n.d. | 33 |
| 977119 | Notch3 | n.d. | n.d. | 35 |
| 977129 | Notch3 | n.d. | n.d. | 27 |
| 977130 | Notch3 | n.d. | n.d. | 28 |
| 977131 | Notch3 | n.d. | n.d. | 17 |
| 977170 | Notch3 | n.d. | n.d. | 16 |

Example 10: Inhibition of the Notch Signaling Pathway In Vivo by a Modified Oligonucleotide Complementary to Notch1

Modified oligonucleotides described above were tested in C57B/6 mice for their effect on mRNA level of Notch1 in mouse lung. Groups of 6 week old male C57B/6 mice were administered 200 μg modified oligonucleotide in 50 μL saline on study day 1, 4, 7, 11, 14 and 19 via oropharyngeal delivery while under anesthesia. Each treatment group that received compound 784563 contained 6 mice, while each control group contained 4 mice (saline, 549144). Mice were sacrificed 48 hours after the last dose, and lung tissue was harvested. Total RNA was isolated from the lung tissue and mRNA levels of Notch1 were measured by RT-qPCR as described above, using primer probe set Mm00627185_m1 (ABI catalog 4351370). Results were normalized to cyclophilin A and are presented as the average percent level of Notch1 mRNA transcript for each treatment group, relative to that of the saline treated group.

TABLE 22 mRNA levels (% saline)

| Compound Number | Notch1 mRNA |
|---|---|
| Saline | 100 |
| 549144 | 105 |
| 784563 | 64 |

Example 11: Effects on Notch Signaling Pathway Inhibition and Trans-Differentiation of Lung Cells by Modified Oligonucleotides Complementary to a Member of the Notch Signaling Pathway Modified oligonucleotides described above were tested in C57B/6 mice for their effects on mRNA levels of cell differentiation markers and members of the Notch signaling pathway in mouse lung. Groups of 8 week old male C57B/6 mice were administered 200 μg modified oligonucleotide in 50 μL saline every other day for 5 days via oropharyngeal delivery while under anesthesia. Each group contained 4 mice. One group of male C57B/6 mice was administered a saline control. Mice were sacrificed 72 hours after the last dose, and lung tissue was harvested. Total RNA was isolated from the lung tissue, and mRNA levels of JAG1, JAG2, and cell differentiation markers were measured by RT-qPCR. JAG1 was detected by Taqman probe Mm00496902_m1 (Thermo Fisher), and JAG2 was detected by Taqman probe Mm01325629_m1 (Thermo Fisher). Notch1 was detected with Mm00627185_m1, and DLL4 was detected with Mm0044619_m1. Other Taqman primer probe sets (ThermoFisher) were used for gene detection as follows: Muc5ac: Mm01276718_m1; Muc5b: Mm00466391_m1; Scgb1a1: Mm01230908_m1; FoxJ1: Mm01267279_m1; and Tubb4a: mM00726185. Results were normalized to cyclophilin A, as detected by primer probe set RTS9317 (forward sequence TCGCCGCTTGCTGCA, designated herein as SEQ ID NO: 34; reverse sequence ATCGGCCGTGATGTCGA, designated herein as SEQ ID NO: 35; probe sequence CCATGGTCAACCCCACCGTGTTC, designated herein as SEQ ID: 36). The normalized results are shown in the tables below as the average percent for each treatment group, relative to that of the saline treated group. The results show that each modified oligonucleotide that is 100% complementary to only one member of the Notch signaling pathway decreased mRNA transcript levels of multiple members of the Notch signaling pathway and decreased mRNA transcript levels of goblet or club cell markers, and/or increased mRNA transcript levels of ciliated cell markers. An entry of "n.d." means that the corresponding data was not analyzed.

TABLE 23 mRNA levels (% saline) in mouse lung

| Compound No. | Target transcript | Notch1 | JAG1 | JAG2 | DLL4 | Notch2 | Notch3 |
|---|---|---|---|---|---|---|---|
| Saline | None | 100 | 100 | 100 | 100 | 100 | 100 |
| 549144 | None | 99 | 97 | 88 | 79 | 90 | 90 |
| 784563 | Notch1 | 54 | 77 | 71 | 41 | 58 | 49 |
| 897368 | JAG1 | 39 | 25 | 46 | 33 | 35 | 27 |
| 897427 | JAG1 | 49 | 25 | 76 | 43 | 49 | 38 |
| 897758 | JAG2 | 57 | 66 | 46 | 55 | 62 | 43 |
| 897763 | JAG2 | 52 | 71 | 51 | 62 | 59 | 51 |
| 797555 | DLL4 | 42 | 52 | 53 | 35 | 45 | 31 |
| 797868 | DLL4 | 57 | 74 | 66 | 55 | 65 | 47 |

TABLE 24 mRNA levels (% saline) in mouse lung

| Compound No. | Target transcript | Goblet Cells Muc5ac mRNA | Club Cells Scgb1a1 mRNA | Ciliated cells FOXJ1 mRNA |
|---|---|---|---|---|
| Saline | none | 100 | 100 | 100 |
| 549144 | none | 130 | 88 | 117 |
| 784563 | Notch1 | n.d. | 54 | 90 |
| 897368 | JAG1 | 61 | 17 | 84 |
| 897427 | JAG1 | 51 | 30 | 206 |
| 897758 | JAG2 | 192 | 60 | 101 |
| 897763 | JAG2 | 111 | 76 | 105 |
| 797555 | DLL4 | 249 | 43 | 75 |
| 797868 | DLL4 | 199 | 94 | 106 |

Example 12: Effects on Notch Signaling Pathway Inhibition and Trans-Differentiation of Lung Cells by Modified Oligonucleotides Complementary to a Member of the Notch Signaling Pathway Modified oligonucleotides described above were tested in A/J mice (Jackson Labs). Groups of 8 week old male A/J mice were administered 200 μg of modified oligonucleotide every other day for 5 days via oropharyngeal delivery while under anesthesia. Each group contained 4 mice. One group of control male A/J mice was administered saline. Mice were sacrificed 72 hours after the last dose, and lung tissue was harvested. Total RNA was isolated from the lung tissue, and mRNA levels of JAG1, JAG2, and lung cell differentiation markers were measured by RT-qPCR using Taqman probe set Mm00496902_m1 (Thermo Fisher) for JAG1, primer probe set RTS35955 (see Example 5) for JAG2, Taqman probe set Mm01230908_m1 for Scgb1a1, and Taqman probe set Mm01267279_m1 for FoXJ1. Results were normalized to cyclophilin A levels and are presented in the tables below as the average mRNA level for each treatment group relative to the saline treated group. The results show that each modified oligonucleotide that is 100% complementary to only one member of the Notch signaling pathway decreased mRNA transcript levels of multiple members of the Notch signaling pathway and decreased mRNA transcript levels of a club cell marker and/or increased mRNA transcript levels of a ciliated cell marker.

TABLE 25 mRNA levels in mouse lung relative to saline treated animals

| Compound No. | Notch signaling pathway | | Ciliated Cells FoxJ1 mRNA | Club cells Scgb1a1 mRNA |
|---|---|---|---|---|
| | JAG1 mRNA | JAG2 mRNA | | |
| Saline | 1.0 | 1.0 | 1.0 | 1.0 |
| 549144 | 0.9 | 1.0 | 0.8 | 0.7 |
| 897368 | 0.2 | 0.4 | 0.9 | 0.3 |
| 897427 | 0.2 | 0.8 | 2.4 | 0.3 |
| 897316 | 0.5 | 0.8 | 1.5 | 0.6 |
| 897372 | 0.5 | 0.6 | 1.9 | 0.5 |
| 897439 | 0.5 | 0.8 | 2.5 | 0.8 |

Example 13: House Dust Mite Model and Methacholine Challenge with Pre-Treatment of Modified Oligonucleotide House dust mite (HDM) is a common allergen that has been previously demonstrated to induce asthma-like disease in mice (Johnson, Am J Respir Crit Care Med Vol 169. pp 378-385, 2004), with increases in airway inflammation, goblet cell hyperplasia, and airway hyperreactivity to methacholine. Modified oligonucleotides described above were tested in A/J mice in combination with administration of HDM and methacholine to induce asthma-like symptoms. Each treatment group contained 4 mice. Modified oligonucleotides and HDM were administered to anesthetized mice via oropharyngeal delivery.

Mice were administered 200 μg of a modified oligonucleotide twice per week for 2 weeks (5 total treatments) before the first HDM treatment (100 μg/mouse/treatment) on day 16. Treatment with modified oligonucleotide twice per week continued until study day 30. HDM treatment was repeated once per week for 3 weeks. One group of mice was administered saline in place of modified oligonucleotide and HDM. 48 hours after the final HDM treatment and 24 hours after the final oligonucleotide treatment, mice were challenged with methacholine, which causes bronchoconstriction. Lung function was measured using the Penh score obtained through unrestrained plethysmography. A higher Penh score indicates more constriction than a lower Penh number. The results in the table below show that mice treated with a modified oligonucleotide complementary to a member of the Notch signaling pathway had improved lung function compared to mice treated with a modified oligonucleotide that is not 100% complementary to a member of the Notch signaling pathway.

72 hours after the final HDM treatment and 48 hours after the final oligonucleotide treatment, mice were sacrificed and lung tissue was harvested for histological analysis and RNA isolation. Sections prepared for histology were stained with Schiff stain in order to detect mucus. The resulting images showed that mucus staining was reduced in both groups of mice treated with a modified oligonucleotide 100% complementary to JAG1 compared to the group of mice treated with a modified oligonucleotide that is not 100% complementary to any member of the Notch signaling pathway. Furthermore, compound 897427, which reduced JAG1 mRNA levels to a greater extent than compound 897372, also reduced mucus staining to a greater extent than compound 897372.

Total RNA was isolated from lung tissue, and mRNA levels were measured by RT-qPCR using primer probe sets described above and normalized to cyclophilin levels. Results are presented in the tables below as the average mRNA level for each treatment group relative to saline treated animals. The results in the tables below show that in an asthma disease model, mice treated with a modified oligonucleotide complementary to a member of the Notch signaling pathway had improved lung function and trans-differentiation to ciliated cells compared to mice treated with a modified oligonucleotide that is not 100% complementary to a member of the Notch signaling pathway.

TABLE 26

Penh scores

| | Methacholine (mg/mL) | | | | | |
|---|---|---|---|---|---|---|
| | 0 | 3 | 6 | 12 | 25 | 50 |
| Treatment group | Penh score | | | | | |
| Naïve (saline + saline) | 0.7 | 0.9 | 1.8 | 3.8 | 4.8 | 7.3 |
| 549144 + HDM | 1.0 | 1.4 | 3.4 | 7.1 | 11.5 | 12.4 |
| 897427 + HDM | 1.0 | 2.2 | 2.4 | 2.9 | 3.4 | 3.8 |
| 897372 + HDM | 1.2 | 1.7 | 2.8 | 4.3 | 8.3 | 10.8 |

TABLE 27 mRNA levels in lung relative to saline treated animals

| Treatment group | Notch signaling pathway JAG1 | Goblet cell markers | | | | Club cell marker Scgb1a1 | Ciliated cell marker FOXJ1 |
|---|---|---|---|---|---|---|---|
| | | Muc5b | Gob5 (Clca1) | Foxa3 | SPDEF | | |
| Naïve (saline + saline) | 1.0 | 1.0 | 1.0 | 1.0 | 1.0 | 1.0 | 1.0 |
| 549144 + HDM | 0.8 | 9.1 | 81.9 | 4.4 | 5.8 | 0.3 | 1.1 |
| 897427 + HDM | 0.5 | 4.5 | 18.9 | 2.2 | 2.7 | 0.2 | 3.4 |
| 897372 + HDM | 0.7 | 7.7 | 38.9 | 2.7 | 4.0 | 0.3 | 2.3 |

Example 14: House Dust Mite Model and Methacholine Challenge, Followed by Treatment with Modified Oligonucleotide Modified oligonucleotides described above were administered to A/J mice after treatment with HDM and methacholine to induce asthma-like symptoms. Modified oligonucleotides and HDM were administered to anesthetized mice via oropharyngeal delivery, as outlined in the table below. Each group contained 4-6 mice. The three groups that received a modified oligonucleotide and the one group that received house dust mites only ("HDM-only") received HDM treatment (100 μg/mouse/treatment) weekly for four weeks. The group of naïve mice received no HDM or oligonucleotide treatment. On day 11, 72 hours after the second HDM treatment, mouse lung function was tested following various doses of methacholine ("methacholine challenge"). After the methacholine challenge, mice in the appropriate groups were administered 200 μg of modified oligonucleotide, as indicated in the table below. Mice were sacrificed on day 12 or day 27, and lung tissue was harvested.

TABLE 28

Study design for each treatment group

| Study Day | Naïve | HDM-only | 549144 | 897427 | 897372 |
|---|---|---|---|---|---|
| 1 | none | HDM | HDM | HDM | HDM |
| 8 | none | HDM | HDM | HDM | HDM |

TABLE 28-continued

Study design for each treatment group

| Study Day | Naïve | HDM-only | 549144 | 897427 | 897372 |
|---|---|---|---|---|---|
| 11 | Methacholine challenge | | | | |
| 11 | none | none | 549144 | 897427 | 897372 |
| 12 | Sac/RNA analysis | | none | none | none |
| 13 | N/A | N/A | 549144 | 897427 | 897372 |
| 14 | N/A | N/A | HDM | HDM | HDM |
| 15 | N/A | N/A | 549144 | 897427 | 897372 |
| 17 | N/A | N/A | 549144 | 897427 | 897372 |
| 20 | N/A | N/A | 549144 | 897427 | 897372 |
| 21 | N/A | N/A | HDM | HDM | HDM |
| 22 | N/A | N/A | 549144 | 897427 | 897372 |
| 25 | N/A | N/A | 549144 | 897427 | 897372 |
| 26 | N/A | N/A | Methacholine challenge | | |
| 27 | N/A | N/A | Sac/RNA analysis | | |

The methacholine challenge doses and results are shown in the table below. Day 11 scores were obtained prior to that day's administration of modified oligonucleotides. The results in the table below show that mice treated with a modified oligonucleotide complementary to a member of the Notch signaling pathway after inducement of asthma-like symptoms generally had improved lung function compared to mice treated with a modified oligonucleotide that is not 100% complementary to a member of the Notch signaling pathway.

Total RNA was isolated from the lung tissue of sacrificed mice, and mRNA levels were measured by RT-qPCR, as described in Example 13. Results are presented in the table below as normalized mRNA levels relative to saline treated animals. The results show that mice treated with a modified oligonucleotide complementary to a member of the Notch signaling pathway after inducement of asthma-like symptoms exhibited increased trans-differentiation to ciliated cells compared to mice treated with a modified oligonucleotide that is not 100% complementary to a member of the Notch signaling pathway.

Sections of lung tissue were prepared for histology and stained with Schiff stain in order to detect mucus. The resulting images showed that mucus staining was reduced in both groups of mice treated with a modified oligonucleotide 100% complementary to JAG1 compared to the group of mice treated with a modified oligonucleotide that is not 100% complementary to any member of the Notch signaling pathway. Furthermore, compound 897427, which reduced JAG1 mRNA levels to a greater extent than compound 897372, also reduced mucus staining to a greater extent than compound 897372. These results show that asthma-like symptoms were reversed following administration of modified oligonucleotides 100% complementary to a member of the Notch signaling pathway.

TABLE 29

Penh scores

| Treatment group, study day | Methacholine (mg/mL) | | | | |
|---|---|---|---|---|---|
| | 0 | 3 | 6 | 12 | 25 |
| | Penh score | | | | |
| Naïve, day 11 | 0.7 | 0.8 | 1.6 | 2.9 | 6.0 |
| HDM-only, day 11 | 0.8 | 2.6 | 4.1 | 7.1 | 9.3 |
| 549144, day 11 | 0.8 | 2.4 | 5.9 | 7.6 | 9.4 |
| 897427, day 11 | 0.7 | 2.9 | 3.8 | 5.8 | 10.3 |
| 897372, day 11 | 0.8 | 2.7 | 4.5 | 7.2 | 10.7 |
| 549144, day 26 | 1.1 | 3.5 | 5.0 | 10.9 | 13.4 |
| 897427, day 26 | 1.2 | 2.0 | 3.4 | 6.6 | 8.6 |
| 897372, day 26 | 1.3 | 1.9 | 5.6 | 9.2 | 12.5 |

TABLE 30 mRNA levels in lung relative to saline treated animals

| Treatment group, study day | Notch signaling pathway JAG1 | Goblet cells Muc5b | Ciliated cells FoxJ1 |
|---|---|---|---|
| Naïve, day 12 | 1.0 | 1 | 1 |
| HDM-only, day 12 | 1.1 | 6.3 | 1.4 |
| 549144, day 27 | 0.7 | 5.9 | 1.1 |
| 897427, day 27 | 0.3 | 1.6 | 1.7 |
| 897372, day 27 | 0.6 | 3.4 | 2.8 |

Example 15: Inhibition of the Notch Signaling Pathway In Vivo by Modified Oligonucleotides Complementary to Notch1, Notch2, or Notch3

Modified oligonucleotides described in Examples 2, 3, and 4 were tested in BALB/c mice. Groups of 8 week old male mice were administered 50 mg/kg modified oligonucleotide once per week for four weeks via subcutaneous delivery. Each group contained 4 mice. One group received PBS via subcutaneous delivery. Mice were sacrificed 48 hours after the last dose, and lung tissue and other tissues were harvested. Total RNA was isolated from the lung tissue and other tissues, and mRNA levels were measured by RT-qPCR.

TABLE 31

Notch1 mRNA levels (% PBS control)

| Compound No. | Target transcript | Liver | Lung | Quadricep | Kidney |
|---|---|---|---|---|---|
| 549144 | None | 102 | 94 | 79 | 92 |
| 784563 | Notch1 | 34 | 57 | 55 | 64 |
| 784586 | Notch1 | 50 | 66 | 66 | 69 |
| 977472 | Notch2 | 105 | 89 | 79 | 98 |
| 977499 | Notch2 | 90 | 88 | 91 | 89 |
| 977129 | Notch3 | 96 | 89 | 88 | 96 |
| 977130 | Notch3 | 75 | 78 | 65 | 86 |

TABLE 32

Notch2 mRNA levels (% PBS control)

| Compound No. | Target transcript | Liver | Lung | Quadricep | Kidney |
|---|---|---|---|---|---|
| 549144 | None | 97 | 102 | 87 | 95 |
| 784563 | Notch1 | 96 | 87 | 112 | 104 |
| 784586 | Notch1 | 102 | 107 | 101 | 107 |
| 977472 | Notch2 | 6 | 41 | 20 | 50 |
| 977499 | Notch2 | 6 | 54 | 45 | 59 |
| 977129 | Notch3 | 97 | 100 | 116 | 105 |
| 977130 | Notch3 | 90 | 91 | 99 | 102 |

TABLE 33

Notch3 mRNA levels (% PBS control)

| Compound No. | Target transcript | Liver | Lung | Quadricep | Kidney |
|---|---|---|---|---|---|
| 549144 | None | 84 | 104 | 104 | 95 |
| 784563 | Notch1 | 87 | 85 | 84 | 97 |
| 784586 | Notch1 | 35 | 66 | 79 | 67 |
| 977472 | Notch2 | 92 | 79 | 98 | 96 |
| 977499 | Notch2 | 106 | 83 | 120 | 92 |
| 977129 | Notch3 | 31 | 29 | 27 | 70 |
| 977130 | Notch3 | 33 | 18 | 20 | 59 |

Plasma levels of liver transaminases were measured using an automated clinical chemistry analyzer (Hitachi Olympus AU400e, Melville, N.Y.). The results are presented in the table below.

TABLE 34

Plasma Transaminases

| Compound No. | ALT (U/L) | AST (U/L) |
|---|---|---|
| 549144 | 25.0 | 58.5 |
| 784563 | 36.3 | 57.3 |
| 784586 | 234.5 | 157.8 |
| 977472 | 89.8 | 109.8 |
| 977499 | 32.8 | 47.3 |
| 977129 | 33.8 | 84.3 |
| 977130 | 38.0 | 68.8 |

Example 16: House Dust Mite Model and Methacholine Challenge, Followed by Treatment with Modified Oligonucleotide Modified oligonucleotides described above were administered to A/J mice after treatment with HDM and methacholine to induce asthma-like symptoms. Modified oligonucleotides and HDM were administered to anesthetized mice as described in Example 14, via oropharyngeal delivery. Each group contained 10-14 mice. A group of naïve mice received no HDM or oligonucleotide treatment, and a group of HDM-only mice received HDM treatment but no modified oligonucleotide. For HDM-only and HDM+oligonucleotide-treated groups, mice were administered HDM (100 μg/mouse/treatment) weekly for 5 weeks. For HDM+ oligonucleotide-treated groups, mice were administered 200 μg/dose of compound no. 549144 (control) or compound no. 897427 (Jag1) three times a week for 3.5 weeks.

A methacholine challenge was performed, as described above, on day 11 (baseline) and day 38. Day 11 scores were obtained prior to that day's administration of modified oligonucleotides, and animals were randomized to normalize the baseline Penh score. The results in the table below show that mice treated with a modified oligonucleotide complementary to a member of the Notch signaling pathway after inducement of asthma-like symptoms generally had improved lung function compared to mice treated with a modified oligonucleotide that is not 100% complementary to a member of the Notch signaling pathway.

TABLE 35

Penh scores on day 38

| Treatment group | Methacholine (mg/mL) | | | |
|---|---|---|---|---|
| | 0 | 3 | 6 | 12 |
| | Penh score | | | |
| Naïve | 0.65 | 0.84 | 1.18 | 2.53 |
| HDM-only | 0.73 | 3.72 | 12.6 | 15.3 |
| HDM + 549144 | 0.94 | 4.10 | 10.5 | 16.4 |
| HDM + 897427 | 1.04 | 1.99 | 4.12 | 7.3 |

Mice were sacrificed, total RNA was isolated from the lung tissue, and mRNA levels were measured by RT-qPCR, as described in Example 13. Results are presented in the table below as normalized mRNA levels relative to naïve animals. The results show that mice treated with a modified oligonucleotide 100% complementary to a member of the Notch signaling pathway after inducement of asthma-like symptoms exhibited increased trans-differentiation to ciliated cells compared to mice treated with a modified oligonucleotide that is not 100% complementary to a member of the Notch signaling pathway.

TABLE 36 mRNA levels in lungs of treated mice relative to naive mice on day 40 (% control)

| Treatment group, study day | Notch signaling pathway JAG1 | Goblet cell marker Muc5b | Ciliated cell marker FoxJ1 |
|---|---|---|---|
| Naïve | 100 | 100 | 100 |
| HDM-only | 58 | 476 | 64 |
| HDM + 549144 | 39 | 363 | 41 |
| HDM + 897427 | 13 | 136 | 66 |

Example 17: Inhibition of the Notch Signaling Pathway by Modified Oligonucleotides Complementary to Hes-1

Modified oligonucleotides 100% complementary to mouse Hes-1 were tested at various doses in HEPA1-6 (mouse hepatoma) cells. The cells were plated at a density of 20,000 cells per well and transfected using electroporation with 0.11 µM, 0.33 µM, 10 µM, or 30 µM modified oligonucleotide, as specified in the tables below. After a treatment period of approximately 24 hours, total RNA was isolated from the cells and Hes-1 mRNA levels were measured by RT-qPCR. Mouse Hes-1 primer probe set RTS38987 was used to measure Hes-1 (Forward sequence GCACAGAAAGTCATCAAAGCC, SEQ ID NO: 219; Reverse sequence ATGTCTGCCTTCTCTAGCTTG, SEQ ID NO: 220; Probe sequence ATTCTTGCCCTTCGCCTCTTCTCC, SEQ ID NO: 221). Hes-1 mRNA levels were normalized according to total RNA content as measured by RIBOGREEN. Results are presented as the percent level of normalized Hes-1 mRNA, relative to that of the untreated control cells. As illustrated in the tables below, Hes-1 mRNA transcript levels were reduced in a dose-dependent manner in cells treated with modified oligonucleotides complementary to Hes-1.

The modified oligonucleotides in the tables below are cEt gapmers (as described in Example 1). The nucleobase sequences of the modified oligonucleotides, shown in the tables below, are 100% complementary to mouse Hes-1 pre-mRNA (GENBANK No. NC_000082.6_TRUNC_30063857_30069296, SEQ ID No. 217), and/or to mouse Hes-1 mRNA (GENBANK No. NM_008235.2, SEQ ID: 218).

TABLE 37

Modified oligonucleotides complementary to Hes-1

| Compound Number | Sequence | SEQ ID 217 top site | SEQ ID 217 stop site | SEQ ID 218 start site | SEQ ID 218 start site | SEQ ID NO. |
|---|---|---|---|---|---|---|
| 1057776 | CACTATTCCAGGACCA | 1545 | 1560 | 45 | 60 | 222 |
| 1057778 | AGCACTATTCCAGGAC | 1547 | 1562 | 47 | 62 | 223 |
| 1057781 | ATCGGTAGCACTATTC | 1553 | 1568 | 53 | 68 | 224 |
| 1057782 | GATCGGTAGCACTATT | 1554 | 1569 | 54 | 69 | 225 |
| 1057784 | GTGATCGGTAGCACTA | 1556 | 1571 | 56 | 71 | 226 |
| 1057788 | CTACTTAGTGATCGGT | 1563 | 1578 | 63 | 78 | 227 |
| 1057789 | GCTACTTAGTGATCGG | 1564 | 1579 | 64 | 79 | 228 |
| 1057796 | TTATTATGTCTTAGGG | 1579 | 1594 | 79 | 94 | 229 |
| 1057797 | TTTATTATGTCTTAGG | 1580 | 1595 | 80 | 95 | 230 |
| 1057799 | GGTTTATTATGTCTTA | 1582 | 1597 | 82 | 97 | 231 |
| 1057800 | AGGTTTATTATGTCTT | 1583 | 1598 | 83 | 98 | 232 |

TABLE 37-continued

Modified oligonucleotides complementary to Hes-1

| Compound Number | Sequence | SEQ ID 217 top site | SEQ ID 217 stop site | SEQ ID 218 start site | SEQ ID 218 start site | SEQ ID NO. |
|---|---|---|---|---|---|---|
| 1057804 | GCAGTTGAAGGTTTAT | 1591 | 1606 | 91 | 106 | 233 |
| 1057805 | AGCAGTTGAAGGTTTA | 1592 | 1607 | 92 | 107 | 234 |
| 1057813 | TTTTTGGAATCCTTCA | 1674 | 1689 | 174 | 189 | 235 |
| 1057906 | GGACTTTACGGGTAGC | 3588 | 3603 | 1099 | 1114 | 236 |
| 1057910 | CGTTTTTAGTGTCCGT | 3625 | 3640 | 1136 | 1151 | 237 |
| 1057975 | AGAGCTTAGTTCTTTG | 2130 | 2145 | 45 | 60 | 238 |
| 1057979 | GTAAGATCCACATGCA | 2154 | 2169 | 47 | 62 | 239 |
| 1057980 | GGTAAGATCCACATGC | 2155 | 2170 | 53 | 68 | 240 |
| 1057987 | CAGTCCTCCTTGTCAG | 2263 | 2278 | 54 | 69 | 241 |
| 1057994 | GGAATGCCGGGAGCTC | 2306 | 2321 | 56 | 71 | 242 |
| 1058018 | GGCAGTAAAATGTAGC | 2490 | 2505 | 63 | 78 | 243 |
| 1058024 | GGCTATAAATAAGACC | 2534 | 2549 | 64 | 79 | 244 |
| 1058030 | GTAACAACTTGGGAGC | 2553 | 2568 | 79 | 94 | 245 |
| 1058031 | AGTAACAACTTGGGAG | 2554 | 2569 | 80 | 95 | 246 |
| 1058043 | CTTCTCGGCTACAGCC | 2590 | 2605 | 82 | 97 | 247 |
| 1058045 | ACCGGCTTCTACCACA | 2624 | 2639 | 83 | 98 | 248 |
| 1058055 | GTGCTAAACCACTGAC | 2693 | 2708 | 91 | 106 | 249 |
| 1058071 | TTCTCCCTAGGTTGGG | 2855 | 2870 | 92 | 107 | 250 |

TABLE 38

Dose response

| Compound Number | Hes-1 mRNA (% control) | | | | IC50 (µM) |
|---|---|---|---|---|---|
| | 1,111 nM | 3,333 nM | 10,000 nM | 30,000 nM | |
| 1057994 | 33 | 35 | 27 | 14 | <1.1 |
| 1057906 | 102 | 88 | 52 | 35 | >30 |
| 1058071 | 102 | 97 | 111 | 94 | >30 |
| 1057782 | 86 | 94 | 79 | 52 | >30 |
| 1057799 | 76 | 60 | 32 | 17 | 4.7 |
| 1057910 | 71 | 65 | 39 | 18 | 5.3 |
| 1058031 | 82 | 80 | 77 | 55 | >30 |
| 1058018 | 80 | 84 | 83 | 71 | >30 |
| 1057987 | 85 | 96 | 90 | 108 | >30 |
| 1058055 | 71 | 68 | 72 | 52 | >30 |
| 1057975 | 94 | 92 | 78 | 58 | >30 |
| 1057778 | 65 | 56 | 37 | 16 | 3.7 |
| 1058043 | 66 | 91 | 105 | 88 | >30 |
| 1058030 | 81 | 64 | 27 | 8 | 4.7 |
| 1057979 | 62 | 56 | 30 | 15 | 3.1 |

TABLE 39

Dose response

| Compound Number | Hes-1 mRNA (% control) | | | | IC50 (µM) |
|---|---|---|---|---|---|
| | 1,111 nM | 3,333 nM | 10,000 nM | 30,000 nM | |
| 1057784 | 100 | 77 | 42 | 19 | 8.5 |
| 1058024 | 105 | 105 | 90 | 70 | >30 |
| 1057797 | 90 | 72 | 41 | 27 | 8.4 |
| 1057788 | 104 | 86 | 51 | 25 | 11.1 |
| 1058045 | 89 | 91 | 77 | 62 | >30 |
| 1057980 | 85 | 64 | 46 | 24 | 7.5 |
| 1057813 | 82 | 73 | 56 | 31 | 11.3 |
| 1057776 | 98 | 89 | 59 | 39 | 17.8 |
| 1057789 | 83 | 78 | 53 | 37 | 13.7 |
| 1057796 | 79 | 73 | 47 | 30 | 9.2 |
| 1057805 | 80 | 58 | 48 | 39 | 9.6 |
| 1057800 | 72 | 54 | 31 | 12 | 3.8 |
| 1057804 | 84 | 50 | 33 | 22 | 5.0 |
| 1057781 | 86 | 74 | 47 | 26 | 8.9 |

Example 18: Inhibition of the Notch Signaling Pathway In Vivo by Modified Oligonucleotides Complementary to Hes-1

Groups of 6 week old male BALB/c mice were administered 50 mg/kg of a modified oligonucleotide described above once per week for 4 weeks via subcutaneous delivery. Each group contained 4 mice. One group was administered only saline as a control. Mice were sacrificed 48 hours after the last dose, and tissues were harvested. Total RNA was isolated from the liver and lung tissue, and mRNA levels of Hes-1 were measured via RT-qPCR as described above, and normalized to Cyclophilin A levels.

TABLE 40

| | mRNA levels | |
|---|---|---|
| Compound Number | Hes-1, lung (% Control) | Hes-1, liver (% control) |
| Saline | 100 | 100 |
| 549144 | 111 | 95 |
| 1057778 | 112 | 53 |

TABLE 40-continued

| | mRNA levels | |
|---|---|---|
| Compound Number | Hes-1, lung (% Control) | Hes-1, liver (% control) |
| 1057781 | 122 | 58 |
| 1057797 | 95 | 21 |
| 1057799 | 86 | 27 |
| 1057800 | 117 | 66 |
| 1057804 | 103 | 67 |
| 1057910 | 110 | 65 |
| 1057979 | 63 | 18 |
| 1057994 | 4 | 2.5 |
| 1058030 | 41 | 15 |

Example 19: Effects on Notch Signaling Pathway Inhibition and Trans-Differentiation of Lung Cells by Modified Oligonucleotides Complementary to Members of the Notch Signaling Pathway Modified oligonucleotides were tested in A/J mice (Jackson Labs). Groups of 8 week old male A/J mice were administered 10 mg/kg of modified oligonucleotide three times in one week via oropharyngeal delivery while under anesthesia. Each group contained 4 mice. One group of control male A/J mice was administered saline, and another group was administered the control oligonucleotide 549144, described herein (see Example 7). Mice were sacrificed 72 hours after the last dose, and lung tissue was harvested. Total RNA was isolated from the lung tissue, and mRNA levels of Hes1, Notch1, Notch2, Notch3, FOXJ1, and Jag1 were measured by RT-qPCR using RTS38987 for Hes1 (See Example 17), RTS1458 for Notch 1 (see Example 2), RTS36982 for Notch 2 (see Example 9), RTS36974 for Notch 3 (see Example 4), Mm01267279 for FoxJ1 (see Example 11), Mm01230908 for Scgb1a1 (see Example 11), and RTS35953 for Jag 1 (Forward sequence GCACAGAAAGTCATCAAAGCC, SEQ ID NO: 219; Reverse sequence ATGTCTGCCTTCTCTAGCTTG, SEQ ID NO: 220; Probe sequence ATTCTTGCCCTTCGCCTCTTCTCC, SEQ ID NO: 221). RNA levels were normalized to cyclophilin A levels and are presented in the tables below as the average, normalized mRNA level for each treatment group relative to the saline treated group. The results show that each modified oligonucleotide that is 100% complementary to only one member of the Notch signaling pathway decreased mRNA transcript levels of multiple members of the Notch signaling pathway and decreased mRNA transcript levels of a club cell marker and/or increased mRNA transcript levels of a ciliated cell marker.

TABLE 41

| mRNA levels in lung of oligonucleotide treated mice relative to saline treated mice | | | | | | | |
|---|---|---|---|---|---|---|---|
| | Notch signaling pathway components | | | | | Ciliated Cell marker | Club cell marker |
| Compound No. | Hes-1 mRNA | Notch1 mRNA | Notch2 mRNA | Notch3 mRNA | Jag1 mRNA | FoxJ1 mRNA | Scgb1a1 mRNA |
| 549144 | 75 | 72 | 71 | 67 | 82 | 71 | 58 |
| 977472 | 48 | 48 | 19 | 57 | 75 | 149 | 16 |
| 977499 | 62 | 70 | 25 | 72 | 102 | 226 | 28 |
| 1057797 | 30 | 63 | 73 | 64 | 70 | 92 | 36 |
| 1057979 | 59 | 77 | 87 | 82 | 88 | 95 | 38 |
| 1058030 | 44 | 66 | 75 | 69 | 68 | 67 | 45 |

Example 20: House Dust Mite Model and Methacholine Challenge with Pre-Treatment of Modified Oligonucleotide Modified oligonucleotides described above were tested in A/J mice in combination with administration of HDM and methacholine to induce asthma-like symptoms as described in Example 13 above. Each treatment group contained 6 mice for mRNA analysis and 8 mice for the methacholine challenge. Modified oligonucleotides and HDM were administered to anesthetized mice via oropharyngeal delivery.

Mice were administered 200 μg of a modified oligonucleotide twice per week for 2 weeks (5 total treatments) before the first HDM treatment (100 μg/mouse/treatment) on day 16. Treatment with modified oligonucleotide twice per week continued until study day 30. HDM treatment was repeated once per week for 3 weeks. One group of mice was administered saline in place of modified oligonucleotide and HDM, and served as the control group to which other groups were compared. 48 hours after the final HDM treatment and 24 hours after the final oligonucleotide treatment, mice were challenged with methacholine, which causes bronchoconstriction. Lung function was measured using the Penh score obtained through unrestrained plethysmography. A higher Penh score indicates more constriction than a lower Penh number.

Total RNA was isolated from lung tissue, and mRNA levels were measured by RT-qPCR using primer probe sets described above and normalized to cyclophilin levels. Results are presented in the tables below as the average mRNA level for each treatment group relative to saline treated animals. The results in the tables below show that in an asthma disease model, mice treated with a modified oligonucleotide complementary to a member of the Notch signaling pathway had improved trans-differentiation to ciliated cells compared to mice treated with a modified oligonucleotide that is not 100% complementary to a member of the Notch signaling pathway.

TABLE 42

Penh scores

| Treatment group | Methacholine (mg/mL) | | | |
|---|---|---|---|---|
| | 0 | 3 | 6 | 12 |
| | Penh score | | | |
| Naïve (saline + saline) | 0.8 | 1.0 | 1.8 | 4.1 |
| 549144 + HDM | 0.9 | 3.8 | 4.8 | 6.1 |
| 977472 + HDM | 1.0 | 1.4 | 3.0 | 7.4 |
| 977499 + HDM | 1.1 | 1.6 | 3.6 | 7.1 |

TABLE 43 mRNA levels in lung of oligonucleotide treated mice relative to saline treated mice

| Treatment group | Notch signaling pathway | | | Goblet cell markers | | Club cell marker | Ciliated cell marker |
|---|---|---|---|---|---|---|---|
| | Notch2 | Jag1 | Jag2 | Muc5b | Muc5ac | Scgb1a1 | FOXJ1 |
| 549144 + HDM | 46 | 78 | 74 | 472 | 3707 | 18 | 56 |
| 977472 + HDM | 21 | 92 | 96 | 184 | 1322 | 21 | 120 |
| 977499 + HDM | 21 | 96 | 88 | 176 | 1110 | 17 | 171 |

Example 21: House Dust Mite Model and Methacholine Challenge, Followed by Treatment with Modified Oligonucleotide Modified oligonucleotides described above were administered to A/J mice after treatment with HDM and methacholine to induce asthma-like symptoms. Modified oligonucleotides and HDM were administered to anesthetized mice as described in the table below, via oropharyngeal delivery. Each group contained 8 mice. A group of naïve mice received no HDM or oligonucleotide treatment and one group received 5 doses of HDM and no oligonucleotide treatment ("HDM-only"). For HDM-only and HDM+oligonucleotide-treated groups, mice were administered HDM (100 µg/mouse/treatment) weekly for 5 weeks. For HDM+ oligonucleotide-treated groups, mice were administered 200 µg/dose of compound no. 549144 (control), compound no. 897427 (Jag1) or compound no. 977472 or 977499 (Notch2) three times a week for 3.5 weeks.

TABLE 44

Study design for each treatment group

| Study Day | Naïve | HDM-only | 549144 | 897427 | 977472 | 977499 |
|---|---|---|---|---|---|---|
| 1 | N/A | HDM | HDM | HDM | HDM | HDM |
| 8 | N/A | HDM | HDM | HDM | HDM | HDM |
| 11 | | | Methacholine challenge | | | |
| 15 | N/A | N/A | 549144 | 897427 | 977472 | 977499 |
| 16 | N/A | HDM | HDM | HDM | HDM | HDM |
| 17 | N/A | N/A | 549144 | 897427 | 977472 | 977499 |
| 19 | N/A | N/A | 549144 | 897427 | 977472 | 977499 |
| 22 | N/A | N/A | 549144 | 897427 | 977472 | 977499 |
| 23 | N/A | HDM | HDM | HDM | HDM | HDM |
| 24 | N/A | N/A | 549144 | 897427 | 977472 | 977499 |
| 26 | N/A | N/A | 549144 | 897427 | 977472 | 977499 |
| 29 | N/A | N/A | 549144 | 897427 | 977472 | 977499 |
| 31 | N/A | N/A | 549144 | 897427 | 977472 | 977499 |
| 32 | N/A | HDM | HDM | HDM | HDM | HDM |
| 33 | N/A | N/A | 549144 | 897427 | 977472 | 977499 |
| 37 | N/A | N/A | 549144 | 897427 | 977472 | 977499 |
| 39 | N/A | N/A | 549144 | 897427 | 977472 | 977499 |
| 40 | | | Methacholine challenge | | | |
| 41 | | | Sac/RNA analysis | | | |

A methacholine challenge was performed, as described above, on day 11 (baseline) and day 40. The results are shown in the table below.

TABLE 45

Penh scores

| Treatment group | Test day | Methacholine (mg/mL) | | | | |
|---|---|---|---|---|---|---|
| | | 0 | 3 | 6 | 12 | 25 |
| | | Penh score | | | | |
| Naïve | 11 | 0.67 | 0.77 | 1.26 | 2.34 | 3.83 |
| HDM-only | 11 | 0.76 | 1.12 | 2.75 | 3.42 | 5.38 |
| HDM + 549144 | 11 | 0.80 | 1.26 | 2.73 | 5.19 | 6.82 |
| HDM + 897427 | 11 | 0.73 | 1.38 | 2.18 | 3.05 | 5.00 |
| HDM + 977472 | 11 | 0.73 | 1.02 | 2.34 | 2.91 | 4.36 |
| HDM + 977499 | 11 | 0.77 | 1.30 | 3.41 | 4.75 | 9.65 |
| Naïve | 40 | 0.82 | 0.82 | 1.00 | 2.54 | 5.32 |
| HDM-only | 40 | 0.85 | 3.94 | 7.33 | 11.6 | 13.3 |
| HDM + 549144 | 40 | 0.94 | 2.45 | 5.64 | 8.59 | 9.70 |
| HDM + 897427 | 40 | 1.24 | 1.67 | 2.56 | 4.13 | 5.59 |
| HDM + 977472 | 40 | 1.86 | 4.20 | 8.43 | 10.1 | 11.4 |
| HDM + 977499 | 40 | 1.31 | 3.03 | 10.86 | 13.5 | 14.4 |

Mice were sacrificed, total RNA was isolated from the lung tissue, and mRNA levels were measured by RT-qPCR, as described in Example 13. Results are presented in the table below as normalized mRNA levels relative to naïve animals. The results show that mice treated with a modified oligonucleotide 100% complementary to a member of the Notch signaling pathway after inducement of asthma-like symptoms exhibited increased trans-differentiation to ciliated cells compared to mice treated with a modified oligonucleotide that is not 100% complementary to a member of the Notch signaling pathway.

TABLE 46 mRNA levels in lung of oligonucleotide treated mice relative to saline treated mice

| Treatment group | Notch signaling pathway | | Goblet cell markers | | | | Ciliated cell marker |
|---|---|---|---|---|---|---|---|
| | Notch2 | Jag1 | Muc5b | Muc5ac | Gob5 (Clca1) | SPDEF | FOXJ1 |
| HDM-only | 73 | 89 | 510 | 1062 | 20419 | 191 | 114 |
| HDM + 549144 | 45 | 76 | 682 | 2294 | 31529 | 285 | 66 |
| HDM + 897427 | 33 | 25 | 214 | 681 | 8325 | 132 | 115 |
| HDM + 977472 | 18 | 62 | 155 | 199 | 1820 | 66 | 92 |
| HDM + 977499 | 20 | 61 | 185 | 337 | 5534 | 97 | 101 |

Example 22: Inhibition of the Notch Signaling Pathway In Vivo by Modified Oligonucleotides Complementary to Jag1 or Notch2

Modified oligonucleotides described in the examples above were tested in BALB/c mice. Groups of 7 week old male mice were administered 50 mg/kg modified oligonucleotide once per week for four weeks via subcutaneous delivery. Each group contained 8 mice. One group received PBS via subcutaneous delivery. Mice were sacrificed 48 hours after the last dose, and tracheal tissue was harvested. Total RNA was isolated from the trachea, and mRNA levels were measured by RT-qPCR.

TABLE 47 mRNA levels in lung of oligonucleotide treated mice relative to saline treated mice

| Compound ID | Notch signaling pathway | | Club Cell marker | Ciliated cell marker |
|---|---|---|---|---|
| | Notch2 | Jag1 | Scgb1a1 | FOXJ1 |
| 549144 | 82 | 69 | 111 | 158 |
| 897427 | 78 | 33 | 47 | 300 |
| 977472 | 39 | 70 | 29 | 502 |
| 977499 | 63 | 78 | 60 | 291 |

What is claimed is:

1. A method of treating a respiratory disorder associated with excessive mucus production in an individual having the respiratory disorder associated with excessive mucus production, the method comprising administering a compound to the individual, thereby treating the respiratory disorder associated with excessive mucus production in the individual, wherein the compound is a modified oligonucleotide complementary to a JAG1 transcript.

2. The method of claim 1, wherein the respiratory disorder associated with excessive mucus production is asthma, chronic obstructive pulmonary disorder (COPD), idiopathic pulmonary fibrosis (IPF), or cystic fibrosis (CF).

3. The method of claim 1, wherein the compound increases trans-differentiation from club cells or goblet cells to ciliated cells, decreases mucus in the lungs, increases lung function, or a combination thereof.

4. A method of inhibiting expression or activity of the Notch signaling pathway in a lung cell, the method comprising contacting the lung cell with a compound, thereby inhibiting expression or activity of a Notch signaling pathway member in the lung cell, wherein the compound is a modified oligonucleotide complementary to a JAG1 transcript.

5. The method of claim 4, wherein the lung cell is in an individual.

6. The method of claim 5, wherein the individual has asthma, chronic obstructive pulmonary disorder (COPD), idiopathic pulmonary fibrosis (IPF), or cystic fibrosis (CF).

7. The method of claim 1, wherein the individual is human.

8. The method of claim 1, wherein the compound inhibits the expression of JAG1.

9. The method of claim 1, wherein the modified oligonucleotide is single-stranded.

10. The method of claim 1, wherein the modified oligonucleotide is part of a double-stranded duplex.

11. The method of claim 1, wherein the modified oligonucleotide is 12 to 30 linked nucleosides in length.

12. The method of claim 1, wherein the modified oligonucleotide comprises at least one modified internucleoside linkage.

13. The method of claim 12, wherein the at least one modified internucleoside linkage is a phosphorothioate internucleoside linkage.

14. The method of claim 1, wherein the modified oligonucleotide comprises at least one modified sugar moiety.

15. The method of claim 14, wherein the at least one modified sugar moiety is a bicyclic sugar moiety or a 2'-O-methoxyethyl modified sugar moiety.

16. The method of claim 14, wherein the at least one modified sugar moiety is a cEt, LNA, or ENA.

17. The method of claim 1, wherein the modified oligonucleotide comprises at least one 5-methylcytosine modified nucleobase.

18. The method of claim 12, wherein each of the at least one modified internucleoside linkage is a phosphorothioate linkage.

19. The method of claim 1, wherein each cytosine nucleobase of the modified oligonucleotide is a 5-methylcytosine.

20. The method of claim 1, wherein the modified oligonucleotide comprises:

a gap segment consisting of 7-11 linked 2'-deoxynucleosides;

a 5' wing segment consisting of 1-7 linked nucleosides; and a 3' wing segment consisting of 1-7 linked nucleosides;

wherein the gap segment is positioned immediately adjacent to and between the 5' wing segment and the 3' wing segment and wherein the nucleoside of each wing segment that is immediately adjacent to the gap segment each comprises a modified sugar.

21. The method of claim 1, wherein the modified oligonucleotide is at least 90% complementary to the JAG1 transcript.

22. The method of claim 1, wherein the modified oligonucleotide is 100% complementary to the JAG1 transcript.

23. The method of claim 1, wherein the compound is administered via inhalation.

24. The method of claim 23, wherein a pharmaceutical composition comprising the compound and at least one pharmaceutically acceptable carrier or diluent is administered.

25. The method of claim 24, wherein the pharmaceutical composition is a solution suitable for administration to an individual using a nebulizer or inhaler.

* * * * *